US008173642B2

(12) United States Patent
Kobayashi et al.

(10) Patent No.: US 8,173,642 B2
(45) Date of Patent: May 8, 2012

(54) AMINODIHYDROTHIAZINE DERIVATIVES

(75) Inventors: Naotake Kobayashi, Osaka (JP); Kazuo Ueda, Osaka (JP); Naohiro Itoh, Shiga (JP); Shinji Suzuki, Osaka (JP); Gaku Sakaguchi, Shiga (JP); Akira Kato, Shiga (JP); Akira Yukimasa, Osaka (JP); Akihiro Hori, Osaka (JP); Yuji Koriyama, Osaka (JP); Hidekazu Haraguchi, Osaka (JP); Ken Yasui, Osaka (JP); Yasuhiko Kanda, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 422 days.

(21) Appl. No.: 12/089,409

(22) PCT Filed: Oct. 23, 2006

(86) PCT No.: PCT/JP2006/321015
§ 371 (c)(1),
(2), (4) Date: Apr. 18, 2008

(87) PCT Pub. No.: WO2007/049532
PCT Pub. Date: May 3, 2007

(65) Prior Publication Data
US 2009/0082560 A1    Mar. 26, 2009

(30) Foreign Application Priority Data

Oct. 25, 2005 (JP) ................... 2005-309642
Mar. 20, 2006 (JP) ................... 2006-076636

(51) Int. Cl.
C07D 417/12 (2006.01)
C07D 417/14 (2006.01)
A61K 31/497 (2006.01)
A61K 31/54 (2006.01)

(52) U.S. Cl. ...................... 514/227.2; 544/53
(58) Field of Classification Search .......... 544/53; 514/227.2
See application file for complete search history.

(56) References Cited

U.S. PATENT DOCUMENTS

| | | | |
|---|---|---|---|
| 3,227,713 A | 1/1966 | Behner et al. | |
| 3,235,551 A * | 2/1966 | Schubert | 544/53 |
| 4,895,841 A | 1/1990 | Sugimoto et al. | |
| 4,906,626 A | 3/1990 | Amrein et al. | |
| 5,100,901 A | 3/1992 | Sugimoto et al. | |
| 5,236,942 A | 8/1993 | Miller | |
| 5,952,374 A | 9/1999 | Clarkson, Jr. et al. | |
| 6,713,276 B2 | 3/2004 | Cordell et al. | |
| 7,183,070 B2 | 2/2007 | Cordell et al. | |
| 2005/0165080 A1 | 7/2005 | Rupp et al. | |
| 2006/0173006 A1 | 8/2006 | Sun et al. | |
| 2006/0183790 A1 | 8/2006 | Cole et al. | |
| 2006/0183792 A1 | 8/2006 | Fobare et al. | |
| 2006/0183943 A1 | 8/2006 | Hu | |
| 2007/0004730 A1 | 1/2007 | Zhou et al. | |
| 2007/0004786 A1 | 1/2007 | Malamas et al. | |
| 2007/0027199 A1 | 2/2007 | Malamas et al. | |
| 2007/0224656 A1 | 9/2007 | Cordell et al. | |
| 2009/0023729 A1 | 1/2009 | Nakamura et al. | |
| 2010/0075957 A1 | 3/2010 | Tamura et al. | |
| 2010/0093999 A1 | 4/2010 | Motoki et al. | |
| 2010/0160290 A1 | 6/2010 | Kobayashi et al. | |
| 2011/0009395 A1 | 1/2011 | Audia et al. | |
| 2011/0046122 A1 | 2/2011 | Andreini et al. | |
| 2011/0065695 A1 | 3/2011 | Beauchamp et al. | |
| 2011/0237576 A1 | 9/2011 | Yonezawa et al. | |

FOREIGN PATENT DOCUMENTS

| | | |
|---|---|---|
| EP | 0 798 292 | 10/1995 |
| EP | 0713704 | 5/1996 |
| EP | 0 718 294 | 6/1996 |
| EP | 1 283 039 A1 | 2/2003 |
| EP | 1 577 294 | 9/2005 |
| EP | 1 942 105 | 7/2008 |
| EP | 2 233 474 | 9/2010 |
| EP | 2305672 | 4/2011 |
| EP | 2 360 155 | 8/2011 |
| GB | 1001093 | 8/1965 |

(Continued)

OTHER PUBLICATIONS

Vippagunta et al, "Crystalline Solids" Advanced Drug Delivery Reviews, vol. 48, pp. 3-26 (2001).*

Edwards et al., "Application of fragment-based lead generation to the discovery of novel, cyclic amidine β-secretase inhibitors with nanomolar potency, cellular activity, and high ligand efficiency", Journal of Medicinal Chemistry., vol. 50, No. 24, 2007, pp. 5912-5925.

(Continued)

Primary Examiner — Kahsay T Habte
(74) Attorney, Agent, or Firm — Hamre, Schumann, Mueller & Larson, P.C.

(57) ABSTRACT

A composition having BACE 1 inhibitory activity containing a compound represented by the general formula (I):

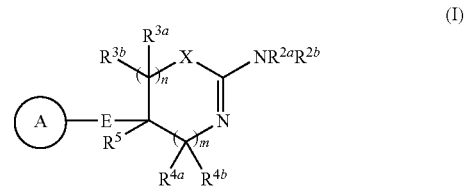

wherein ring A is an optionally substituted carbocyclic group or an optionally substituted heterocyclic group;
E is lower alkylene;
X is S, O, or $NR^1$;
$R^1$ is a hydrogen atom or lower alkyl;
$R^{2a}$, $R^{2b}$, $R^{3a}$, $R^{3b}$, $R^{4a}$ and $R^{4b}$ is each independently a hydrogen atom, halogen, or hydroxy etc.;
n and m are each independently an integer of 0 to 3;
n+m is an integer of 0 to 3;
$R^5$ is a hydrogen atom or substituted lower alkyl;
its pharmaceutically acceptable salt, or a solvate thereof.

13 Claims, No Drawings

FOREIGN PATENT DOCUMENTS

| | | | |
|---|---|---|---|
| JP | 62120374 A * | 6/1987 | |
| JP | 8-231521 A | 9/1996 | |
| JP | 9-67355 A | 3/1997 | |
| JP | 10-505862 | 12/1999 | |
| JP | 11-349572 | 12/1999 | |
| JP | 2005-509651 A | 4/2004 | |
| JP | 2004-149429 A | 5/2004 | |
| JP | 2005-517634 A | 6/2005 | |
| JP | 2005-526005 A | 9/2005 | |
| JP | 2005-531520 A | 10/2005 | |
| JP | 2006-519758 | 8/2006 | |
| JP | 2009-051828 | 3/2009 | |
| WO | 94/12165 | 6/1994 | |
| WO | 95/09619 | 4/1995 | |
| WO | 96/009286 | 3/1996 | |
| WO | WO 96/14842 A1 | 5/1996 | |
| WO | 97/07098 | 2/1997 | |
| WO | 01/19788 | 3/2001 | |
| WO | 01/78709 | 10/2001 | |
| WO | WO 01/87293 A1 | 11/2001 | |
| WO | WO 02/096897 A1 | 12/2002 | |
| WO | WO 03/039446 | 5/2003 | |
| WO | WO 03/040115 | 5/2003 | |
| WO | WO 03/040142 | 5/2003 | |
| WO | WO 03/082191 | 10/2003 | |
| WO | WO 2004/014843 A1 | 2/2004 | |
| WO | WO 2004/043916 A1 | 5/2004 | |
| WO | 2004/096795 | 11/2004 | |
| WO | 2005/014555 | 2/2005 | |
| WO | 2005/032493 | 4/2005 | |
| WO | WO 2005/058311 A1 | 6/2005 | |
| WO | WO 2005/097767 A1 | 10/2005 | |
| WO | 2005/111031 | 11/2005 | |
| WO | 2006/041404 | 4/2006 | |
| WO | WO 2006/014104 A1 | 4/2006 | |
| WO | WO 2006/041405 A1 | 4/2006 | |
| WO | 2006/065204 | 6/2006 | |
| WO | 2006/065277 | 6/2006 | |
| WO | 2006/138265 | 12/2006 | |
| WO | 2006/138304 | 12/2006 | |
| WO | WO 2006/138192 | 12/2006 | |
| WO | WO 2006/138217 | 12/2006 | |
| WO | WO 2007/005366 | 1/2007 | |
| WO | WO 2007/005404 | 1/2007 | |
| WO | WO 2007/016012 | 2/2007 | |
| WO | WO 2007/038271 | 4/2007 | |
| WO | 2007/049532 | 5/2007 | |
| WO | 2007/058580 | 5/2007 | |
| WO | WO 2007/058582 | 5/2007 | |
| WO | WO 2007/058583 | 5/2007 | |
| WO | WO 2007/058601 | 5/2007 | |
| WO | WO 2007/058602 | 5/2007 | |
| WO | 2007/073284 | 6/2007 | |
| WO | WO 2007/078813 | 7/2007 | |
| WO | 2007/114771 | 10/2007 | |
| WO | 2007/120096 | 10/2007 | |
| WO | 2007/146225 | 12/2007 | |
| WO | 2008/011560 | 1/2008 | |
| WO | WO 2008/073370 | 6/2008 | |
| WO | 2008/103351 | 8/2008 | |
| WO | 2008/133273 | 11/2008 | |
| WO | 2008/133274 | 11/2008 | |
| WO | 2009/010454 | 1/2009 | |
| WO | WO 2009/134617 | 11/2009 | |
| WO | 2009/151098 | 12/2009 | |
| WO | WO 2010/013302 | 2/2010 | |
| WO | WO 2010/013794 | 2/2010 | |
| WO | 2010/047372 | 4/2010 | |
| WO | 2010/113848 | 10/2010 | |
| WO | 2010/128058 | 11/2010 | |
| WO | 2011/005738 | 1/2011 | |
| WO | 2011/009897 | 1/2011 | |
| WO | 2011/009898 | 1/2011 | |
| WO | 2011/009943 | 1/2011 | |
| WO | 2011/020806 | 2/2011 | |
| WO | 2011/029803 | 3/2011 | |
| WO | 2011/044181 | 4/2011 | |
| WO | 2011/044184 | 4/2011 | |
| WO | 2011/044185 | 4/2011 | |
| WO | 2011/044187 | 4/2011 | |
| WO | 2011/058763 | 5/2011 | |
| WO | 2011/069934 | 6/2011 | |
| WO | 2011/070029 | 6/2011 | |
| WO | 2011/070781 | 6/2011 | |
| WO | 2011/071057 | 6/2011 | |
| WO | 2011/071109 | 6/2011 | |
| WO | 2011/071135 | 6/2011 | |
| WO | 2011/077726 | 6/2011 | |
| WO | 2011/080176 | 7/2011 | |

OTHER PUBLICATIONS

Cohen et al. "Synthesis of 2-Amino-5, +-dihydro-4H-1, 3-thiazines and Related Compounds by Acid Catalyzed Cyclization of Allylic Isothiuronium Salts." Journal of Heterocyclic Chemistry 14(5), 1977, p. 717-723.

Kuo et al. "A Synthesis of Estrone via Novel Intermediates. Mechanism of Coupling Reaction of a Vinyl Carbinol with a β Diketone." Journal of Organic Chemistry 33(8), Aug. 1968, p. 3126-3132.

Liebscher et al. "2-Arylimino-3-Thiazolines—Formation of Unusual Tautomers of 2-Arylamino-Thiazolines—A Revision." Tetrahedron Letters, 26(35), 1985, p. 4179-4180.

Fernández et al. "Syntheses and Spectral Properties of β-Iodoureas ans 2-Amino-4, 4-diphenyl-2-oxazolines." Journal of Heterocyclic Chemistry, 28(3), Apr.-May 1991, p. 777-780.

Schaumann et al. "Stickstoffhaltige Fünfring-Heterocyclen aus Carbodiimiden orderKeteniminen mit 3-Dimethylamino-2H-azirinen." Liebigs Annalen der Chemie, 1981, p. 290-305.

Fernández et al. "Syntheses of β-iodourea derivatives of carbohydrates and glycosylamino-ozazolines." Carbohydrate Research, 216, 1991, p. 21-32.

Cambie et al. "vic-Iodothiocyanates and Iodoisothiocyanates. Part 2. New Syntheses of Thiazolidin-2-ones and 2-Amino-thiazolines." Journal of the Chemical Society, Perkin Transactions I, 3, 1979, p. 765-770.

Kondrat'Eva et al. "Noncyclic dimer of 4-methyl-2-(dimenthylamino)oxazole." Akademii Nauk SSSR, Seriya Khimicheskaya, 7, 1977, p. 1680-1682.

Hünig et al. "Azo dyes by oxidative coupling, XVIII. Synthesis of 3-substituted 2-thiazolone hydrazones and 2-thiazolone benzenesulfonylhydrazones." Ann. 647, 1961, p. 66-76.

Koriyama et al., "Reversal of diastereofacial selectivity in the nucleophilic addition reaction to chiral N-sulfinimine and application to the synthesis of indrizidine 223AB," Tetrahedron, vol. 58, 2002, pp. 9621-9628.

Fujisawa et al., "Switchover of diastereofacial selectivity in the condensation reaction of optically active N-sulfinimine with ester enolate," Tetrahedron Letters, vol. 37, No. 22, 1996, pp. 3881-3884.

Vilaivan et al., "Recent Advances in Catalytic Asymmetric Addition to Imines and Related C=N Systems," Current Organic Chemistry, vol. 9, 2005, pp. 1315-1392.

Hua et al., "N-Alkylidenesulfinamides," Sulfur Reports, vol. 21, 1999, pp. 211-239.

Savoca et al., "1,5-Diazabicyclo[4.3.0]non-5-ene[1]," Encyclopedia of Reagents for Organic Synthesis, 2006, 10 pages total.

Creeke et al., "Synthesis and elaboration of heterocycles via iodocyclisation of unsaturated thioureas," Tetrahedron Letters, 1989, vol. 30, No. 33, pp. 4435-4438.

Mellor et al., A general route to spirocycles by radical additions to exocyclic unsaturated sulphides and related compounds, Tetrahedron Letters, 1991, vol. 32, No. 48, pp. 7111-7114.

Murai et al., "Iodo-cyclization of N-homoallyl thioamides leading to 2,4-diaryl-5,6-dihydro-4H-1,3-thiazines," Chemistry Letters, 2004, vol. 33, No. 5, pp. 508-509.

Singh et al., "Synthesis of heterocyclic compounds via enamines. Part 8.[†] Acid-catalysed transformations in a 4,4,6-trimethyl-1,4-dihydropyrimidine-2(3H)-thione derivatives and related compounds," J. Chem. Soc., Perkin Trans. 1, 1980, pp. 1013-1018.

Vippagunta et al. "Crystalline Solids". Advanced Drug Delivery Reviews, vol. 48, 2001, pp. 3-26.

Gavezzotti. "Are Crystal Structures Predictable". Accounts of Chemical Research, vol. 27, 1994, pp. 309-314.

Kondrat'eva et al., "Noncyclic dimer of 4-methyl-2-dimethlaminooxazole," Izvestiya Akademii Nauk SSSR, Seriya Khimicheskaya, No. 7, Jul. 1977, pp. 1680-1682 (with English translation).

Database Registry [Online], Chemical Abstracts Service, Columbus, Ohio, US; May 29, 2007, "2H-Indol-2-ome,4-(-2-amino-5,6-dihydro-4-methyl-4H-1,3-thiazin-4-yl)-1,3-dihydro-", XP002646872, Database accession No. 935998-84-8.

Schubert et al., "Neue synthesen von 2-Amino-5,6-dihydro-4H-1,3-thiazinen," Archiv der Pharmazie, 1968, vol. 301, No. 10, pp. 750-762.

Huang et al., "Pharmacophore model construction of β-secretase inhibitors," 2008, Acta Chimica Sinica, vol. 66, No. 16, pp. 1889-1897 (English language abstract provided).

Specification for co-pending U.S. Appl. No. 12/997,802, filed Dec. 13, 2010 entitled Sulfur-Containing Heterocyclic Derivative Having Beta Secretase Inhibitory Activity.

Clark, et al., "Antitumor Imidazotetrazines. 32.1 Synthesis of Novel Imidazotetrazinones and Related Bicyclic Heterocycles to Probe the Mode of Action of the Antitumor Drug Temozolomide", J. Med. Chem., vol. 38, 1995, pp. 1493-1504.

Congreve, et al., "Application of Fragment Screening by X-ray Crystallography to the Discovery of Aminopyridines as Inhibitors of β-Secretase§", J. Med. Chem., vol. 50, 2007, pp. 1124-1132.

Huang, et al., "Progress in the Development of Nonpeptidomimetic BACE 1 Inhibitors for Alzheimer's Disease", Current Medicinal Chemistry, vol. 16, 2009, pp. 1806-1820.

Goodyer et al., "Synthesis of N-benzyl- and N-phenyl-2-amino-4,5-dihydrothiazoles and thioureas and evaluation as modulators of the isoforms of nitric oxide synthase," Bioorganic & Medicinal Chemistry, 2003, vol. 11, pp. 4189-4206.

Siddiqui et al., "Some extensions of Von Bruan (BrCN) reaction on organic bases," Proc. Pakistan Acad. Sci., 1988, vol. 25, No. 3, pp. 231-240.

Ozawa et al., Pharmacological actions of 2-Aminoethylisothiuronium (AET) derivatives. II), Yakugaku Zasshi, 1968, vol. 88, No. 2, pp. 156-162 (English language abstract provided).

Curtis et al., The byozynsethis of Phenols. Part VIII. The synthesis of (2-carboxy-3,5-dihydroxyphynyl)propan-2-one (C-acetyl-o-orsellinic acid). Journal of the Chemical Society, 1964, pp. 5382-5385.

Burton et al., "Addition reactions of quinones. Part I. The reaction of cysteine and thiourea and its derivatives with some quinones," Journal of the Chemical Society, 1952, pp. 2193-2196.

Matsui, "Yomo bochuzai no kenkyu (the 6$^{th}$ report) Kagaku kozo to yomo shokugai boshi koka tono kankei (III)," Journal of Synthetic Organic Chemistry, Japan, 1950, vol. 8, No, 10, pp. Ho61-Ho65 (and International Search Report issued in PCT/JP2010/055528, which corresponds to co-pending application U.S. Appl. No. 13/260,103).

Desai et al., "The condensation of thiocarbamides with monochloroacetic acide and the conversion of arylformamidinethiolacetic acids into pseudothiohydantoin derivatives," Recuil des Travaux Chimiques des Pays-Bas et de la Belgique, 1935, pp. 118-121.

Cole et al., "Acylguanidines as small-molecule beta-secretase inhibitors," J. Med. Chem., 2006, pp. 6158-6161.

Co-pending U.S. Appl. No. 13/260,103, entitled Isothiourea Derivatives or Isourea Derivatives Having Bace I Inhibitory Activity, filed Sep. 23, 2011.

* cited by examiner

AMINODIHYDROTHIAZINE DERIVATIVES

TECHNICAL FIELD

The present invention relates to a compound which has reducing effect to produce amyloid β protein and is useful as an agent for treating disease induced by production, secretion and/or deposition of amyloid β protein.

BACKGROUND ART

In the brain of Alzheimer's patient, the peptide composed of about 40 amino acids residue as is called amyloid β protein, that accumulates to form insoluble specks (senile specks) outside nerve cells is widely observed. It is concerned that this senile specks kill nerve cells to cause Alzheimer's disease. The therapeutic agents for Alzheimer's disease, such as decomposition agents of amyloid β protein and amyloid β vaccine, are under investigation.

Secretase is an enzyme which cleaves amyloid β precursor protein (APP) in cell and produce amyloid β protein. The enzyme which controls the production of N terminus of amyloid β protein is called as BACE 1 (beta-site APP-cleaving enzyme 1, β-secretase). It is thought that inhibition of this enzyme leads to reduction of producing amyloid β protein and that the therapeutic agent for Alzheimer's disease will be created by the inhibition.

Patent Literature 1 describes the compounds which are similar to those of the present invention, and the compounds have NO synthase enzyme inhibitory activity and are useful for dementia.

Patent literatures 2 to 4 and Non-patent Literatures 1 and 2 describe the compounds which are similar to those of the present invention, and are useful for hypertensive agent, analgesic like morphine, or tranquilizers, intermediate for medicine, analgesic respectively.

Patent Literature 5 to 13 are known as BACE 1 inhibitor, however, all compounds in these literatures have different structures from the present invention.

[Patent Literature 1] International Patent Application Publication WO96/014842
[Patent Literature 2] U.S. Pat. No. 3,235,551
[Patent Literature 3] U.S. Pat. No. 3,227,713
[Patent Literature 4] JP Application Publication H09-067355
[Patent Literature 5] International Patent Application Publication WO01/187293
[Patent Literature 6] International Patent Application Publication WO04/014843
[Patent Literature 7] JP Application Publication 2004-149429
[Patent Literature 8] International Patent Application Publication WO02/96897
[Patent Literature 9] International Patent Application Publication WO04/043916
[Patent Literature 10] International Patent Application Publication WO2005/058311
[Patent Literature 11] International Patent Application Publication
[Patent Literature 12] International Patent Application Publication WO2005/097767
[Patent Literature 13] International Patent Application Publication. WO2006/041405
[Non-Patent Literature 1] Journal of Heterocyclic Chemistry, 14, 717-723 (1977)
[Non-Patent Literature 2] Journal of Organic Chemistry, 33, 8, 3126-3132 (1968)

DISCLOSURE OF INVENTION

Problems to be Solved by the Invention

The present invention provides compounds which have reducing effects to produce amyloid β protein, especially BACE 1 inhibitory activity, and are useful as an agent for treating disease induced by production, secretion and/or deposition of amyloid β protein.

Means to Solve the Problems

The present invention provides:
(a) a composition having BACE 1 inhibitory activity containing a compound represented by the general formula (I):

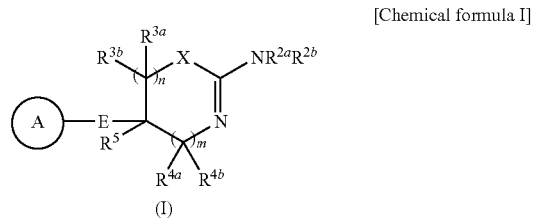

[Chemical formula 1]

wherein ring A is an optionally substituted carbocyclic group or an optionally substituted heterocyclic group;

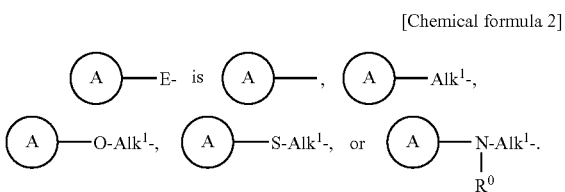

[Chemical formula 2]

$Alk^1$ is lower alkylene or lower alkenylene;
$R^0$ is a hydrogen atom, lower alkyl or acyl;
X is S, O, or $NR^1$;
$R^1$ is a hydrogen atom or lower alkyl;
$R^{2a}$ and $R^{2b}$ are each independently a hydrogen atom, hydroxy, optionally substituted lower alkyl optionally substituted lower alkenyl, optionally substituted amino, optionally substituted amidino, optionally substituted acyl optionally substituted carbamoyl, optionally substituted carbamoylcarbonyl optionally substituted lower alkylsulfonyl, optionally substituted arylsulfonyl an optionally substituted carbocyclic group or an optionally substituted heterocyclic group;
$R^{3a}$, $R^{3b}$, $R^{4a}$ and $R^{4b}$ are each independently a hydrogen atom, halogen, hydroxy, optionally substituted lower alkyl optionally substituted lower alkenyl optionally substituted acyl carboxy, optionally substituted lower alkoxycarbonyl optionally substituted amino, optionally substituted carbamoyl an optionally substituted carbocyclic group or an optionally substituted heterocyclic group;
n and m are each independently an integer of 0 to 3;
n+m is an integer of 1 to 3;
each $R^{3a}$, each $R^{3b}$, each $R^{4a}$, and each $R^{4b}$ may be independently different;
$R^5$ is a hydrogen atom, optionally substituted lower alkyl, optionally substituted lower alkenyl, optionally substituted lower alkynyl, an optionally substituted carbocyclic group or an optionally substituted heterocyclic group;

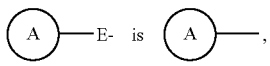

when
$R^5$ and ring A can be taken together to form

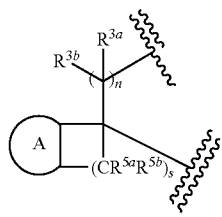

wherein $R^{5a}$ and $R^{5b}$ are each independently a hydrogen atom or lower alkyl;
s is an integer of 1 to 4;
each $R^{5a}$ and each $R^{5b}$ may be different;
with the proviso that the compound wherein n+m is 2; $R^5$ is a hydrogen atom; and
ring A is non-substituted phenyl is excluded,
its pharmaceutically acceptable salt, or a solvate thereof,
(a1) a composition having BACE 1 inhibitory activity containing a compound represented by the general formula (I):

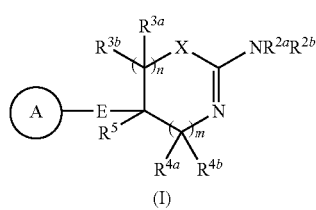

wherein ring A is an optionally substituted carbocyclic group or an optionally substituted heterocyclic group;

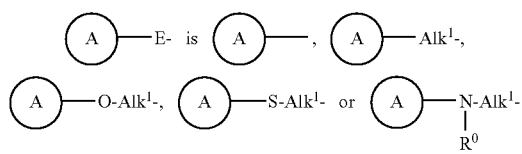

$Alk^1$ is lower alkylene;
$R^0$ is a hydrogen atom, lower alkyl or acyl;
X is S, O, or $NR^1$;
$R^1$ is a hydrogen atom or lower alkyl;
$R^{2a}$ and $R^{2b}$ are each independently a hydrogen atom, hydroxy, optionally substituted lower alkyl, optionally substituted lower alkenyl, optionally substituted amino, optionally substituted amidino, optionally substituted acyl, optionally substituted carbamoyl, optionally substituted lower alkylsulfonyl optionally substituted arylsulfonyl an optionally substituted carbocyclic group or an optionally substituted heterocyclic group;

$R^{3a}$, $R^{3b}$, $R^{4a}$, and $R^{4b}$ are each independently a hydrogen atom, halogen, hydroxy, optionally substituted lower alkyl, optionally substituted lower alkenyl optionally substituted acyl, carboxy, optionally substituted lower alkoxycarbonyl, optionally substituted amino, optionally substituted carbamoyl, an optionally substituted carbocyclic group or an optionally substituted heterocyclic group;
n and m are each independently an integer of 0 to 3;
n+m is an integer of 1 to 3;
each $R^{3a}$, each $R^{3b}$, each $R^{4a}$, and each $R^{4b}$ may be independently different;
$R^5$ is a hydrogen atom, optionally substituted lower alkyl optionally substituted lower alkenyl, optionally substituted lower alkynyl, an optionally substituted carbocyclic group or an optionally substituted heterocyclic group;

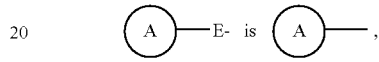

when
$R^5$ and ring A can be taken together to form

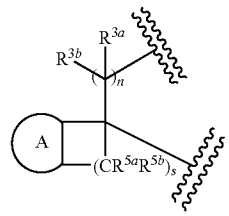

wherein $R^{5a}$ and $R^{5b}$ are each independently a hydrogen atom or lower alkyl;
s is an integer of 1 to 4;
each $R^{5a}$ and each $R^{5b}$ may be different;
with the proviso that the compound wherein n+m is 2; $R^5$ is a hydrogen atom; and
ring A is non-substituted phenyl is excluded,
its pharmaceutically acceptable salt, or a solvate thereof,
(b) a composition having BACE 1 inhibitory activity according to (a), wherein X is S,
(c) a composition having BACE 1 inhibitory activity according to (a), wherein n is 2, and m is 0,
(d) a composition having BACE 1 inhibitory activity according to (a), wherein E is a bond,
(e) a compound represented by the general formula (I):

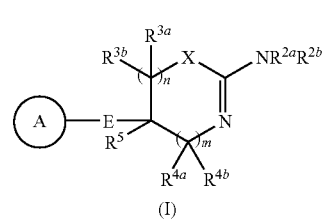

wherein each symbols are the same as described in (a), with the proviso that the compounds as shown below;
i) wherein n+m is 2, $R^5$ is a hydrogen atom, and ring A is non-substituted phenyl;

ii) wherein n is 2, m is 0, $R^{2a}$ is a hydrogen atom, $R^{2b}$ is a hydrogen atom or acetyl $R^5$ is methyl and ring A is phenyl or 4-methoxyphenyl;

iii) wherein n is 2, m is 0, $R^{2a}$ is a hydrogen atom, $R^{2b}$ is a hydrogen atom or acetyl, $R^5$ is ethyl, and ring A is 3,4-dimethoxyphenyl;

iv) wherein n is 2, m is 0, $R^{2a}$ is a hydrogen atom, $R^{2b}$ is a hydrogen atom or acetyl, and $R^5$ and ring A is phenyl;

v) wherein n is 2, m is 0, $R^{2a}$ and $R^{2b}$ is a hydrogen atom, $R^5$ and ring A are taken together to form

[Chemical formula 8]

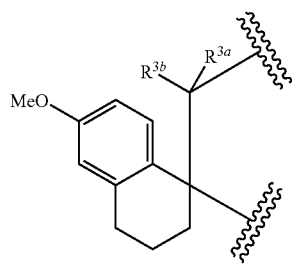

wherein Me is methyl, and each symbols are the same as described above; and vi) wherein n+m is 2,
$R^5$ is a hydrogen atom,
ring A is phenyl substituted with one or two substituent(s) selected from the group of hydroxy, halogen, lower alkyl, lower alkoxy, nitro, amino, lower alkylcarbonylamino, mercapto, lower alkylthio, and carbamoyl,
non-substituted phenyl,
or non-substituted naphthyl; are excluded,
its pharmaceutically acceptable salt, or a solvate thereof, (f) the compound according to (e), wherein X is S, its pharmaceutically acceptable salt, or a solvate thereof, (g) the compound according to (e) or (f), wherein n is 2, and m is 0, its pharmaceutically acceptable salt, or a solvate thereof, (h) the compound according to any one of (e) to (g), wherein $R^5$ is optionally substituted lower alkyl optionally substituted lower alkenyl optionally substituted lower alkynyl, an optionally substituted carbocyclic group or an optionally substituted heterocyclic group,
its pharmaceutically acceptable salt, or a solvate thereof, (i) the compound according to any one of (e) to (h), wherein $R^{2a}$ is a hydrogen atom;
$R^{2b}$ is a hydrogen atom, optionally substituted lower alkyl optionally substituted acyl, optionally substituted lower alkylsulfonyl or optionally substituted amidino, its pharmaceutically acceptable salt, or a solvate thereof, (j) the compound according to any one of (e) to (h), wherein $NR^{2a}R^{2b}$ is represented by the formula:

[Chemical formula 9]

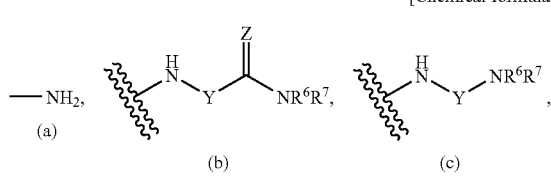

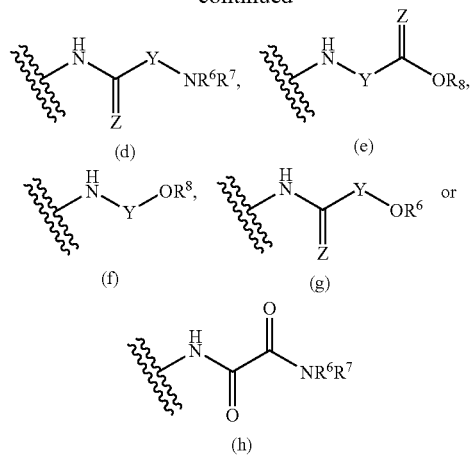

$R^6$, $R^7$, and $R^8$ are each independently a hydrogen atom, lower alkyl or acyl Y is optionally substituted lower alkylene, optionally substituted lower alkenylene or optionally substituted lower alkylene;

Z is O or S;

its pharmaceutically acceptable salt, or a solvate thereof, (k) the compound according to any one of (e) to (j), wherein ring A is substituted phenyl,
its pharmaceutically acceptable salt, or a solvate thereof, (l) the compound according to any one of (e) to (j), wherein ring A is represented by the formula:

[Chemical formula 10]

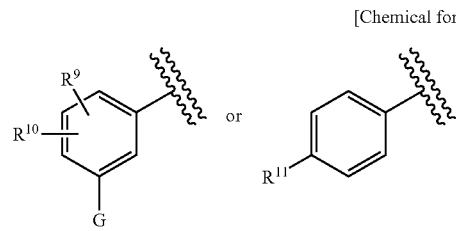

wherein $R^9$, $R^{10}$ and $R^{11}$ are hydrogen atom or G;

G is halogen, hydroxy, cyano, nitro, mercapto, optionally substituted lower alkyl optionally substituted lower alkoxy, optionally substituted lower alkenyl, optionally substituted lower alkynyl, optionally substituted acyl, optionally substituted acyloxy, carboxy, optionally substituted lower alkoxycarbonyl optionally substituted lower alkoxycarbonyloxy, optionally substituted aryloxycarbonyloxy, optionally substituted amino, optionally substituted carbamoyl, optionally substituted carbamoyloxy, optionally substituted lower alkylthio, optionally substituted arylthio, optionally substituted lower alkylsulfonyl, optionally substituted arylsulfonyl optionally substituted lower alkylsulfinyl, optionally substituted arylsulfinyl, optionally substituted lower alkylsulfonyloxy, optionally substituted arylsulfonyloxy, an optionally substituted carbocyclic group, optionally substituted carbocyclicoxy, an optionally substituted heterocyclic group or optionally substituted heterocyclicoxy;

each G may be independently different;

its pharmaceutically acceptable salt, or a solvate thereof, (m) the compound according to (l), wherein G is represented by the formula:

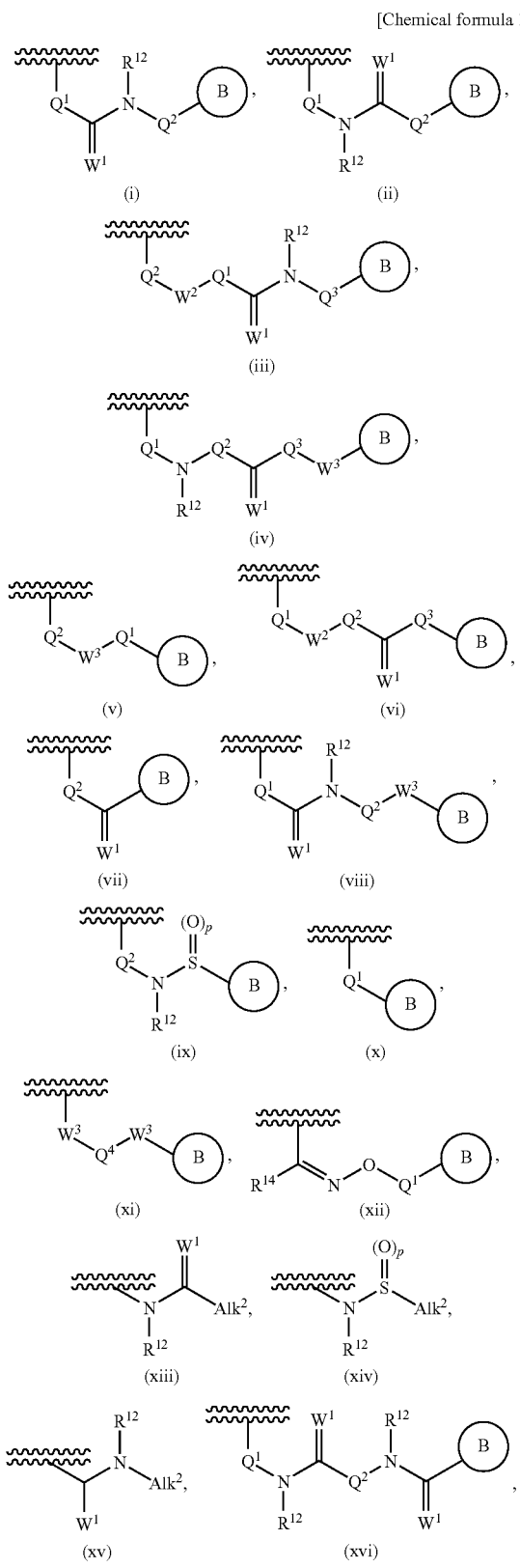

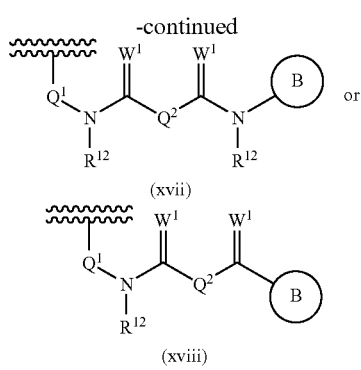

$Q^1$, $Q^2$, and $Q^3$ are each independently a bond, optionally substituted lower alkylene, or optionally substituted lower alkenylene;

$Q^4$ is optionally substituted lower alkylene or optionally substituted lower alkenylene;

$W^1$ and $W^2$ are each independently O or S;

$W^3$ is O, S or $NR^{12}$;

$R^{12}$ is a hydrogen atom, lower alkyl hydroxy lower alkyl lower alkoxy lower alkyl lower alkoxycarbonyl lower alkyl, carbocyclic lower alkyl or acyl;

$R^{14}$ is a hydrogen atom or lower alkyl;

ring B is an optionally substituted carbocyclic group or an optionally substituted heterocyclic group;

$Alk^2$ is optionally substituted lower alkyl;

p is 1 or 2;

if there are multiple $W^1$, multiple $W^3$, and multiple $R^{12}$, each may be independently different;

in (xii), the position of an oxygen atom may be cis or trans to a substituent $R^{14}$, its pharmaceutically acceptable salt, or a solvate thereof, (n) the compound according to (m), wherein ring B is aryl optionally substituted with one or more substituents selected from the group of halogen, hydroxy, optionally substituted lower alkyl, optionally substituted lower alkoxy, optionally substituted acyl optionally substituted amino, cyano, optionally substituted carbamoyl an optionally substituted carbocyclic group, optionally substituted carbocyclicoxy or an optionally substituted heterocyclic group, or heteroaryl optionally substituted with one or more substituents selected from the group of halogen, hydroxy, optionally substituted lower alkyl, optionally substituted lower alkoxy, optionally substituted acyl, optionally substituted amino, cyano, optionally substituted carbamoyl, an optionally substituted carbocyclic group, optionally substituted carbocyclicoxy or an optionally substituted heterocyclic group, its pharmaceutically acceptable salt, or a solvate thereof (o) the compound according to (m), wherein G is represented by the formula:

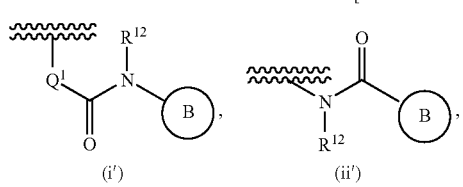

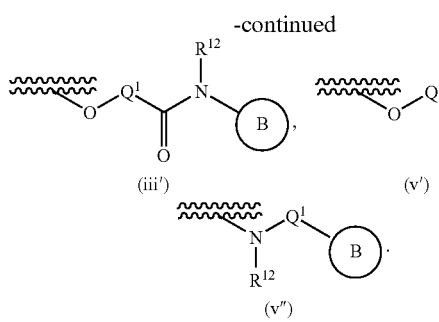

wherein, each symbols are the same as described above,
its pharmaceutically acceptable salt, or a solvate thereof, (p) the compound according to any one of (e) to (o), wherein $R^5$ is C1 to C3 alkyl, its pharmaceutically acceptable salt, or a solvate thereof, (q) the compound according to any one of (e) to (o), wherein $R^5$ is methyl,
its pharmaceutically acceptable salt, or a solvate thereof, (r) the compound according to any one of (e) to (q), wherein $R^{3a}$ and $R^{3b}$ are each independently a hydrogen atom, halogen, hydroxy, optionally substituted lower alkyl optionally substituted lower alkoxy or optionally substituted aryl,
its pharmaceutically acceptable salt, or a solvate thereof, (s) the compound according to any one of (e) to (q), wherein $R^{3a}$ and $R^{3b}$ are both hydrogen atoms,
its pharmaceutically acceptable salt, or a solvate thereof (t) a pharmaceutical composition containing the compound according to any one of (e) to (s),
its pharmaceutically acceptable salt, or a solvate thereof as an active ingredient, (u) a composition having BACE 1 inhibitory activity containing the compound according to any one of (e) to (a),
its pharmaceutically acceptable salt, or a solvate thereof, (v) a composition having BACE 1 inhibitory activity containing the compound according to any one of (a) to (d) or (u) as amyloid β reducing agent, (w) a composition having BACE 1 inhibitory activity according to any one of (a) to (d), (u) or (v) as therapeutic agent for disease induced by production, secretion and/or deposition of amyloid β protein, (x) a composition having BACE 1 inhibitory activity according to any one of (a) to
(d), (u) or (v) as therapeutic agent for Alzheimer's disease.

in addition, the present invention provides:

(y) a method for treating disease induced by production, secretion and/or deposition of amyloid β protein comprising administering the compound as defined in any one of formula (I) in above (a),
its pharmaceutically acceptable salt, or a solvate thereof, (z) use of compound as defined in any one of formula (I) in above (a),
its pharmaceutically acceptable salt, or a solvate thereof, in the manufacture of a medicament for the treatment of disease induced by production, secretion and/or deposition of amyloid β protein, (aa) a method for treating Alzheimer's disease characterizing in administering the compound as defined in any one of formula (I) in above (a),
its pharmaceutically acceptable salt, or a solvate thereof, (ab) use of compound as defined in any one of formula (I) in above (a),
its pharmaceutically acceptable salt, or a solvate thereof, in the manufacture of a medicament for the treatment of Alzheimer's disease.

Effect of the Invention

The compounds in this invention are useful as an agent for treating disease such as Alzheimer's disease induced by production, secretion and/or deposition of amyloid β protein.

BEST MODE FOR CARRYING OUT THE INVENTION

As used herein, the "halogen" includes fluorine, chlorine, bromine, and iodine. A halogen part of the "halogeno lower alkyl", the "halogeno lower alkoxy", the "halogeno acyl", the "halogeno lower alkylthio" and the "halogeno lower alkoxycarbonyl" is the same.

The "lower alkyl" includes a straight or branched alkyl of a carbon number of 1 to 15, preferably a carbon number of 1 to 10, further preferably a carbon number of 1 to 6, and more further preferably a carbon number of 1 to 3, and examples include methyl ethyl, n-propyl isopropyl n-butyl, isobutyl sec-butyl tert-butyl, n-pentyl, isopentyl, neopentyl, hexyl isohexyl n-heptyl isoheptyl, n-octyl, isooctyl, n-nonyl, and n-decyl.

A lower alkyl part of the "carbocyclic lower alkyl", the "lower alkoxy", the "halogeno lower alkyl", the "halogeno lower alkoxy", the "halogeno lower alkylthio", the "hydroxy lower alkyl", the "lower alkoxycarbonyl", the "halogeno lower alkoxycarbonyl", the "lower alkoxycarbonyl lower alkyl", the "lower alkoxycarbonyloxy", the "lower alkylamino", the "lower alkylcarbonylamino", the "lower alkoxycarbonylamino", the "lower alkoxy lower alkyl", the "lower alkylcarbamoyl", the "hydroxy lower alkylcarbamoyl", the "amino lower alkyl", the "hydroxy imino lower alkyl", the "lower alkoxy imino lower alkyl", the "lower alkylthio", the "lower alkylsulfonyl", the "lower alkyl sulfamoyl", the "lower alkylsulfinyl", the "lower alkylsulfonyloxy", the "lower alkoxycarbonyl lower alkynyl", the "lower alkylthio lower alkyl", the "aryl lower alkyl", the "aryl lower alkylamino", the "aryl lower alkoxycarbonyl", the "aryl lower alkylcarbamoyl", the "heterocyclic group lower alkylamino" and the "heterocyclic group lower alkylcarbamoyl" is the same as that of the aforementioned "lower alkyl".

The example of the "optionally substituted lower alkyl" as a substituent of ring A is lower alkyl optionally substituted with one or more substituents selected from the "substituent group α", "hydroxyimino" and "lower alkoxyimino"; the group defined as above (i), (ii), (iv), (vi), (viii), (x) (wherein each $Q^1$ is optionally substituted lower alkylene); the group defined as (iii), (v), (vii), (ix) (wherein $Q^2$ is optionally substituted lower alkylene); and the group (xii).

In other "optionally substituted lower alkyl" is optionally substituted with one or more substituents selected from the "substituent group α".

The "substituent group α" is selected from the group of halogen, hydroxy, lower alkoxy, hydroxy lower alkoxy, lower alkoxy lower alkoxy, acyl acyloxy, carboxy, lower alkoxycarbonyl, amino, acylamino, lower alkylamino, lower alkylthio, carbamoyl, lower alkylcarbamoyl, hydroxy lower alkylcarbamoyl sulfamoyl lower alkylsulfamoyl lower alkylsulfinyl cyano, nitro, aryl and heterocyclic group.

Especially as a substituent of the "optionally substituted lower alkyl" in $Alk^2$, halogen, hydroxy, lower alkoxy, lower alkoxy lower alkoxy, lower alkoxycarbonyl, amino, acylamino, lower alkylamino and/or lower alkylthio are preferable.

The example of the "optionally substituted lower alkoxy" as a substituent of ring A is lower alkoxy optionally substituted with one or more substituents selected from the above "substituent group α"; above (iii) wherein $Q^1$ is optionally substituted lower alkylene, $Q^2$ is a bond, $W^2$ is O; above (v) wherein $Q^1$ is optionally substituted lower alkylene, $Q^2$ is a bond, $W^3$ is O; above (vi) wherein $Q^1$ is a bond, $Q^2$ is optionally substituted lower alkylene, $W^2$ is O; or above (xi) wherein $Q^4$ is optionally substituted lower alkylene, $W^2$ is O.

In other case, the substituents of the "optionally substituted lower alkoxy", the "optionally substituted lower alkoxycarbonyl", the "optionally substituted lower alkoxycarbonyloxy", the "optionally substituted lower alkylsulfonyl", the "optionally substituted lower alkylsulfinyl", the "optionally substituted lower alkylsulfonyloxy" and the "optionally substituted lower alkylthio" are one or more substituents selected from the "substituent group α".

The "lower alkenyl" includes a straight or branched alkenyl of a carbon number of 2 to 15, preferably a carbon number of 2 to 10, further preferably a carbon number of 2 to 6 and more further preferably a carbon number of 2 to 4 having one or more double bonds at an arbitrary position. Specifically examples include vinyl allyl propenyl isopropenyl, butenyl isobutenyl prenyl butadienyl pentenyl isopentenyl hexenyl, isohexenyl, hexadienyl, heptenyl octenyl nonenyl decenyl, undecenyl, dodenyl, tridecenyl tetradecenyl, and pentadecenyl.

The "lower alkynyl" includes a straight or branched alkynyl of a carbon number of 2 to 10, preferably a carbon number of 2 to 8, further preferably a carbon number of 3 to 6, having one or more triple bonds at an arbitrary position. Specifically, examples include ethynyl, propenyl butynyl pentynyl hexynyl, heptynyl, octynyl nonynyl, and decynyl. These may further have a double bond at an arbitrary position.

A lower alkynyl part of the "lower alkoxycarbonyl lower alkynyl" is the same as that of above "lower alkynyl".

The example of the "optionally substituted lower alkenyl" as a substituent of ring A is lower alkenyl optionally substituted with one or more substituents selected from the above "substituent group α"; above (i), (ii), (iv), (vi), (viii) or (x), wherein $Q^1$ is optionally substituted lower alkenylene; (iii), (v), (vii) or (ix), wherein $Q^2$ is optionally substituted lower alkenylene.

In other case, the substituents of the "optionally substituted lower alkenyl" and the "optionally substituted lower alkynyl" are one or more substituents selected from the "substituent group α".

The example of the "optionally substituted lower amino" as a substituent of ring A is amino optionally substituted with one or more substituents selected from the group of lower alkyl acyl hydroxy, lower alkoxy, lower alkoxycarbonyl, a carbocyclic group and a heterocyclic group; (ii), wherein $Q^1$ is a bond; (iv), wherein $Q^1$ is a bond; (v), wherein $Q^2$ is a bond, $W^8$ is $NR^{12}$; (ix), wherein $Q^2$ is a bond; (xiii); or (xiv).

The example of the "optionally substituted carbamoyl" as a substituent of ring A is carbamoyl optionally substituted with one or more substituents selected from the group of lower alkyl, acyl, hydroxy, lower alkoxy, lower alkoxycarbonyl a carbocyclic group and a heterocyclic group; (i), (viii), wherein each $Q^1$ is bond; or (xv).

In other case, the substituents of the "optionally substituted amino", the "optionally substituted amidino", the "optionally substituted carbamoyl", the "optionally substituted carbamoylcarbonyl", and the "optionally substituted carbamoyloxy" are one or two substituents selected from the group of lower alkyl acyl, hydroxy, lower alkoxy, lower alkoxycarbonyl, a carbocyclic group and a heterocyclic group, and the like.

The "acyl" includes aliphatic acyl of a carbon number of 1 to 10, carbocyclic carbonyl and heterocyclic carbonyl. Specifically, formyl, acetyl, propynoyl, butylyl, isobutynyl, valeryl, pivaloyl, hexanoyl, acryloyl, propioloyl, methacryloyl, crotonoyl, benzoyl, cyclohexanecarbonyl, pyridinecarbonyl, furancarbonyl, thiophenecarbonyl, benzothiazolcarbonyl, pyrazinecarbonyl, piperidinecarbonyl, thiomorpholinocarbonyl, and the like.

The part of the acyl of the "halogenoacyl", the "acylamino" and the "acyloxy" is the same as the aforementioned "acyl".

The substituent of the "optionally substituted acyl" and "optionally substituted acyloxy" is one or more substituents selected from the group of the "substituent group α". The ring part of the "carbocyclic carbonyl" and the "heterocyclic carbonyl" is optionally substituted with one or more substituents selected from the group of "lower alkyl"; the "substituent group α"; and "lower alkyl substituted with one or more substituents selected from the group of the substituent α".

The "carbocyclic group" includes cycloalkyl cycloalkenyl aryl and non-aromatic fused carbocyclic group.

The "cycloalkyl" includes a carbocyclic group of a carbon number of 3 to 10, preferably a carbon number of 3 to 8, further preferably a carbon number of 4 to 8, and examples include, cyclopropyl, cyclobutyl cyclopentyl cyclohexyl cycloheptyl, cyclooctyl cyclononyl and cyclodecyl and the like.

The "cycloalkenyl" includes cycloalkenyl having one or more double bonds at an arbitrary position in a ring of the aforementioned cycloalkyl and examples include cyclopropenyl cyclobutenyl cyclopentenyl, cyclohexenyl, cycloheptenyl, cyclooctynyl and cyclohexadienyl, and the like.

The "aryl" includes phenyl naphthyl, anthryl, and phenanthryl and the like, and phenyl is particularly preferable.

The "non-aromatic fused a carbocyclic group" includes group fused with two or more ring groups selected from the group of the above "cycloalkyl", the "cycloalkenyl" and the "aryl". Specifically, examples include indanyl indenyl, tetrahydronaphthyl and fluorenyl and the like.

The carbocyclic part of the "carbocyclicoxy", and the "carbocyclic lower alkyl" is the same as the aforementioned "carbocyclic group".

The aryl part of the "aryl lower alkyl", the "aryloxy", the "aryloxycarbonyl", the "aryloxycarbonyloxy", the "aryl lower alkoxycarbonyl", the "arylthio", the "arylamino", the "aryl lower alkylamino", the "arylsulfonyl", the "arylsulfonyloxy", the "arylsulfinyl", the "arylsulfamoyl", the "arylcarbamoyl" and the "aryl lower alkylcarbamoyl" is the same as the aforementioned "aryl".

The "heterocyclic group" includes a heterocyclic group having one or more heteroatoms arbitrary selected from O, S, and N in a ring, specifically includes a 5- to 6-membered heteroaryl such as pyrrolyl, imidazolyl, pyrazolyl, pyridyl, pyridazinyl, pyrimidinyl pyrazinyl, triazolyl triazinyl tetrazolyl isoxazolyl oxazolyl oxadiazolyl, isothiazolyl thiazolyl thiadiazolyl isothiazolyl furyl and thienyl; a bicyclic fused heterocyclic group such as indolyl isoindolyl indazolyl indolizinyl indolinyl isoindolinyl quinolyl isoquinolyl cinnolinyl, phthalazinyl, quinazolinyl naphthridinyl quinoxalinyl purinyl pteridinyl benzopyranyl, benzimidazolyl benzioxazolyl benzoxazolyl benzoxadiazolyl, benzoisothiazolyl benzothiazolyl, benzothiadiazolyl benzofuryl, isobenzofuryl benzothienyl benzotriazolyl imidazopyridyl pyrazolopyridyl triazolopyridyl imidazothiazolyl pyrazinopyridazinyl, quinazolinyl, quinolyl isoquinolyl, naphthyridinyl, dihydrobenzofuryl tetrahydroquinolyl tetrahydroisoquinolyl, dihydrobenzoxazine, tetrahydrobenzothienyl; a tricyclic fused heterocyclic group such as carbazolyl acridinyl, xanthenyl phenothiazinyl phenoxathiinyl, phenoxazinyl dibenzofuryl and imidazoquinolyl; a non-aromatic heterocyclic group such as dioxanyl, thiiranyl oxyranyl oxathioranyl azethidinyl, thianyl pyrrolidinyl pyrrolinyl imidazolidinyl imidazolinyl pyrazolidinyl pyrazolinyl piperidyl, piperazinyl, morpholinyl morpholino, thiomorpholinyl thiomorpholino, dihydropyridyl, dihydrobenzoimidazolyl tetrahydropyridyl tetrahydrofuryl tetrahydropyranyl tetrahydrothiazolyl, tetrahydroisothiazolyl dihydroxadinyl hexahydroazepinyl tetrahydroazepyinyl. Preferable is a 5- to 6-membered heteroaryl, or a non-aromatic heterocyclic group.

The heterocyclic part of the "heterocyclicoxy", the "heterocyclic thio", the "heterocyclic carbonyl", the "heterocyclic amino", the "heterocyclic carbonylamino", the "heterocyclic sulfamoyl", the "heterocyclic sulfonyl", the "heterocyclic carbamoyl", the "heterocyclicoxycarbonyl", the "heterocyclic lower alkylamino" and the "heterocyclic lower alkyl carbamoyl" is the same as the aforementioned "heterocyclic group".

The example of the substituent of the "optionally substituted carbocyclic group" and the "optionally substituted heterocyclic group" in ring A is;

the substituent α, wherein preferable is for example, halogen, hydroxy, acyl, acyloxy, carboxy, lower alkoxycarbonyl, carbamoyl, amino, lower alkylamino, lower alkylthio;

lower alkyl optionally substituted with one or more substituents selected from the group of substituent α, wherein preferable is halogen, hydroxy, lower alkoxy, lower alkoxycarbonyl, and the like;

amino lower alkyl substituted with one or more substituents selected from the group of substituent α, wherein preferable is acyl, lower alkyl and/or lower alkoxy, and the like; hydroxyimino lower alkyl; lower alkoxyimino lower alkyl;

lower alkenyl optionally substituted with one or more substituents selected from the group of substituent α, wherein preferable is lower alkoxycarbonyl, halogen and/or halogeno lower alkoxycarbonyl, and the like;

lower alkynyl optionally substituted with one or more substituents selected from the group of substituent α, wherein preferable is for example, lower alkoxycarbonyl, lower alkoxy optionally substituted with one or more substituents selected from the group of substituent α, wherein preferable is for example, lower alkyl carbamoyl and/or hydroxy lower alkyl carbamoyl, lower alkylthio optionally substituted with one or more substituents selected from the group of substituent α, lower alkylamino substituted with one or more substituents selected from the group of substituent α, lower alkylsulfonyl optionally substituted with one or more substituents selected from the group of substituent α, aryl lower alkoxycarbonyl optionally substituted with one or more substituents selected from the group of substituent α, azido, and lower alkyl, acyl substituted with one or more substituents selected from the group of substituent α, cycloalkyl optionally substituted with one or more substituents selected from the group of substituent α, azido, and lower alkyl, lower alkylsulfinyl optionally substituted with one or more substituents selected from the group of substituent α, sulfamoyl, aryl optionally substituted with one or more substituents selected from the group of substituent α, azido, and lower alkyl, heterocyclic optionally group substituted with one or more substituents selected from the group of substituent α, azido, and lower alkyl, aryloxy optionally substituted with one or more substituents selected from the group of substituent α, azido, and lower alkyl, heterocyclicoxy optionally substituted with one or more substituents selected from the group of substituent α, azido, and lower alkyl, arylthio optionally substituted with one or more substituents selected from the group of substituent α, azido, and lower alkyl, heterocyclicthio optionally substituted with one or more substituents selected from the group of substituent α, azido, and lower alkyl, arylamino optionally substituted with one or more substituents selected from the group of substituent α, azido, and lower alkyl, heterocyclicamino optionally substituted with one or more substituents selected from the group of substituent α, azido, and lower alkyl, aryl lower alkylamino optionally substituted with one or more substituents selected from the group of substituent α, azido, and lower alkyl, heterocyclic lower alkylamino optionally substituted with one or more substituents selected from the group of substituent α, azido, and lower alkyl, lower alkyl sulfamoyl optionally substituted with one or more substituents selected from the group of substituent α, aryl sulfamoyl optionally substituted with one or more substituents selected from the group of substituent α, azido, and lower alkyl, heterocyclic sulfamoyl optionally substituted with one or more substituents selected from the group of substituent α, azido, and lower alkyl, arylsulfonyl optionally substituted with one or more substituents selected from the group of substituent α, azido, and lower alkyl, heterocyclic sulfonyl optionally substituted with one or more substituents selected from the group of substituent α, azido, and lower alkyl, aryl carbamoyl optionally substituted with one or more substituents selected from the group of substituent α, azido, and lower alkyl, heterocyclic carbamoyl optionally substituted with one or more substituents selected from the group of substituent α, azido, and lower alkyl, aryl lower alkylcarbamoyl optionally substituted with one or more substituents selected from the group of substituent α, azido, and lower alkyl, heterocyclic lower alkylcarbamoyl optionally substituted with one or more substituents selected from the group of substituent α, azido, and lower alkyl, aryloxycarbonyl optionally substituted with one or more substituents selected from the group of substituent α, azido, and lower alkyl, heterocyclicoxycarbonyl optionally substituted with one or more substituents selected from the group of substituent α, azido, and lower alkyl, lower alkylenedioxy optionally substituted with halogen; oxo; azido;

[Chemical formula 13]

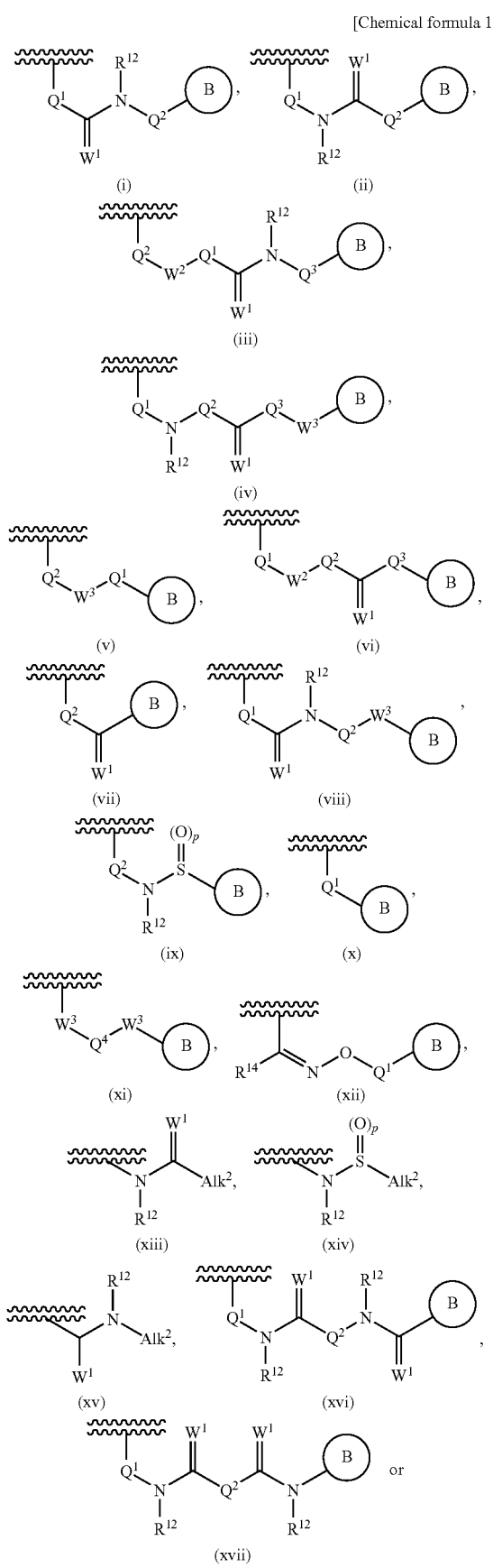
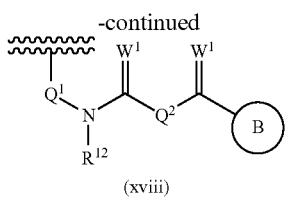

(xviii)

wherein $Q^1$, $Q^2$ and $Q^3$ are each independently a bond, optionally substituted lower alkylene or optionally substituted lower alkenylene;
$Q^4$ is optionally substituted lower alkylene or optionally substituted lower alkenylene;
$W^1$ and $W^2$ are each independently O or S;
$W^3$ is O, S or $NR^{12}$;
$R^{12}$ is a hydrogen atom, lower alkyl, hydroxy lower alkyl, lower alkoxy lower alkyl, lower alkoxycarbonyl lower alkyl, carbocyclic group lower alkyl or acyl;
$R^{14}$ is a hydrogen atom or lower alkyl;
ring B is an optionally substituted carbocyclic group or an optionally substituted heterocyclic group;
$Alk^2$ is optionally substituted lower alkyl;
and the ring A is optionally substituted with one or more substituents selected from these groups.

If there are multiple $W^1$, multiple $W^3$, and multiple $R^{12}$, each may be independently different.

In addition, an oxygen atom in (xii) may be cis or trans position to the substituent $R^{14}$. The substituent of the "substituted phenyl" is, in the same way, phenyl substituted with one or two substituents selected preferably from the group of the substituent α or (i) to (xv).

The substituent of the "optionally substituted carbocyclic group" or the "optionally substituted heterocyclic group" in ring B is optionally substituted with one or more substituents selected from the following group of, for example;
the substituent α, wherein preferable is halogen, hydroxy, lower alkoxy, carboxy, lower alkoxycarbonyl, acyl, amino, lower alkylamino, acylamino, carbamoyl, lower alkylcarbamoyl, cyano, and nitro, and the like;
lower alkyl optionally substituted with one or more substituents selected from the group of the substituent α, wherein preferable is halogen, hydroxy, and lower alkoxy, and the like; amino lower alkyl substituted with one or more substituents selected from the group of substituent α;
hydroxyimino lower alkyl;
lower alkoxyimino lower alkyl;
lower alkenyl optionally substituted with one or more substituents selected from the group of substituent α;
lower alkynyl optionally substituted with one or more substituents selected from the group of substituent α;
lower alkoxy optionally substituted with one or more substituents selected from the group of substituent α, wherein preferable is halogen, hydroxy, and the like;
lower alkylthio optionally substituted with one or more substituents selected from the group of substituent α, wherein preferable is halogen;
lower alkylamino substituted with one or more substituents selected from the group of substituent α, wherein preferable is amino;
lower alkylsulfonyl optionally substituted with one or more substituents selected from the group of substituent α;
aryl lower alkoxycarbonyl optionally substituted with one or more substituents selected from the group of substituent α and lower alkyl;
acyl substituted with one or more substituents selected from the group of substituent α, wherein preferable is halogen;

lower alkylsulfonyl optionally substituted with one or more substituents selected from the group of substituent α; sulfamoyl;
lower alkyl sulfamoyl optionally substituted with one or more substituents selected from the group of substituent α;
cycloalkyl optionally substituted with one or more substituents selected from the group of substituent α azido and lower alkyl;
aryl optionally substituted with one or more substituents selected from the group of substituent a azido and lower alkyl;
heterocyclic group optionally substituted with one or more substituents selected from the group of substituent α, azido and lower alkyl, wherein preferable is halogen, lower alkyl, and the like; aryloxy optionally substituted with one or more substituents selected from the group of substituent α, azido and lower alkyl;
heterocyclicoxy optionally substituted with one or more substituents selected from the group of substituent α, azido and lower alkyl;
arylthio optionally substituted with one or more substituents selected from the group of substituent α, azido and lower alkyl, wherein preferable is halogen, hydroxy, lower alkoxy, acyl, and the like;
heterocyclic thio optionally substituted with one or more substituents selected from the group of substituent α, azido and lower alkyl;
arylamino optionally substituted with one or more substituents selected from the group of substituent α, azido and lower alkyl, wherein preferable is halogen, hydroxy, lower alkoxy, acyl;
heterocyclic amino optionally substituted with one or more substituents selected from the group of substituent α, azido and lower alkyl;
aryl lower alkylamino optionally substituted with one or more substituents selected from the group of substituent α, azido and lower alkyl, wherein preferable is halogen, hydroxy, lower alkoxy, acyl;
heterocyclic lower alkylamino substituted with one or more substituents selected from the group of substituent α, azido and lower alkyl;
arylsulfamoyl substituted with one or more substituents selected from the group of substituent a azido and lower alkyl;
heterocyclic sulfamoyl substituted with one or more substituents selected from the group of substituent α, azido and lower alkyl;
arylsulfonyl optionally substituted with one or more substituents selected from the group of substituent α, azido and lower alkyl;
heterocyclic sulfonyl optionally substituted with one or more substituents selected from the group of substituent α, azido and lower alkyl;
arylcarbamoyl optionally substituted with one or more substituents selected from the group of substituent α, azido and lower alkyl;
heterocyclic carbamoyl optionally substituted with one or more substituents selected from the group of substituent α, azido and lower alkyl;
aryl lower alkylcarbamoyl optionally substituted with one or more substituents selected from the group of substituent α, azido and lower alkyl;
heterocyclic lower alkylcarbamoyl optionally substituted with one or more substituents selected from the group of substituent α, azido and lower alkyl;
aryloxy carbonyl optionally substituted with one or more substituents selected from the group of substituent α, azido and lower alkyl;
heterocyclicoxycarbonyl optionally substituted with one or more substituents selected from the group of substituent α, azido and lower alkyl;
lower alkylenedioxy optionally substituted with halogen; oxo; and the like.

In other case, the substituent of the "optionally substituted carbocyclic group", the "optionally substituted heterocyclic group", the "optionally substituted carbocyclicoxy", the "optionally substituted arylsulfonyl", the "optionally substituted aryloxycarbonyloxy", the "optionally substituted heterocyclicoxy", the "optionally substituted arylsulfinyl", the "optionally substituted arylsulfonyloxy", the "optionally substituted arylthio" is one or more substituents selected from the group of "lower alkyl" and the "substituent α".

"heteroaryl" include aromatic ring group in the aforementioned "heterocyclic group".

The substituent of the "optionally substituted 5- to 6-membered heteroaryl" is the same as the substituent of the "optionally substituted heterocyclic group" in the aforementioned "ring B". Preferable is one or more substituent selected from lower alkyl and a substituent α.

The "lower alkylene" includes a straight or branched bivalent carbon chain of a carbon number of 1 to 10, preferably a carbon number of 1 to 6, further preferably a carbon number of 1 to 3. Specifically, examples include methylene, dimethylene, trimethylene, tetramethylene, and methyltrimethylene, and the like.

The part of lower alkylene of the "lower alkylenedioxy" is the same as the aforementioned "lower alkylene".

The "lower alkenylene" includes a straight or branched bivalent carbon chain of a carbon number of 2 to 10, preferably a carbon number of 2 to 6, further preferably a carbon number of 2 to 4 having double bond at an arbitrary position. Specifically, examples include vinylene, propenylene, butenylene, butadienylene, methylpropenylene, pentenylene, and hexenylene, and the like.

The "lower alkenylene" includes a straight or branched bivalent carbon chain of a carbon number of 2 to 10, preferably a carbon number of 2 to 6, further preferably a carbon number of 2 to 4 having triple bond at an arbitrary position. Specifically, examples include ethynylene, propynylene, butynylene, pentynylene, and hexynylene, and the like.

The substituent of the "optionally substituted lower alkylene", the "optionally substituted lower alkenylene", the "optionally substituted lower alkynylene" is the substituent α, preferable is halogen, hydroxy and the like.

The "each $R^{3a}$, each $R^{3b}$, each $R^{4a}$, and each $R^{4b}$ may be independently different" means when n is 2 or 3, two or three $R^{3a}$ may be independently different, and two or three $R^{3b}$ may be independently different. In the same way, when m is 2 or 3, two or three $R^{4a}$ may be independently different, and two or three $R^{4b}$ may be independently different.

[Chemical formula 14]

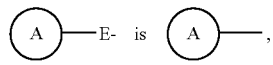

The case that
R⁵ and ring A can be taken together to form

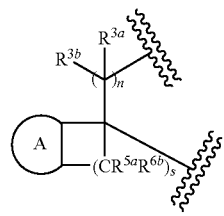

means for example, include the following structures.

[Chemical formula 15]

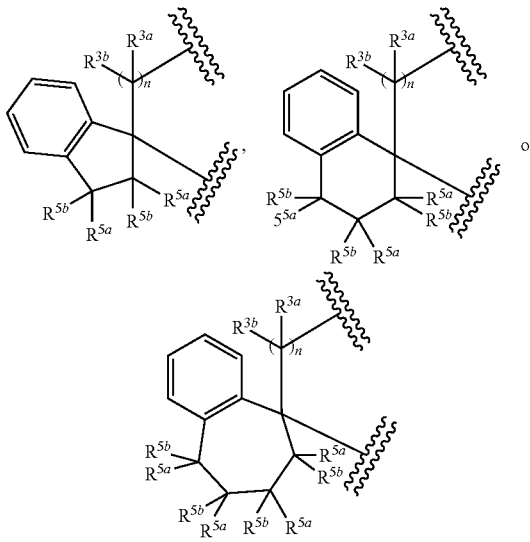

wherein each symbols are the same as described above; preferably, $R^{5a}$ and $R^{5b}$ are all hydrogen atoms.

In this description, "solvate" includes, for example, a solvate with an organic solvent and a hydrate, and the like. When hydrate is formed, arbitrary number of water molecules may be coordinated.

The compound (I) includes a pharmaceutically acceptable salt. Examples include salts with alkali metals (lithium, sodium or potassium, and the like), alkaline earth metals (magnesium or calcium, and the like), ammonium, organic bases or amino acids, and salts with inorganic acids (hydrochloric acid, sulfuric acid, nitric acid, hydrobromic acid, phosphoric acid or hydroiodic acid, and the like), and organic acid (acetic acid, trifluoroacetic acid, citric acid, lactic acid, tartaric acid, oxalic acid, maleic acid, fumaric acid, manderic acid, glutaric acid, malic acid, benzoic acid, phthalic acid, benzenesulfonic acid, p-toluenesulfonic acid, methanesulfonic acid, or ethanesulfonic acid, and the like). Particularly, hydrochloric acid, phosphoric acid, tartaric acid, or methanesulfonic acid is preferable. These salts can be formed by a conventional method.

In addition, the compound (I) is not limited to a specific isomer, but includes all possible isomers (keto-enol isomer, imine-enamine isomer, diastereo isomer, optical isomer, and rotational isomer, and the like) and racemates. For example, the compound (I), wherein $R^{2a}$ is a hydrogen atom, includes following tautomer.

[Chemical formula 16]

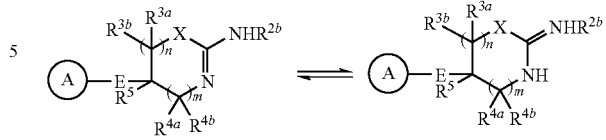

The compound (I) in this invention can be prepared by the process described in, for example Non-patent Document 1 or following process.

The synthesis of aminodihydrothiazine ring; Method A

[Chemical formula 17]

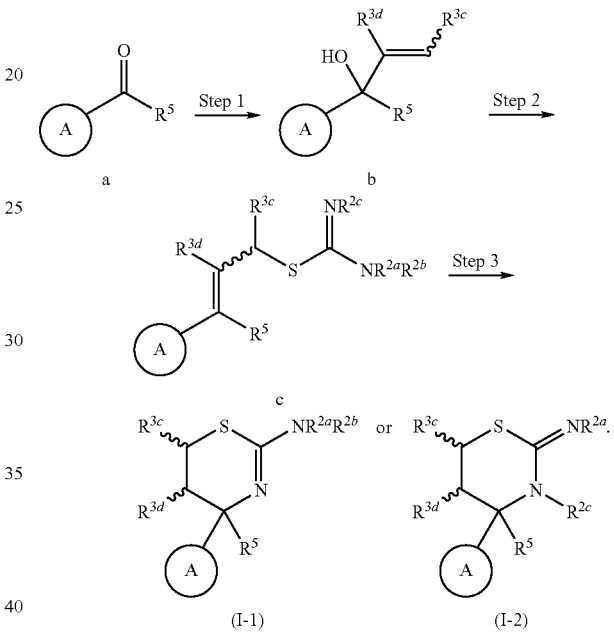

In formula, at least either $R^{2b}$ or $R^{2c}$ is a hydrogen atom, either $R^{3c}$ or $R^{3d}$ is each independently a hydrogen atom, halogen, hydroxy, optionally substituted lower alkyl, optionally substituted lower alkenyl, optionally substituted acyl, carboxy, optionally substituted lower alkoxycarbonyl, optionally substituted amino, optionally substituted carbamoyl, an optionally substituted carbocyclic group or an optionally substituted heterocyclic group. Other symbols are the same as described above.

(Step 1)

To a solution of compound (a), which is commercially available or prepared by known method, in appropriate solvent or mixture of solvents, such as ether, tetrahydrofuran, and the like is added the Grignard reagent having substituent corresponds to the target compound; for example vinylmagnesium chloride, vinylmagnesium bromide, or propenylmagnesium bromide, and the like; at −100° C. to 50° C., preferably −80° C. to 0° C. The mixture is reacted for 0.2 to 24 hours, preferably 0.5 to 5 hours, to obtain compound (b).

(Step 2)

The compound (b) in solvent, such as toluene or absence of solvent is treated with thiourea derivatives having substituent corresponds to the target compound, such as thiourea, N-methylthiourea, N,N'-dimethylthiourea, and the like in the presence of an acid or mixture of acids, such as acetic acid, trifluoroacetic acid, hydrochloric acid, or sulfuric acid, and the like. The mixture is reacted at −20° C. to 100° C., preferably 0° C. to 50° C. for 0.5 to 120 hours, preferably 1 to 72 hours, to obtain the compound (c).

(Step 3)

The compound (c) in solvent, such as toluene or absence of solvent is treated with an acid or mixture of acids, such as trifluoroacetic acid, methanesulfonic acid, trifluoromethanesulfonic acid, and the like. The mixture is reacted at −20° C. to 100° C., preferably 0° C. to 50° C. for 0.5 to 120 hours, preferably 1 to 72 hours, to obtain the compound (I-2), wherein $R^{2b}$ is a hydrogen atom, or the compound (I-1), wherein $R^{2c}$ is a hydrogen atom.

The synthesis of aminodihydrothiazine ring; Method B

[Chemical formula 18]

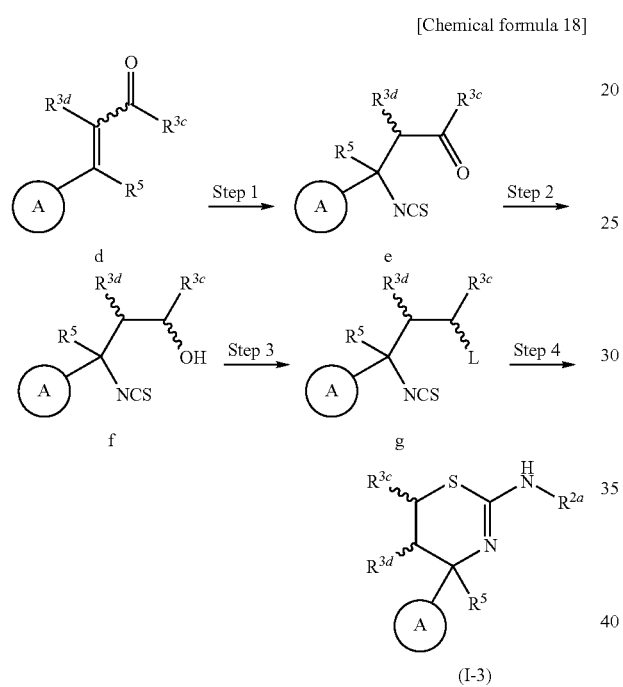

In formula, L is leaving group such as halogen or sulfonyloxy, and the like. Other symbols are the same as described above.

(Step 1)

The compound (d) which is commercially available or prepared by known method is reacted with thiocyanic acid; for example, sodium thiocyanic acid, ammonium thiocyanic acid, and the like; in solvent; for example, toluene, chloroform, tetrahydrofuran, and the like; in the presence of acid; for example, water, hydrochloric acid, sulfuric acid, and the like; at 0° C. to 160° C., preferably 20° C. to 100° C. for 0.5 to 24 hours, preferably 1 to 12 hours, to obtain the compound (e).

(Step 2)

To the compound (e) in solvent or mixture of solvents; for example, tetrahydrofuran, methanol, ethanol, water, and the like; in the presence or the absence of buffer like sodium dihydrogen phosphate, and the like; reducing agent; for example sodium borohydride, and the like; is added and the mixture is reacted at −80° C. to 50° C., preferably −20° C. to 20° C. for 0.1 to 24 hours, preferably 0.5 to 12 hours, to obtain the compound (f).

(Step 3)

The compound (f) in the presence or the absence of solvent; for example, toluene, dichloromethane, and the like; is reacted with halogenating agent; for example thionyl chloride, phosphorus oxychloride, carbon tetrabromide-triphenylphosphine, and the like; at −80° C. to 50° C., preferably −20° C. to 20° C. for 0.1 to 24 hours, preferably 0.5 to 12 hours, to obtain the compound (g). Alternatively, the compound (f) in the presence or the absence of solvent; for example, toluene, dichloromethane, and the like; under base; for example triethylamine, and the like; is reacted with sulfonating agent; for example, methanesulfonyl chloride, p-toluenesulfonylchloride, and the like; at −80° C. to 50° C., preferably −20° C. to 20° C. for 0.1 to 24 hours, preferably 0.5 to 12 hours, to obtain the compound (g).

(Step 4)

To the compound (g) in solvent or mixture of solvents, for example methanol ethanol, water, and the like; is reacted with primary amine; for example, ammonia or methylamine, and the like; at −20° C. to 80° C., preferably 0° C. to 40° C. for 0.5 to 48 hours, preferably 1 to 24 hours, to obtain the compound (I-3).

The synthesis of aminodihydrothiazine ring; Method C

[Chemical formula 19]

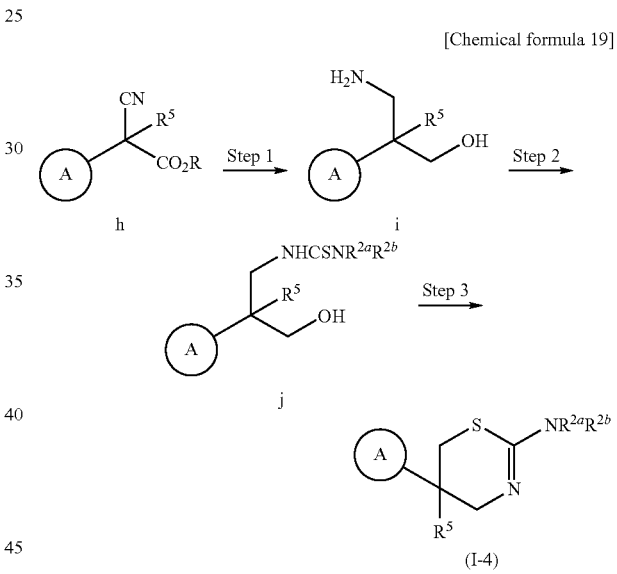

In formula, R is a hydrogen atom or protective groups of carboxyl group. Other symbols are the same as described above.

(Step 1)

The compound (h) which is commercially available or prepared by known method is reacted with reducing agent; for example, lithium aluminium hydride, diisobutyl aluminium hydride, and the like; in solvent; for example tetrahydrofuran, ether, and the like; at −80° C. to 150° C., preferably 25° C. to 100° C. for 0.1 to 24 hours, preferably 0.5 to 12 hours, to obtain the compound (i).

(Step 2)

The compound (i) in solvent; for example, toluene, chloroform, tetrahydrofuran, and the like; in the presence or the absence of base; for example, diisopropylethylamine, triethylamine, pyridine, sodium hydroxide, and the like; is reacted with corresponding isothiocyanate; for example, 4-methoxybenzylisothiocyanate, t-butylisothiocyanate, and the like; or corresponding thiocarbamoylhalide; for example, N,N-dimethylthiocarbamoylchloride, N,N-diethylthiocarbamoylchloride, and the like; at 0° C. to 150° C., preferably 20° C. to 100° C. for 0.5 to 120 hours, preferably 1 to 72 hours, to obtain the compound (j).
(Step 3)

The compound (j) in solvent; for example, acetonitrile, toluene, dichloromethane, and the like; is reacted with halogenating agent; for example thionyl chloride, phosphorus oxychloride, carbon tetrabromide-triphenylphosphine, and the like; at −80° C. to 50° C., preferably −20° C. to 20° C. for 0.1 to 24 hours, preferably 0.5 to 12 hours, or alternatively, the compound (j) in solvent; for example, toluene, dichloromethane, and the like; in the presence of base; for example triethylamine, and the like; is reacted with sulfonating agent; for example, methanesulfonyl chloride, p-toluenesulfonylchloride, and the like; at −80° C. to 50° C., preferably −20° C. to 20° C. for 0.1 to 24 hours, preferably 0.5 to 12 hours. The obtained halogenated compound or sulfonylated compound is reacted with base; for example, diisopropylamine, potassium carbonate, sodium hydrogencarbonate, sodium hydride, sodium hydroxide, and the like; at 0° C. to 150° C., preferably 20° C. to 100° C. for 0.5 to 120 hours, preferably 1 to 72 hours, to obtain the compound (I-4).

The synthesis of aminodihydrothiazine ring; Method D
The synthesis of aminothiazoline ring; Method A
The synthesis of tetrahydrothiazepine ring; Method A N,N-dimethylformamide, tetrahydrofuran, and the like; at 0° C. to 200° C., preferably 40° C. to 150° C. for 0.5 to 24 hours, preferably 1 to 12 hours, to obtain the compound (l).
(Step 2)

The compound (l) is reacted with reducing agent; for example, lithium aluminium hydride, diisobutyl aluminium hydride, and the like; in solvent; for example tetrahydrofuran, ether, and the like; at −80° C. to 150° C., preferably 25° C. to 100° C. for 0.1 to 24 hours, preferably 0.5 to 12 hours, to obtain the compound (m).
(Step 3)

The compound (m) in solvent; for example, toluene, chloroform, tetrahydrofuran, and the like; is reacted with corresponding isothiocyanate; for example, methylisothiocyanate, ethylisothiocyanate, and the like; or corresponding thiocarbamoylhalide; for example, N,N-dimethylthiocarbamoylchloride, N,N-diethylthiocarbamoylchloride, and the like; at 0° C. to 150° C., preferably 20° C. to 100° C. for 0.5 to 120 hours, preferably 1 to 72 hours, to obtain the compound (n).
(Step 4)

The compound (n) in solvent; for example, acetonitrile, toluene, dichloromethane and the like; is reacted with halogenating agent; for example thionyl chloride, phosphorus oxychloride, carbon tetrabromide-triphenylphosphine, and the like; at 80° C. to 50° C., preferably −20° C. to 20° C. for 0.1 to 24 hours, preferably 0.5 to 12 hours, or alternatively, the compound (n) in solvent; for example, toluene, dichloromethane, and the like; in the presence of base; for example diisopropylethylamine, triethylamine, and the like; is reacted with sulfonating agent; for example, methanesulfonyl chloride, p-toluenesulfonylchloride, and the like; at −80° C. to 50° C., preferably −20° C. to 20° C. for 0.1 to 24 hours, preferably 0.5 to 12 hours. The obtained halogenated compound or sulfonylated compound is reacted with base; for example, diisopropylamine, potassium carbonate, sodium hydrogencarbonate, sodium hydride, sodium hydroxide, and the like; at 0° C. to 150° C., preferably 20° C. to 100° C. for 0.5 to 120 hours, preferably 1 to 72 hours, to obtain the compound (I-6).

The synthesis of aminodihydrothiazine ring; Method E
The synthesis of aminothiazoline ring; Method B
The synthesis of tetrahydrothiazepine ring; Method B

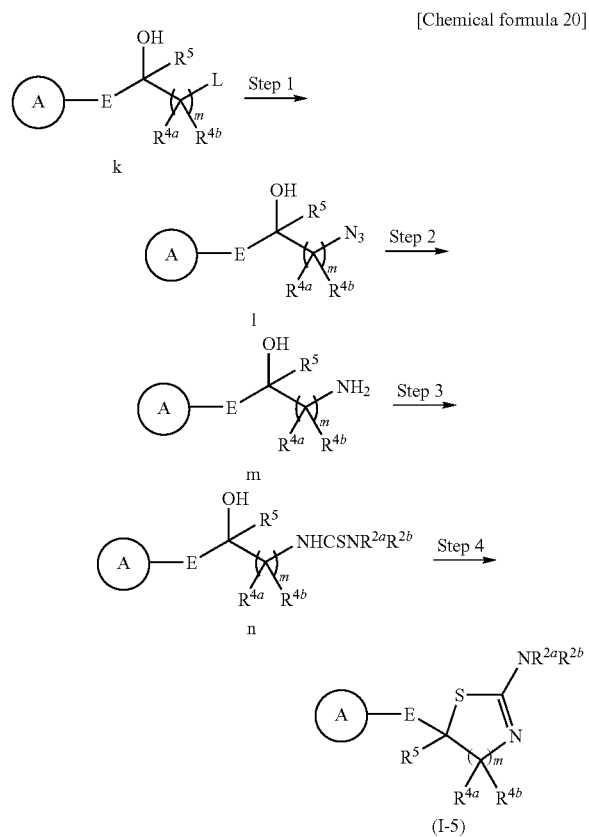

[Chemical formula 20]

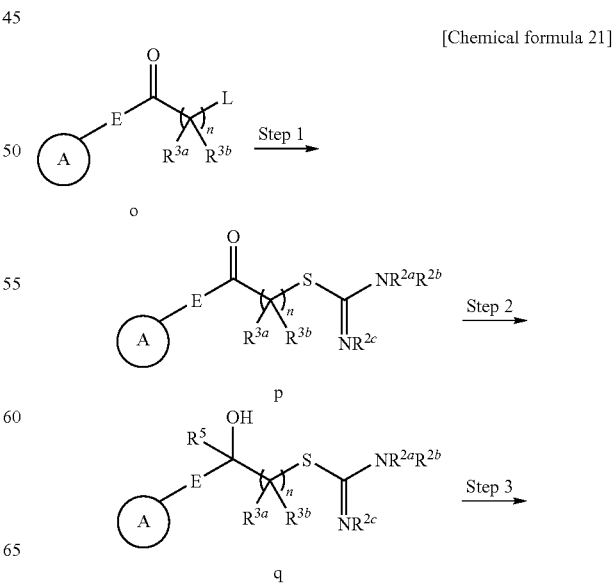

[Chemical formula 21]

In formula, L is leaving group such as halogen or sulfonyloxy, and the like; m is an integer of 1 to 3; and the other symbols are the same as described above.
(Step 1)

The compound (k) which is commercially available or prepared by known method is reacted with azide reagent; for example, sodium azide, and the like; in solvent; for example -continued

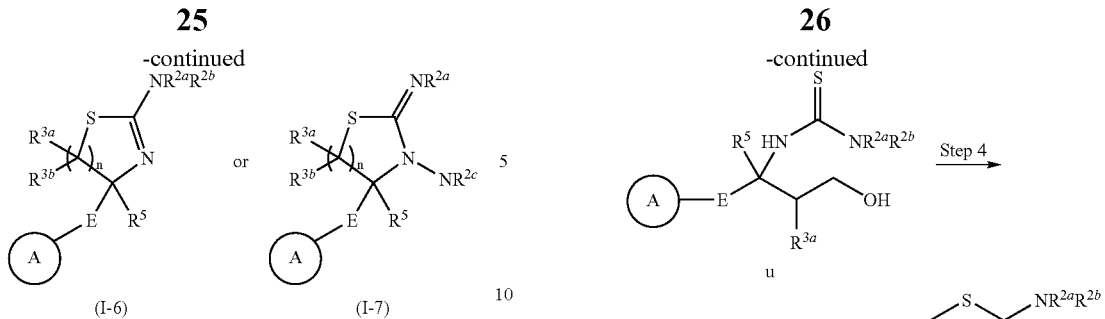

(I-6)  (I-7)

In formula, at lease one of $R^{2b}$ and $R^{2c}$ is a hydrogen atom, n is an integer of 1 to 3, and the other symbols are the same as described above.

(Step 1)

The compound (o) which is commercially available or prepared by known method is reacted with substituted thiourea; for example, thiourea, N-methylthiourea, N,N,-dimethylthiourea, N,N'-dimethylthiourea, and the like; in solvent; for example, ethanol, methanol, tetrahydrofuran, toluene, and the like; at −20° C. to 200° C., preferably 0° C. to 150° C. for 0.5 to 200 hours, preferably 1 to 120 hours, to obtain the compound (p).

(Step 2)

To the compound (p) in solvent or mixture of solvents; for example, ether, tetrahydrofuran, and the like; the Grignard reagent having substituent corresponding to target compound; for example methylmagnesium chloride, ethylmagnesium bromide, or benzylmagnesium bromide, and the like; is added at 100° C. to 50° C., preferably −80° C. to 30° C., and the mixture is reacted for 0.2 to 24 hours, preferably 0.5 to 5 hours, to obtain the compound (q).

(Step 3)

To the compound (q) in the presence or the absence of solvent; for example, toluene, and the like; acid or mixture of acids, such as trifluoroacetic acid, methanesulfonic acid, trifluoromethanesulfonic acid, and the like; is added and the mixture is reacted at −20° C. to 100° C., preferably 0° C. to 50° C. for 0.5 to 200 hours, preferably 1 to 150 hours, to obtain the compound (I-6)(wherein $R^{2c}$ is H), or the compound (I-7)(wherein $R^{2b}$ is H).

The synthesis of aminodihydrothiazine ring; Method F

[Chemical formula 22]

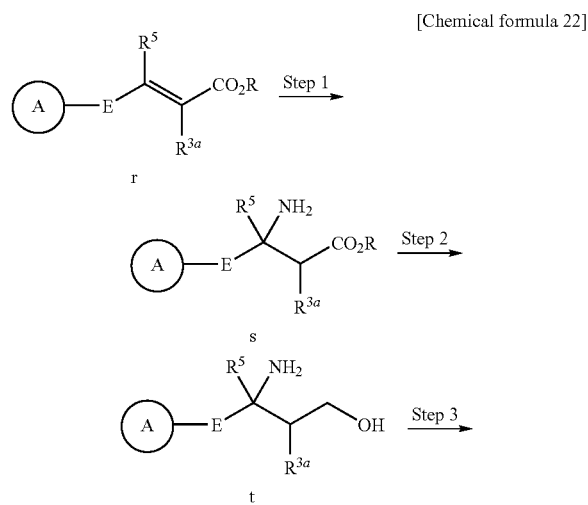

-continued

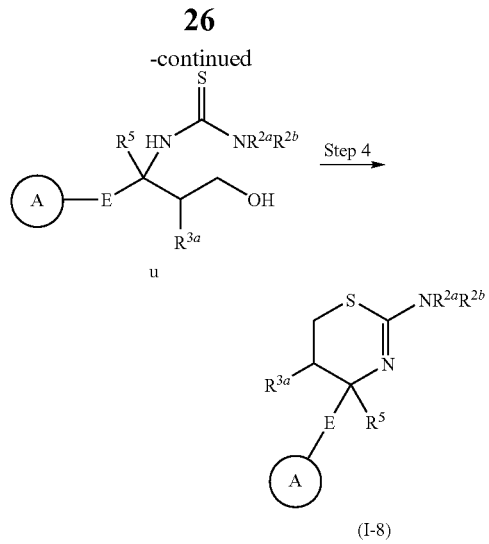

(I-8)

In formula, each symbols are the same as described above.

(Step 1)

The compound (r) which is commercially available or prepared by known method is reacted with ammonium chloride in solvent; for example, acetic acid, and the like; at 0° C. to 200° C., preferably 10° C. to 100° C. for 0.1 to 100 hours, preferably 0.5 to 24 hours, to obtain the compound (s).

(Step 2)

The compound (a) is reacted with reducing agent; for example, lithium aluminium hydride, diisobutyl aluminium hydride, and the like; in solvent; for example tetrahydrofuran, ether, and the like; at −80° C. to 150° C., preferably 0° C. to 100° C. for 0.1 to 24 hours, preferably 0.5 to 12 hours, to obtain the compound (t).

(Step 3)

The compound (t) in solvent; for example, toluene, chloroform, tetrahydrofuran, and the like; in the presence or the absence of base; for example, diisopropylethylamine, triethylamine, pyridine, sodium hydroxide, and the like; is reacted with corresponding isothiocyanate; for example, 4-methoxybenzylisothiocyanate, t-butylisothiocyanate, and the like; or corresponding carbamoylhalide; for example, N,N-dimethylthiocarbamoylchloride, N,N-diethylthiocarbamoylchloride, and the like; at 0° C. to 150° C., preferably 200° C. to 100° C. for 0.5 to 120 hours, preferably 1 to 72 hours, to obtain the compound (u).

(Step 4)

The compound (u) in solvent; for example, acetonitrile, toluene, dichloromethane, and the like; is reacted with halogenating agent; for example thionyl chloride, phosphorus oxychloride, carbon tetrabromide-triphenylphosphine, and the like; at −80° C. to 60° C., preferably −20° C. to 20° C. for 0.1 to 24 hours, preferably 0.5 to 12 hours, or alternatively, the compound (u) in solvent; for example, toluene, dichloromethane, and the like; in the presence of base; for example triethylamine, and the like; is reacted with sulfonating agent; for example, methanesulfonyl chloride, p-toluenesulfonylchloride, and the like; at −80° C. to 50° C., preferably −20° C. to 20° C. for 0.1 to 24 hours, preferably 0.5 to 12 hours. The obtained halogenated compound or sulfonylated compound is reacted with base; for example, diisopropylamine, potassium carbonate, sodium hydrogencarbonate, sodium hydride, sodium hydroxide, and the like; at 0° C. to 150° C., preferably 20° C. to 100° C. for 0.5 to 120 hours, preferably 1 to 72 hours, to obtain the compound (I-8).

The synthesis of aminodihydrooxazine ring; Method A

The synthesis of aminotetrahydrooxazepine ring; Method A

[Chemical formula 23]

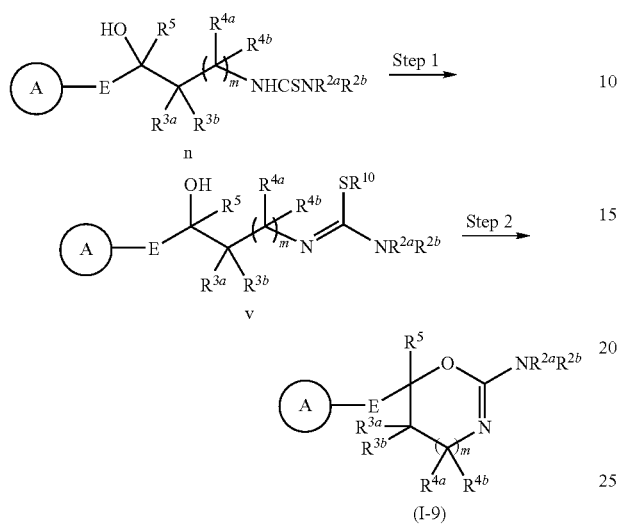

(I-9)

In formula, each symbols are the same as described above.

(Step 1)

The compound (n) which is obtained by Step 3 (the compound (m) to the compound (n)) of "The synthesis of aminodihydrothiazine ring; Method D", in solvent; for example, methanol, ethanol, N,N-dimethylformamide, tetrahydrofuran, and the like; in the presence or the absence of base; for example, diisopropylethylamine, triethylamine, pyridine, sodium hydroxide, and the like; is reacted with alkylating agent; for example, methyl iodide, dimethyl sulfate, benzyl bromide, and the like; at 0° C. to 200° C., preferably 40° C. to 150° C. for 0.1 to 48 hours, preferably 0.5 to 24 hours, to obtain the compound (v).

(Step 2)

The compound (v) in solvent; for example, N,N-dimethylformamide, tetrahydrofuran, dichloromethane, and the like; in the presence or the absence of base; for example, diisopropylethylamine, triethylamine, pyridine, sodium hydroxide, and the like; is reacted with metallic oxide; for example, silver oxide, mercury oxide, manganese dioxide, and the like; at 0° C. to 200° C. preferably 10° C. to 150° C. for 1 to 120 hours, preferably 0.5 to 100 hours, to obtain the compound (I-9).

The synthesis of aminodihydrooxazine ring; Method B

The synthesis of aminoxazoline ring

The synthesis of aminotetrahydrooxazepine ring; Method B

[Chemical formula 24]

In formula, $R^{15}$ is optionally substituted lower alkyl; for example, t-butyl, benzyl, and the like; $R^{16}$ is hydrogen atom or lower alkyl; n is an integer of 1 to 3, and the other symbols are the same as described above.

(Step 1)

The compound (w) which is commercially available or prepared by known method in solvent; for example, toluene, t-butylalcohol, tetrahydrofuran, and the like; in the presence of base; for example, diisopropylethylamine, triethylamine, pyridine, and the like; is reacted with azide reagent; for example, diphenyl phosphoryl azide, and the like; at 0° C. to 200° C., preferably 40° C. to 150° C. for 1 to 48 hours, preferably 0.5 to 24 hours, to obtain the compound (x).

(Step 2)

The compound (x in solvent; for example, toluene, xylene, N,N-dimethylformamide, tetrahydrofuran, and the like; is reacted with alcohol; for example, t-butylalcohol, 3,4-dimethoxybenzylalcohol, 4-methoxybenzylalcohol, and the like; at 0° C. to 300° C., preferably 50° C. to 200° C. for 1 to 800 hours, preferably 5 to 500 hours, to obtain the compound (y).

(Step 3)

The compound (y) in the presence or the absence of solvent; for example, water, toluene, dichloromethane, methanol 1,4-dioxane, acetic acid, ethyl acetate, and the like; in the presence of acid; for example, hydrochloric acid, sulfuric acid, hydrobromic acid, trifluoroacetic acid, and the like; at 0° C. to 200° C., preferably 25° C. to 150° C. for 0.1 to 48 hours, preferably 0.6 to 24 hours, to obtain the compound (z).

(Step 4)

The compound (z) in solvent; for example, toluene, chloroform, tetrahydrofuran, and the like; in the presence of base; for example, diisopropylethylamine, triethylamine, pyridine, and the like; is reacted with corresponding isothiocyanate, or thiocarbamoylhalide corresponding to target compound; for example, N,N-dimethylthiocarbamoylchloride, N,N-diethylthiocarbamoylchloride, and the like; at 0° C. to 150° C., preferably 20° C. to 100° C. for 0.5 to 120 hours, preferably 1 to 72 hours, to obtain the compound (aa).

(Step 6)

The compound (aa) in solvent; for example, methanol ethanol N,N-dimethylformamide, tetrahydrofuran, and the like; in the presence or the absence of base; for example, diisopropylethylamine, triethylamine, pyridine, sodium hydroxide, and the like; is reacted with alkylating agent; for example, methyl iodide, dimethyl sulfate, benzyl bromide, and the like; at 0° C. to 200° C., preferably 40° C. to 150° C. for 1 to 48 hours, preferably 0.5 to 24 hours, to obtain the compound (ab).

(Step 6)

The compound (ab) in solvent; for example, N,N-dimethylformamide, tetrahydrofuran, dichloromethane, and the like; in the presence of base; for example, diisopropylethylamine, triethylamine, pyridine, sodium hydroxide, and the like; is reacted with metallic oxide; for example, silver oxide, mercury oxide, manganese dioxide, and the like; at 0° C. to 200° C., preferably 10° C. to 150° C. for 1 to 120 hours, preferably 0.5 to 100 hours, to obtain the compound (I-10).

The synthesis of aminotetrahydropyrimidine ring

[Chemical formula 25]

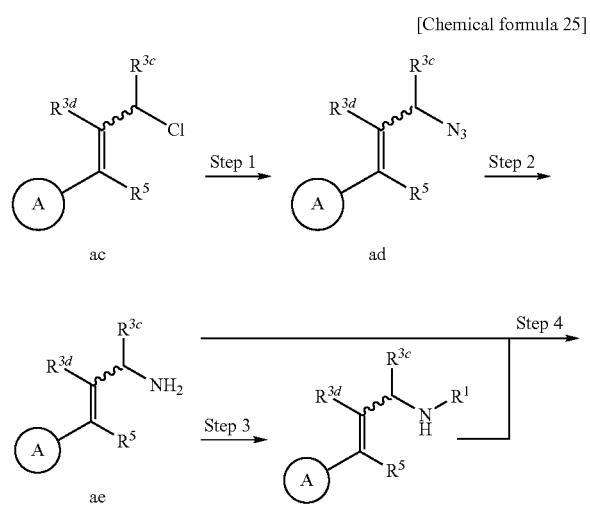

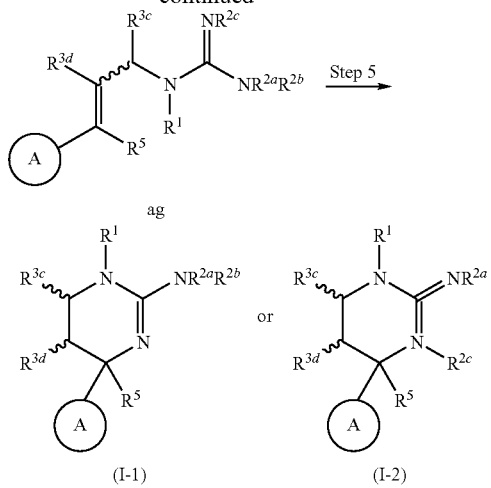

In formula, each symbols are the same as described above.

(Step 1)

To the compound (ac) prepared by known method in solvent; for example, N,N-dimethylformamide, methanol and the like; is reacted with azide reagent; for example, sodium azide, lithium azide, and the like; at 20° C. to 150° C., preferably 50° C. to 100° C. for 0.5 to 120 hours, preferably 1 to 72 hours, to obtain the compound (ad).

(Step 2)

To the suspension of lithium aluminium hydride in solvent; for example, tetrahydrofuran, or ether, and the like; the compound (ad) dissolved in solvent; for example, tetrahydrofuran, or diethyl ether, and the like; is added under nitrogen atmosphere, at −80° C. to 20° C., preferably −30° C. to 0° C., and the mixture is reacted for 1 minute to 10 hours, preferably 10 minutes to 1 hour, or alternatively to the compound (ad) in solvent; for example, ethanol, isopropanol, or n-butanol, and the like; Raney-Nickel is added at 10° C. to 110° C., preferably 50° C. to 80° C., and reacted for 1 minute to 10 hours, preferably 10 minutes to 1 hour, to obtain the compound (ae).

(Step 3)

The compound (ae) in solvent; for example, tetrahydrofuran, dichloromethane, and the like; in the presence of acid; for example, acetic acid, or propionic acid, and the like; is reacted with reducing agent; for example, sodium cyanoborohydride, sodium triacetoxyborohydride, and the like; at −60° C. to 100° C., preferably 0° C. to 50° C., for 0.1 to 48 hours, preferably 0.5 to 24 hours, or the compound (ae) in solvent; for example, tetrahydrofuran, N,N-dimethylformamide, and the like; in the presence of dehydrating agent; for example, 1-ethyl-3-(3-dimethylaminopropyl)carbodiimide-N-hydroxybenzotriazole, carbonyldiimidazole, and the like; or in the presence of base; for example, triethylamine, potassium carbonate, and the like; is reacted with carboxylic acid; for example, formic acid, acetic acid, and the like; at −50° C. to 100° C., preferably 0° C. to 50° C. for 0.1 to 48 hours, preferably 0.6 to 16 hours, to obtain the compound (af). And next, to the suspension of lithium aluminium hydride in solvent; for example, tetrahydrofuran, or diethyl ether, and the like; the aforementioned amide compound dissolved in solvent; for example, tetrahydrofuran, or ether, and the like; is added at −50° C. to 60° C., preferably 0° C. to 50° C., and the mixture is reacted for 1 minute to 48 hours, preferably 10 minutes to 10 hours, to obtain the compound (af).

(Step 4)

The compound (ae) or the compound (af) in solvent; for example, acetonitrile, tetrahydrofuran, N,N-dimethylformamide, and the like; is reacted with 3,5-dimethylpyrazole-1-carboxamidine or S-methylthiourea at 0° C. to 150° C., preferably 20° C. to 100° C., and the mixture is reacted for 0.5 to 120 hours, preferably 1 to 24 hours, to obtain the compound (ag).

(Step 5)

To the compound (ag) (wherein at least either $R^{2b}$ or $R^{2c}$ is a hydrogen atom) in the presence or the absence of solvent; for example, toluene, and the like; acid; for example, trifluoroacetic acid, methanesulfonic acid, trifluoromethanesulfonic acid, and the like, or the mixture thereof; is added and the mixture is reacted at −20° C. to 100° C., preferably 0° C. to 50° C., and the mixture is reacted for 0.5 to 120 hours, preferably 1 to 72 hours, to obtain the compound (I-2) (wherein $R^{2b}$ is a hydrogen atom) or the compound (I-1) (wherein $R^{2c}$ is a hydrogen atom) respectively. Proviso, if $R^{2a}$, $R^{2b}$, and $R^{2c}$ have fragile structure under acidic condition; for example, t-butyloxycarbonyl, and the like; $R^{2a}$, $R^{2b}$, and $R^{2c}$ in the compound (I-1) or the compound (I-2) may be transformed into a hydrogen atom.

The synthesis of aminothiazoline ring; Method C

[Chemical formula 26]

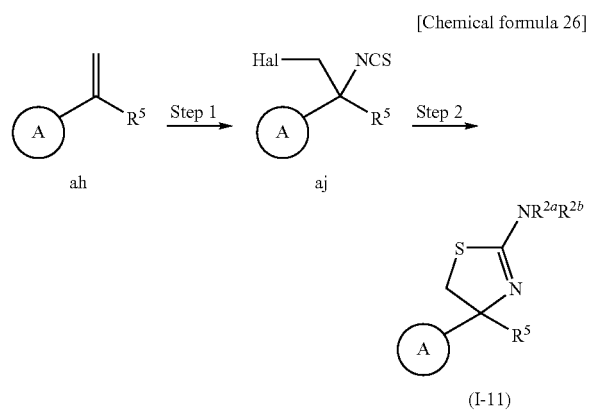

In formula, Hal is halogen, and other symbols are the same as described above.

(Step 1)

The compound (ah) which is commercially available or prepared by known method in solvent; for example, toluene, chloroform, tetrahydrofuran, and the like; or in mixed-solvent; for example, chloroform-water, and the like; is reacted with halogen; for example, including iodine, bromine, chorine; phase transfer catalyst; for example, sodium thiocyanic acid, ammonium thiocyanic acid, and the like; at 0° C. to 150° C., preferably 20° C. to 100° C., for 0.5 to 48 hours, preferably 1 to 24 hours, to obtain the compound (ai).

(Step 2)

The compound (ai) in solvent; for example, toluene, chloroform, tetrahydrofuran, and the like; is reacted with amine having substituent corresponding to target compound; for example ammonia, methylamine, diethylamine, and the like; at 0° C. to 150° C., preferably 20° C. to 100° C., for 0.5 to 48 hours, preferably 1 to 24 hours, to obtain the compound (I-11).

The aminoacyl derivative-1

[Chemical formula 27]

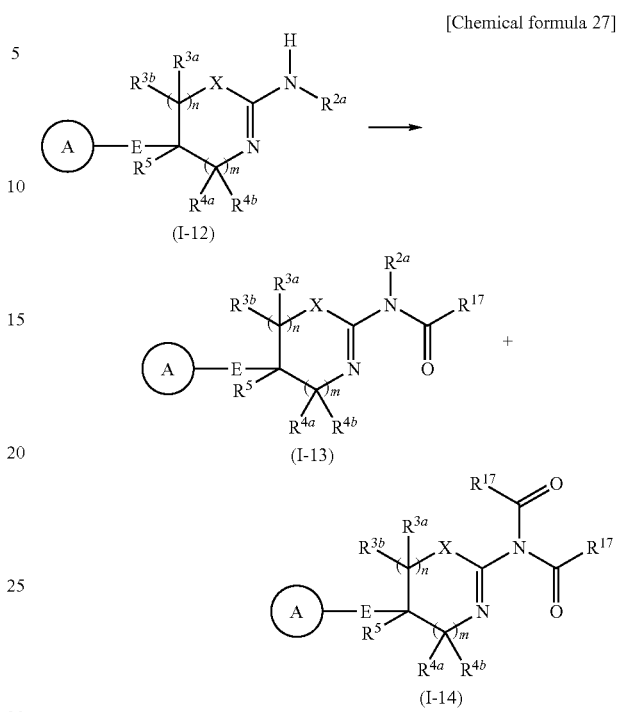

In formula, $R^{17}$ is optionally substituted lower alkyl, an optionally substituted carbocyclic group or an optionally substituted heterocyclic group, and the other symbols are the same as described above.

The compound (I-12) wherein $R^{2b}$ is a hydrogen atom in the presence or the absence of solvent; for example, tetrahydrofuran, dichloromethane, and the like; in the presence of base; for example, pyridine, triethylamine, and the like; is reacted with acylating agent having substituent corresponding to target compound; for example, benzoyl chloride, 2-furoyl chloride, acetic anhydride, and the like; at −80° C. to 100° C., preferably −20° C. to 40° C., for 0.1 to 24 hours, preferably 1 to 12 hours, or alternatively, the compound (I-12) in solvent; for example, N,N-dimethylformamide, tetrahydrofuran, dichloromethane, and the like; in the presence of dehydrating agent; for example, dicyclohexylcarbodiimide, carbonyldiimidazole, and the like; is reacted with carboxylic acid having substituent corresponding to target compound; for example, amino acid, glycolic acid, and the like; at −80° C. to 100° C., preferably −20° C. to 40° C., for 0.1 to 24 hours, preferably 1 to 12 hours, to obtain the compound (I-13) and/or the compound (I-14) (wherein $R^{2a}$ is a hydrogen atom).

The guanidino derivatives

[Chemical formula 28]

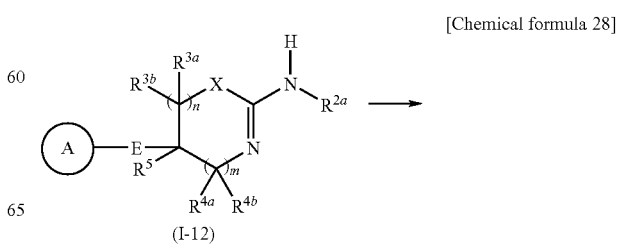

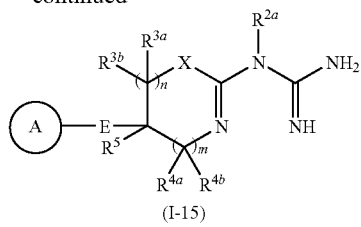

(I-15)

In formula, each symbols are the same as described above.

The compound (I-12) wherein $R^{2b}$ is a hydrogen atom in solvent; for example, acetonitrile, tetrahydrofuran, N,N-dimethylformamide, and the like; in the presence or the absence of base; for example, triethylamine, sodium hydrogencarbonate, and the like; is reacted with 3,6-dimethylpyrazole-1-carboxamidine, or S-methylisothiourea etc. at 0° C. to 150° C., preferably 20° C. to 100° C., for 0.5 to 120 hours, preferably 1 to 24 hours, to obtain the compound (I-16).

The carbamoyl derivatives

[Chemical formula 29]

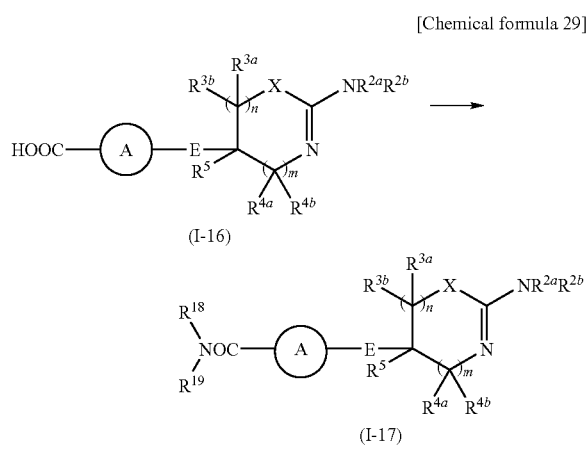

In formula, $CONR^{18}R^{19}$ is optionally substituted carbamoyl, and the other symbols are the same as described above.

The compound (I-16) having a carboxyl group as substituent of ring A in solvent; for example, N,N-dimethylformamide, tetrahydrofuran, dichloromethane, and the like; in the presence of dehydrating agent; for example, dicyclohexylcarbodiimide, carbonyldiimidazole, dicyclohexylcarbodiimide-N-hydroxybenzotriazole, and the like; is reacted with primary amine or secondary amine (aniline, 2-aminopyridine, dimethylamine etc.) at −80° C. to 100° C., preferably −20° C. to 40° C., for 0.1 to 24 hours, preferably 1 to 12 hours, to obtain the compound (I-17).

The acylamino derivative-2

[Chemical formula 30]

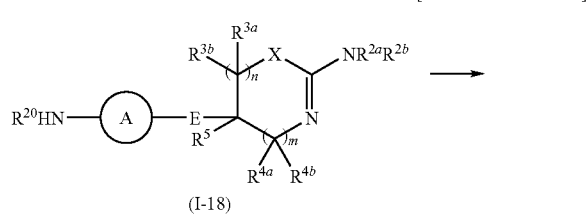

(I-18)

(I-19)

In formula, $NHR^{20}$ is optionally substituted amino; $NR^{20}COR^{21}$ is optionally substituted acyl amino, optionally substituted ureido, carboxy amino having substituent on oxygen atom, and the other symbols are the same as described above.

The compound (I-18) having an optionally substituted amino group on ring A in the presence or the absence of solvent; for example, tetrahydrofuran, dichloromethane, and the like; in the presence or the absence of base; for example, pyridine, triethylamine, and the like; is reacted with reagent including acid chloride, acid anhydride, chloroformate ester derivatives, isocyanate derivatives (benzoyl chloride, 2-furoyl chloride, acetic anhydride, benzyl chloroformate, di-t-butyl dicarbonate, phenyl isocyanate etc.), at −80° C. to 100° C., preferably −20° C. to 40° C., for 0.1 to 24 hours, preferably 1 to 12 hours. Or alternatively, the compound (I-18) having an optionally substituted amino group on ring A in solvent; for example, N,N-dimethylformamide, tetrahydrofuran, dichloromethane, and the like; in the presence of dehydrating agent; for example, dicyclohexylcarbodiimide, carbonyldiimidazole, dicyclohexylcarbodiimide-N-hydroxybenzotriazole, and the like; is reacted with carboxylic acid having substituent corresponding to target compound; for example, benzoic acid, 2-pyridinecarboxylic acid, and the like; at −80° C. to 100° C., preferably −20° C. to 40° C., for 0.1 to 24 hours, preferably 1 to 12 hours, to obtain the compound (I-19).

The alkylamino derivatives

[Chemical formula 31]

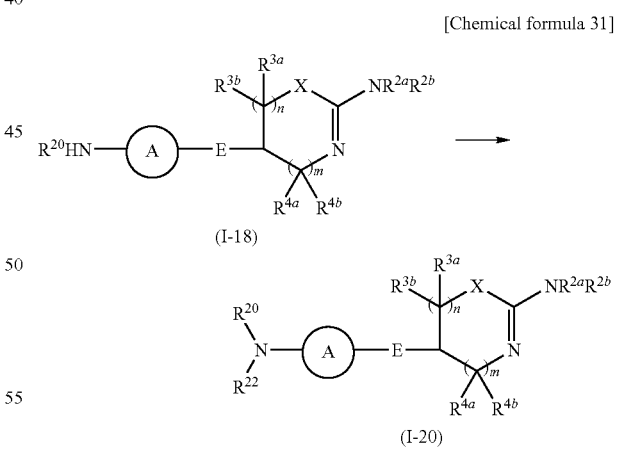

In formula, $NHR^{20}$ is optionally substituted amino, $R^{22}$ is lower alkyl.

The compound (I-18) having an amino group on ring A in solvent; for example, dichloromethane, tetrahydrofuran, and the like; in the presence or the absence of acid; for example, acetic acid, and the like; is reacted with aldehyde having substituent corresponding to target compound; for example, benzaldehyde, pyridine-2-carboaldehyde, and the like; and reducing agent; for example, sodium borohydride, sodium triacetoxyborohydride, and the like; at −80° C. to 100° C., preferably 0° C. to 40° C., for 0.5 to 150 hours, preferably 1 to 24 hours, to obtain the compound (I-20).

The substituted alkoxy derivatives

[Chemical formula 32]

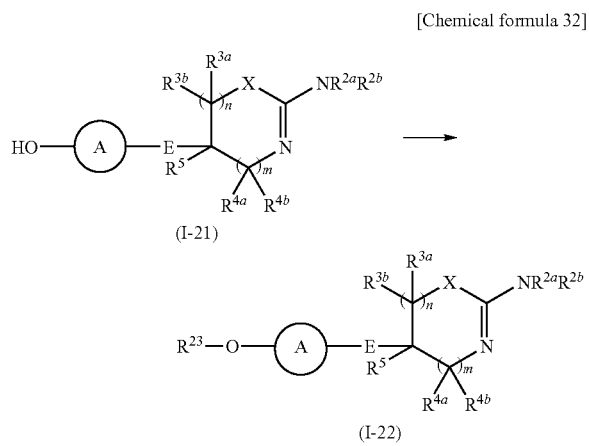

In formula, $R^{23}$ is optionally substituted lower alkyl an optionally substituted carbocyclic group or an optionally substituted heterocyclic group, etc., and the other symbols are the same as described above.

The compound (I-21) having a hydroxy group as substituent of A ring in solvent; for example, N,N-dimethylformamide, tetrahydrofuran, and the like; in the presence of base; for example potassium carbonate, sodium hydroxide, sodium hydride, and the like; is reacted with alkylating agent having substituent corresponding to target compound; for example, benzylchloride, methyl iodide, and the like; at −80° C. to 100° C., preferably 0° C. to 40° C., for 0.5 to 160 hours, preferably 1 to 24 hours, or alternatively, the compound (I-18) in solvent; for example, N,N-dimethylformamide, tetrahydrofuran, and the like; under Mitsunobu reagent; for example triphenylphosphine-azodicarboxylic acid ethyl ester, and the like; is reacted with alcohol; for example, 2-aminoethanol, and the like; at −80° C. to 100° C., preferably 0° C. to 40° C., for 0.5 to 72 hours, preferably 1 to 24 hours, to obtain the compound (I-22).

The introduction of substituent with palladium coupling reaction

[Chemical formula 33]

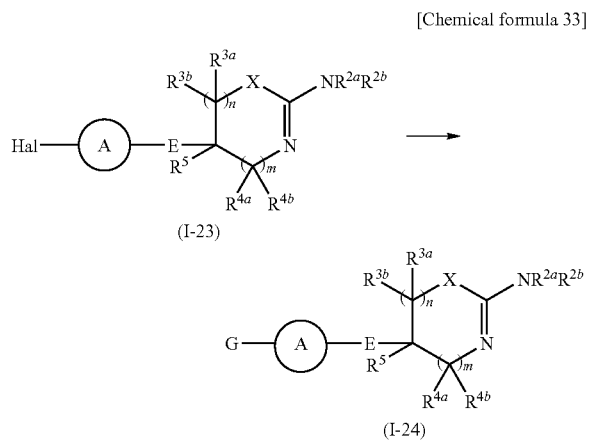

In formula, Hal is halogen, G is optionally substituted lower alkenyl, optionally substituted lower alkynyl, optionally substituted lower alkoxycarbonyl, an optionally substituted carbocyclic group or an optionally substituted heterocyclic group etc., and the other symbols are the same as described above.

The compound (I-23) having halogen as substituent of A ring in solvent; for example, tetrahydrofuran, N,N-dimethylformamide, 1,2-dimethoxyethane, methanol and the like; in the presence of base; for example, triethylamine, sodium carbonate, and the like; palladium catalyst; for example, palladium acetate, palladium chloride, and the like; and ligand; for example triphenylphosphine, and the like; is reacted with compound having substituent corresponding to target compound (styrene, propargyl alcohol aryl boronic acid, carbon monoxide), with or without microwave irradiation, at −80° C. to 150° C., preferably 0° C. to 100° C., for 0.5 to 72 hours, preferably 1 to 24 hours, to obtain the compound (I-24).

The oxime derivatives

[Chemical formula 34]

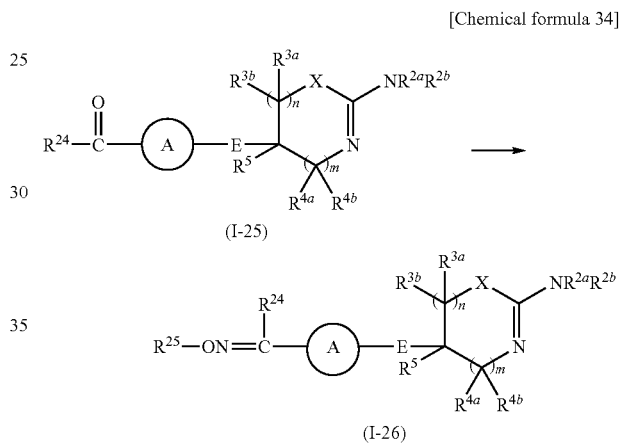

In formula, in $R^{24}$ is a hydrogen atom or optionally substituted lower alkyl etc., $R^{25}$ is a hydrogen atom, optionally substituted lower alkyl, optionally substituted lower alkenyl or an optionally substituted carbocyclic group or an optionally substituted heterocyclic group etc., and the other symbols are the same as described above.

The compound (I-25) having an acyl group as substituent of A ring in solvent; for example, methanol, ethanol and the like; in the presence or the absence of additives; for example, potassium acetate, and the like; is reacted with hydroxylamine having substituent corresponding to target compound (hydroxylamine, methoxylamine, O-benzylhydroxylamine, etc.) or the salt thereof, at 0° C. to 100° C., preferably 0° C. to 40° C., for 0.5 to 150 hours, preferably 1 to 72 hours, to obtain the compound (I-26).

In all of above mentioned steps, if a compound having substituent which interrupts the reaction; (for example, hydroxy, mercapto, amino, formyl, carbonyl carboxyl, etc.), the substituent of the compound is protected by methods described in Protective Groups in Organic Synthesis, Theodora W Green (John Wiley & Sons) beforehand, and is deprotected at preferable step.

The compound (I) in this invention presented below; in particular, X is S, and E is a bond or methylene; is preferable.

1) A compound represented by the general formula (I'),

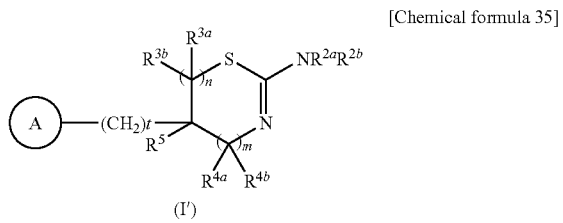

in formula, t is 0 or 1, the other symbols are the same as above (a), with the proviso that the compounds represented below;
i) wherein n+m is 2, $R^5$ is a hydrogen atom, and ring A is unsubstituted phenyl;
ii) wherein n is 2, m is 0, $R^{2a}$ is a hydrogen atom, $R^{2b}$ is a hydrogen atom or acetyl, $R^5$ is methyl and ring A is phenyl or 4-methoxyphenyl;
iii) wherein n is 2, m is 0, $R^{2a}$ is a hydrogen atom, $R^{2b}$ is a hydrogen atom or acetyl,
$R^5$ is ethyl, and ring A is 3,4-dimethoxyphenyl;
iv) wherein n is 2, m is 0, $R^{28}$ is a hydrogen atom, $R^{2b}$ is a hydrogen atom or acetyl,
$R^5$ and ring A are phenyl;
v) wherein n is 2, m is 0, $R^{28}$ and $R^{2b}$ is a hydrogen atom, $R^5$ and ring A are taken together to form

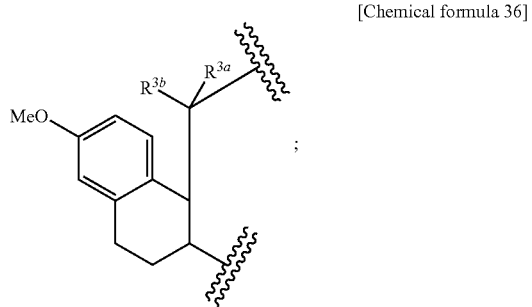

and
vi) the compound, wherein n+m is 1 or 2; $R^5$ is a hydrogen atom; ring A is phenyl substituted by one or two substituent selected from hydroxy, halogen, lower alkyl, lower alkoxy, nitro, amino, lower alkyl carbonylamino, mercapto, lower alkylthio, carbamoyl, lower alkylamino, lower alkyl carbamoyl and lower alkoxycarbonyl; non-substituted phenyl or non-substituted naphthyl; are excluded.

In addition, in formula (I'), preferable is the compound represented below.
2) The compound, wherein n is 1 and m is 0 (this compound is represented by nm-1),
3) the compound, wherein n is 2 and m is 0 (this compound is represented by nm-2),
4) the compound, wherein n is 3 and m is 0 (this compound is represented by nm-3),
5) the compound, wherein $R^{2a}$ is a hydrogen atom; $R^{2b}$ is a hydrogen atom, optionally substituted lower alkyl optionally substituted acyl, optionally substituted lower alkylsulfonyl, or optionally substituted amidino (this compound is represented by R2-1),
6) the compound, wherein $R^{2a}$ is a hydrogen atom; $R^{2b}$ is a hydrogen atom, optionally substituted lower alkyl or optionally substituted acyl (this compound is represented by R2-2), 7) the compound, wherein $NR^{2a}R^{2b}$ is represented by the following formula:

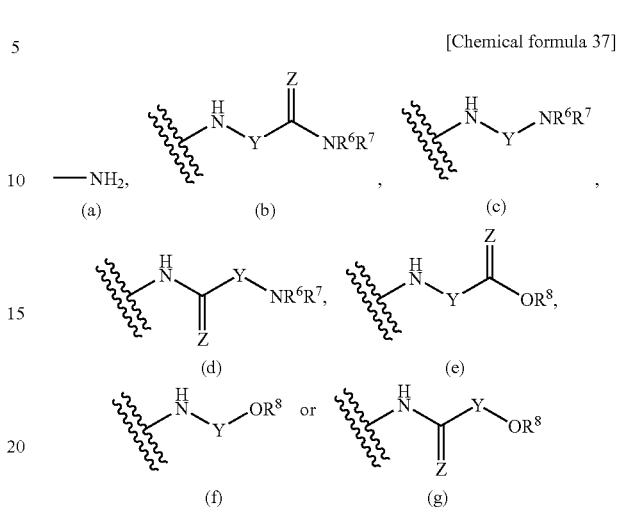

wherein each symbols are the same as described above.
$R^6$, $R^7$ and $R^8$ are each independently a hydrogen atom, lower alkyl or acyl,
Y is optionally substituted lower alkylene, optionally substituted lower alkenylene or optionally substituted lower alkynylene,
Z is O or S (this compound is represented by R2-3),
8) the compound, wherein $NR^{2a}R^{2b}$ is $NH_2$ (this compound is represented by R2-4),
9) the compound, wherein ring A is substituted phenyl or substituted pyridyl (this compound is represented by A-1),
10) the compound, wherein ring A is represented by the following formula:

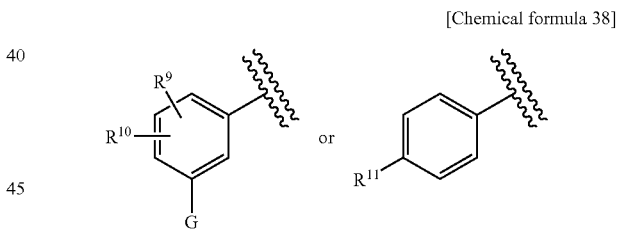

wherein $R^9$, $R^{10}$ and $R^{11}$ is a hydrogen atom or G,
G is halogen, hydroxy, cyano, nitro, mercapto, optionally substituted lower alkyl optionally substituted lower alkoxy, optionally substituted lower alkenyl, optionally substituted lower alkynyl optionally substituted acyl optionally substituted acyloxy, carboxy, optionally substituted lower alkoxycarbonyl optionally substituted lower alkoxycarbonyloxy, optionally substituted aryloxycarbonyloxy, optionally substituted amino, optionally substituted carbamoyl, optionally substituted carbamoyloxy, optionally substituted lower alkylthio, optionally substituted arylthio, optionally substituted lower alkylsulfonyl, optionally substituted arylsulfonyl optionally substituted lower alkylsulfinyl, optionally substituted arylsulfinyl optionally substituted lower alkylsulfonyloxy, optionally substituted arylsulfonyloxy, optionally substituted sulfamoyl an optionally substituted carbocyclic group, optionally substituted carbocyclicoxy, an optionally substituted heterocyclic group or optionally substituted heterocyclicoxy, each G may be different (this compound is represented by A-2), 11) the compound, wherein ring A is represented by the following formula:

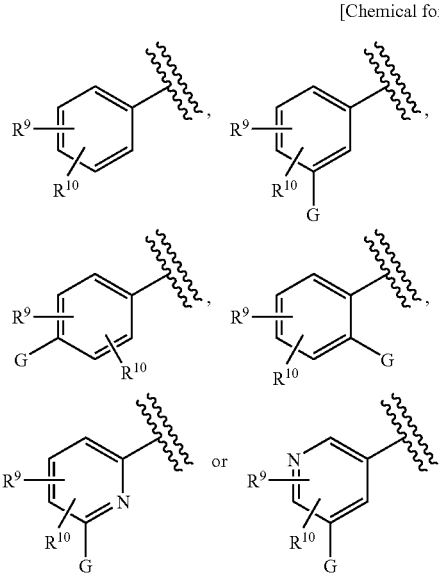

[Chemical formula 39]

wherein $R^9$ and $R^{10}$ are each independently a hydrogen atom, halogen, hydroxy, optionally substituted lower alkyl, cyano, nitro, optionally substituted lower alkoxy, optionally substituted acyl, optionally substituted amino, optionally substituted carbamoyl optionally substituted carbamoyloxy, optionally substituted lower alkylsulfonyl, optionally substituted arylsulfonyl, optionally substituted lower alkylsulfonyloxy, optionally substituted arylsulfonyloxy, an optionally substituted carboncyclic group, optionally substituted carbocyclicoxy, an optionally substituted heterocyclic group or optionally substituted heterocyclicoxy, G is the same as described above 10) (this compound is represented by A-3), 12) the compound, wherein ring A is represented by the following formula:

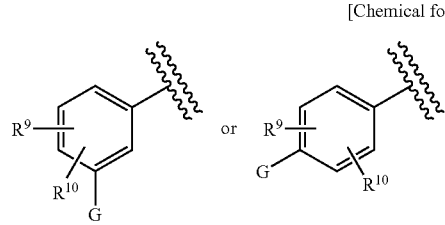

[Chemical formula 40]

wherein $R^9$ and $R^{10}$ is the same as described in 11), G is the same as described in 10) (this compound is represented by A-4), 13) the compound, wherein ring A, $R^9$, and $R^{10}$ are defined in 11), G is optionally substituted amino (this compound is represented by A-6), 14) the compound, wherein ring A, $R^9$ and $R^{10}$ are defined in 11), G is optionally substituted arylcarbonylamino or optionally substituted heterocyclic carbonylamino, 15) the compound, wherein ring A, $R^9$ and $R^{10}$ are defined in 11), G is optionally substituted heterocyclic carbonylamino (this compound is represented by A-6), 16) the compound, wherein ring A is defined in 11), G is represented by the following formula:

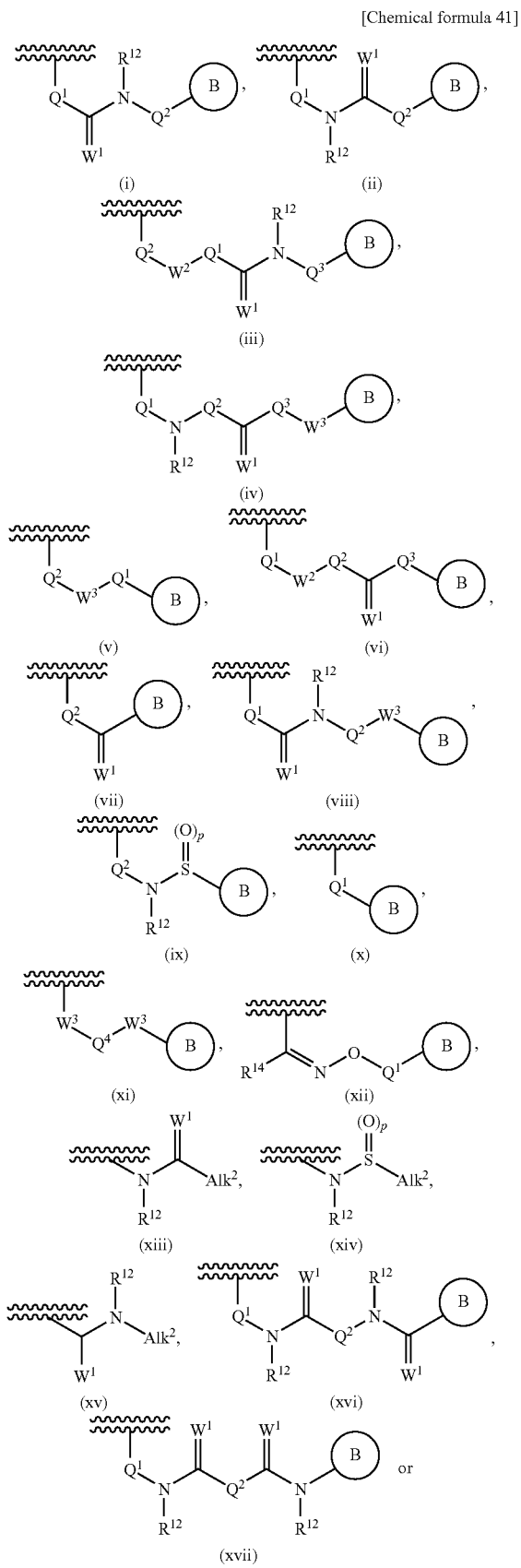

[Chemical formula 41]

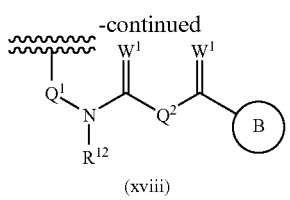

(xviii)

wherein $Q^1$, $Q^2$ and $Q^3$ are each independently a bond, optionally substituted lower alkylene or optionally substituted lower alkenylene;
$Q^4$ is optionally substituted lower alkylene or optionally substituted lower alkenylene;
$W^1$ and $W^2$ are each independently O or S; $W^3$ is O, S or $NR^{12}$;
$R^{12}$ is a hydrogen atom, lower alkyl, hydroxy lower alkyl lower alkoxy lower alkyl, lower alkoxycarbonyl lower alkyl, carbocyclic lower alkyl or acyl,
$R^{14}$ is hydrogen atom or lower alkyl;
ring B is an optionally substituted carbocyclic group or an optionally substituted heterocyclic group;
$Alk^2$ is optionally substituted lower alkyl;
$R^9$ and $R^{10}$ are the same as described in 11) (this compound is represented by A-7),
17) the compound, wherein ring A, $R^9$ and $R^{10}$ are the group defined in 11); G is the group defined in 16); ring B is aryl optionally substituted with one or more substituents selected from halogen, hydroxy, optionally substituted lower alkyl, optionally substituted lower alkoxy, optionally substituted acyl optionally substituted amino, cyano, optionally substituted carbamoyl an optionally substituted carbocyclic group, optionally substituted carbocyclicoxy or an optionally substituted heterocyclic group or
heteroaryl optionally substituted with one or more substituents selected from halogen, hydroxy, optionally substituted lower alkyl, optionally substituted lower alkoxy, optionally substituted acyl optionally substituted amino, cyano, optionally substituted carbamoyl an optionally substituted carbocyclic group, optionally substituted carbocyclicoxy or an optionally substituted heterocyclic group; and the other symbols are the same as described in 16) (this compound is represented by A-8),
18) the compound, wherein ring A, $R^9$ and $R^{10}$ are defined in 11), G is represented by the following formula:

[Chemical formula 42]

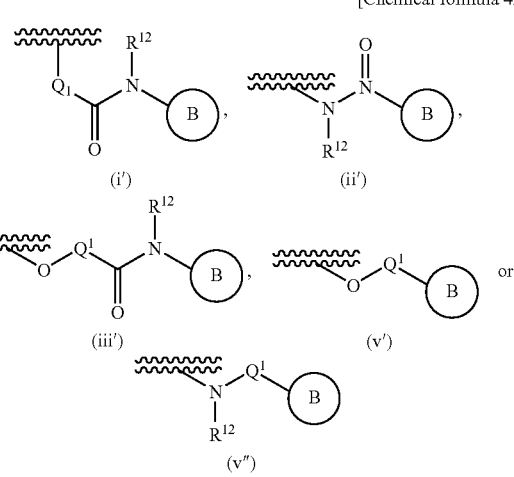

in formula, wherein each symbols are the same as described in 16) (this compound is represented by A-9), 19) the compound, wherein ring A is represented by the following formula:

[Chemical formula 43]

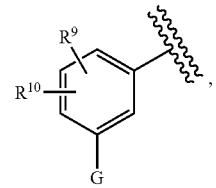

G is defined in 16), ring B is optionally substituted aryl or optionally substituted heteroaryl, either $R^9$ or $R^{10}$ is a hydrogen atom; and the other is a hydrogen atom, halogen, optionally substituted lower alkyl, cyano, nitro, optionally substituted lower alkoxy, optionally substituted amino, optionally substituted carbamoyl, optionally substituted lower alkylsulfonyl, an optionally substituted carbocyclic group or an optionally substituted heterocyclic group (this compound is represented by A-10),
20) the compound, wherein ring A is represented by the following formula:

[Chemical formula 44]

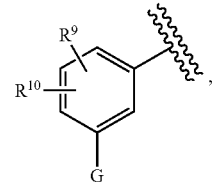

G is defined in 18), the other symbols are the same as described in 19) (this compound is represented by A-11),
21) the compound, wherein ring A is represented by the following formula:

[Chemical formula 45]

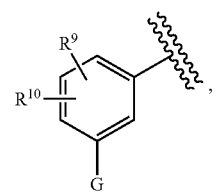

G is defined in 16), ring B is optionally substituted phenyl 5- to 6-membered heteroaryl benzothiazolyl or benzothienyl $R^9$ and $R^{10}$ are the same as described in 19) (this compound is represented by A-12),
22) the compound, wherein ring A is represented by the following formula:

[Chemical formula 46]

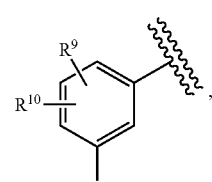

G is defined in 18), ring B is defined in 21), $R^9$ and $R^{10}$ are the same as described in 19) (this compound is represented by A-13), 23) the compound, wherein ring A is represented by the following formula:

[Chemical formula 47]

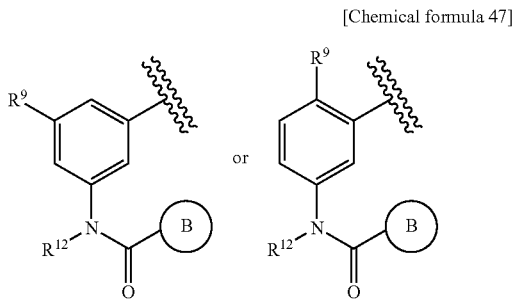

wherein $R^9$ is a hydrogen atom, halogen, optionally substituted lower alkyl, cyano, nitro, optionally substituted lower alkoxy, optionally substituted amino, optionally substituted carbamoyl optionally substituted lower alkylsulfonyl an optionally substituted carbocyclic group or an optionally substituted heterocyclic group, ring B is the same as described in 21); $R^{12}$ is a hydrogen atom or lower alkyl (this compound is represented by A-14), 24) the compound, wherein $R^5$ is a hydrogen atom or C1 to C3 alkyl (this compound is represented by R5-1), 25) the compound, wherein $R^5$ is C1 to C3 alkyl (this compound is represented by R5-2), 26) the compound, wherein $R^5$ is methyl (this compound is represented by R5-3), 27) the compound, wherein $R^{3a}$ and $R^{3b}$ are each independently a hydrogen atom, halogen, hydroxy, optionally substituted lower alkyl optionally substituted lower alkoxy or optionally substituted aryl (this compound is represented by R3-1), 28) the compound wherein, $R^{3a}$ is a hydrogen atom, halogen, hydroxy, optionally substituted lower alkyl, optionally substituted lower alkoxy or optionally substituted aryl $R^{3b}$ is a hydrogen atom, one $R^3$ is a hydrogen atom when n is 2, one or two $R^{2a}$ is (are) a hydrogen atom when n is 3 (this compound is represented by R3-2), 29) the compound, wherein $R^{3a}$ and $R^{3b}$ are all hydrogen atoms (this compound is represented by R3-3), and in a compound represented by the general formula (I'), a compound, wherein the combination of n, m, $R^{2a}$, $R^{2b}$, ring A, $R^5$, $R^{3a}$, and $R^{3b}$ (m, $R^2$, A, $R^5$, $R^3$) is the following compound.

(nm, $R^2$, A, $R^5$, $R^3$)=
(nm-1,R2-1,A-1,R5-1,R3-1), (nm-1,R2-1,A-1,R5-1,R3-2),
(nm-1,R2-1,A-1,R5-2,R3-1), (nm-1,R2-1,A-1,R5-2,R3-2),
(nm-1,R2-1,A-1,R5-3,R3-1), (nm-1,R2-1,A-1,R5-3,R3-2),
(nm-1,R2-1,A-2,R5-1,R3-1), (nm-1,R2-1,A-2,R5-1,R3-2),
(nm-1,R2-1,A-2,R5-2,R3-1), (nm-1,R2-1,A-2,R5-2,R3-2),
(nm-1,R2-1,A-2,R5-3,R3-1), (nm-1,R2-1,A-2,R5-3,R3-2),
(nm-1,R2-1,A-3,R5-1,R3-1), (nm-1,R2-1,A-3,R5-1,R3-2),
(nm-1,R2-1,A-3,R5-2,R3-1), (nm-1,R2-1,A-3,R5-2,R3-2),
(nm-1,R2-1,A-3,R5-3,R3-1), (nm-1,R2-1,A-3,R5-3,R3-2),
(nm-1,R2-1,A-4,R5-1,R3-1), (nm-1,R2-1,A-4,R5-1,R3-2),
(nm-1,R2-1,A-4,R5-2,R3-1), (nm-1,R2-1,A-4,R5-2,R3-2),
(nm-1,R2-1,A-4,R5-3,R3-1), (nm-1,R2-1,A-4,R5-3,R3-2),
(nm-1,R2-1,A-5,R5-1,R3-1), (nm-1,R2-1,A-5,R5-1,R3-2),
(nm-1,R2-1,A-5,R5-2,R3-1), (nm-1,R2-1,A-5,R5-2,R3-2),
(nm-1,R2-1,A-5,R5-3,R3-1), (nm-1,R2-1,A-5,R5-3,R3-2),
(nm-1,R2-1,A-6,R5-1,R3-1), (nm-1,R2-1,A-6,R5-1,R3-2),
(nm-1,R2-1,A-6,R5-2,R3-1), (nm-1,R2-1,A-6,R5-2,R3-2),
(nm-1,R2-1,A-6,R5-3,R3-1), (nm-1,R2-1,A-6,R5-3,R3-2),
(nm-1,R2-1,A-7,R5-1,R3-1), (nm-1,R2-1,A-7,R5-1,R3-2),
(nm-1,R2-1,A-7,R5-2,R3-1), (nm-1,R2-1,A-7,R5-2,R3-2),
(nm-1,R2-1,A-7,R5-3,R3-1), (nm-1,R2-1,A-7,R5-3,R3-2),
(nm-1,R2-1,A-8,R5-1,R3-1), (nm-1,R2-1,A-8,R5-1,R3-2),
(nm-1,R2-1,A-8,R5-2,R3-1), (nm-1,R2-1,A-8,R5-2,R3-2),
(nm-1,R2-1,A-8,R5-3,R3-1), (nm-1,R2-1,A-8,R5-3,R3-2),
(nm-1,R2-1,A-9,R5-1,R3-1), (nm-1,R2-1,A-9,R5-1,R3-2),
(nm-1,R2-1,A-9,R5-2,R3-1), (nm-1,R2-1,A-9,R5-2,R3-2),
(nm-1,R2-1,A-9,R5-3,R3-1), (nm-1,R2-1,A-9,R5-3,R3-2),
(nm-1,R2-1,A-10,R5-1,R3-1), (nm-1,R2-1,A-9,R5-3,R3-1),
(nm-1,R2-1,A-9,R5-3,R3-2), (nm-1,R2-1,A-10,R5-1,R3-1),
(nm-1,R2-1,A-10,R5-1,R3-2), (nm-1,R2-1,A-10,R5-2,R3-1), (nm-1,R2-1,A-10,R5-2,R3-2), (nm-1,R2-1,A-10,R-3,R3-1), (nm-1,R2-1,A-10,R5-3,R3-2), (nm-1,R2-1,A-1,R5-1,R3-1), (nm-1,R2-1,A-11,R5-1,R3-2), (nm-1,R2-1,A-11,R5-2,R3-1), (nm-1,R2-1,A-11,R5-2,R3-2), (nm-1,R2-1,A-11,R5-3,R3-1), (nm-1,R2-1,A-11,R5-3,R3-2), (nm-1,R2-1,A-12,R5-1,R3-1), (nm-1,R2-1,A-12,R5-1,R3-2), (nm-1,R2-1,A-12,R5-2,R3-1), (nm-1,R2-1,A-12,R5-2,R3-2), (nm-1,R2-1,A-12,R5-3,R3-1), (nm-1,R2-1,A-12,R5-3,R3-2), (nm-1,R2-1,A-13,R5-1,R3-1), (nm-1,R2-1,A-13,R5-1,R3-2), (nm-1,R2-1,A-13,R5-2,R3-1), (nm-1,R2-1,A-13,R5-2,R3-2), (nm-1,R2-1,A-13,R5-3,R3-1), (nm-1,R2-1,A-13,R5-3,R3-2), (nm-1,R2-1,A-14,R5-1,R3-1), (nm-1,R2-1,A-14,R5-1,R3-2), (nm-1,R2-1,A-14,R5-2,R3-1), (nm-1,R2-1,A-14,R5-2,R3-2), (nm-1,R2-1,A-14,R5-3,R3-1), (nm-1,R2-1,A-14,R5-3,R3-2), (nm-1,R2-2,A-1,R5-1,R3-1), (nm-1,R2-2,A-1,R5-1,R3-2), (nm-1,R2-2,A-1,R5-2,R3-1), (nm-1,R2-2,A-1,R5-2,R3-2), (nm-1,R2-2,A-1,R5-3,R3-1), (nm-1,R2-2,A-1,R5-3,R3-2), (nm-1,R2-2,A-2,R5-1,R3-1), (nm-1,R2-2,A-2,R5-1,R3-2), (nm-1,R2-2,A-2,R5-2,R3-1), (nm-1,R2-2,A-2,R5-2,R3-2), (nm-1,R2-2,A-2,R5-3,R3-1), (nm-1,R2-2,A-2,R5-3,R3-2), (nm-1,R2-2,A-3,R5-1,R3-1), (nm-1,R2-2,A-3,R5-1,R3-2), (nm-1,R2-2,A-3,R5-2,R3-1), (nm-1,R2-2,A-3,R5-2,R3-2), (nm-1,R2-2,A-3,R5-3,R3-1), (nm-1,R2-2,A-3,R5-3,R3-2), (nm-1,R2-2,A-4,R5-1,R3-1), (nm-1,R2-2,A-4,R5-1,R3-2), (nm-1,R2-2,A-4,R5-2,R3-1), (nm-1,R2-2,A-4,R5-2,R3-2), (nm-1,R2-2,A-4,R5-3,R3-1), (nm-1,R2-2,A-4,R5-3,R3-2), (nm-1,R2-2,A-5,R5-1,R3-1), (nm-1,R2-2,A-5,R5-1,R3-2), (nm-1,R2-2,A-5,R5-2,R3-1), (nm-1,R2-2,A-5,R5-2,R3-2), (nm-1,R2-2,A-5,R5-3,R3-1), (nm-1,R2-2,A-5,R5-3,R3-2), (nm-1,R2-2,A-6,R-1,R3-1), nm-1,R2-2,A-6,R5-1,R3-2), (nm-1,R2-2,A-6,R5-2,R3-1), (nm-1,R2-2,A-6,R5-2,R3-2), (nm-1,R2-2,A-6,R5-3,R3-1), (nm-1,R2-2,A-6,R5-3,R3-2), (nm-1,R2-2,A-7,R5-1,R3-1), (nm-1,R2-2,A-7,R5-1,R3-2), (nm-1,R2-2,A-7,R5-2,R3-1), (nm-1,R2-2,A-7,R5-2,R3-2), (nm-1,R2-2,A-7,R5-3,R3-1), (nm-1,R2-2,A-7,R5-3,R3-2), (nm 1,R2-2,A-8,R5-1,R3-1), (nm-1,R2-2,A-8,R5-1,R3-2), (nm-1,R2-2,A-8,R5-2,R3-1), (nm-1,R2-2,A-8,R5-2,R3-2), (nm-1,R2-2,A-8,R5-3,R3-1), (nm-1,R2-2,A-8,R5-3,R3-2), (nm 1,R2-2,A-9,R5-1,R3-1), (nm-1,R2-2,A-9,R5-1,R3-2), (nm-1,R2-2,A-9,R5-2,R3-1), (nm-1,R2-2,A-9,R5-2,R3-2), (nm-1,R2-2,A-9,R5-3,R3-1), (nm-1,R2-2,A-9,R5-3,R3-2), (nm-1,R2-2,A-10,R5-1,R3-1), (nm-1,R2-2,A-10,R5-1,R3-2), (nm-1,R2-2,A-10,R5-2,R3-1), (nm-1,R2-2,A-10,R5-2,R3-2), (nm-1,R2-2,A-10,R5-3,R3-1), (nm-1,R2-2,A-10,R5-3,R3-2), (nm-1,R2-2,A-11,R5-1,R3-1), (nm-1,R2-2,A-11,R5-1,R3-2), (nm-1,R2-2,A-11,R5-2,R3-1), (nm-1,R2-2,A-11,R5-2,R3-2), (nm-1,R2-2,A-11,R5-3,R3-1), (nm-1,R2-2,A-11,R5-3,R3-2), (nm-1,R2-2,A-12,R6-1,R3-1), (nm-1,R2-2,A-12,R-1,R3-2), (nm-1,R2-2,A-12,R5-2,R3-1), (nm-1,R2-2,A-12,R5-2,R3-2), (nm-1,R2-2,A-12,R5-3,R3-1), (nm-1,R2-2,A-12,R5-3,R3-2), (nm-1,R2-2,A-13,R5-1,R3-1), (nm-1,R2-2,A-13,R5-1,R3-2), (nm-1,R2-2,A-13,R5-2,

R3-1), (nm-1,R2-2,A-13,R5-2,R3-2), (nm-1,R2-2,A-13,R5-3,R3-1), (nm-1,R2-2,A-13,R5-3,R3-2), (nm-1,R2-2,A-14,R5-1,R3-1), (nm-1,R2-2,A-14,R5-1,R3-2), (nm-1,R2-2,A-14,R5-2,R3-1), (nm-1,R2-2,A-14,R5-2,R3-2), (nm-1,R2-2,A-14,R5-3,R3-1), (nm-1,R2-2,A-14,R5-3,R3-2), (nm-1,R2-3,A-1,R5-1,R3-1), (nm-1,R2-3,A-1,R5-1,R3-2), (nm-1,R2-3,A-1,R5-2,R3-1), (nm-1,R2-3,A-1,R5-2,R3-2), (nm-1,R2-3,A-1,R5-3,R3-1), (nm-1,R2-3,A-1,R5-3,R3-2), (nm-1,R2-3,A-2,R5-1,R3-1), (nm-1,R2-3,A-2,R5-1,R3-2), (nm-1,R2-3,A-2,R5-2,R3-1), (nm-1,R2-3,A-2,R5-2,R3-2), (nm-1,R2-3,A-2,R5-3,R3-1), (nm-1,R2-3,A-2,R5-3,R3-2), (nm-1,R2-3,A-3,R5-1,R3-1), (nm-1,R2-3,A-3,R-1,R3-2), (nm-1,R2-3,A-3,R5-2,R3-1), (nm-1,R2-3,A-3,R5-2,R3-2), (nm-1,R2-3,A-3,R5-3,R3-1), (nm-1,R2-3,A-3,R5-3,R3-2), (nm-1,R2-3,A-4,R-1,R3-1), (nm-1,R2-3,A-4,R5-1,R3-2), (nm-1,R2-3,A-4,R5-2,R3-1), (nm-1,R2-3,A-4,R5-2,R3-2), (nm-1,R2-3,A-4,R5-3,R3-1), (nm-1,R2-3,A-4,R5-3,R3-2), (nm-1,R2-3,A-5,R5-1,R3-1), (nm-1,R2-3,A-5,R5-1,R3-2), (nm-1,R2-3,A-5,R5-2,R3-1), (nm-1,R2-3,A-5,R5-2,R3-2), (nm-1,R2-3,A-6,R5-3,R3-1), (nm-1,R2-3,A-5,R5-3,R3-2), (nm-1,R2-3,A-6,R5-1,R3-1), (nm-1,R2-3,A-6,R5-1,R3-2), (nm-1,R2-3,A-6,R5-2,R3-1), (nm-1,R2-3,A-6,R5-2,R3-2), (nm-1,R2-3,A-6,R5-3,R3-1), (nm-1,R2-3,A-6,R5-3,R3-2), (nm-1,R2-3,A-7,R5-1,R3-1), (nm-1,R2-3,A-7,R5-1,R3-2), (nm-1,R2-3,A-7,R5-2,R3-1), (nm-1,R2-3,A-7,R5-2,R3-2), (nm-1,R2-3,A-7,R5-3,R3-1), (nm-1,R2-3,A-7,R5-3,R3-2), (nm-1,R2-3,A-8,R-1,R3-1), (nm-1,R2-3,A-8,R5-1,R3-2), (nm-1,R2-3,A-8,R5-2,R3-1), (nm-1,R2-3,A-8,R5-2,R3-2), (nm-1,R2-3,A-8,R5-3,R3-1), (nm-1,R2-3,A-8,R5-3,R3-2), (nm-1,R2-3,A-9,R5-1,R3-1), (nm-1,R2-3,A-9,R5-1,R3-2), (nm-1,R2-3,A-9,R5-2,R3-1), (nm-1,R2-3,A-9,R5-2,R3-2), (nm-1,R2-3,A-9,R5-3,R3-1), (nm-1,R2-3,A-9,R5-3,R3-2), (nm-1,R2-3,A-10,R5-1,R3-1), (nm-1,R2-3,A-10,R5-1,R3-2), (nm-1,R2-3,A-10,R5-2,R3-1), (nm-1,R2-3,A-10,R5-2,R3-2), (nm-1,R2-3,A-10,R5-3,R3-1), (nm-1,R2-3,A-10,R5-3,R3-2), (nm-1,R2-3,A-11,R5-1,R3-1), (nm-1,R2-3,A-11,R5-1,R3-2), (nm-1,R2-3,A-11,R5-2,R3-1), (nm-1,R2-3,A-11,R5-2,R3-2), (nm-1,R2-3,A-11,R5-3,R3-1), (nm-1,R2-3,A-11,R5-3,R3-2), (nm-1,R2-3,A-12,R5-1,R3-1), (nm-1,R2-3,A-12,R5-1,R3-2), (nm-1,R2-3,A-12,R5-2,R3-1), (nm-1,R2-3,A-12,R5-2,R3-2), (nm-1,R2-3,A-12,R5-3,R3-1), (nm-1,R2-3,A-12,R5-3,R3-2), (nm-1,R2-3,A-13,R6-1,R3-1), (nm-1,R2-3,A-13,R5-1,R3-2), (nm-1,R2-3,A-13,R5-2,R3-1), (nm-1,R2-3,A-13,R5-2,R3-2), (nm-1,R2-3,A-13,R5-3,R3-1), (nm-1,R2-3,A-13,R5-3,R3-2), (nm-1,R2-3,A-14,R5-1,R3-1), (nm-1,R2-3,A-14,R5-1,R3-2), (nm-1,R2-3,A-14,R5-2,R31), (nm 1,R2-3,A-14,R5-2,R3-2), (nm-1,R2-3,A-14,R5-3,R3-1), (nm-1,R2-3,A-14,R5-3,R3-2), (nm-1,R2-4,A-1,R5-1,R3-1), (nm-1,R2-4,A-1,R5-1,R3-2), (nm-1,R2-4,A-1,R5-2,R3-1), (nm-1,R2-4,A-1,R5-2,R3-2), (nm-1,R2-4,A-1,R5-3,R3-1), (nm-1,R2-4,A-1,R5-3,R3-2), (nm-1,R2-4,A-2,R5-1,R3-1), (nm-1,R2-4,A-2,R5-1,R3-2), (nm-1,R2-4,A-2,R5-2,R3-1), (nm-1,R2-4,A-2,R5-2,R3-2), (nm-1,R2-4,A-3,R5-1,R3-2), (nm-1,R2-4,A-3,R5-2,R3-1), (nm-1,R2-4,A-3,R5-2,R3-2), (nm-1, R2-4,A-3,R5-3,R3-1), (nm-1,R2-4,A-3,R5-3,R3-2), (nm-1,R2-4,A-4,R-5-1,R3-1), (nm-1,R2-4,A-4,R5-1,R3-2), (nm-1,R2-4,A-4,R5-2,R3-1), (nm-1,R2-4,A-4,R5-2,R3-2), (nm-1,R2-4,A-4,R5-3,R3-1), (nm-1,R2-4,A-4,R5-3,R3-2), (nm-1,R2-4,A-5,R5-1,R3-1), (nm-1,R2-4,A-5,R5-1,R3-2), (nm-1,R2-4,A-5,R5-2,R3-1), (nm-1,R2-4,A-5,R5-2,R3-2), (nm-1,R2-4,A-5,R5-3,R3-1), (nm 1,R2-4,A-5,R5-3,R3-2), (nm-1,R2-4,A-6,R5-1,R3-1), (nm-1,R2-4,A-6,R5-1,R3-2), (nm-1,R2-4,A-6,R5-2,R3-1), (nm-1,R2-4,A-6,R5-2,R3-2), (nm-1,R2-4,A-6,R5-3,R3-1), (nm 1,R2-4,A-6,R5-3,R3-2), (nm-1,R2-4,A-7,R5-1,R3-1), (nm-1,R2-4,A-7,R5-1,R3-2), (nm-1,R2-4,A-7,R5-2,R3-1), (nm-1,R2-4,A-7,R5-2,R3-2), (nm-1,R2-4,A-7,R5-3,R3-1), (nm-1,R2-4,A-7,R5-3,R3-2), (nm-1,R2-4,A-8,R5-1,R3-1), (nm-1,R2-4,A-8,R5-1,R3-2), (nm-1,R2-4,A-8,R5-2,R3-1), (nm-1,R2-4,A-8,R5-2,R3-2), (nm-1,R2-4,A-8,R5-3,R3-1), (nm-1,R2-4,A-8,R5-3,R3-2), (nm-1,R2-4,A-9,R5-1,R3-1), (nm-1,R2-4,A-9,R5-1,R3-2), (nm-1,R2-4,A-9,R5-2,R3-1), (nm-1,R2-4,A-9,R5-2,R3-2), (nm-1,R2-4,A-9,R5-3,R3-1), (nm-1,R2-4,A-9,R5-3,R3-2), (nm-1,R2-4,A-10,R5-1,R3-1), (nm 1,R2-4,A-10,R5-1,R3-2), (nm-1,R2-4,A-10,R5-2,R3-1), (nm-1,R2-4,A-10,R4-2,R3-2), (nm-1,R2-4,A-10,R5-3,R3-1), (nm-1,R2-4,A-10,R5-3,R3-2), (nm-1,R2-4,A-11, R5-1,R3-1), (nm-1,R2-4,A-11,R5-R3-2), (nm-1,R2-4,A-11,R5-2,R3-1), (nm-1,R2-4,A-11,R5-2,R3-2), (nm-1,R2-4,A-11, R5-3,R3-1), (nm-1,R2-4,A-11,R5-3,R3-2), (nm-1,R2-4,A-12,R5-1,R3-1), (nm-1,R2-4,A-12,R5-1,R3-2, (nm-1,R2-4,A-12,R5-2,R3-1), (nm-1,R2-4,A-12,R5-2,R3-2), (nm-1,R2-4,A-12,R5-3,R3-1), (nm-1,R2-4,A-12,R5-3,R3-2), (nm-1,R2-4,A-13,R5-1,R31), (nm-1,R2-4,A-13,R5-1,R3-2), (nm-1,R2-4,A-13,R5-2,R3-1), (nm-1,R2-4,A-13,R5-2,R3-2), (nm-1,R2-4,A-13,R5-3,R3-1), (nm-1,R2-4,A-13,R5-3,R3-2), (nm-1,R2-4,A-14,R5-1,R3-1), (nm-1,R2-4,A-14,R5-1,R3-2), (nm-1,R2-4,A-14,R5-2,R3-1), (nm-1,R2-4,A-14,R5-2,R3-2), (nm-1,R2-4,A-14,R5-3,R3-1), (nm-1,R2-4,A-14,R5-3,R3-2), (nm-2,R2-1,A-1,R5-1,R3-1), (nm-2,R2-1,A-1,R5-1,R3-2), (nm-2,R2-1,A-1,R5-2,R3-1), (nm-2,R2-1,A-1,R5-2,R3-2), (nm-2,R2-1,A-1,R5-3,R3-1), (nm-2,R2-1,A-1,R5-3,R3-2), (nm-2,R2-1,A-2,R5-1,R3-1), (nm-2,R2-1,A-2,R5-1,R3-2), (nm-2,R2-1,A-2,R5-2,R3-1), (nm-2,R2-1,A-2,R5-2,R3-2), (nm-2,R2-1,A-2,R5-3,R3-1), (nm-2,R2-1,A-2,R5-3,R3-2), (nm-2,R2-1,A-3,R5-1,R3-1), (nm-2,R2-1,A-3,R5-1,R3-2), (nm-2,R2-1,A-3,R5-2,R3-1), (nm-2,R2-1,A-3,R5-2,R3-2), (nm-2,R2-1,A-3,R5-3,R3-1), (nm-2,R2-1,A-3,R5-3,R3-2), (nm-2,R2-1,A-4,R5-1,R3-1), (nm-2,R2-1,A-4,R5-1,R3-2), (nm-2,R2-1,A-4,R5-2,R3-1), (nm-2,R2-1,A-4,R5-2,R3-2), (nm-2,R2-1,A-4,R5-3,R3-1), (nm-2,R2-1,A-4,R5-3,R3-2), (nm-2,R2-1,A-5,R5-2,R3-2), (nm-2,R2-1,A-5,R5-3,R3-1), (nm-2,R2-1,A-5,R5-3,R3-2), (nm-2,R2-1,A-6,R5-1,R3-1), (nm-2,R2-1,A-6,R5-1,R3-2), (nm-2,R2-1,A-6,R5-2,R3-1), (nm-2,R2-1,A-6,R5-2,R3-2), (nm-2,R2-1,A-6,R5-3,R3-1), (nm-2,R2-1,A-6,R5-3,R3-2), (nm-2,R2-1,A-7,R5-1,R3-1), (nm-2,R2-1,A-7,R5-1,R3-2), (nm-2,R2-1,A-7,R5-2,R3-1), (nm-2,R2-1,A-7,R5-2,R3-2), (nm-2,R2-1,A-7,R5-3,R3-1), (nm-2,R2-1,A-7,R5-3,R3-2), (nm-2,R2-1,A-8,R5-1,R3-1), (nm-2,R2-1,A-8,R5-1,R3-2), (nm-2,R2-1,A-8,R5-2,R3-1), (nm-2,R2-1,A-8,R5-2,R3-2), (nm-2,R2-1,A-8,R5-3,R3-1), (mm-2,R2-1,A-8,R5-3,R3-2), (nm-2,R2-1,A-9,R5-1,R3-1), (nm-2,R2-1,A-9,R5-1,R3-2), (nm-2,R2-1,A-9,R5-2,R3-1), (nm-2,R2-1,A-9,R5-2,R3-2), (nm-2,R2-1,A-9,R5-3,R3-1), (nm-2,R2-1,A-9,R5-3,R3-2), (nm-2,R2-1,A-10,R5-1,R3-1), (nm-2,R2-1,A-10,R5-1,R3-2), (nm-2,R2-1,A-10,R5-2,R3-1), (nm-2,R2-1,A-10,R5-2,R3-2), (nm-2,R2-1,A-10,R5-3,R3-1), (nm-2,R2-1,A-10,R5-3,R3-2), (nm-2,R2-1,A-11,R5-1,R3-1), (nm-2,R2-1,A-11,R5-1,R3-2), (nm-2,R2-1,A-11,R5-2,R3-1), (nm-2,R2-1,A-11,R5-2,R3-2), (nm-2,R2-1,A-11,R5-3,R3-1), (nm-2,R2-1,A-11,R5-3,R3-2), (nm-2,R2-1,A-12,R5-1, R3-1), (nm-2,R2-1,A-12,R5-1,R3-2), (nm-2,R2-1,A-12,R5-2,R3-1), (nm-2,R2-1,A-12,R5-2,R3-2), (nm-2,R2-1,A-12,R5-3,R3-1), (nm-2,R2-1,A-12,R5-3,R3-2), (nm-2,R2-1,A-13,R5-2,R3-2), (nm-2,R2-1,A-13,R5-3,R3-1), (nm-2,R2-1,A-13,R5-3,R3-2), (nm-2,R2-1,A-14; R5-1,R3-1), (nm-2,R2-1,A-14,R5-1,R3-2), (nm-2,R2-1,A-14,R5-2,R3-1), (nm-2,R2-1,A-14,R5-2,R3-2), (nm-2,R2-1,A-14,R5-3,R3-1), (nm-2,R2-1,A-14,R5-3,R3-2), (nm-2,R2-2,A-1,R5-1,R3-1), (nm-2,R2-2,A-1,R5-1,R3-2), (nm-2,R2-2,A-1,R5-2,R3-1), (nm-2,R2-2,A-1,R5-2,R3-2), (nm-2,R2-2,A-1,R5-3,R3-1), (nm-2,R2-2,A-1,R-3,R3-2), (nm-2,R2-2,A-2,R5-1,R3-1), (nm-2,R2-2,A-2,R5-1,R3-2), (nm-2,R2-2,A-2,R-5-2,R3-1), (nm-2,R2-2,A-2,R5-2,R3-2), (nm-2,R2-2,A-2,R5-3,

R3-1), (nm-2,R2-2,A-2,R5-3,R3-2), (nm-2,R2-2,A-3,R5-1, R3-1), (nm-2,R2-2,A-3,R5-1,R3-2), (nm-2,R2-2,A-3,R5-2, R3-1), (nm-2,R2-2,A-3,R5-2,R3-2), (nm-2,R2-2,A-3,R5-3, R3-1), (nm-2,R2-2,A-3,R5-3,R3-2), (nm-2,R2-2,A-4,R5-1, R3-1), (nm-2,R2-2,A-4,R5-1,R3-2), (nm-2,R2-2,A-4,R5-2, R3-1), (nm-2,R2-2,A-4,R5-2,R3-2), (nm-2,R2-2,A-4,R5-3, R3-1), (nm-2,R2-2,A-4,R5-3,R3-2), (nm-2,R2-2,A-5,R5-1, R3-1), (nm-2,R2-2,A-5,R5-1,R3-2), (nm-2,R2-2,A-5,R5-2, R3-1), (nm-2,R2-2,A-5,R5-2,R3-2), (nm-2,R2-2,A-5,R5-3, R3-1), (nm-2,R2-2,A-5,R5-3,R3-2), (nm-2,R2-2,A-6,R5-1, R3-1), (nm-2,R2-2,A-6,R5-1,R3-2), (nm-2,R2-2,A-6,R5-2, R3-1), (nm-2,R2-2,A-6,R5-2,R3-2), (nm-2,R2-2,A-6,R5-3, R3-1), (nm-2,R2-2,A-6,R5-3,R3-2), (nm-2,R2-2,A-7,R5-1, R3-1), (nm-2,R2-2,A-7,R5-1,R3-2), (nm-2,R2-2,A-7,R5-2, R3-1), (nm-2,R2-2,A-7,R5-2,R3-2), (nm-2, R2-2,A-7,R5-3, R3-1), (nm-2,R2-2,A-7,R5-3,R3-2), (nm-2,R2-2,A-8,R5-1, R3-1), (nm-2,R2-2,A-8,R5-1,R3-2), (nm-2,R2-2,A-8,R5-2, R3-1), (nm-2,R2-2,A-8,R5-2,R3-2), (nm-2,R2-2,A-8,R5-3, R3-1), (nm-2,R2-2,A-8,R5-3,R3-2), (nm-2,R2-2,A-9,R5-1, R3-1), (nm-2,R2-2,A-9,R5-1,R3-2), (nm-2,R2-2,A-9,R5-2, R3-1), (nm-2,R2-2,A-9,R5-2,R3-2), (nm-2,R2-2,A-9,R5-3, R3-1), (nm-2,R2-2,A-9,R5-3,R3-2), (nm-2,R2-2,A-10,R5-1, R3-1), (nm-2,R2-2,A-10,R5-1,R3-2), (nm-2,R2-2,A-10,R5-2,R3-1), (nm-2,R2-2,A-10,R5-2,R3-2), (nm-2,R2-2,A-10, R5-3,R3-1), (nm-2,R2-2,A-10,R5-3,R3-2), (nm-2,R2-2,A-11,R5-1,R3-1), (nm-2,R2-2,A-11,R5-1,R3-2), (nm-2,R2-2,A-11,R5-2,R3-1), (nm-2,R2-2,A-11,R5-2,R3-2), (nm-2,R2-2,A-11,R5-3,R3-1), (nm-2,R2-2,A-11,R5-3,R3-2), (nm-2,R2-2,A-12,R5-1,R3-1), (nm-2,R2-2,A-12,R5-1,R3-2), (nm-2,R2-2,A-12,R5-2,R3-1), (nm-2,R2-2,A-12,R5-2,R3-2), (nm-2,R2-2,A-12,R5-3,R3-1), (nm-2,R2-2,A-12,R5-3,R3-2), (nm-2,R2-2,A-13,R5-1,R3-1), (nm-2,R2-2,A-13,R5-1,R3-2), (mm-2,R2-2,A-13,R5-2,R3-1), (nm-2,R2-2,A-13,R5-2,R3-2), (nm-2,R2-2,A-13,R5-3,R3-1), (nm-2,R2-2,A-13,R5-3,R3-2), (nm-2,R2-2,A-14,R5-1,R3-1), (nm-2,R2-2,A-14,R5-1,R3-2), (nm-2,R2-2,A-14,R5-2,R3-1), (nm-2,R2-2,A-14,R5-2,R3-2), (nm-2,R2-2,A-14,R5-3,R3-1), (nm-2,R2-2,A-14,R5-3,R3-2), (nm-2,R2-3,A-1,R5-1,R3-1), (nm-2,R2-3,A-1,R5-1,R3-2), (nm-2,R2-3,A-1,R5-2,R3-1), (nm-2,R2-3,A-1,R5-2,R3-2), (nm-2,R2-3,A-1,R5-3,R3-1), (nm-2,R2-3,A-1,R5-2,R3-1), (nm-2,R2-3,A-2,R5-1, R3-1), (nm-2,R2-3,A-2,R5-1,R3-2), (nm-2,R2-3,A-2,R5-2,R31), (nm-2,R2-3,A-2,R5-2,R3-2), (nm-2,R2-3,A-2,R5-3,R3-1), (nm-2,R2-3,A-2,R5-3,R3-2), (nm-2,R2-3,A-3,R5-1,R3-1), (nm-2,R2-3,A-3,R5-1,R3-2), (nm-2,R2-3,A-3,R5-2,R3-1), (nm-2,R2-3,A-3,R5-2,R3-2), (nm-2,R2-3,A-3,R5-3,R3-1), (nm-2,R2-3,A-3,R-5-3,R3-1), (nm-2,R2-3,A-4,R5-1,R3-2), (nm-2,R2-3,A-4,R5-2,R3-1), (nm-2,R2-3,A-4,R5-2,R3-2), (nm-2,R2-3,A-4,R5-3,R3-1), (nm-2,R2-3,A-4,R5-3,R3-2), (nm-2,R2-3,A-5,R5-1,R3-1), (nm-2,R2-3,A-5,R5-1,R3-2), (nm-2,R2-3,A-5,R5-2,R3-1), (nm-2,R2-3,A-5,R5-2,R3-2), (nm-2,R2-3,A-5,R5-3,R3-1), (nm-2,R2-3,A-5,R5-3,R3-2), (nm-2,R2-3,A-6,R5-1,R3-1), (nm-2,R2-3,A-6,R5-1,R3-2), (nm-2,R2-3,A-6,R5-2,R3-1), (nm-2,R2-3,A-6,R5-2,R3-2), (nm-2,R2-3,A-6,R5-3,R3-1), (nm-2,R2-3,A-6,R5-3,R3-2), (nm-2,R2-3,A-7,R5-1,R3-1), (nm-2,R2-3,A-7,R5-1,R3-2), (nm-2,R2-3,A-7,R5-2,R3-1), (nm-2,R2-3,A-7,R5-2,R3-2), (nm-2,R2-3,A-7,R5-3,R3-1), (nm-2,R2-3,A-7,R5-3,R3-2), (nm-2,R2-3,A-8,R5-1,R3-1), (nm-2,R2-3,A-8,R5-1,R3-2), (nm-2,R2-3,A-8,R5-2,R3-1), (nm-2,R2-3,A-8,R5-2,R3-2), (nm-2,R2-3,A-8,R5-3,R3-1), (nm-2,R2-3,A-8,R5-3,R3-2), (nm-2,R2-3,A-9,R5-1,R3-1), (nm-2,R2-3,A-9,R5-1,R3-2), (nm-2,R2-3,A-9,R5-2,R3-1), (nm-2,R2-3,A-9,R5-2,R3-2), (nm-2,R2-3,A-9,R5-3,R3-1), (nm-2,R2-3,A-9,R5-3,R3-2), (nm-2,R2-3,A-10,R5-1,R3-1), (nm-2,R2-3,A-10,R5-1,R3-2), (nm-2,R2-3,A-10,R5-2,R3-1), (nm-2,R2-3,A-10,R5-2,R3-2), (nm-2,R2-3,A-10,R5-3,R3-1), (nm-2,R2-3,A-10,R5-3,R3-2), (nm-2,R2-3,A-11,R5-1,R3-1), (nm-2,R2-3,A-11,R5-1,R3-2), (nm-2,R2-3,A-11,R5-2,R3-1), (nm-2,R2-3,A-11,R5-2,R3-2), (nm-2,R2-3,A-11,R5-3,R3-1), (nm-2,R2-3,A-11,R5-3,R3-2), (nm-2,R2-3,A 12,R5-1,R3-1), (nm-2,R2-3,A 12,R5-1,R3-2), (nm-2,R2-3,A-12,R5-2,R3-1), (nm-2,R2-3,A-12,R5-2,R3-2), (nm-2,R2-3,A-12,R5-3,R3-1), (nm-2,R2-3,A-12,R5-3,R3-2), (nm-2,R2-3,A-13,R5-1,R3-1), (nm-2,R2-3,A-13,R5-1,R3-2), (nm-2,R2-3,A-13,R5-2,R3-1), (nm-2,R2-3,A-13,R5-2,R3-2), (nm-2,R2-3,A-13,R5-3,R3-1), (nm-2,R2-3,A-13,R5-3,R3-2), (nm-2,R2-3,A-14,R5-1,R3-1), (nm-2,R2-3,A-14,R5-1,R3-2), (nm-2,R2-3,A-14,R5-2,R3-1), (nm-2,R2-3,A-14,R5-2,R3-2), (nm-2,R2-3,A-14,R5-3,R3-1), (nm-2,R2-3,A-14,R5-3,R3-2), (nm-2,R2-4,A 1,R5-1,R3-1), (nm-2,R2-4,A-1,R5-1,R3-2), (nm-2,R2-4,A-1,R5-2,R3-1), (nm-2,R2-4,A-1,R5-2,R3-2), (nm-2,R2-4,A-1,R5-3,R3-1), (nm-2,R2-4,A-1,R5-3,R3-2), (nm-2,R2-4,A-2,R5-1,R3-1), (nm-2,R2-4,A-2,R5-1,R3-2), (nm-2,R2-4,A-2,R5-2,R3-1), (nm-2,R2-4,A-2,R5-2,R3-2), (nm-2,R2-4,A-2,R5-3,R3-1), (nm-2,R2-4,A-2,R5-3,R3-2), (nm 2,R2-4,A-3,R5-1,R3-1), (nm-2,R2-4,A-3,R5-1,R3-2), (nm-2,R2-4,A-3,R5-2,R3-1), (nm-2,R2-4,A-3,R5-2,R3-2), (nm-2,R2-4,A-3,R5-3,R3-1), (nm-2,R2-4,A-3,R5-3,R3-2), (nm-2,R2-4,A-4,R5-1,R3-1), (nm-2,R2-4,A-4,R5-1,R3-2), (nm-2,R2-4,A-4,R5-2,R3-1), (nm-2,R2-4,A-4,R5-2,R3-2), (nm-2,R2-4,A-4,R5-3,R3-1), (nm-2,R2-4,A-4,R5-3,R3-2), (nm-2,R2-4,A-5,R5-1,R3-1), (nm-2,R2-4,A-5,R5-1,R3-2), (nm-2,R2-4,A-5,R5-2,R3-1), (nm-2,R2-4,A-5,R5-2,R3-2), (nm-2,R2-4,A-5,R5-3,R3-1), (nm-2,R2-4,A-5,R5-3,R3-2), (nm-2,R2-4,A-6,R5-1,R3-1), (nm-2,R2-4,A-6,R5-1,R3-2), (nm-2,R2-4,A-6,R5-2,R3-1), (nm-2,R2-4,A-6,R5-2,R3-2), (nm-2,R2-4,A-6, R5-3,R3-1), (nm-2,R2-4,A-6,R5-3,R3-2), (nm-2,R2-4,A-7,R5-1,R3-1), (nm-2,R2-4,A-7,R5-1,R3-2), (nm-2,R2-4,A-7,R5-2,R3-1), (nm-2,R2-4,A-7,R5-2,R3-2), (nm-2,R2-4,A-7,R5-3,R3-1), (nm-2,R2-4,A-7,R5-3,R3-2), (nm-2,R2-4,A-8,R5-1,R3-1), (nm-2,R2-4,A-8,R5-1,R3-2), (nm-2,R2-4,A-8,R5-2,R3-1), (nm-2,R2-4,A-8,R5-2,R3-2), (nm-2,R2-4,A-8,R5-3,R3-1), (nm-2,R2-4,A-8,R5-3,R3-2), (nm-2,R2-4,A-9,R5-1,R3-1), (nm-2,R2-4,A-9,R5-1,R3-2), (nm-2,R2-4,A-9,R5-2,R3-1), (nm-2,R2-4,A-9,R5-2,R3-2), (nm-2,R2-4,A-9,R5-3,R3-1), (nm-2,R2-4,A-9,R5-3,R3-2), (nm-2,R2-4,A-10,R5-1,R3-1), (nm-2,R2-4,A-10,R5-1,R3-2), (nm-2,R2-4,A-10,R5-2,R3-1), (nm-2,R2-4,A-10,R5-2,R3-2), (nm-2,R2-4,A-10,R5-3,R3-1), (nm-2,R2-4,A-10,R5-3,R3-2), (nm-2,R2-4,A-11,R5-1,R3-1), (nm-2,R2-4,A-11,R5-1,R3-2), (nm-2,R2-4,A-11,R5-2,R3-1), (nm-2,R2-4,A-11,R5-2,R3-2), (nm-2,R2-4,A-11,R5-3,R3-1), (nm-2,R2-4,A-11,R5-3,R3-2), (nm-2,R2-4,A-12,R5-1,R3-1), (nm-2,R2-4,A-12,R5-1,R3-2), (nm-2,R2-4,A-12,R5-2,R3-1), (nm-2,R2-4,A-12,R5-2,R3-2), (nm-2,R2-4,A-12,R5-3,R3-1), (nm-2,R2-4,A-12,R5-3,R3-2), (nm-2,R2-4,A-13,R5-1,R3-1), (nm-2,R2-4,A-13,R5-1,R3-2), (nm-2,R2-4,A-13,R5-2,R3-1), (nm-2,R2-4,A-13,R5-2,R3-2), (nm-2,R2-4,A-13,R5-3,R3-1), (nm-2,R2-4,A-13,R5-3,R3-2), (nm-2,R2-4,A-14,R5-1,R31), (nm-2,R2-4,A-14,R5-1,R3-2), (nm-2,R2-4,A-14,R5-2,R3-1), (nm-2,R2-4,A-14,R5-2,R3-2), (nm-2,R2-4,A-14,R5-3,R3-1), (nm-2,R2-4,A-14,R5-3,R3-2), (nm-3,R2-1,A-1,R5-1,R3-1), (nm-3,R2-1,A-1,R5-1,R3-2), (nm-3,R2-1,A-1,R5-2,R3-1), (nm-3,R2-1,A-1,R5-2,R3-2), (nm-3,R2-1,A-1,R5-3,R3-1), (nm-3,R2-1,A-1,R5-3,R3-2), (nm-3,R2-1,A-2,R5-1,R3-1), (nm-3,R2-1,A-2,R5-1,R3-2), (nm-3,R2-1,A-2,R5-2,R3-1), (nm-3,R2-1,A-2,R5-2,R3-2), (nm-3,R2-1,A-2,R5-3,R3-1), (nm-3,R2-1,A-2,R5-3,R3-2), (nm-3,R2-1,A-3,R5-1,R3-1), (nm-3,R2-1,A-3,R5-1,R3-2), (nm-3,R2-1,A-3,R5-2,R3-1), (nm-3,R2-1,A-3,R5-2,R3-2), (nm-3,R2-1,A-3,R5-3,R3-1), (nm-3,R2-1,A-3,R5-3,R3-2), (nm-3,R2-1,A-4,R5-1,R3-1), (nm-3,R2-1,A-4,R5-1,R3-2), (nm-3,R2-1,A-4,R5-2,R3-1), (nm-3,R2-1,A-4,R5-2,R3-2), (nm-3,R2-1,A-4,R5-3,R3-1), (nm-3,R2-1,A-4,R5-3,R3-2), (nm-3,R2-1,A-5,R5-1,R3-1), (nm-3,R2-1,A-5,R5-1,R3-2), (nm-3,R2-1,A-6,R5-2,R3-1), (nm-3,R2-1,A-5,R5-2,R3-2), (nm-3,R2-1,A-5,R5-3,R3-1), (nm-3,R2-1,A-5,R5-3,R3-2), (nm-3,R2-1,A-6,R5-1,R3-1), (nm-3,R2-1,A-6,R5-1,R3-2), (nm-3,R2-1,A-6,R5-2,R3-1), (nm-3,R2-1,A-6,R5-2,R3-2), (nm-3,R2-1,A-6,R5-3,R3-1), (nm-3,R2-1,A-6,R5-3,R3-2), (nm-3,R2-1,A-7,R5-1,R3-1), (nm-3,R2-1,A-7,R5-1,R3-2), (nm-3,R2-1,A-7,R5-2,R3-1), (nm-3,R2-1,A-7,R5-2,R3-2), (nm-3,R2-1,A-7,R5-3,R3-1), (nm-3,R2-1,A-7,R5-3,R3-2), (nm-3,R2-1,A-8,R5-1,R3-1), (nm-3,R2-1,A-8,R5-1,R3-2), (nm-3,R2-1,A-8,R5-2,R3-1), (nm-3,R2-1,A-8,R5-2,R3-2), (nm-3,R2-1,A-8,R5-3,R3-1), (nm-3,R2-1,A-8,R5-3,R3-2, (nm-3,R2-1,A-9,R5-1,R3-1), (nm-3,R2-1,A-9,R5-1,R3-2), (nm-3,R2-1,A-9,R5-2,R3-1), (nm-3,R2-1,A-9,R5-2,R3-2), (nm-3,R2-1,A-9,R5-3,R3-1), (nm-3,R2-1,A-9,R5-3,R3-2), (nm-3,R2-1,A-10,R-1,R3-1), (nm-3,R2-1,A-10,R5-1,R3-2), (nm-3,R2-1,A-10,R5-2,R3-1), (nm-3,R2-1,A-10,R5-2,R3-2), (nm-3,R2-1,A-10,R5-3,R3-1), (nm-3,R2-1,A-10,R5-3,R3-2), (nm-3,R2-1,A-11,R5-1,R3-1), (nm-3,R2-1,A-11,R5-1,R3-2), (nm-3,R2-1,A-11,R5-2,R3-1), (nm-3,R2-1,A-11,R5-2,R3-2), (nm-3,R2-1,A-11,R5-3,R3-1), (nm-3,R2-1,A-11,R5-3,R3-2), (nm-3,R2-1,A-12,R5-1,R3-1), (nm-3,R2-1,A-12,R5-1,R3-2), (nm-3,R2-1,A-12,R5-2,R3-1), (nm-3,R2-1,A-12,R5-2,R3-2), (nm-3,R2-1,A-12,R5-3,R3-1), (nm-3,R2-1,A-12,R5-3,R3-2), (nm-3,R2-1,A-13,R5-1,R3-1), (nm-3,R2-1,A-13,R5-1,R3-2), (nm-3,R2-1,A-13,R5-2,R3-1), (nm-3,R2-1,A-13,R5-2,R3-2), (nm-3,R2-1,A-13,R5-3,R3-1), (nm-3,R2-1,A-13,R5-3,R3-2), (nm-3,R2-1,A-14,R5-1,R3-1), (nm-3,R2-1,A-14,R5-1,R3-2), (nm-3,R2-1,A-14,R5-2,R3-1), (nm-3,R2-1,A-14,R5-2,R3-2), (nm-3,R2-1,A-14,R5-3,R3-1), (nm-3,R2-1,A-14,R5-3,R3-2), (nm-3,R2-2,A-1,R5-1,R3-1), (nm-3,R2-2,A-1,R5-1,R3-2), (nm-3,R2-2,A-1,R5-2,R31), (nm-3,R2-2,A-1,R5-2,R3-2), (nm-3,R2-2,A-1,R5-3,R3-1), (nm-3,R2-2,A-1,R5-3,R3-2), (nm-3,R2-2,A-2,R5-1,R3-1), (nm-3,R2-2,A-2,R5-1,R3-2), (nm-3,R2-2,A-2,R5-2,R3-1), (nm-3,R2-2,A-2,R5-2,R3-2, (nm-3,R2-2,A-2,R5-3,R3-1), (nm-3,R2-2,A-2,R5-3,R3-2), (nm-3,R2-2,A-3,R5-1,R3-1), (nm-3,R2-2,A-3,R5-1,R3-2), (nm-3,R2-2,A-3,R5-2,R3-1), (nm-3,R2-2,A-3,R5-2,R3-2), (nm-3,R2-2,A-3,R5-3,R3-1), (nm-3,R2-2,A-3,R5-3,R3-2), (nm-3,R2-2,A-4,R5-1,R3-1), (nm-3,R2-2,A-4,R5-1,R3-2), (nm-3,R2-2,A-4,R5-2,R3-1), (nm-3,R2-2,A-4,R5-2,R3-2), (nm-3,R2-2,A-4,R5-3,R3-1), (nm-3,R2-2,A-4,R5-3,R3-2), (nm-3,R2-2,A-5,R5-1,R3-1), (nm-3,R2-2,A-5,R5-1,R3-2), (nm-3,R2-2,A-5,R5-2,R31), (nm-3,R2-2,A-5,R5-2,R3-2), (nm-3,R2-2,A-5,R5-3,R3-1), (nm-3,R2-2,A-5,R5-3,R3-2), (nm-3,R2-2,A-6,R5-1,R3-1), (nm-3,R2-2,A-6,R5-1,R3-2), (nm-3,R2-2,A-6,R5-2,R3-1), (nm-3,R2-2,A-6,R5-2,R3-2), (nm-3,R2-2,A-6,R5-3,R3-1), (nm-3,R2-2,A-6,R5-3,R3-2), (nm-3,R2-2,A-7,R5-1,R3-1), (nm-3,R2-2,A-7,R5-1,R3-2), (nm-3,R2-2,A-7,R5-2,R3-1), (nm-3,R2-2,A-7,R5-2,R3-2), (nm-3,R2-2,A-7,R5-3,R3-1), (nm-3,R2-2,A-7,R5-3,R3-2), (nm-3,R2-2,A-8,R5-1,R3-1), (nm-3,R2-2,A-8,R5-1,R3-2), (nm-3,R2-2,A-8,R5-2,R3-1), (nm-3,R2-2,A-8,R5-2,R3-2), (nm-3,R2-2,A-8,R5-3,R3-1), (nm-3,R2-2,A-8,R5-3,R3-2), (nm-3,R2-2,A-9,R5-1,R3-1), (nm-3,R2-2,A-9,R5-1,R3-2), (nm-3,R2-2,A-9,R5-2,R3-1), (nm-3,R2-2,A-9,R5-2,R3-2), (nm-3,R2-2,A-9,R5-3,R3-1), (nm-3,R2-2,A-9,R5-3,R3-2), (nm-3,R2-2,A-10,R5-1,R3-1), (nm-3,R2-2,A-10,R5-1,R3-2), (nm-3,R2-2,A-10,R5-2,R3-1), (nm-3,R2-2,A-10,R5-2,R3-2), (nm-3,R2-2,A-10,R5-3,R3-1), (nm-3,R2-2,A-10,R5-3,R3-2), (nm-3,R2-2,A-11,R5-1,R3-1), (nm-3,R2-2,A-11,R5-1,R3-2), (nm-3,R2-2,A-11,R5-2,R3-1), (nm-3,R2-2,A-11,R5-2,R3-2), (nm-3,R2-2,A-11,R5-3,R3-1), (nm-3,R2-2,A-11,R5-3,R3-2), (nm-3,R2-2,A-12,R5-1,R3-1), (nm-3,R2-2,A-12,R5-1,R3-2), (nm-3,R2-2,A-12,R5-2,R3-1), (nm-3,R2-2,A-12,R5-2,R3-2), (nm-3,R2-2,A-12,R5-3,R3-1), (nm-3,R2-2,A-12,R5-3,R3-2), (nm-3,R2-2,A-13,R5-1,R3-1), (nm-3,R2-2,A-13,R5-1,R3-2), (nm-3,R2-2,A-13,R5-2,R3-1), (nm-3,R2-2,A-13,R5-2,R3-2), (nm-3,R2-2,A-13,R5-3,R3-1), (nm-3,R2-2,A-13,R5-3,R3-2), (nm-3,R2-2,A-14,R5-1,R3-1), (nm-3,R2-2,A-14,R5-1,R3-2), (nm-3,R2-2,A-14,R5-2,R3-1), (nm-3,R2-2,A-14,R5-2,R3-2), (nm-3,R2-2,A-14,R5-3,R3-1), (nm-3,R2-2,A-14,R5-3,R3-2), (nm-3,R2-3,A-1,R5-1,R3-1), (nm-3,R2-3,A-1,R5-1,R3-2), (nm-3,R2-3,A-1,R5-2,R3-1), (nm-3,R2-3,A-1,R5-2,R3-2), (nm-3,R2-3,A-1,R5-3,R3-1), (nm-3,R2-3,A-1,R5-3,R3-2), (nm-3,R2-3,A-2,R5-1,R3-1), (nm-3,R2-3,A-2,R5-1,R3-2), (nm-3,R2-3,A-2,R5-2,R3-1), (nm-3,R2-3,A-2,R5-2,R3-2), (nm-3,R2-3,A-2,R5-3,R3-1), (nm-3,R2-3,A-2,R5-3,R3-2), (nm-3,R2-3,A-3,R5-1,R3-1), (nm-3,R2-3,A-3,R5-1,R3-2), (nm-3,R2-3,A-3,R5-2,R3-1), (nm-3,R2-3,A-3,R5-2,R3-2), (nm-3,R2-3,A-3,R5-3,R3-1), (nm-3,R2-3,A-3,R5-3,R3-2), (nm-3,R2-3,A-4,R5-1,R3-1), (nm-3,R2-3,A-4,R5-1,R3-2), (nm-3,R2-3,A-4,R5-2,R3-1), (nm-3,R2-3,A-4,R5-2,R3-2), (nm-3,R2-3,A-4,R5-3,R3-1), (nm-3,R2-3,A-4,R5-3,R3-2), (nm-3,R2-3,A-5,R5-1,R3-1), (nm-3,R2-3,A-5,R5-1,R3-2), (nm-3,R2-3,A-5,R5-2,R3-1), (nm-3,R2-3,A5,R5-2,R3-2), (nm-3,R2-3,A-5,R5-3,R3-1), (nm-3,R2-3,A-5,R5-3,R3-2), (nm-3,R2-3,A-6,R5-1,R3-1), (nm-3,R2-3,A-6,R5-1,R3-2), (nm-3,R2-3,A-6,R5-2,R3-1), (nm-3,R2-3,A-6,R5-2,R3-2), (nm-3,R2-3,A-6,R5-3,R3-1), (nm-3,R2-3,A-6,R5-3,R3-2), (nm-3,R2-3,A-7,R5-1,R3-1), (nm-3,R2-3,A-7,R5-1,R3-2), (nm-3,R2-3,A-7,R5-2,R3-1), (nm-3,R2-3,A-7,R5-2,R3-2), (nm-3,R2-3,A-7,R5-3,R3-1), (nm-3,R2-3,A-7,R5-3,R3-2), (nm-3,R2-3,A-8,R5-1,R3-1), (nm-3,R2-3,A-8,R5-1,R3-2), (nm-3,R2-3,A-8,R5-2,R3-1), (nm-3,R2-3,A-8,R5-2,R3-2), (nm-3,R2-3,A-8,R5-3,R3-1), (nm-3,R2-3,A-8,R5-3,R3-2), (nm-3,R2-3,A-9,R5-1,R3-1), (nm-3,R2-3,A-9,R5-1,R3-2), (nm-3,R2-3,A-9,R5-2,R3-1), (nm-3,R2-3,A-9,R5-2,R3-2), (nm-3,R2-3,A-9,R5-3,R3-1), (nm-3,R2-3,A-9,R5-3,R3-2), (nm-3,R2-3,A-10,R5-1,R3-1), (nm-3,R2-3,A-10,R5-1,R3-2), (nm-3,R2-3,A-10,R5-2,R3-1), (nm-3,R2-3,A-10,R5-2,R3-2), (nm-3,R2-3,A-10,R5-3,R3-1), (nm-3,R2-3,A-10,R5-3,R3-2), (nm-3,R2-3,A-11,R5-1,R3-1), (nm-3,R2-3,A-11,R5-1,R3-2), (nm-3,R2-3,A-11,R5-2,R3-1), (nm-3,R2-3,A-11,R5-2,R3-2), (nm-3,R2-3,A-11,R5-3,R3-1), (nm-3,R2-3,A-11,R5-3,R3-2), (nm-3,R2-3,A-12,R5-1,R3-1), (nm-3,R2-3,A-12,R5-1,R3-2), (nm-3,R2-3,A-12,R5-2,R3-1), (nm-3,R2-3,A-12,R5-2,R3-2), (nm-3,R2-3,A-12,R5-3,R3-1), (nm-3,R2-3,A-12,R5-3,R3-2), (nm-3,R2-3,A-13,R5-1,R3-1), (nm-3,R2-3,A-13,R5-1,R3-2), (nm-3,R2-3,A-13,R5-2,R3-1), (nm-3,R2-3,A-13,R5-2,R3-2), (nm-3,R2-3,A-13,R5-3,R3-1), (nm-3,R2-3,A-13,R5-3,R3-2), (nm-3,R2-3,A-14,R5-1,R3-1), (nm-3,R2-3,A-14,R5-1,R3-2), (nm-3,R2-3,A-14,R5-2,R3-1), (nm-3,R2-3,A-14,R5-2,R3-2), (nm-3,R2-3,A-14,R5-3,R3-1), (nm-3,R2-3,A-14,R5-3,R3-2), (nm-3,R2-4,A-1,R5-1,R3-1), (nm-3,R2-4,A-1,R5-1,R32), (nm-3,R2-4,A-1,R5-2,R3-1), (nm-3,R2-4,A-1,R5-2,R3-2), (nm-3,R2-4,A-1,R5-3,R3-1), (nm-3,R2-4,A-1,R5-3,R3-2), (nm-3,R2-4,A-2,R5-1,R3-1), (nm-3,R2-4,A-2,R5-1,R3-2), (nm-3,R2-4,A-2,R5-2,R3-1), (nm-3,R2-4,A-2,R5-2,R3-2), (nm-3,R2-4,A-2,R5-3,R3-1), (nm-3,R2-4,A-2,R5-3,R3-2), (nm-3,R2-4,A-3,R5-1,R3-1), (nm-3,R2-4,A-3,R5-1,R3-2), (nm-3,R2-4,A-3,R5-2,R3-1), (nm-3,R2-4,A-3,R5-2,R3-2), (nm-3,R2-4,A-3,R5-3,R3-1), (nm-3,R2-4,A-3,R5-3,R3-2), (nm-3,R2-4,A-4,R5-1,R3-1), (nm-3,R2-4,A-4,R5-1,R3-2), (nm-3,R2-4,A-4,R5-2,R3-1), (nm-3,R2-4,A-4,R5-2,R3-2), (nm-3,R2-4,A-4,R5-3,R3-1), (nm-3,R2-4,A-4,R5-3,R3-2), (nm-3,R2-4,A-6,R5-1,R3-1), (nm-3,R2-4,A-5,R5-1,R3-2), (nm-3,R2-4,A-5,R5-2,R3-1), (nm-3,R2-4,A-5,R5-2,R3-2), (nm-3,R2-4,A-5,R5-3,R3-1), (nm-3,R2-4,A-5,R5-3,R3-2), (nm-3,R2-4,A-6,R5-1,R31), (nm-3,R2-4,A-6,R5-1,R3-2), (nm-3,R2-4,A-6,R5-2,R3-1), (nm-3,R2-4,A-6,R5-2,

R3-2), (nm-3,R2-4,A-6,R5-3,R3-1), (nm-3,R2-4,A-6,R5-3, R3-2), (nm-3,R2-4,A-7,R5-1,R3-1), (nm-3,R2-4,A-7,R5-1, R3-2), (nm-3,R2-4,A-7,R5-2,R3-1), (nm-3,R2-4,A-7,R5-2, R3-2), (nm-3,R2-4,A-7,R5-3,R3-1), (nm-3,R2-4,A-7,R5-3, R3-2), (nm-3,R2-4,A-8,R5-1,R3-1), (nm-3,R2-4,A-8,R5-1, R3-2), (nm-3,R2-4,A-8,R5-2,R3-1), (nm-3,R2-4,A-8,R5-2, R3-2), (nm-3,R2-4,A-8,R5-3,R3-1), (nm-3,R2-4,A-8,R5-3, R3-2), (nm-3,R2-4,A-9,R5-1,R3-1), (nm-3,R2-4,A-9,R5-1, R3-2), (nm-3,R2-4,A-9,R5-2,R3-1), (nm-3,R2-4,A-9,R5-2, R3-2), (nm-3,R2-4,A-9,R5-3,R3-1), (nm-3,R2-4,A-9,R5-3, R3-2), (nm-3,R2-4,A-10,R5-1,R3-1), (nm-3,R2-4,A-10,R5-1,R3-2), (nm-3,R2-4,A-10,R5-2,R3-1), (nm-3,R2-4,A-10,R5-2,R3-2), (nm-3,R2-4,A-10,R5-3,R3-1), (nm-3,R2-4,A-10,R5-3,R3-2), (nm-3,R2-4,A-11,R5-1,R3-1), (nm-3,R2-4,A-11,R5-1,R3-2), (nm-3,R2-4,A-11,R5-2,R3-1), (nm-3,R2-4,A-11,R5-2,R3-2), (nm-3,R2-4,A-11,R5-3,R3-1), (nm-3,R2-4,A-11,R5-3,R3-2), (nm-3,R2-4,A-12,R5-1,R3-1), (nm-3,R2-4,A-12,R5-1,R3-2), (nm-3,R2-4,A-12,R5-2,R3-1), (nm-3,R2-4,A-12,R5-2,R3-2), (nm-3,R2-4,A-12,R5-3,R3-1), (nm-3,R2-4,A-12,R5-3,R3-2), (nm-3,R2-4,A-13,R5-1,R3-1), (nm-3,R2-4,A-13,R5-1,R3-2), (nm-3,R2-4,A-13,R5-2,R3-1), (nm-3,R2-4,A-13,R5-2,R3-2), (nm-3,R2-4,A-13,R5-3,R3-1), (nm-3,R2-4,A-13,R5-3,R3-2), (nm-3,R2-4,A-14,R5-1,R3-1), (nm-3,R2-4,A-14,R5-1,R3-2), (nm-3,R2-4,A-14,R5-2,R3-1), (nm-3,R2-4,A-14,R5-2,R3-2), (nm-3,R2-4,A-14,R5-3,R3-1), (nm-3,R2-4,A-14,R5-3,R3-2), (nm-3,R2-4,A-14,R5-3,R3-3).

In a compound represented by the general formula (I'), a compound, wherein the combination of n, m, $R^{2a}$, $R^{2b}$, ring A, $R^5$, $R^{3a}$, and $R^{3b}$ (m, $R^2$, A, $R^5$, $R^3$) is one of the above compound, and E is a bond.

The compounds of the invention can be employed in the treatment and/or prevention of disease associated with the generation, secretion or deposition of β-amyloid protein, such as dementia of the Alzheimer's type (Alzheimer's disease, senile dementia of Alzheimer type), Down's syndrome, memory impairment, prion disease (Creutzfeldt-Jakob disease), mild cognitive impairment (MCI), Dutch type of hereditary cerebral hemorrhage with amyloidosis, cerebral amyloid angiopathy, other type of degenerative dementia, mixed dementia with Alzheimer's and vascular type, dementia with Parkinson's Disease, dementia with progressive supranuclear palsy, dementia with Cortico-basal degeneration, Alzheimer's disease with diffuse Lewy body disease, age-related macular degeneration, Parkinson's Disease, amyloid angiopathy and so on.

The compounds of the invention can be administered in combination with other pharmaceutical agents such as other therapeutic drugs for Alzheimer's disease, acetylcholinesterase inhibitors and so on. The compounds of the invention can be treated with concomitantly with the anti-dementia agents such as Donepezil Hydrochloride, Tacrine, Galantamine, Rivastigmine, Zanapezil, Memantine, Vinpocetine.

When the present compound is administered to a human, it can be administered orally as powders, granules, tablets, capsules, pills, solutions, or the like, or parenterally as injectables, suppositories, transdermal absorbable agents, absorbable agents, or the like. In addition, the present compound can be formulated into pharmaceutical preparations by adding pharmaceutical additives such as excipients, binders, wetting agents, disintegrating agents, lubricants and the like, which are suitable for formulations and an effective amount of the present compound.

A dose is different depending on state of disease, an administration route, and an age and a weight of a patient, and is usually 0.1 μg to 1 g/day, preferably 0.01 to 200 mg/day when orally administered to an adult, and is usually 0.1 μg to 10 g/day, preferably 0.1 to 2 g/day when parenterally administered.

Following examples and test examples illustrate the present invention in more detail, but the present invention is not limited by these examples.

In example, the meaning of each abbreviation is following.

Me methyl

Et ethyl iPr or $Pr^i$ isopropyl

Ph phenyl

Bn benzyl

Boc t-butoxycarbonyl

TBDPS t-butyldiphenylsilyl

Example 1

The Synthesis of Compound 588

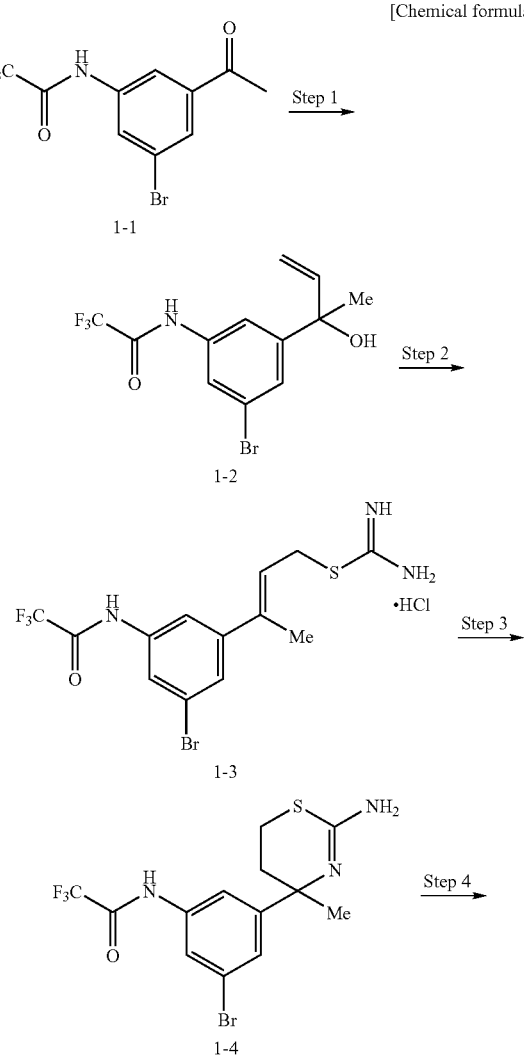

[Chemical formula 48]

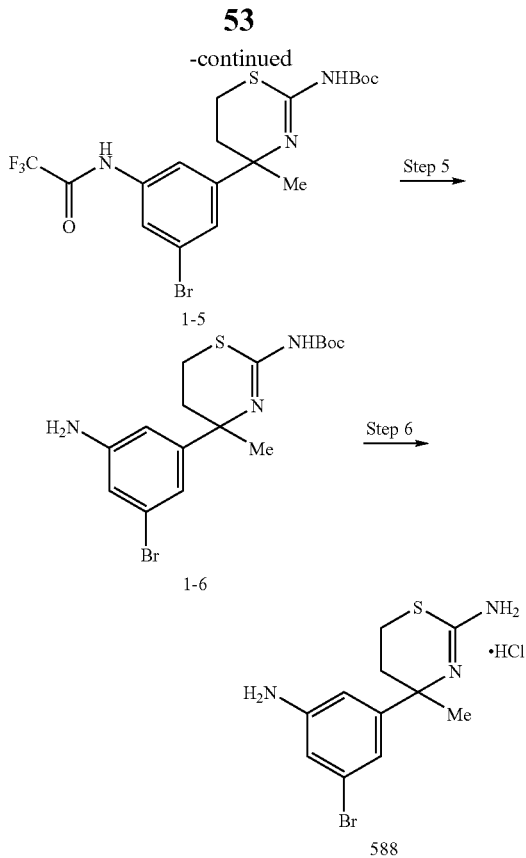

Step 1

Under nitrogen atmosphere, the compound (1-1)(7.98 g) was dissolved into diethyl ether (330 ml)-tetrahydrofuran (36 ml), vinylmagnesium chloride in tetrahydrofuran solution (1.32 mol/L, 44.8 ml) was added under cooling with dryice-acetone bath, and stirred for 20 min. Then, the reaction solution was stirred for 30 min under cooling with ice-water bath and stirred for 35 min at room temperature. And then, saturated ammonium chloride solution was added to the mixture, the mixture was extracted with ethyl acetate, and organic layer was washed with saturated ammonium chloride solution, saturated sodium hydrogencarbonate solution, and brine, and dried over anhydrous magnesium sulfate, and the solvent was evaporated. Then, the residue was purified by silica gel column chromatography to afford the compound (I-2)(6.00 g).

$^1$H-NMR (CDCl$_3$): 1.63 (3H, s), 2.08 (1H, br), 5.20 (1H, dd, J=10.6, 1.6 Hz), 5.31 (1H, dd, J=17.1, 1.6 Hz), 6.09 (1H, m), 7.46 (1H, m), 7.62 (1H, dd, J=3.4, 2.6 Hz), 7.80 (1H, dd, J=3.9, 2.6 Hz), 8.06 (1H, br)

Step 2

The compound (1-2)(6.36 g) was dissolved into acetic acid (30 ml), and added thiourea (1.50 g), 1 mol/L hydrochloride-acetic acid solution (20.7 ml). The reaction mixture was stirred at room temperature for 3 hours, then stirred at 40° C. for 3 hours, then stirred at room temperature for 66 hours, and at 40° C. for 19 hours. Thiourea (0.450 g), and 1 mol/L hydrochloric acid-acetic acid solution (7.53 ml) was added, and stirred at 40° C. for 23 hours. After the consumption of the compound (1-2), the solvent was evaporated under reduced pressure, then the obtained residue was crystallized from methanol-diethyl ether to afford the compound (I-3)(5.23 g) as crystal. On the other hand, mother liquid was evaporated under reduced pressure, and the compound (I-3)(3.00 g) was obtained as crude solid product.

$^1$H-NMR (DMSO-d$_6$): 2.09 (3H, s), 4.10 (2H, d, J=7.3 Hz), 5.94 (1H, t, J=7.7 Hz), 7.50 (1H, s), 7.75 (1H, s), 7.87 (1H, s), 9.17 (3H, br), 11.46 (1H, s)

Step 3

The compound (1-3)(5.23 g) dissolved in trifluoroacetic acid (26 ml) was added methanesulfonic acid (2.14 ml) dropwise under cooling with ice-water bath. After addition, the reaction mixture was stirred at room temperature for 3.5 hours. After the consumption of the compound (1-3), the solvent was evaporated under reduced pressure. To the residue obtained was added water and sodium carbonate, and then extracted with ethyl acetate. The organic layer was washed with saturated sodium hydrogencarbonate solution, and was dried over anhydrous magnesium sulfate, and the solvent was evaporated under reduced pressure to afford the compound (1-4)(4.90 g) as crude product.

$^1$H-NMR (CDCl$_3$): 1.53 (3H, s), 1.90 (1H, m), 2.09 (1H, m), 2.74 (1H, m), 2.97 (1H, m), 4.32 (2H, br), 7.34 (1H, t, J=1.6 Hz), 7.37 (1H, t, J=1.8 Hz), 7.86 (1H, t, J=1.8 Hz)

Step 4

Under nitrogen atmosphere, the compound (I-4)(4.90 g) dissolved in tetrahydrofuran was added di-t-butyl-dicarbonate (2.97 g) and triethylamine (1.89 ml) under cooling with ice-water bath and then stirred for 2 hours. The reaction mixture was stirred at room temperature for 3 hours. The reaction mixture was added water, and then extracted with ethyl acetate. The organic layer was washed with water, and dried over anhydrous magnesium sulfate, then the solvent was evaporated under reduced pressure. Then the obtained residue was crystalized from ethyl acetate-diethyl ether to afford the compound (I-5)(4.62 g) as crystal.

$^1$H-NMR (CDCl$_3$): 1.36 (9H, s), 1.72 (3H, s), 2.10 (1H, m), 2.41 (1H, m), 2.62 (1H, m), 2.75 (1H, m), 7.22 (1H, s), 7.48 (1H, s), 8.29 (1H, s)

Step 5

The compound (1-6)(1.00 g) was dissolved into tetrahydrofuran (8.7 ml), and 1 mol/L lithium hydroxide (4.43 ml) was added and stirred at 50° C. for 4 hours. Water was added to the reaction mixture, and the mixture was extracted with ethyl acetate, and the organic layer was washed with water, brine successively, and dried over anhydrous magnesium sulfate, and the solution was evaporated under reduced pressure. The obtained residue was purified by medium-pressured silica gel column chromatography to afford the compound (I-6)(0.668 g).

$^1$H-NMR (CDCl$_3$): 1.51 (9H, s), 1.63 (3H, s), 2.06 (1H, m), 2.40 (1H, m), 2.68-2.74 (2H, m), 3.83 (2H, br), 6.51 (1H, t, J=1.8 Hz), 6.72-6.74 (2H, m)

Step 6

The compound (1-6)(20.0 mg) was dissolved into 4 mol/L hydrochloric acid in 1,4-dioxane, and the mixture was stirred for 16 hours. The reaction solvent was evaporated under reduced pressure and the obtained residue was crystallized from methanol-diethyl ether to afford the compound (588) (14.7 mg).

$^1$H-NMR (DMSO-d$_6$): 1.59 (3H, s), 2.09-2.76 (4H, m), 6.44 (1H, t, J=1.6 Hz), 6.60 (1H, t J=1.9 Hz), 6.71 (1H, t, J=2.0 Hz), 10.4 (1H, s)

Example 2

The Synthesis of Compound 835

[Chemical formula 49]

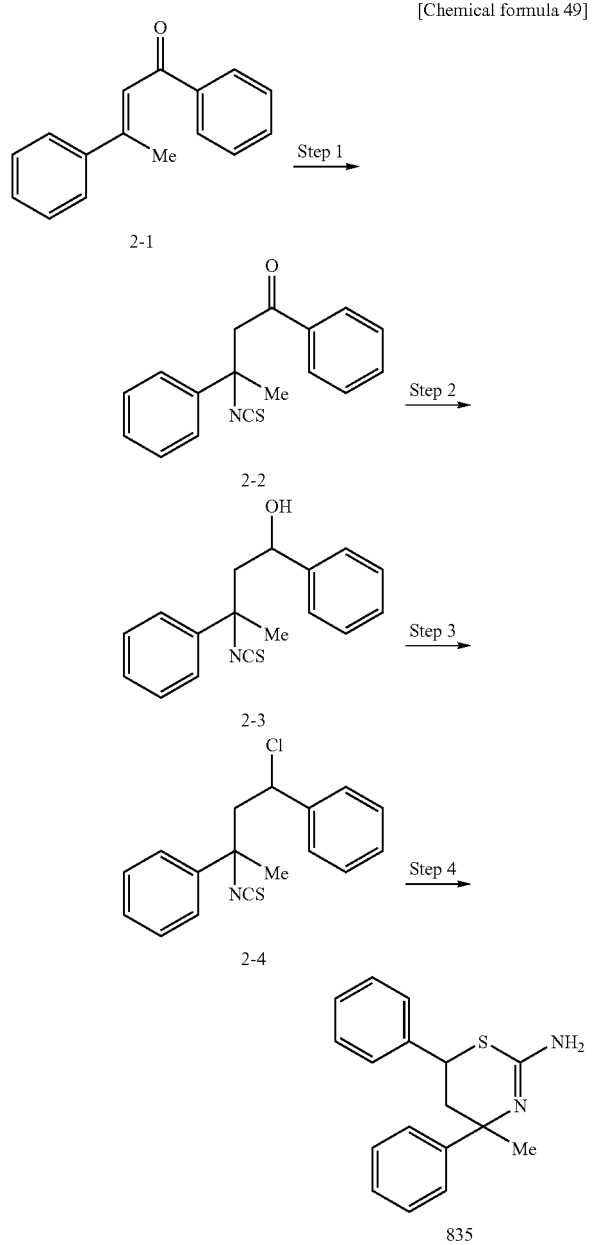

Step 1

The compound (2-1)(2020 mg) was dissolved into chloroform (20 ml), then water (4 ml) and sodium thiocyanic acid (1470 mg) were added at room temperature with stirring, and then sulfuric acid (1.94 ml) was added dropwise under cooling with ice-water bath. After an addition was complete, the reaction mixture was warmed to room temperature and then stirred for 345 minutes, then stirred at 60° C. overnight. Because the compound (2-1) was remained (checked by TLC), the reaction mixture was cooled to room temperature, then sodium thiocyanic acid (1470 mg), water (5 ml) and sulfuric acid (1.94 ml) were added successively. After the reaction mixture was warmed to 60° C., the mixture was stirred for 1 day. Saturated sodium carbohydrate solution was added to the reaction mixture to be basic condition under cooling with ice-water bath, and then the reaction mixture was extracted with ethyl acetate. The organic layer was washed with brine, then dried over anhydrous magnesium sulfate. The solvent was evaporated and the obtained residue was purified by silica gel column chromatography to afford the compound (2-2)(968 mg).

$^1$H-NMR (CDCl$_3$, 270 MHz): 1.99 (3H, s), 3.55 (1H, d, J=16.1 Hz), 3.69 (1H, d, J=16.1 Hz), 7.12-7.64 (8H, m), 7.82-7.95 (2H, m)

Step 2

The compound (2-2)(842 mg) was dissolved into ethanol (8.4 ml), sodium dihydrogen phosphate, sodium borohydride (113.2 mg), and water (2.8 ml), were added successively under cooling with ice-water bath with stirring, and the mixture was stirred for 30 minutes. After the consumption of the compound (2-2)(checked by TLC), ethyl acetate and water were added to the reaction mixture under cooling with ice-water bath, and then stirred for a few minutes. The reaction mixture was extracted with ethyl acetate. The organic layer was washed with water, brine successively, and dried over anhydrous magnesium sulfate. The solvent was evaporated to afford the compound (2-3)(904.8 mg) as crude product.

Step 3

To a solution of compound (2-3)(900 mg) in toluene (10 ml) was added a solution of thionyl chloride (0.7 ml) in toluene (5 ml) under cooling with ice-water bath, and then stirred for 1 hour. After the consumption of the compound (2-3)(checked by TLC), the reaction solvent was evaporated under reduced pressure to afford the compound (2-4)(1076.8 mg) as crude product.

Step 4

The compound (2-4)(1070 mg) was dissolved into about 7 mol/L ammonia in methanol (20 ml) at room temperature, then the mixture was stirred for 1 day. After the consumption of the compound (2-4)(checked by TLC), the reaction solvent was evaporated under reduced pressure to afford the compound (835)(2633 mg) as crude product.

Example 3

The Synthesis of Compound 561

[Chemical formula 50]

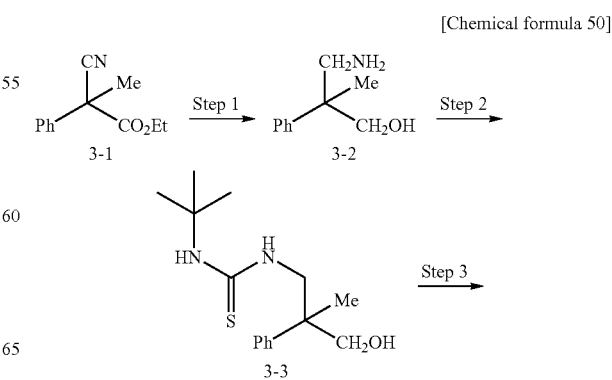

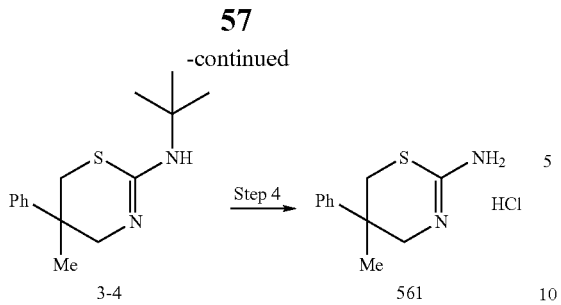

Step 1

To tetrahydrofuran (30 ml) under cooling with ice-water bath with string, lithium aluminium hydride (0.63 g) was added portionwise, then a solution of compound (3-1)(1.94 g) in tetrahydrofuran (40 ml) was added dropwise. The reaction mixture was reacted for 20 minutes at room temperature, then reacted for 3 hours under reflux. Then ice was added in small portions under cooling, and then stirred for 1 day at room temperature. The reaction mixture was filtered and the filtrate was evaporated under reduced pressure, and the residue was purified by silica gel column chromatography to afford the compound (3-2)(0.90 g).

$^1$H-NMR (CDCl$_3$): 1.22 (3H, s), 3.08 (1H, d, J=12.5 Hz), 3.34 (1H, d, J=12.5 Hz), 3.85 (1H, d, J=11.0 Hz), 4.11 (1H, d, J=11.0 Hz), 7.21-7.25 (1H, m), 7.34-7.40 (2H, m), 7.46-7.50 (2H, m).

Step 2

The compound (3-2)(0.90 g) was dissolved into tetrahydrofuran (15 ml), t-butylisothiocyanate (0.69 g) in tetrahydrofuran (5 ml) was added under cooling with ice-water bath with stirring. The reaction mixture was stirred for 3 days at room temperature, water was added and extracted with dichloromethane. The organic layer was dried over anhydrous magnesium sulfate, then the solvent was evaporated under reduced pressure. The residue was purified by silica gel column chromatography to afford the compound (3-3)(1.33 g).

$^1$H-NMR (CDCl$_3$): 1.12 (9H, s), 1.34 (3H, s), 3.15 (1H, br), 3.76 (1H, d, J=11.2 Hz), 3.87 (1H, dd, J=14.2, 4.6 Hz), 4.13 (1H, d, J=11.2 Hz), 4.23 (1H, dd, J=14.2, 6.6 Hz), 5.18 (1H, br), 6.01 (1H, br), 7.23-7.28 (1H, m), 7.34-7.41 (4H, m).

Step 3

The compound (3-3)(315 mg) was dissolved into acetonitrile (3 ml), triphenylphosphine (440 mg), and carbon tetrachloride (520 mg) in acetonitrile (3 ml) were added under cooling with ice-water bath with stirring. The reaction mixture was stirred for 1 hour at room temperature, and then potassium carbonate (460 mg) was added and stirred for 2 days at room temperature. Then water was added to the reaction mixture and the mixture was extracted with dichloromethane. The organic layer was dried over anhydrous magnesium sulfate, and then the solvent was evaporated under reduced pressure. The residue was purified by silica gel column chromatography to afford the compound (3-4)(0.23 g).

$^1$H-NMR (CDCl$_3$): 1.30 (9H, s), 1.36 (3H, s), 3.13 (1H, d, J=12.2 Hz), 3.24 (1H, dd, J=12.2, 2.3 Hz), 3.51 (1H, br), 3.53 (1H, d, J=15.2 Hz), 3.99 (1H, dd, J=15.2, 2.3 Hz), 7.20-7.25 (1H, m), 7.30-7.36 (2H, m), 7.39-7.43 (2H, m).

Step 4

To the compound (3-4)(0.22 g), conc. hydrochloric acid (4.5 ml) was added, then stirred for 2 hours under reflux, and then the reaction solvent was evaporated under reduced pressure. The obtained residue was crystallized from methanol-diethyl ether to afford the compound (561)(0.16 g).

$^1$H-NMR (DMSO-d$_6$): 1.33 (3H, 8), 3.33-3.49 (2H, m), 3.65-3.96 (2H, m), 7.29 (1H, t. J=7.6 Hz), 7.40 (2H, t. J=7.6 Hz), 7.48 (2H, t. J=7.6 Hz).

Example 4

The Synthesis of Compound 534

[Chemical formula 51]

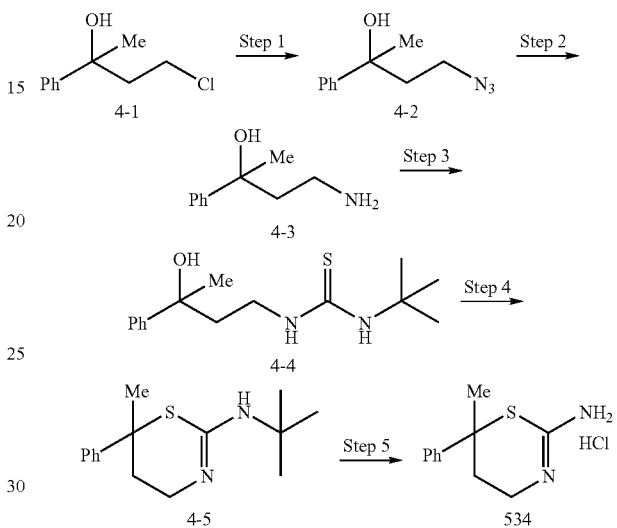

Step 1

The compound (4-1)(0.72 g) was dissolved into N,N-dimethylformamide (15 ml), then sodium azide (0.31 g) was added. The reaction mixture was stirred at 100° C. for 13 hours, then water was added and the mixture was extracted with diethyl ether, the organic layer was dried over anhydrous magnesium sulfate to afford the compound (4-2)(0.71 g) as crude product.

Step 2

To a solution of the compound (4-2)(0.71 g) in tetrahydrofuran (10 ml), lithium aluminium hydride (0.14 g) was added portionwise under cooling with ice-water bath with stirring, then stirred for 2 hours at room temperature. After the consumption of the starting material, ice was added in small portions, then stirred for 18 hours at room temperature. The reaction mixture was filtered then filtrate was evaporated under reduced pressure to afford the compound (4-3)(0.89 g) as crude product.

Step 3

The compound (4-3)(0.89 g) was dissolved into tetrahydrofuran (10 ml), then t-butylisothiocyanate (0.56 g) in tetrahydrofuran (5 ml) was added under cooling with ice-water bath with stirring. The reaction mixture was stirred for 4 hours at room temperature, and water was added, and then extracted with dichloromethane, and the organic layer was dried over anhydrous magnesium sulfate. Then the residue was purified by silica gel column chromatography to afford the compound (4-4)(0.72 g).

$^1$H-NMR (CDCl$_3$): 1.39 (9H, s), 2.08 (3H, s), 2.09-2.15 (2H, m), 3.37-3.44 (1H, m), 3.80-3.87 (1H, m), 5.97 (1H, br.), 6.86 (1H, br.), 7.28-7.43 (5H, m).

Step 4

The compound (4-4)(120 mg) was dissolved into acetonitrile (2 ml), triphenylphosphine (170 mg), and carbon tetrachloride (200 mg) in acetonitrile (1 ml) were added under cooling with ice-water bath with stirring. The reaction mixture was stirred for 5 hours at room temperature, and then potassium carbonate (177 mg) was added and stirred for 5 days at room temperature. Then water was added to the reaction mixture and the mixture was extracted with dichloromethane, the organic layer was dried over anhydrous magnesium sulfate, then the solvent was evaporated under reduced pressure. The residue was purified by silica gel column chromatography to afford the compound (4-5)(0.06 g).

$^1$H-NMR (CDCl$_3$): 1.35 (9H, s), 1.59 (3H, s), 1.91 (1H, ddd, J=13.5, 8.8, 5.0 Hz), 2.06 (1H, dt, J=13.5, 5.0 Hz), 3.00 (1H, ddd, J=15.1, 8.8, 5.0 Hz), 3.30 (1H, dt, J=15.1, 5.0 Hz), 7.24-7.38 (5H, m).

Step 5

To the compound (4-5)(0.06 g), conc. hydrochloric acid (3 ml) was added, then the mixture was stirred for 1 hour under reflux, and the solvent was evaporated under reduced pressure. The obtained residue was crystallized from methanol-water to afford the compound (534)(0.02 g).

$^1$H-NMR (DMSO-d$_6$): 1.43 (3H, s), 1.77 (1H, dt. J=8.4, 3.4 Hz), 2.11 (1H, d. J=9.2 Hz), 2.48-2.50 (1H, m), 2.83-2.99 (1H, m), 6.12 (1H, br), 6.65 (1H, br), 7.21-7.24 (1H, m), 7.31-7.37 (4H, m).

Example 5

The Synthesis of Compound 1008

[Chemical formula 52]

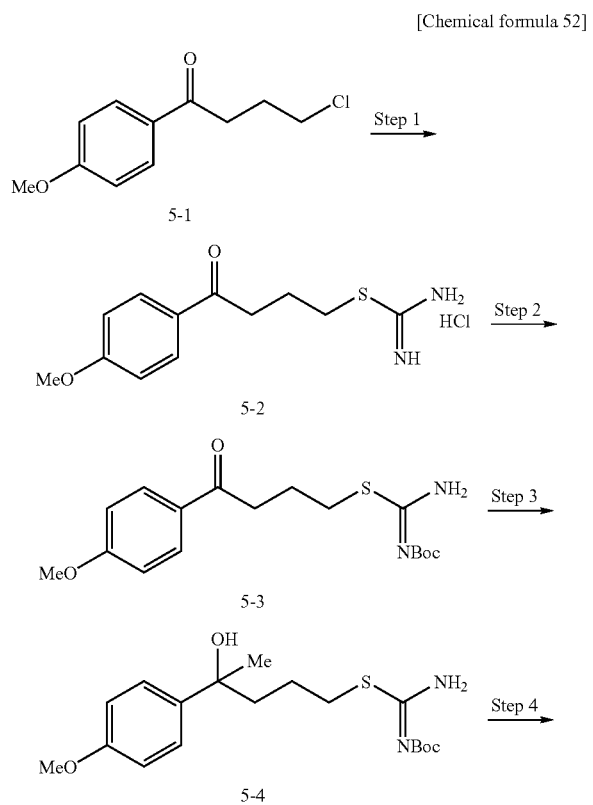

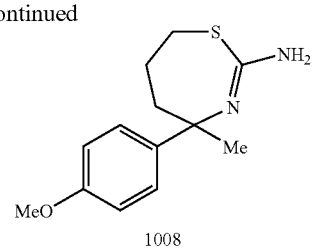

Step 1

The compound (5-1)(3.00 g) was dissolved into ethanol (30 ml), and thiourea (1.13 g) was added, and then the mixture was refluxed for 26 hours, and the solvent was evaporated under reduced pressure. The obtained residue was crystallized from ethyl acetate/hexane to afford the compound (5-2) (4.03 g).

$^1$H-NMR (DMSO-d6): 1.95 (2H, quint, J=6.8 Hz), 3.13 (2H, t, J=6.8 Hz), 3.21 (2H, t, J=6.8 Hz), 3.85 (3H, 8), 7.06 (2H, d, J=8.8 Hz), 7.95 (2H, d, J=8.8 Hz), 9.18 (4H, br).

Step 2

The compound (5-2)(1.00 g) was dissolved into tetrahydrofuran (25 ml), then di-t-butyl-dicarbonate (1.74 g), and triethylamine (0.88 g) were added, and then the mixture was stirred for 3 hours at room temperature. Water was added to the reaction mixture, and the mixture was extracted with dichloromethane. The organic layer was dried over anhydrous magnesium sulfate, and then the solvent was evaporated under reduced pressure. The residue was purified by silica gel column chromatography to afford the compound (5-3)(1.24 g).

$^1$H-NMR (CDCl$_3$): 1.50 (9H, s), 2.07-2.17 (2H, m), 2.98 (2H, t, J=7.8 Hz), 3.09 (2H, t, J=6.3 Hz), 6.95 (2H, d, J=8.9 Hz), 7.95 (2H, d, J=8.9 Hz).

Step 3

The compound (5-3)(1.18 g) was dissolved into tetrahydrofuran (12 ml), then 0.9 mol/1 methylmagnesium bromide in tetrahydrofuran solution (10.1 ml) was added under cooling with acetonitrile-dryice bath with stirring, and then reaction mixture was stirred for 1 hour, then stirred for 30 minutes at room temperature. After the reaction, saturated ammonium chloride solution was added under cooling with ice-water bath with stirring, then the mixture was extracted with diethyl ether, and the organic layer was dried over anhydrous magnesium sulfate, and then the solvent was evaporated under reduced pressure. The obtained residue was purified by silica gel column chromatography to afford the compound (5-4) (0.39 g).

$^1$H-NMR (CDCl$_3$): 1.51 (9H, s), 1.63 (3H, s), 1.65-1.65 (2H, m), 1.87-1.91 (2H, m), 2.96-3.12 (2H, m), 6.86 (2H, d, J=8.9 Hz), 7.36 (2H, d, J=8.9 Hz).

Step 4

The compound (5-4)(0.24 g) was dissolved into trifluoroacetic acid (6 ml), and stirred for 20 hours at room temperature, then the reaction solvent was evaporated under reduced pressure. To the residue, water and saturated sodium hydrogencarbonate was added, and then extracted with dichloromethane. The organic layer was dried over anhydrous sodium sulfate, and then the solvent was evaporated under reduced pressure. The residue was purified by silica gel column chromatography to afford the compound (1008)(0.06 g).

¹H-NMR (CDCl₃): 1.54 (3H, s), 1.77-1.87 (1H, m), 1.90-1.97 (1H, m), 2.20-2.36 (2H, m), 2.67-2.79 (2H, m), 3.81 (3H, s), 5.30 (2H, br), 6.87 (2H, d, J=9.0 Hz), 7.33 (2H, d, J=9.0 Hz).

Example 6

The Synthesis of Compound 783

[Chemical formula 53]

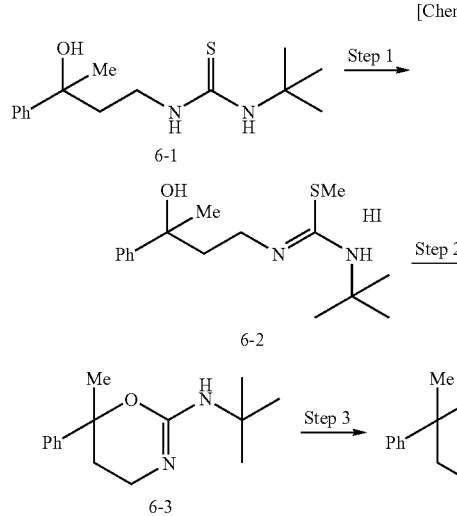

Step 1

The compound (6-1)(0.55 g) was dissolved into methanol (7 ml), and methyl iodide (0.36 g) was added at room temperature with stirring. The mixture was stirred at room temperature for 18 hours, then the reaction solvent was evaporated under reduced pressure to afford the compound (6-2) (0.92 g) as crude product.

Step 2

The compound (6-2)(0.92 g) was dissolved into tetrahydrofuran (7 ml), then triethylamine (0.24 g) and silver oxide (1.1 g) was added. The mixture was stirred at room temperature for 3 days, then the insolubles was removed by filtration, then the filtrate was evaporated under reduced pressure, and then the obtained residue was purified by silica gel column chromatography to afford the compound (6-3)(0.31 g).

¹H-NMR (CDCl₃): 1.35 (9H, s), 1.60 (3H, s), 1.92 (1H, ddd, J=9.2, 5.8, 3.4 Hz), 2.07 (1H, dt, J=9.2, 3.4 Hz), 3.00 (1H, ddd, J=9.2, 5.8, 3.4 Hz), 3.30 (1H, dt, J=9.2, 3.4 Hz), 7.24-7.38 (5H, m).

Step 3

To the compound (6-3)(0.22 g), conc. hydrochloric acid (3 ml) was added, then the mixture was stirred for 1 hour under reflux, and then the reaction solvent was evaporated under reduced pressure. The obtained residue was crystallized from water to afford the compound (783)(0.13 g).

¹H-NMR (DMSO-d₆): 1.44 (3H, s), 1.78 (1H, dt. J=12.4, 4.2 Hz), 2.12 (1H, d. J=8.9 Hz), 2.51-2.52 (1H, m), 2.96 (1H, d. J=4.2 Hz), 6.12 (1H, br), 6.66 (1H, br), 7.21-7.24 (1H, m), 7.32-7.37 (4H, m).

Example 7

The Synthesis of Compound 69

[Chemical formula 54]

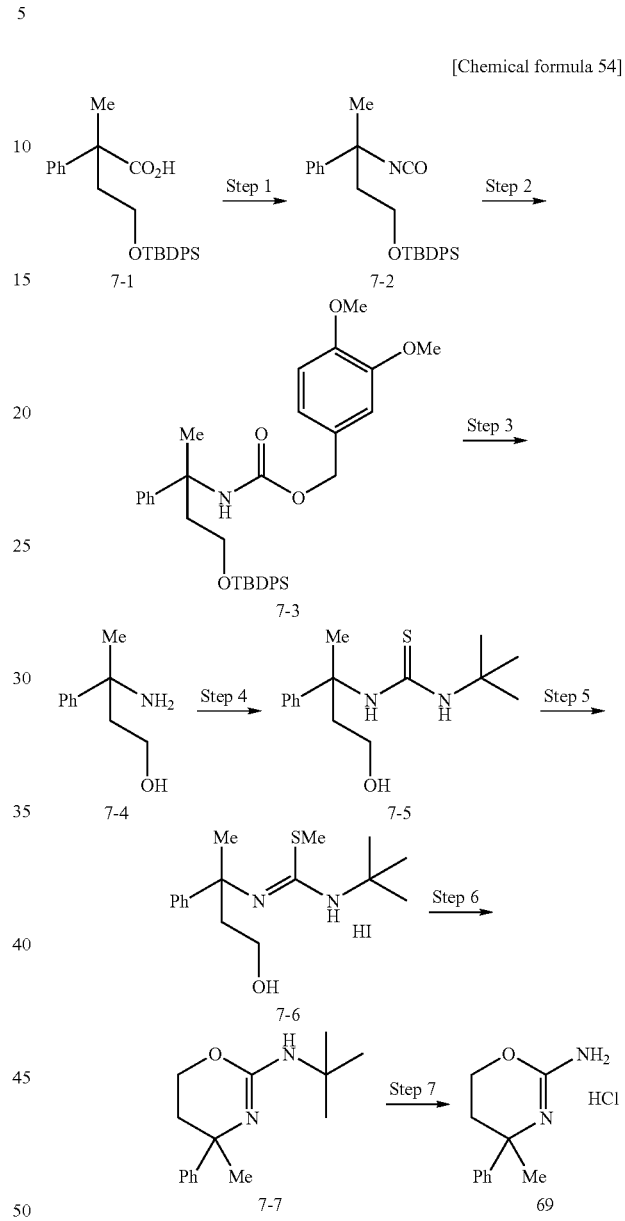

Step 1

A solution of the compound (7-1)(1.93 g), diphenylphosphoryl azide (1.60 g), and triethylamine (0.59 g) in toluene (20 ml) was stirred at 80° C. for 3 hours, and water was added, and then the mixture was extracted with diethyl ether. The organic layer was dried over anhydrous sodium sulfate, and then the solvent was evaporated under reduced pressure. The obtained residue was purified by silica gel column chromatography to afford the compound (7-2)(1.69 g).

¹H-NMR (CDCl₃): 1.00 (9H, a), 1.72 (3H, s), 2.17-2.22 (2H, m), 3.49-3.58 (1H, m), 3.70-3.80 (1H, m), 7.20-7.42 (10H, m), 7.58-7.63 (5H, m).

Step 2

The compound (7-2)(1.68 g) was dissolved into toluene (9 ml), and 3,4-dimethoxybenzylalcohol (0.79 g) was added, the mixture was refluxed for 8 hours. To the reaction mixture, water was added, then the mixture was extracted with dichloromethane, and the organic layer was dried over anhydrous sodium sulfate, and the solvent was evaporated under reduced pressure. The obtained residue was purified by silica gel column chromatography to afford the compound (7-3)(2.09 g).

$^1$H-NMR (CDCl$_3$): 1.03 (9H, s), 1.87 (3H, s), 2.04 (2H, m), 3.48 (1H, m), 3.51 (1H, m), 3.62 (3H, s), 3.65 (3H, s), 4.95 (1H, d, J=12.2 Hz), 5.03 (1H, d, J=12.2 Hz), 6.80-7.09 (3H, m), 7.22-7.42 (10H, m), 7.56-7.64 (5H, m).

Step 3

The compound (7-3)(2.09 g) was dissolved into 1,4-dioxane (15 ml), and 4 mol/L hydrochloric acid-1,4-dioxane (15 ml) solution was added, then stirred at room temperature for 24 hours. To the reaction mixture, water and 1 mol/L-sodium hydroxide solution were added and extracted with dichloromethane, then the organic layer was dried over anhydrous sodium sulfate, and then the solvent was evaporated under reduced pressure. The obtained residue was purified by silica gel column chromatography to afford the compound (7-4) (0.45 g).

$^1$H-NMR (CDCl$_3$): 1.57 (3H, s), 1.07-1.98 (2H, m), 3.48-3.56 (1H, m), 3.72-3.86 (1H, m), 7.23-7.45 (15H, m).

Step 4

The compound (7-4)(0.44 g) was dissolved into tetrahydrofuran (16 ml), t-butylisothiocyanate (0.41 g) and diisopropylethylamine (0.46 g) were added. After the mixture was stirred at room temperature for 3 days, water was added, and extracted with dichloromethane, then the organic layer was dried over anhydrous sodium sulfate, and then the solvent was evaporated under reduced pressure. The obtained residue was purified by silica gel column chromatography to afford the compound (7-5)(0.17 i).

$^1$H-NMR (CDCl$_3$): 1.79 (3H, s), 1.82-2.20 (2H, m), 3.71-3.81 (2H, m), 5.09 (1H, br), 7.30-7.52 (5H, m).

Step 5

The compound (7-5)(0.17 g) was dissolved into tetrahydrofuran (3.4 ml), then methyl iodide (0.11 g) was added at room temperature with stirring. The mixture was stirred for 23 hours, the reaction solvent was evaporated under reduced pressure to afford the compound (7-6)(0.28 g) as crude product.

Step 6

The compound (7-6)(0.28 g) was dissolved into tetrahydrofuran (5 ml), then triethylamine (74 mg) and silver oxide (0.34 g) were added. The mixture was stirred at room temperature for 20 hours, then insolubles were removed by filtration, and then the filtrate was evaporated under reduced pressure. The obtained residue was purified by silica gel column chromatography to afford the compound (7-7)(0.14 g).

$^1$H-NMR (CDCl$_3$): 1.36 (9H, s), 1.49 (3H, s), 1.96-2.09 (2H, m), 2.77-3.83 (1H, m), 4.05-4.10 (1H, m), 7.19 (1H, t, J=7.3 Hz), 7.31 (2H, t, J=7.3 Hz), 7.44 (2H, d, J=7.3 Hz).

Step 7

To the compound (7-7)(0.12 g) conc. hydrochloric acid (9 ml) was added, then stirred for 1 hour under reflux, and then the reaction solvent was evaporated under reduced pressure. The obtained residue was crystallized from methanol-water to afford the compound (69)(0.10 g).

$^1$H-NMR (DMSO-d$_6$): 1.65 (3H, s), 2.28-2.35 (1H, m), 2.39-2.44 (1H, m), 3.97 (1H, dt, J=7.8, 3.0 Hz), 4.53 (1H, dt, J=7.8, 3.0 Hz), 7.32-7.44 (5H, m), 8.44 (2H, br), 10.33 (1H, s).

Example 8

The Synthesis of Compound 256

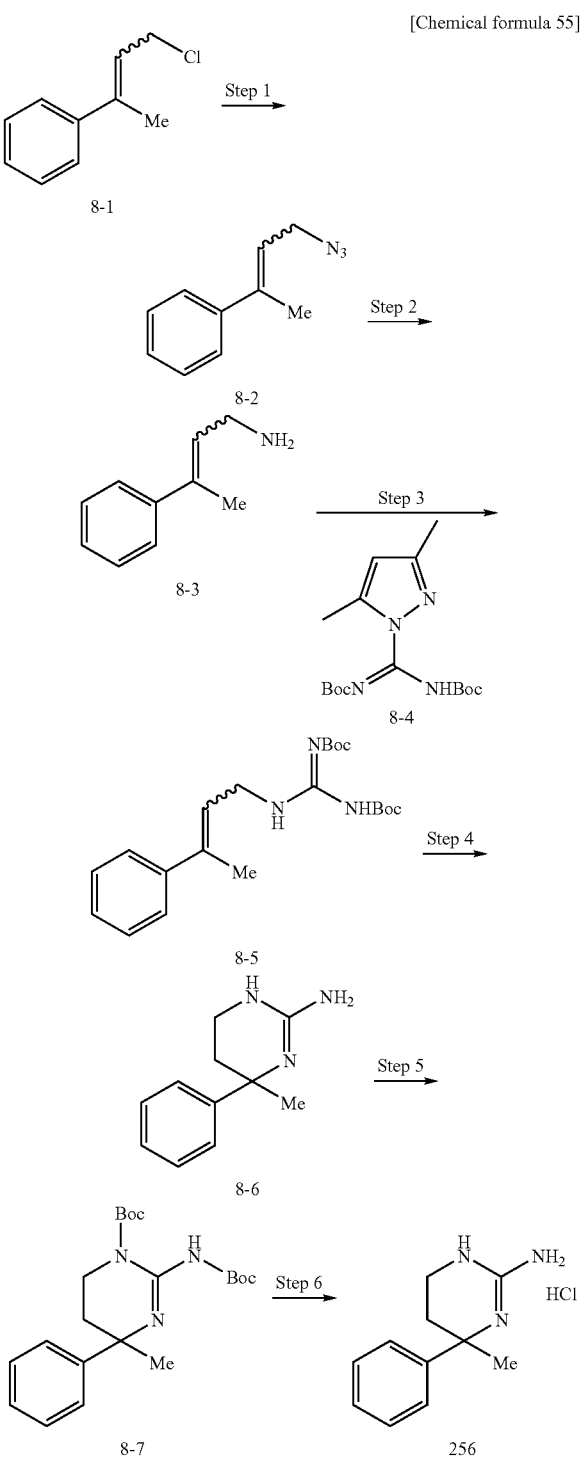

[Chemical formula 55]

Step 1

The compound (8-1)(4890 mg) was dissolved into N,N-dimethylformamide (100 ml), then sodium azide (5720 mg) was added at room temperature with stirring, and the solution was warmed to 80° C., and stirred for 12 hours. After the consumption of the compound (8-1)(checked by TLC), the reaction mixture was cooled to room temperature, then diethyl ether and water were added, and then the mixture was extracted with diethyl ether. The organic layer was washed with brine, and dried over magnesium sulfate. The solvent was evaporated under reduced pressure to afford the compound (8-2)(4940 mg) as crude product.

Step 2

To the suspension of lithium aluminium hydride (1080 mg) in tetrahydrofuran (90 ml) under nitrogen atmosphere under cooling with ice-water bath, the compound (8-2)(4940 mg) in tetrahydrofuran (15 ml) solution was added, the reaction mixture was stirred for 30 minutes. After the consumption of the compound (8-2)(checked by TLC), 1 mol/L sodium hydroxide solution was added under cooling with ice-water bath, then stirred for a while. The generated gel was removed with filtration, and the mother liquid was extracted with diethyl ether. The organic layer was washed with brine, and dried over magnesium sulfate. The solvent was evaporated under reduced pressure to afford the compound (8-3)(4219.1 mg) as crude product.

Step 3

The compound (8-3)(800 mg) was dissolved into acetonitrile (16 ml), the compound (8-4)(1840 mg) was added with stirring at room temperature, and stirred for 13 hours. After the consumption of the compound (8-3)(checked by TLC), the reaction solvent was evaporated under reduced pressure, the obtained residue was purified by silica gel column chromatography to afford the compound (8-5)(1550.7 mg).

8-5-(Z) $^1$H-NMR (CDCl$_3$, 270 MHz): 1.49 (18H, s), 2.06 (3H, d, J=1.4 Hz), 3.91-4.00 (2H, m), 5.54 (1H, td, J=7.1, 1.4 Hz), 7.12-7.41 (5H, m), 8.17-8.25 (1H, m), 11.47 (1H, s)

8-5-(E): $^1$H-NMR (CDCl$_3$, 270 MHz): 1.49 (9H, s), 1.52 (9H, s), 2.09 (3H, d, J=1.5 Hz), 4.24 (21, dd, J=6.6, 5.3 Hz), 6.80 (1H, td, J=6.6, 1.5 Hz), 7.21-7.48 (5H, m), 8.28-8.38 (1H, m), 11.51 (1H, s)

Step 4

The compound (8-5)(474.1 mg) was dissolved into trifluoroacetic acid (4.6 ml) under cooling with ice-water bath, then warmed to room temperature, and stirred for 4 hours. After the consumption of the compound (8-5)(checked by NMR), the reaction mixture was poured into floating ice—1 mol/L sodium hydroxide solution to be neutralized, then the mixture was extracted with ethyl acetate. The organic layer was washed with brine, and dried over magnesium sulfate. The solvent was evaporated under reduced pressure to afford the compound (8-6)(326.4 mg) as crude product.

Step 5

The compound (8-6)(326.4 mg) was dissolved into 1,4-dioxane (2.4 ml), sodium hydroxide (195 mg) and water (1.2 ml) were added successively, then di-t-butyl dicarbonate (0.84 ml) was added under cooling with ice-water bath. The reaction mixture was warmed to room temperature, and stirred for 15 hours, then the consumption of the compound (8-6) was checked by LC-MS. After added water to the reaction mixture, the mixture was extracted with ethyl acetate. The organic layer was washed with brine, and dried over magnesium sulfate. The solvent was evaporated under reduced pressure, and the obtained residue was purified by silica gel column chromatography to afford the compound (8-7)(113.6 mg).

$^1$HNMR (CDCl$_3$, 400 MHz): 1.46 (9H, s), 1.51 (9H, s), 1.64 (3H, m), 2.06 (1H, ddd, J=13.4, 11.4, 5.0 Hz), 2.27 (1H, dt, J=13.4, 4.6 Hz), 3.15 (1H, ddd, J=12.9, 11.3, 4.6 Hz), 3.70 (1H, dt, J=12.9, 4.7 Hz), 7.23-7.29 (1H, m), 7.33-7.38 (4H, m)

Step 6

The compound (8-7)(110 mg) was dissolved into 4 mol/L hydrochloric acid-1,4-dioxane solution (1 ml) under cooling ice-water bath, the mixture was warmed to room temperature, and stirred for 2 days, then the consumption of the compound (8-7) was checked by LC-MS, and diethyl ether and water were added at room temperature. After separation of diethyl ether layer, water layer was evaporated under reduced pressure. To the obtained residue, methanol was added, then the generated crystal was filtered. The methanol in mother liquid was evaporated under reduced pressure to afford the compound (256)(69 mg).

$^1$H-NMR (DMSO-d$_6$, 400 MHz): 1.57 (3H, a), 1.87-1.96 (1H, m), 2.30 (1H, dt, J=13.6, 3.8 Hz), 2.60 (1H, td, J=12.0, 3.7 Hz), 3.25 (1H, ddd, J=12.8, 8.2, 4.4 Hz), 6.93 (2H, s), 7.27-7.44 (5H, m), 7.94 (1H, s), 8.63 (1H, s)

Example 9

The Synthesis of Compound 24

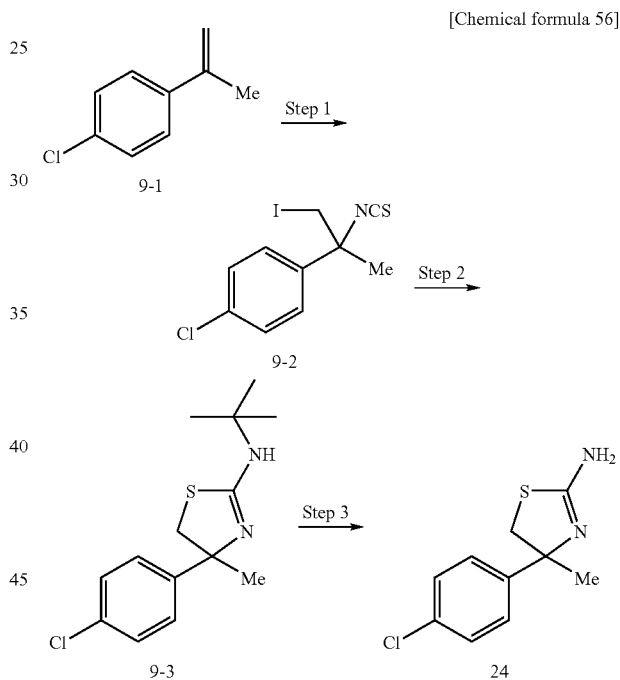

Step 1

The compound (9-1)(0.39 g) was dissolved into chloroform (20 ml), iodine (1.53 g), potassium thiocyanate (1.25 g), catalytic amount of tetrabutylammonium chloride, and water (1 ml) were added at room temperature, then stirred for 15 hours. To the reaction mixture, 10% thiosodium sulfate solution and water were added, and the mixture was extracted with dichloromethane. The organic layer was dried over anhydrous sodium sulfate, the solvent was evaporated under reduced pressure. The obtained residue was purified by silica gel column chromatography to afford the compound (9-2) (0.56 g).

$^1$H-NMR (CDCl$_3$): 1.95 (3H, s), 3.62 (2H, s), 7.30-7.40 (4H, m).

Step 2

To a solution of the compound (9-2)(0.56 g) in tetrahydrofuran (10 ml), t-butylamine (0.24 g) was added and stirred at room temperature for 18 hours. The reaction solvent was evaporated under reduced pressure, then the obtained residue was purified by silica gel column chromatography to afford the compound (9-3)(190 mg).

$^1$H-NMR (CDCl$_3$): 1.43 (9H, s), 1.56 (3H, s), 3.27 (1H, d, J=10.6 Hz), 3.36 (1H, d, J=10.6 Hz), 7.28 (2H, d, J=8.2 Hz), 7.43 (2H, d, J=8.2 Hz).

Step 3

To the compound (9-3)(190 mg), conc. hydrochloric acid (3 ml) was added, then stirred at 100° C. for 3 hours. To the reaction mixture, 6 mol/L sodium hydroxide was added to neutralize, the mixture was extracted with dichloromethane. The organic layer was dried with anhydrous sodium sulfate, and the solvent was evaporated under reduced pressure. The obtained residue was purified by silica gel column chromatography, then crystallized from dichloromethane/n-hexane to afford the compound (24)(110 mg).

$^1$H-NMR (CDCl$_3$): 1.62 (3H, s), 3.47 (1H, d, J=10.6 Hz), 3.52 (1H, d, J=10.6 Hz), 4.59 (2H, br), 7.29 (2H, d, J=8.6 Hz), 7.39 (2H, d, J=8.6 Hz).

Example 10

The Synthesis of Compound 48

[Chemical formula 57]

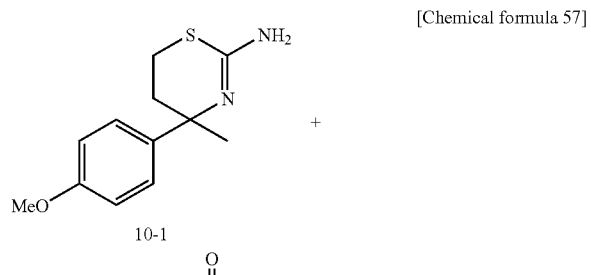

Step 1

The compound (10-1)(79.6 mg) and (10-2)(120 mg) were dissolved into N,N-dimethylformamide (3 ml), then 1-hydroxybenzotriazole (54.6 mg) and N,N'-diisopropylcarbodiimide (0.063 ml) were added, then the reaction mixture was stirred overnight at room temperature. Then after the consumption of the compound (10-1), water was added, and the mixture was extracted with ethyl acetate. The organic layer was washed with brine, and dried over magnesium sulfate, and the solvent was evaporated under reduced pressure. The obtained residue was purified by silica gel column chromatography to afford the compound (10-3)(110.2 mg) as crude product of diastereomer.

$^1$H-NMR (CDCl$_3$): 0.78-1.00 (6H, m), 1.14 (9/2H, s), 1.16 (9/2H, s) 1.62 (3/2H, s), 1.54 (3/2H, s) 1.86-2.28 (3H, m), 2.56-2.89 (2H, m), 3.80 (3/2H, s), 3.81 (3/2H, 5) 4.04-4.14 (1H, m), 6.80-6.91 (2H, m), 7.08-7.22 (2H, m), 7.30-7.51 (6H, m), 7.61-7.76 (4H, m)

Step 2

The compound (10-3)(100 mg) was dissolved into tetrahydrofuran (3 ml) under nitrogen atmosphere, then 1 mol/L tetrabutylammonium fluoride in tetrahydrofuran (0.18 ml) was added at 0° C. with stirring, then the reaction mixture was stirred at 0° C. for 5 minutes. After the consumption of the compound (10-3), water was added, and the mixture was extracted with ethyl acetate. The organic layer was washed with brine, and dried over magnesium sulfate, then the solvent was evaporated under reduced pressure. The obtained residue was purified by silica gel column chromatography to afford the compound (48)(40.7 mg) as a mixture of diastereomers.

$^1$H-NMR (CDCl$_3$): 0.80-0.90 (3H, m) 1.01-1.12 (3H, m) 1.70 (3H, m), 2.02-2.31 (2H, m) 2.39-2.55 (1H, m), 2.61-2.90 (2H, m) 3.63-3.70 (1H, m) 3.81 (3H, m), 3.96-4.08 (1H, m) 6.87-6.96 (2H, m), 7.13-7.22 (2H, m)

Example 11

The Synthesis of Compound 707

[Chemical formula 58]

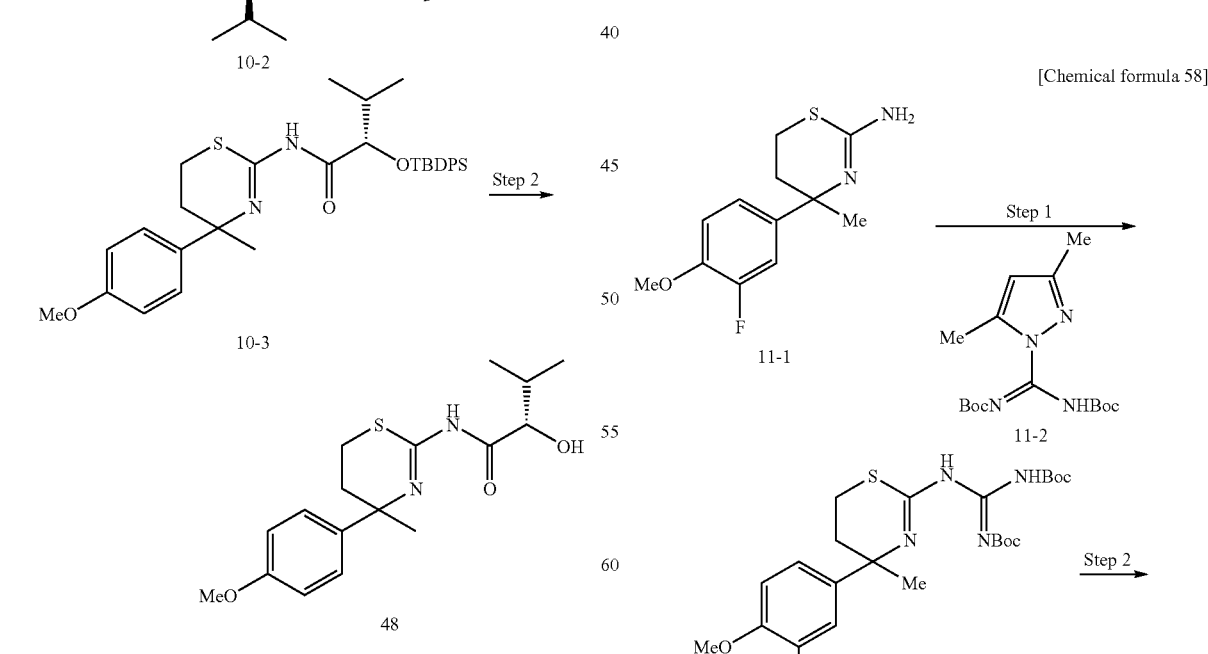

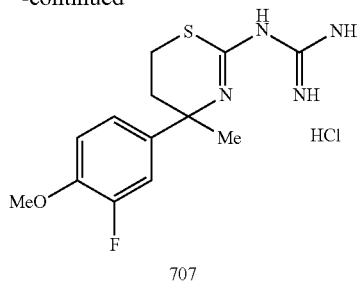

707

Step 1

The compound (11-1)(150 mg) was dissolved into acetonitrile (5 ml), then the compound (11-2)(219.6 mg) was added at room temperature with stirring, and then the reaction mixture was warmed to 60° C., and stirred for 25 hours. The compound (11-1) was remained (checked by TLC). The reaction solvent was evaporated under reduced pressure, then the obtained residue was purified by silica gel column chromatography to afford the compound (11-1)(211.4 mg).

¹H-NMR (CDCl₃, 400 MHz): 1.46 (9H, s), 1.50 (9H, s), 1.57 (3H, s), 1.90 (1H, ddd, J=13.7, 10.0, 3.8 Hz) 2.11 (1H, ddd, J=13.7, 6.5, 3.7 Hz) 2.68-2.76 (1H, m), 2.86-2.93 (1H, m), 3.88 (3H, s), 6.91 (1H, t, J=8.6 Hz) 6.99-7.03 (1H, m), 7.06 (1H, dd, J=13.0, 2.2 Hz), 10.14 (1H, s), 13.93 (1H, s)

Step 2

The compound (11-3)(210 mg) was dissolved into 4 mol/L hydrochloric acid in 1,4-dioxane (4 ml) under cooling with ice-water bath, then the mixture was warmed to room temperature and stirred for 67 hours. After the consumption of the compound (11-3)(checked by LC/MS), the reaction solvent was evaporated under reduced pressure. The obtained residue was crystallized from methanol-diethyl ether, and crystal was collected by filtration and washed with diethyl ether to afford compound (707)(140.2 mg).

¹H-NMR (DMSO-d₆, 400 MHz): 1.56 (3H, s), 1.90-2.01 (1H, m), 2.43-2.62 (2H, m), 2.95-3.03 (1H, m), 3.84 (3H, s), 7.10-7.27 (3H, m), 7.76 (3H, br s), 8.26 (1H, br s), 9.42 (1H, s)

Example 12

The Synthesis of Compound 845

[Chemical formula 59]

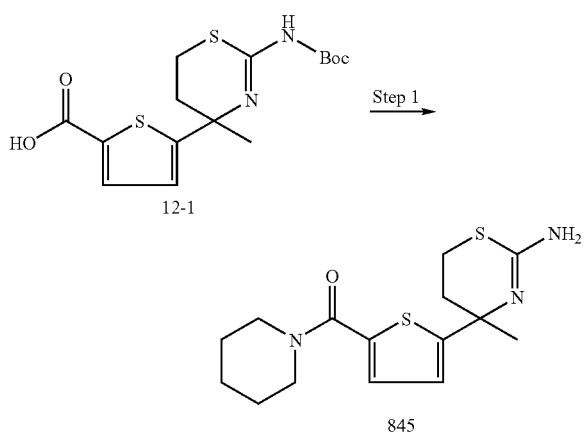

Step 1

The compound (12-1)(50 mg) and piperidine (17.9 mg) were dissolved into N,N-dimethylformamide (2 ml), then O-(7-azabenzotriazo-1-yl)-1,1,3,3-tetramethyluronium-hexafluorophosphate (79.8 mg) was added, and then the mixture was stirred at room temperature for 40 hours. After the consumption of the compound (12-1), the solvent was evaporated under reduced pressure with heating. To the obtained residue, saturated sodium hydrogencarbonate solution was added, and extracted with ethyl acetate. The organic layer was washed with brine, and dried over magnesium sulfate, then the solvent was evaporated under reduced pressure. The obtained residue was purified by silica gel column chromatography to afford the compound (845)(30.7 mg).

¹H-NMR (CDCl₃): 1.60 (3H, s), 1.51-1.82 (6H, m), 1.87-1.98 (1H, m), 2.09-2.19 (1H, m), 2.91-2.97 (2H, m), 3.64-3.68 (4H, m), 6.73 (1H, d, J=4.05 Hz), 7.14 (1H, d, J=4.05 Hz)

Example 13

The Synthesis of Compound 1262

[Chemical formula 60]

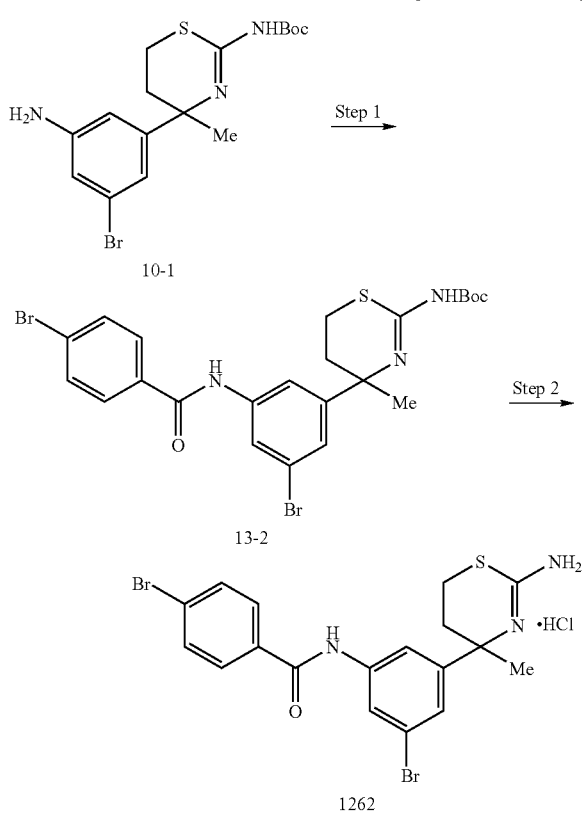

Step 1

The compound (13-1)(50.0 mg) was dissolved into tetrahydrofuran (1 ml) under nitrogen atmosphere, then triethylamine (19 μl), and 4-bromobenzoyl chloride (30.1 mg) were added under cooling with ice-water bath, and stirred for 40 minutes. The reaction solvent was evaporated under reduced pressure, and then the obtained residue was dissolved into ethyl acetate. The solution was washed with saturated sodium hydrogencarbonate solution, and dried over magnesium sulfate, and then the solvent was evaporated under reduced pressure. The generated crystal was collected by filtration to afford the compound (13-2)(57.2 mg).

$^1$H-NMR (CDCl$_3$): 1.48 (9H, s), 1.68 (3H, s), 2.08 (1H, m), 2.44 (1H, m), 2.65 (1H, m), 2.76 (1H, m), 7.18 (1H, s), 7.32 (1H, s), 7.64 (2H, d, J=8.2 Hz), 7.78 (2H, d, J=8.2 Hz), 8.15 (1H, s), 8.25 (1H, br)

Step 2

The compound (13-2)(62.3 mg) was dissolved into 4 mol/L hydrochloric acid-1,4-dioxane and stirred for 24 hours. The reaction solvent was evaporated under reduced pressure. The obtained residue was crystallized from methanol/diethyl ether to afford the compound (1262)(44.7 mg).

$^1$H-NMR (DMSO-d$_6$): 1.67 (3H, s), 2.10 (1H, m), 2.50-2.61 (3H, m), 7.33 (1H, s), 7.74 (1H, s), 7.77 (2H, d, J=8.6 Hz), 7.91 (2H, d, J=8.6 Hz), 8.08 (1H, s), 10.6 (1H, s)

Example 14

The Synthesis of Compound 753

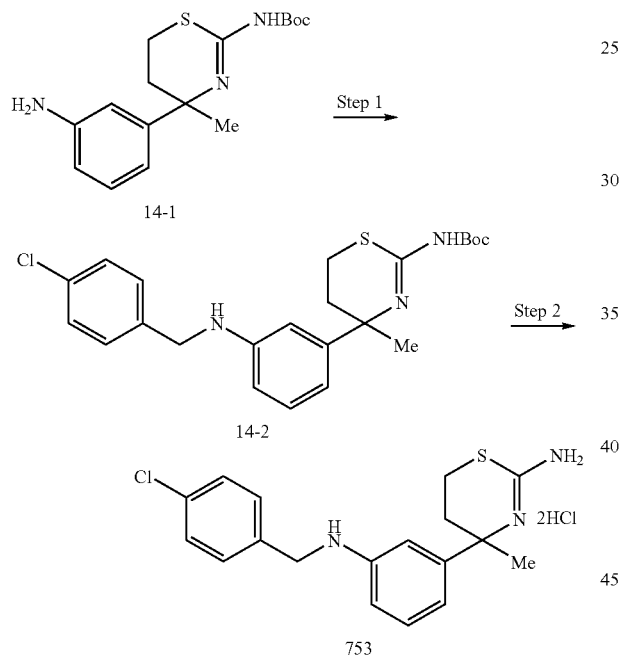

[Chemical formula 61]

Step 1

The compound (14-1)(46 mg) was dissolved into dichloromethane (2 ml), then 4-chlorobenzaldehyde (20 mg) and acetic acid (17 mg) was added at room temperature, and then stirred for 20 minutes, and then sodium triacetoxyborohydride (45 mg) was added under cooling with ice-water bath. The mixture was stirred at room temperature for 14 hours, and then water was added and extracted with dichloromethane. The organic layer was dried over sodium sulfate, and then the solvent was evaporated under reduced pressure. The obtained residue was purified by silica gel column chromatography to afford the compound (14-2)(52 mg).

$^1$H-NMR (CDCl$_3$): 1.50 (9H, s), 1.64 (3H, s), 2.02-2.10 (1H, m), 2.40 (1H, dt, J=14.0, 4.1 Hz), 2.62-2.74 (2H, m), 4.30 (2H, s), 6.49 (1H, ddd, J=, 7.8, 2.0, 0.8 Hz), 6.52 (1H, t, J=2.0 Hz), 6.60 (1H, ddd, J=, 7.8, 2.0, 0.8 Hz), 7.16 (1H, t, J=7.8 Hz), 7.18-7.33 (4H, m).

Step 2

To the compound (14-2)(52 mg), 4 mol/L hydrochloric acid in 1,4-dioxane solution (4 ml) was added, then the mixture was stirred at room temperature for 4 days, and then the reaction solvent was evaporated under reduced pressure. The obtained residue was crystallized from methanol/diethyl ether to afford the compound (753)(42 mg).

$^1$H-NMR (DMSO-d$_6$): 1.58 (3H, a), 2.00 (1H, ddd, J=, 14.3, 11.3, 3.3 Hz), 2.49-2.57 (2H, m), 3.07 (1H, dt, J=12.7, 3.3 Hz), 4.27 (2H, s), 6.47 (1H, d, J=8.2 Hz), 6.51-6.63 (2H, m), 7.08 (1H, t, J=8.2 Hz), 7.37 (4H, s), 8.80 (2H, br).

Example 15

The Synthesis of Compound 1135

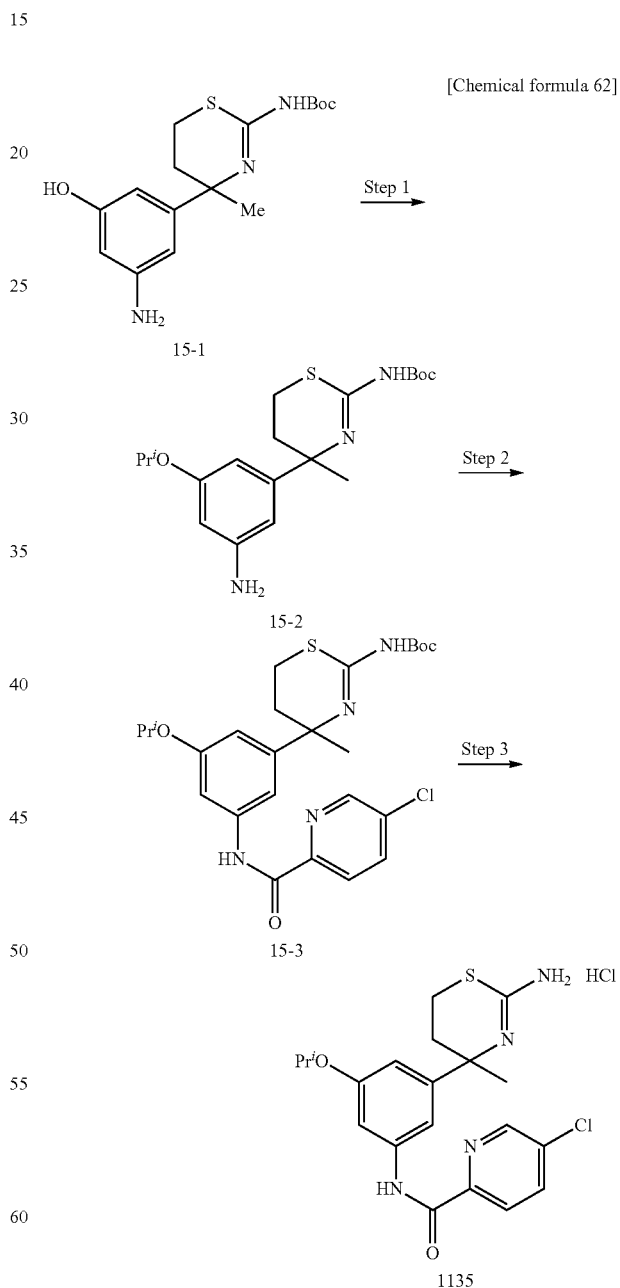

[Chemical formula 62]

Step 1

To a solution of the compound (16-1)(101 mg), 2-propanol (56 iii), and triphenylphosphine (189 mg) in tetrahydrofuran (2 ml), diethyl azodicarboxylate (2.2 mol/L) in toluene (328 µl) was added dropwise, then stirred for 1 hour at room temperature. After the consumption of the compound (15-1), the solvent was evaporated under reduced pressure. The obtained residue was purified by silica gel column chromatography to afford the compound (15-2)(280 mg) as a mixture of triphenylphosphine oxide and diethyl hydrazodicarboxylate.

Step 2

To the suspension of 5-chloropyridine-2-carboxylic acid (47 mg) in toluene (1 ml), N,N-dimethylformamide (1 drop) and thionylchloride (91 µl) were added and stirred at 100° C. for 1 hour. The solvent was evaporated under reduced pressure, then the obtained residue was dissolved into tetrahydrofuran (1 ml), and then the mixture of the compound (15-2) (280 mg), and pyridine (194 µl) in tetrahydrofuran (0.5 ml) were added dropwise at 0° C. and stirred for 10 minutes. After the consumption of the compound (15-2), water was added and the mixture was extracted with ethyl acetate. The organic layer was washed with water, and then the solvent was evaporated under reduced pressure. The obtained residue was purified by silica gel column chromatography to afford the compound (15-3)(68 mg) as a mixture of diethyl hydrazodicarboxylate.

Step 3

To the compound (15-3)(68 mg) as a mixture of diethyl hydrazodicarboxylate, 4 mol/L in hydrochloric acid in 1,4-dioxane solution (1 ml) was added, then the mixture was stirred at room temperature for 16 hours. After the consumption of the compound (44), the reaction solvent was evaporated under reduced pressure. The obtained residue was crystallized from 2-propanol/diethyl ether to afford the compound (1135)(36 mg).

$^1$H-NMR (DMSO-$d_6$): 1.30 (3H, d, J=6.4 Hz), 1.31 (3H, d, J=6.4 Hz), 1.65 (3H, s), 2.04-2.11 (1H, m), 2.50-2.64 (2H, m), 3.12-3.16 (1H, m), 4.61 (1H, sep, J=6.4 Hz), 6.66 (1H, t, J=2.0 Hz), 7.48 (1H, t, J=2.0 Hz), 7.60 (1H, t, J=2.0 Hz), 8.16 (1H, dd, J=8.4, 0.8 Hz), 8.22 (1H, dd, J=8.4, 2.4 Hz), 8.79 (1H, dd, J=2.4, 0.8 Hz), 10.33 (1H, s), 10.72 (1H, s).

Example 16

The Synthesis of Compound 161

[Chemical formula 63]

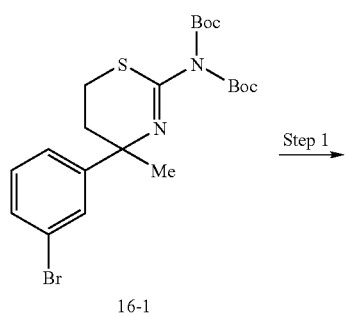

16-1

→ Step 1

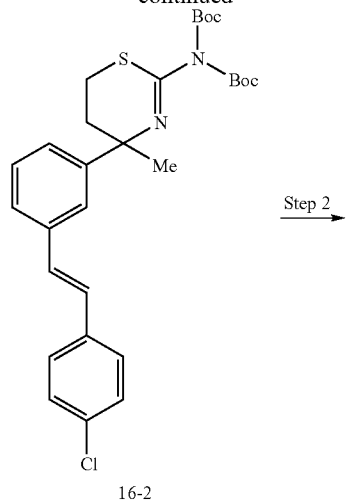

16-2

→ Step 2

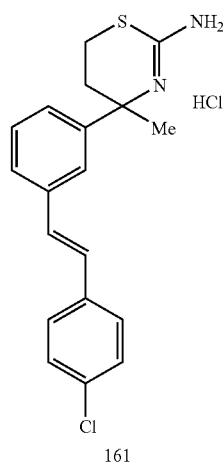

161

Step 1

The compound (16-1)(200 mg), palladium acetate (4.7 mg), and tri-(o-tolyl)phosphine (12.5 mg), were dissolved into N,N-dimethylformamide (2 ml) under nitrogen atmosphere, then n-butylamine (0.196 ml), and p-chlorostyrene (0.074 ml) were added at room temperature with stirring, then the solution was warmed to 80° C., and stirred for 3 hours. After the consumption of the compound (16-1)(checked by TLC), the reaction mixture was cooled to room temperature, and saturated ammonium chloride solution was added to the mixture. The mixture was extracted with ethyl acetate, the organic layer was washed with water and brine, and dried over magnesium sulfate, and then the solvent was evaporated under reduced pressure. The obtained residue was purified by silica gel column chromatography to afford the compound (16-2)(213.1 mg).

$^1$H-NMR (CDCl$_3$, 400 MHz): 1.54 (18H, B), 1.64 (3H, s), 1.96 (1H, ddd, J=13.7, 9.1, 4.0 Hz) 2.10 (1H, ddd, J=13.7, 8.1, 3.4 Hz) 2.86 (1H, ddd, J=12.3, 9.1, 3.4 Hz), 3.03 (1H, ddd, J=12.3, 8.1, 4.0 Hz), 7.08 (1H, d, J=16.4 Hz) 7.15 (1H, d, J=16.4 Hz), 7.27-7.40 (5H, m) 7.44 (2H, d, J=8.8 Hz), 7.58 (1H, s)

Step 2

The compound (16-2)(213 mg) was dissolved into 4 mol/L hydrochloric acid in 1,4-dioxane (5 ml) under cooling with ice-water bath, then the mixture was warmed to room temperature and stirred for 63 hours. After the consumption of the compound (16-2)(checked by LC/MS), the reaction mixture was diluted with diethyl ether. The generated crystal was collected by filtration, and washed with diethyl ether to afford the compound (161)(108.6 mg).

$^1$H-NMR (DMSO-d$_6$, 400 MHz): 1.69 (3H, s), 2.08-2.18 (1H, m), 2.56-2.70 (2H, m), 3.13-3.20 (1H, m), 7.23 (1H, d, J=8.0 Hz), 7.31 (1H, d, J=17.0 Hz), 7.35 (1H, d, J=17.0 Hz), 7.45 (2H, d, J=8.6 Hz), 7.46 (1H, t, 7.6 Hz), 7.59 (1H, d, J=2.0 Hz), 7.61-7.64 (1H, m), 7.64 (2H, d, J=8.6 Hz), 8.53-9.50 (21, br), 10.67 (1H, br 9)

Example 17

The Synthesis of Compound 597

[Chemical formula 64]

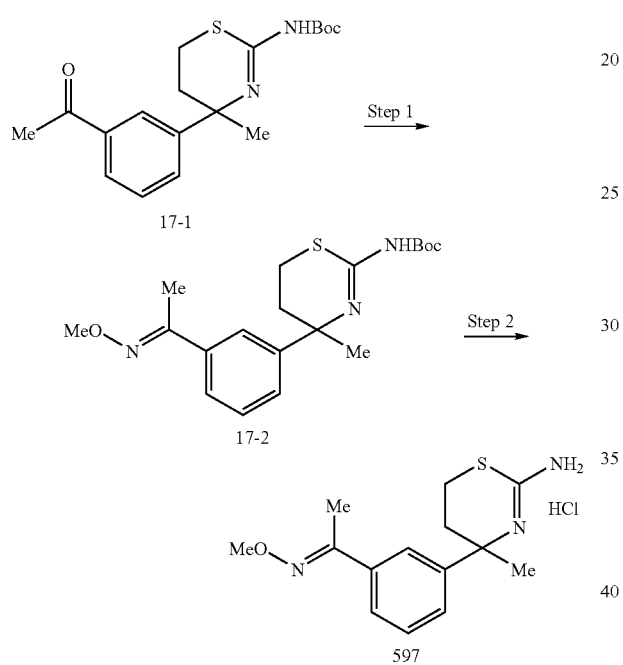

Step 1

The solution of compound (17-1)(135 mg), O-methxylhydroxylamine hydrochloride (39 mg), and potassium acetate (27 mg) in methanol (3 ml) was stirred at room temperature for 16 hours, then water was added. The mixture was extracted with dichloromethane, the organic layer was dried over anhydrous sodium sulfate, then the solvent was evaporated under reduced pressure. The obtained residue was purified by silica gel column chromatography to afford the compound (17-2)(110 mg).

$^1$H-NMR (CDCl$_3$): 1.51 (9H, s), 1.70 (3H, s), 2.14 (1H, ddd, J=14.4, 11.4, 3.4 Hz), 2.22 (3H, s), 2.48 (1H, m), 2.65 (1H, dt, J=12.6, 11.4 Hz), 2.78 (1H, ddd, J=12.6, 6.6, 3.4 Hz), 4.00 (3H, s), 7.30 (1H, d, J=7.8 Hz), 7.38 (1H, d, J=7.8 Hz), 7.54-7.57 (2H, m).

Step 2

To the compound (17-2)(110 mg), 4 mol/L hydrochloric acid in 1,4-dioxane (4.5 ml) solution was added and stirred for 4 days at room temperature, then the reaction solvent was evaporated under reduced pressure. The obtained residue was crystallized from methanol/diethyl ether to afford compound (597)(65 mg).

$^1$H-NM (DMSO-d$_6$): 1.67 (3H, s), 2.08-2.15 (1H, m), 2.20 (3H, s), 2.56-2.64 (2H, m), 3.14-3.17 (1H, m), 3.92 (3H, s), 7.37 (1H, d, J=8.0 Hz), 7.48 (1H, d, J=8.0 Hz), 7.66 (1H, s), 7.62 (1H, d, J=8.0 Hz).

The other compounds were synthesized in the same way. The structural formulas and physical constants are shown below.

TABLE 1

| Compound No. | Chemical structure |
|---|---|
| 1 | 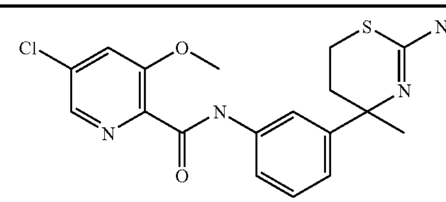 |
| 2 | 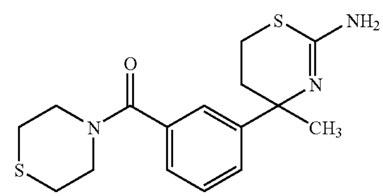 |
| 3 | 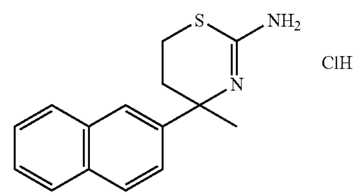 |
| 4 | 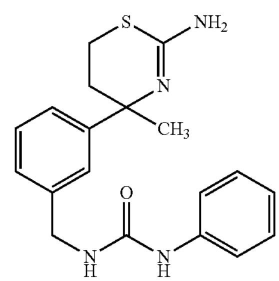 |
| 5 | 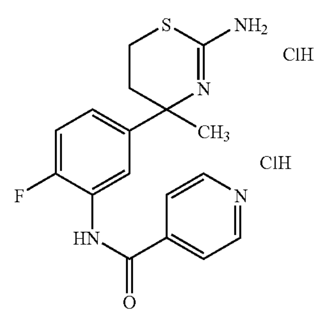 |
| 6 | 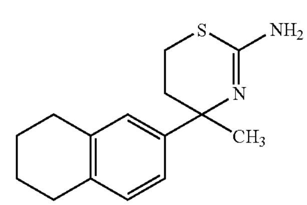 |

TABLE 1-continued
| Compound No. | Chemical structure |
|---|---|
| 7 | 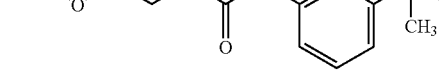 |
| 8 | 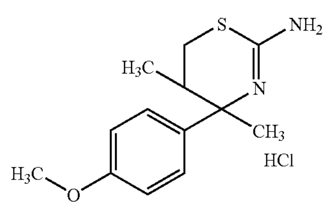 |
| 9 | 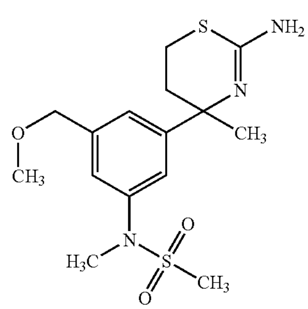 |
TABLE 2
| | |
|---|---|
| 10 | 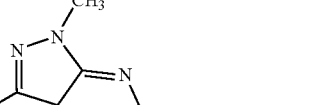 |
| 11 | 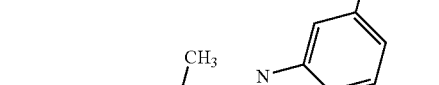 |
| 12 | 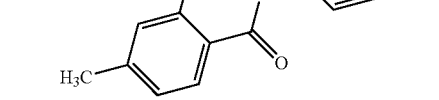 |
| 13 |  |
| 14 | |
| 15 | |
| 18 | |

TABLE 2-continued
| 17 | 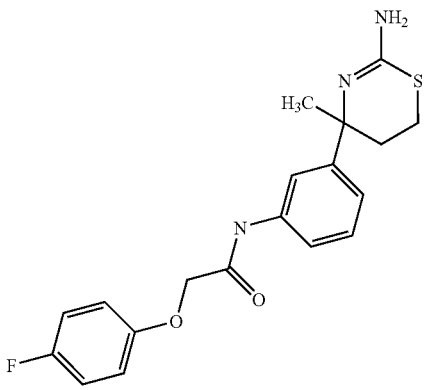 |
| --- | --- |
| 18 | 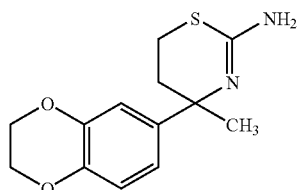 |
TABLE 3
| 19 | 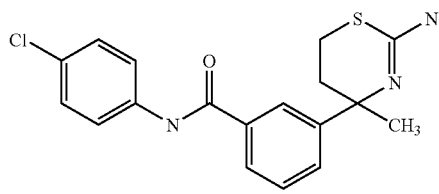 |
| --- | --- |
| 20 | |
| 21 | 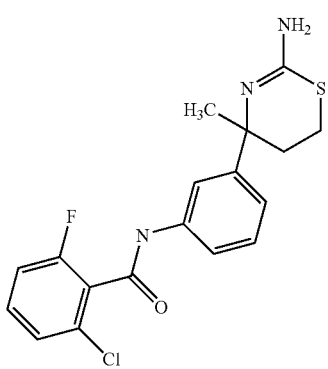 |
TABLE 3-continued
| 22 | 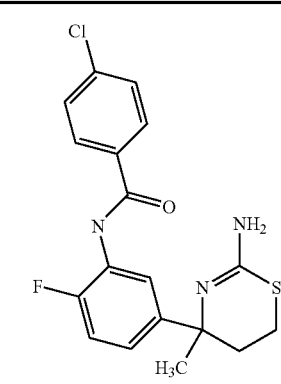 |
| --- | --- |
| 23 | 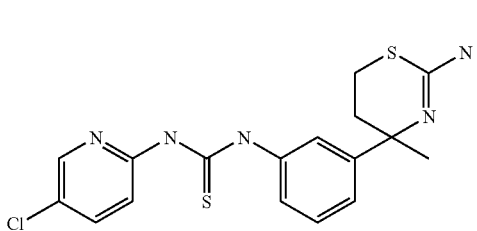 |
| 24 | 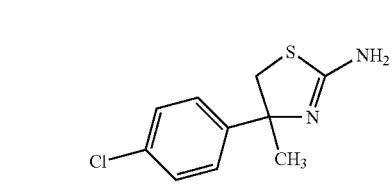 |
| 25 | 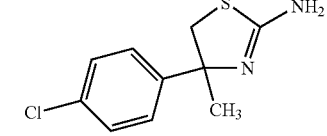 |
| | 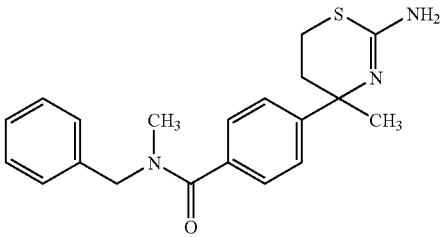 |
| 26 | 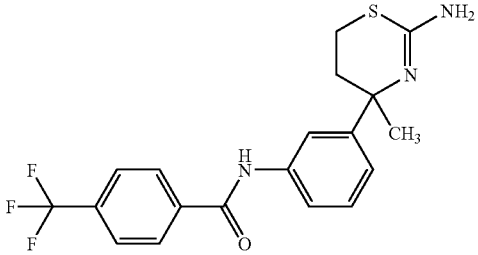 |
| 27 | 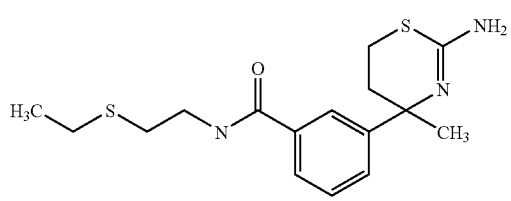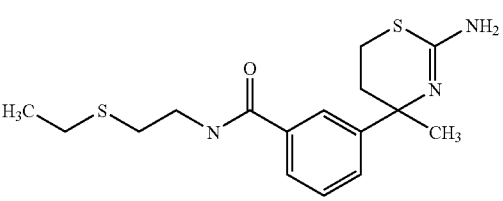 |

TABLE 3-continued
28 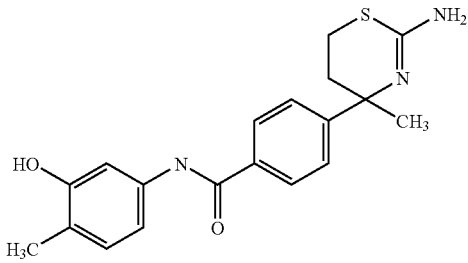
TABLE 4
29 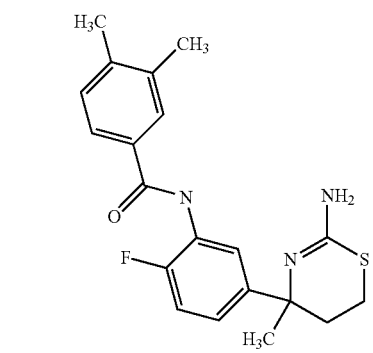
30 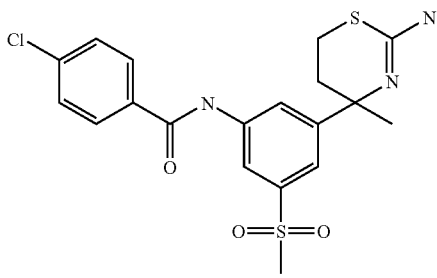
31 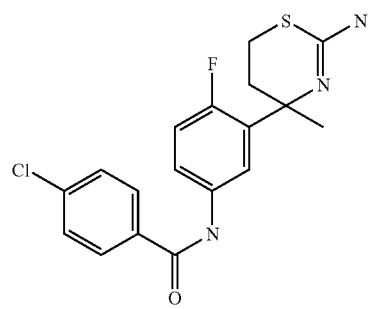
32 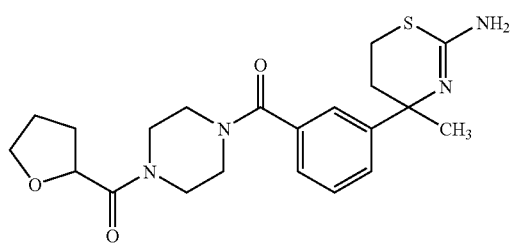
TABLE 4-continued
33 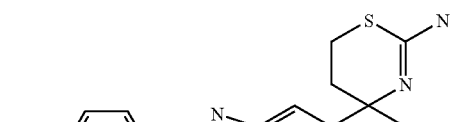
34 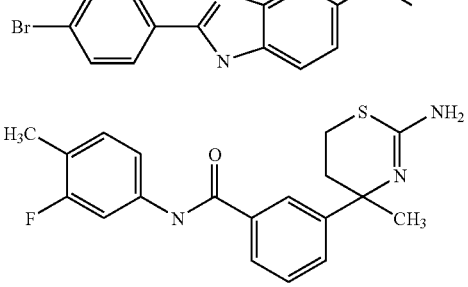
35 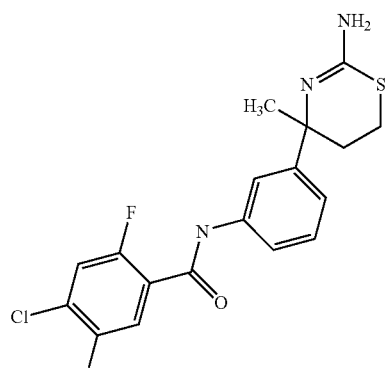
36 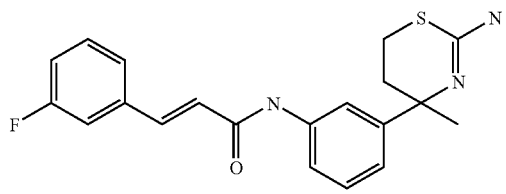
37 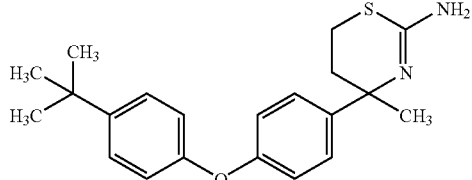
38 
39 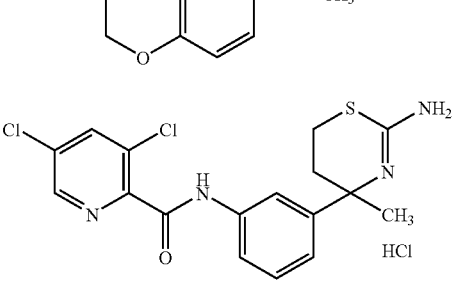
HCl

TABLE 5
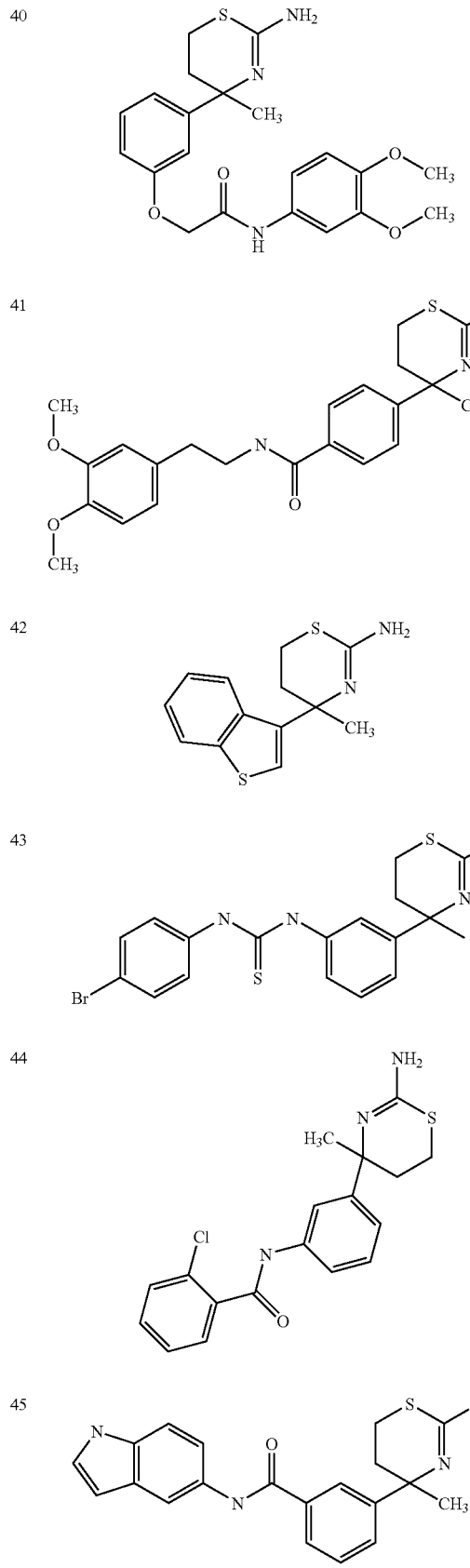
TABLE 5-continued
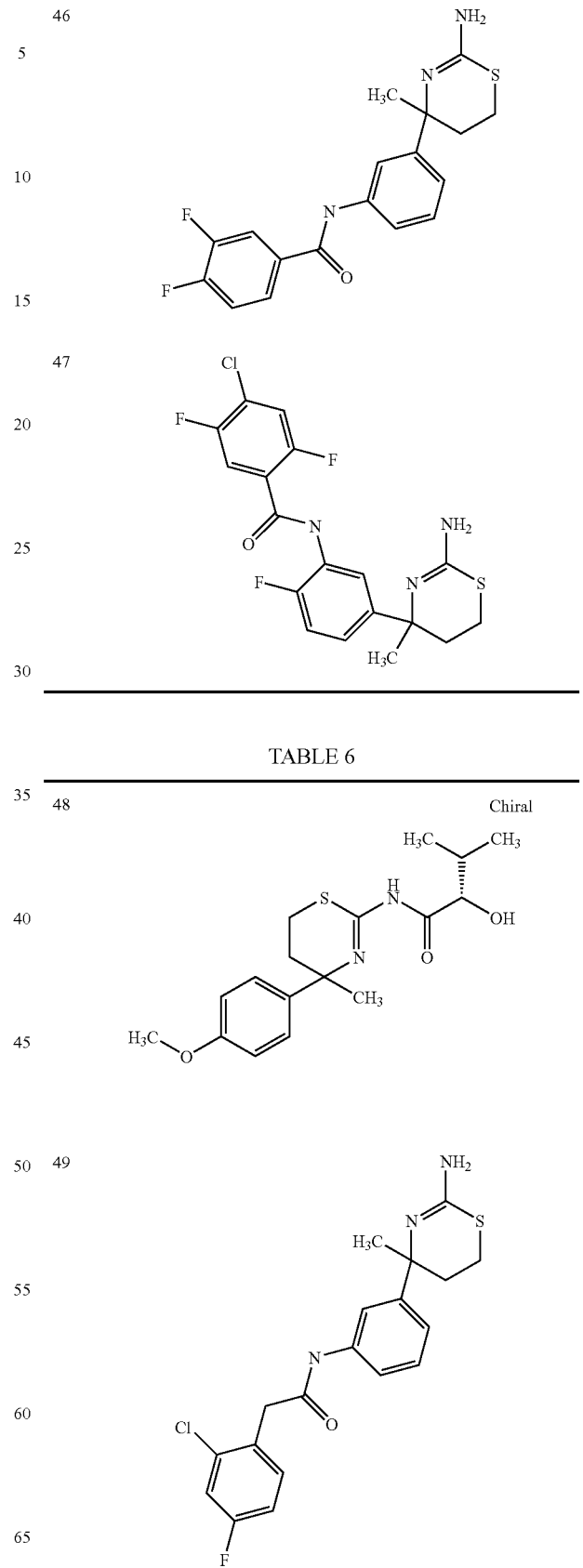

TABLE 6-continued
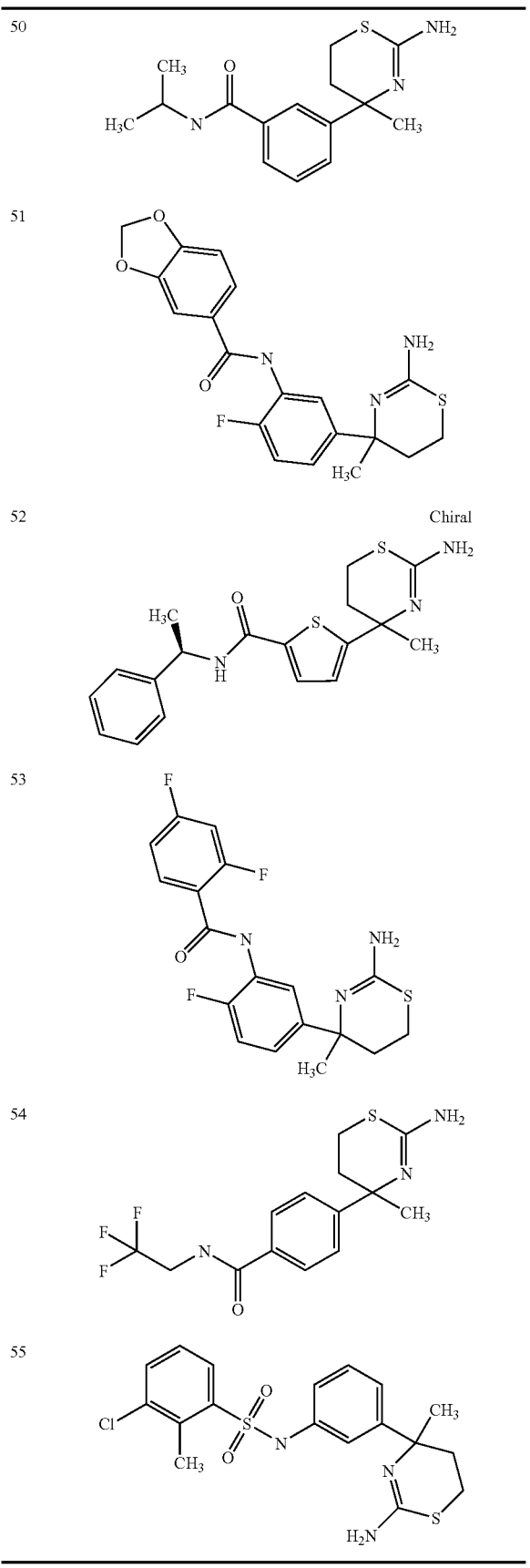
TABLE 7
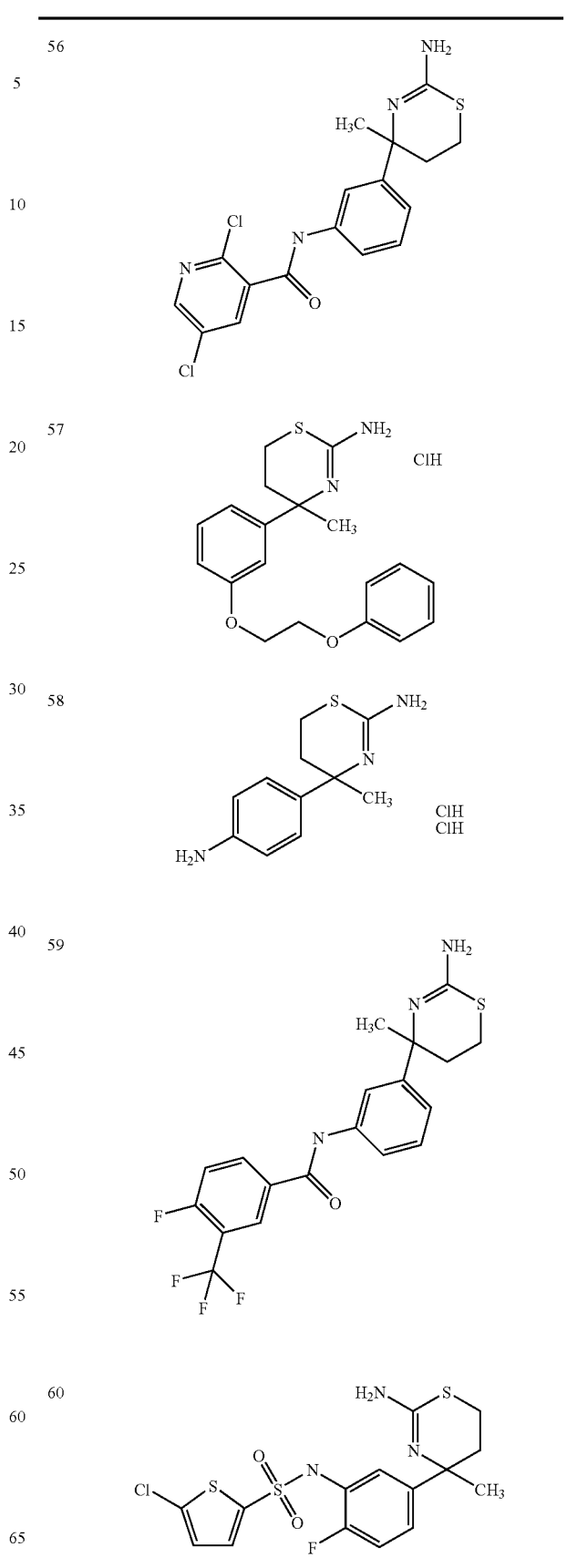

TABLE 7-continued
61 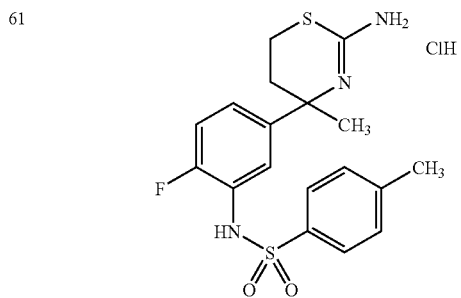
62 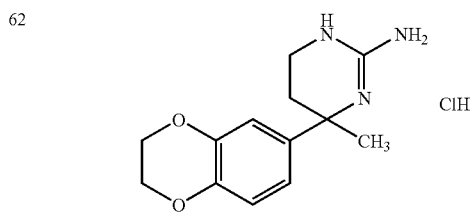
63 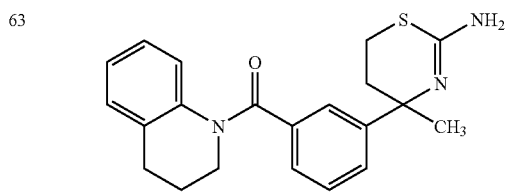
64 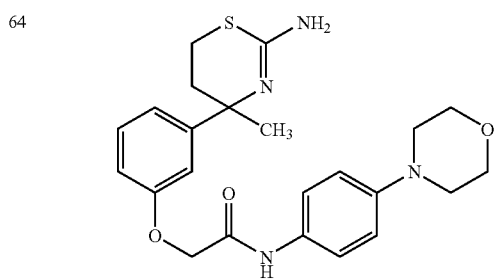
65 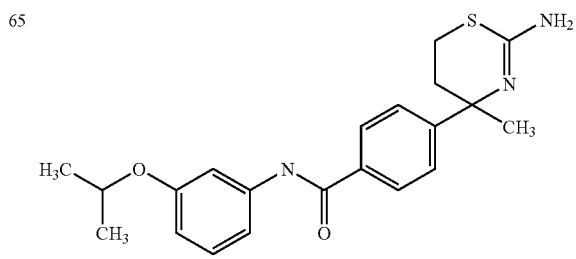
TABLE 8
66 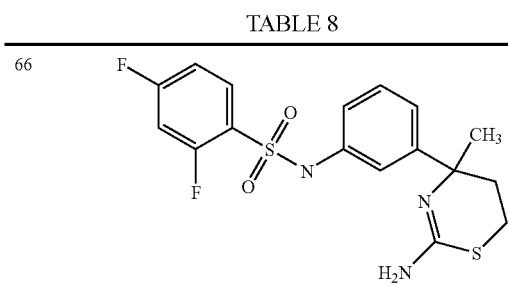
TABLE 8-continued
67 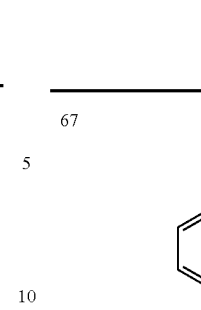
68 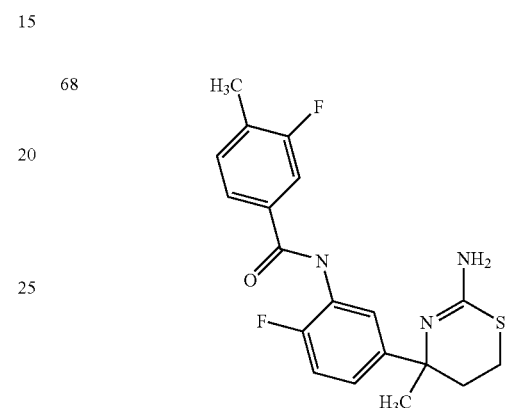
69
70
71 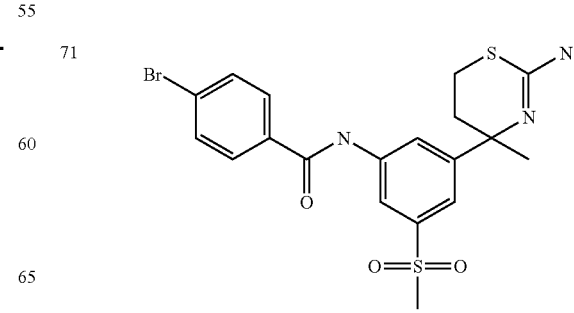

TABLE 8-continued
| 72 | 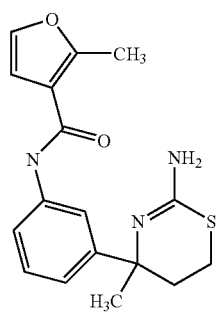 |
|---|---|
| 73 | 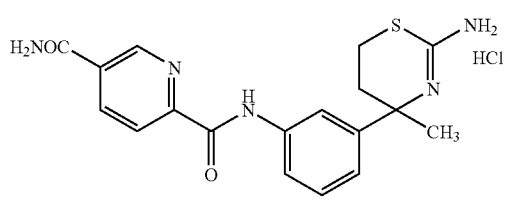 |
| 74 | 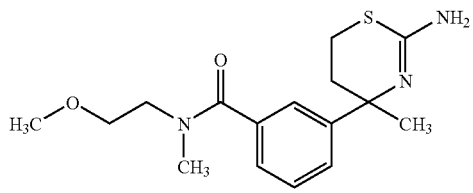 |
TABLE 9
| 75 | 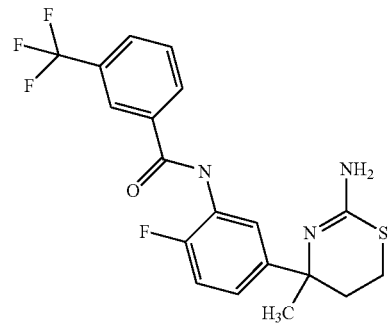 |
|---|---|
| 76 | 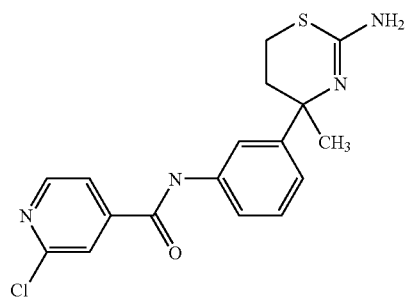 |
TABLE 9-continued
| 77 | 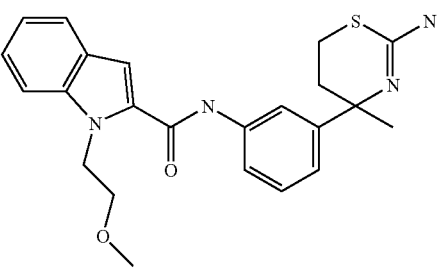 |
|---|---|
| 78 | 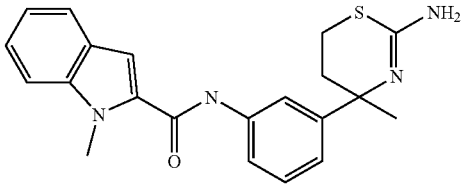 |
| 79 | 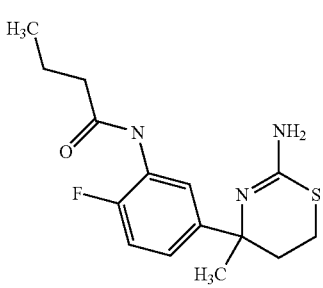 |
| 80 | 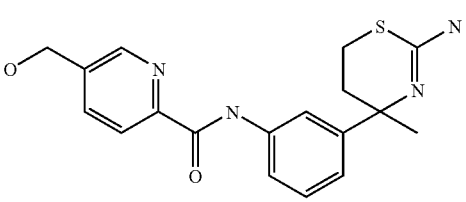 |
| 81 | 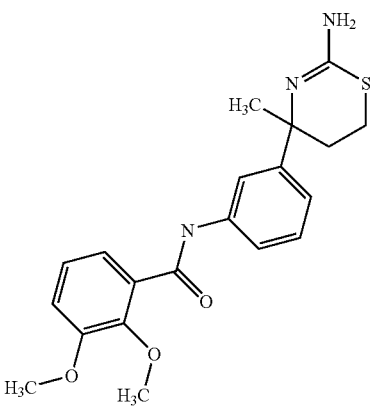 |

TABLE 9-continued
82 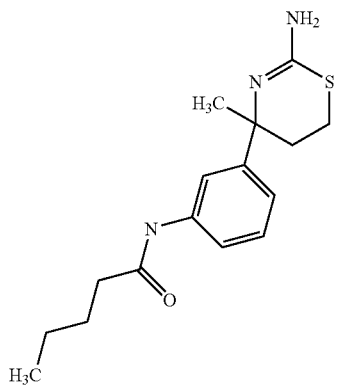
TABLE 10
83 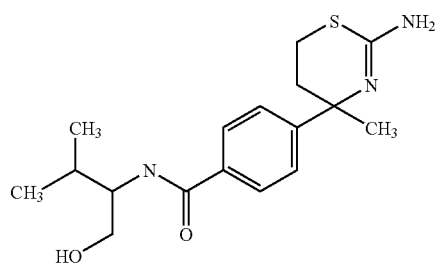
84 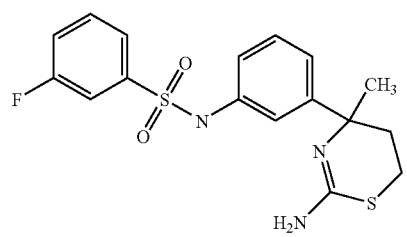
85 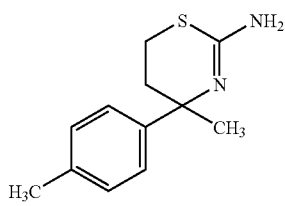
86 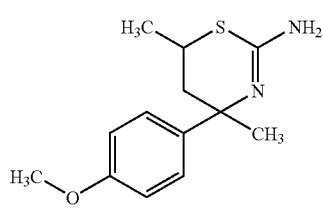
TABLE 10-continued
87 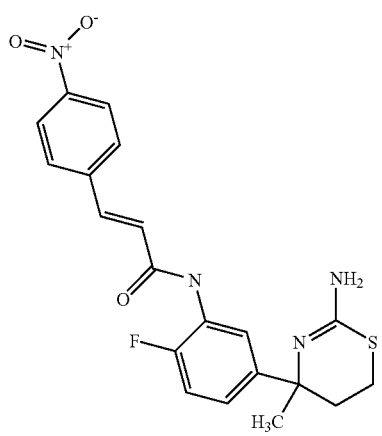
88 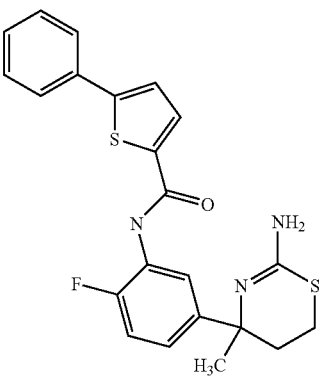
89 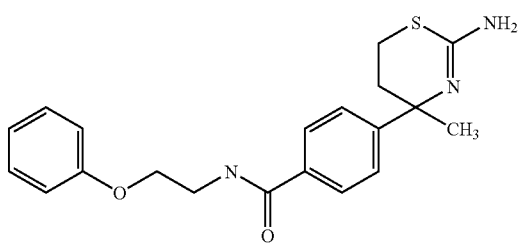
90 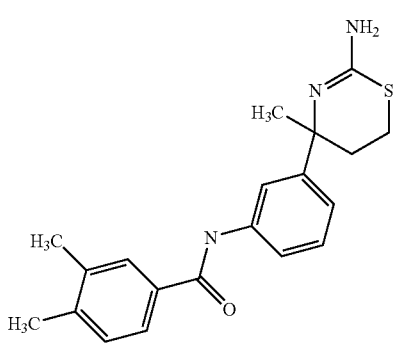

TABLE 10-continued
91 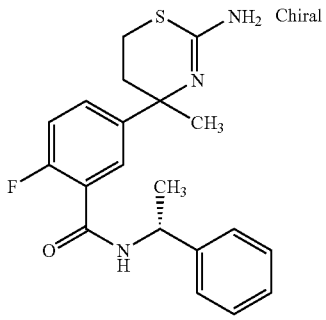 Chiral
TABLE 11
92 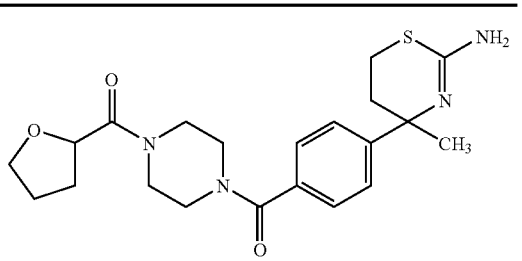
93 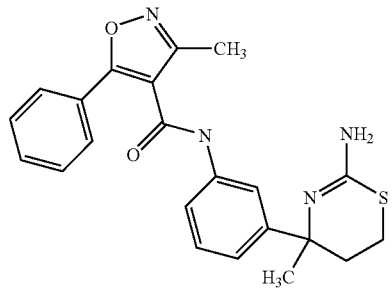
94 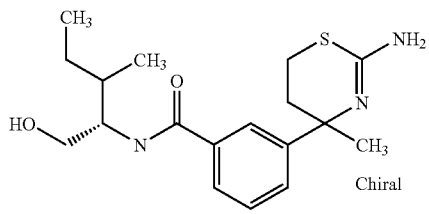 Chiral
95 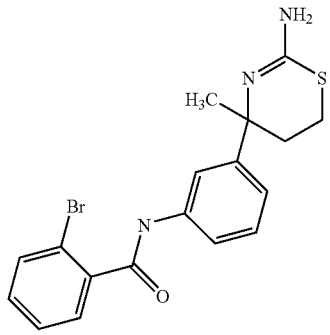
TABLE 11-continued
96 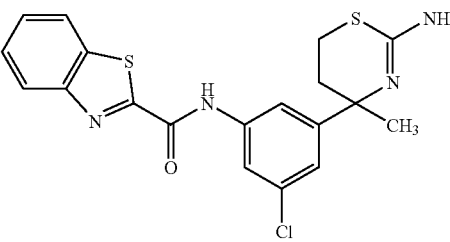
97 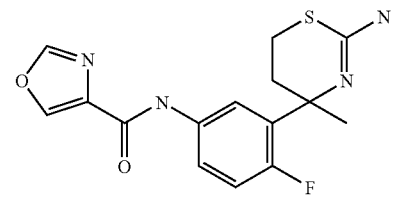
98 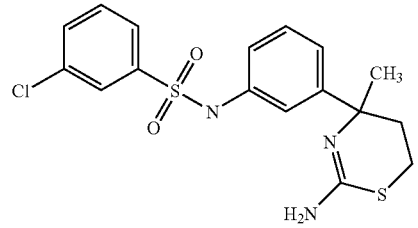
99 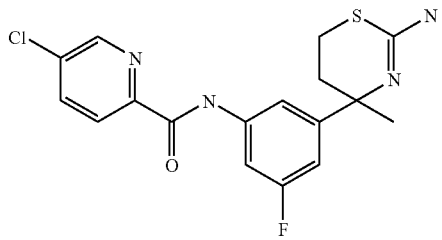
100 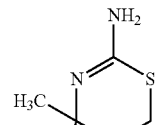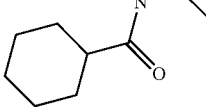
101 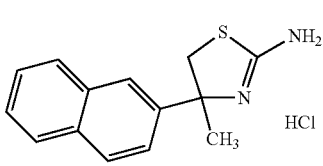 HCl TABLE 12
102 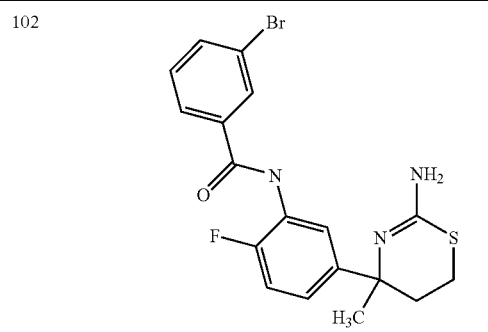
103 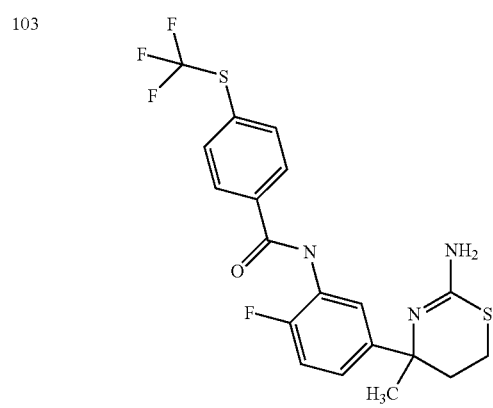
104 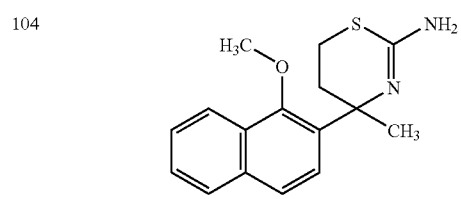
105 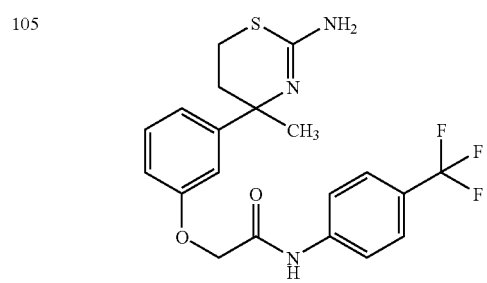
106 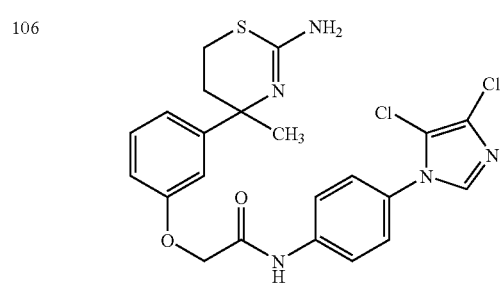
TABLE 12-continued
107 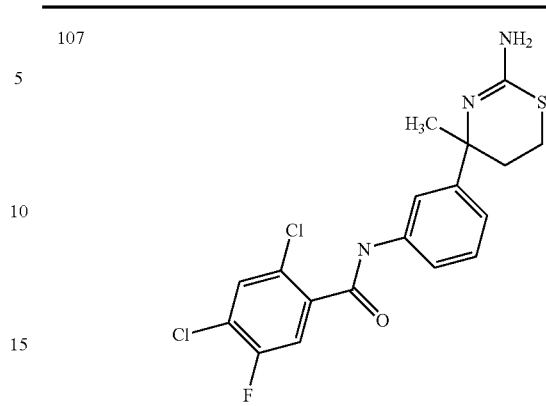
108 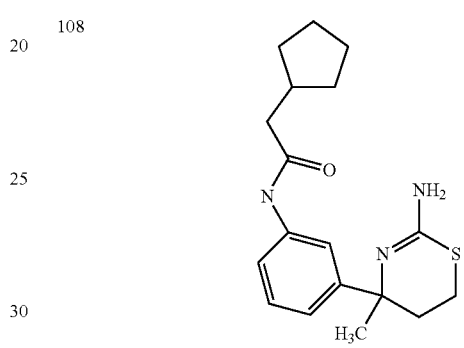
109 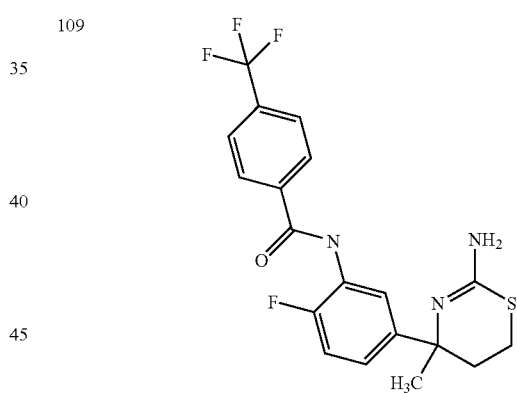
TABLE 13
110 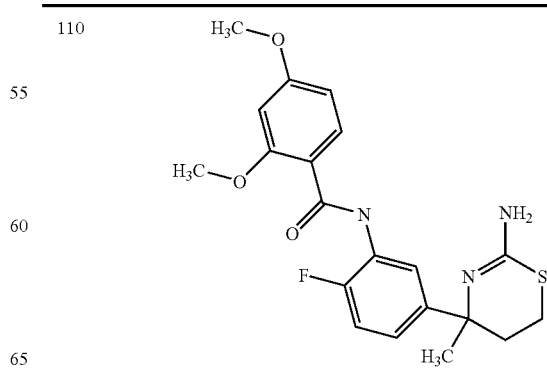

TABLE 13-continued
| | |
|---|---|
| 111 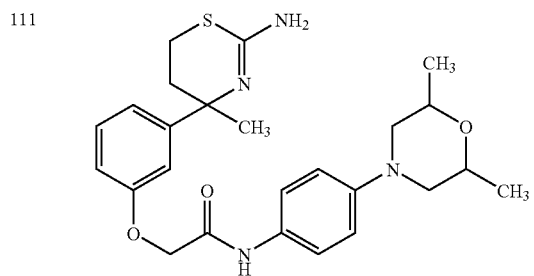 | 118 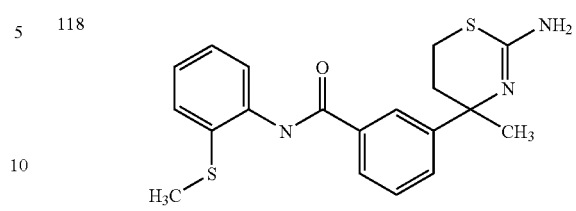 |
| 112 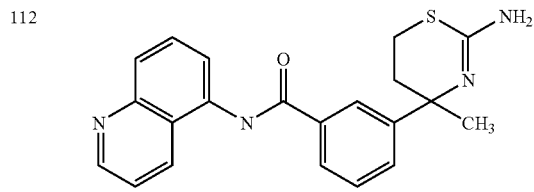 | 119 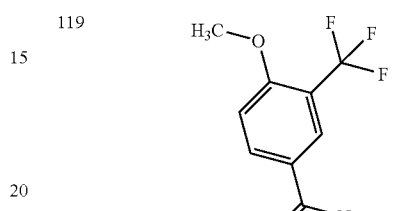 |
| 113 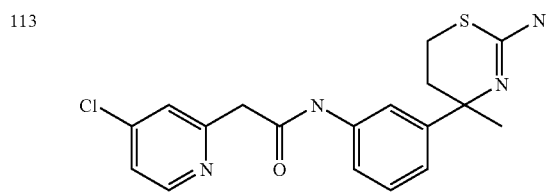 | |
| 114 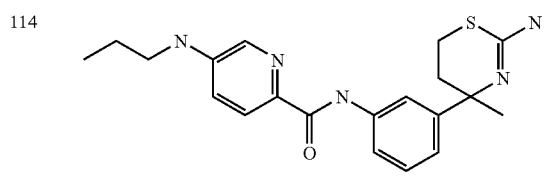 | TABLE 14 |
| 115 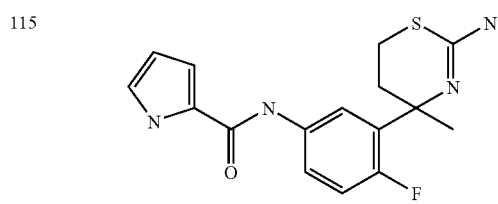 | 120 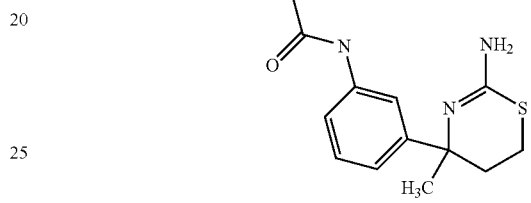 |
| 116 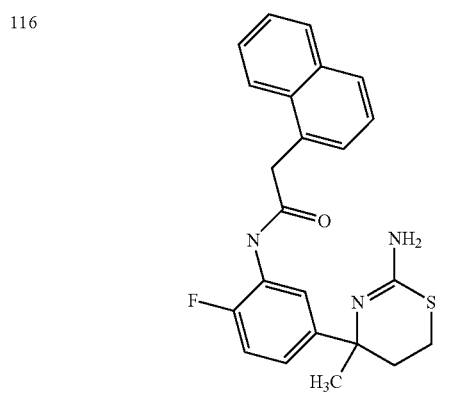 | 121 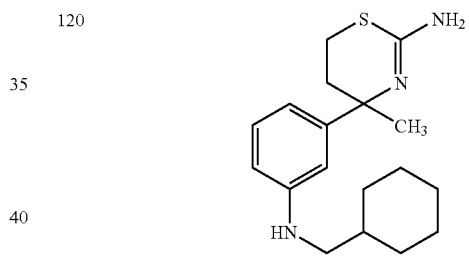 ClH |
| 117 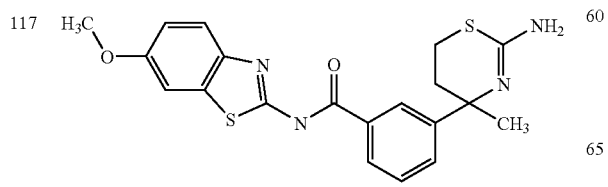 | 122 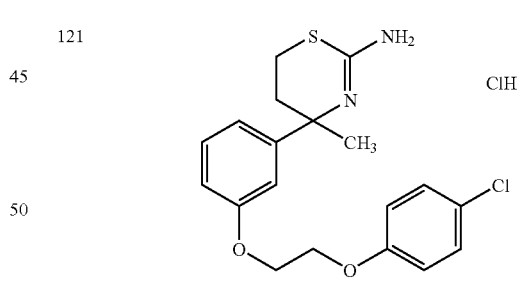 |

TABLE 14-continued
| 124 | 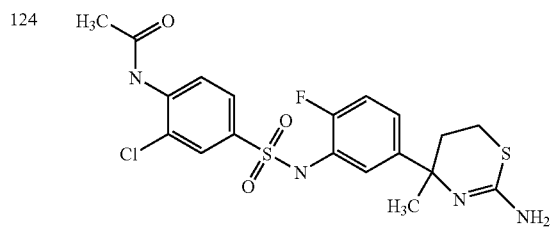 |
|---|---|
| 125 | 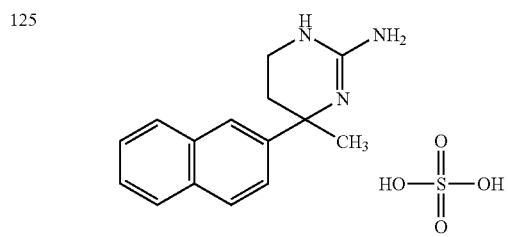 |
| 126 | 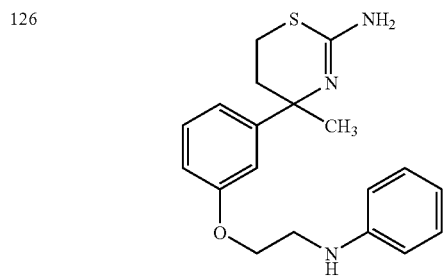 |
| 127 | 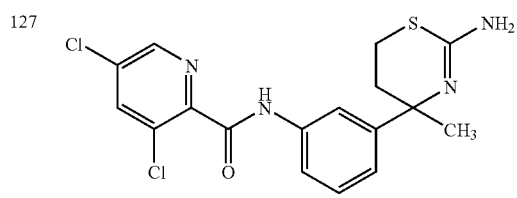 |
| 128 | 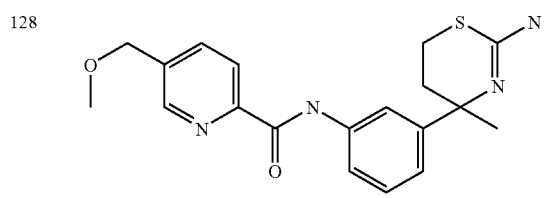 |
| 129 | 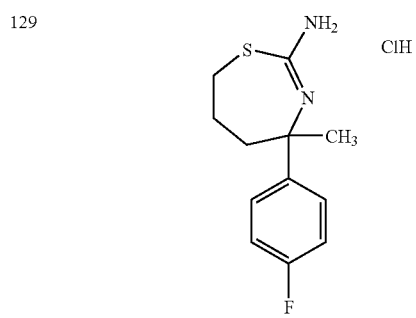 |
TABLE 14-continued
| 130 | 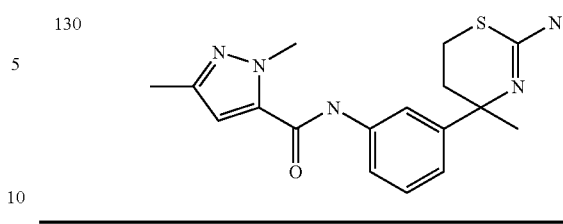 |
TABLE 15
| 131 | |
|---|---|
| 132 | 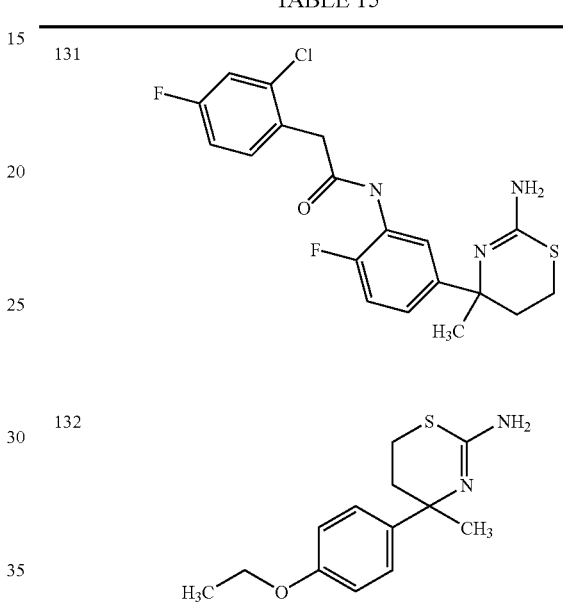 |
| 133 | |
| 134 | 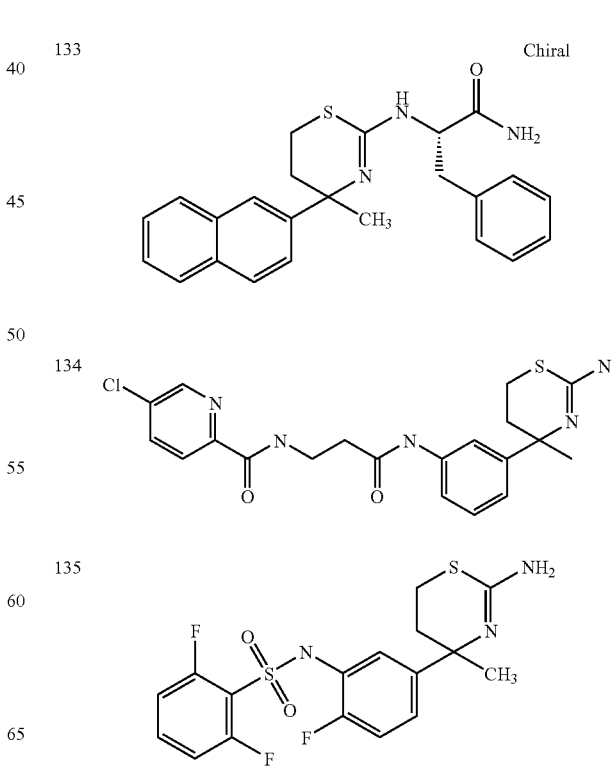 |
| 135 | |

TABLE 15-continued
136 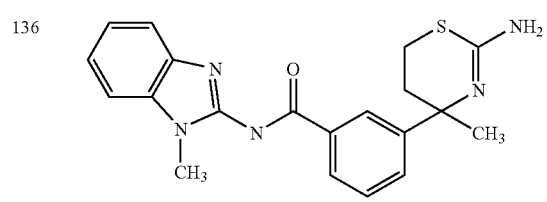
137 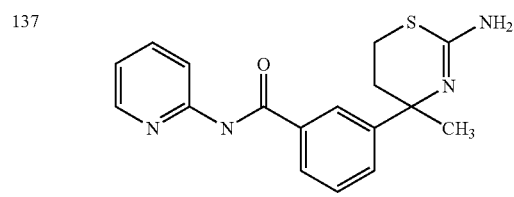
138 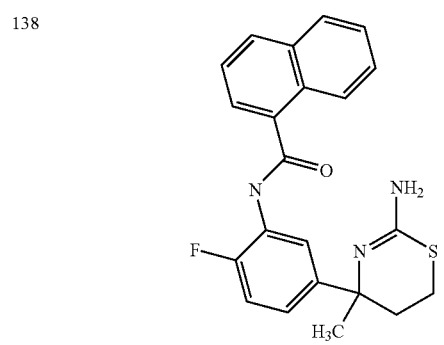
139 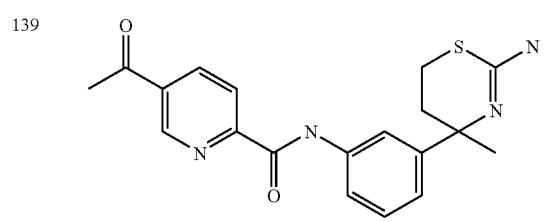
140 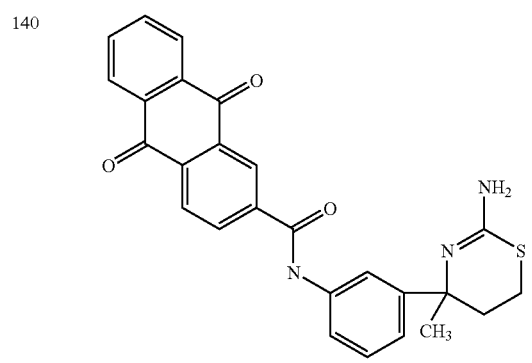
141 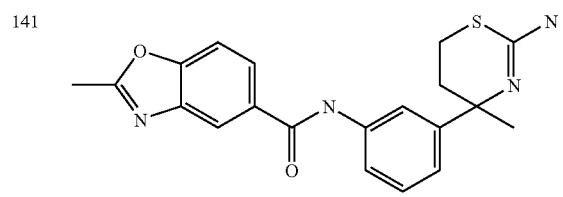
TABLE 16
142 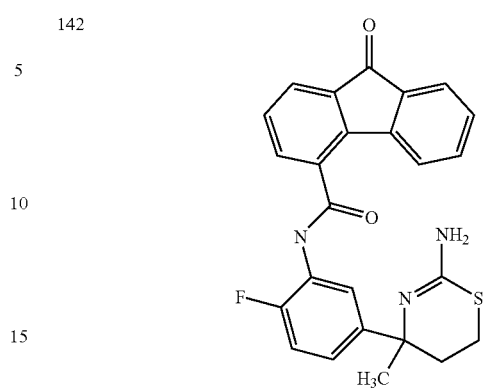
143 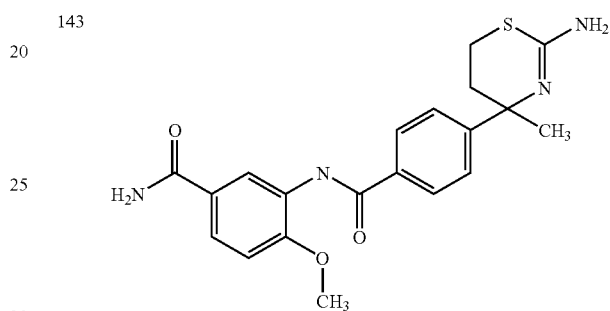
144 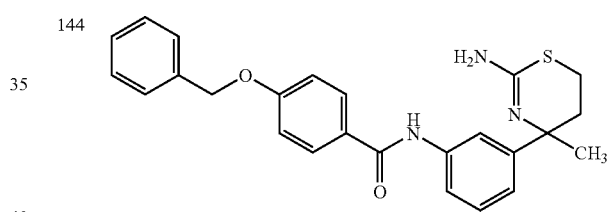
145 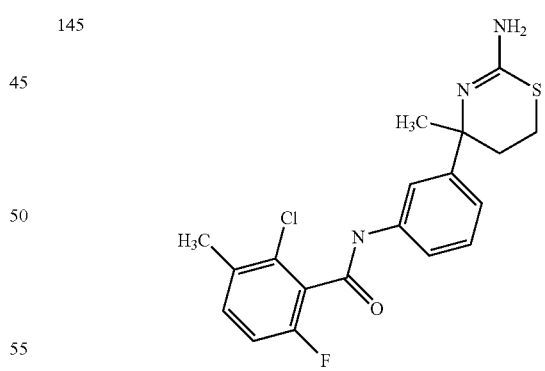
146 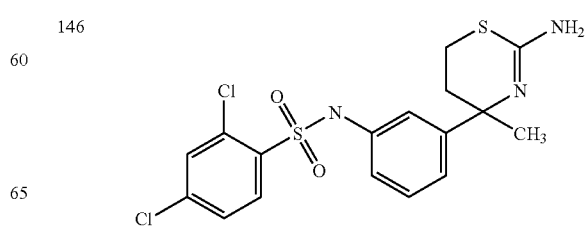

TABLE 16-continued
147 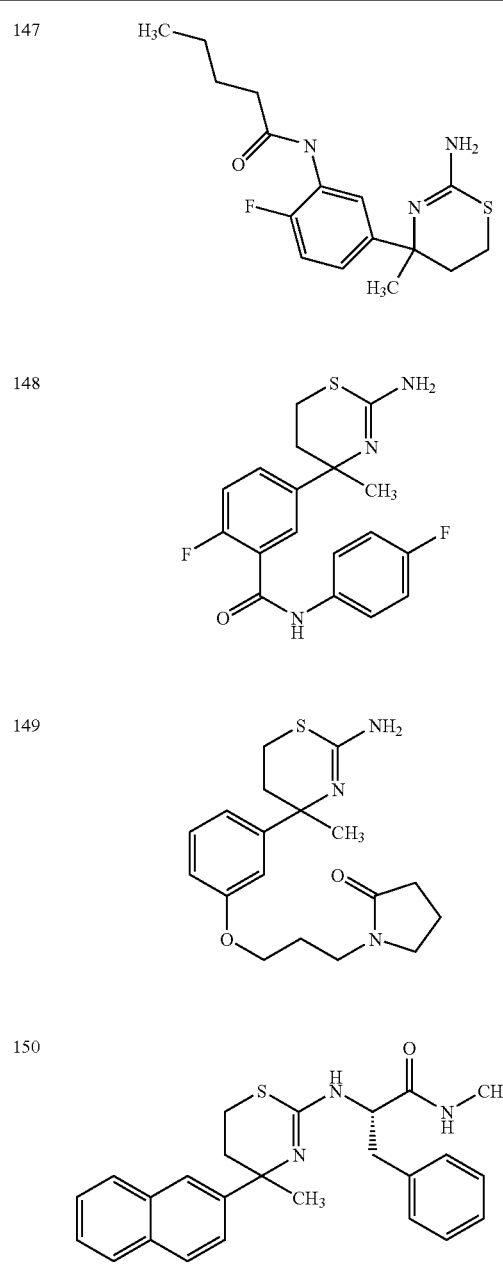
148
149
150 Chiral
TABLE 17
151
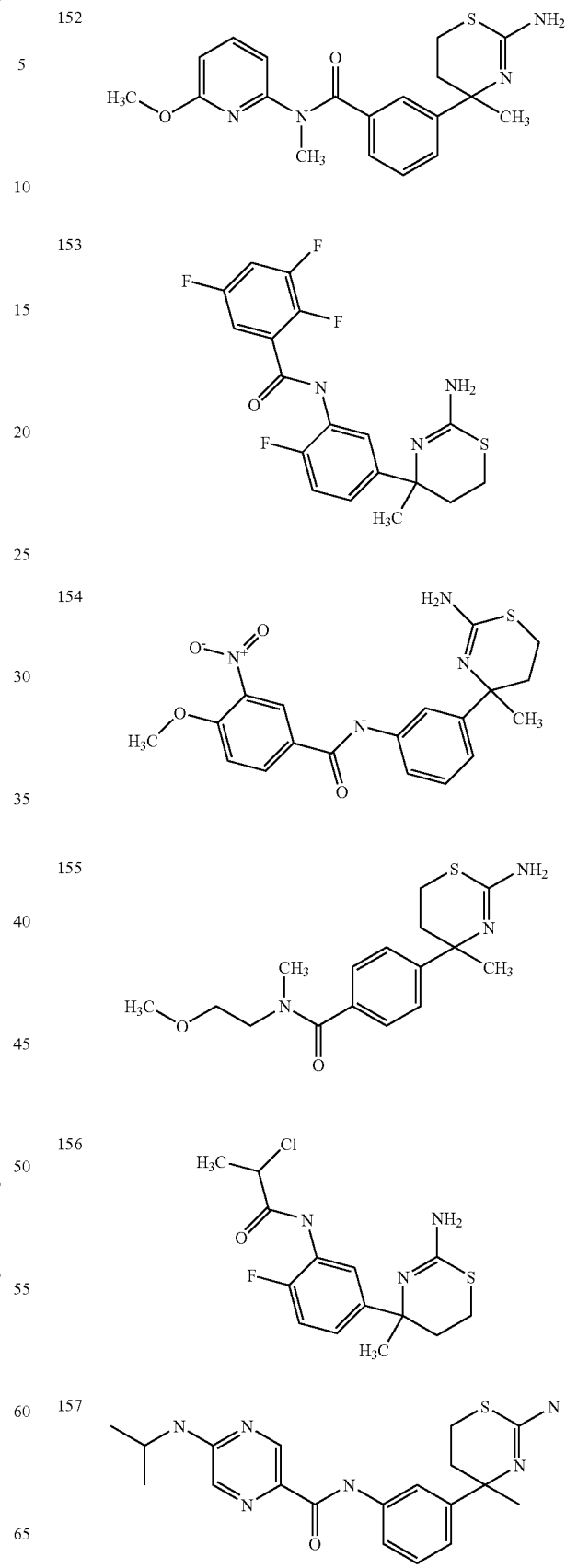
TABLE 17-continued
152
153
154
155
156
157

TABLE 17-continued
158 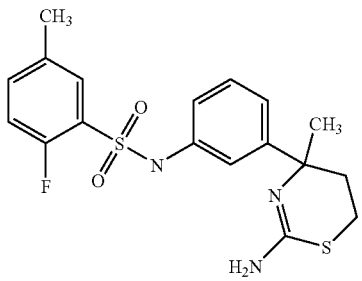
159 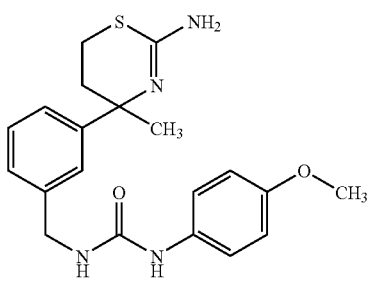
TABLE 18
160 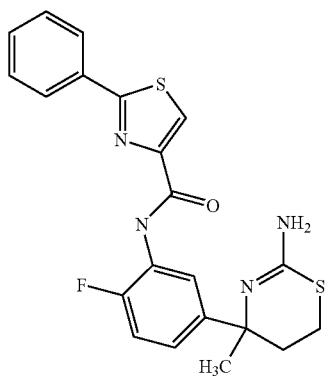
161 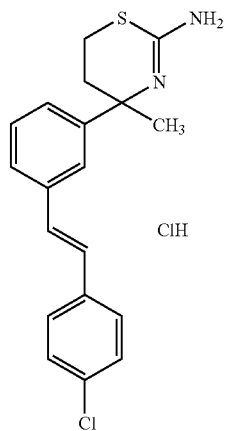
TABLE 18-continued
162 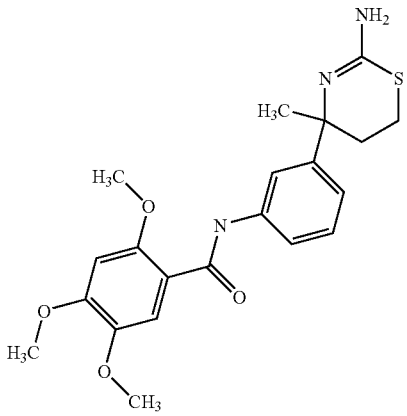
163 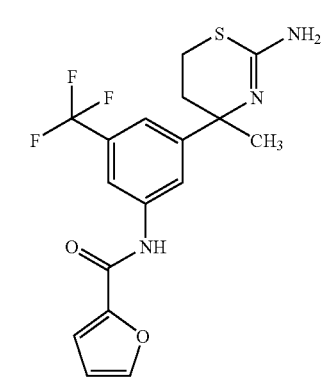
164 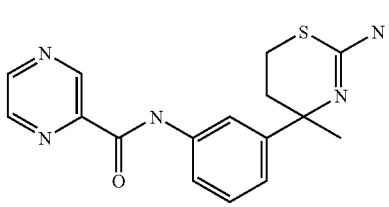
165 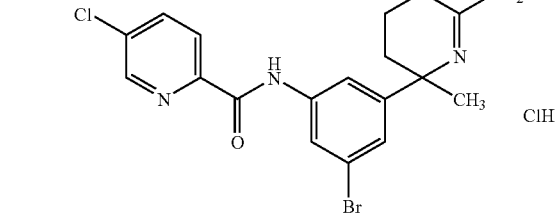
166 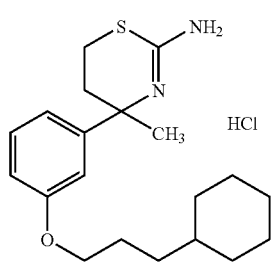

TABLE 19
167 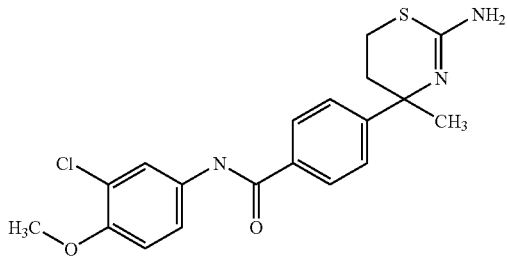
168 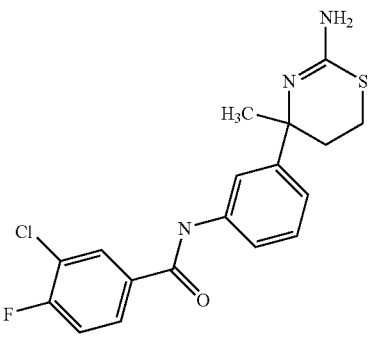
169 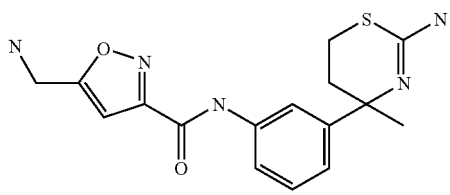
170 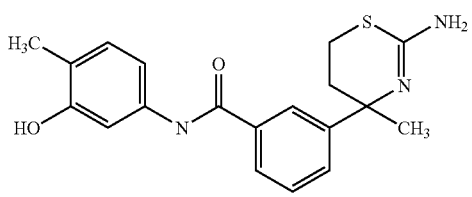
171 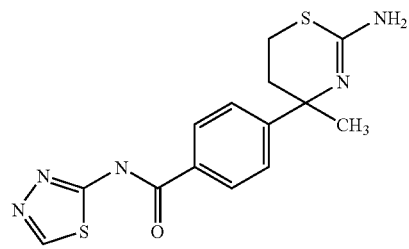
172 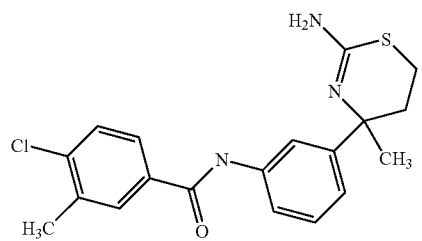
TABLE 19-continued
173 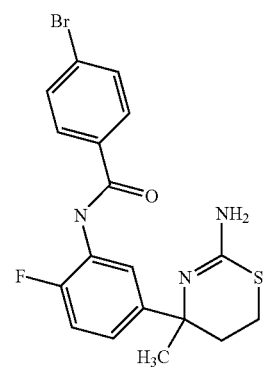
174 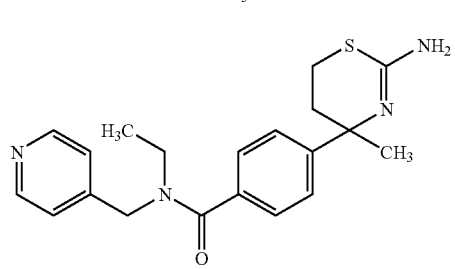
175 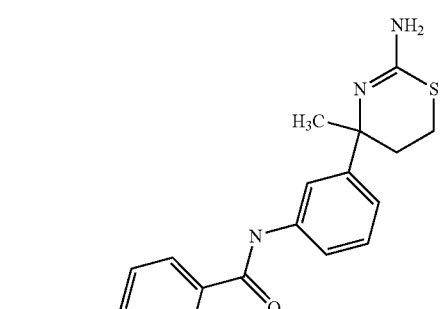
176 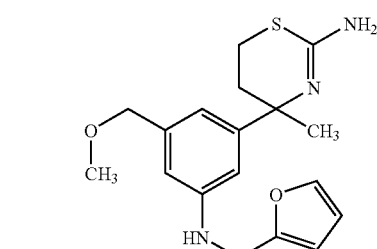
TABLE 20
177 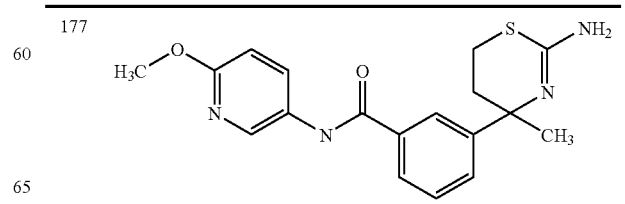

TABLE 20-continued
178 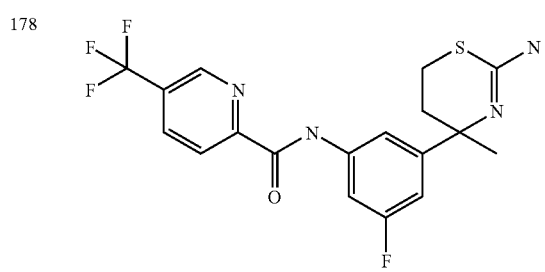
179 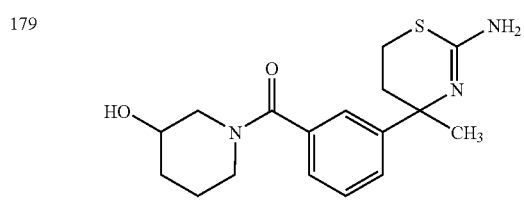
180 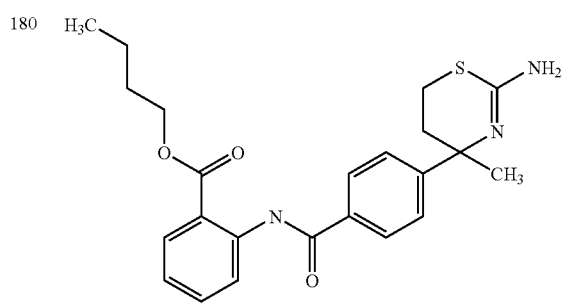
181 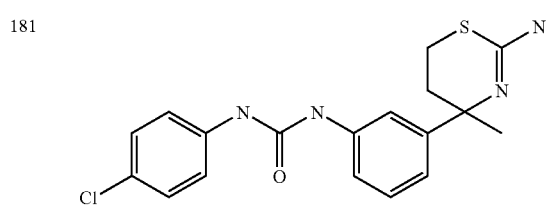
182 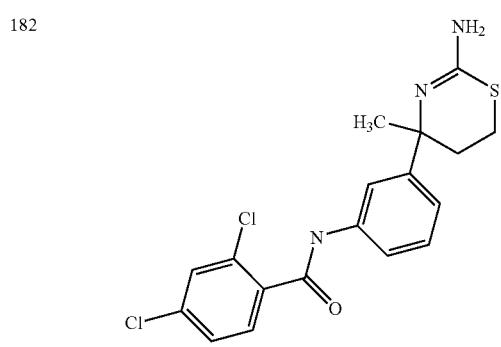
TABLE 20-continued
183 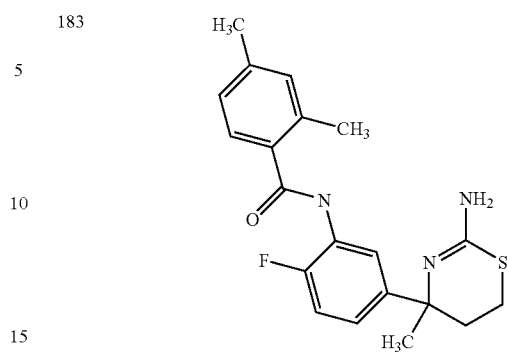
184 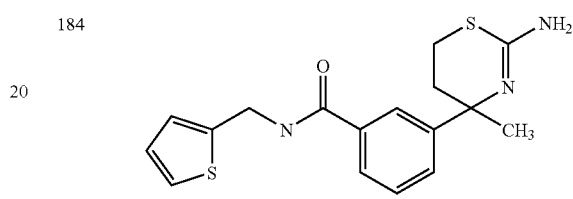
185 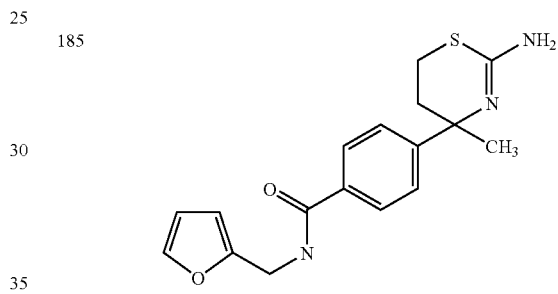
186 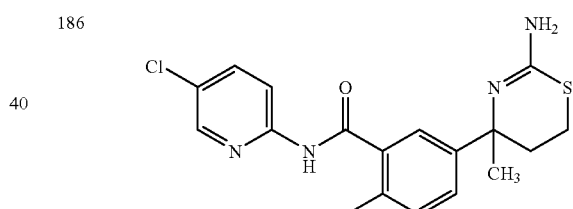
187 
188 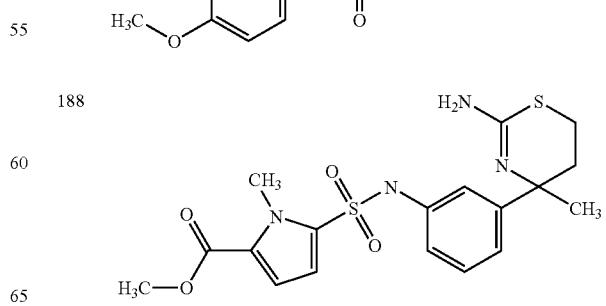

TABLE 21
189 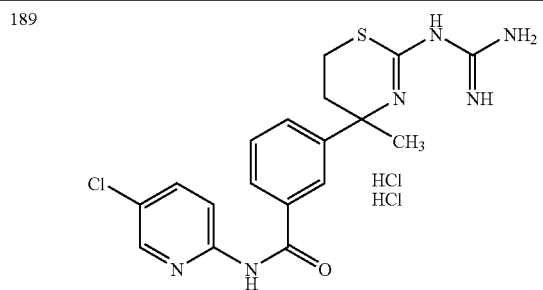 HCl HCl
190 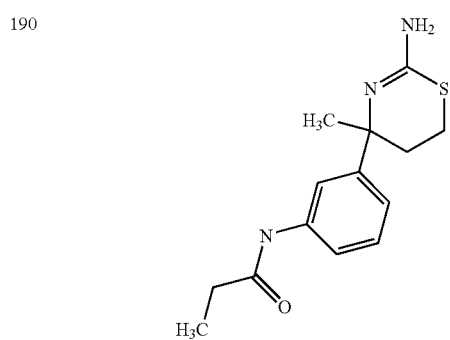
191 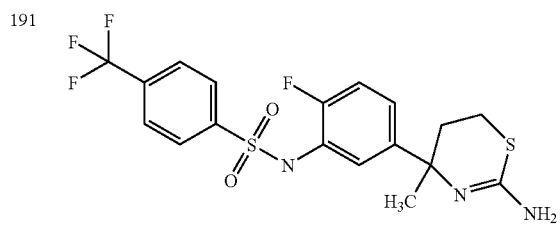
192 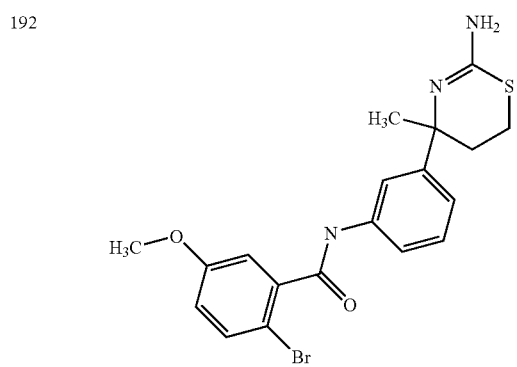
193 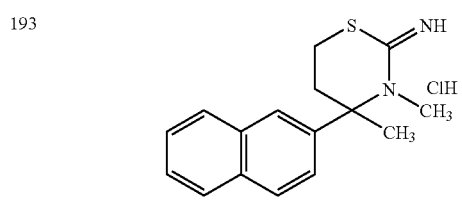
TABLE 21-continued
194 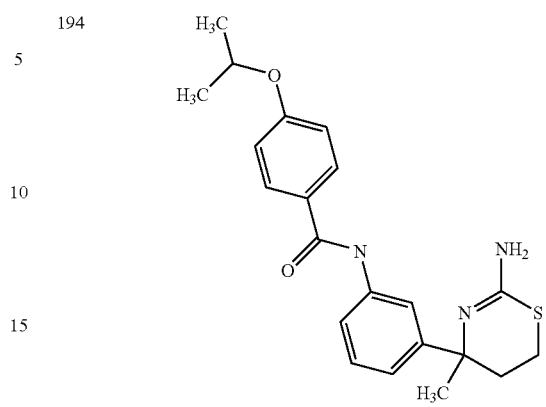
195 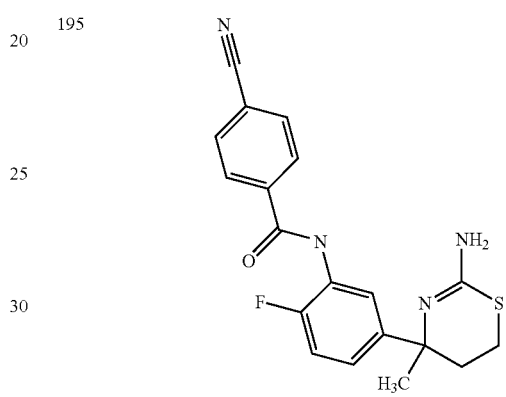
196 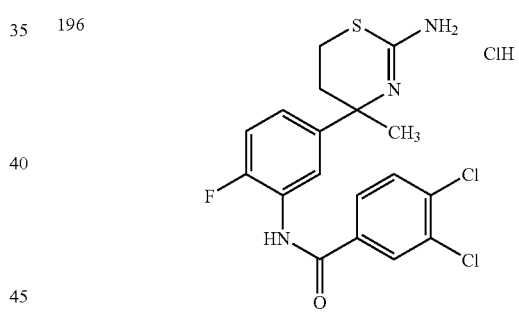 ClH
TABLE 22
197 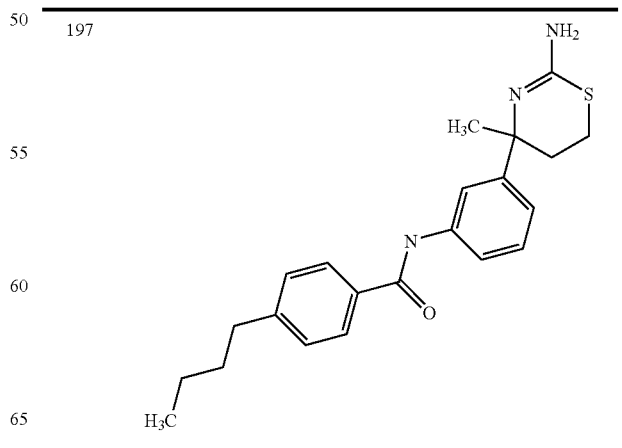

TABLE 22-continued
| | |
|---|---|
| 198 | 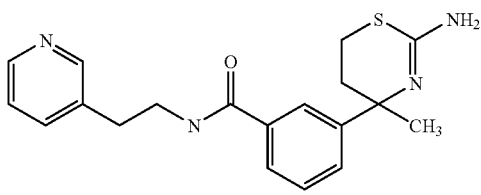 |
| 199 | 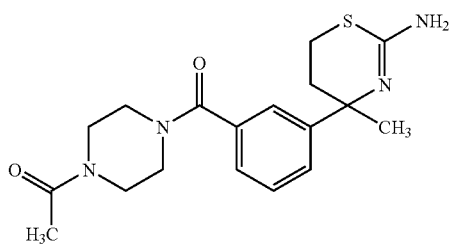 |
| 200 | 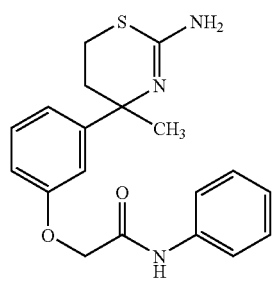 |
| 201 | 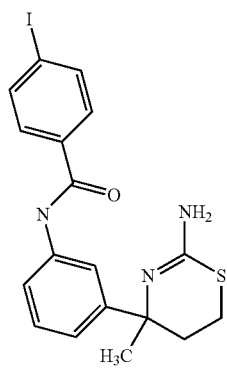 |
| 202 | 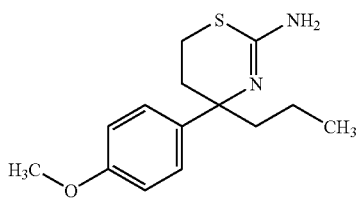 |
| 203 | 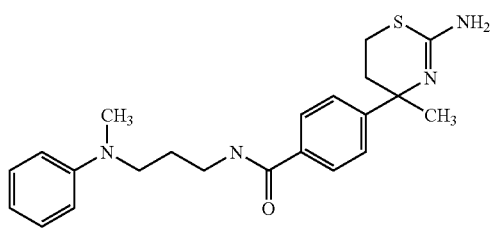 |
TABLE 22-continued
| | |
|---|---|
| 204 | 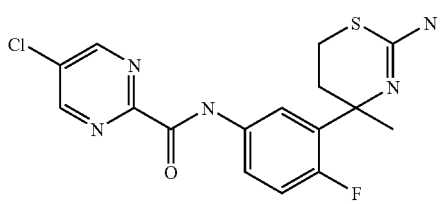 |
| 205 | 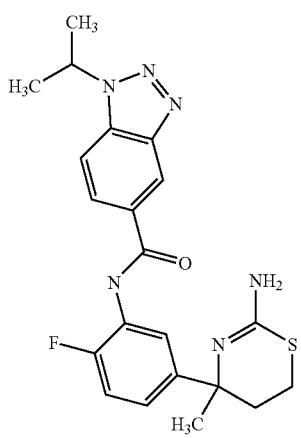 |
| 206 | 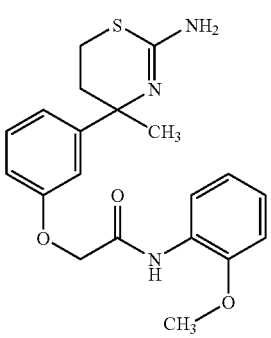 |
TABLE 23
| | |
|---|---|
| 207 | 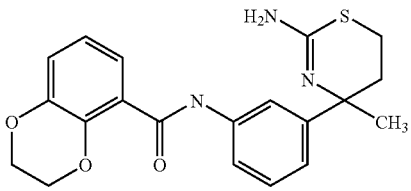 |
| 208 | 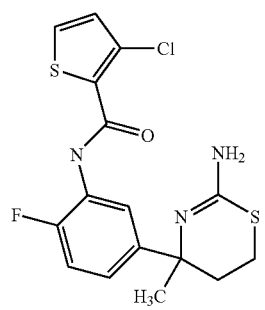 |

TABLE 23-continued
209 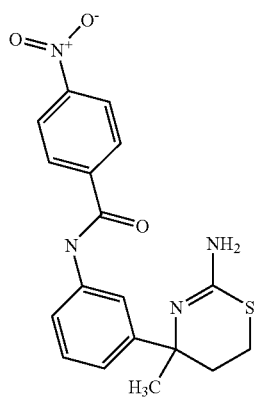
210 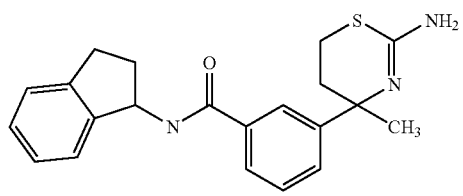
211 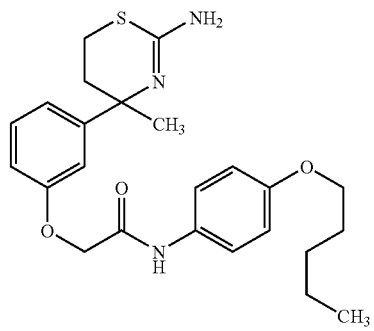
212 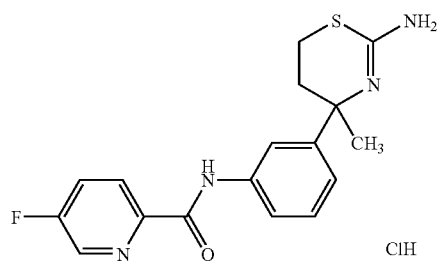 ClH
213 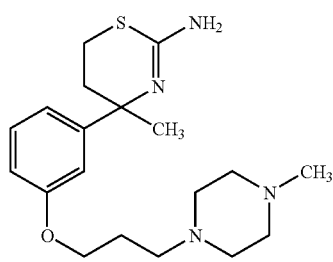
214 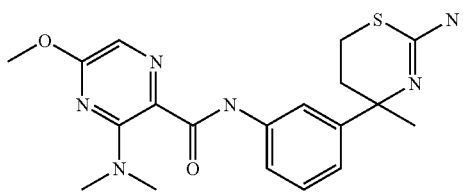
TABLE 23-continued
215 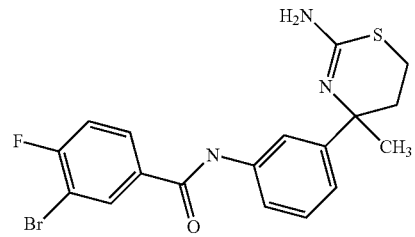
TABLE 24
216 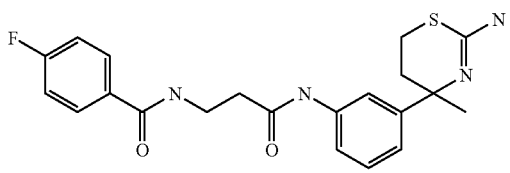
217 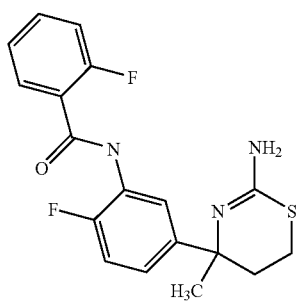
218 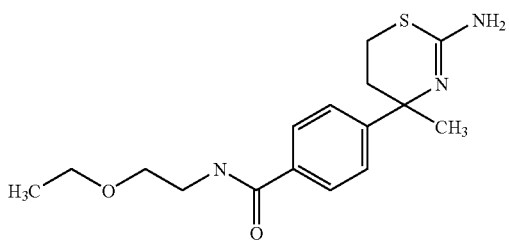
219 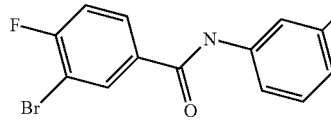
220 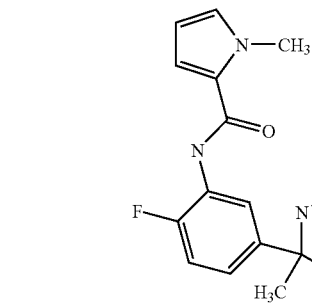 ClH
ClH TABLE 24-continued
| | |
|---|---|
| 221 | 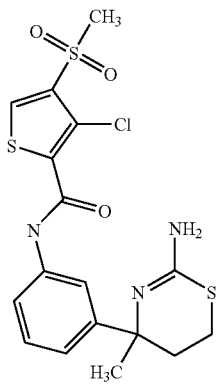 |
| 222 | 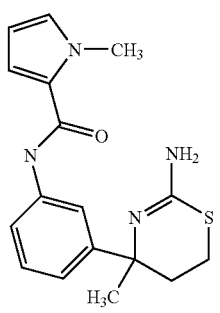 |
| 223 | 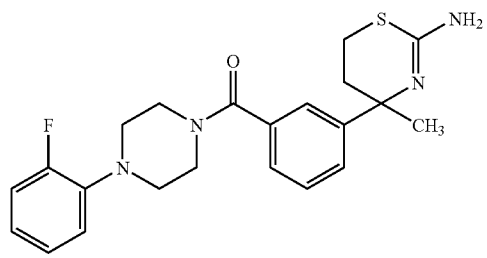 |
| 224 | 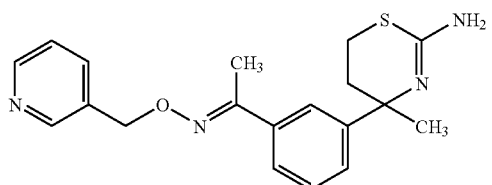 |
TABLE 25
| | |
|---|---|
| 225 | 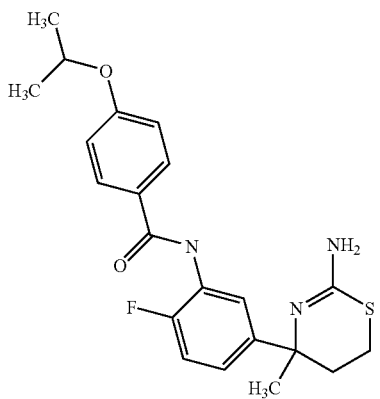 |
TABLE 25-continued
| | |
|---|---|
| 226 | 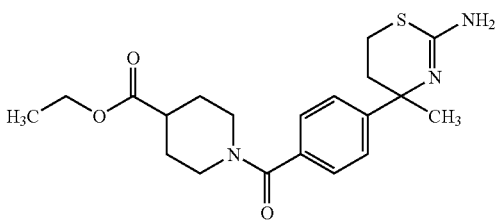 |
| 227 | 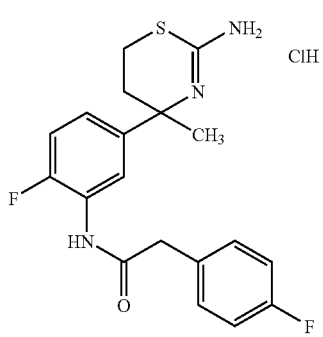 ClH |
| 228 | 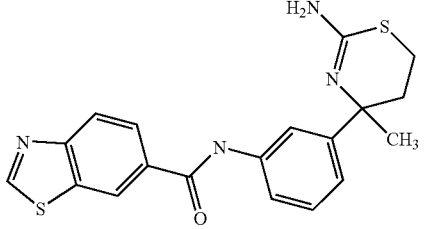 |
| 229 | 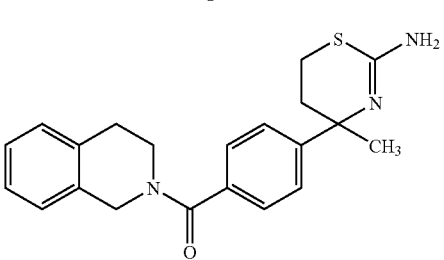 |
| 230 | 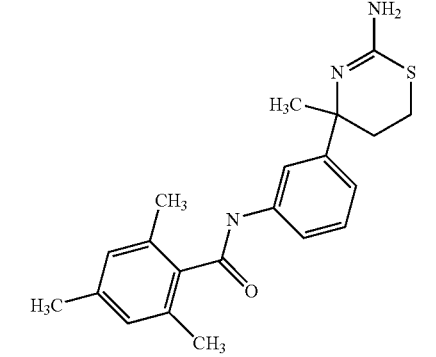 |
| 231 | 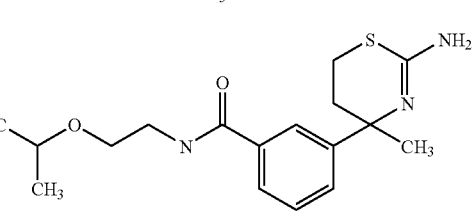 |

119
TABLE 25-continued
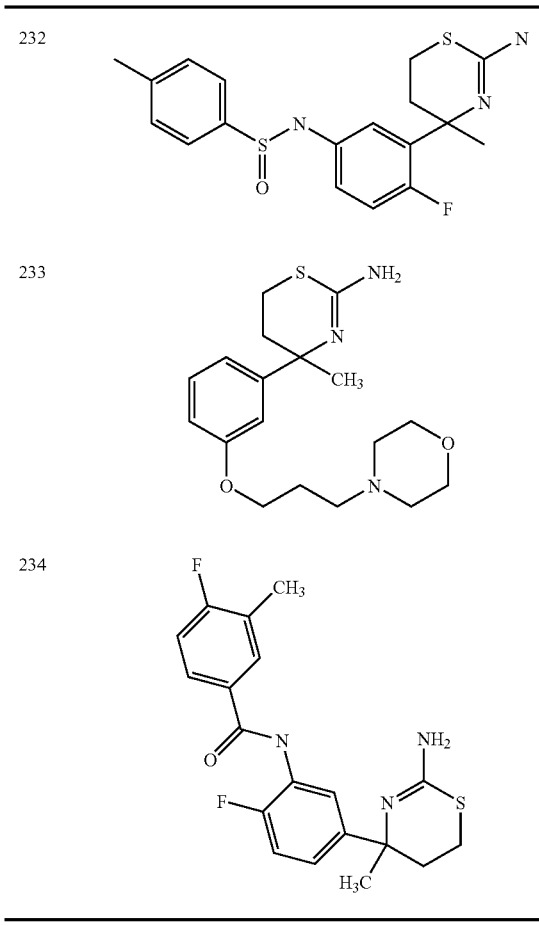
TABLE 26
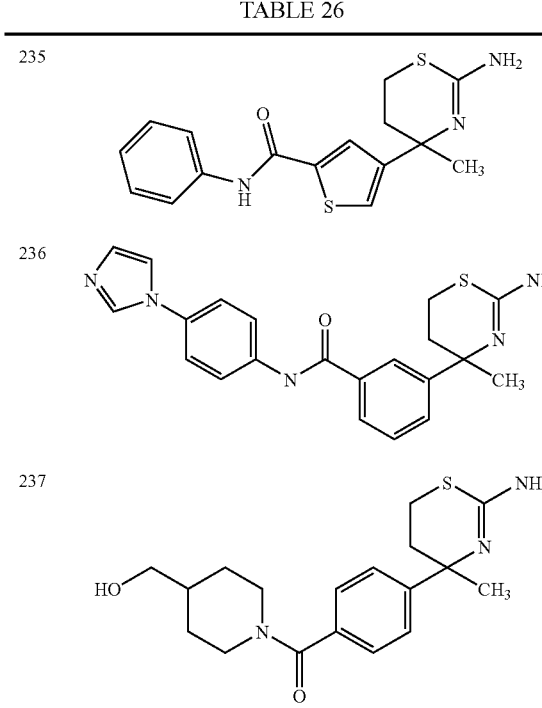
120
TABLE 26-continued
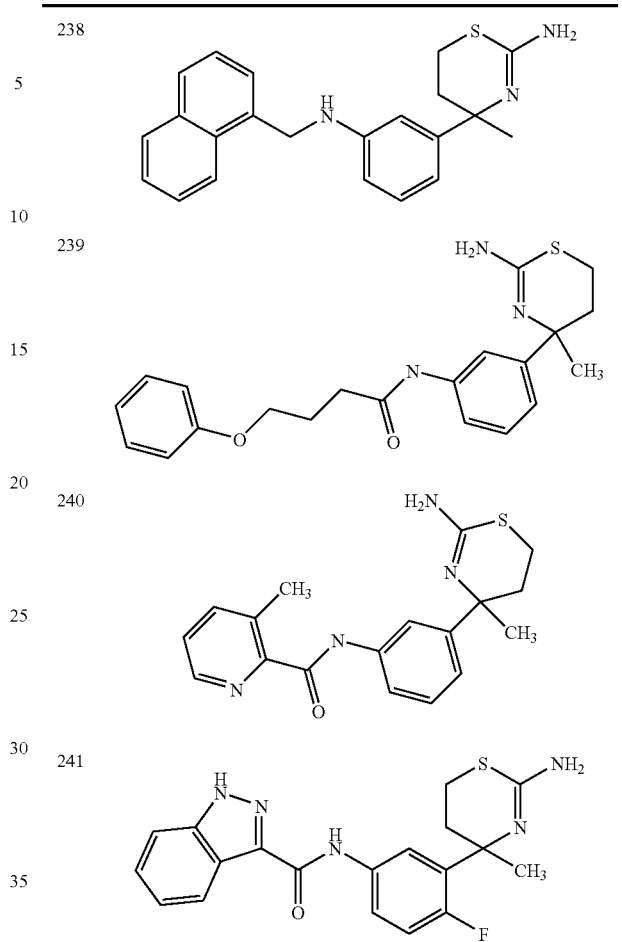
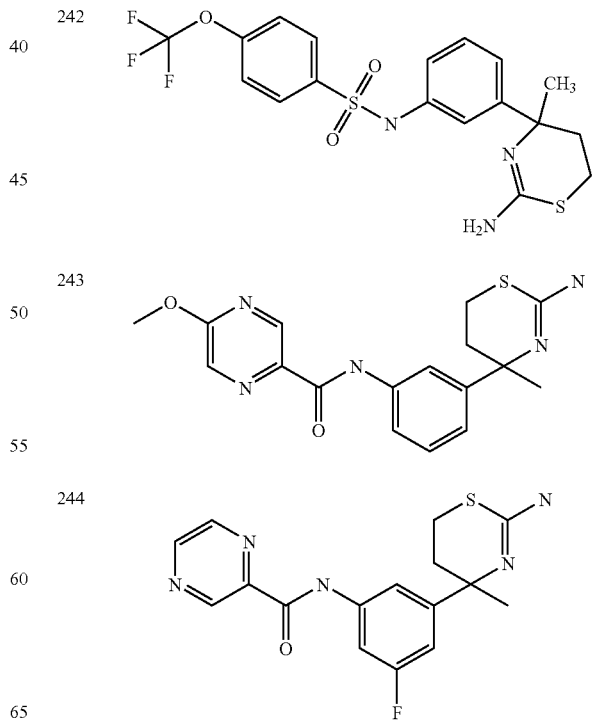

TABLE 26-continued
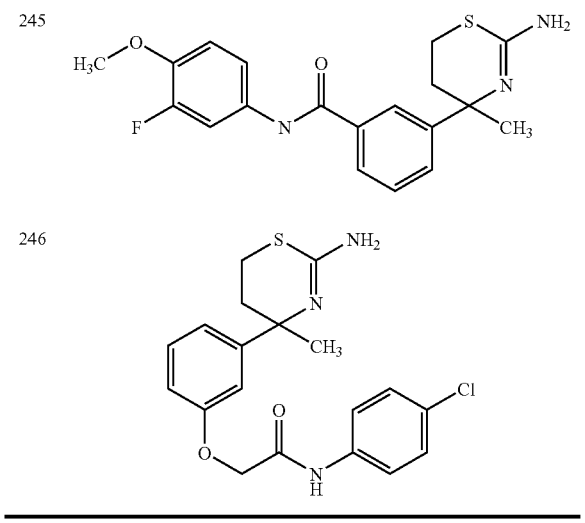
TABLE 27
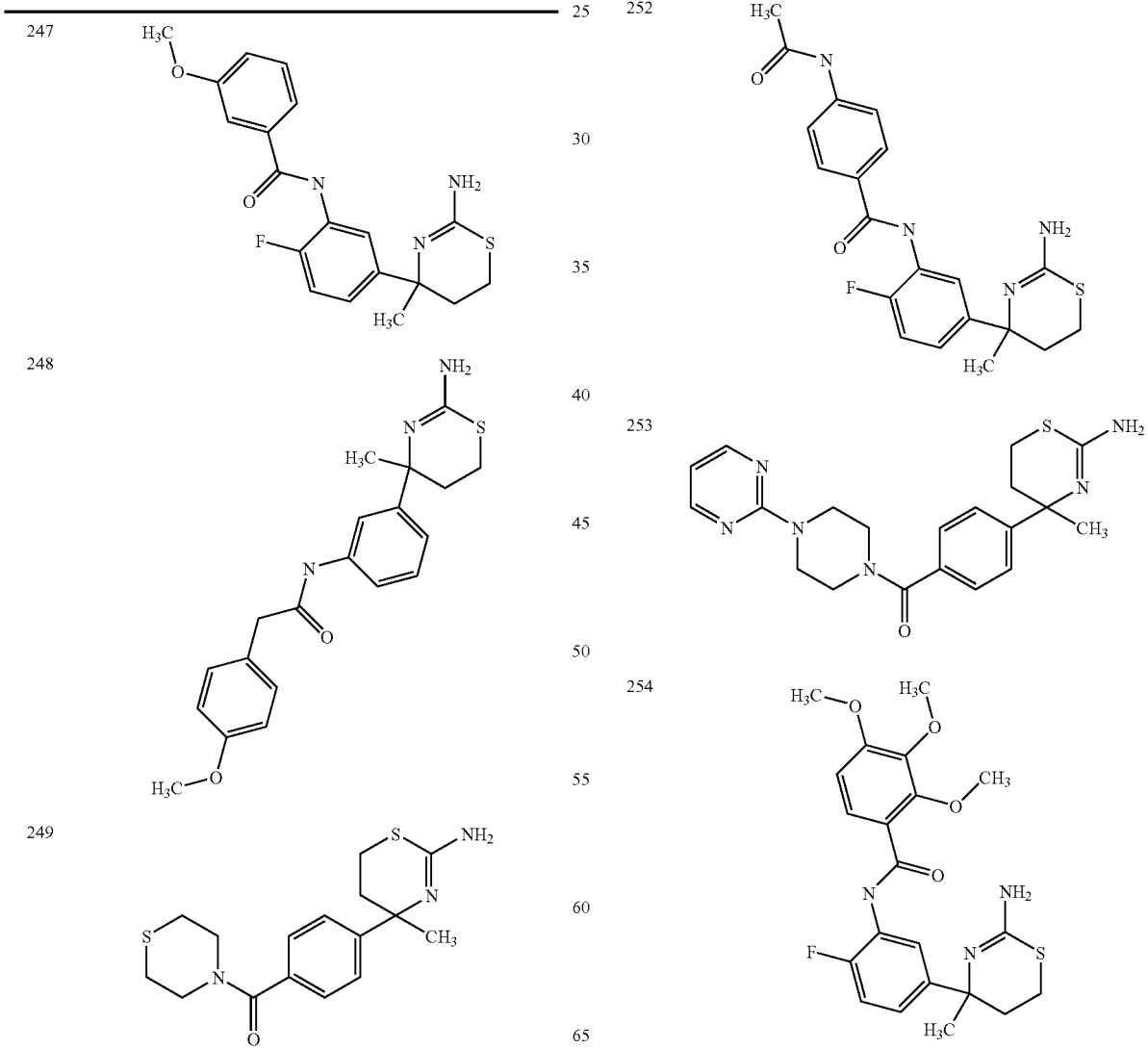
TABLE 27-continued
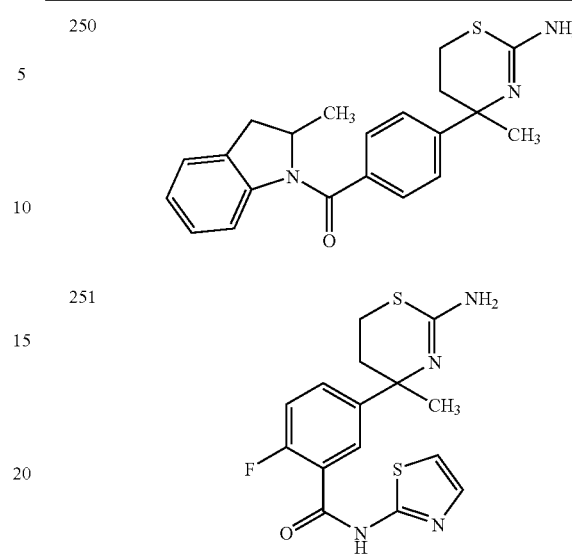

TABLE 27-continued
255 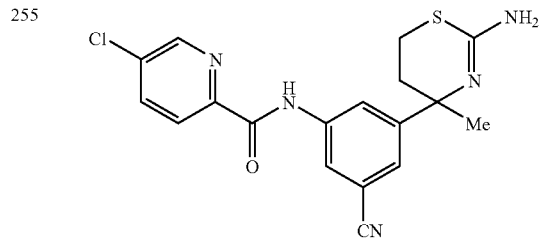
TABLE 28
256 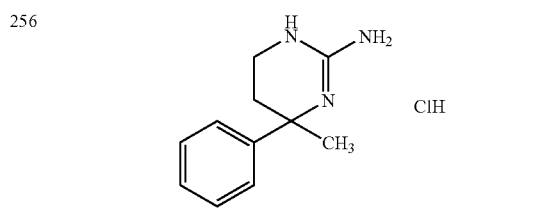
257 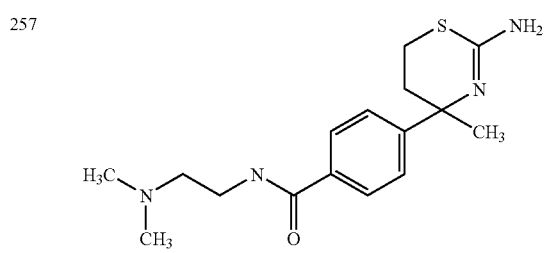
258 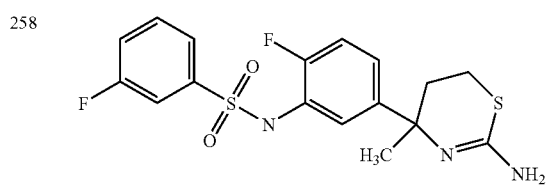
259 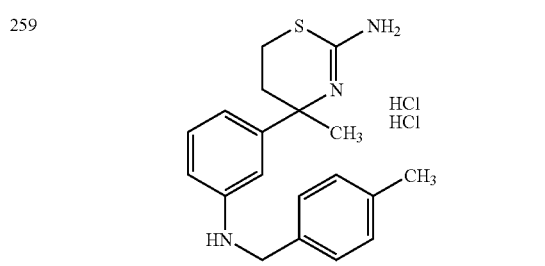
260 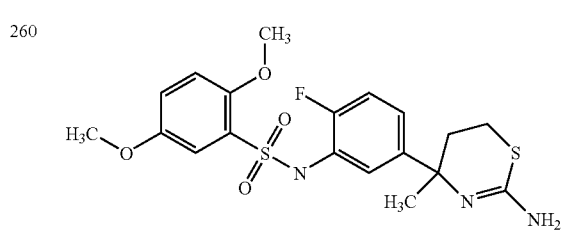
TABLE 28-continued
261 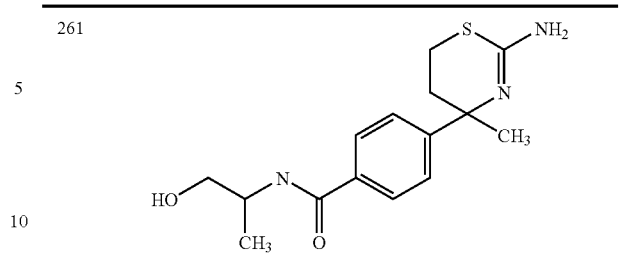
262 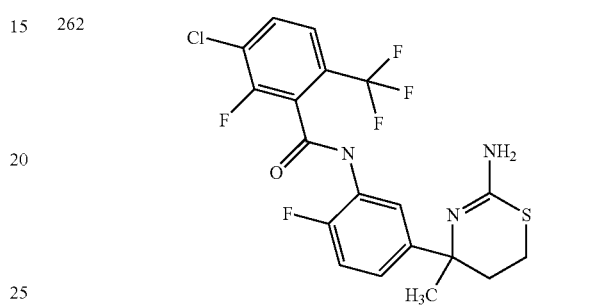
263 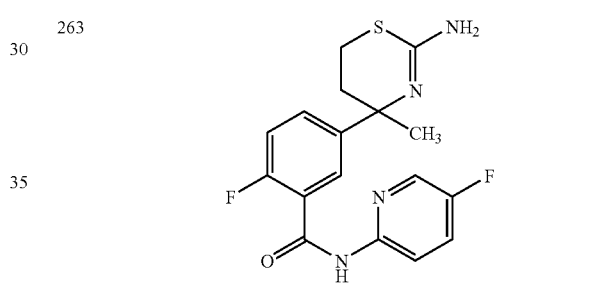
264 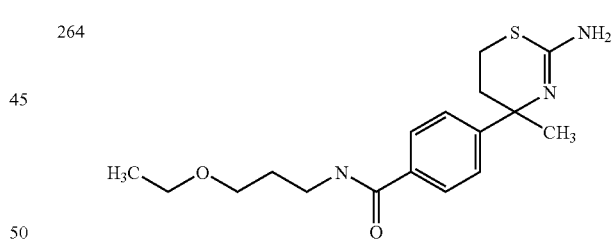
265 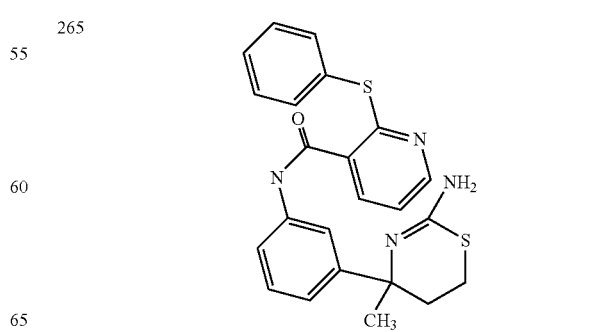

TABLE 28-continued
266 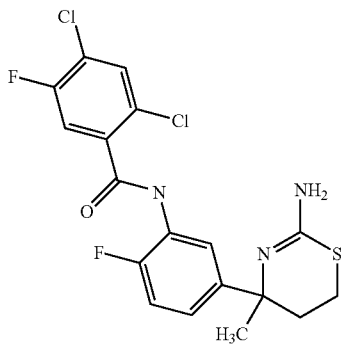
TABLE 29
267 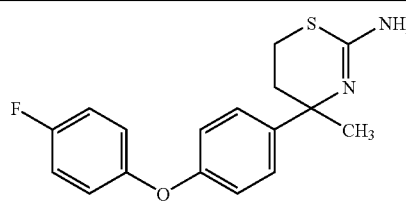
268 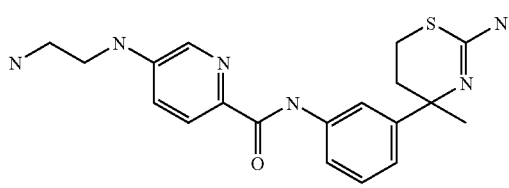
269 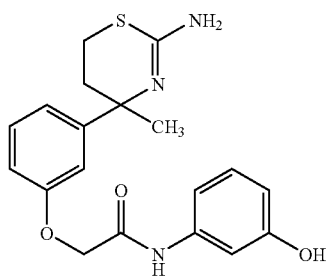
270 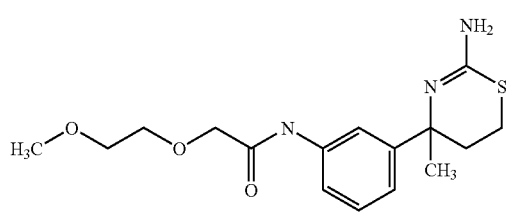
TABLE 29-continued
271 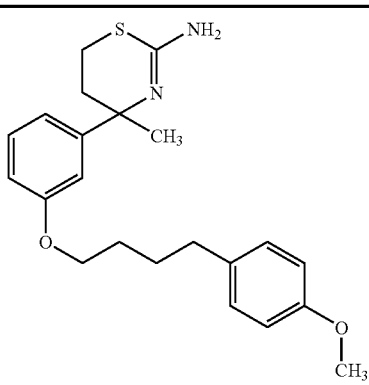
272 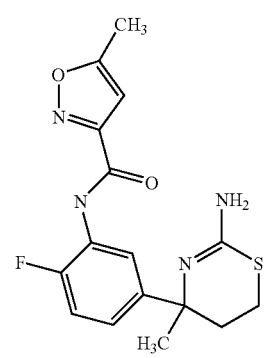
273 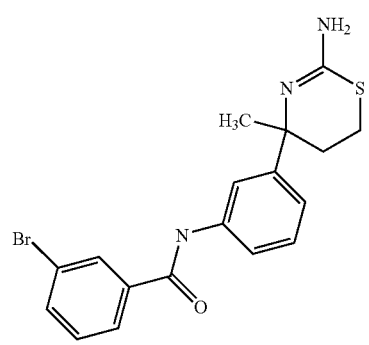
274 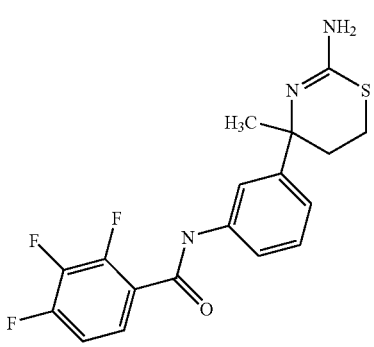
275 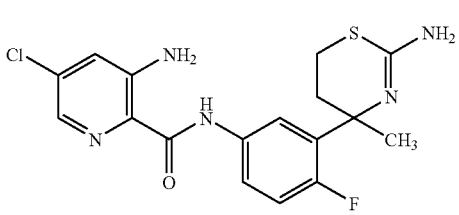

TABLE 30
276 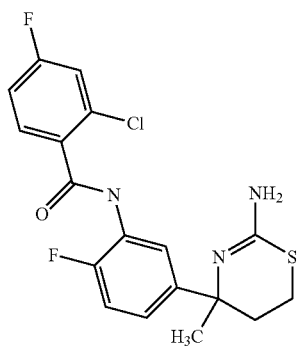
277 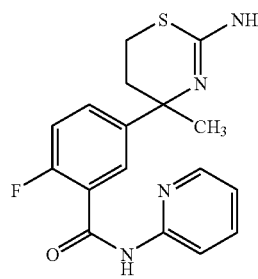
278 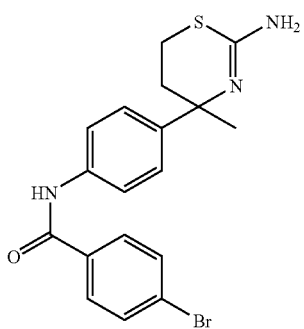
279 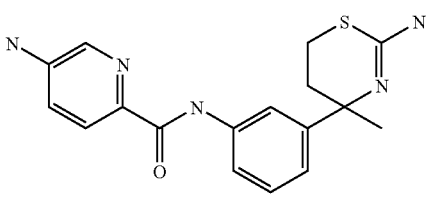
280 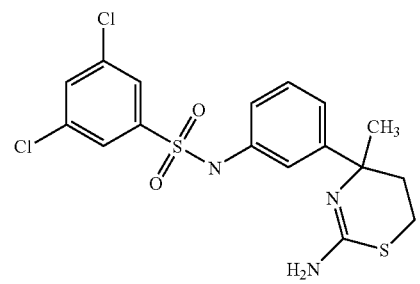
TABLE 30-continued
281 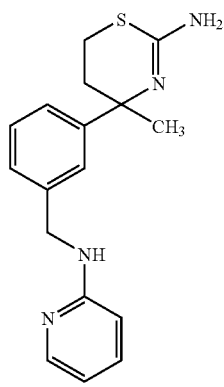
282 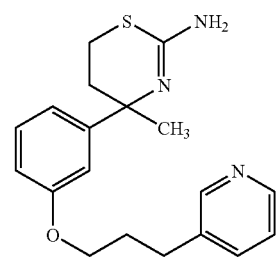
283 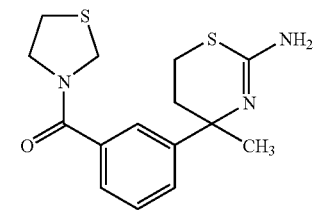
284 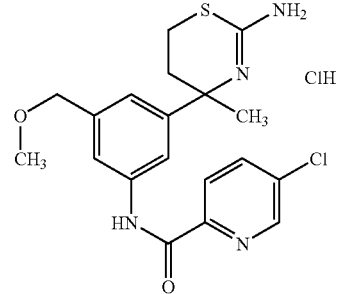
TABLE 31
285 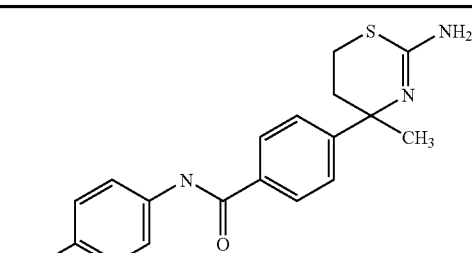

TABLE 31-continued
286 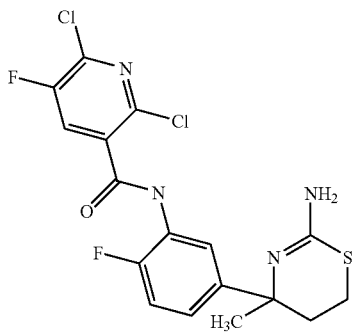
287 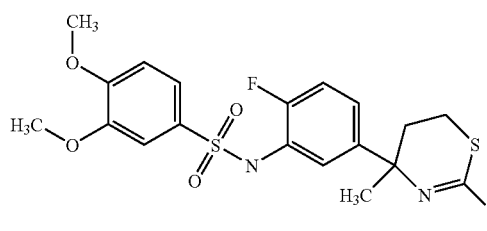
288 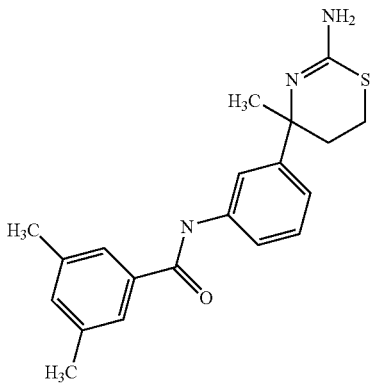
289 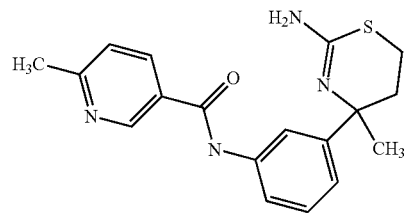
290 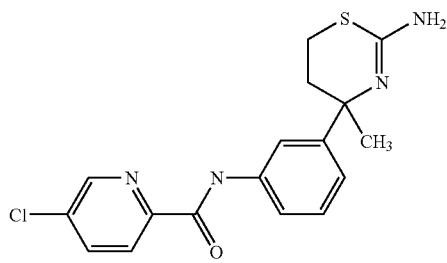
TABLE 31-continued
291 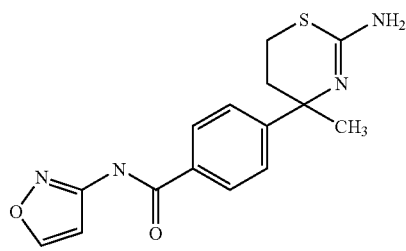
292 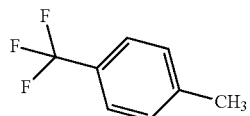
293 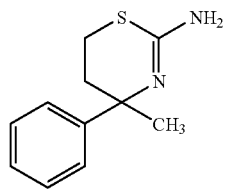
TABLE 32
294 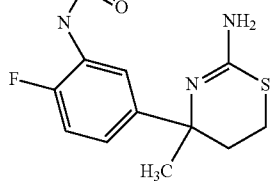
295 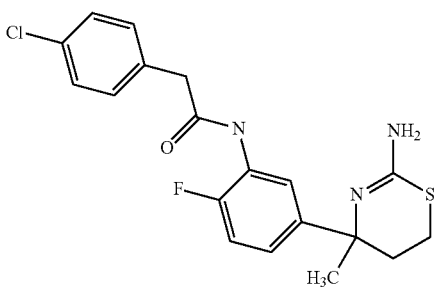

TABLE 32-continued
296 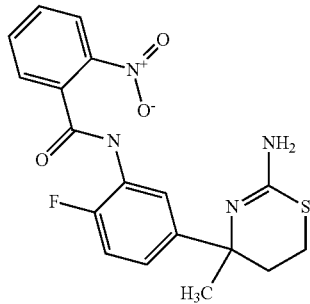
297 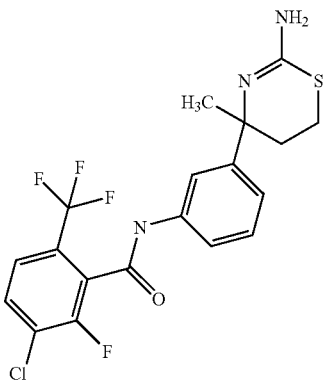
298 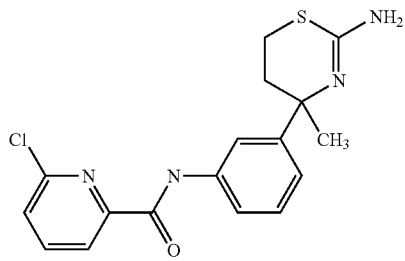
299 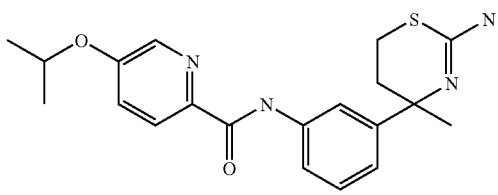
300 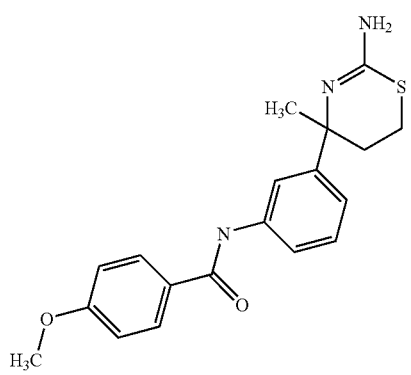
TABLE 32-continued
301 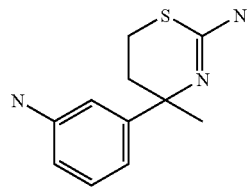
302 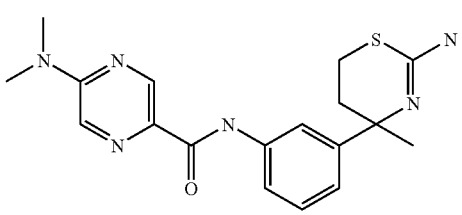
TABLE 33
303 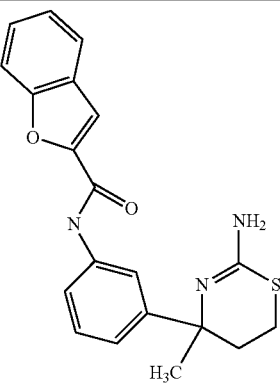
304 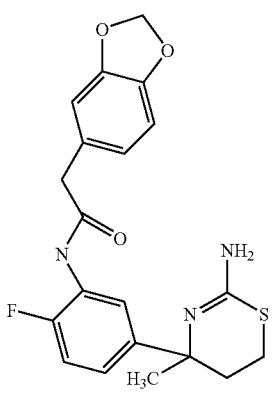
305 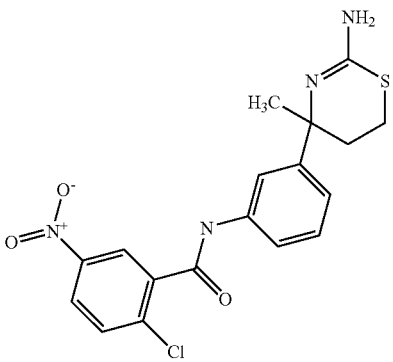

133
TABLE 33-continued
306 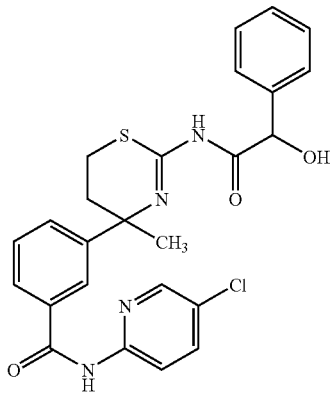
307 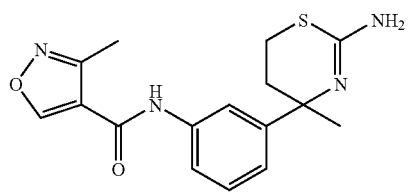
308 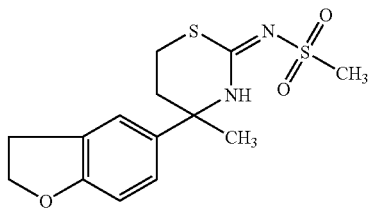
309 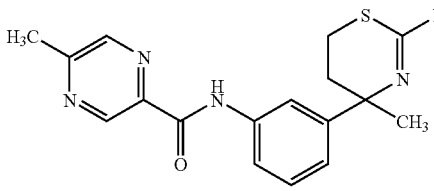
TABLE 34
310 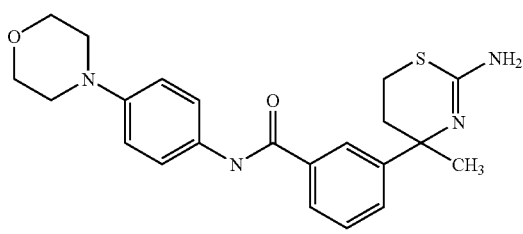
134
TABLE 34-continued
311 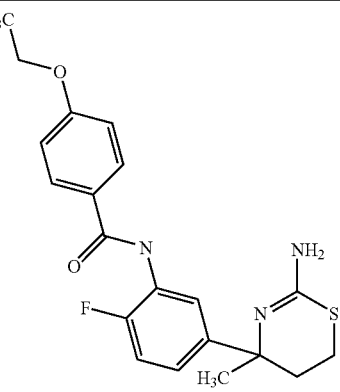
312 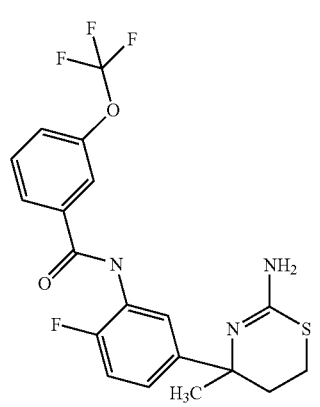
313 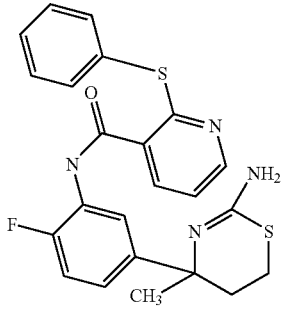
314 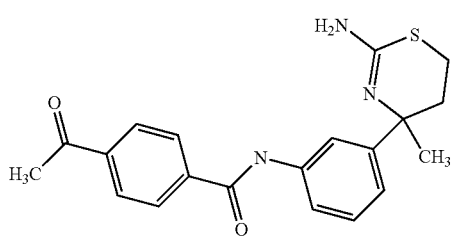
315 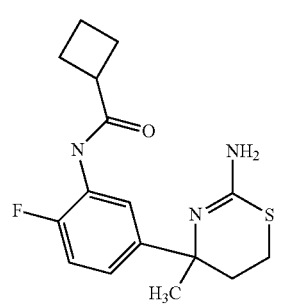

TABLE 34-continued
316 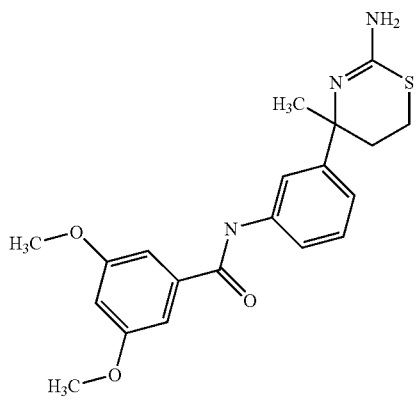
317 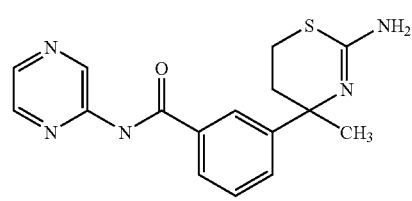
TABLE 35
318 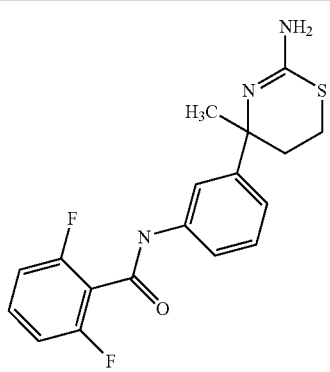
319 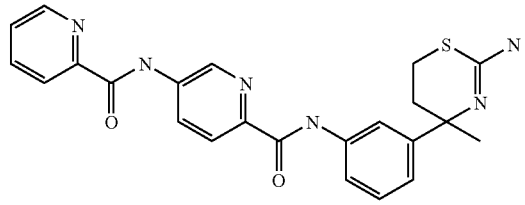
320 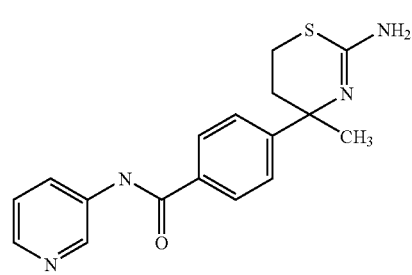
TABLE 35-continued
321 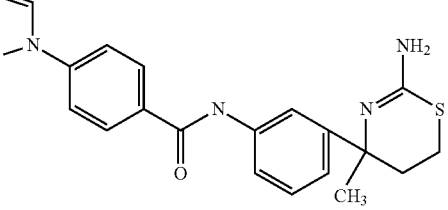
322 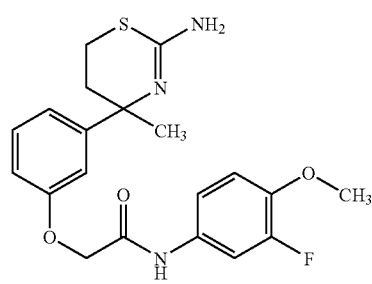
323 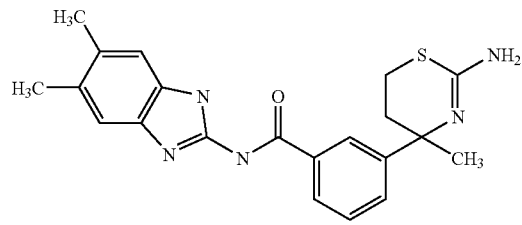
324 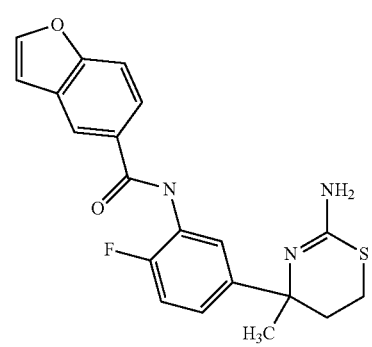
325 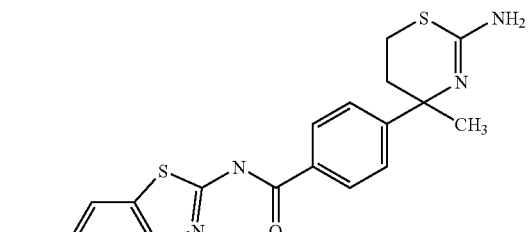
326 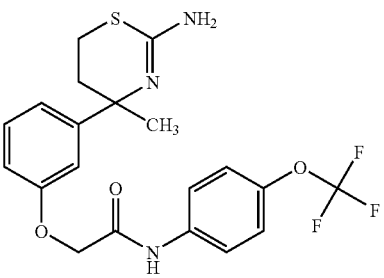

TABLE 35-continued
327 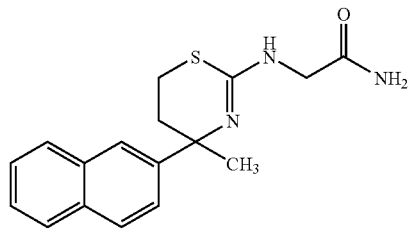
328 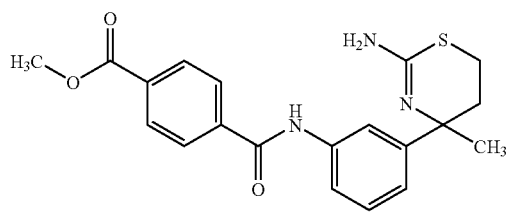
TABLE 36
329 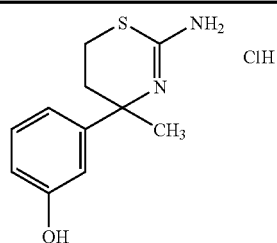
330 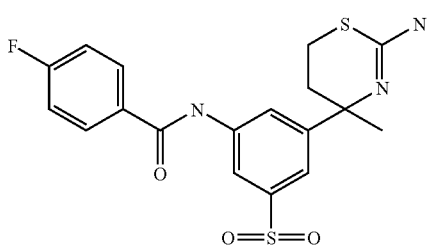
331 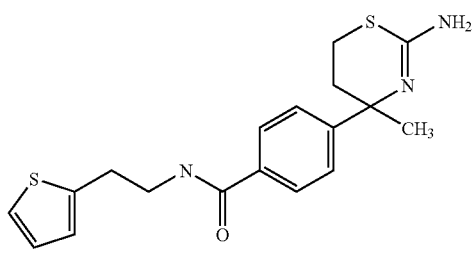
332 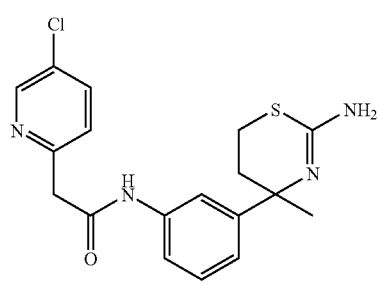
TABLE 36-continued
333 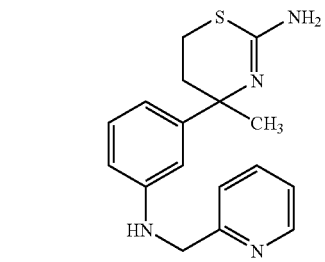
334 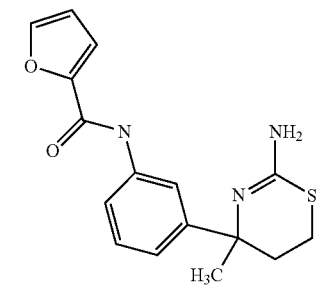
335 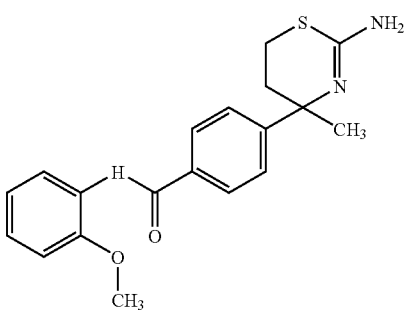
336 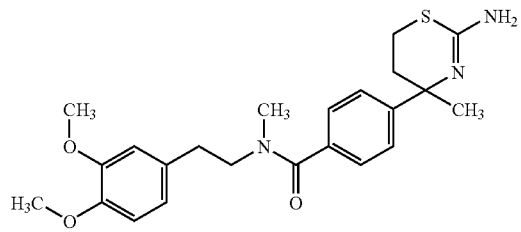
337

TABLE 36-continued
338 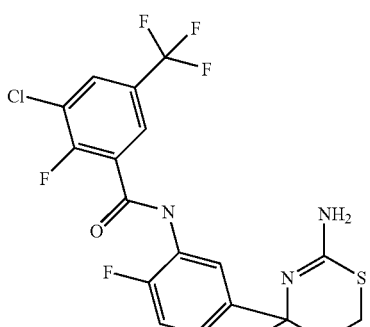
339 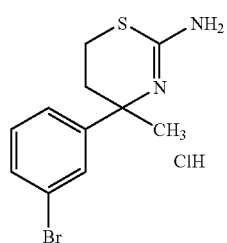
TABLE 37
340 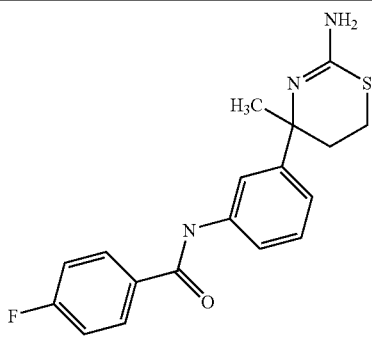
341 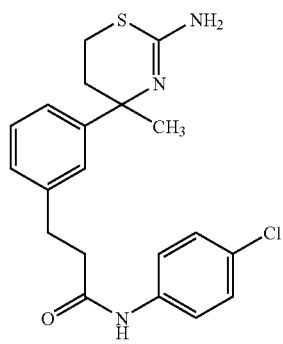
342 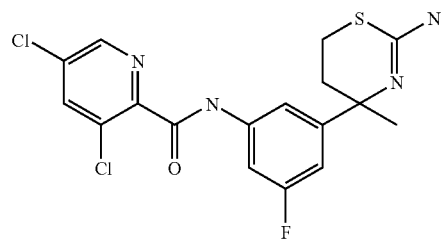
TABLE 37-continued
343 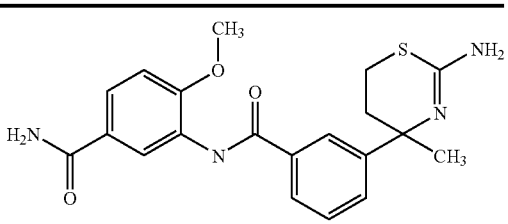
344 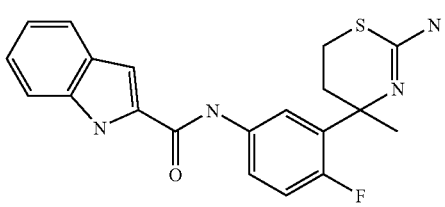
345 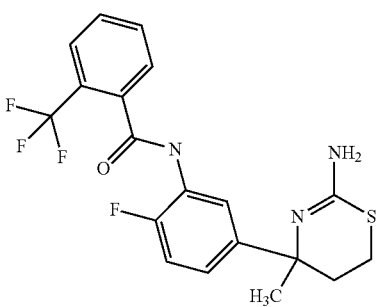
346 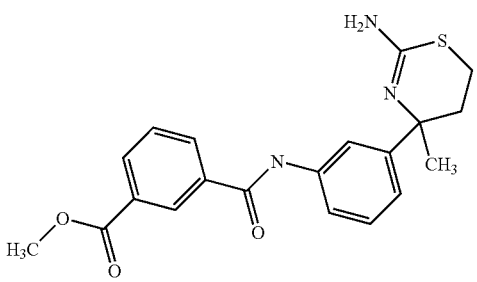
347 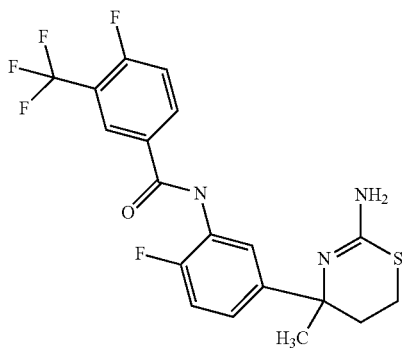
348 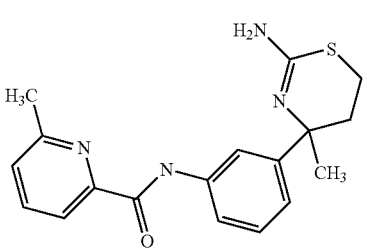

TABLE 38
349 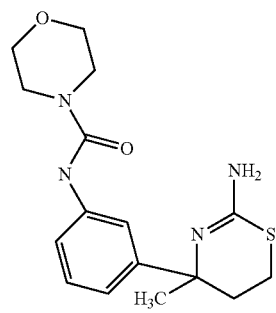
350 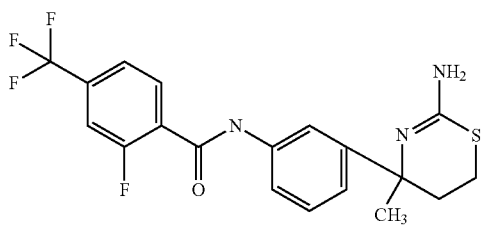
351 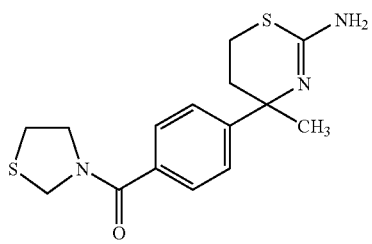
352 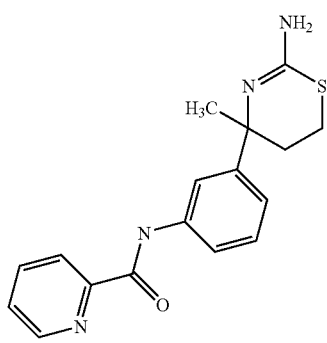
353 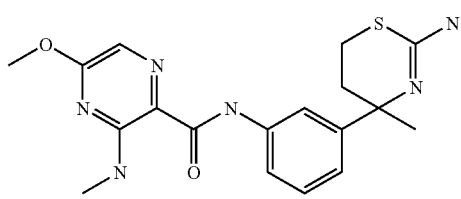
TABLE 38-continued
354 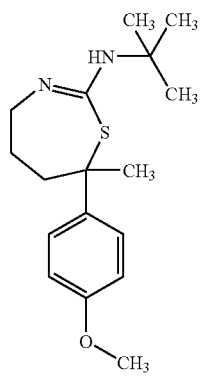
355 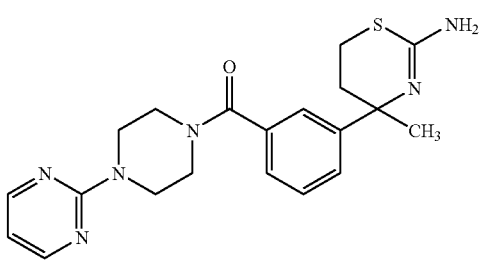
356 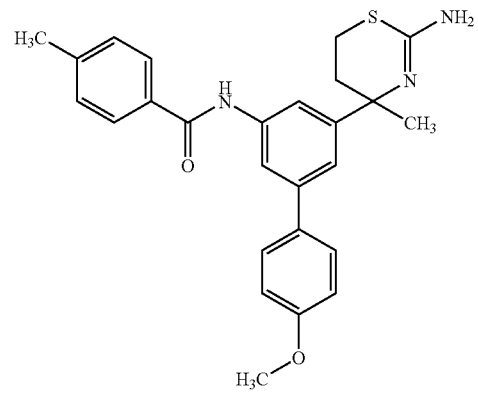
357 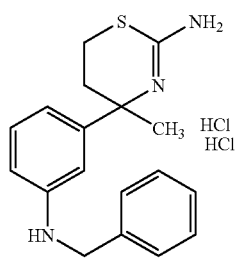
TABLE 39
358 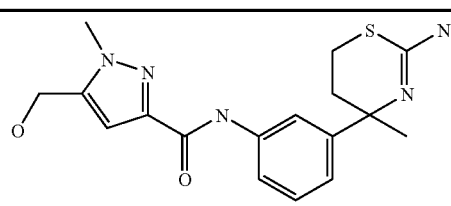

TABLE 39-continued
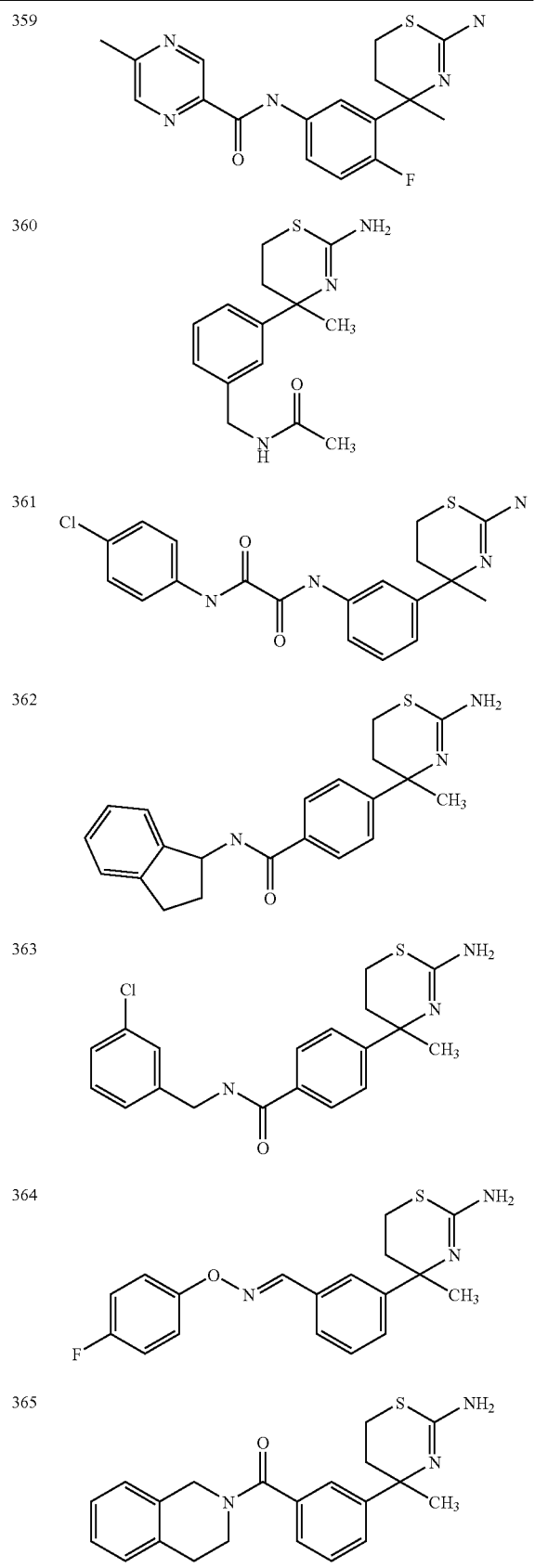
TABLE 39-continued
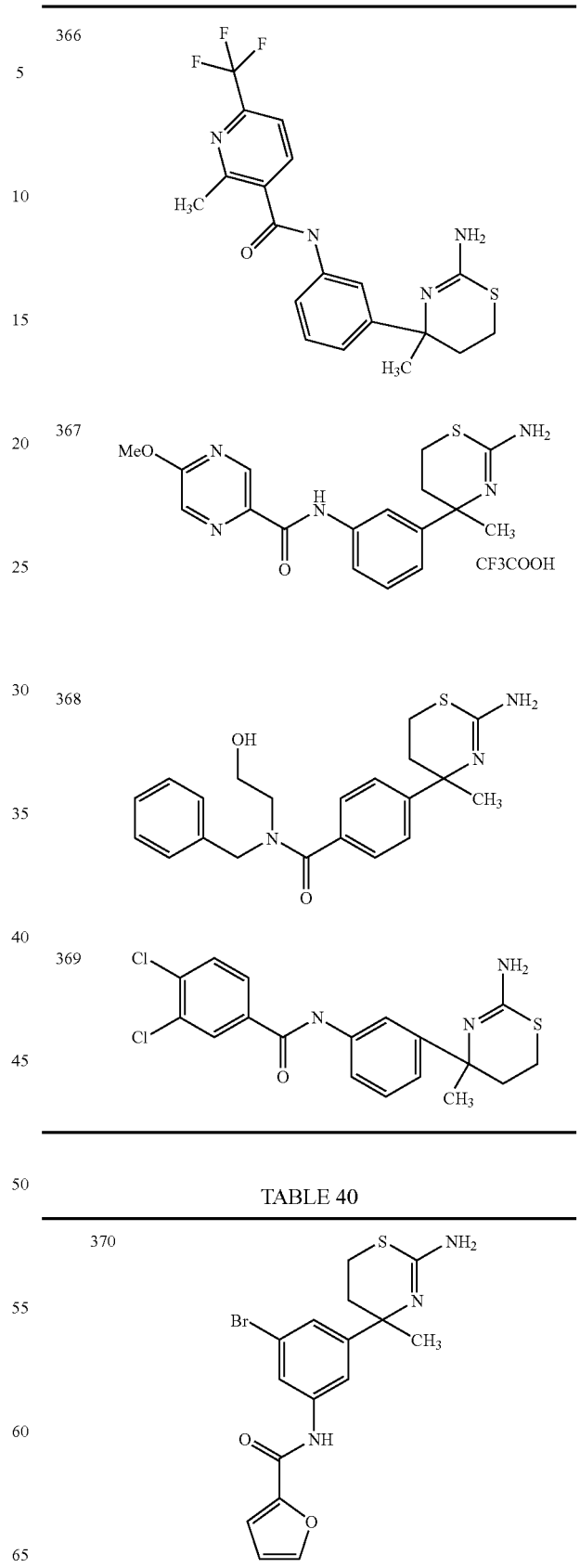
TABLE 40

TABLE 40-continued
371 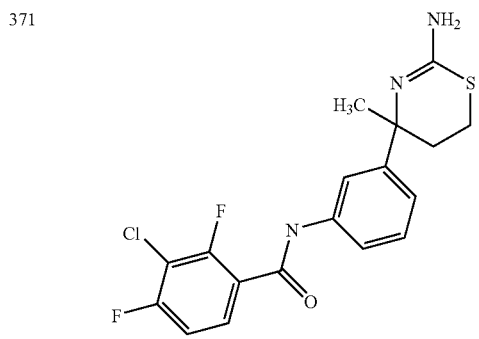
372 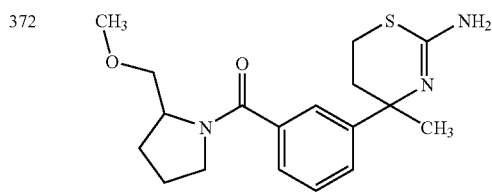
373 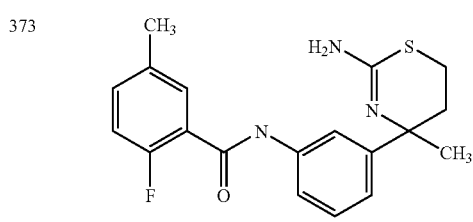
374 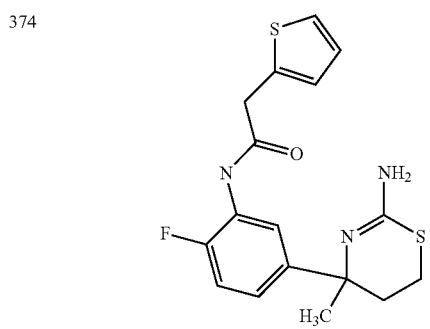
375 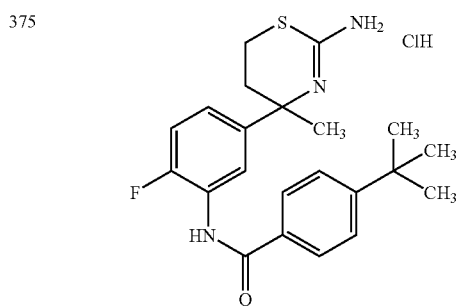
TABLE 40-continued
376 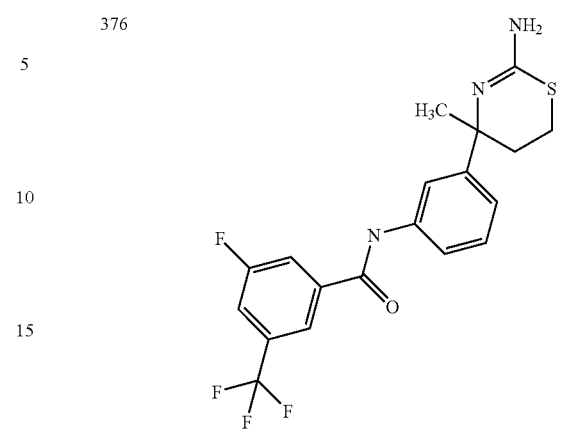
377 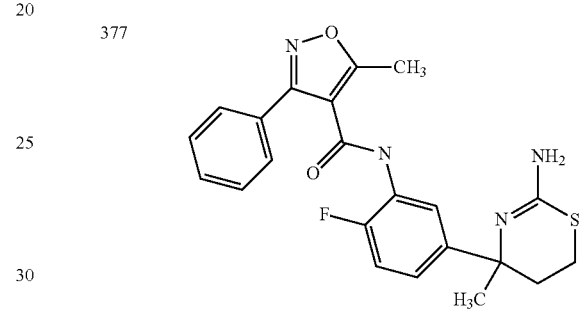
378 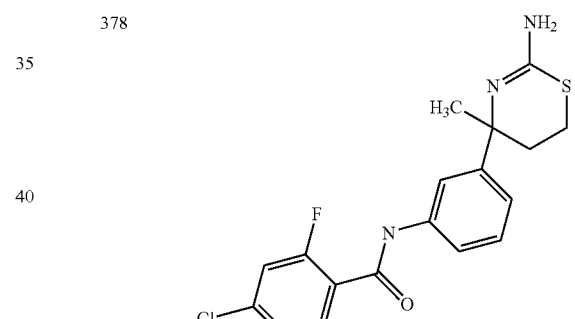
TABLE 41
379
380
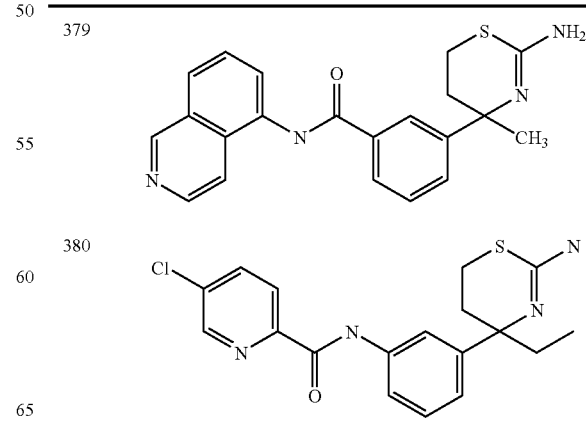

TABLE 41-continued
381 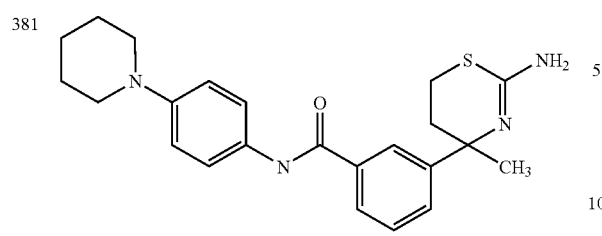
382 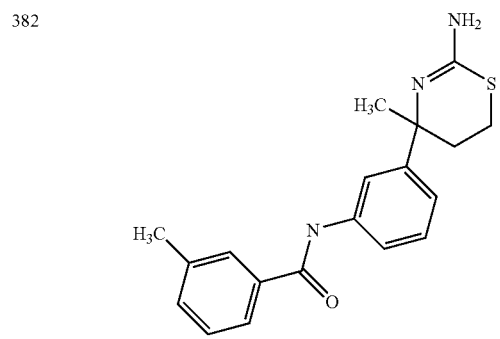
383 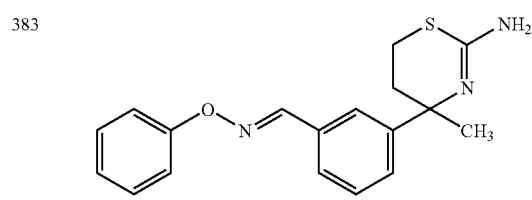
384 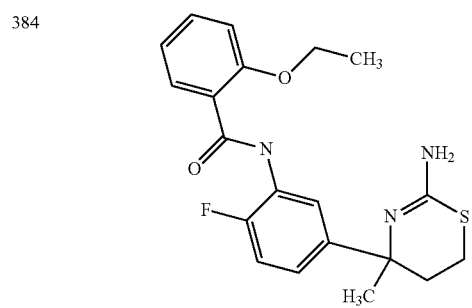
385 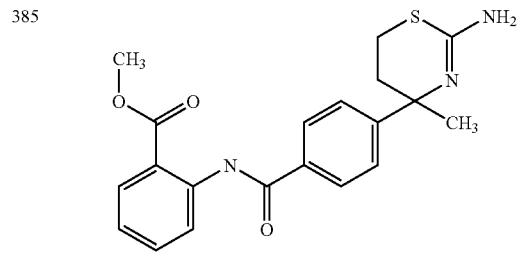
386 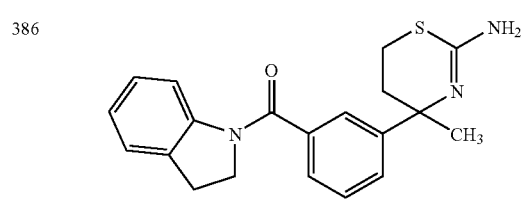
TABLE 41-continued
387 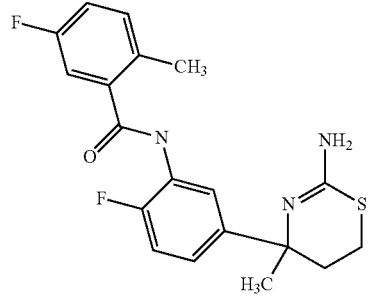
388 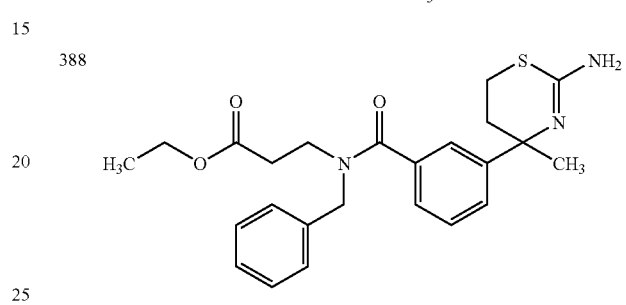
389 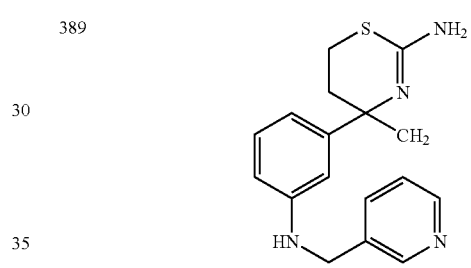
TABLE 42
390 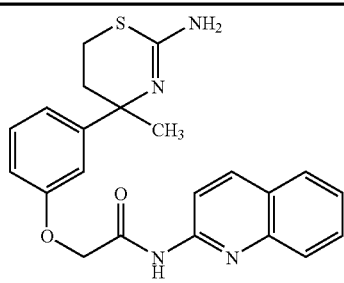
391 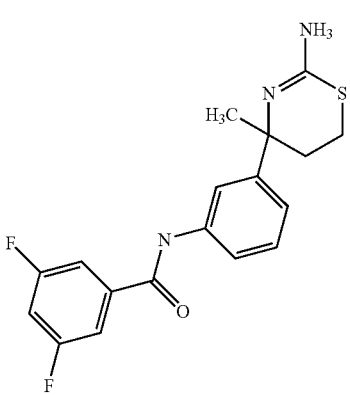

TABLE 42-continued
392 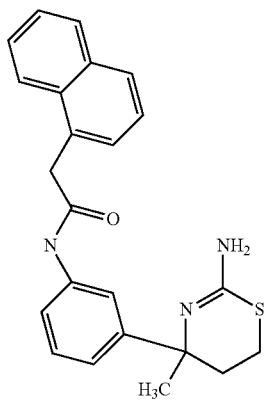
393 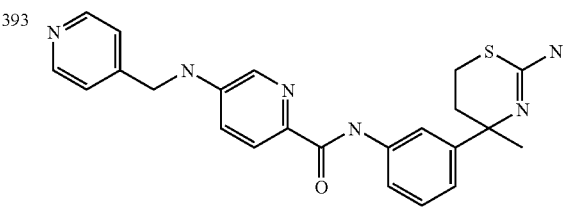
394 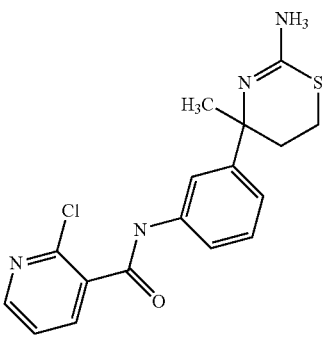
395 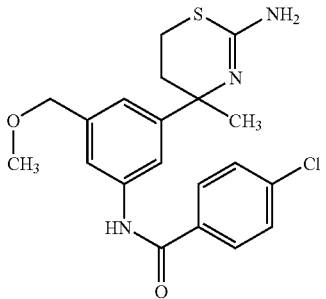
396 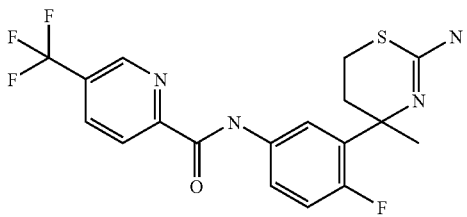
TABLE 42-continued
397 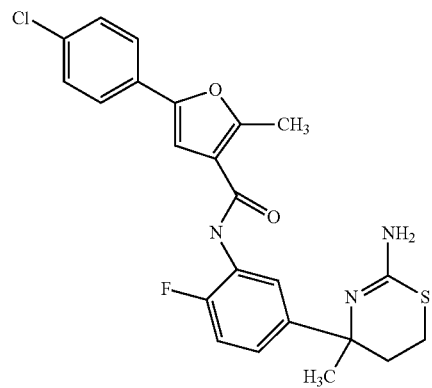
TABLE 43
398 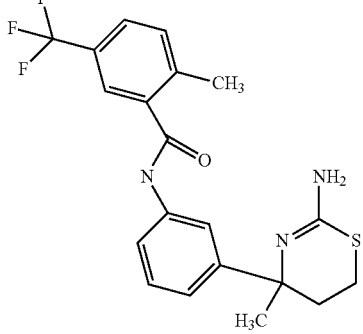
399 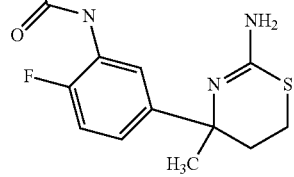
400 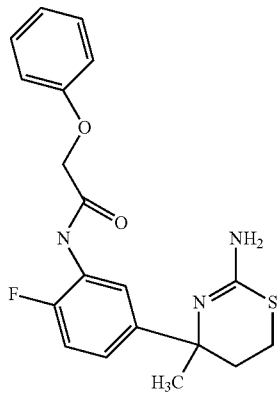

TABLE 43-continued
| | |
|---|---|
| 401 | 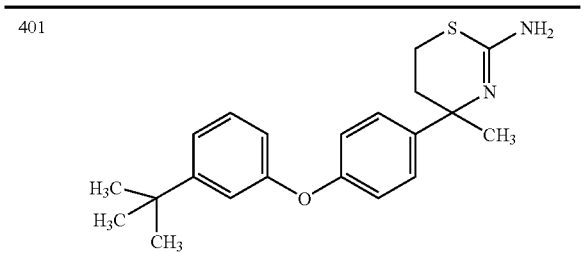 |
| 402 | 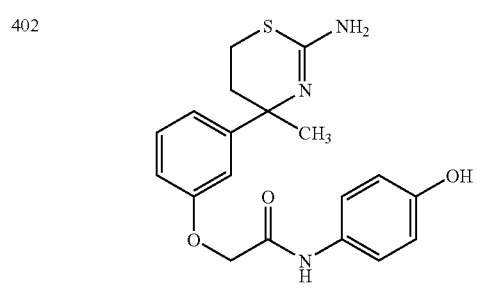 |
| 403 | 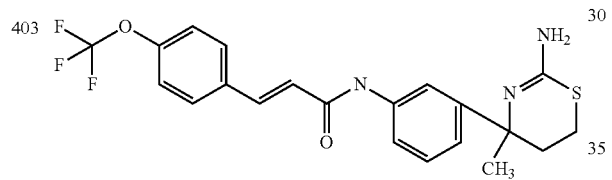 |
| 404 | 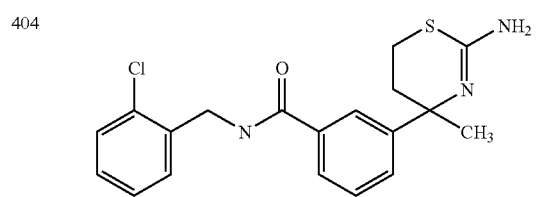 |
| 405 | 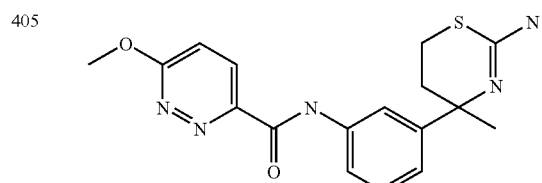 |
| 406 | 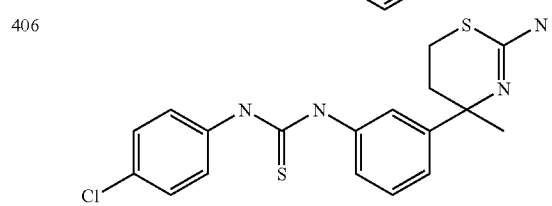 |
TABLE 43-continued
| | |
|---|---|
| 407 | 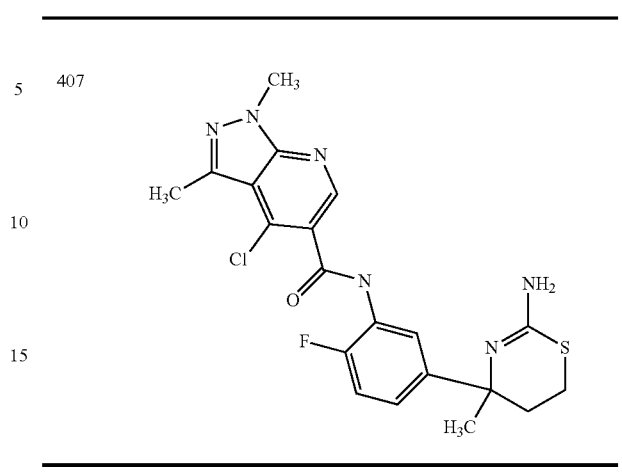 |
TABLE 44
| | |
|---|---|
| 408 | 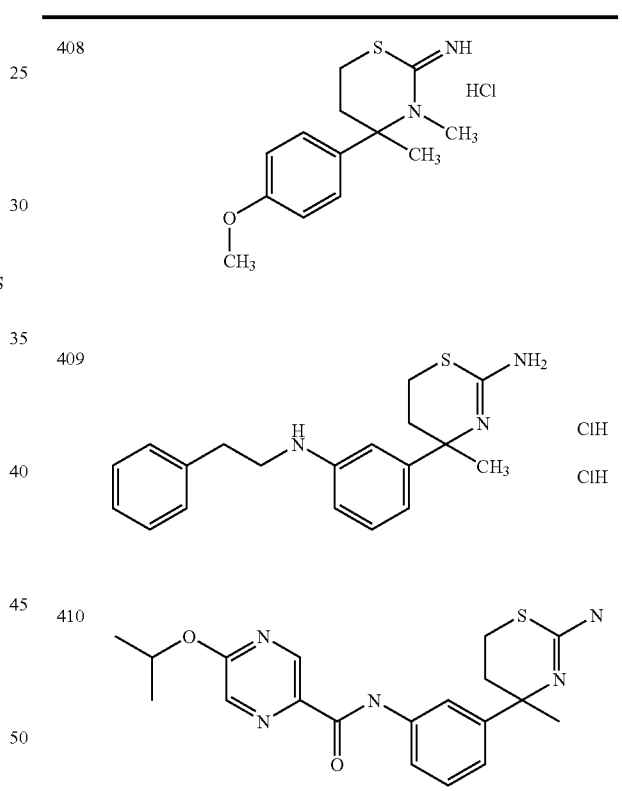 |
| 409 | |
| 410 | |
| 411 | 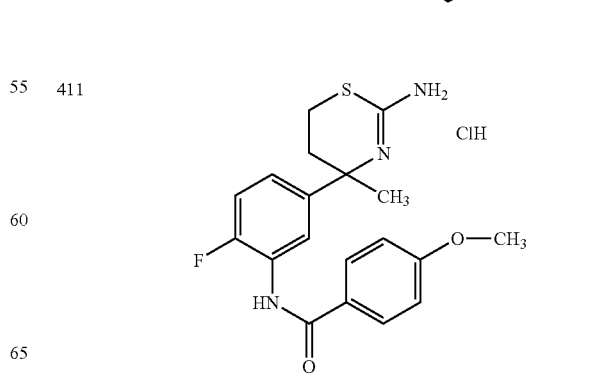 |

TABLE 44-continued
412 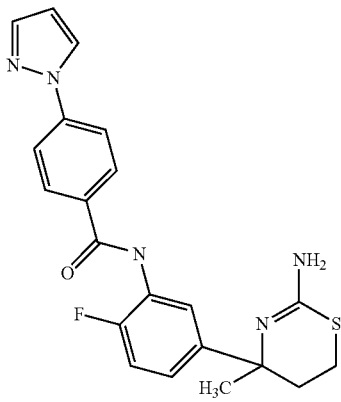
413 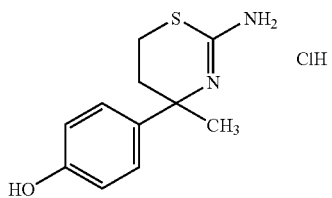 ClH
414 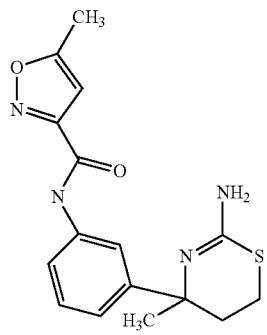
415 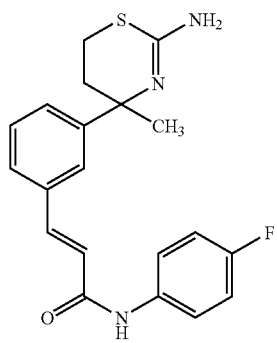
416 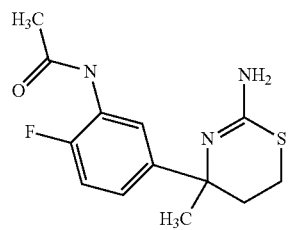
TABLE 45
417 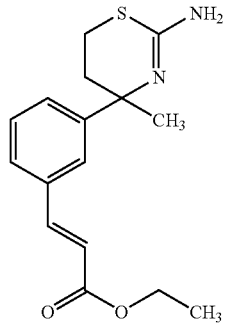
418 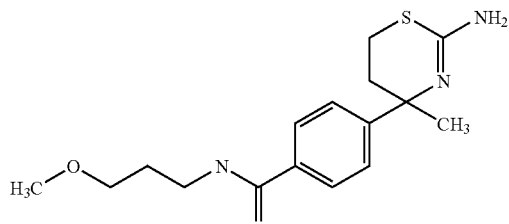
419 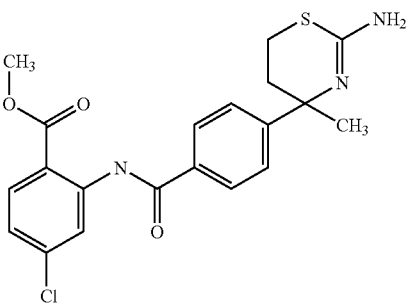
420 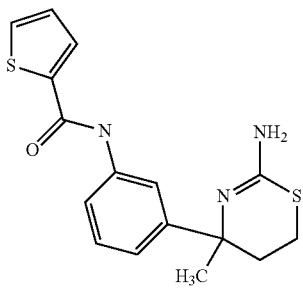

TABLE 45-continued
421
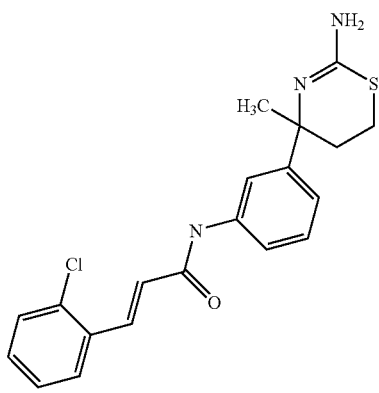
422
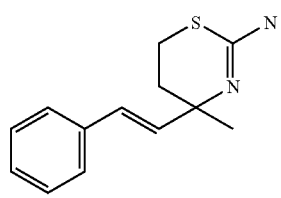
TABLE 45-continued
423
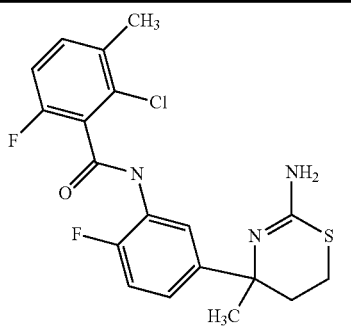
424
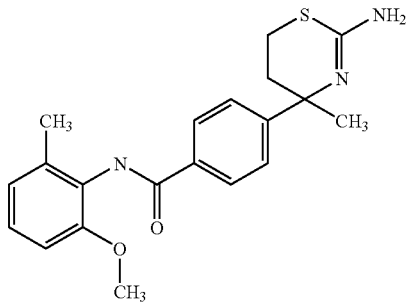
TABLE 46
425
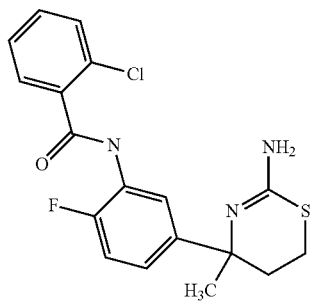
426
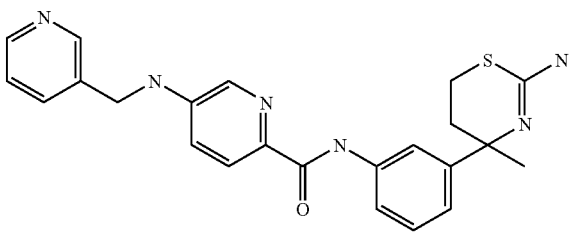
427
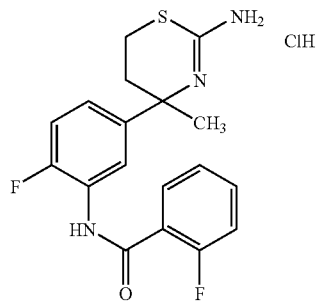

TABLE 46-continued
| | |
|---|---|
| 428 | 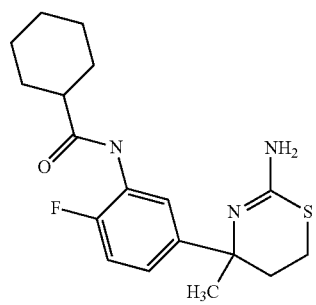 |
| 429 | 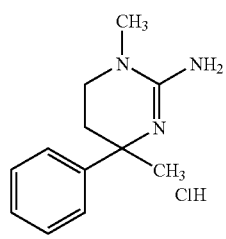 |
| 430 | 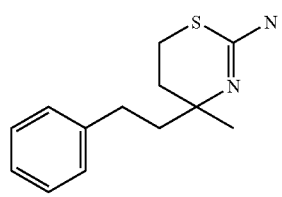 |
| 431 | 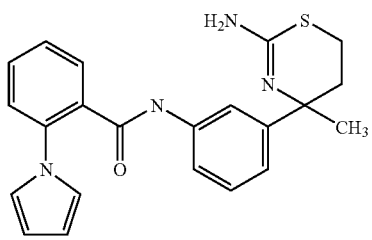 |
| 432 | 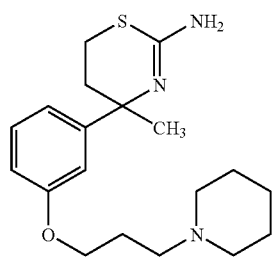 |
| 433 | 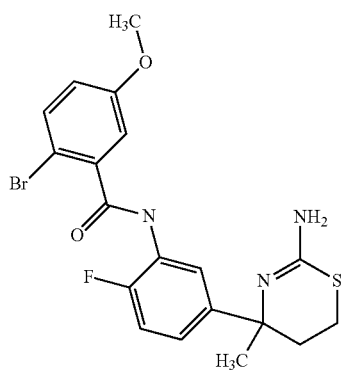 |

TABLE 47
434 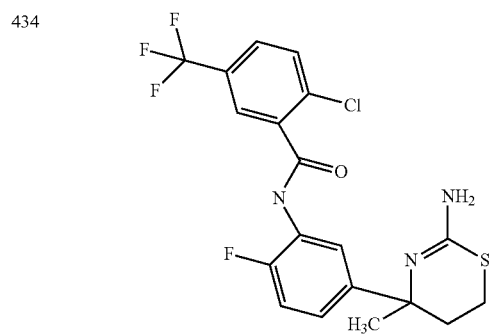
435 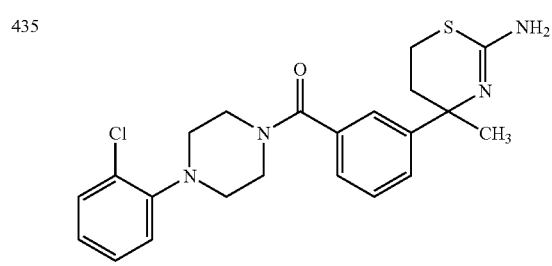
436 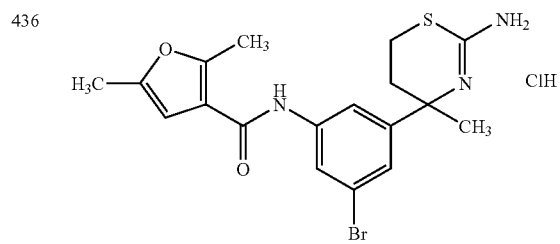
437 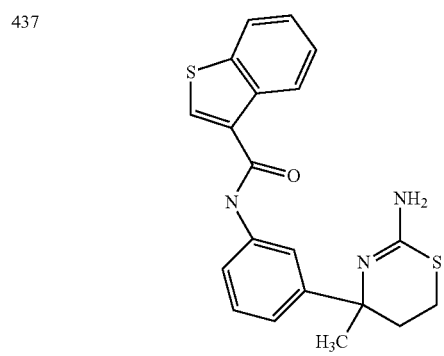
438 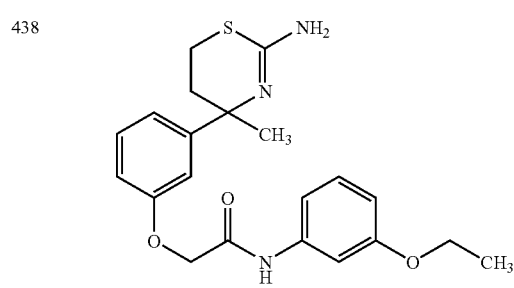
TABLE 47-continued
439 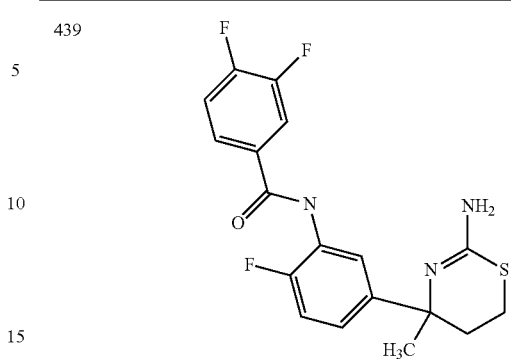
440 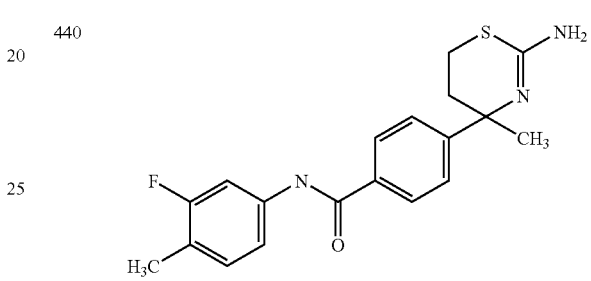
441 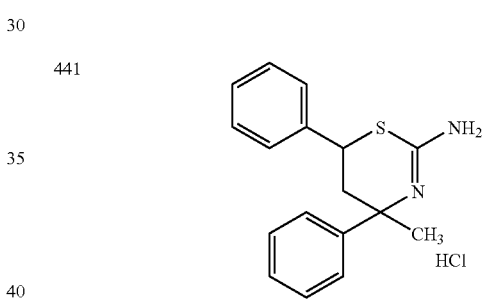
442 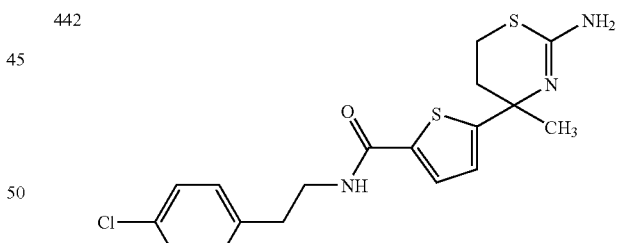
TABLE 48
443 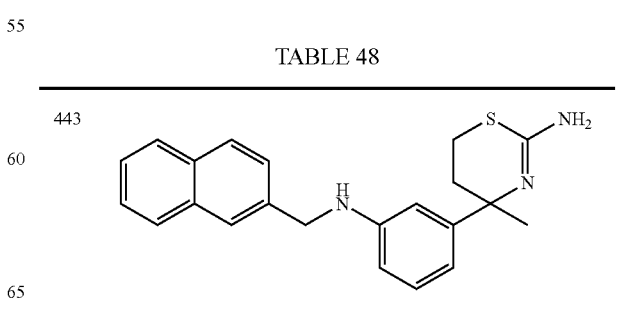

TABLE 48-continued
444 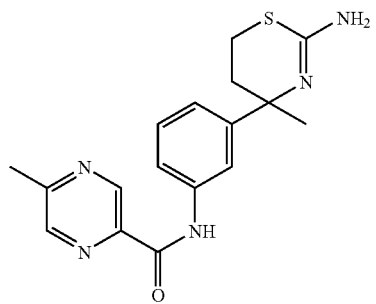
445 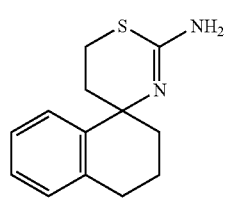
446 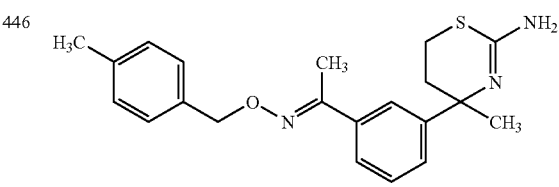
447 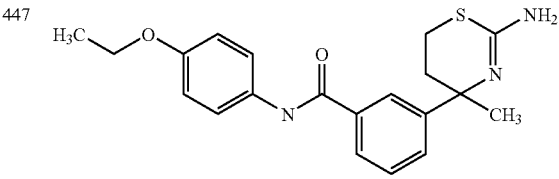
448 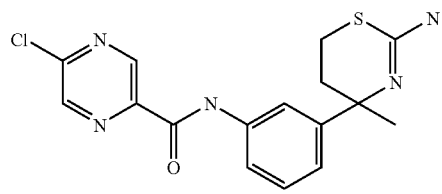
449 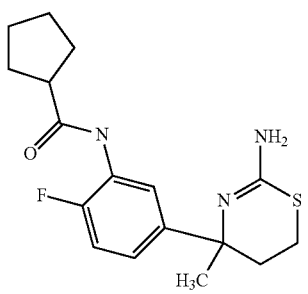
TABLE 48-continued
450 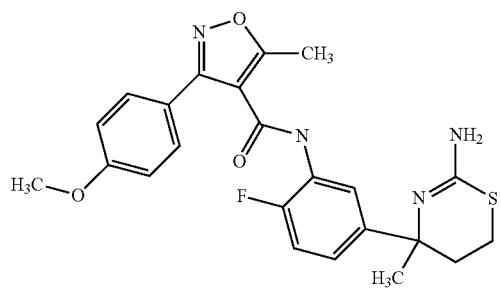
451 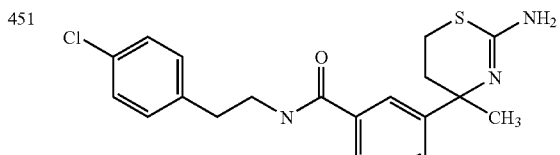
452 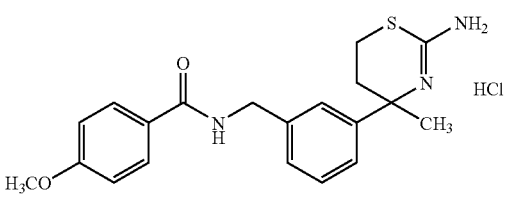
HCl
453 
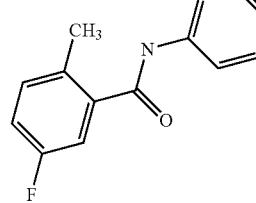
TABLE 49
454 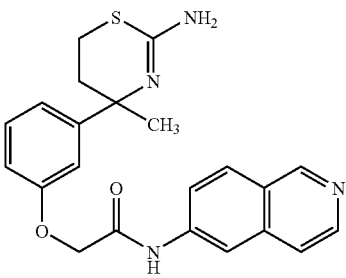

TABLE 49-continued
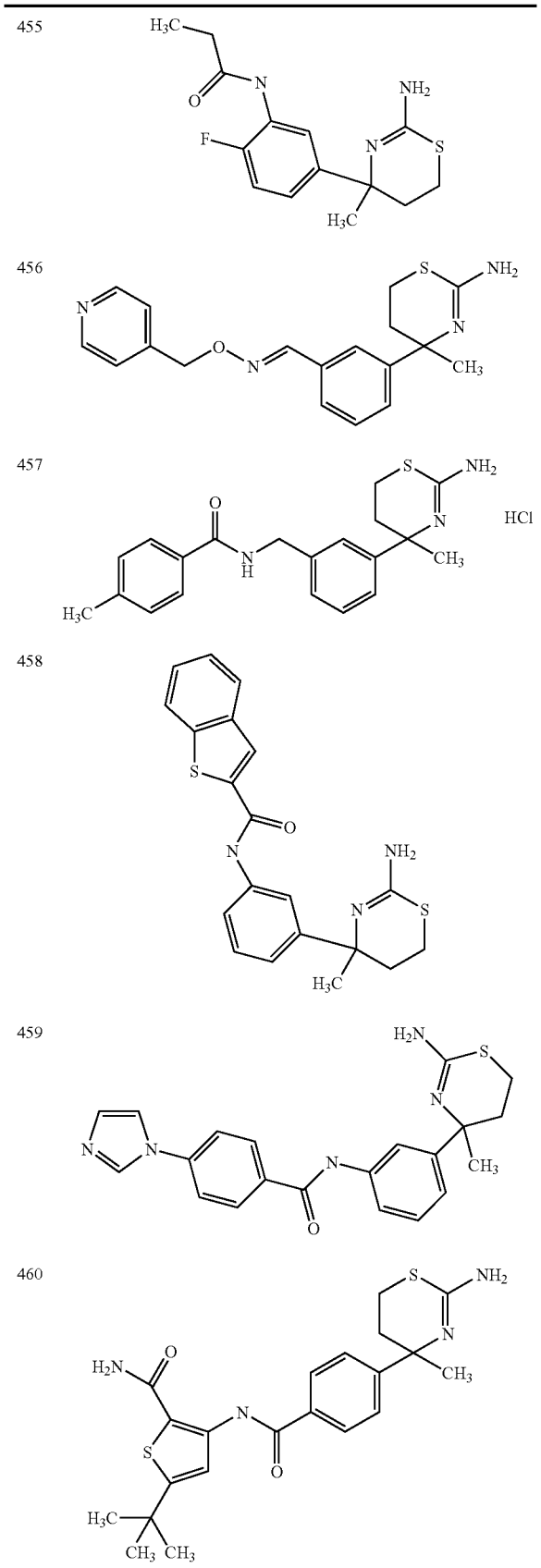
TABLE 49-continued
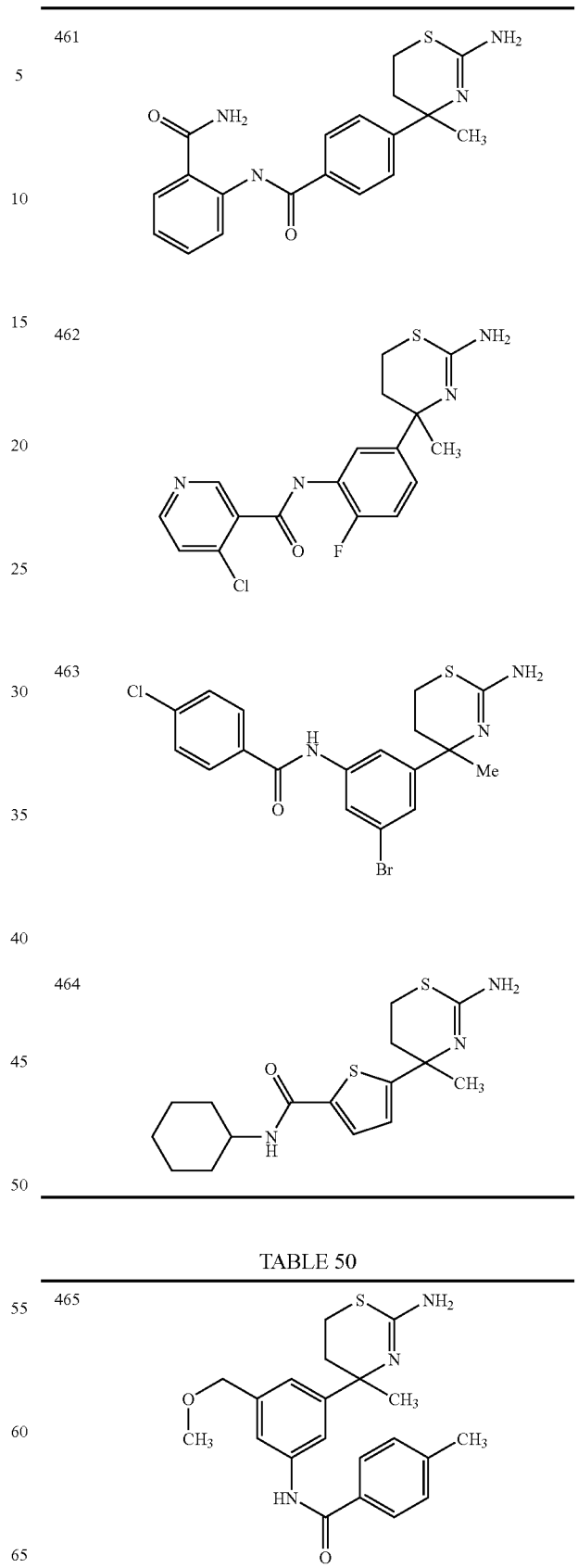
TABLE 50

TABLE 50-continued
| 466 | 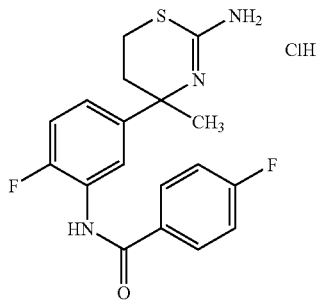 |
| --- | --- |
| 467 | 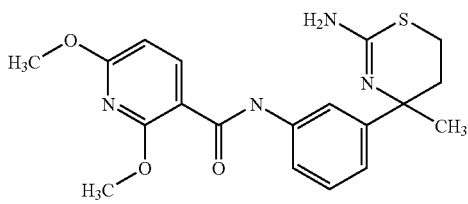 |
| 468 | 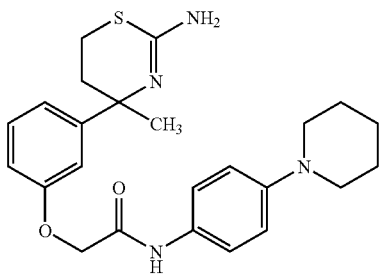 |
| 469 | 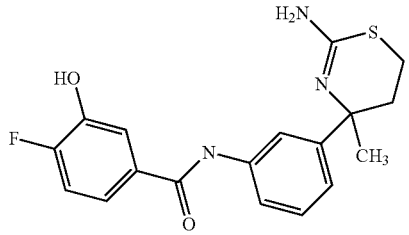 |
| 470 | 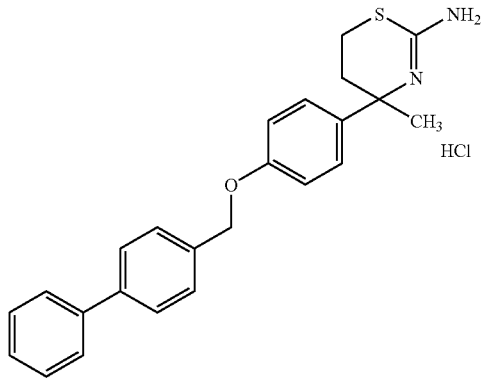 |
TABLE 50-continued
| 471 | 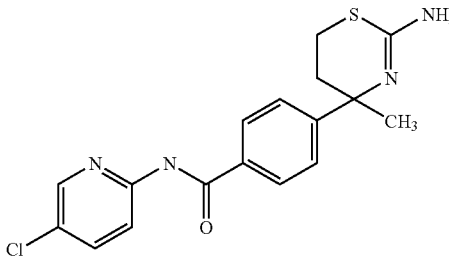 |
| --- | --- |
| 472 | 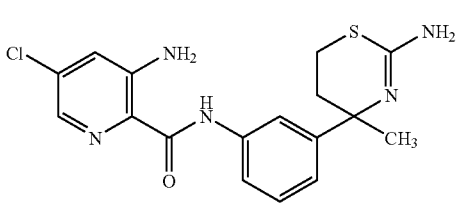 |
| 473 | 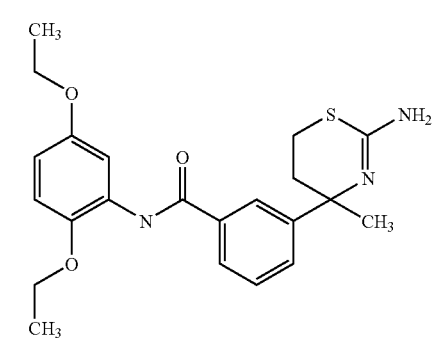 |
| 474 | 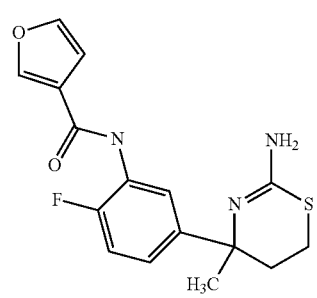 |
TABLE 51
| 475 | 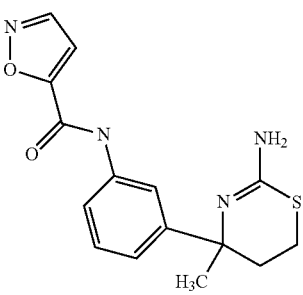 |
| --- | --- |

TABLE 51-continued
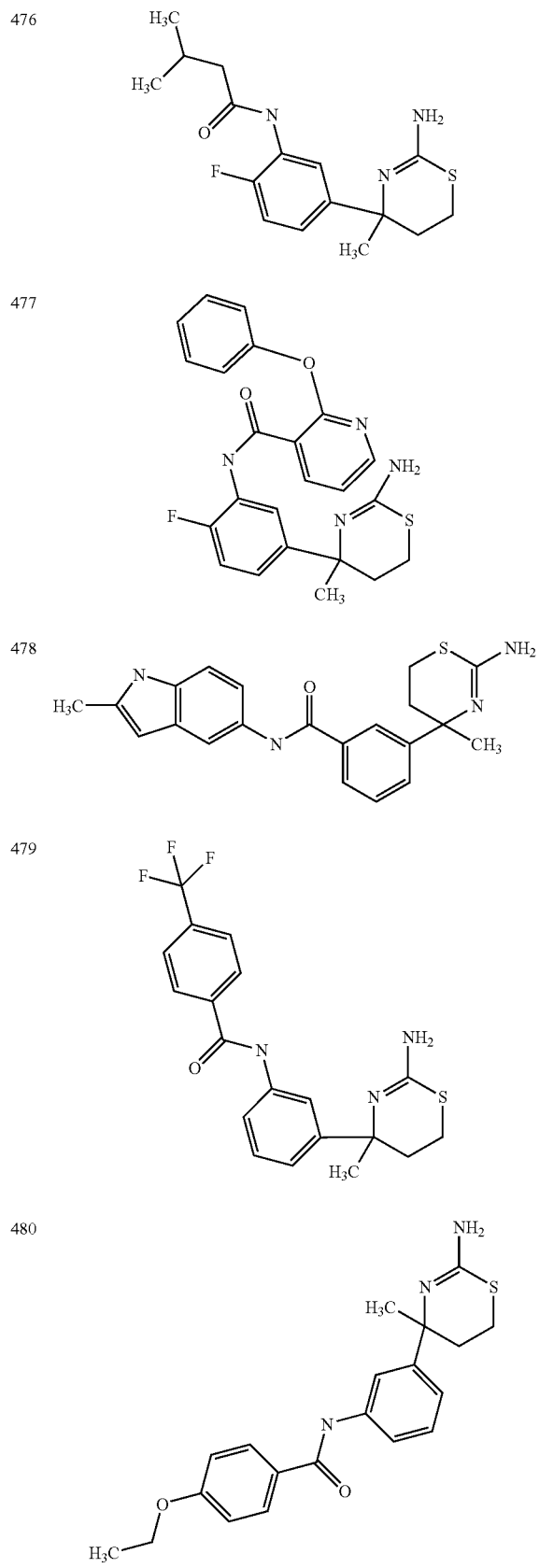
TABLE 51-continued
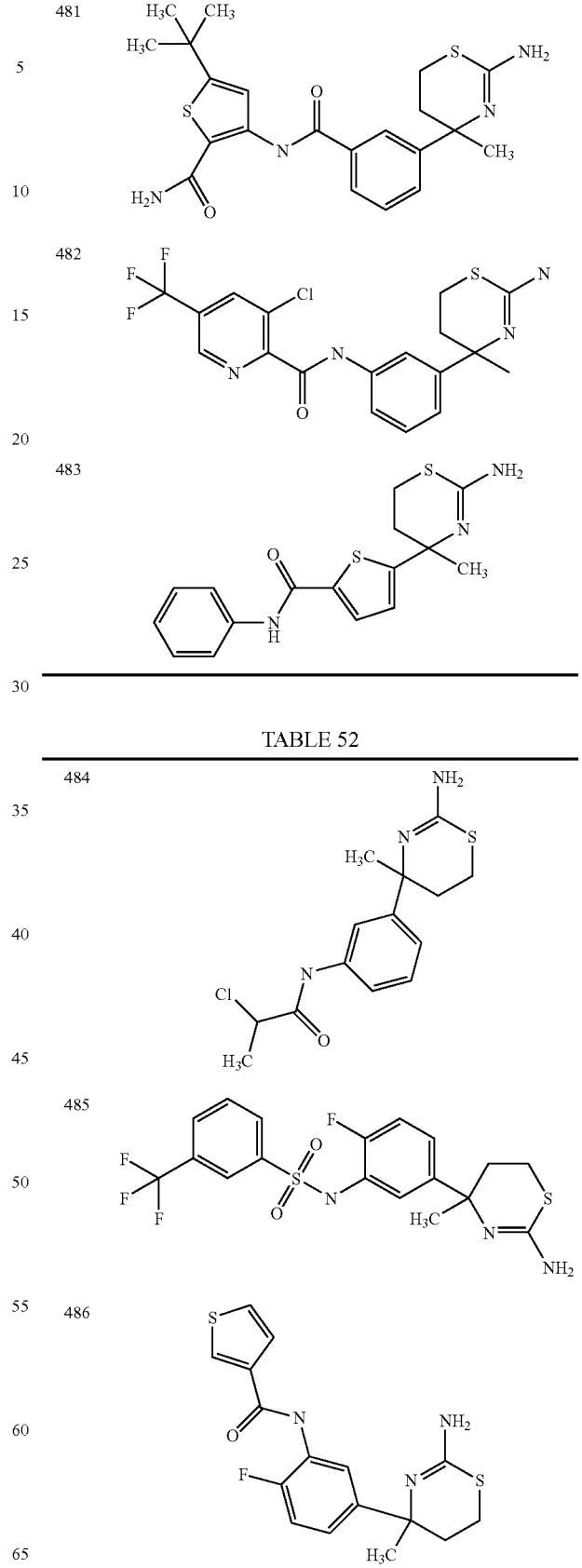
TABLE 52
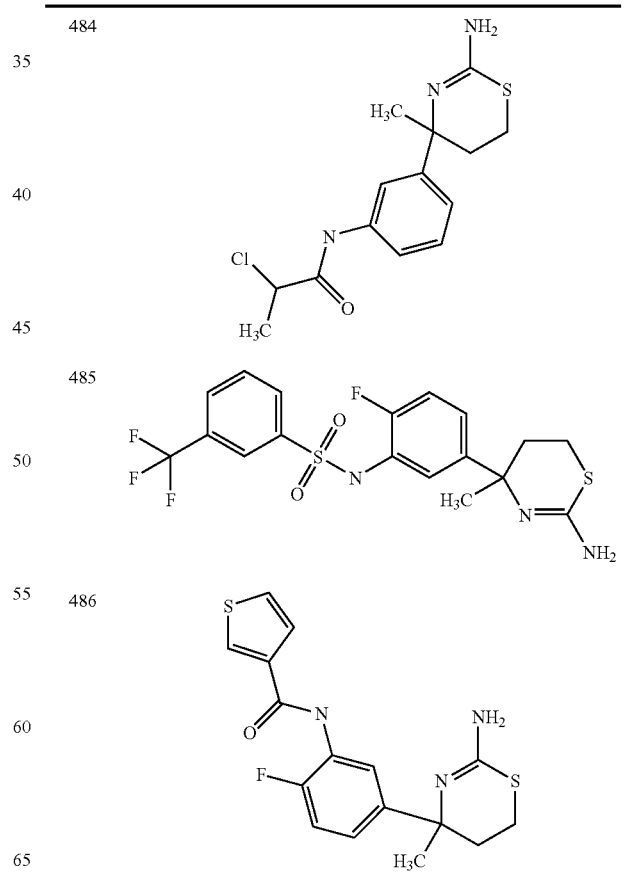

TABLE 52-continued
| | |
|---|---|
| 487 | 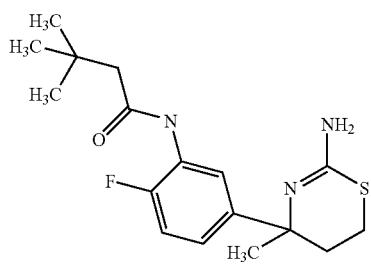 |
| 488 | 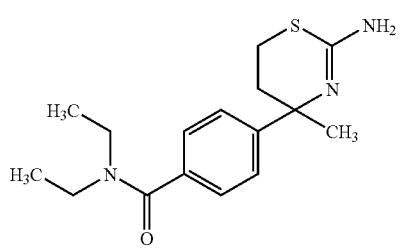 |
| 489 | 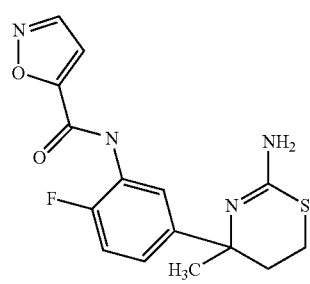 |
| 490 | 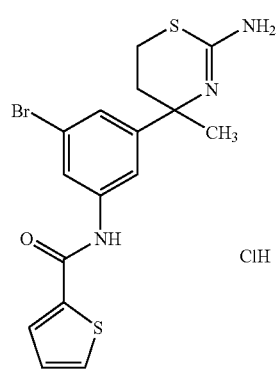 |
| 491 | 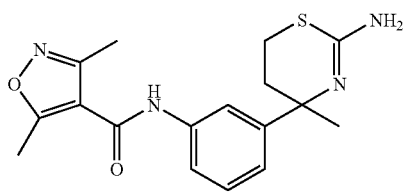 |
TABLE 52-continued
| | |
|---|---|
| 492 | 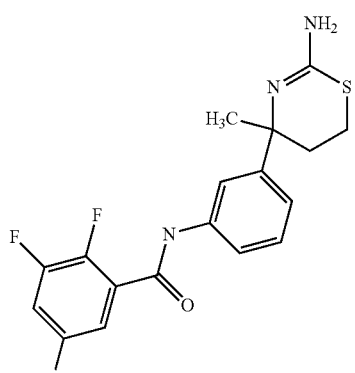 |
TABLE 53
| | |
|---|---|
| 493 | 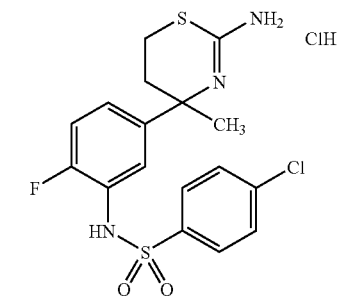 |
| 494 | 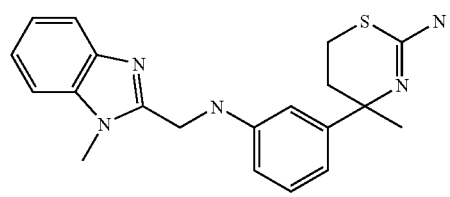 |
| 495 | 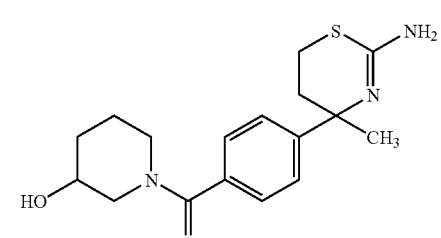 |
| 496 | 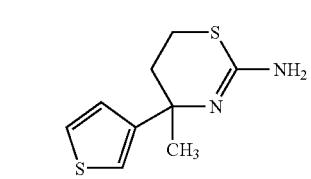 |
| 497 | 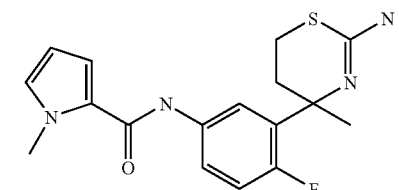 |

TABLE 53-continued
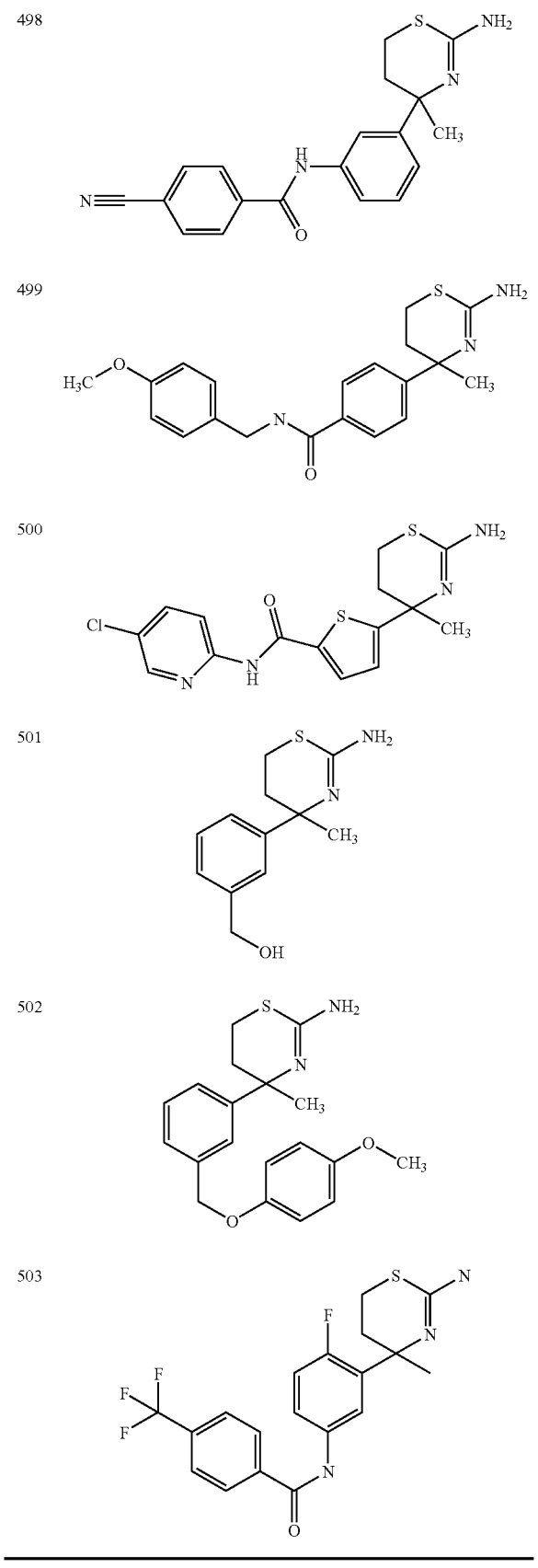
TABLE 54
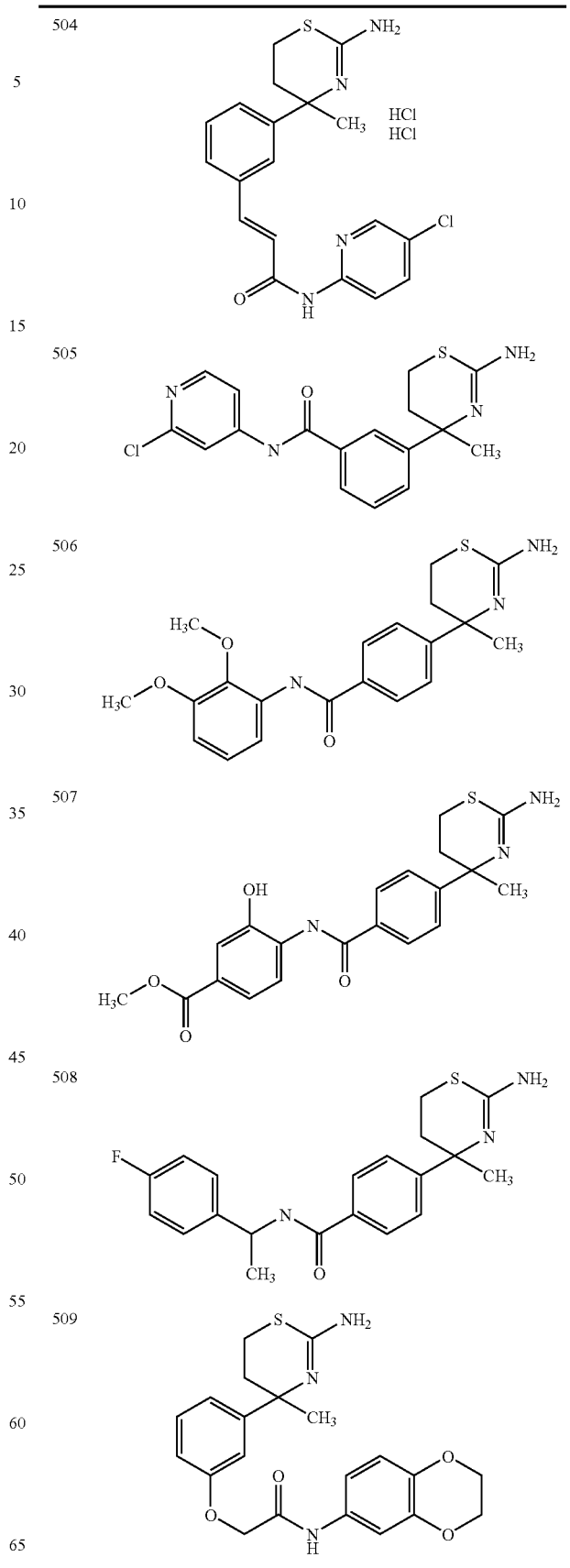

TABLE 54-continued
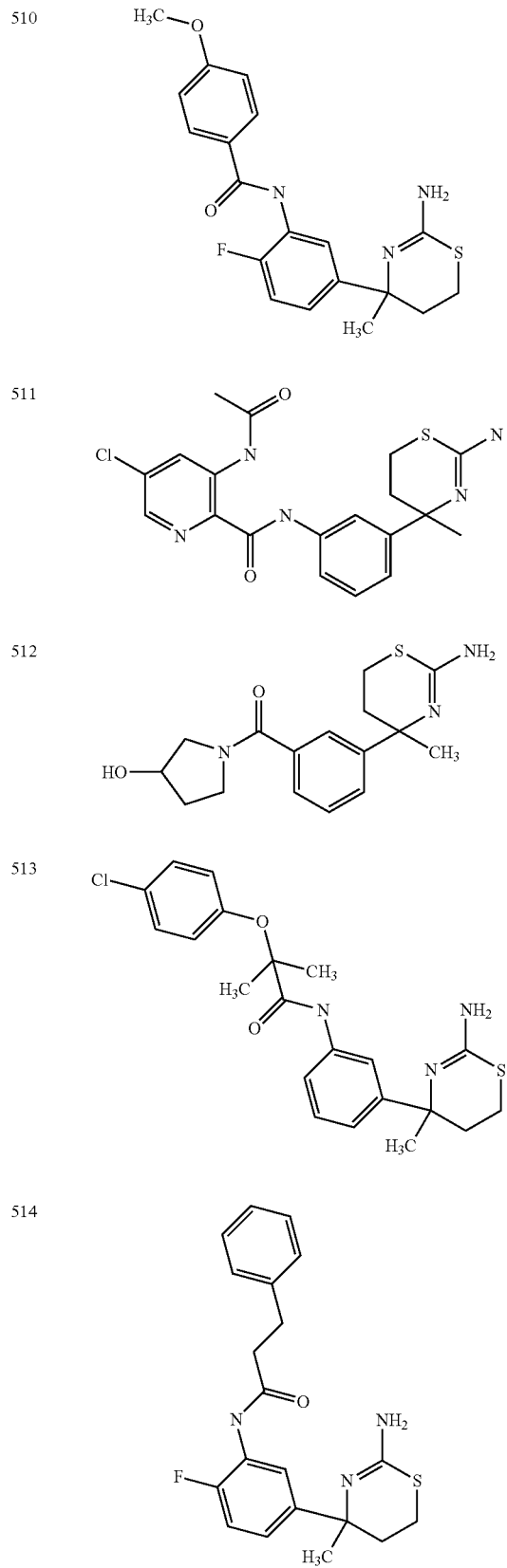
TABLE 55
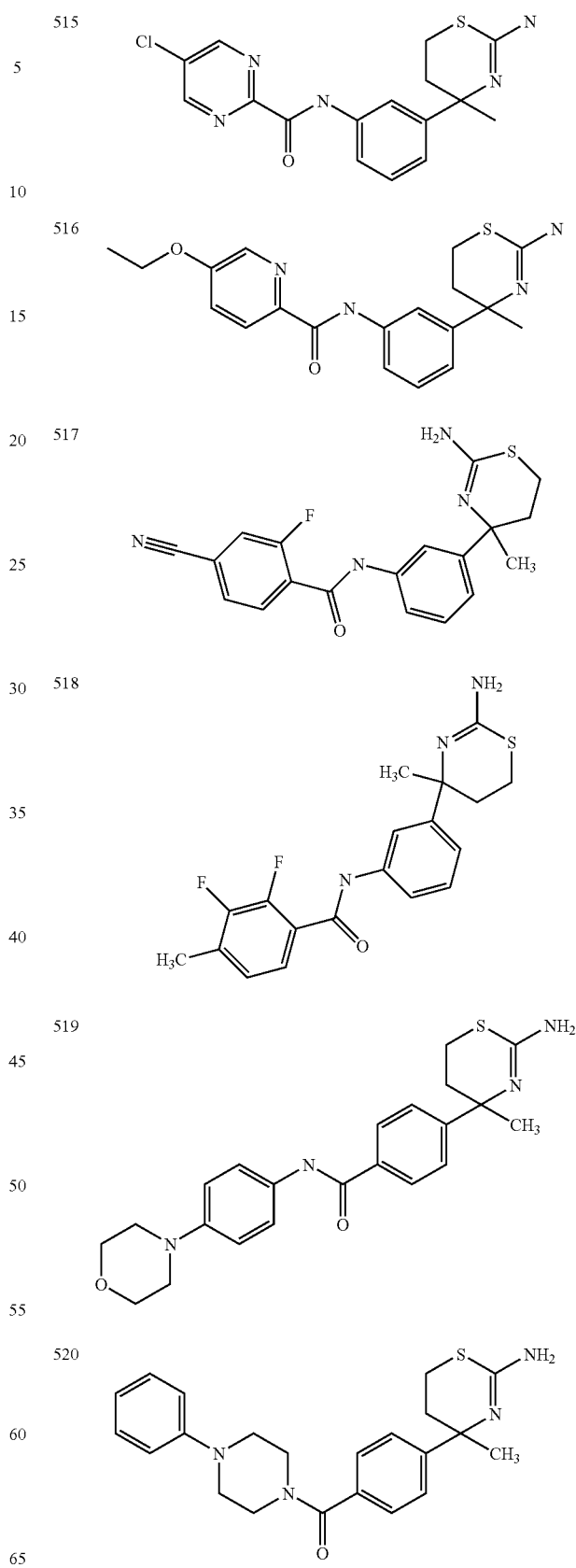

TABLE 55-continued
521 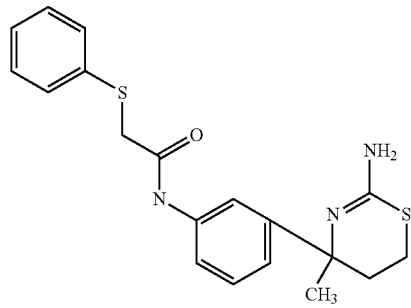
522 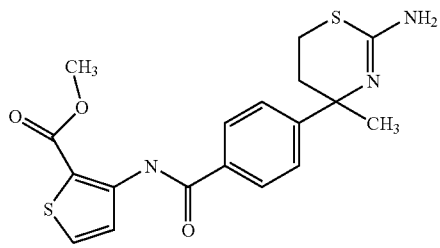
523 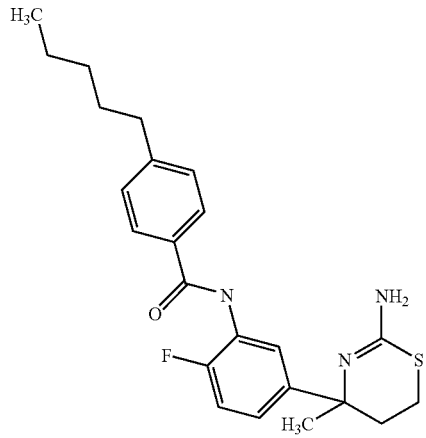
524 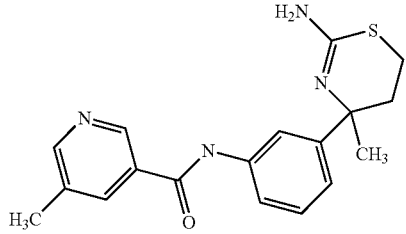
TABLE 56
525 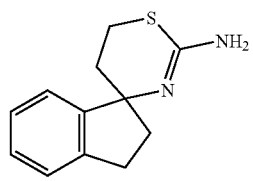
TABLE 56-continued
526 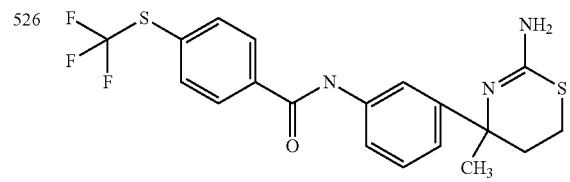
527 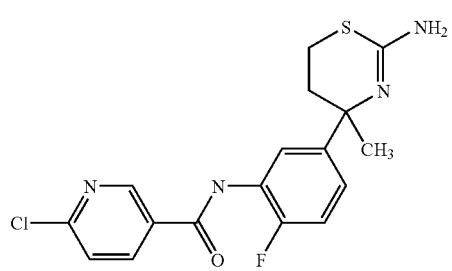
528 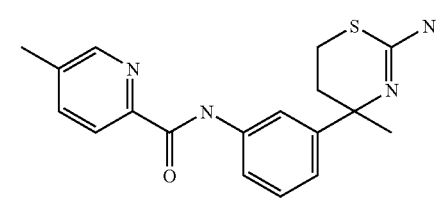
529 
530 
531 

TABLE 56-continued
| | |
|---|---|
| 532 | 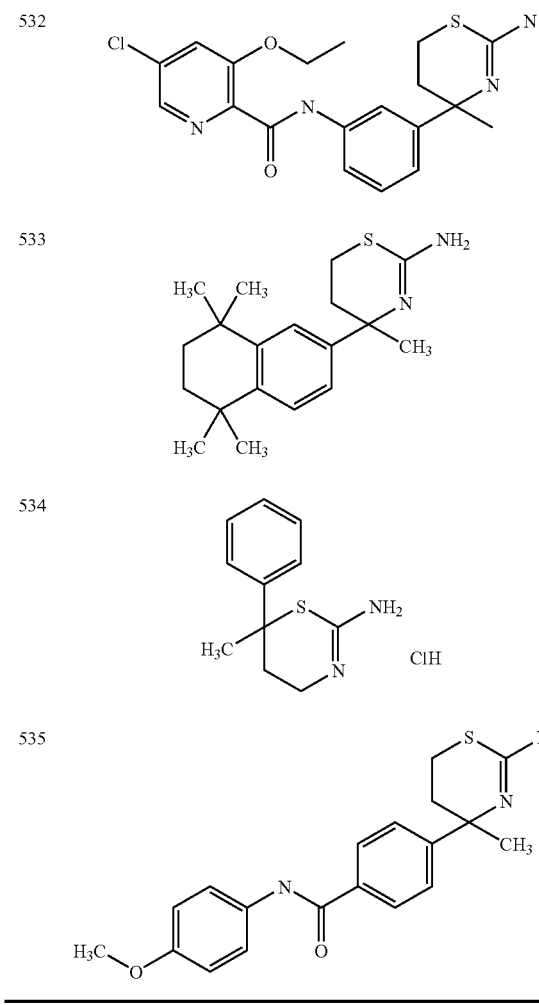 |
| 533 | |
| 534 | |
| 535 | |
TABLE 57
| | |
|---|---|
| 536 | 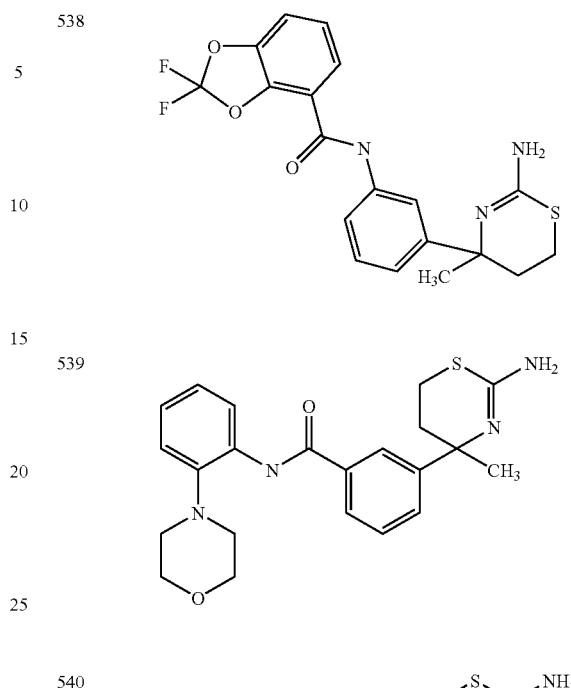 |
| 537 | |
TABLE 57-continued
| | |
|---|---|
| 538 | 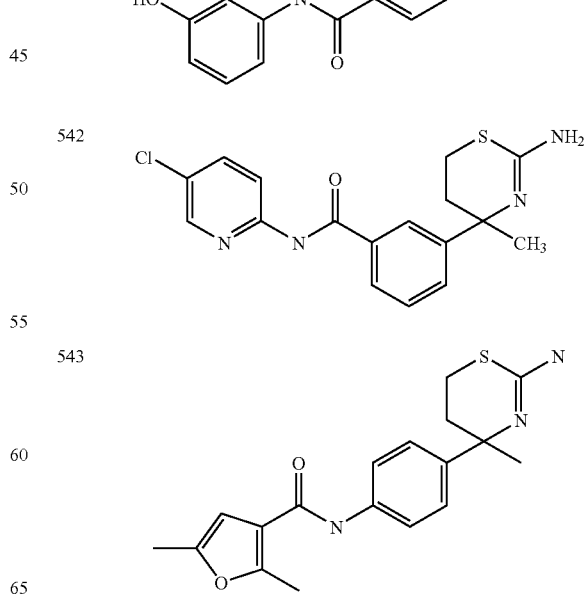 |
| 539 | |
| 540 | |
| 541 | |
| 542 | |
| 543 | |
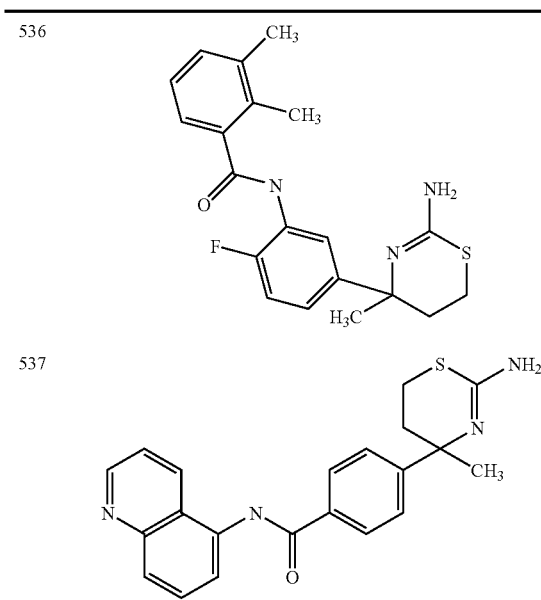

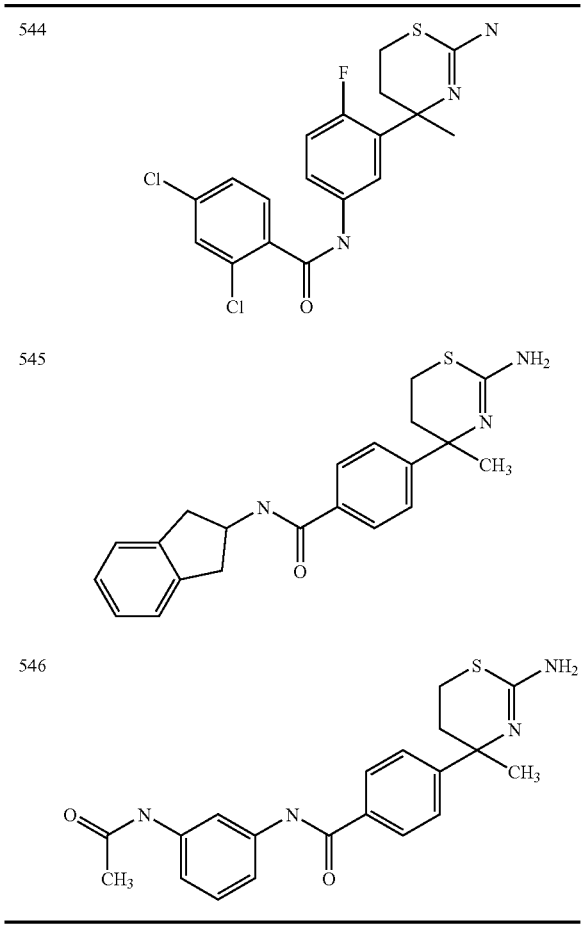

TABLE 58-continued
555 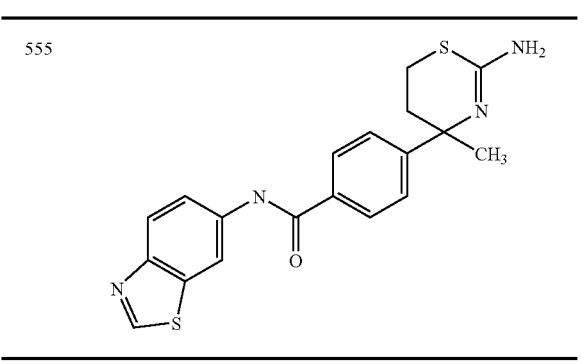
TABLE 59
556 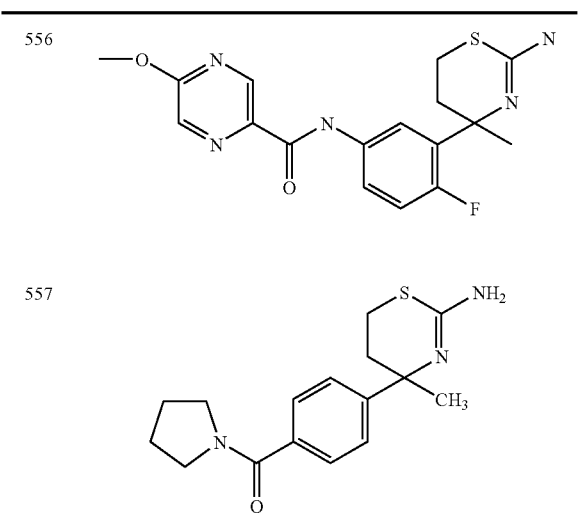
557
558
559 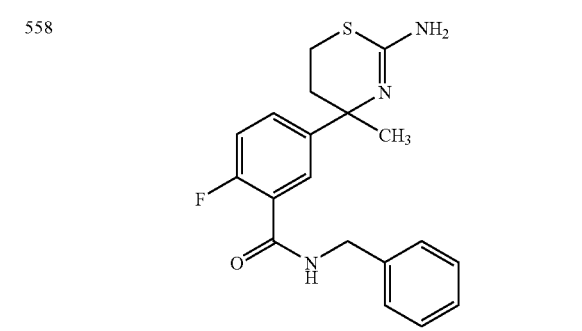
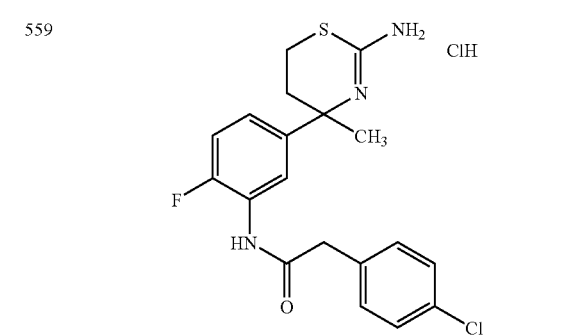
TABLE 59-continued
560 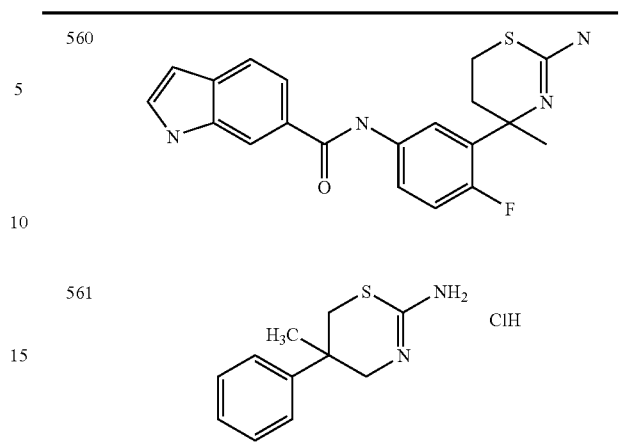
561
562 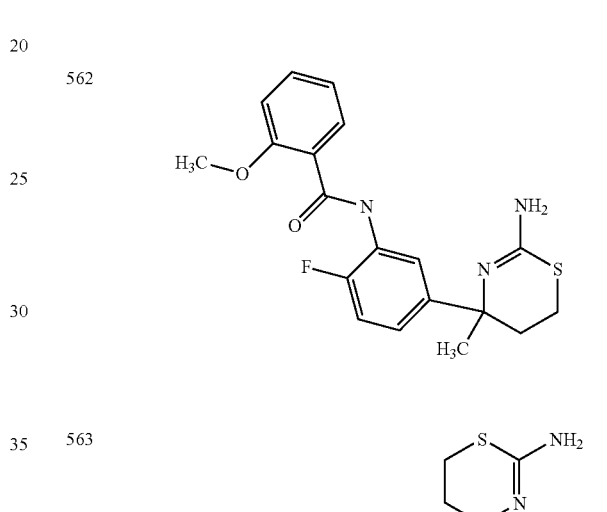
563 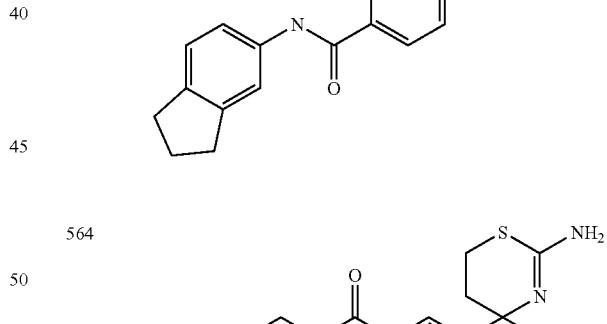
564
565 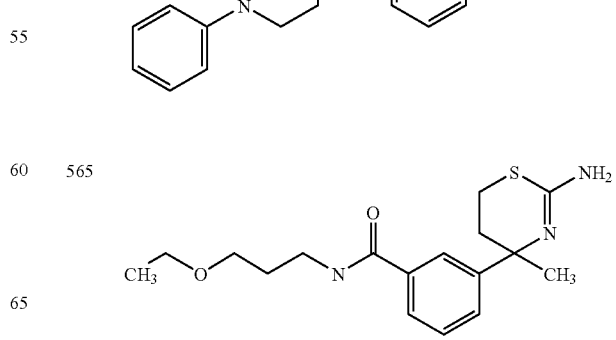

TABLE 59-continued
| 566 | 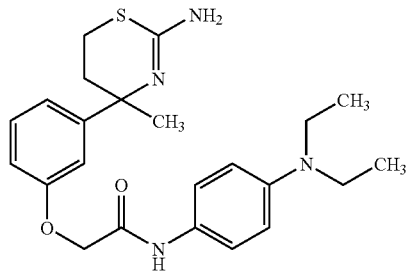 |
TABLE 60
| 567 | 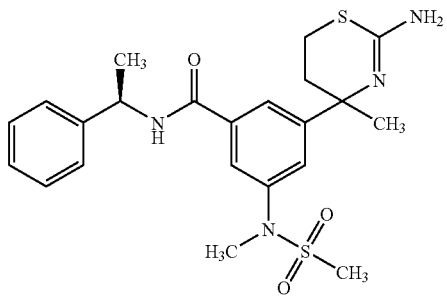 |
| 568 | 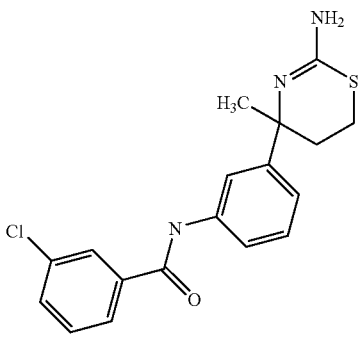 |
| 569 | 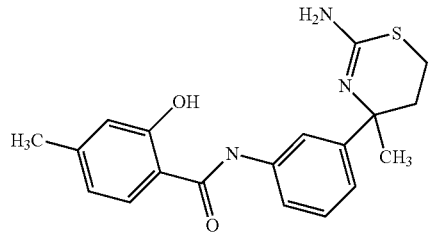 |
| 570 | 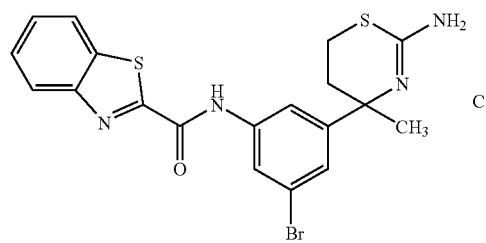 ClH |
TABLE 60-continued
| 571 | 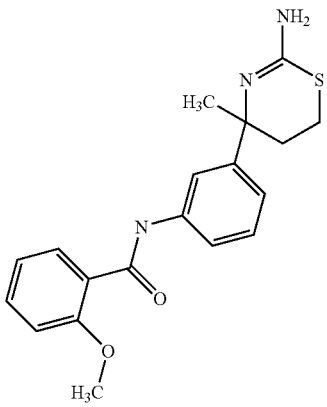 |
| 572 | 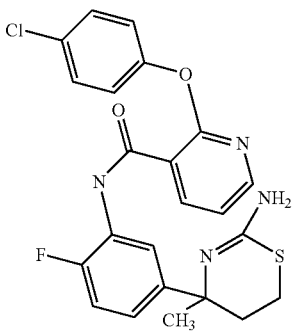 |
| 573 | 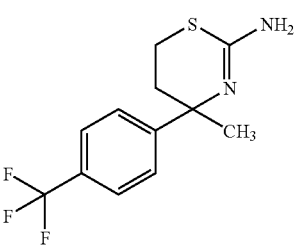 |
| 574 | 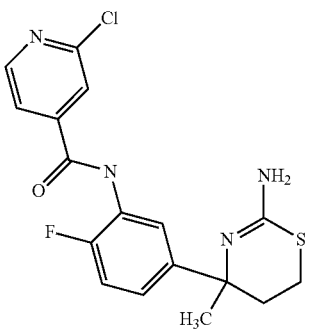 |

TABLE 61
575 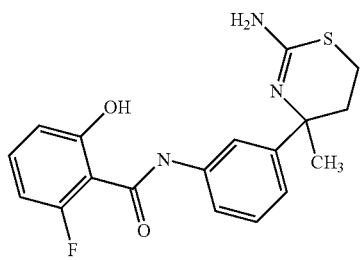
576 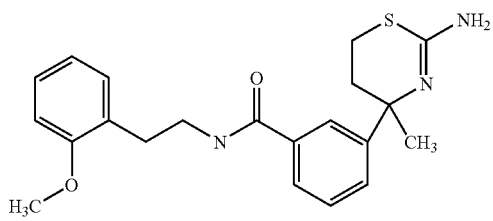
577 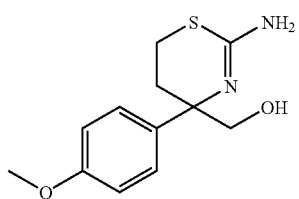
578 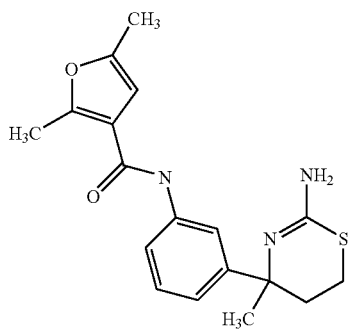
579 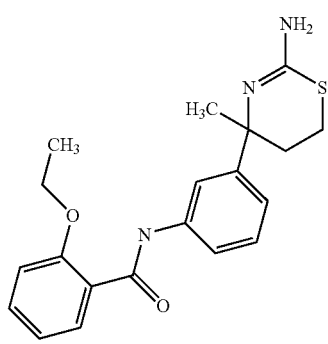
580 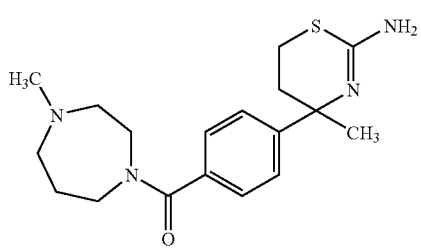
TABLE 61-continued
581 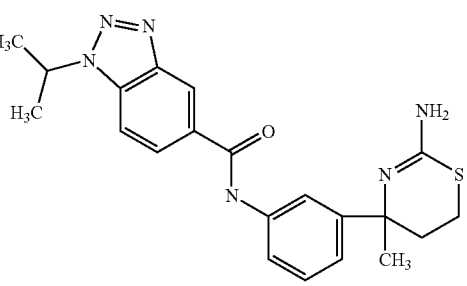
582 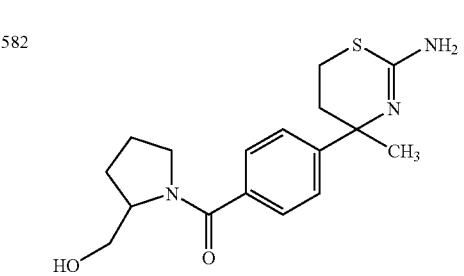
583 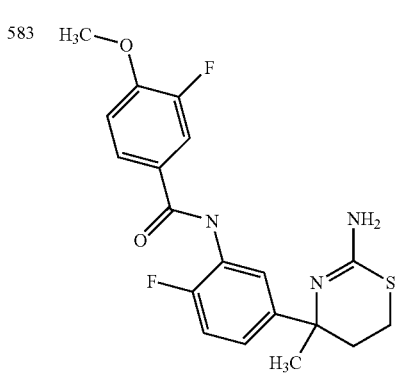
584 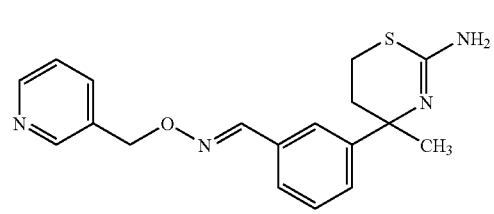
TABLE 62
585 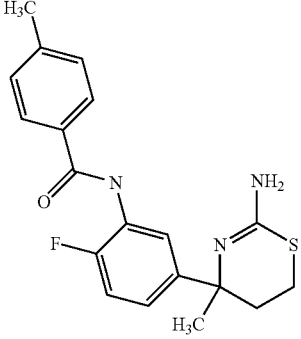

TABLE 62-continued
586 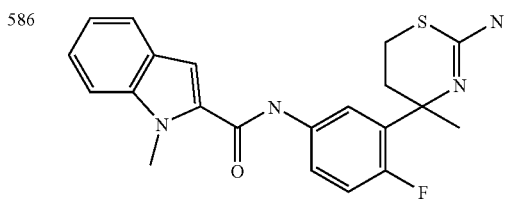
587 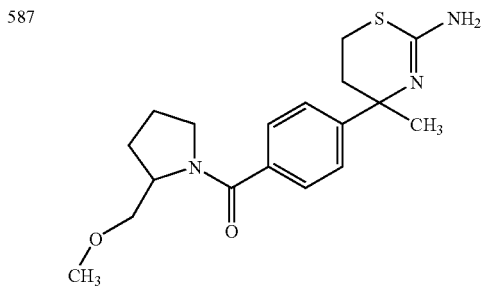
588 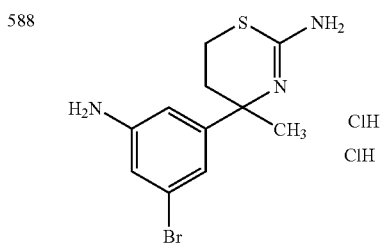
589 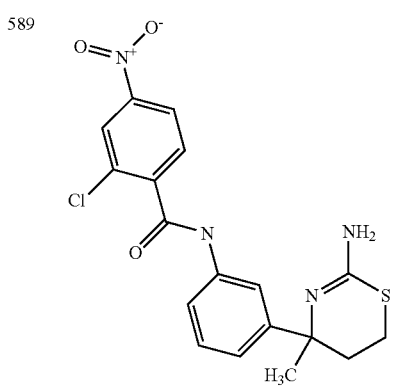
590 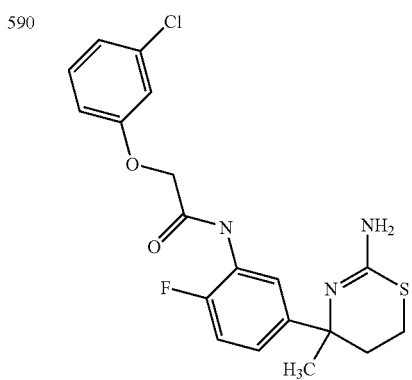
TABLE 62-continued
591 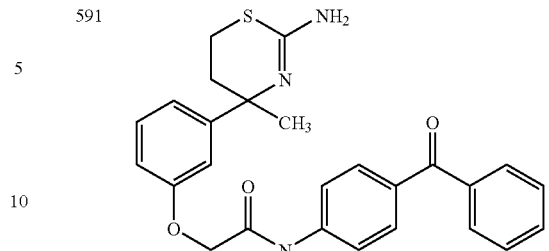
TABLE 63
592 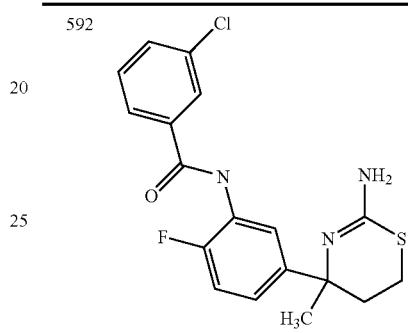
593 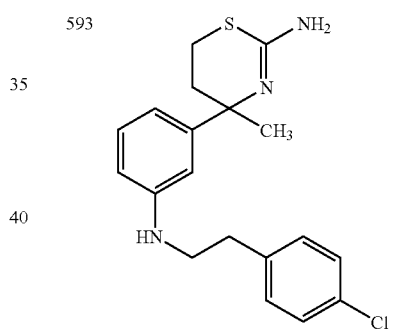
594 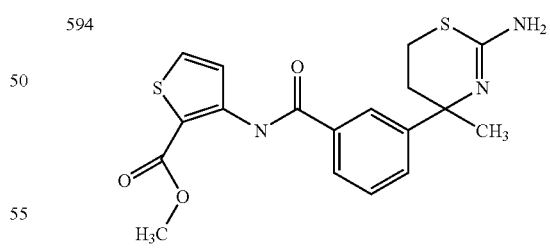
595 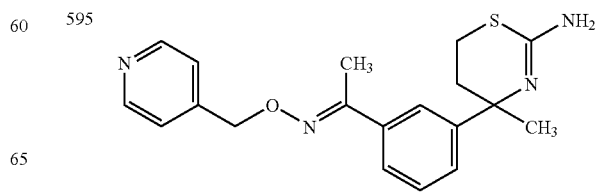

TABLE 63-continued
596 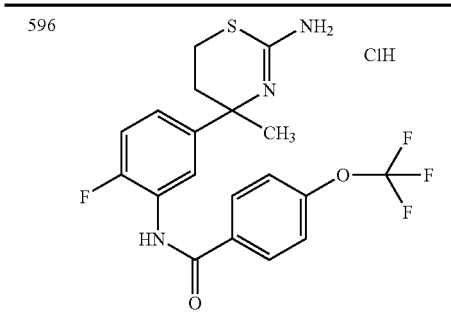
597 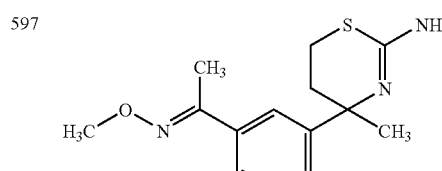
598 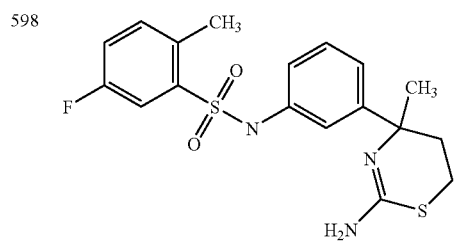
599 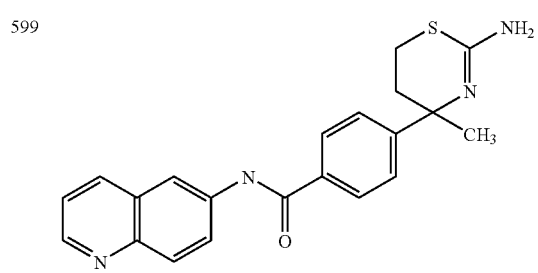
TABLE 63-continued
600 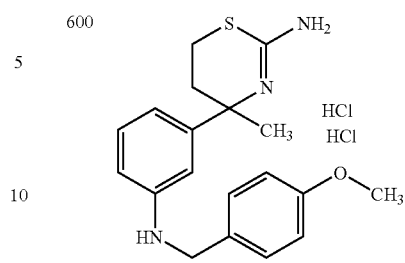
601 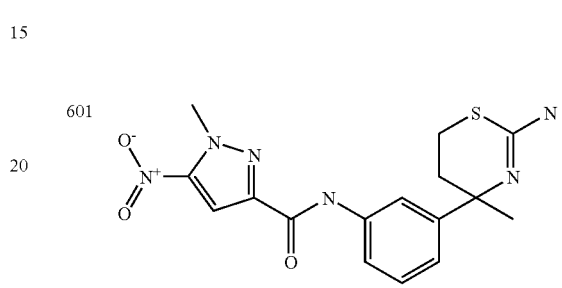
602 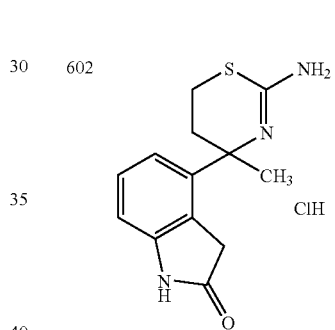
TABLE 64
603 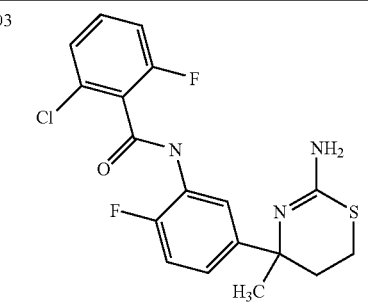
604 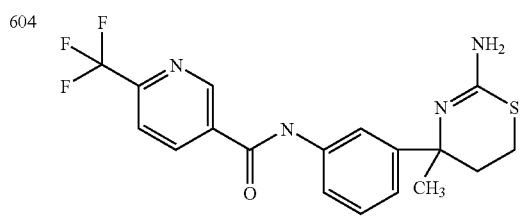

TABLE 64-continued
605 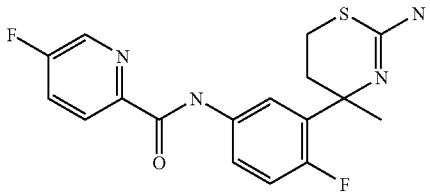
606 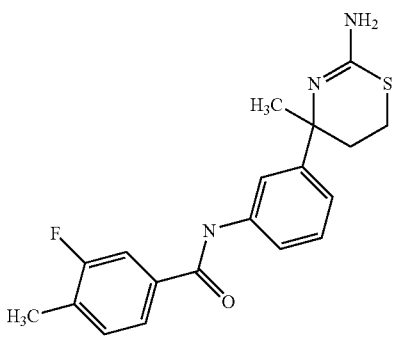
607 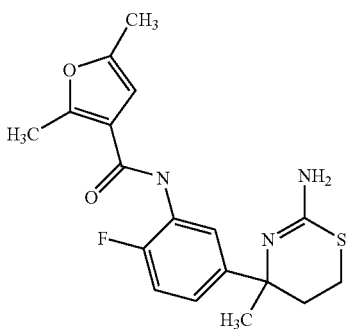
608 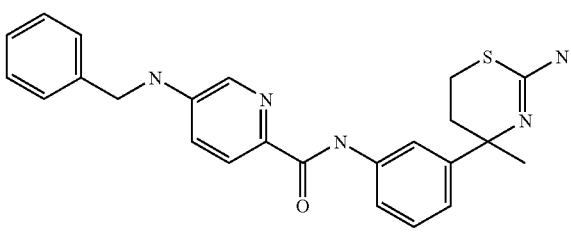
609 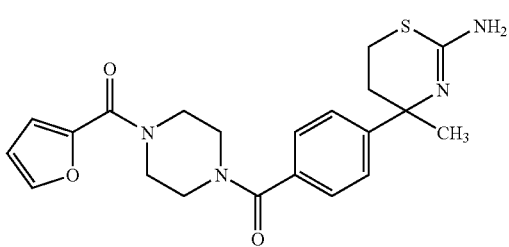

TABLE 64-continued
610 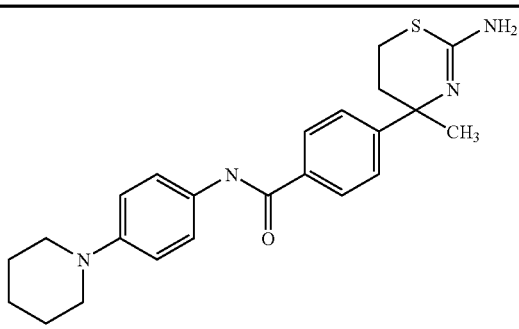
611 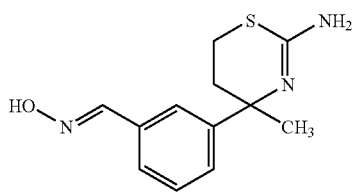
612 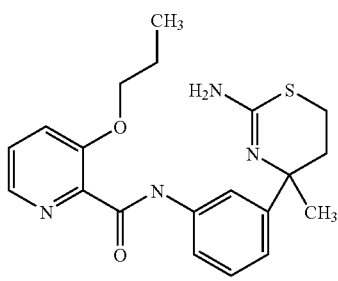
613 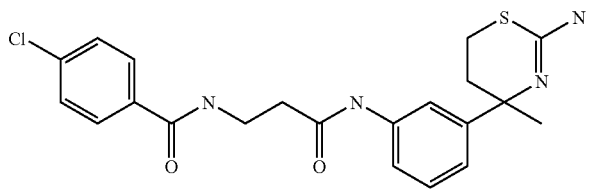
TABLE 65
614 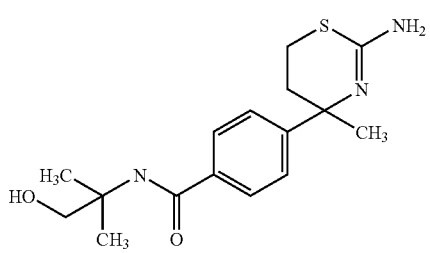
615 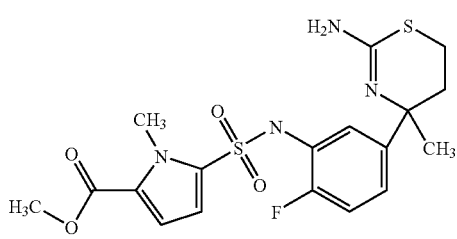
TABLE 65-continued
616 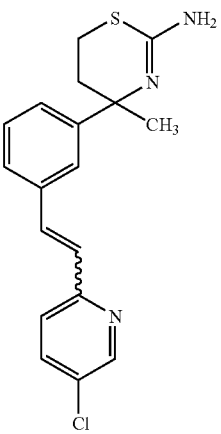

TABLE 65-continued
617 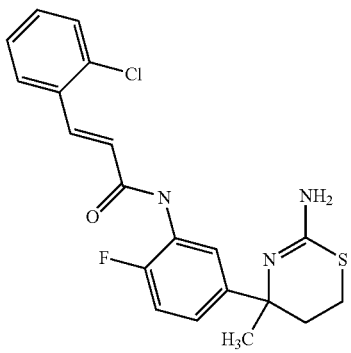
618 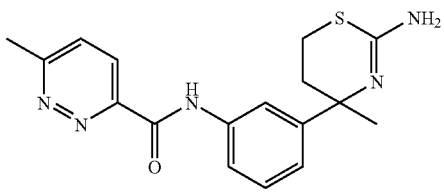
619 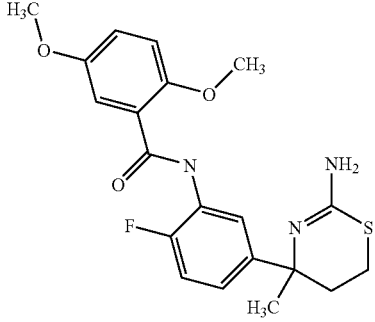
620 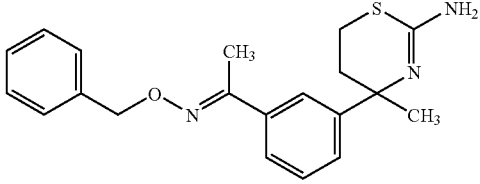
621 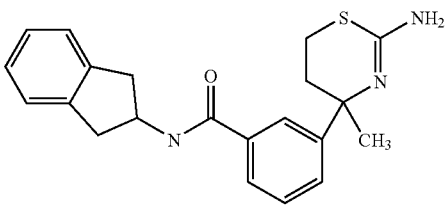
623 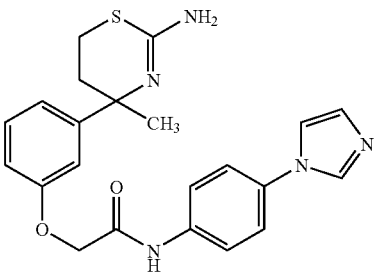
624 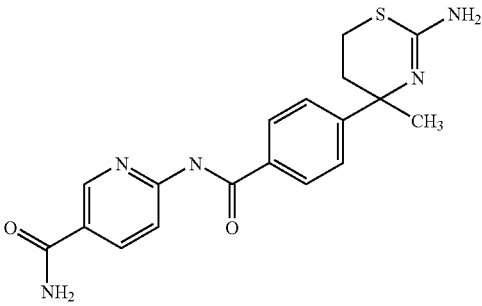
TABLE 66
625 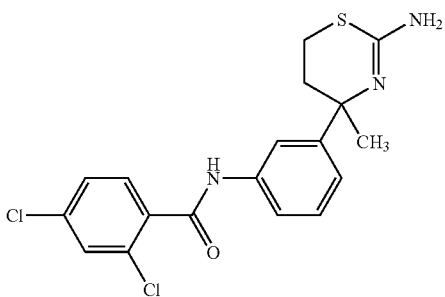

TABLE 66-continued
626
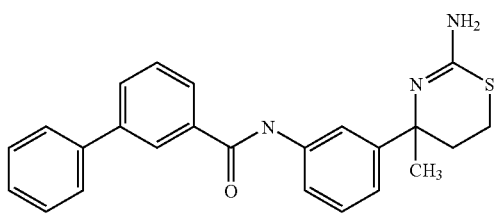
627
628
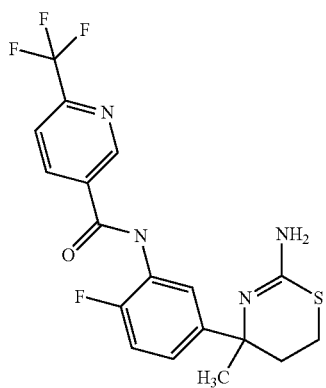
629
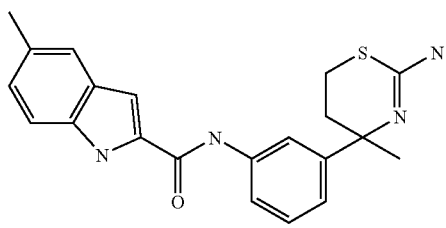
630
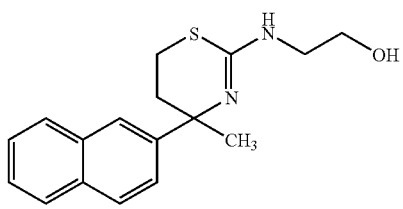
631
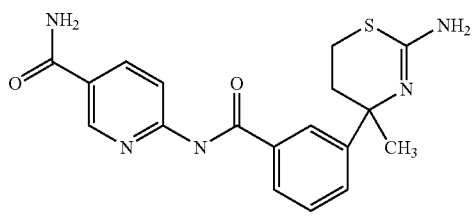

TABLE 66-continued
632 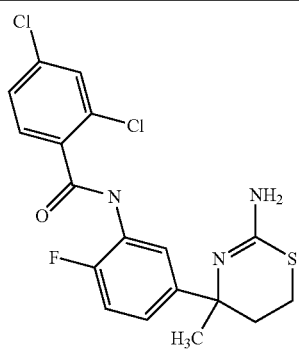
633 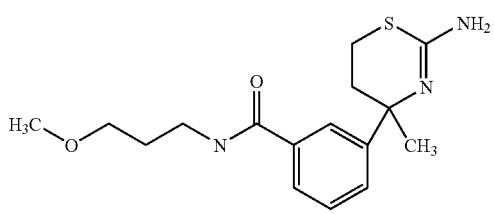
634 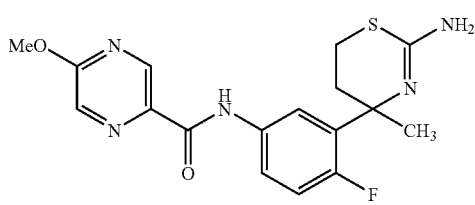
635 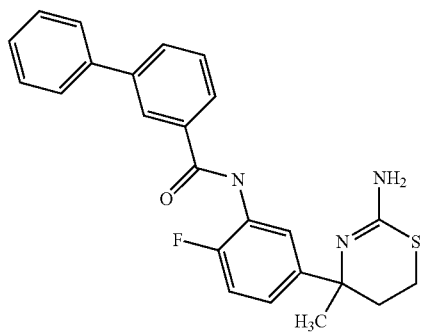
TABLE 67
636 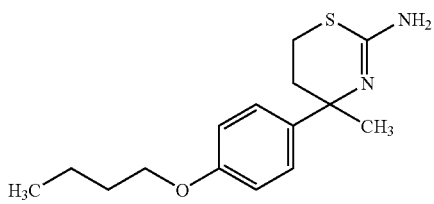
TABLE 67-continued
637 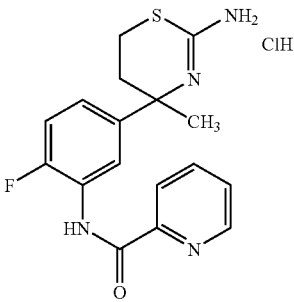

TABLE 67-continued
638 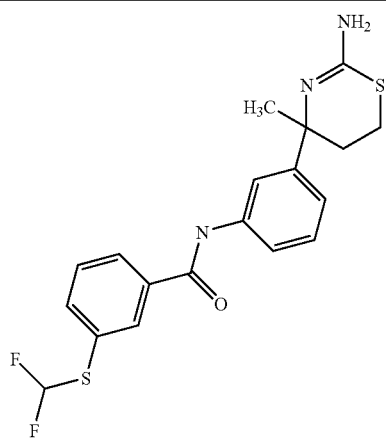
639 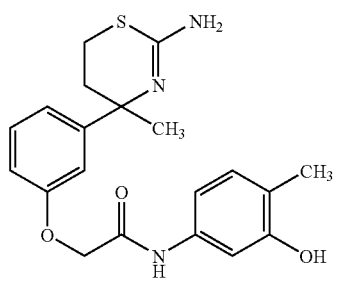
640 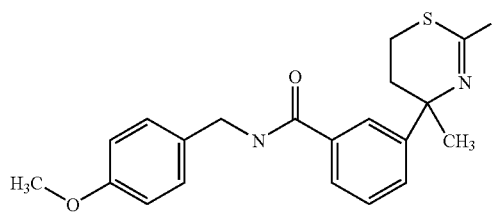
TABLE 67-continued
641 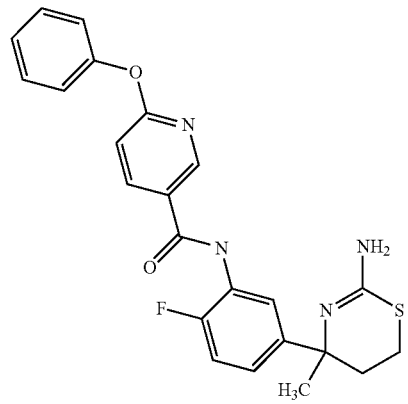
642 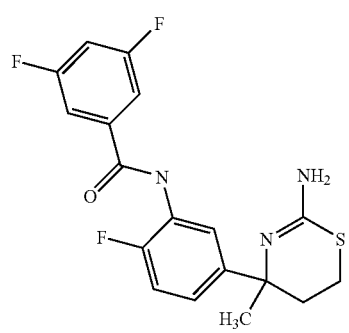
643 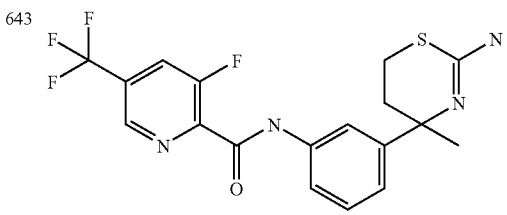
TABLE 68
644 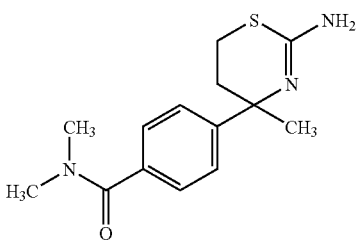
645 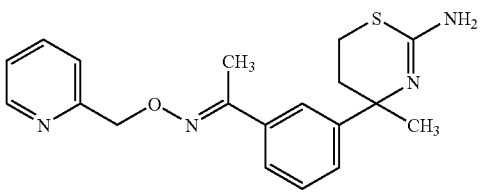

TABLE 68-continued

| 646 | (structure) |
| 647 | (structure) |
| 648 | (structure) |
| 649 | (structure) |
| 650 | (structure) |
| 651 | (structure) |
| 652 | (structure) |

TABLE 68-continued
653 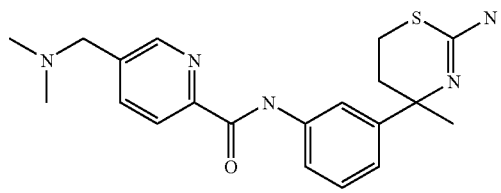
654 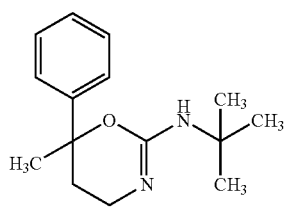
655 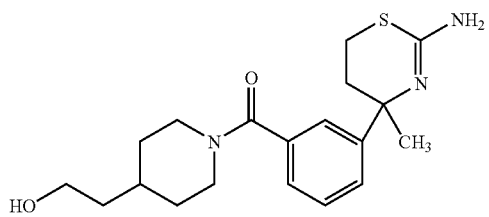
656 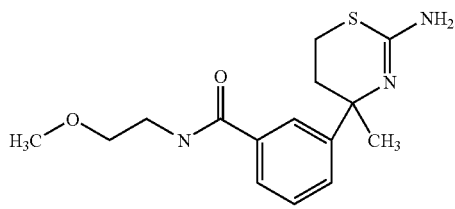
TABLE 69
657 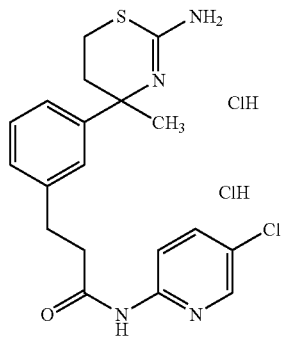
658 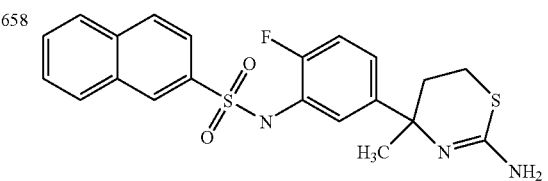
TABLE 69-continued
659 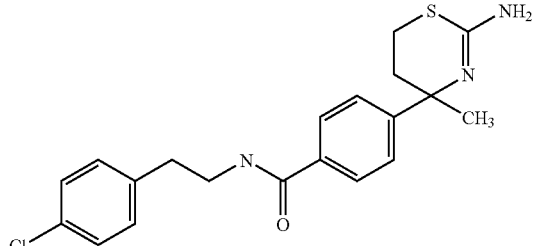
660 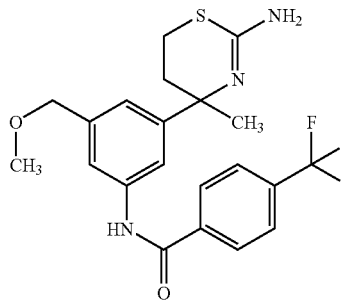

TABLE 69-continued
661 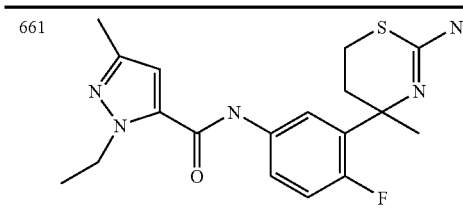
662 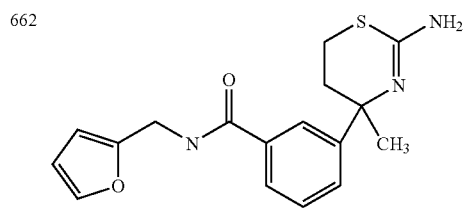
663 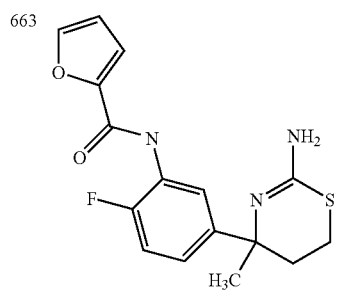
TABLE 69-continued
664 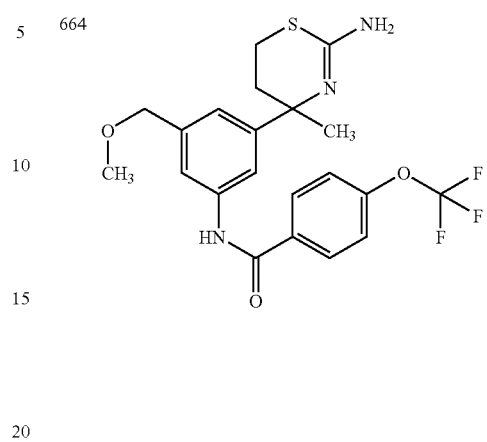
665 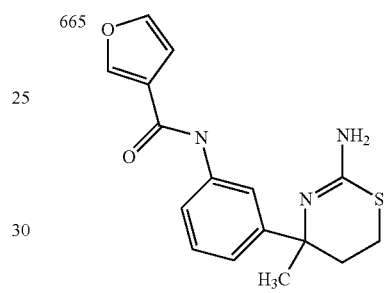
TABLE 70
666 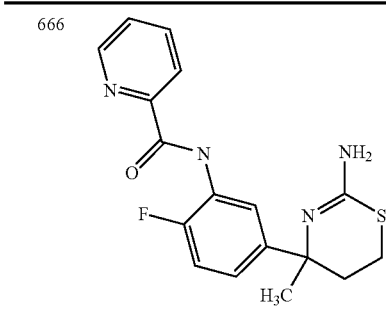
667 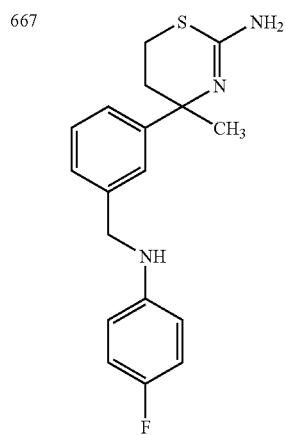

TABLE 70-continued
668 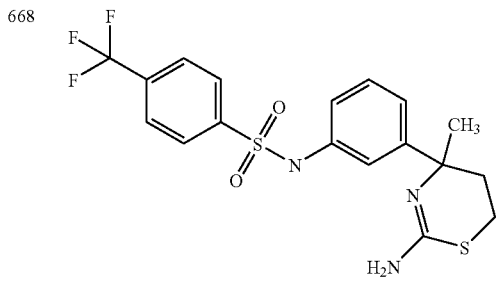
669
670 
671
672
673

TABLE 70-continued
674
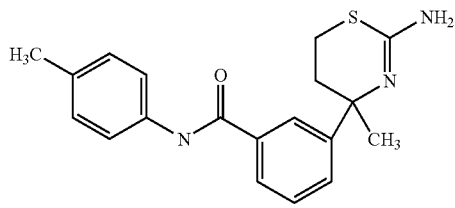
TABLE 71
675
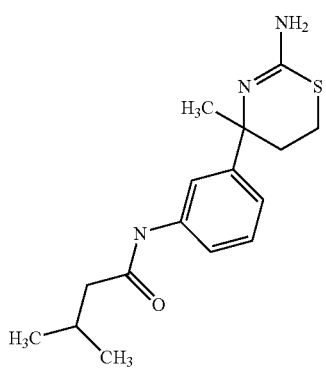
676
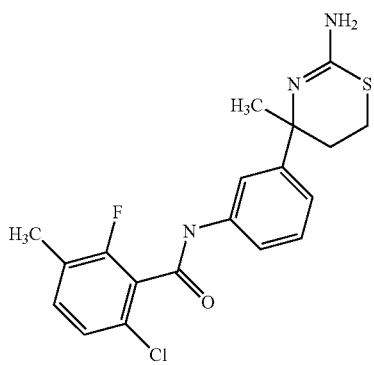
677
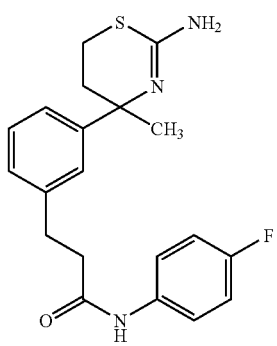
678
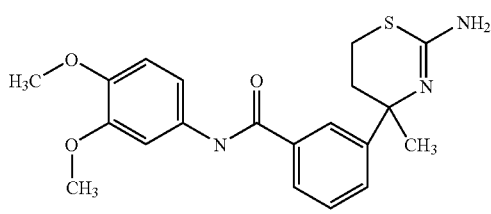
TABLE 71-continued
679
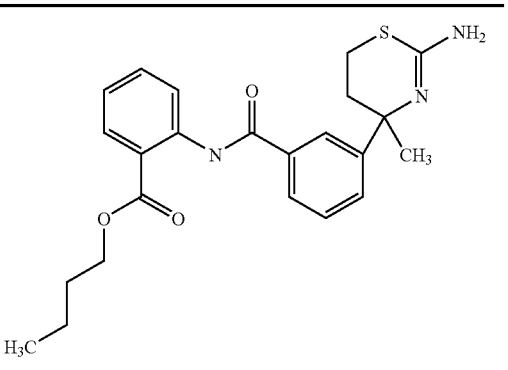
680
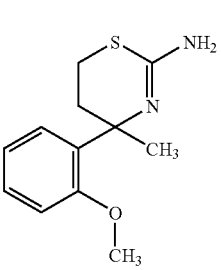
681
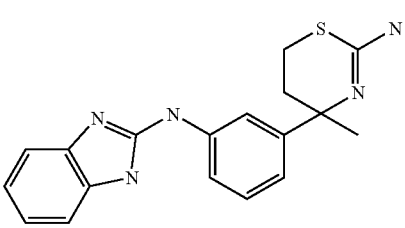
682
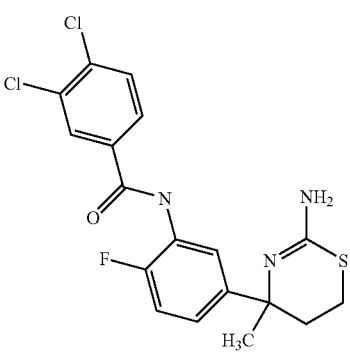

TABLE 71-continued
683 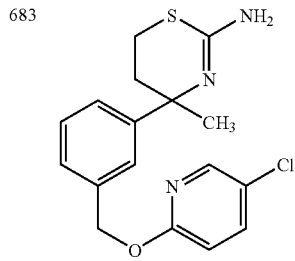
TABLE 72
684 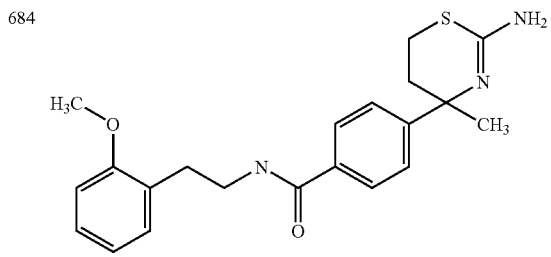
685 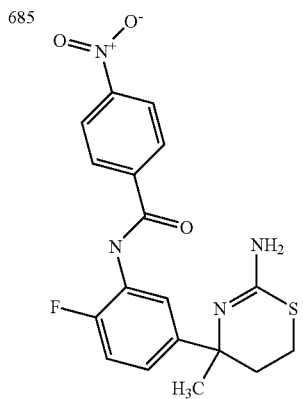
686 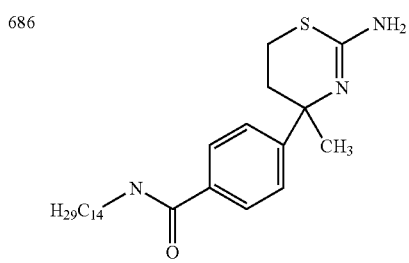
687 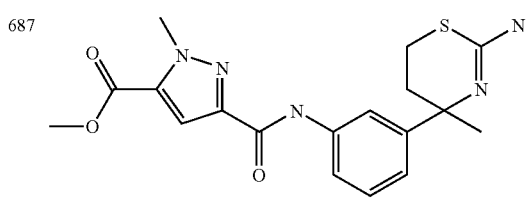
TABLE 72-continued
688 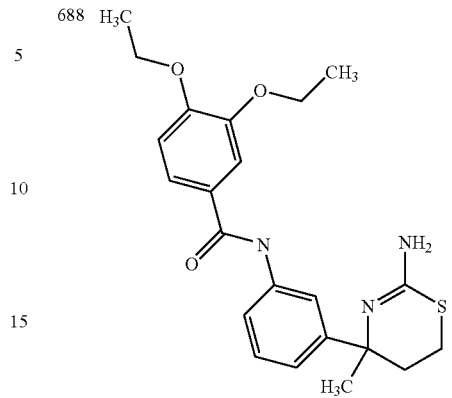
689 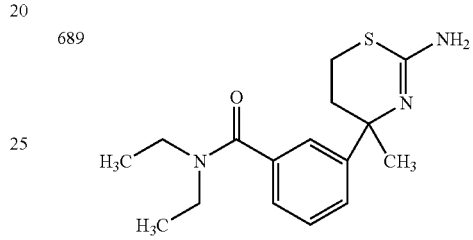
690 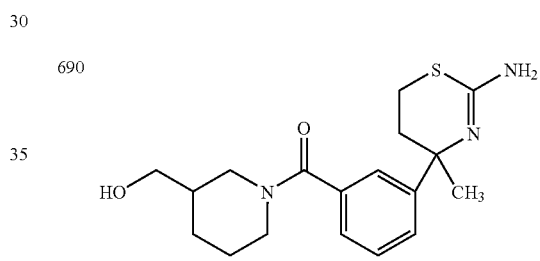
691 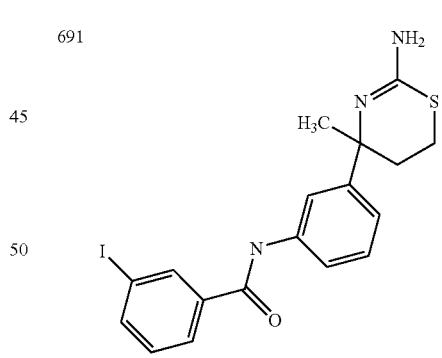
692 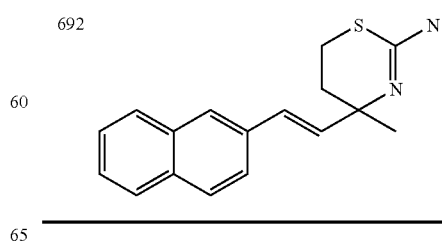

TABLE 73
693 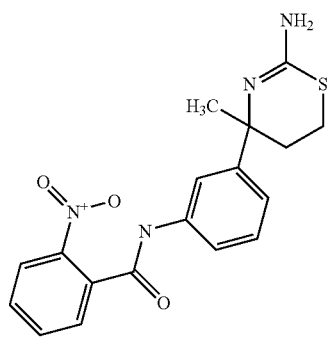
694 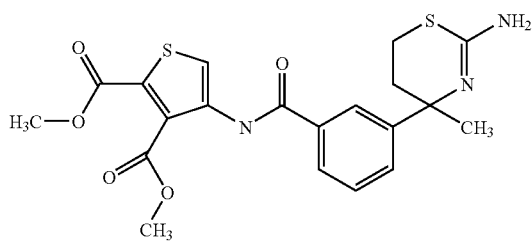
695 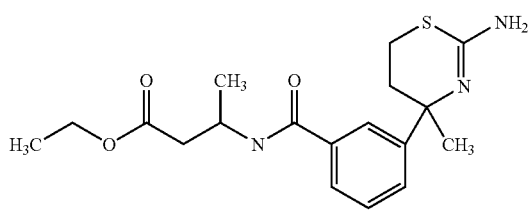
696 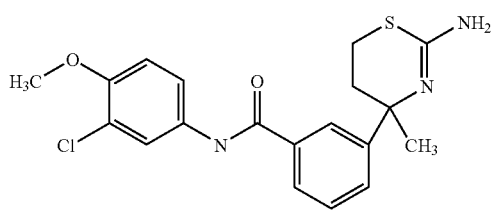
697 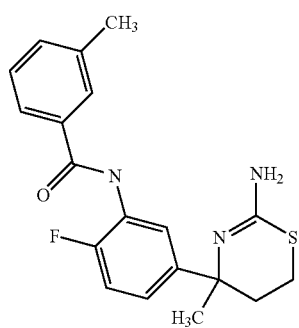
698 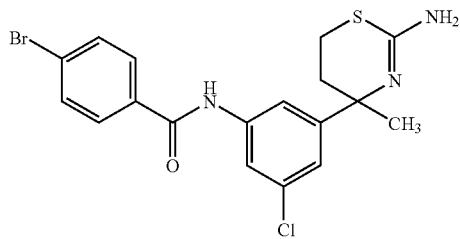

TABLE 73-continued
699 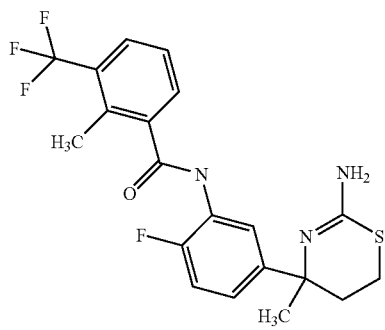
700 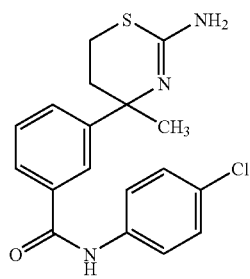
701 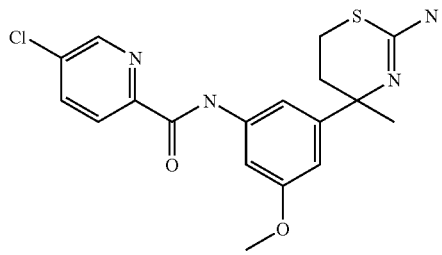
702 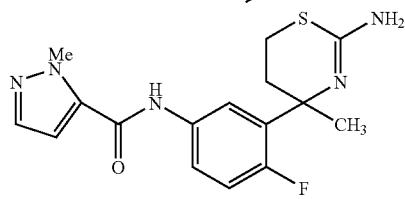
TABLE 74
703 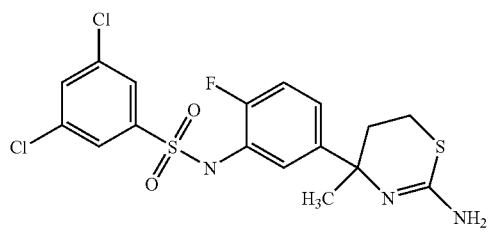
704 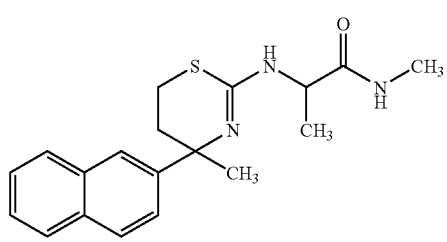
TABLE 74-continued
705 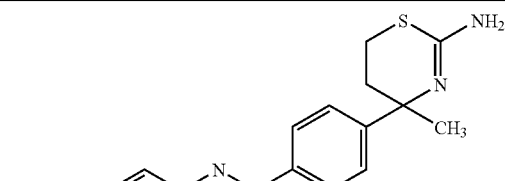
706 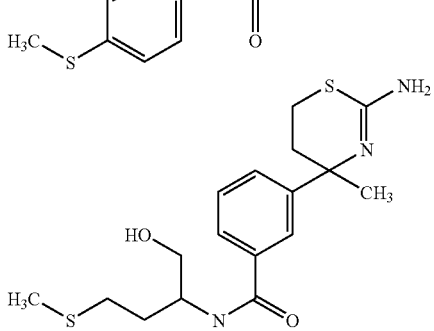

TABLE 74-continued
707
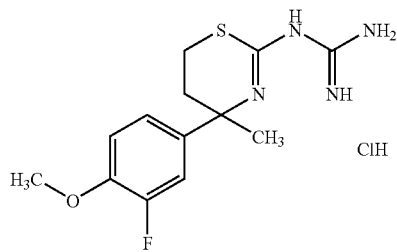
ClH
708
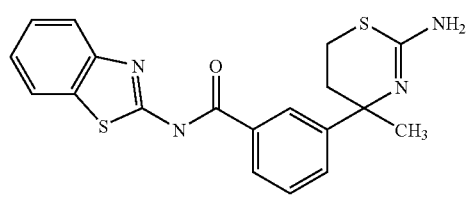
709
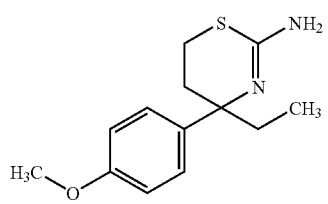
TABLE 74-continued
710
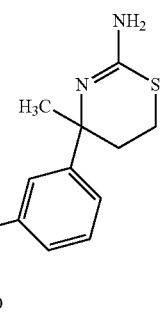
711
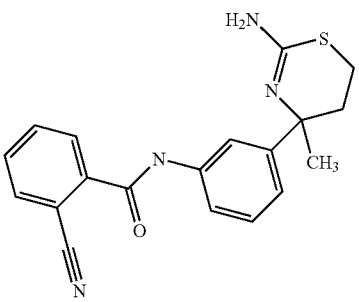
712
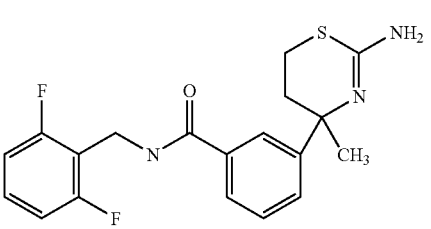
TABLE 75
713
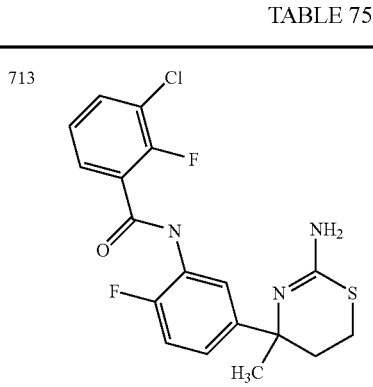

TABLE 75-continued
714 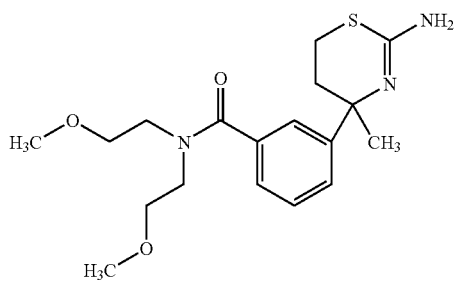
715 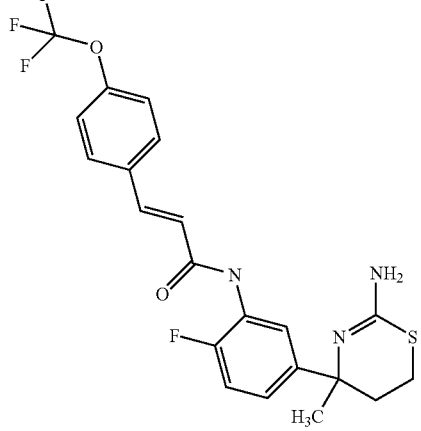
716 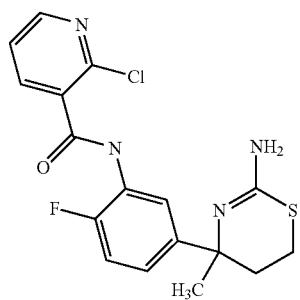
717 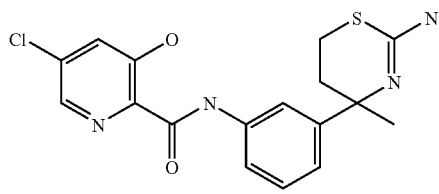
718 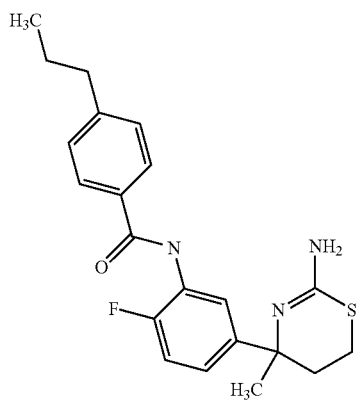

TABLE 75-continued
719 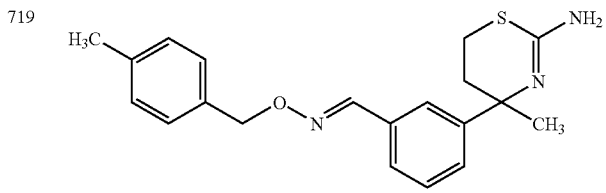
TABLE 76
720 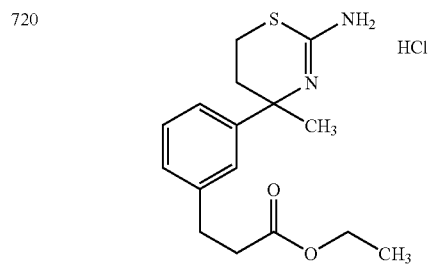
721 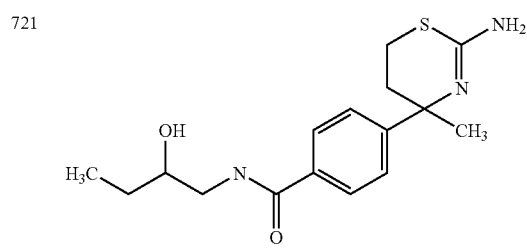
722 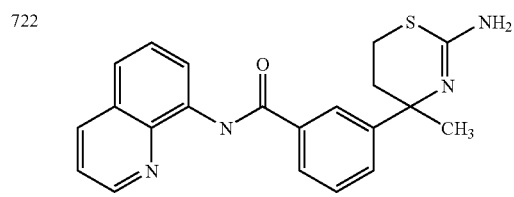
723 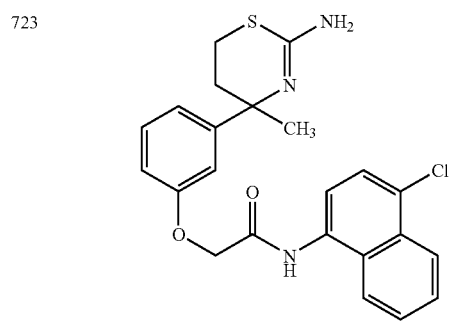
724 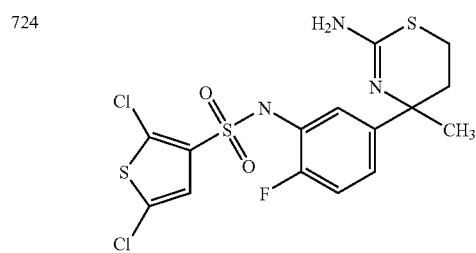
TABLE 76-continued
725 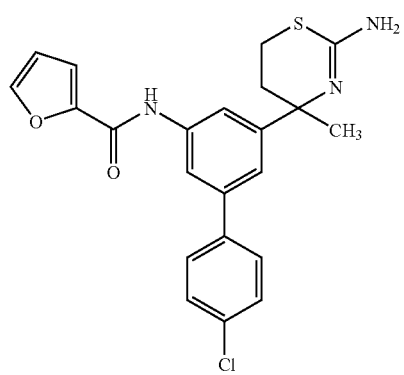
726 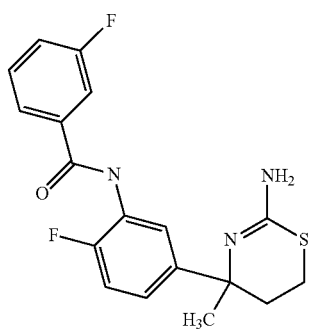
727 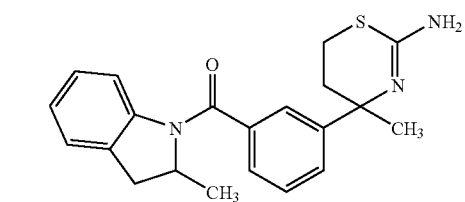
728 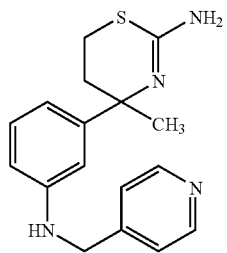

TABLE 76-continued
729 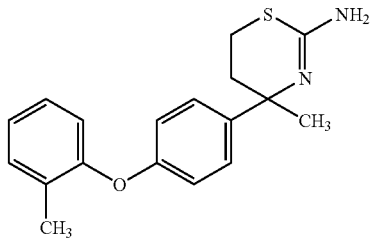
TABLE 77
730 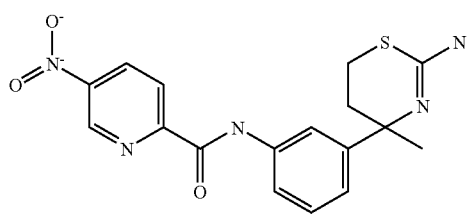
731 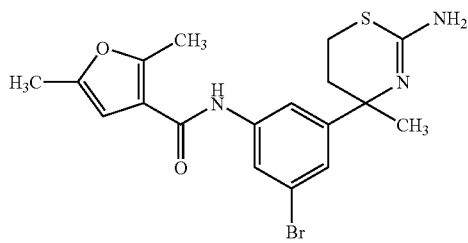
732 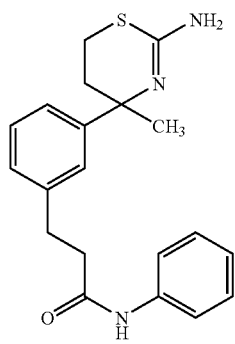
734 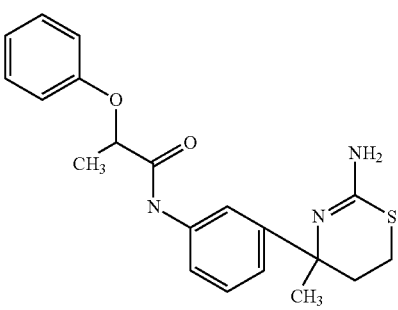
TABLE 77-continued
735 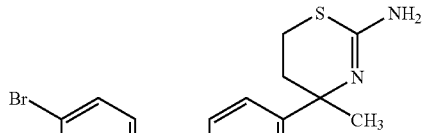
736 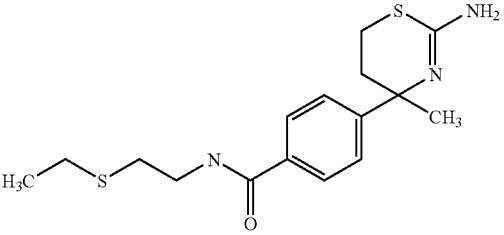
737 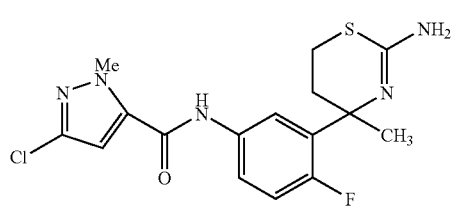
738 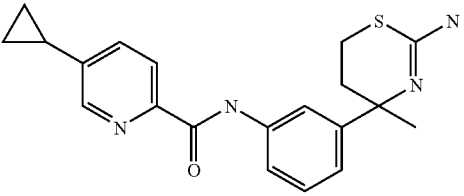
739 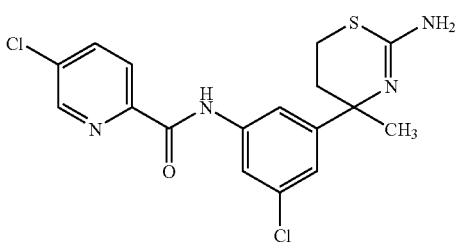
740 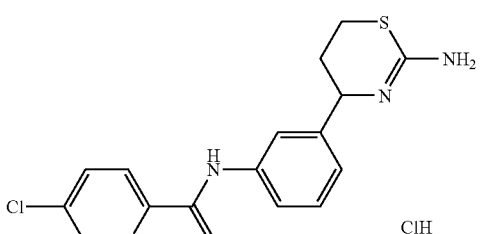
ClH TABLE 78
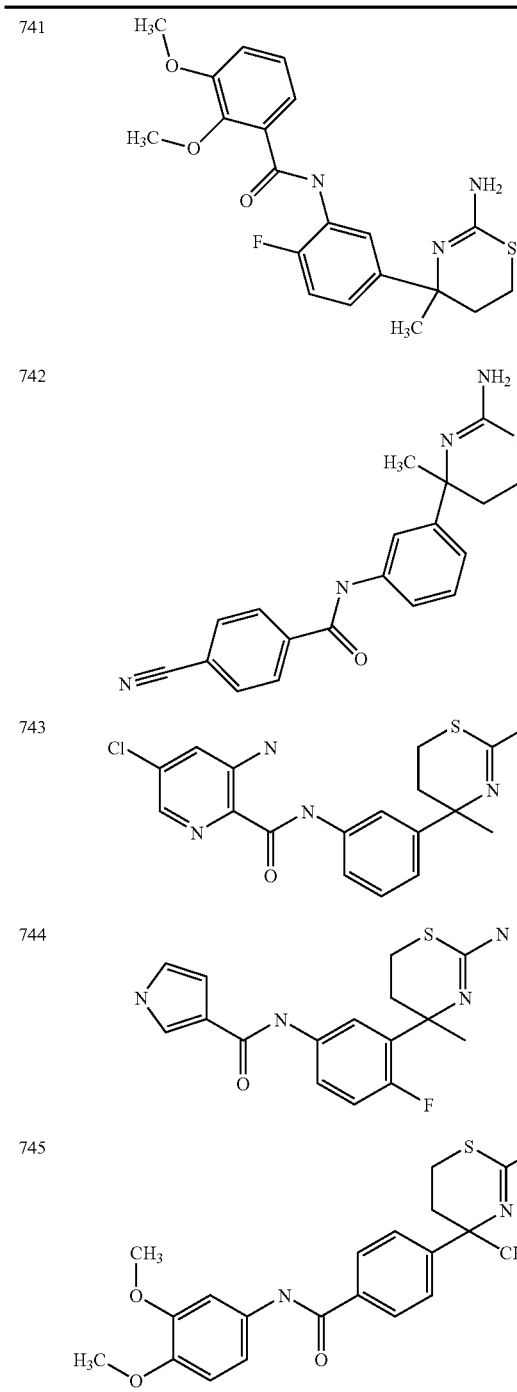
TABLE 78-continued
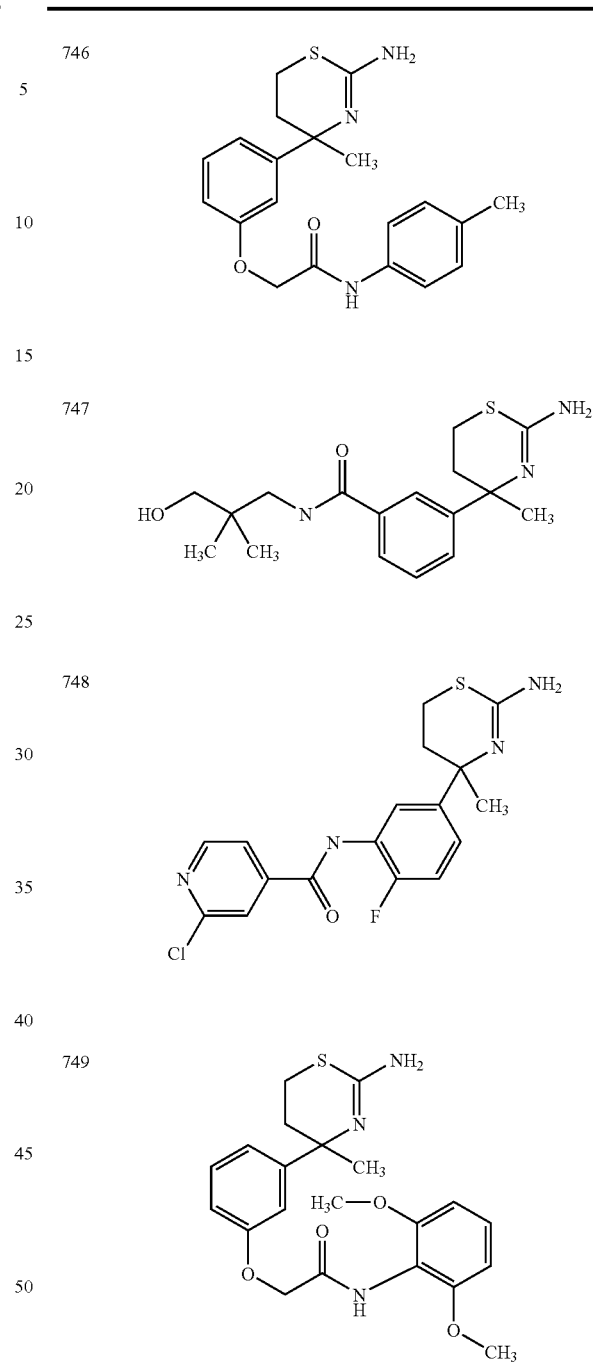
TABLE 79
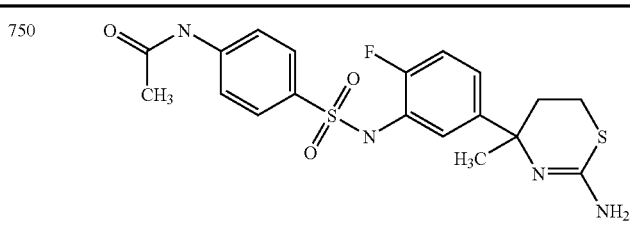

TABLE 79-continued
| | |
|---|---|
| 751 | 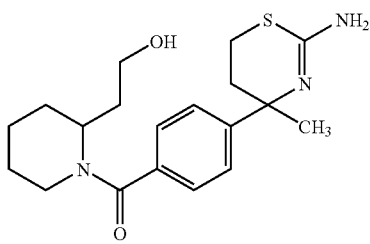 |
| 752 | 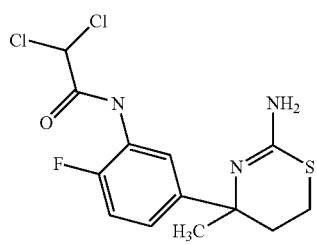 |
| 753 | 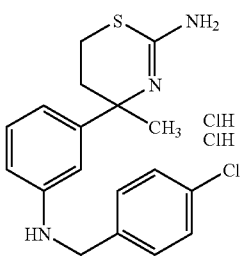 |
| 754 | 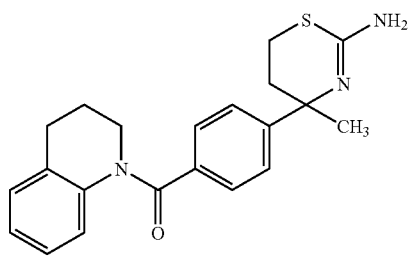 |
| 755 | 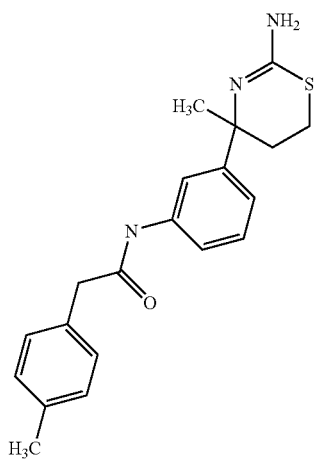 |

TABLE 79-continued
756 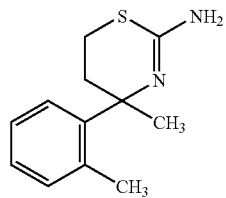
757 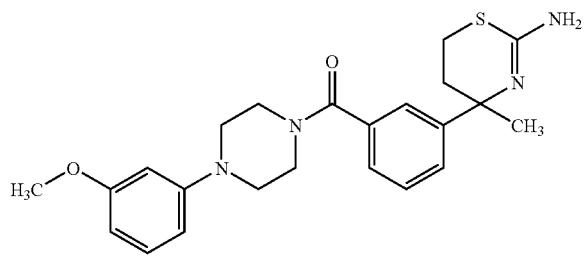
758 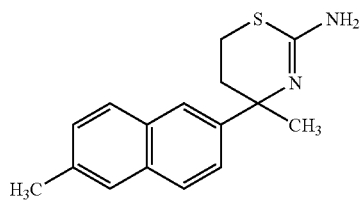
759 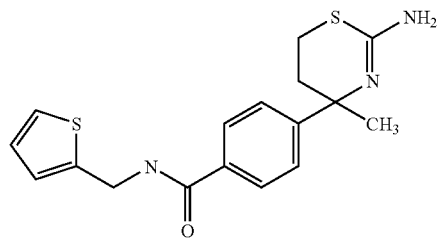
| TABLE 80 | | TABLE 80-continued | |
|---|---|---|---|
| 760 | 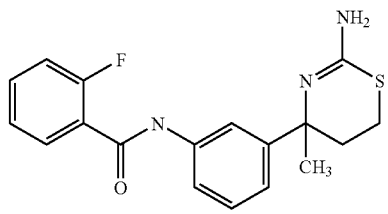 | 762 | 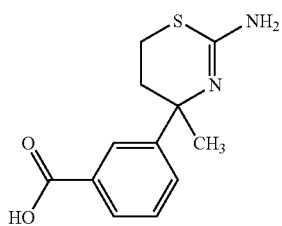 |
| 761 | 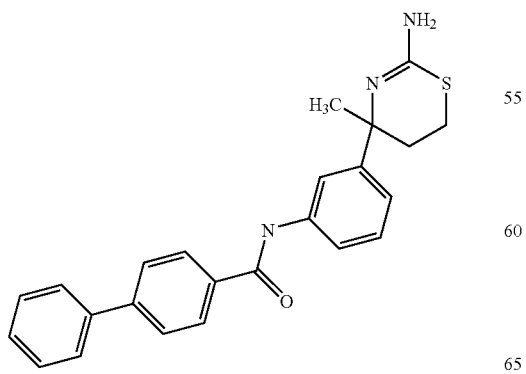 | 763 | 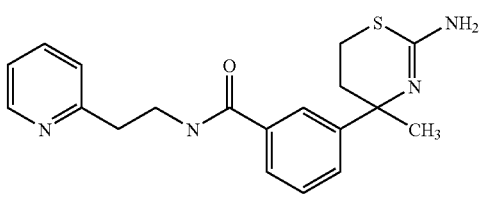 |

TABLE 80-continued
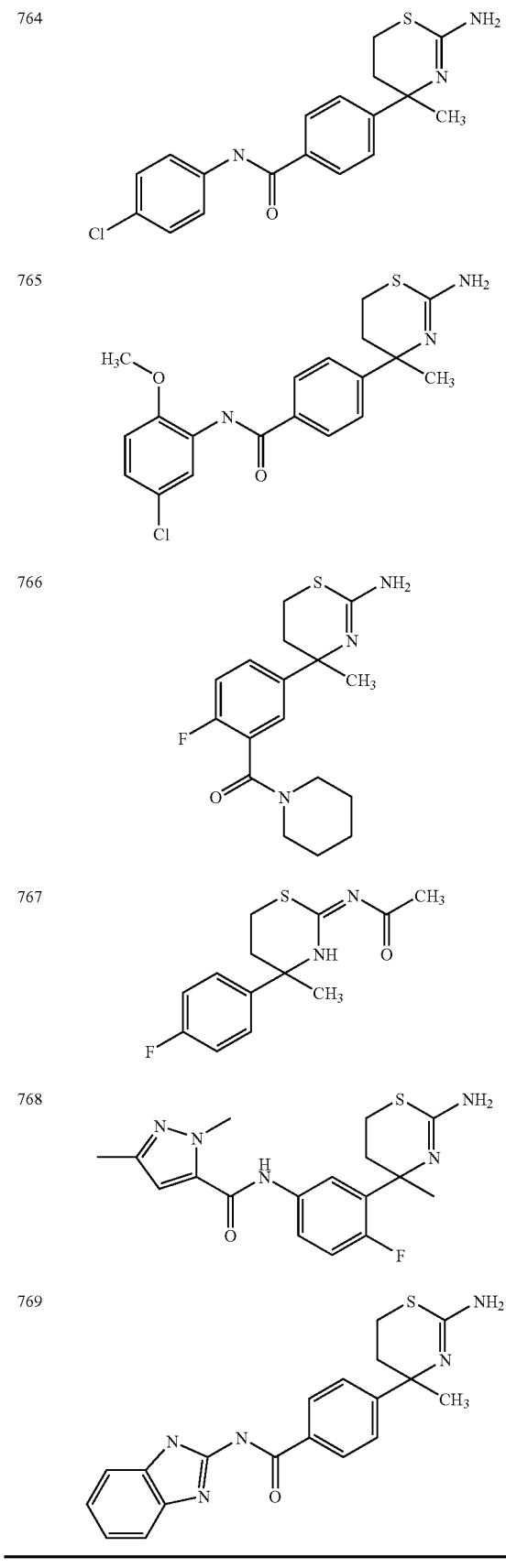
TABLE 81
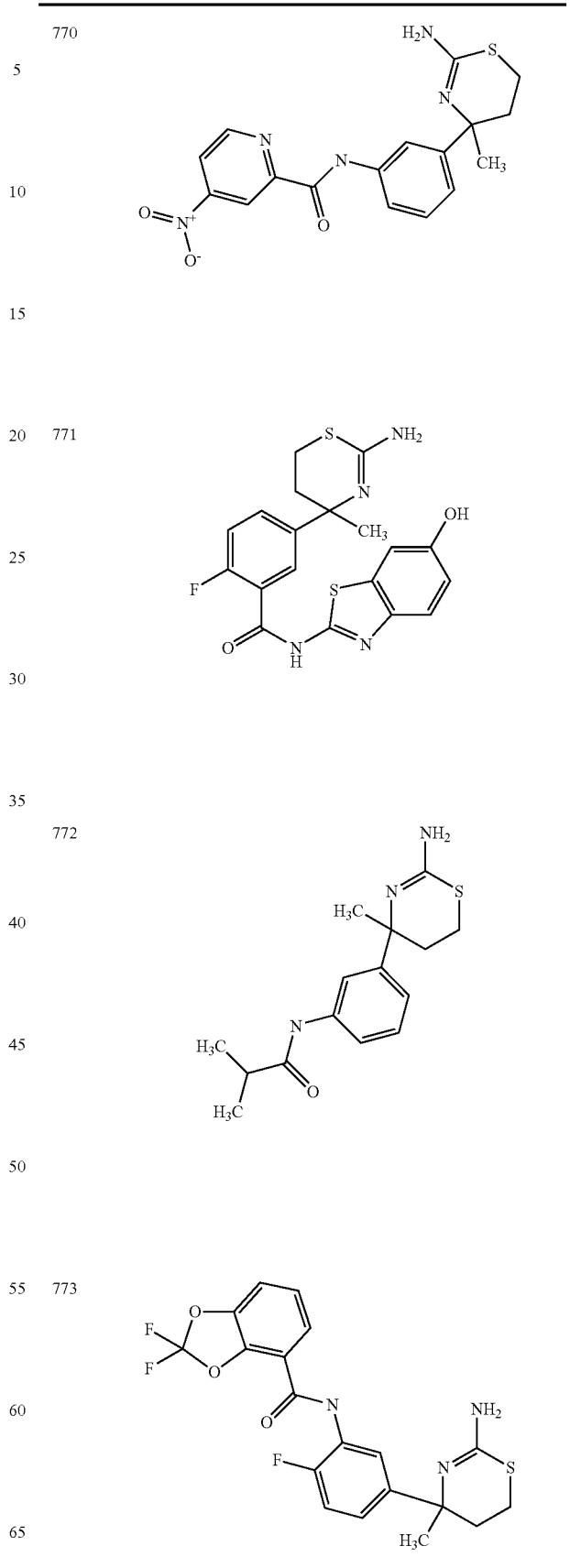

TABLE 81-continued
774 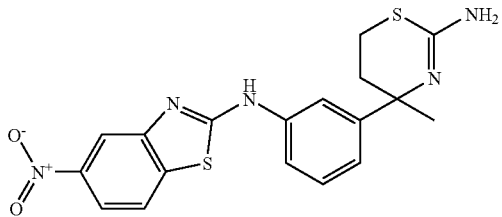
775 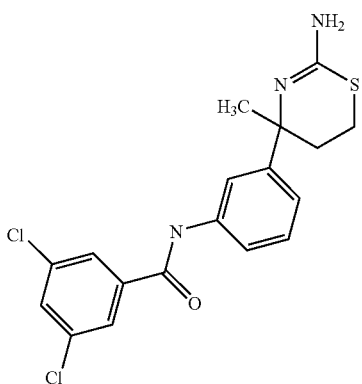
776 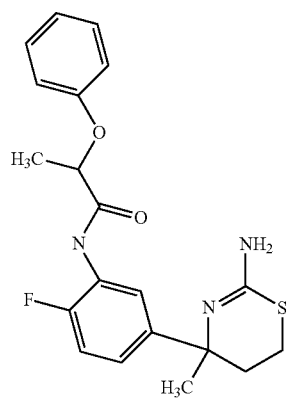
777 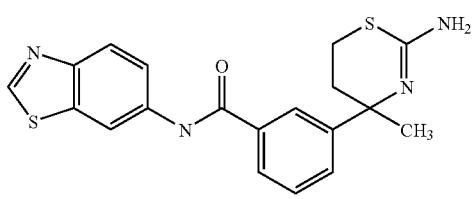
TABLE 82
778 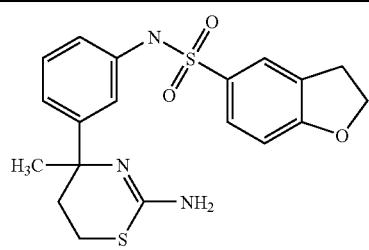
779 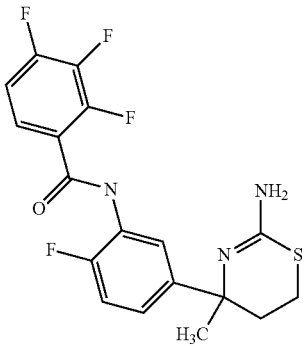
780 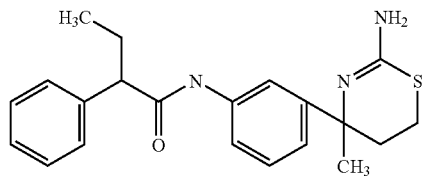

TABLE 82-continued
781 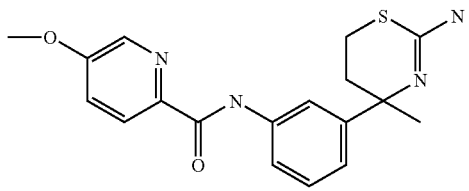
782 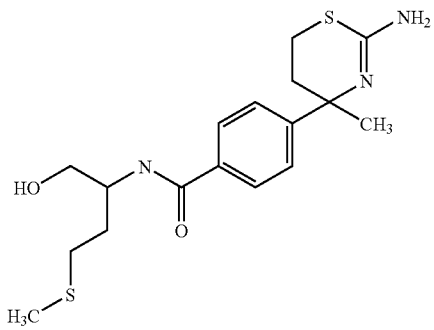
783 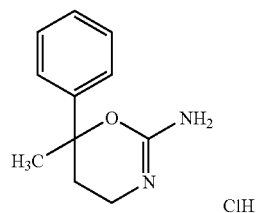
784 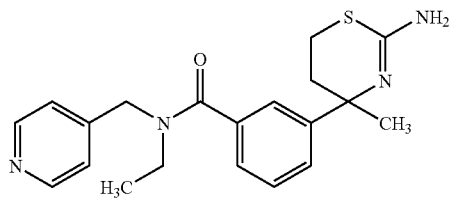
785 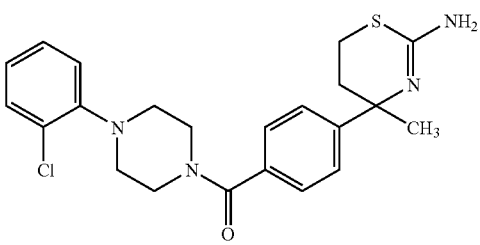
786 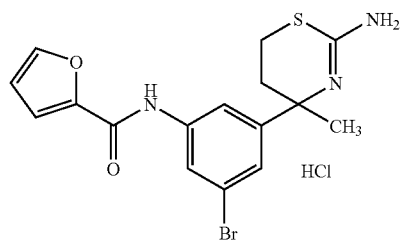

TABLE 82-continued
| 787 | 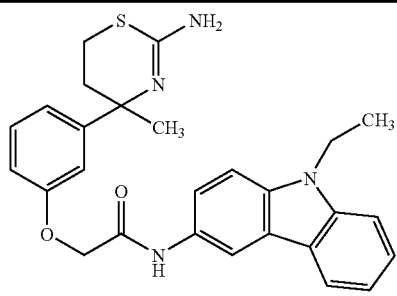 |
| 788 | 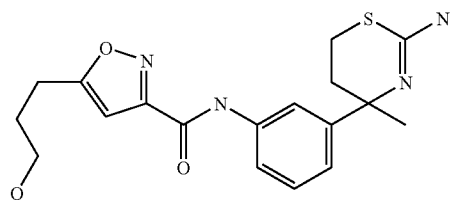 |
| 789 | 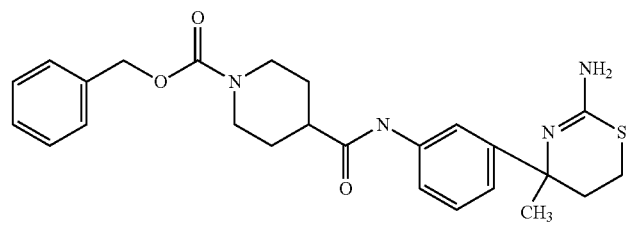 |
TABLE 83
| 790 | 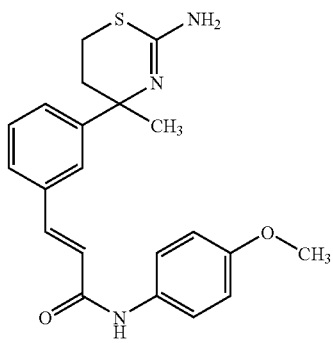 |
| 791 | 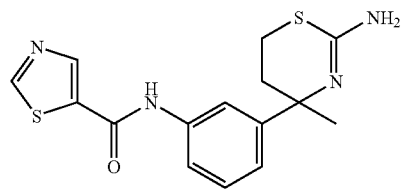 |
| 792 | 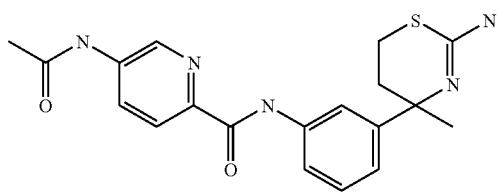 |

TABLE 83-continued
793
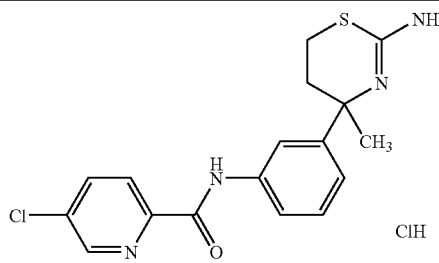
794
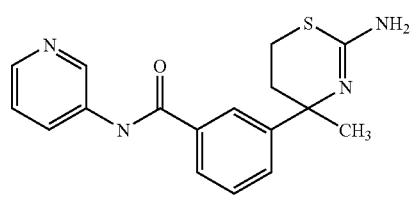
795
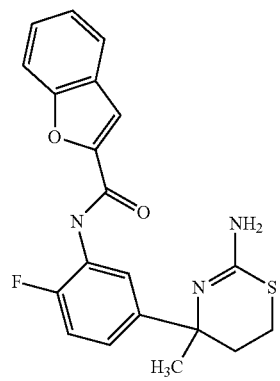
796
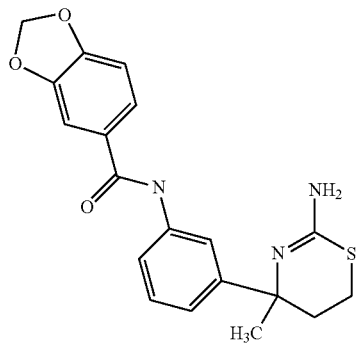
797
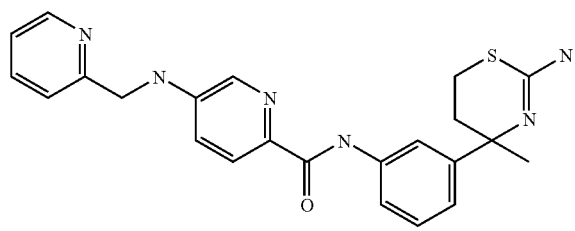

TABLE 83-continued
798 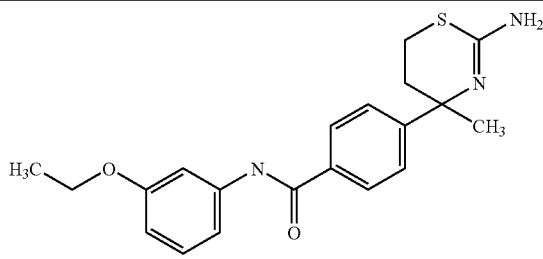
TABLE 84
799 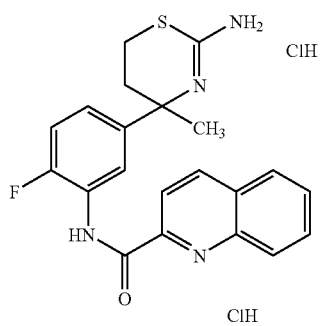
800 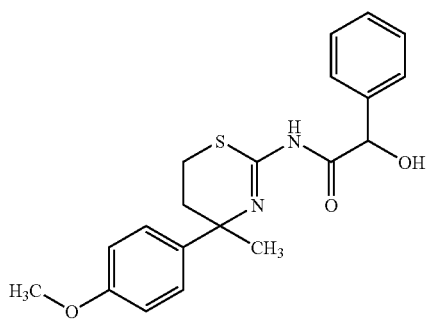
801 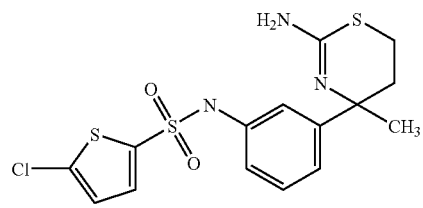
802 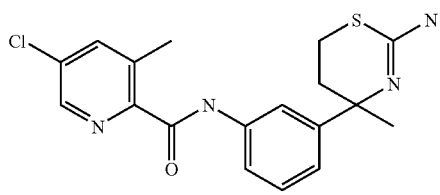
TABLE 84-continued
803 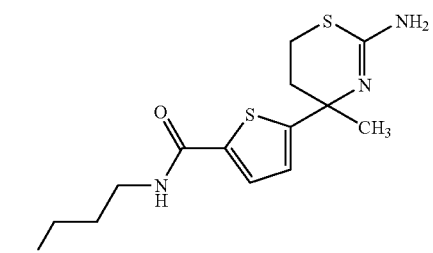
804 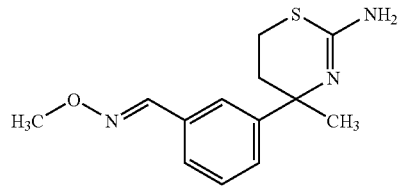
805 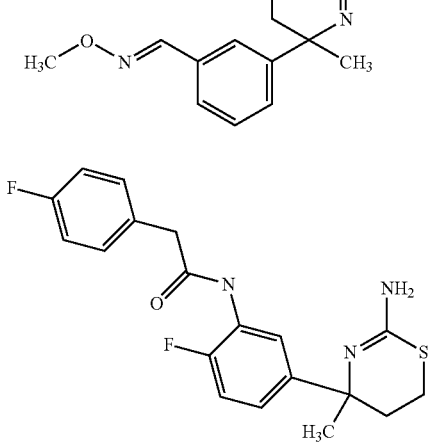
806 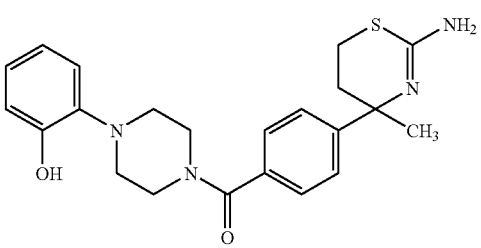
807 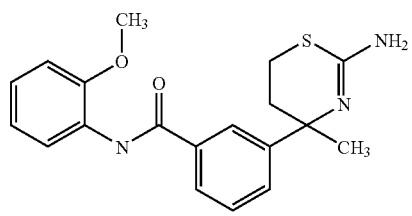

TABLE 84-continued
808 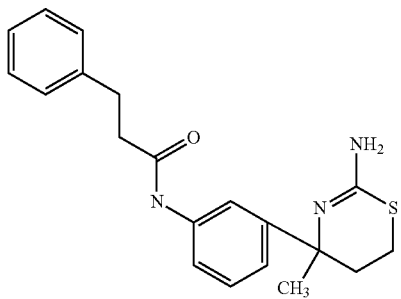
809 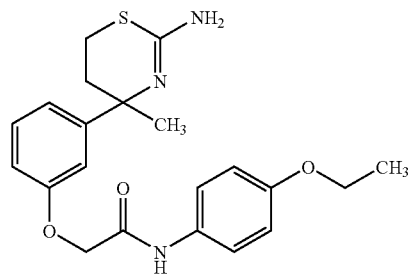
TABLE 85
810 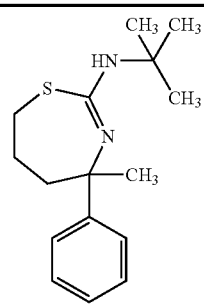
811 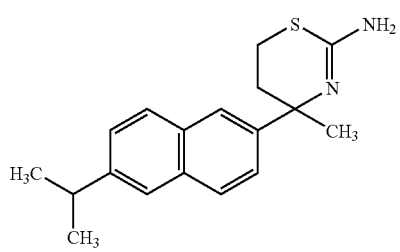
812 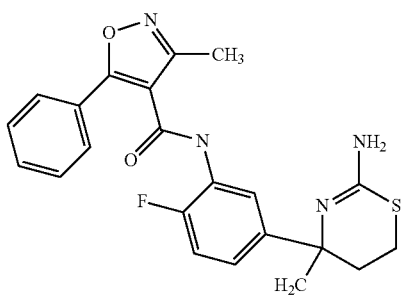
813 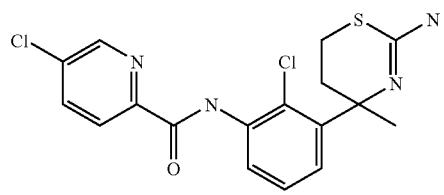

TABLE 85-continued
| 814 | 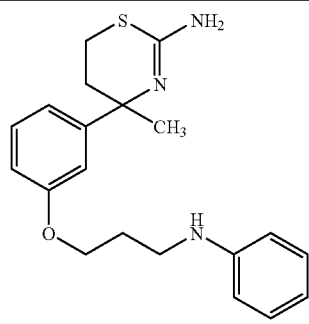 |
| 815 | 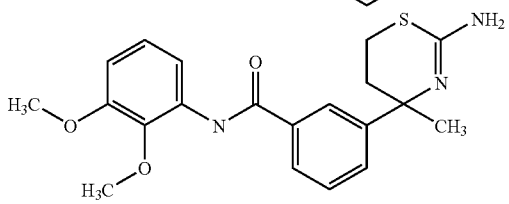 |
| 816 | 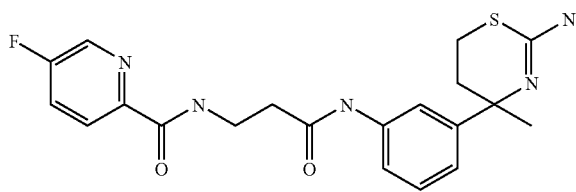 |
| 817 | 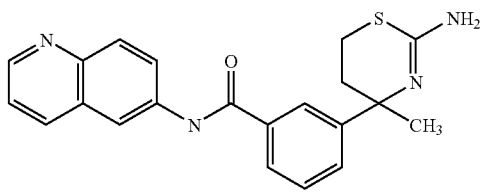 |
| 818 | 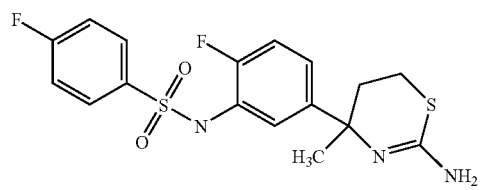 |
TABLE 86
| 819 | 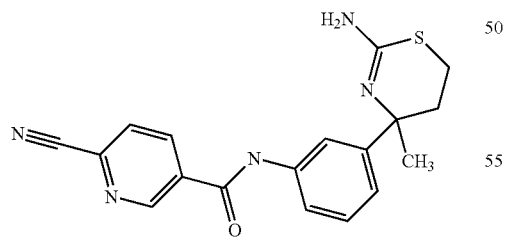 |
| 820 | 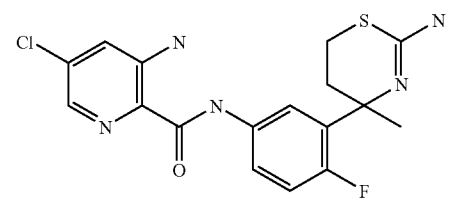 |
| 821 | 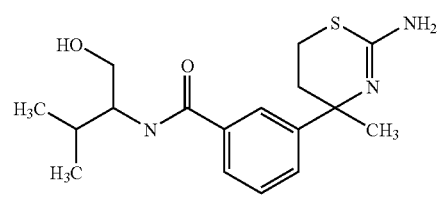 |
| 822 | 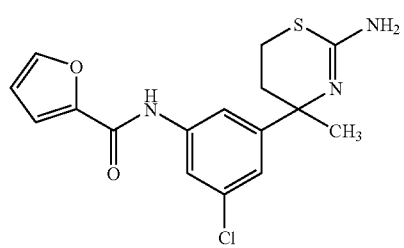 |

TABLE 86-continued
823 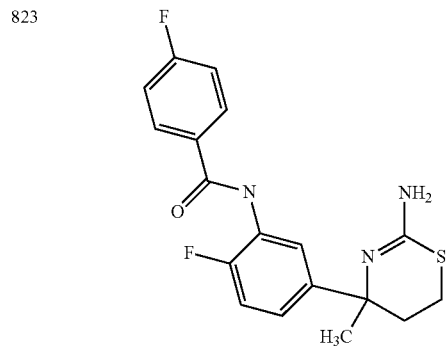
824 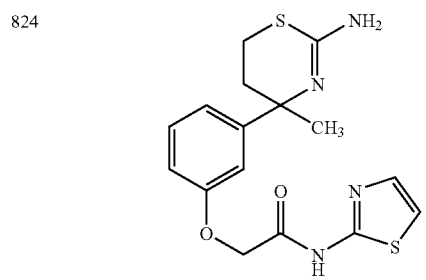
825 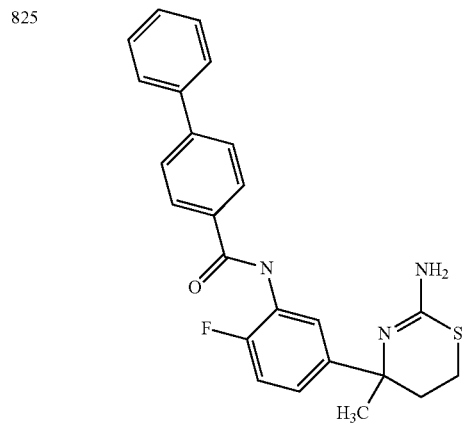
826 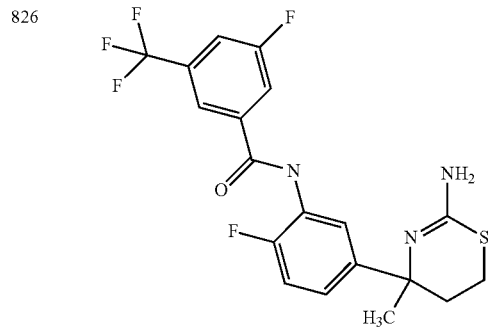
827 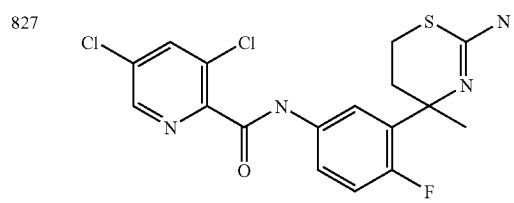
TABLE 87
828 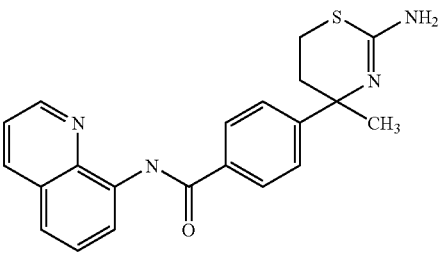
829 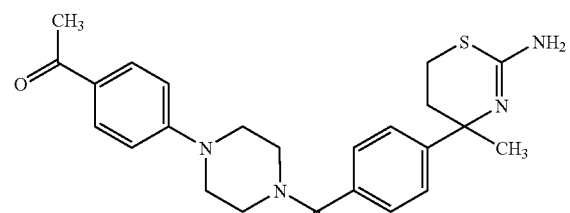
830 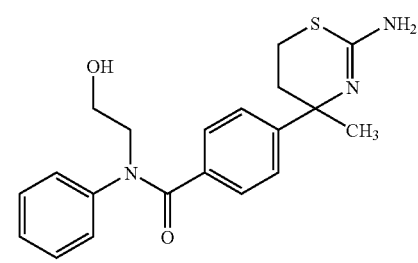
831 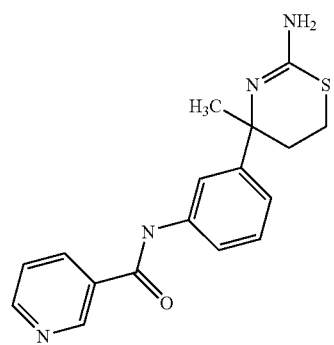
832 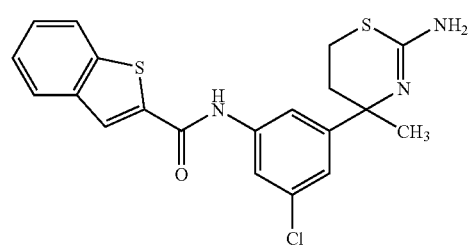

TABLE 87-continued
| 833 | 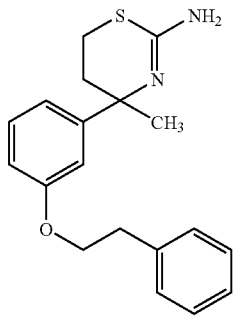 |
| 834 | 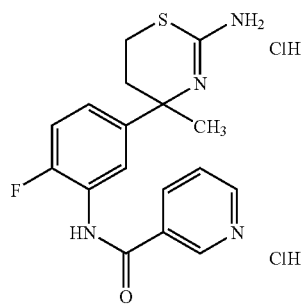 |
| 835 | 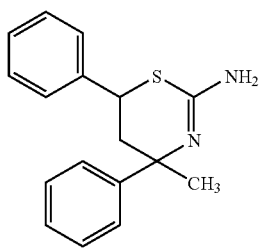 |
| 836 | 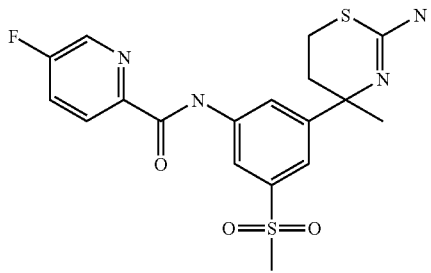 |
TABLE 88
| 837 | 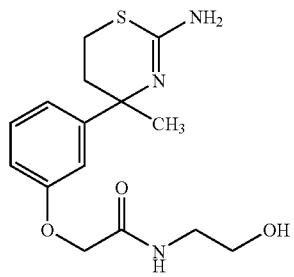 |
TABLE 88-continued
| 838 | 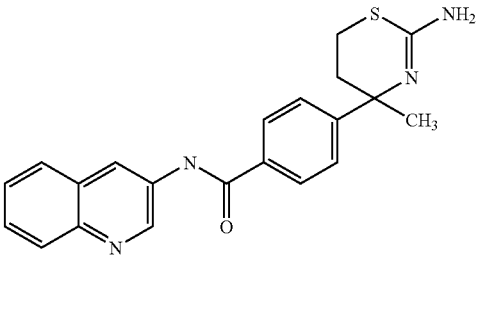 |
| 839 | 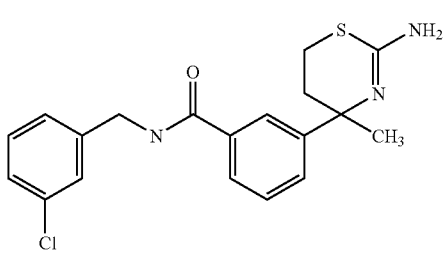 |
| 840 | 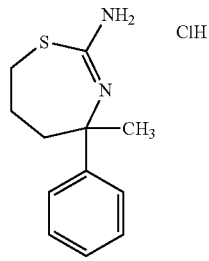 |
| 841 | 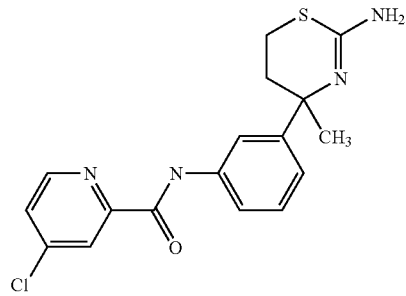 |

TABLE 88-continued
842 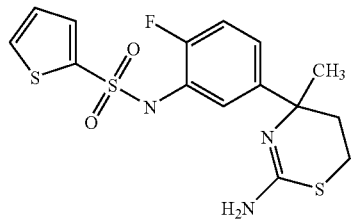
843 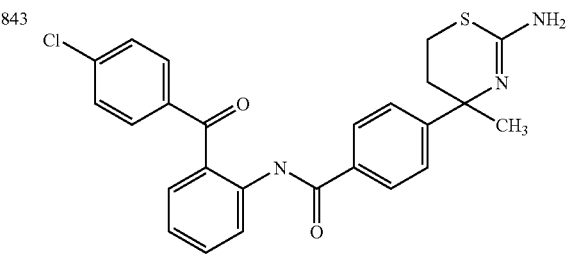
TABLE 88-continued
844 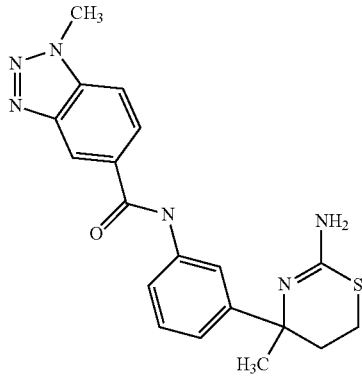
845 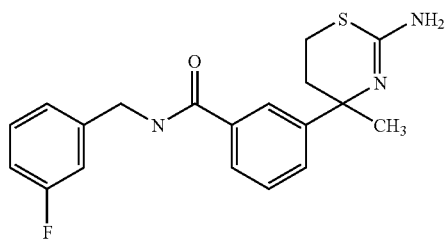
TABLE 89
846 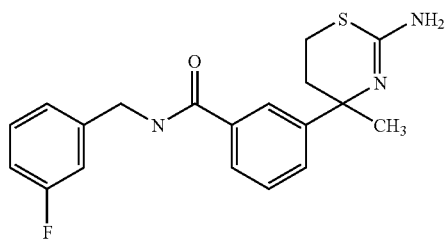
847 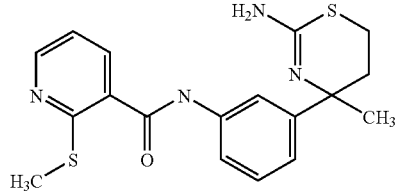
848 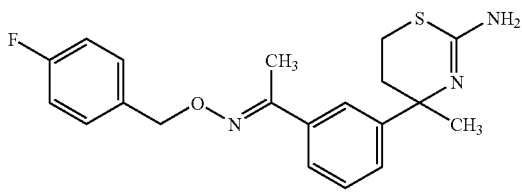

TABLE 89-continued
| | |
|---|---|
| 849 | 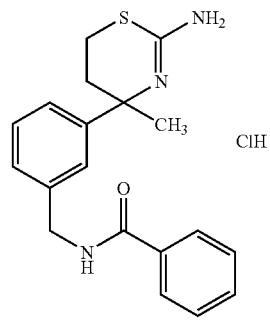 ClH |
| 850 | 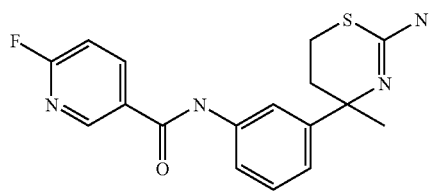 |
| 851 | 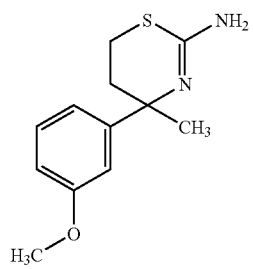 |
| 852 | 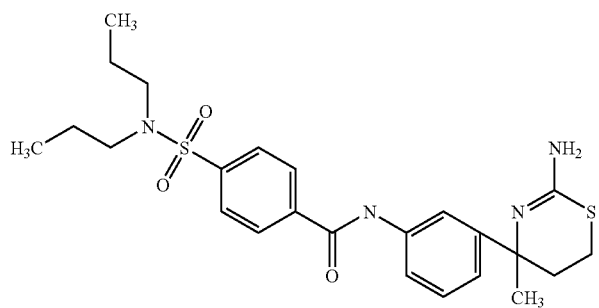 |
| 853 | 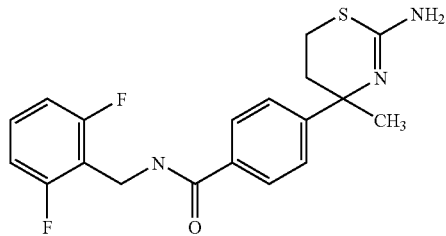 |
| 854 | 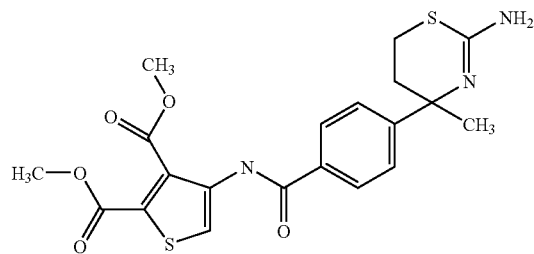 |

TABLE 89-continued
855 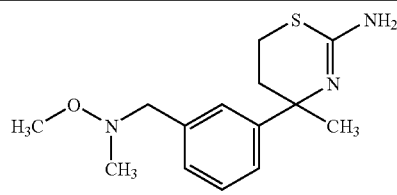
TABLE 90
856 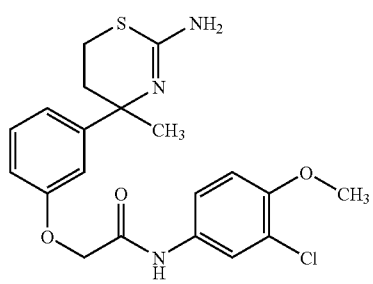
857 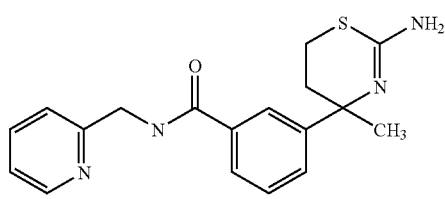
858 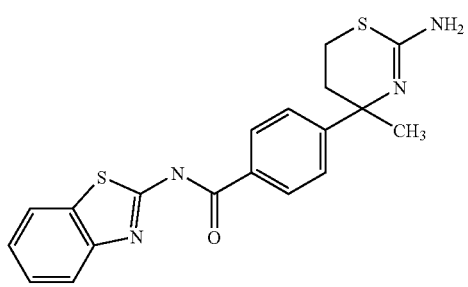
859 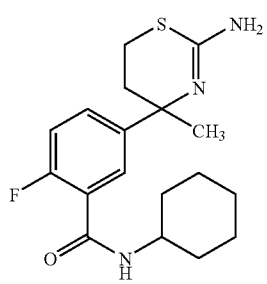
860 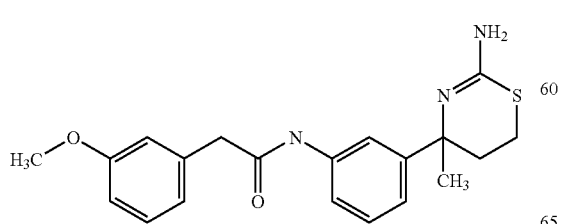
TABLE 90-continued
861
862
863
864
865

TABLE 91
866 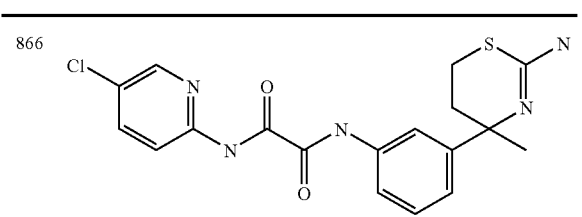
867 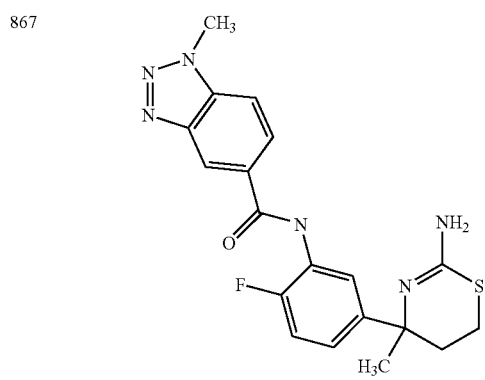
868 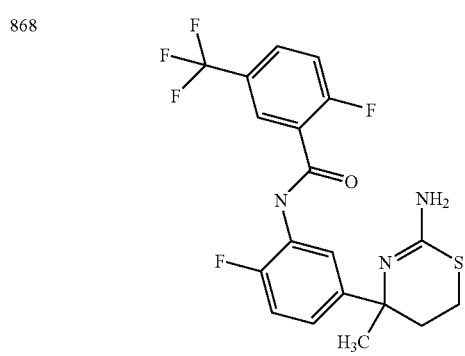
869 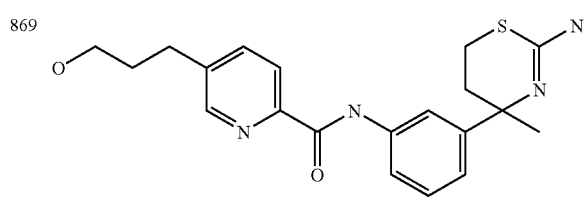
870 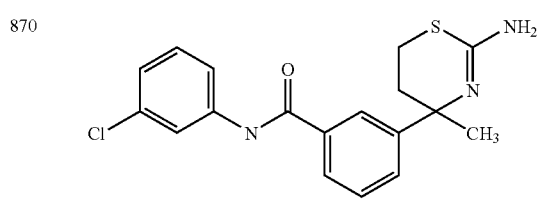
871 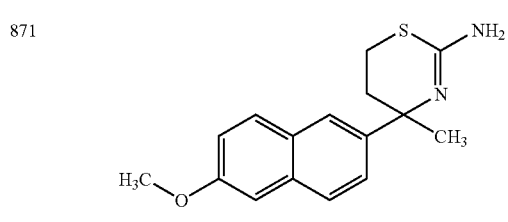
TABLE 91-continued
872 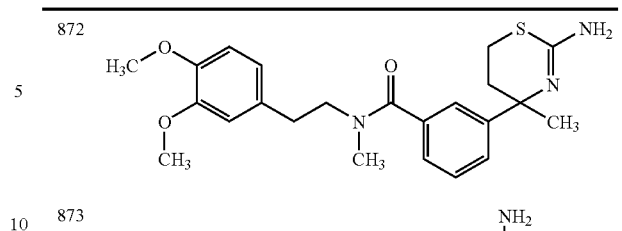
873 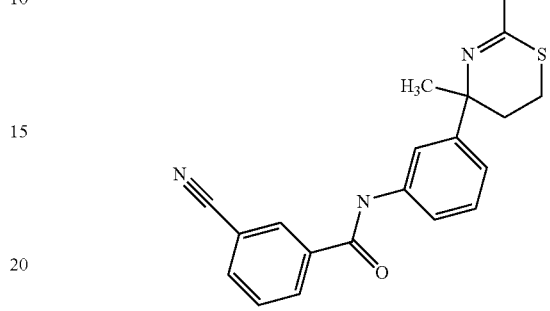
874 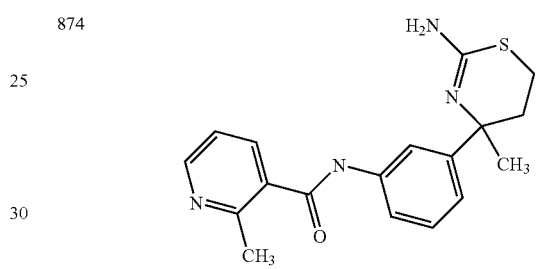
875 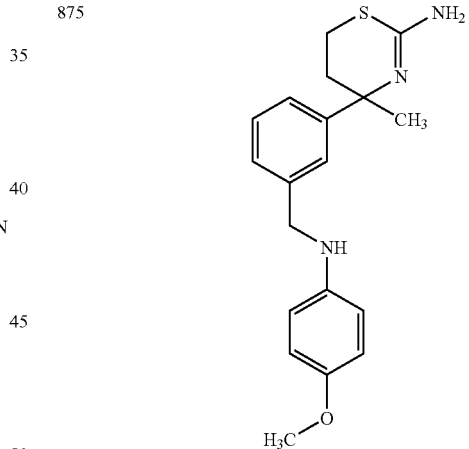
TABLE 92
876 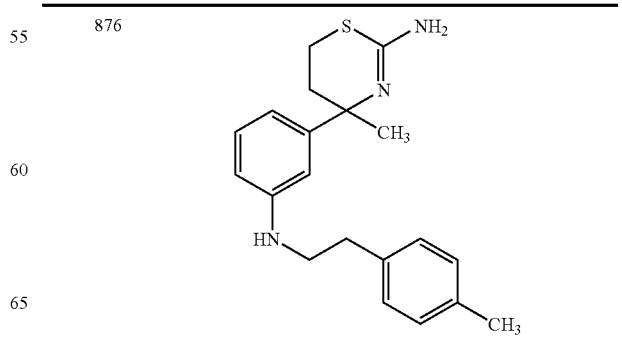

TABLE 92-continued
877 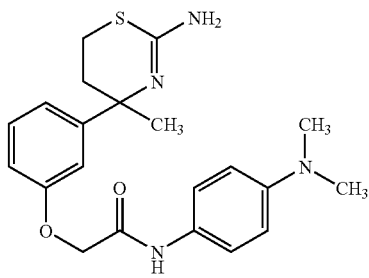
878 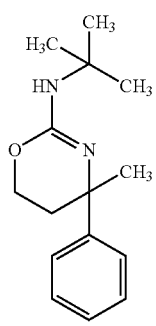
879 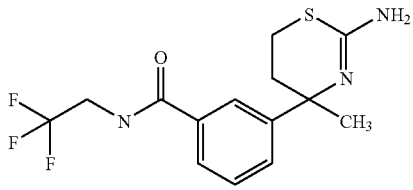
880 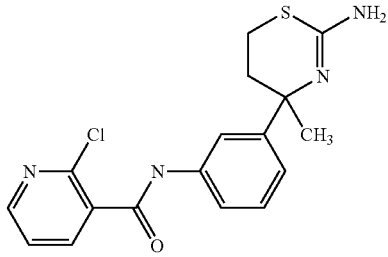
881 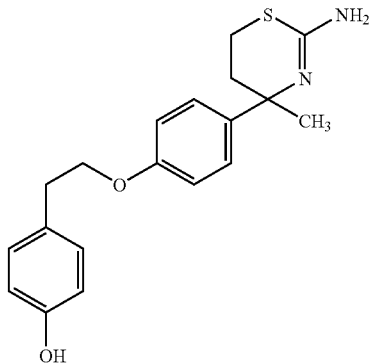
TABLE 92-continued
882 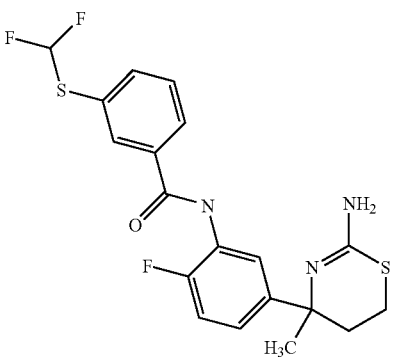
883 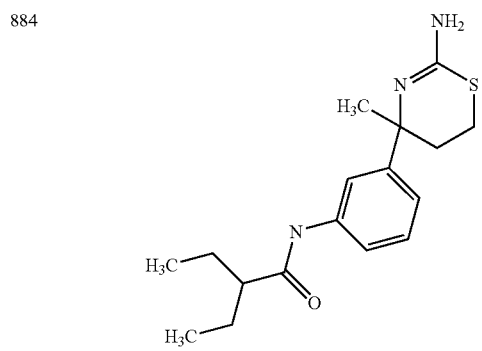
Chiral
TABLE 93
884 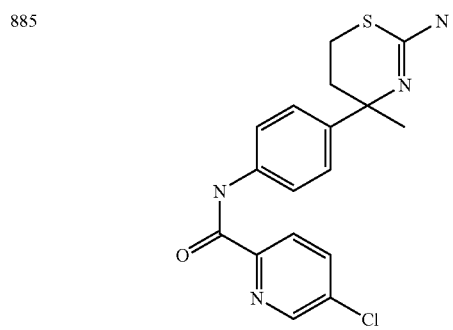
885

TABLE 93-continued
886 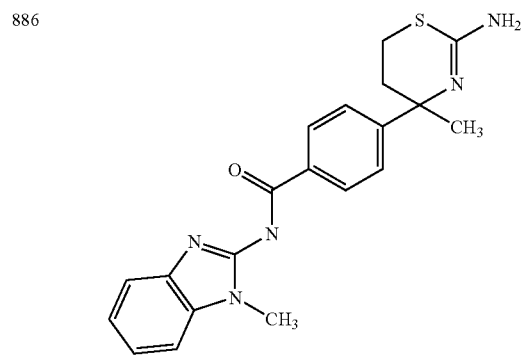
887 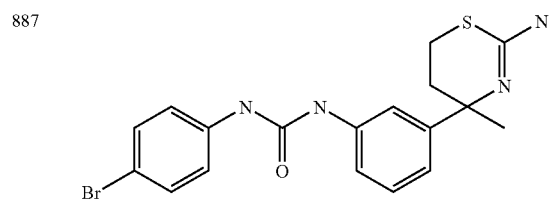
888 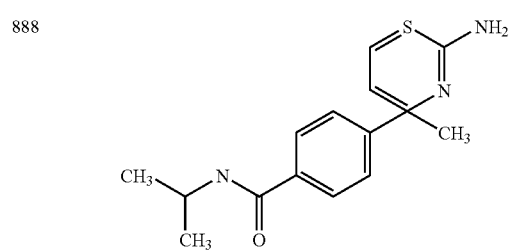
889 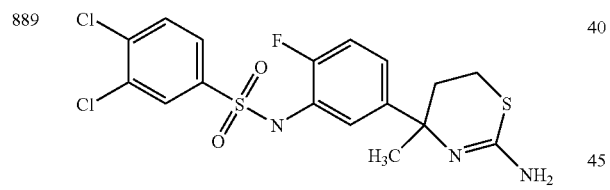
890 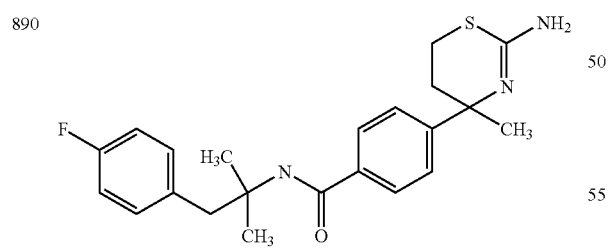
891 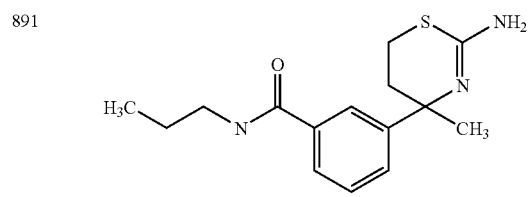
TABLE 93-continued
892 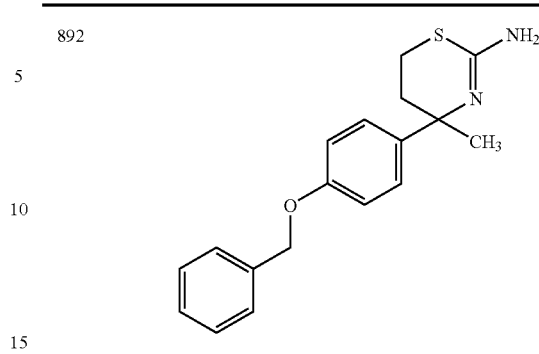
893 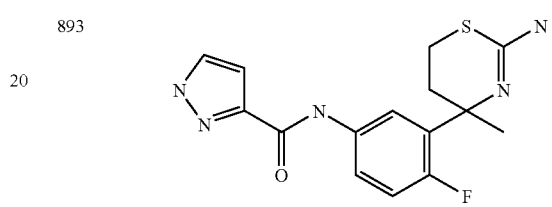
894 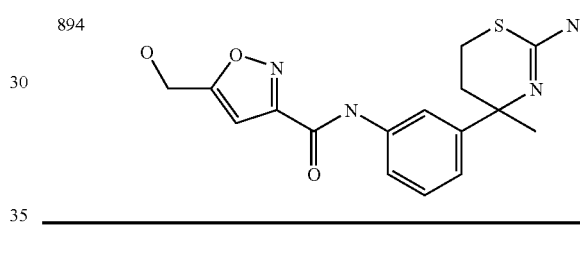
TABLE 94
895 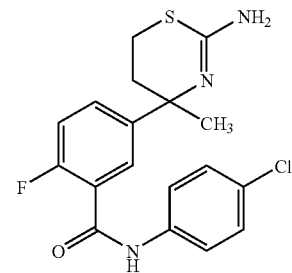
896 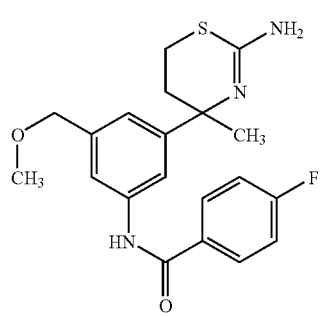

TABLE 94-continued
897 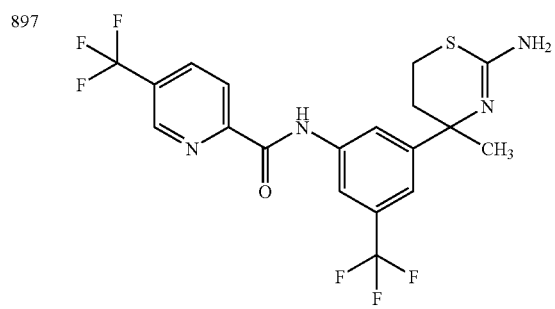
898 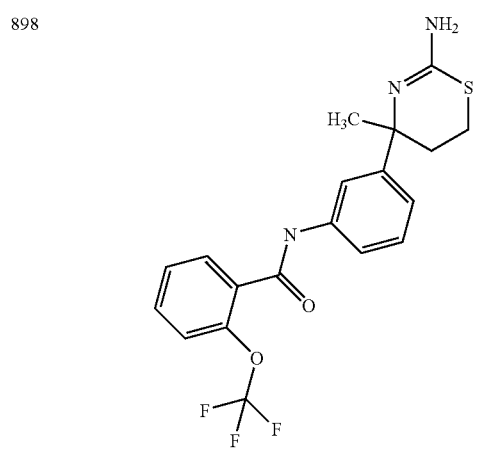
899 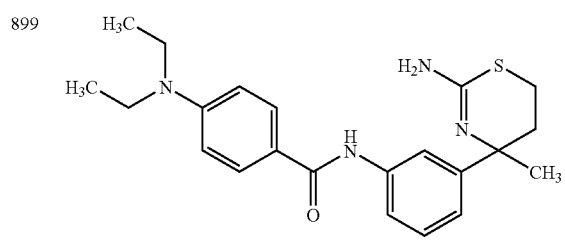
900 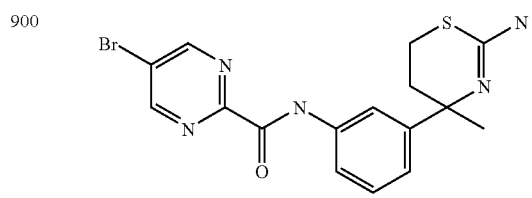
901 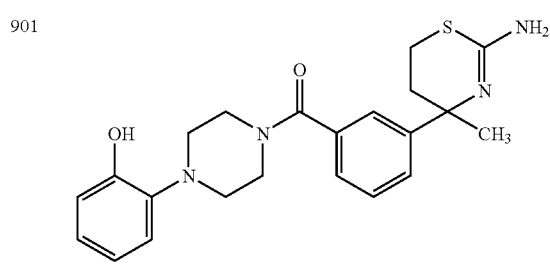
TABLE 94-continued
902 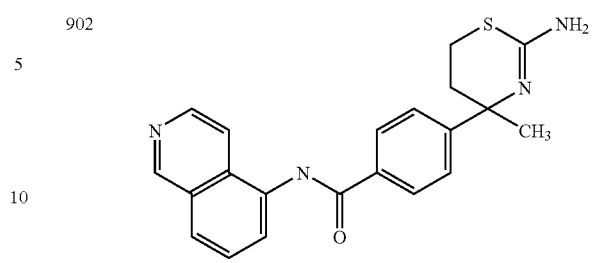
903 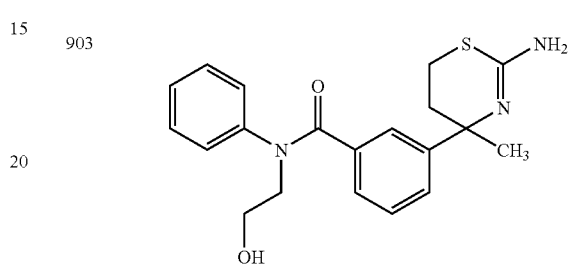
904 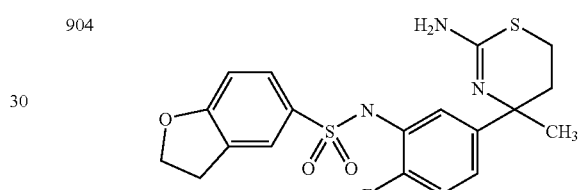
TABLE 95
905 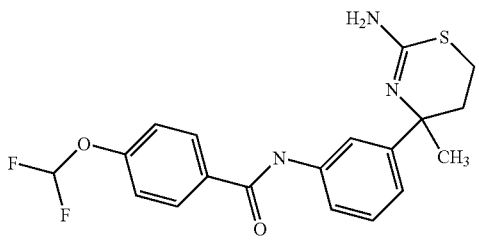
906 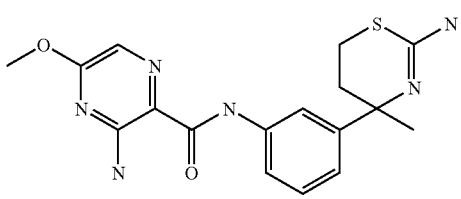
907 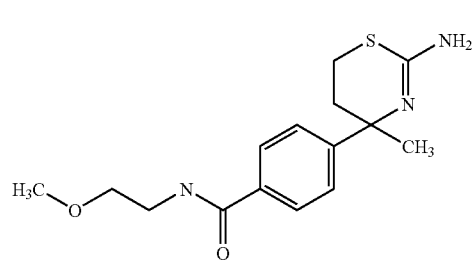

TABLE 95-continued
908 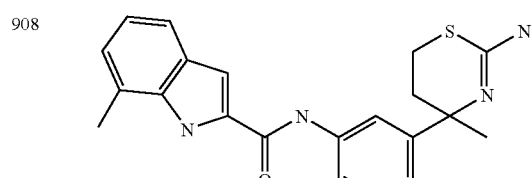
909 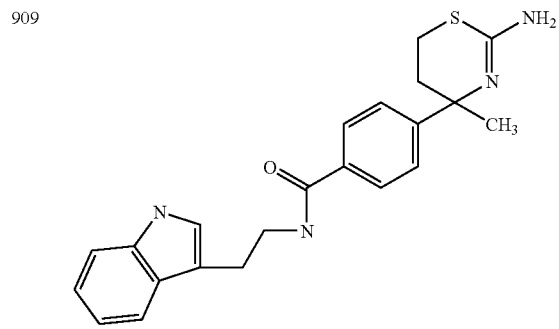
910 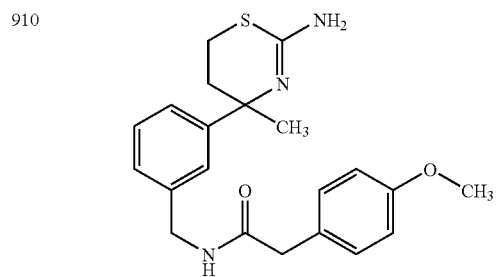
911 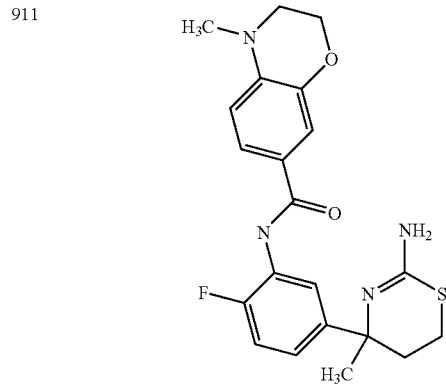
912 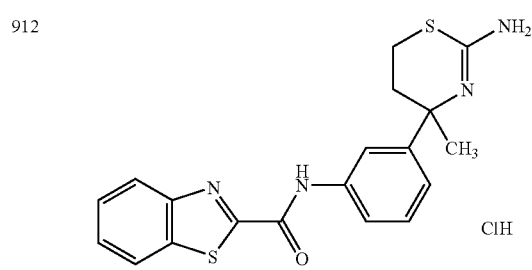
TABLE 95-continued
913 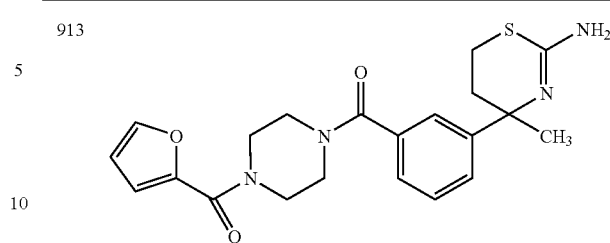
914 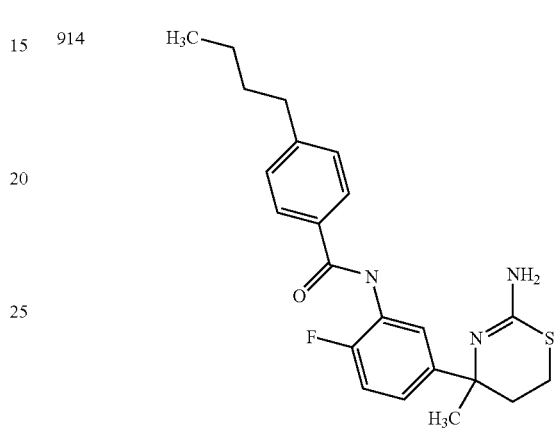
TABLE 96
915 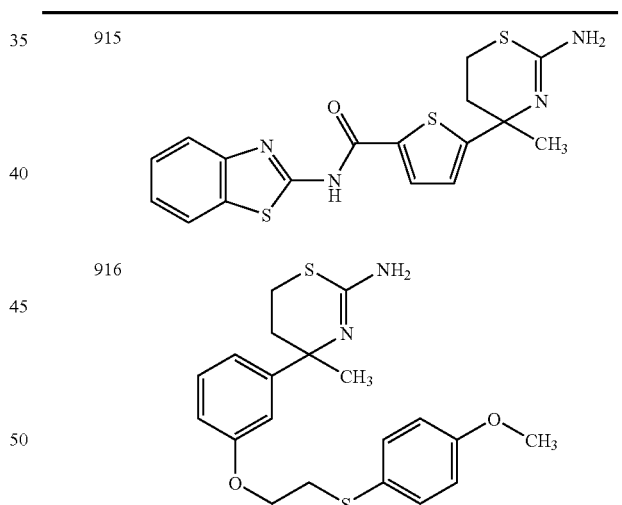
916 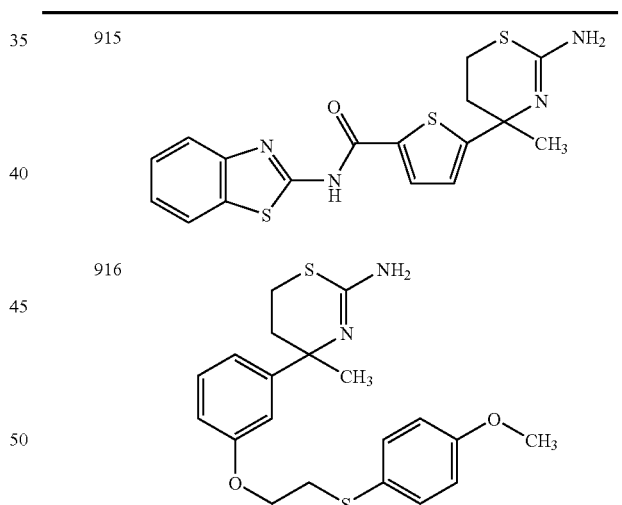
917 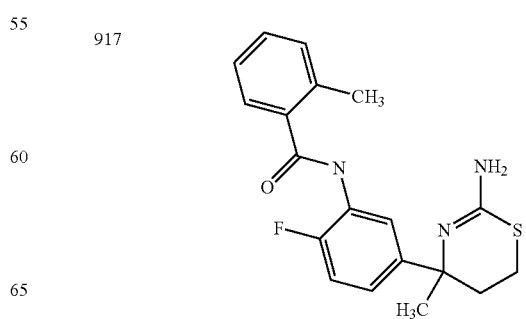

TABLE 96-continued
918 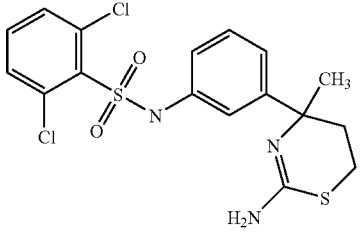
919 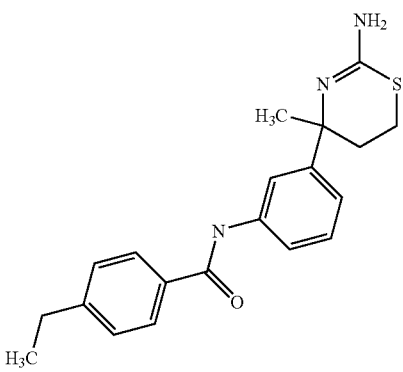
920 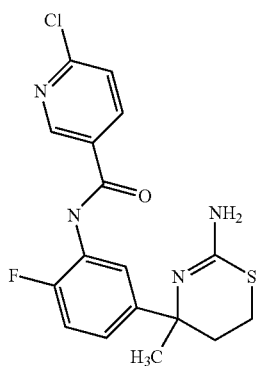
921 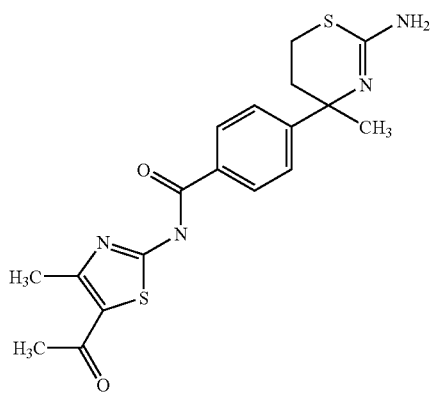
922 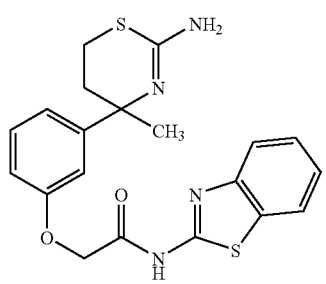
TABLE 96-continued
TABLE 97
923 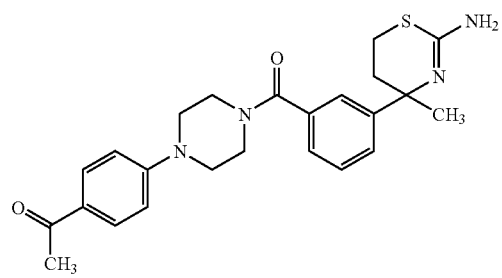
924 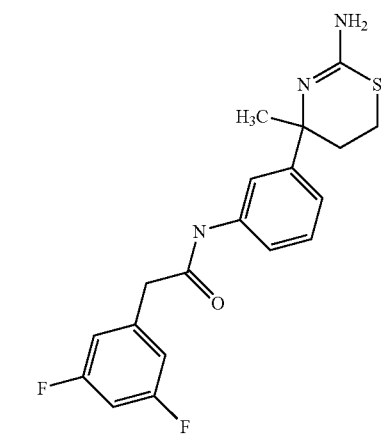
925 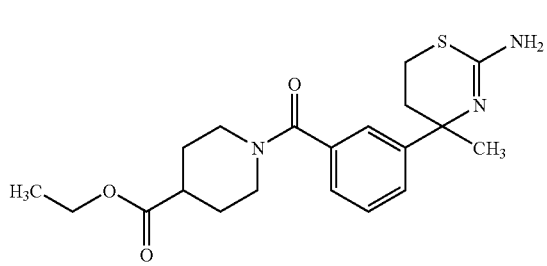
926 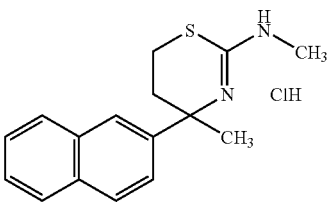
927 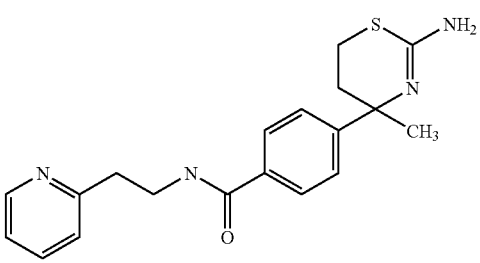

TABLE 97-continued
928 
929 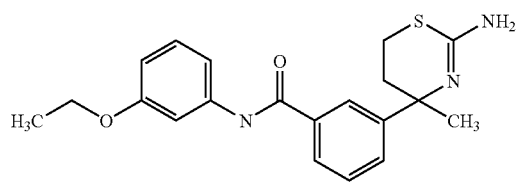
930 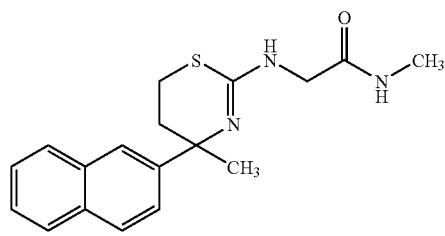
931 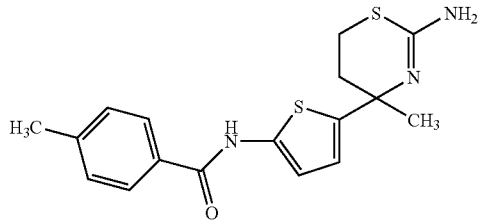
932 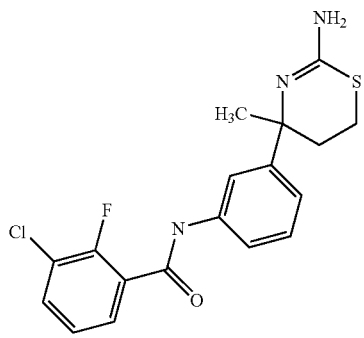
TABLE 98
933 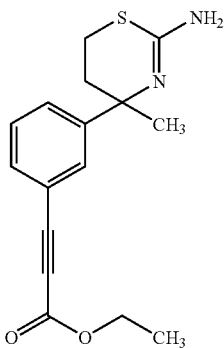
934
935
936
937 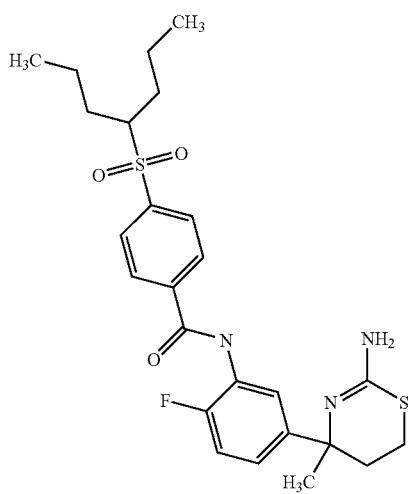

TABLE 98-continued
938 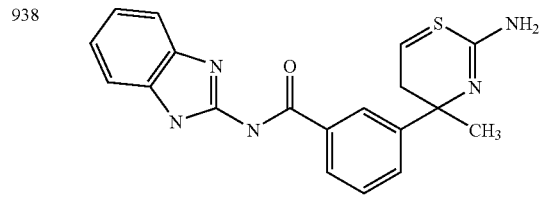
939 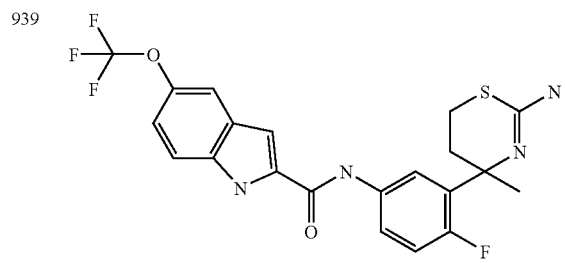
940 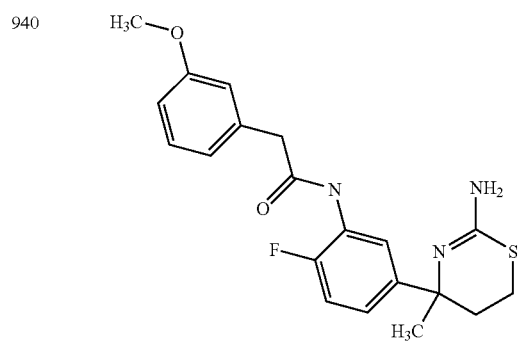
TABLE 99
941 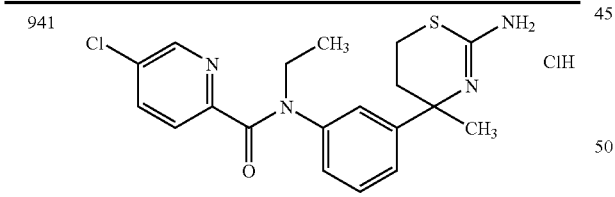
942 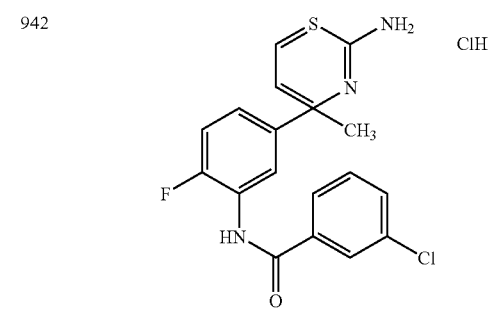
TABLE 99-continued
943 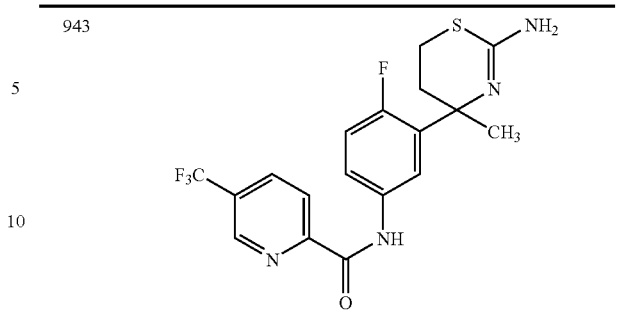
944 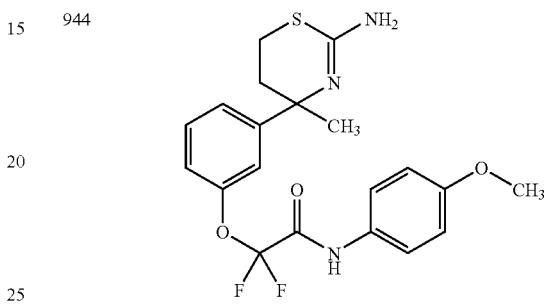
945 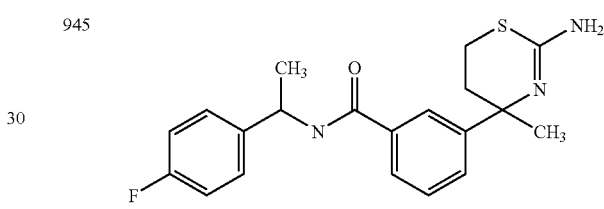
946 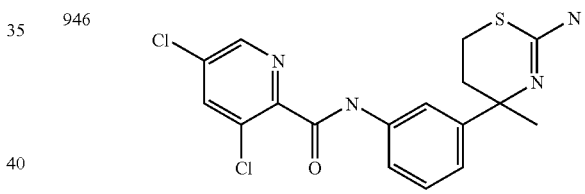
947 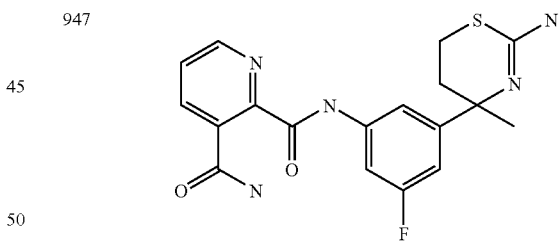
948 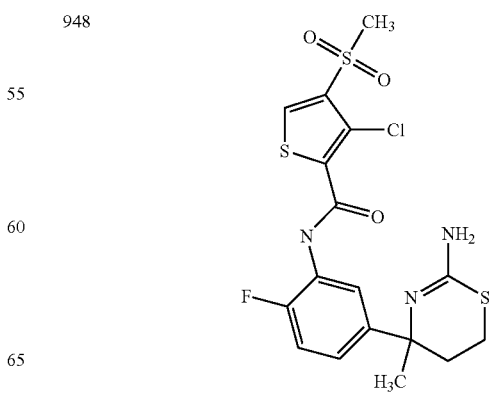

TABLE 99-continued
949
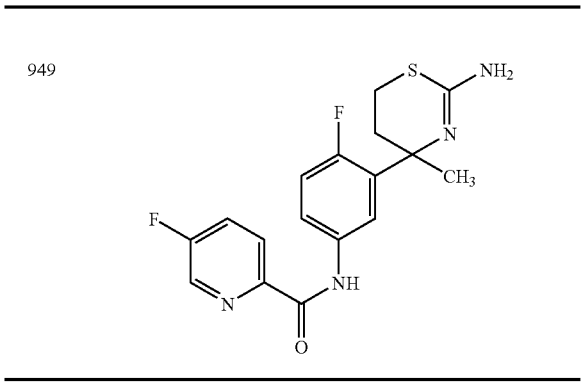
TABLE 100
950
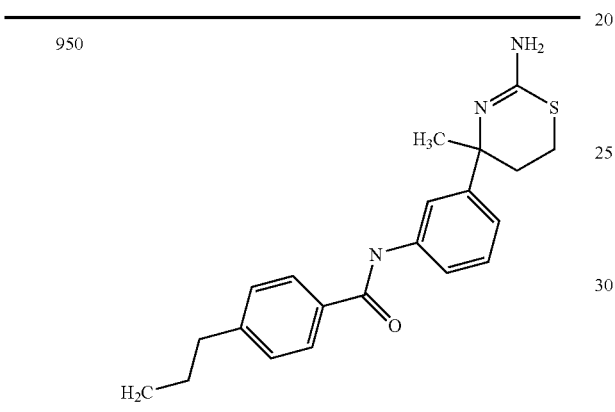
951
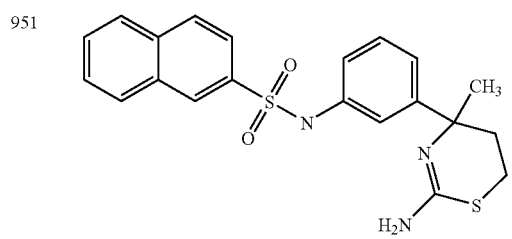
952
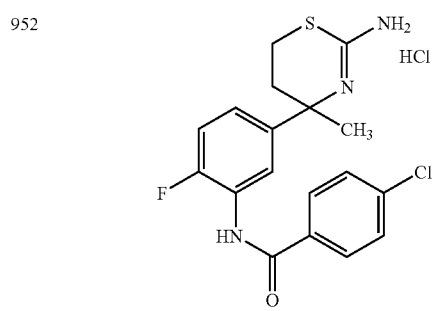
953
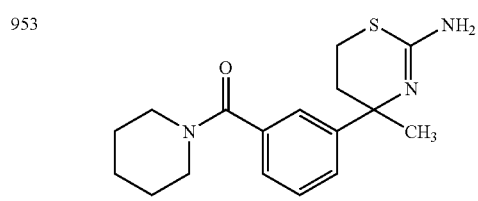
TABLE 100-continued
954
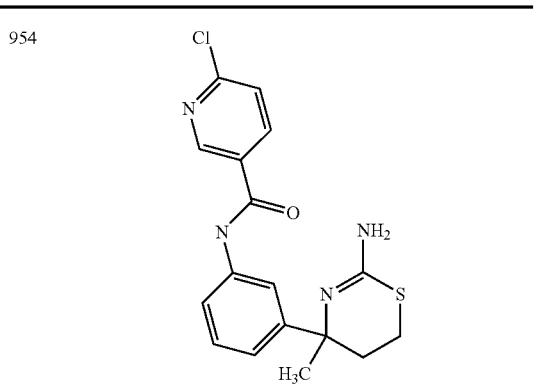
955
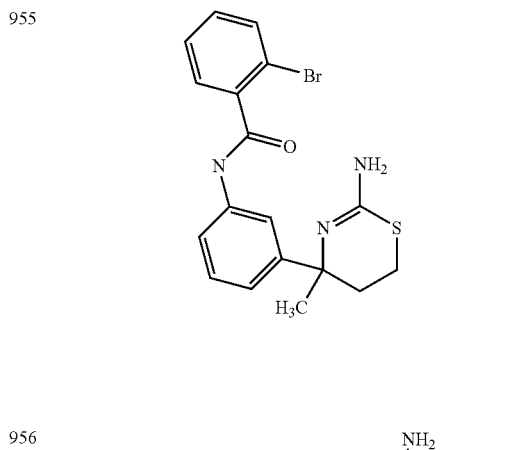
956
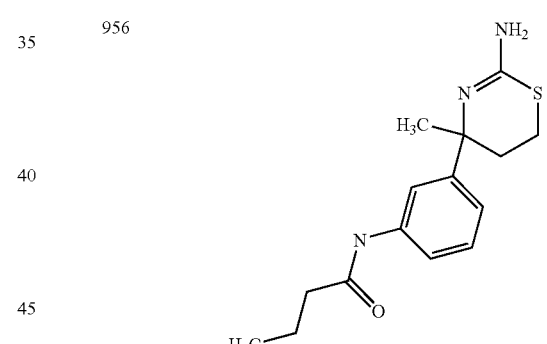
957
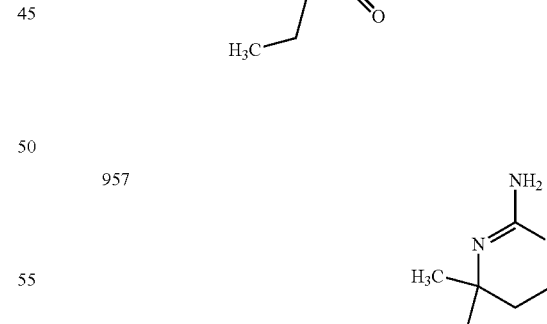
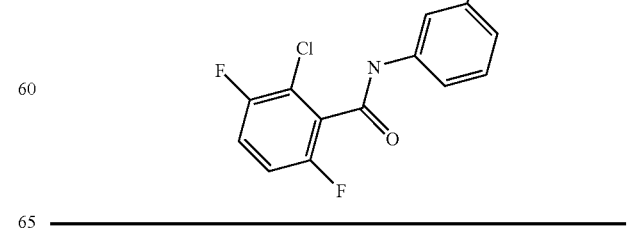

TABLE 101
958 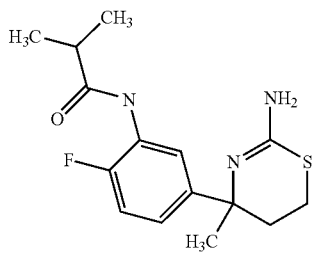
959 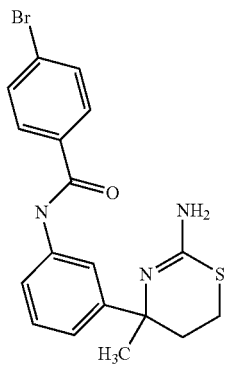
960 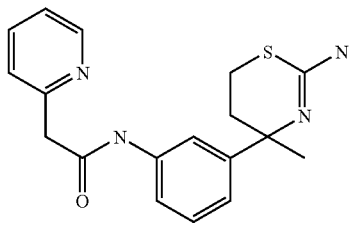
961 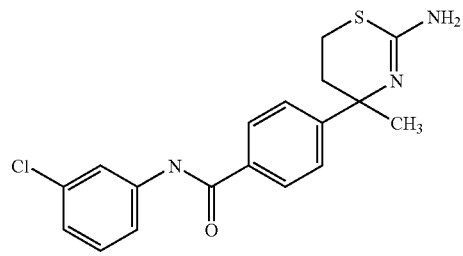
962 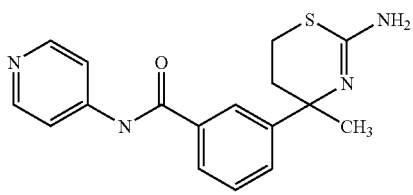
TABLE 101-continued
963 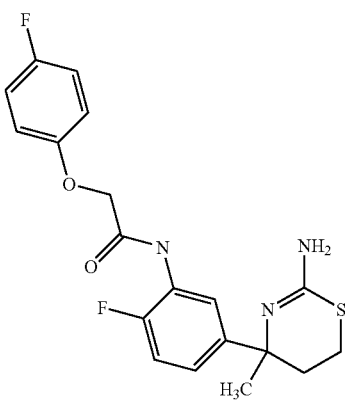
964 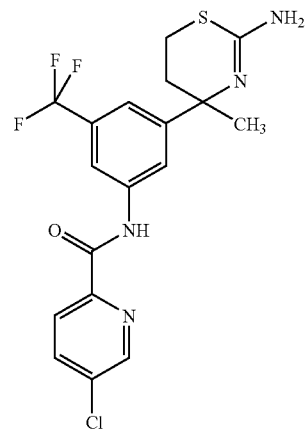
TABLE 102
965 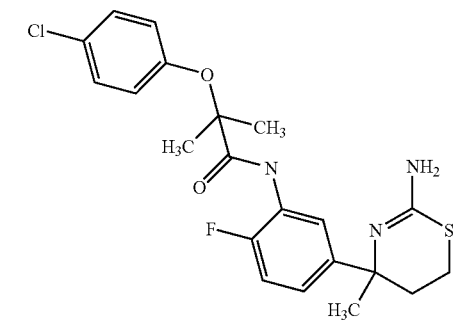
966 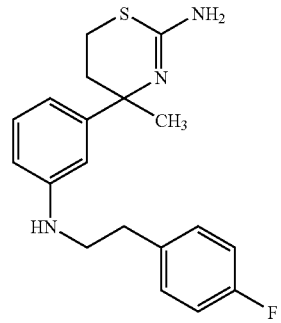

TABLE 102-continued
967 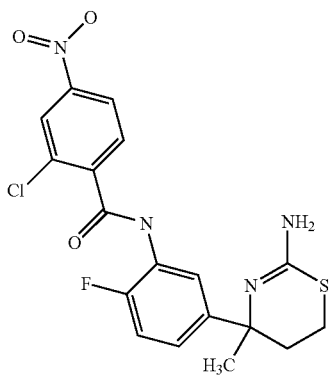
968 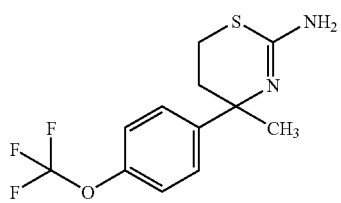
969 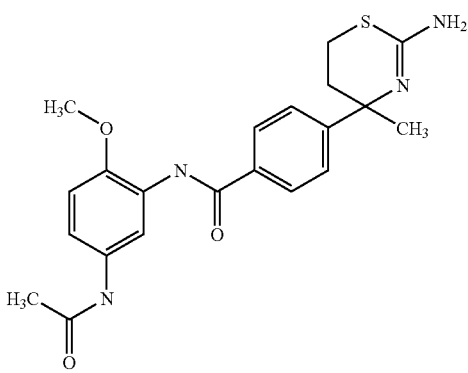
970 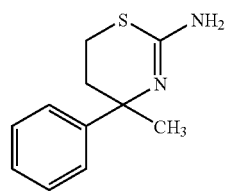
971 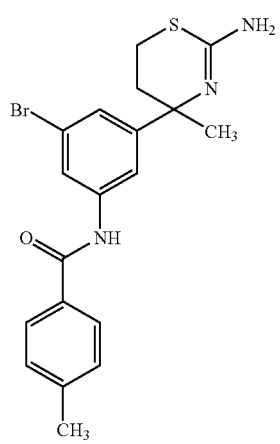
TABLE 102-continued
972 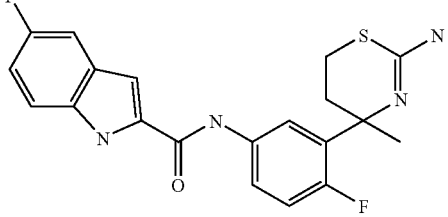
TABLE 103
973 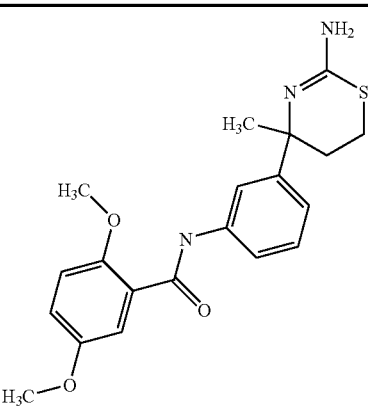
974 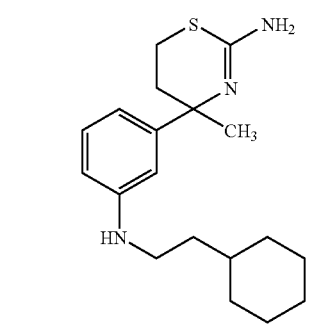
975 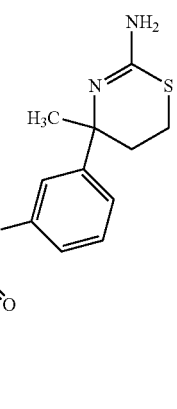

TABLE 103-continued
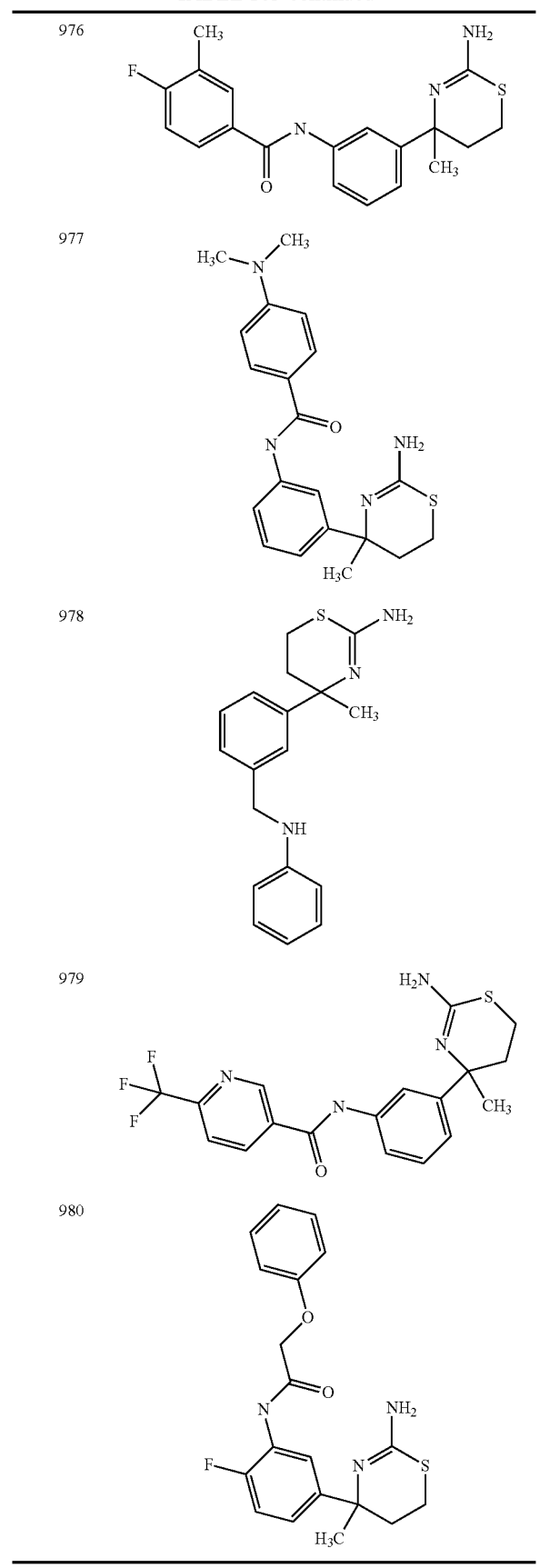
TABLE 104
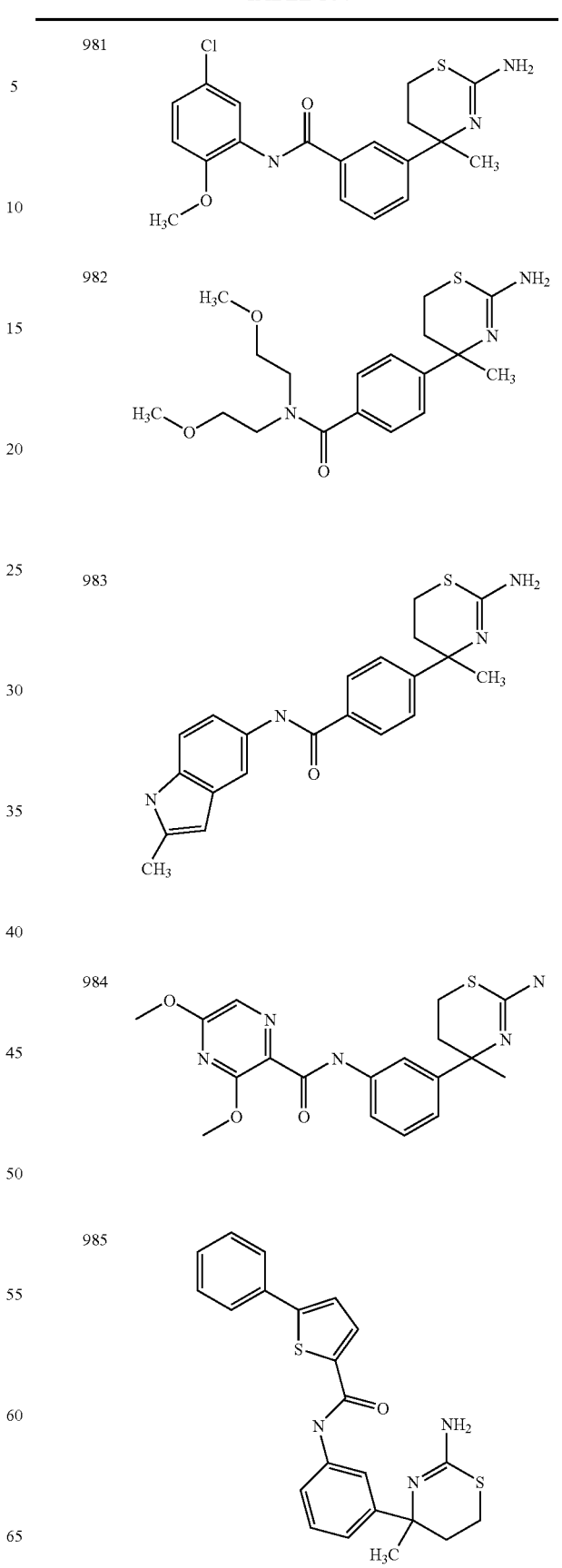

283
TABLE 104-continued
986 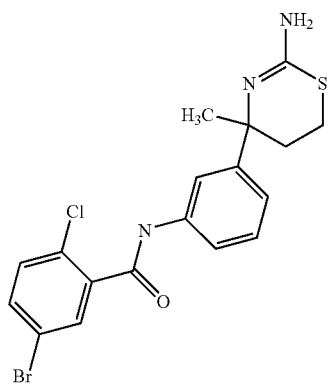
987 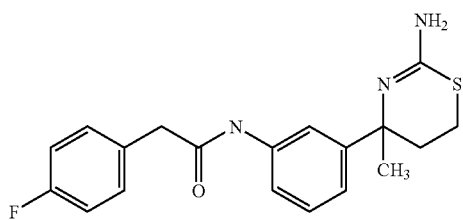
988 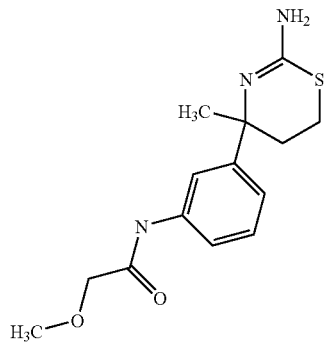
989 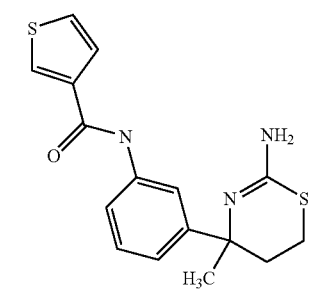
TABLE 105
990 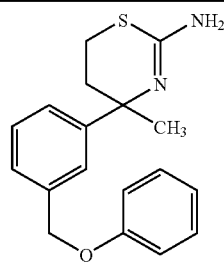
284
TABLE 105-continued
991 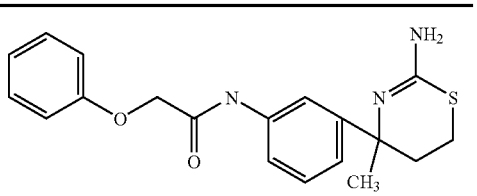
992 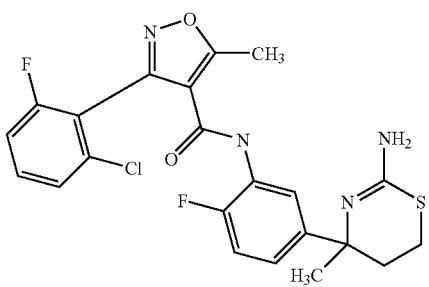
993 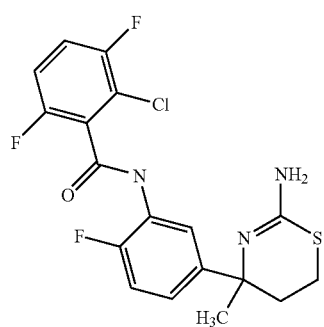
994 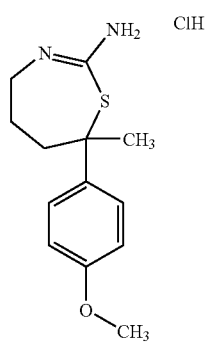
995 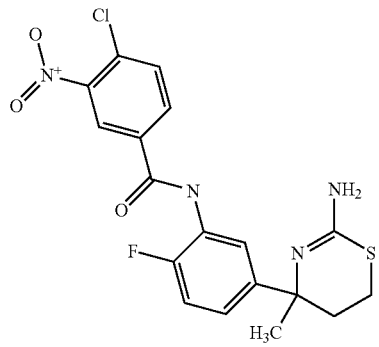

TABLE 105-continued
996 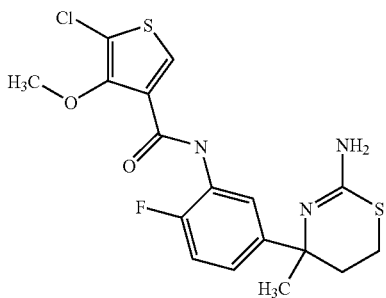
997 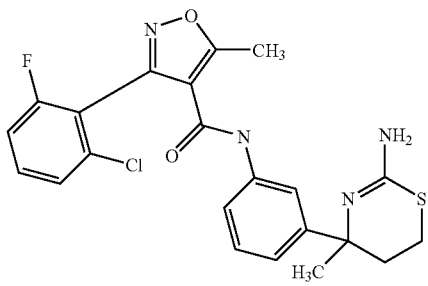
998 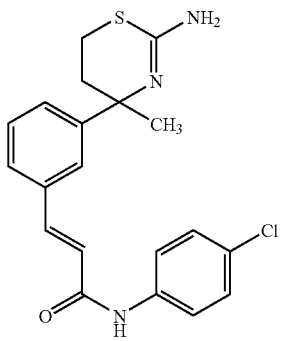
TABLE 106
999 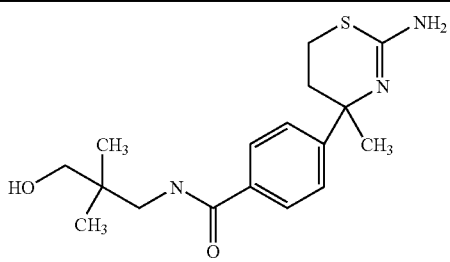
1000 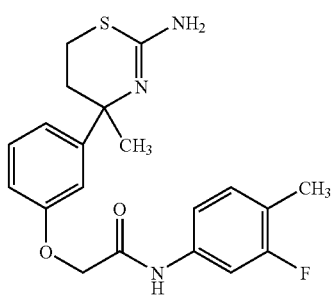
TABLE 106-continued
1001 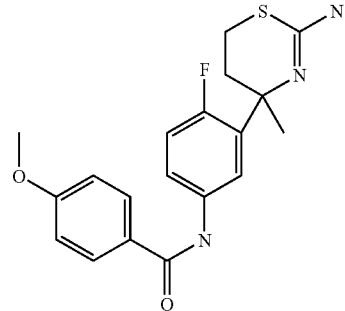
1002 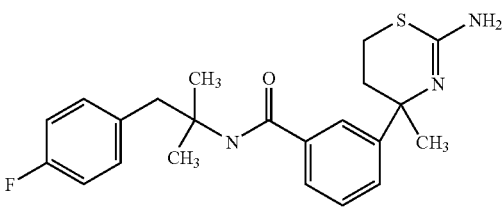
1003 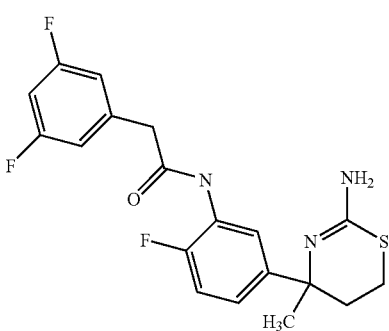
1004 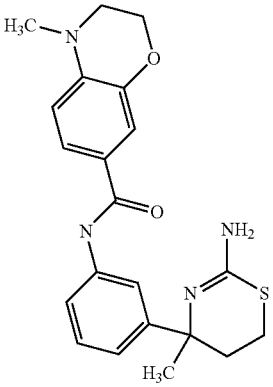
1005 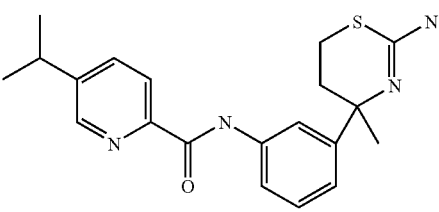

TABLE 106-continued
1006 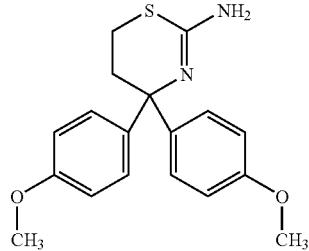
1007 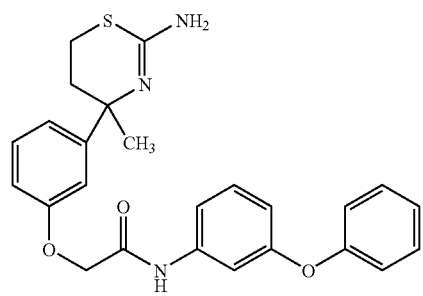
TABLE 107
1008 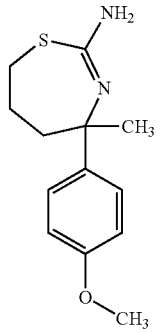
1009 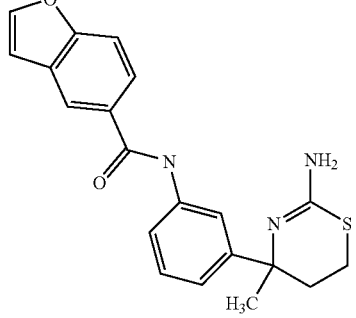
1010 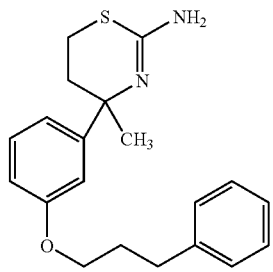
TABLE 107-continued
1011 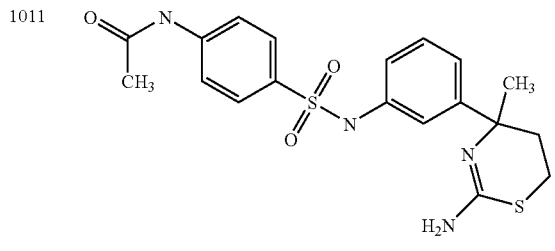
1012 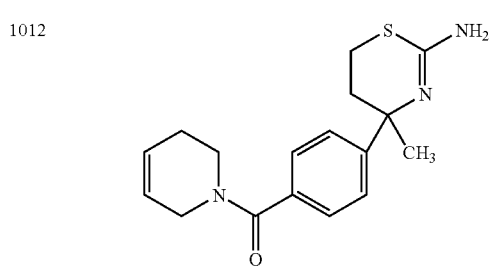
1013 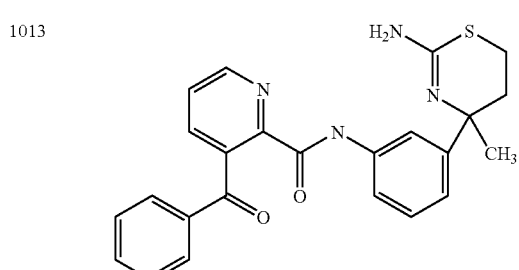
1014 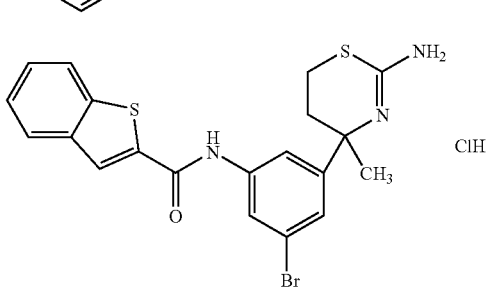 ClH
1015 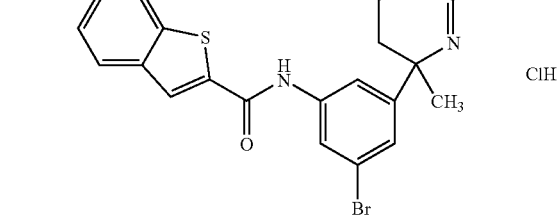
1016 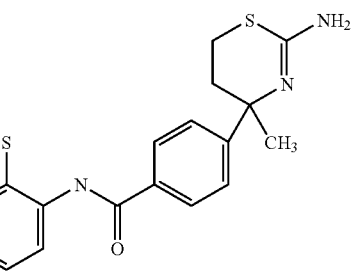

TABLE 107-continued 1017 (structure)

TABLE 108

1018 (structure)

1019 (structure)

1020 (structure)

1021 (structure)

TABLE 108-continued 1022 (structure)

1023 (structure)

1024 (structure)

1025 (structure)

TABLE 109
1026 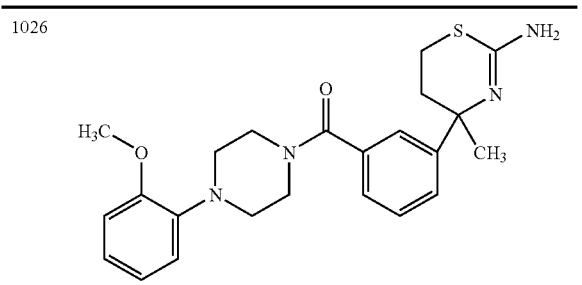
1027 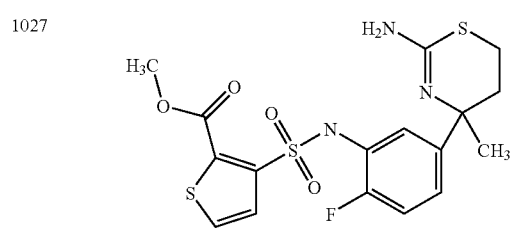
1028 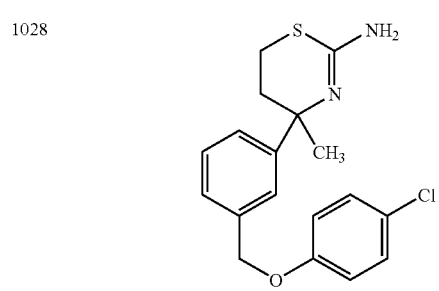
1029 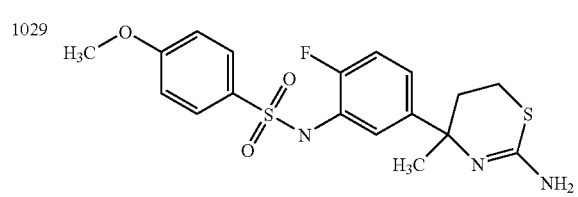
1030 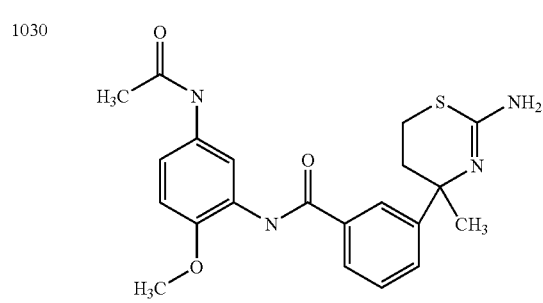
1031 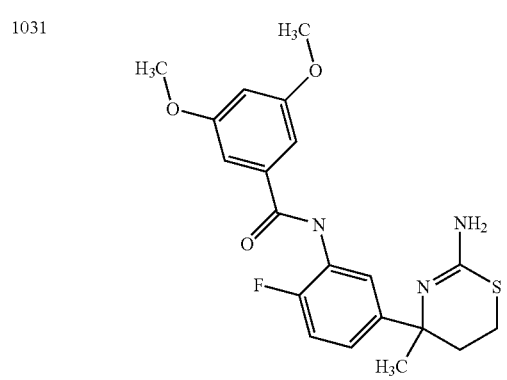
TABLE 109-continued
1032 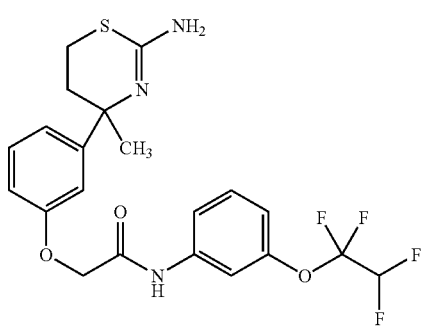
1033 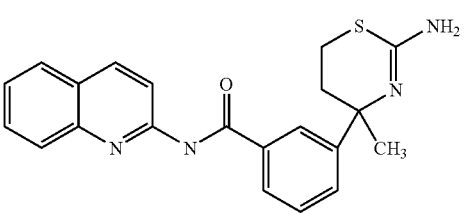
1034 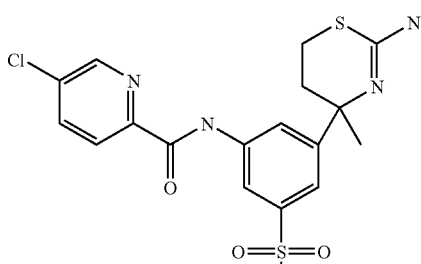
1035 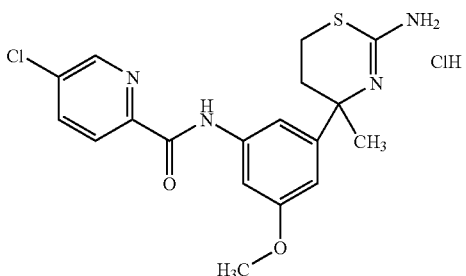
TABLE 110
1036 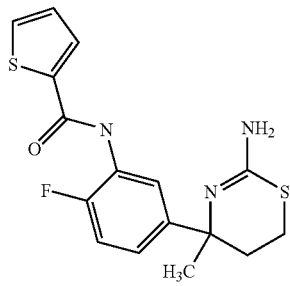

TABLE 110-continued
| | |
|---|---|
| 1037 | 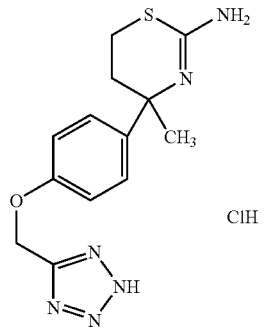 ClH |
| 1038 | 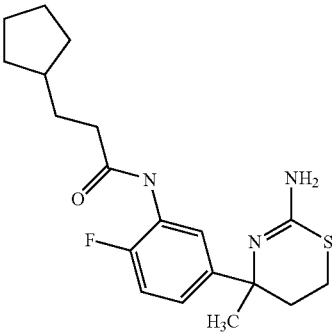 |
| 1039 | 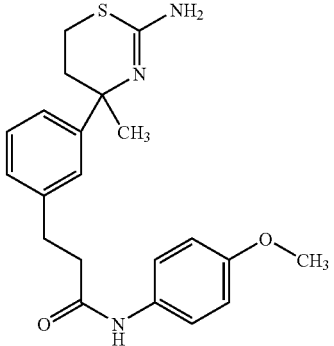 |
| 1040 | 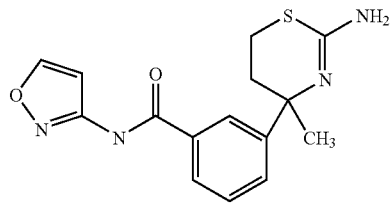 |
| 1041 | 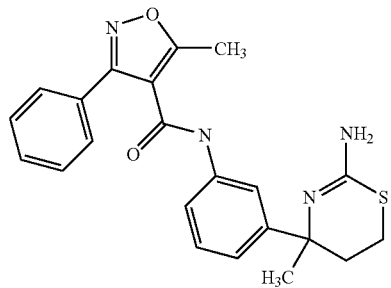 |
TABLE 110-continued
| | |
|---|---|
| 1042 | 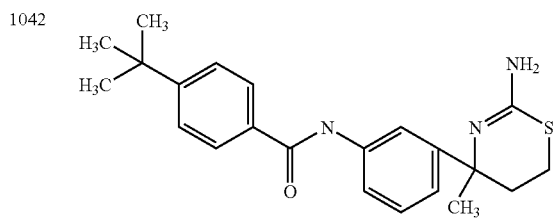 |
| 1043 | 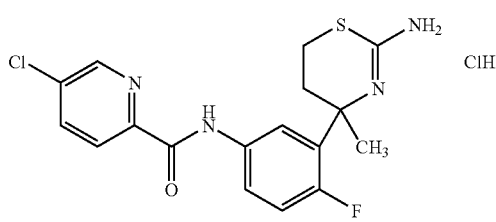 ClH |
| 1044 | 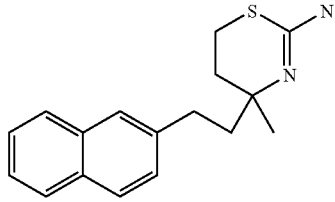 |
TABLE 111
| | |
|---|---|
| 1045 | 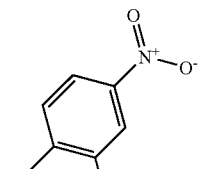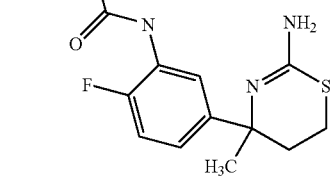 |
| 1046 | 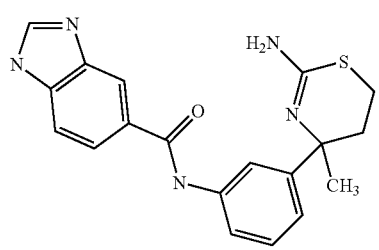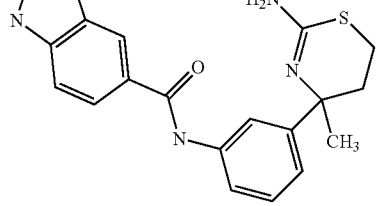 |

TABLE 111-continued
1047 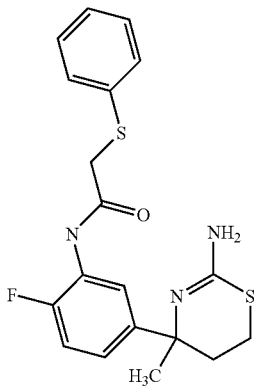
1048 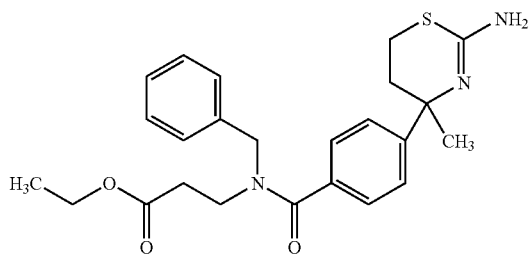
1049 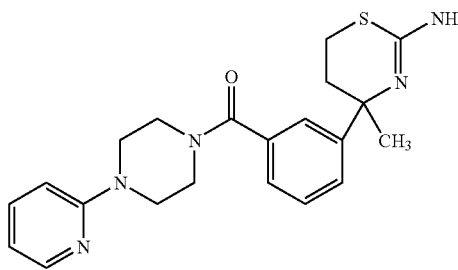
1050 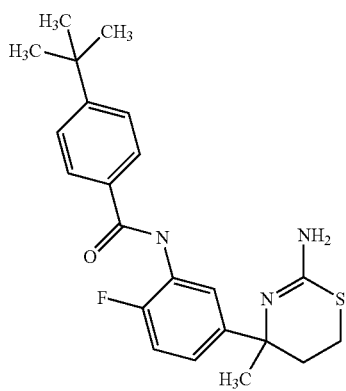
1051 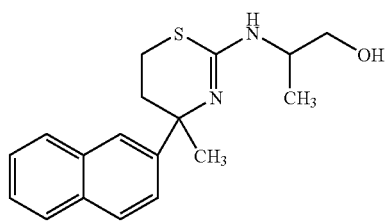
TABLE 111-continued
1052 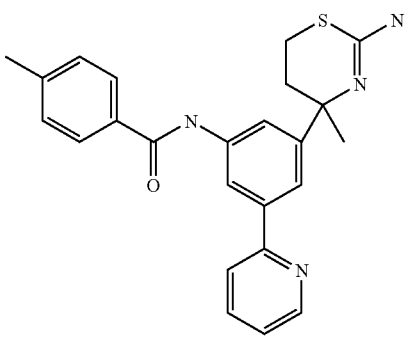
TABLE 112
1053 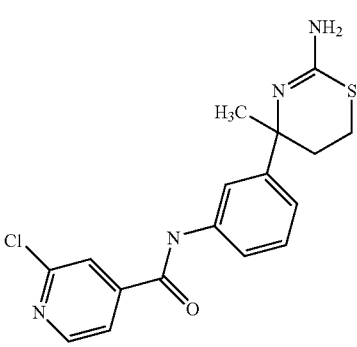
1054 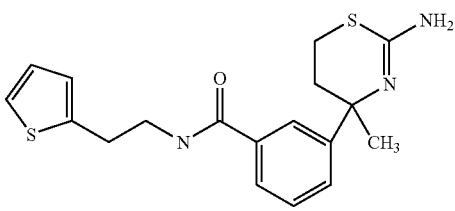
1055 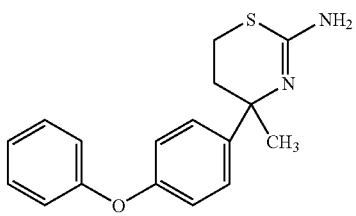
1056 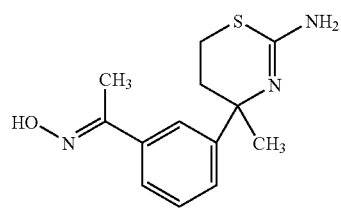

TABLE 112-continued
1057 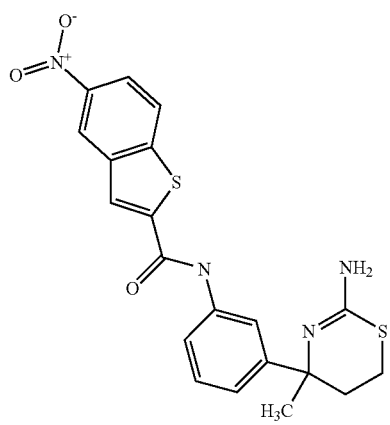
1058 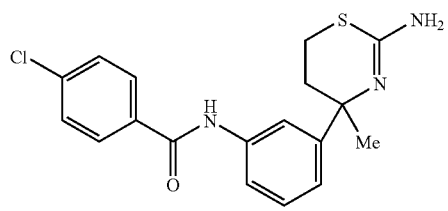
1059 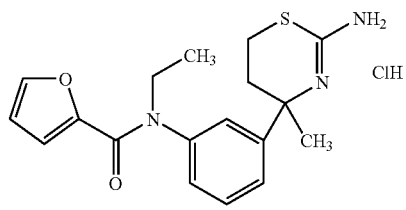 ClH
1060 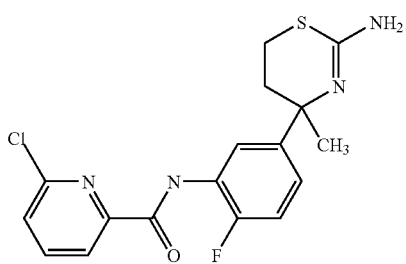
1061 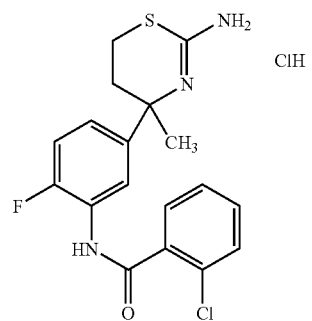 ClH
TABLE 112-continued
1062 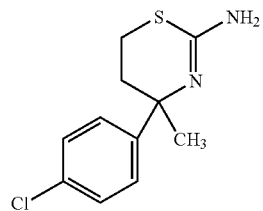
TABLE 113
1063 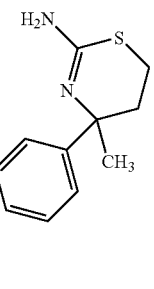
1064 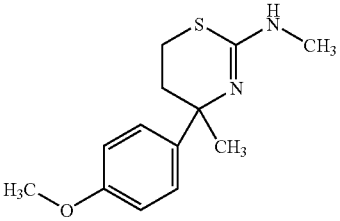
1065 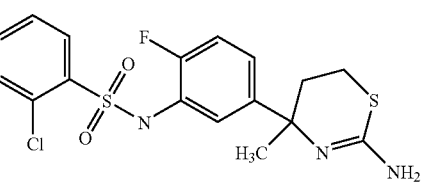
1066 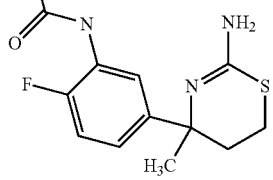

TABLE 113-continued
1067 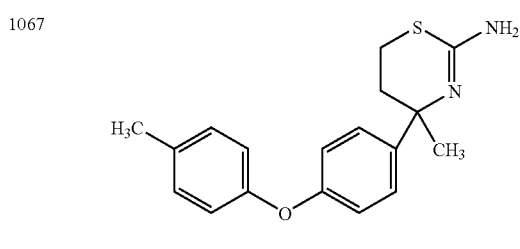
1068 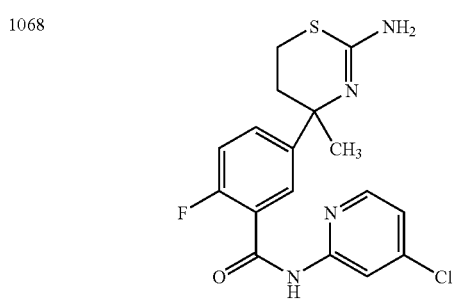
1069 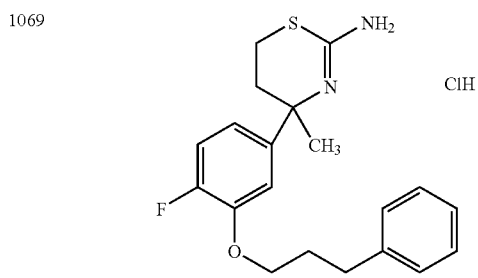
1070 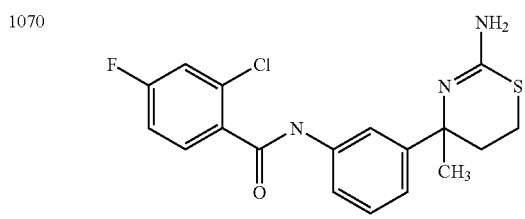
1071 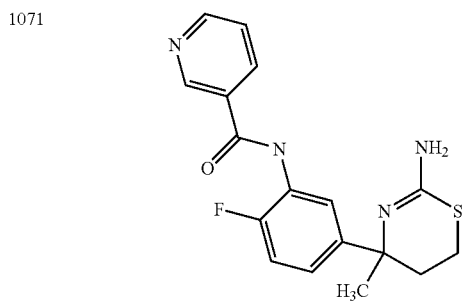
TABLE 114
1072 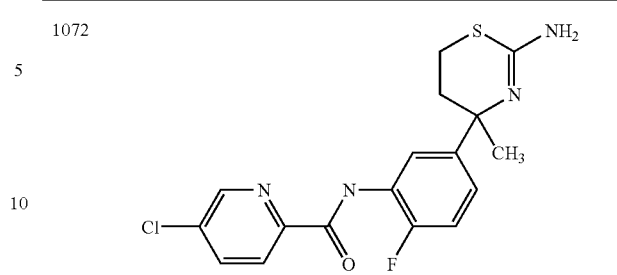
1073 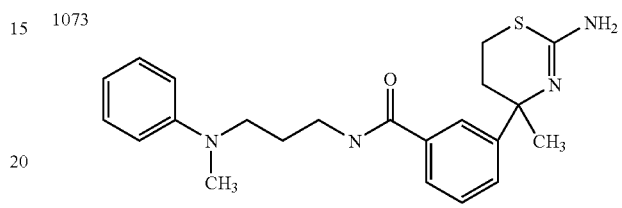
1074 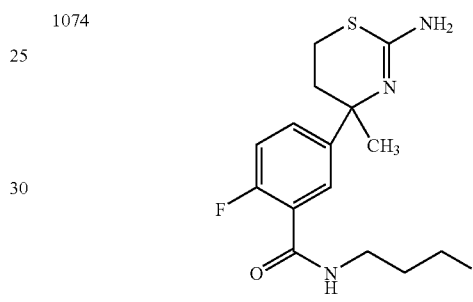
1075 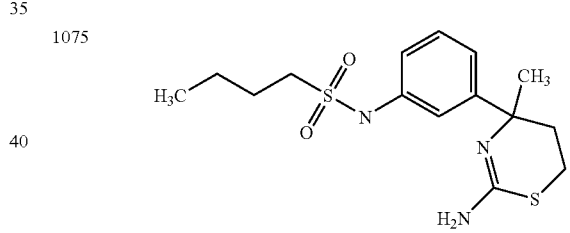
1076 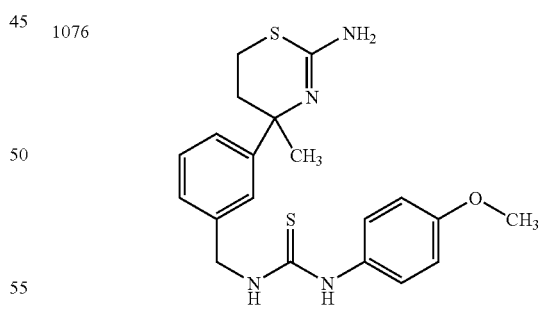
1077 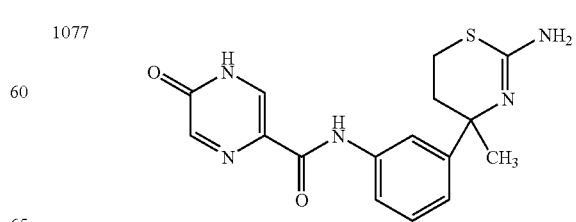

TABLE 114-continued
1078 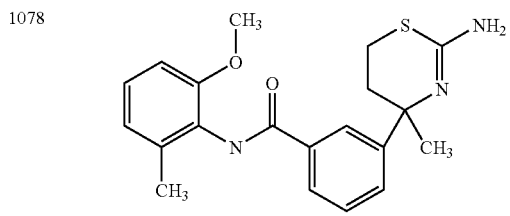
1079 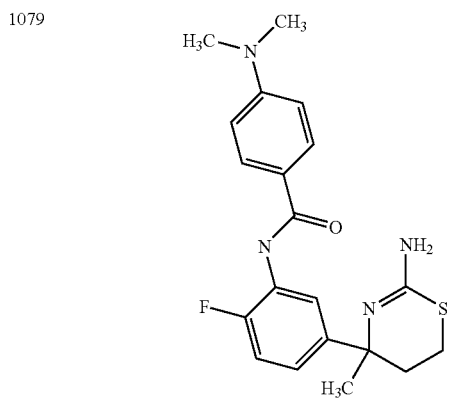
1080 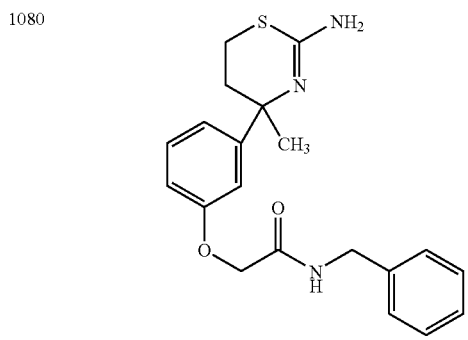
TABLE 115
1081 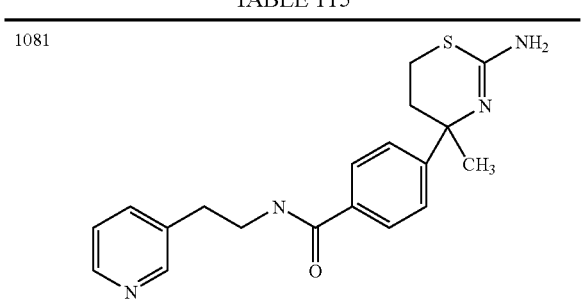
1082 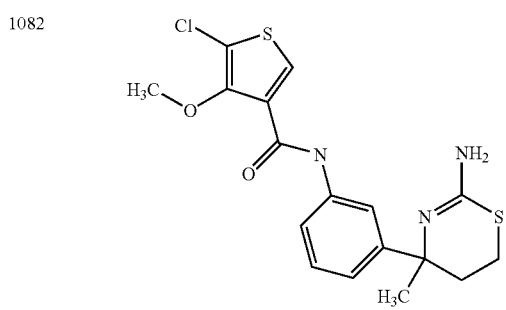
TABLE 115-continued
1083 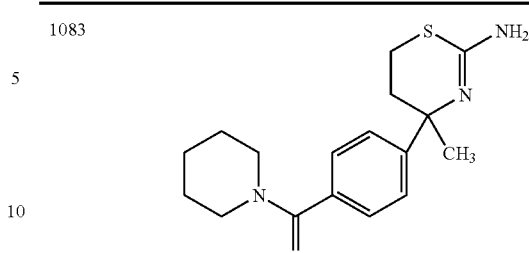
1084 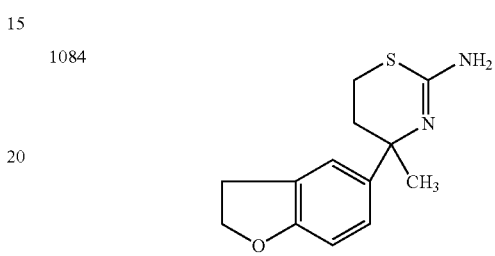
1085 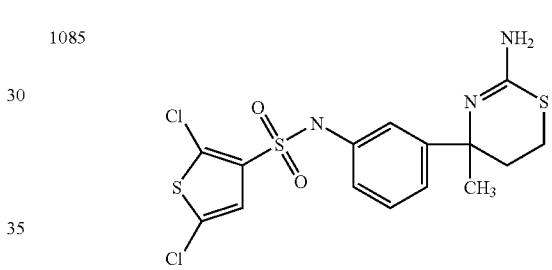
1086 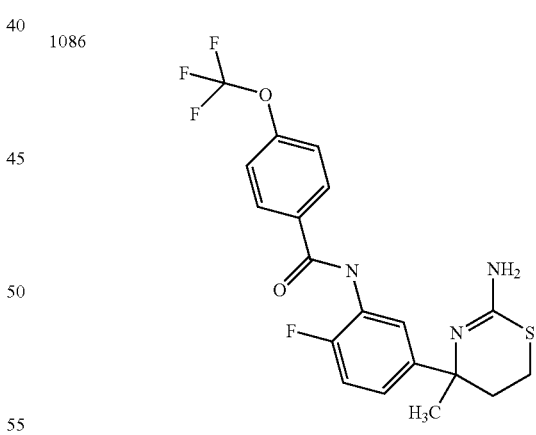
1087 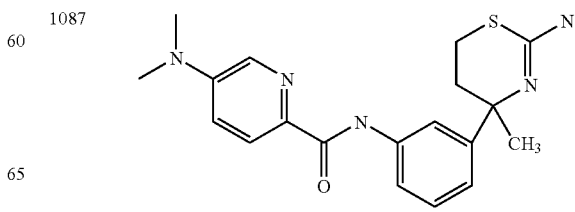

TABLE 115-continued
1088 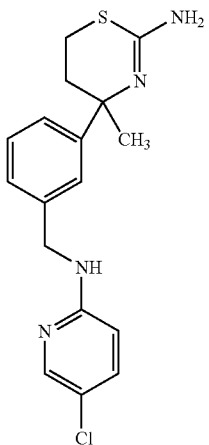
1089 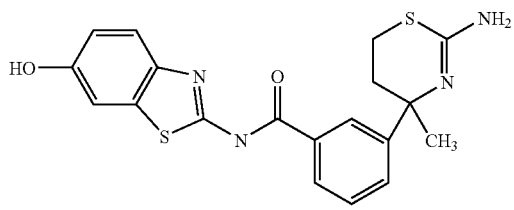
1090 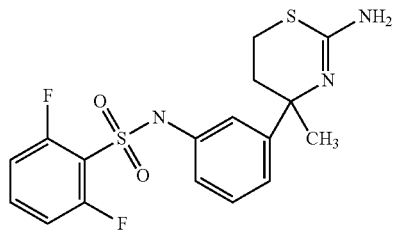
TABLE 116
1091 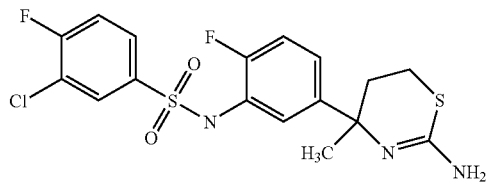
1092 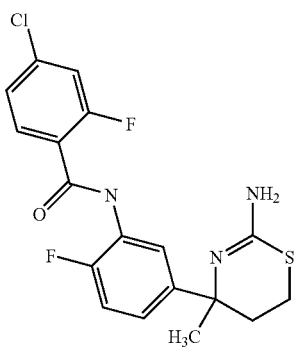
TABLE 116-continued
1093 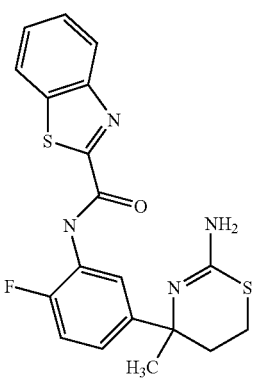
1094 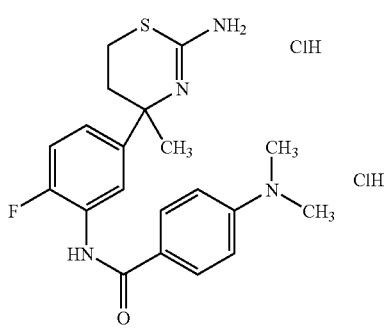
1095 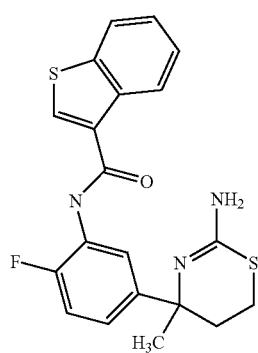
1096 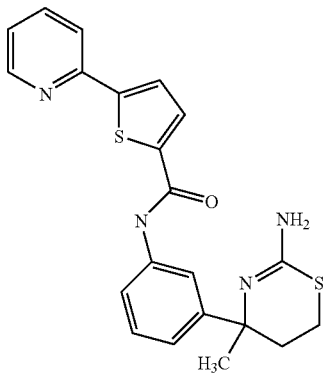
1097 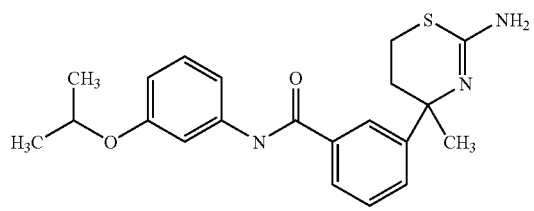

TABLE 116-continued
1098
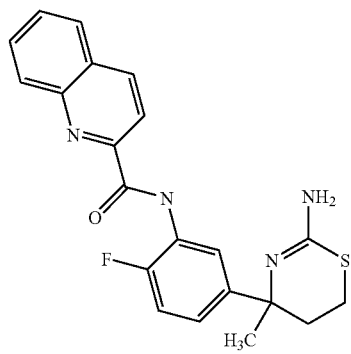
TABLE 117
1099
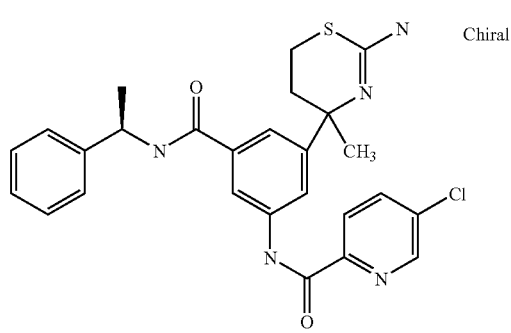
Chiral
1100
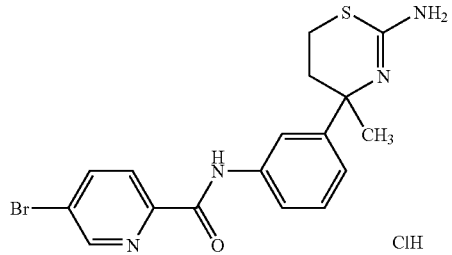
ClH
1101
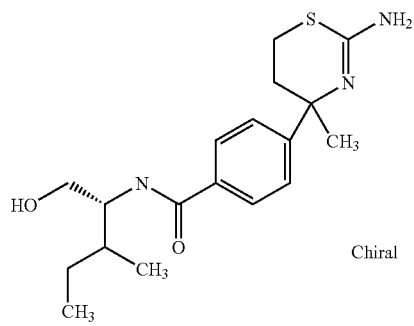
Chiral
TABLE 117-continued
1102
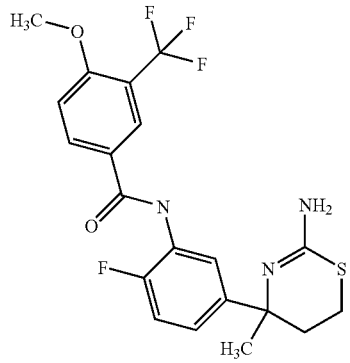
1103
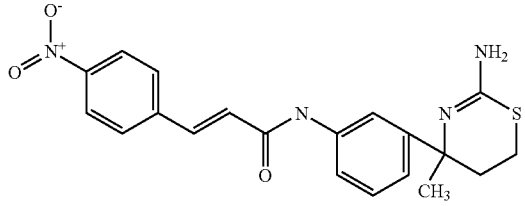
1105
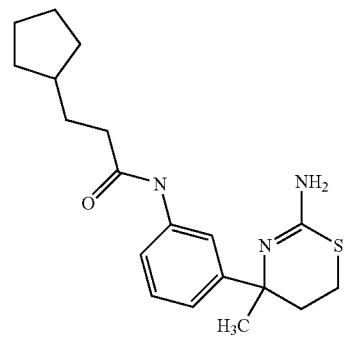
1106
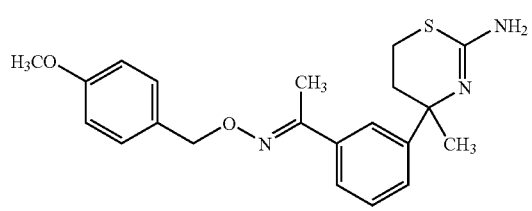
1107

TABLE 118
1108 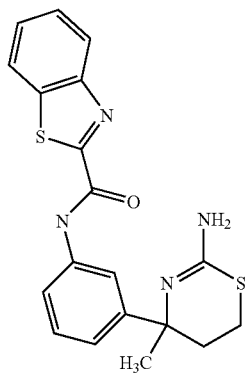
1109 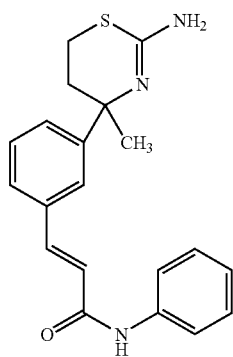
1110 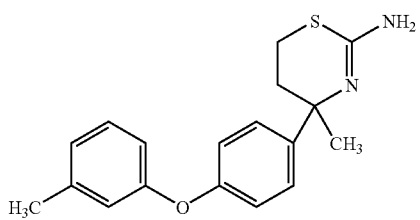
1111 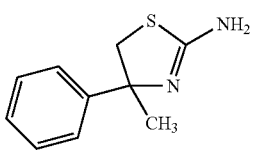
1112 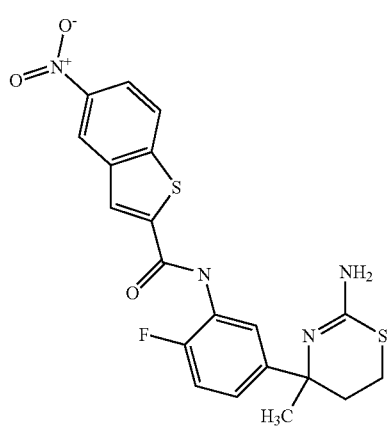
TABLE 118-continued
1113 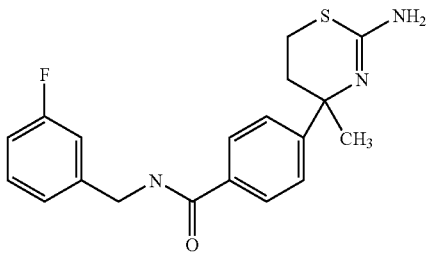
1114 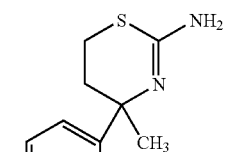
1115 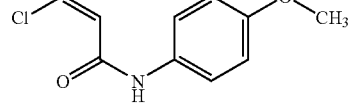
TABLE 119
1116 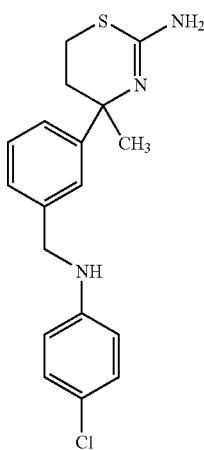

TABLE 119-continued
1117 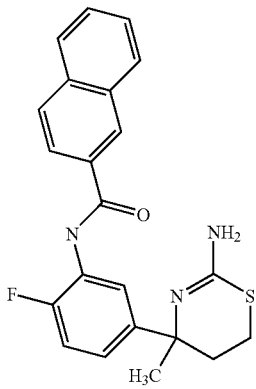
1118 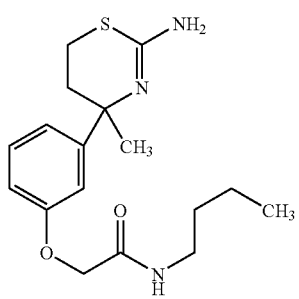
1119 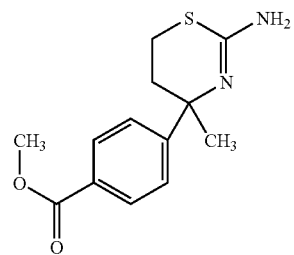
1120 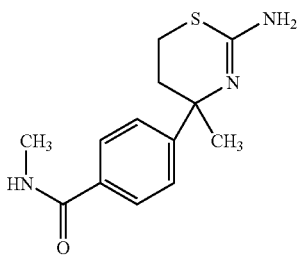
1121 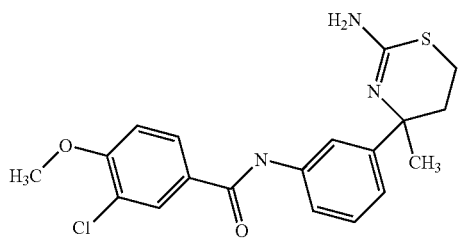
TABLE 119-continued
1122 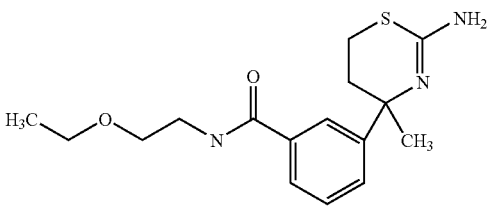
1123 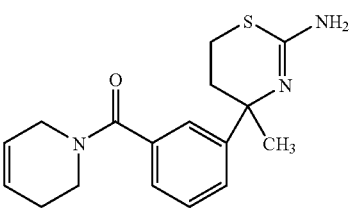
1124 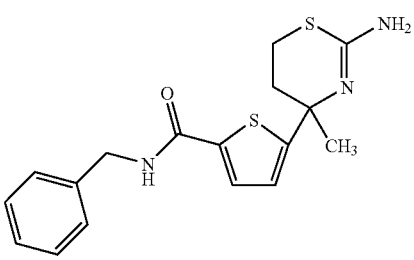
TABLE 120
1125 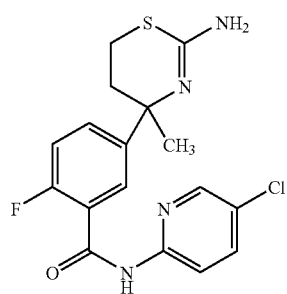
1126 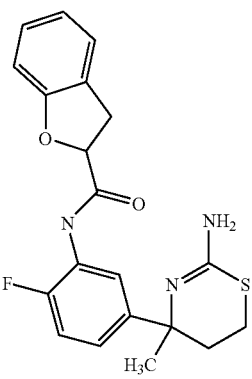

TABLE 120-continued
| 1127 | 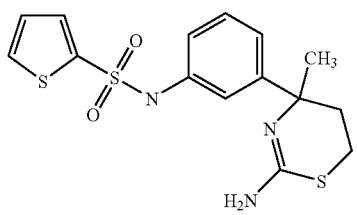 |
|---|---|
| 1128 | 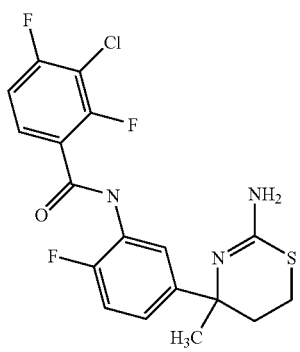 |
| 1129 | 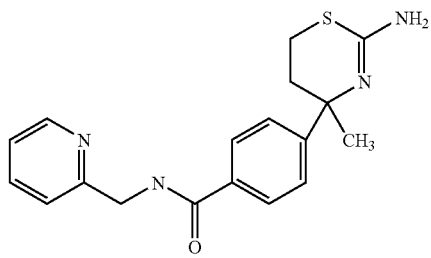 |
| 1130 | 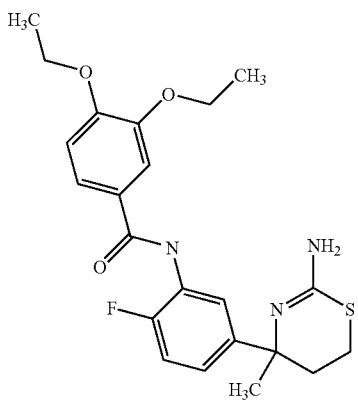 |
| 1131 | 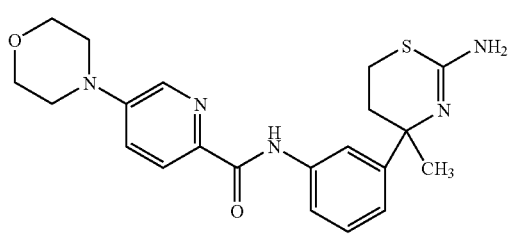 |
TABLE 120-continued
| 1132 | 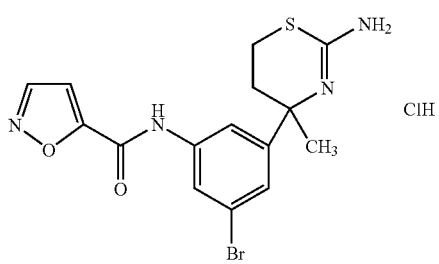 ClH |
TABLE 121
| 1133 | 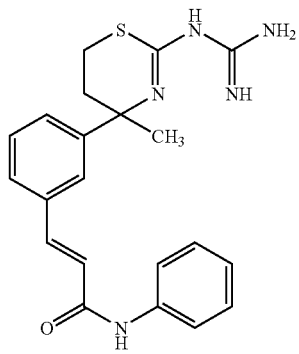 |
|---|---|
| 1134 | 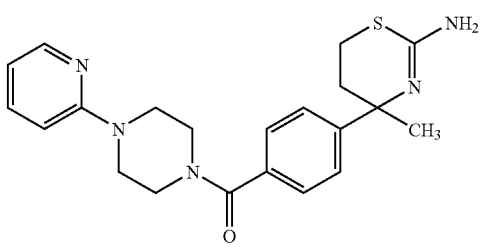 |
| 1135 | 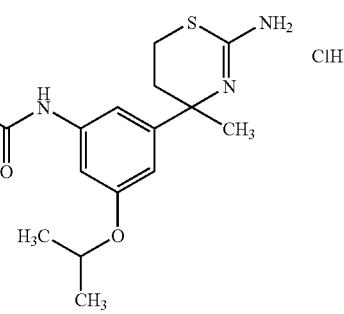 ClH |
| 1136 | 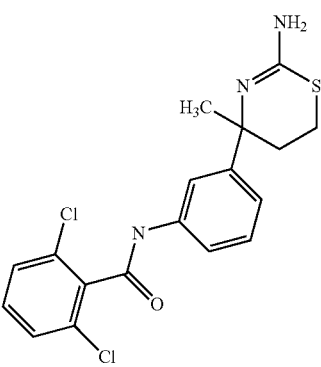 |

TABLE 121-continued
1137 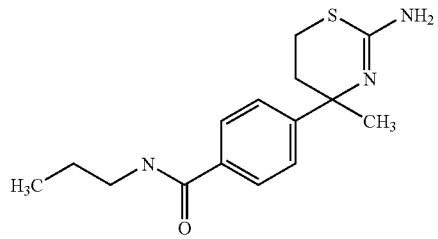
1138 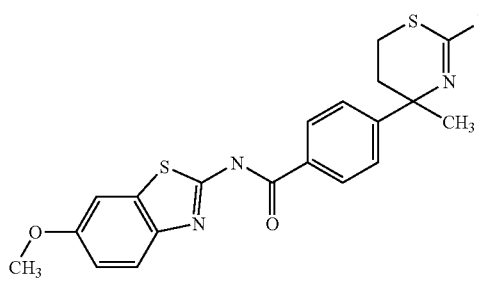
1139 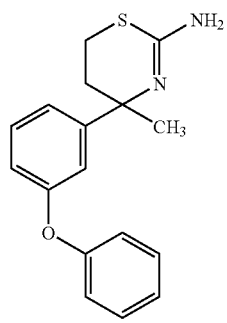
1140 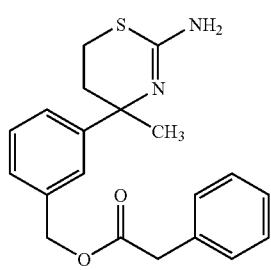
TABLE 122
1141 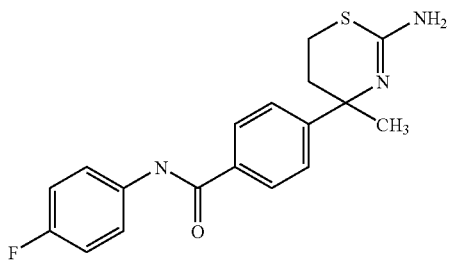
TABLE 122-continued
1142 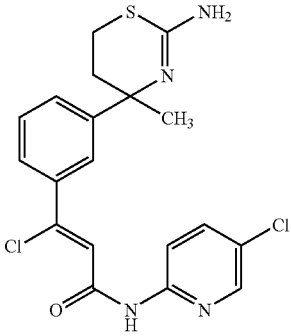
1143 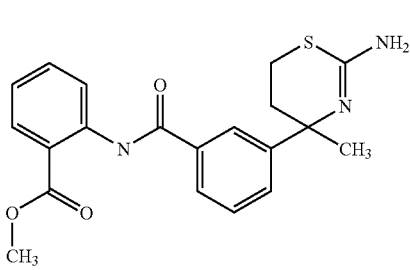
1144 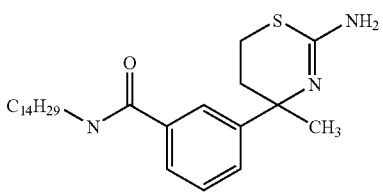
1145 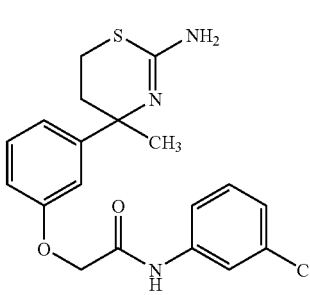
1146 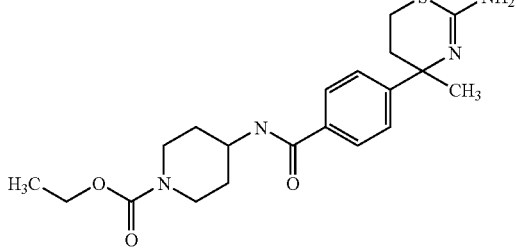
1147 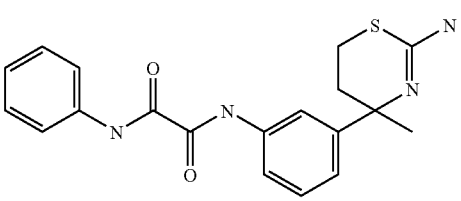

TABLE 122-continued
1148 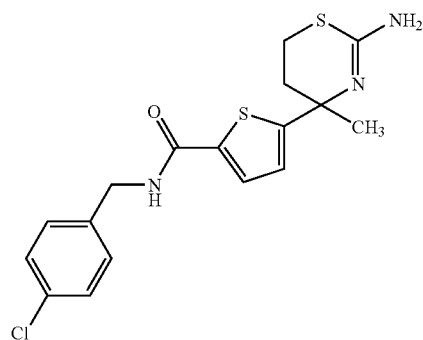
1149 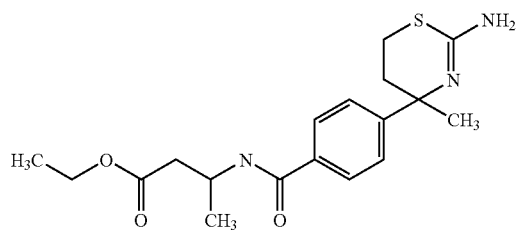
1150 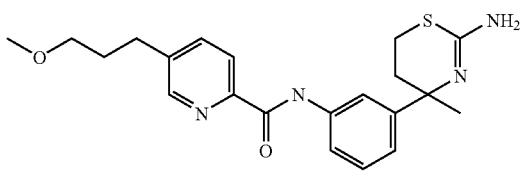
1151 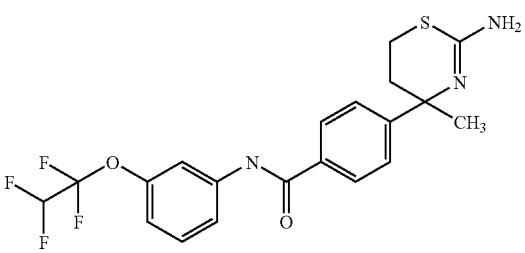
1152 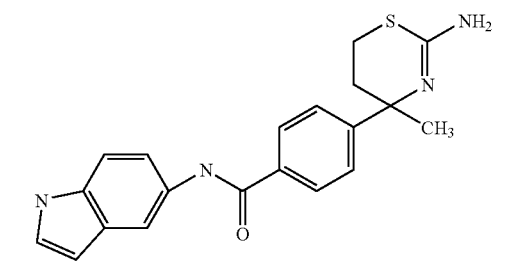
TABLE 123
1153 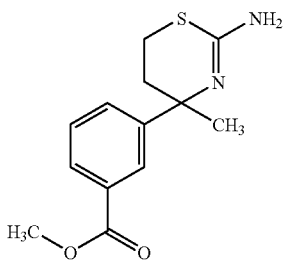
TABLE 123-continued
1154 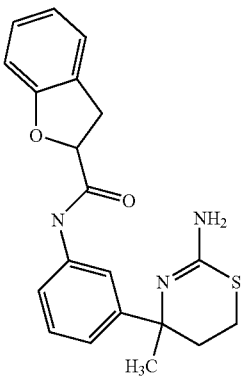
1155 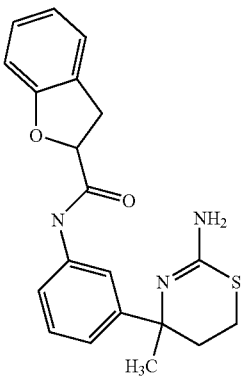
1156 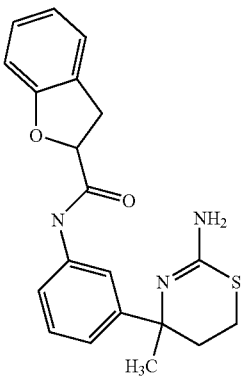
1157 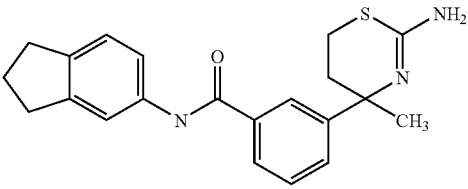
1158 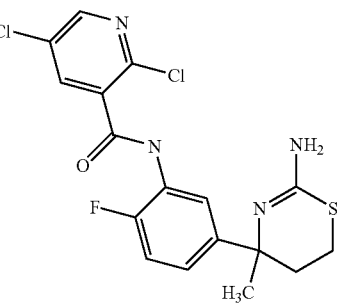

TABLE 123-continued
1159 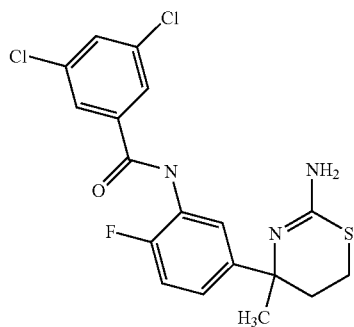
1160 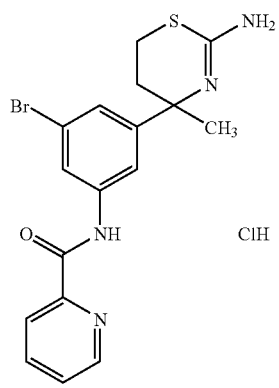
ClH
TABLE 124
1161 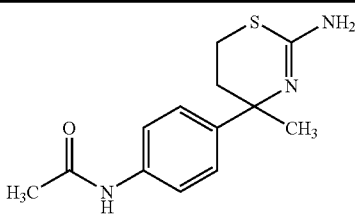
1162 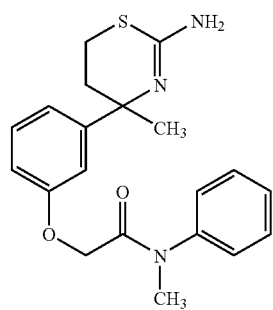
1163 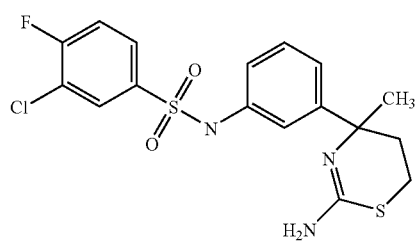
TABLE 124-continued
1164 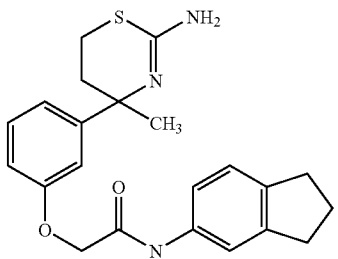
1165 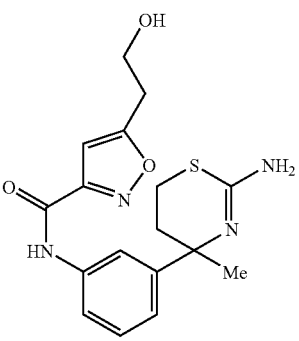
1166 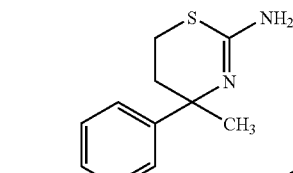
1167 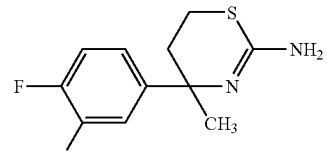
1168 

TABLE 125
1169 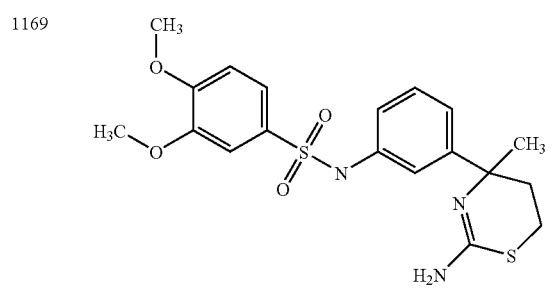
1170 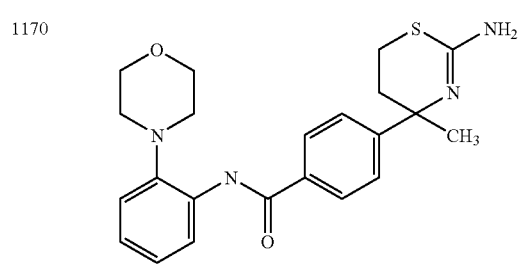
1171 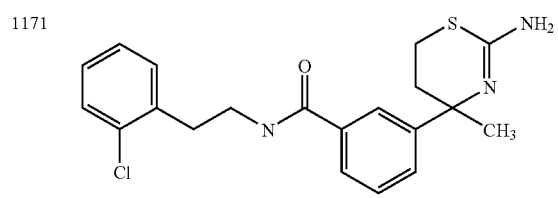
1172 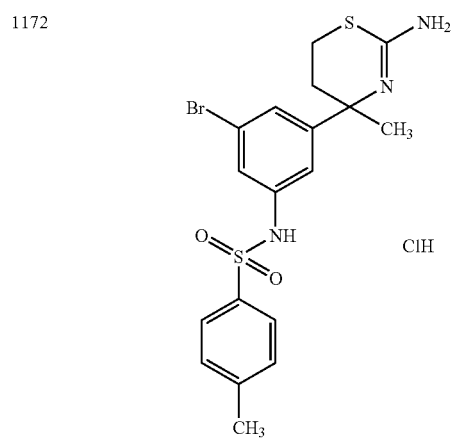
1173 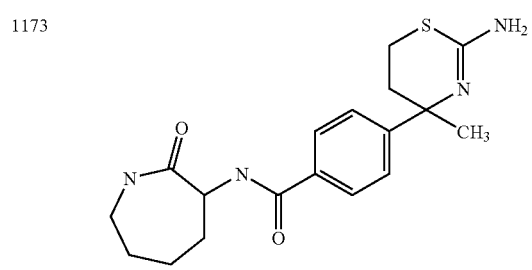
TABLE 125-continued
1174 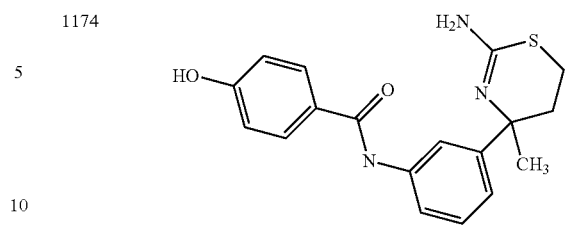
1175 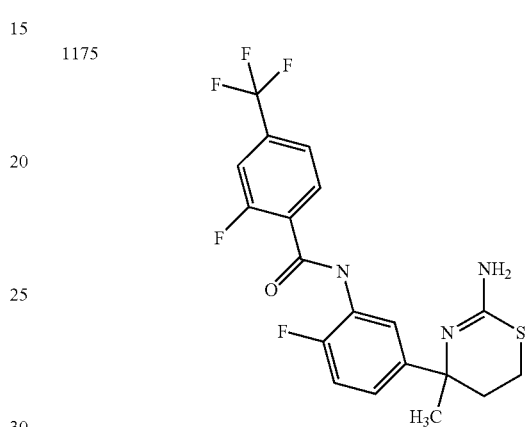
1176 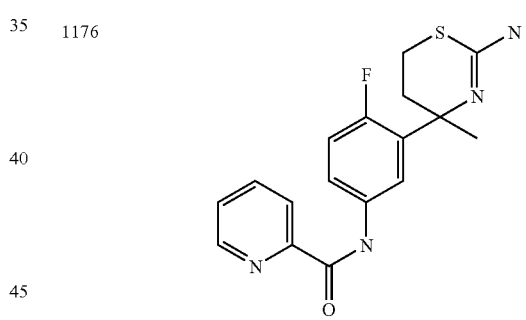
1177 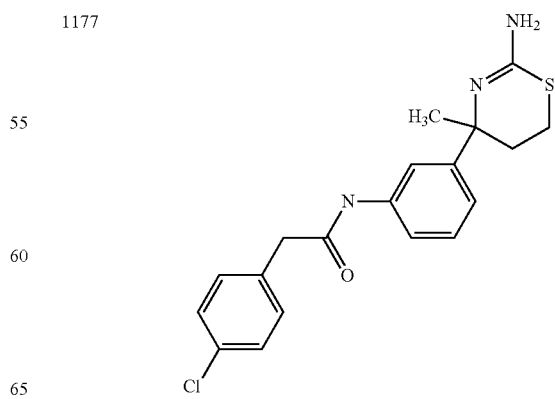

TABLE 126
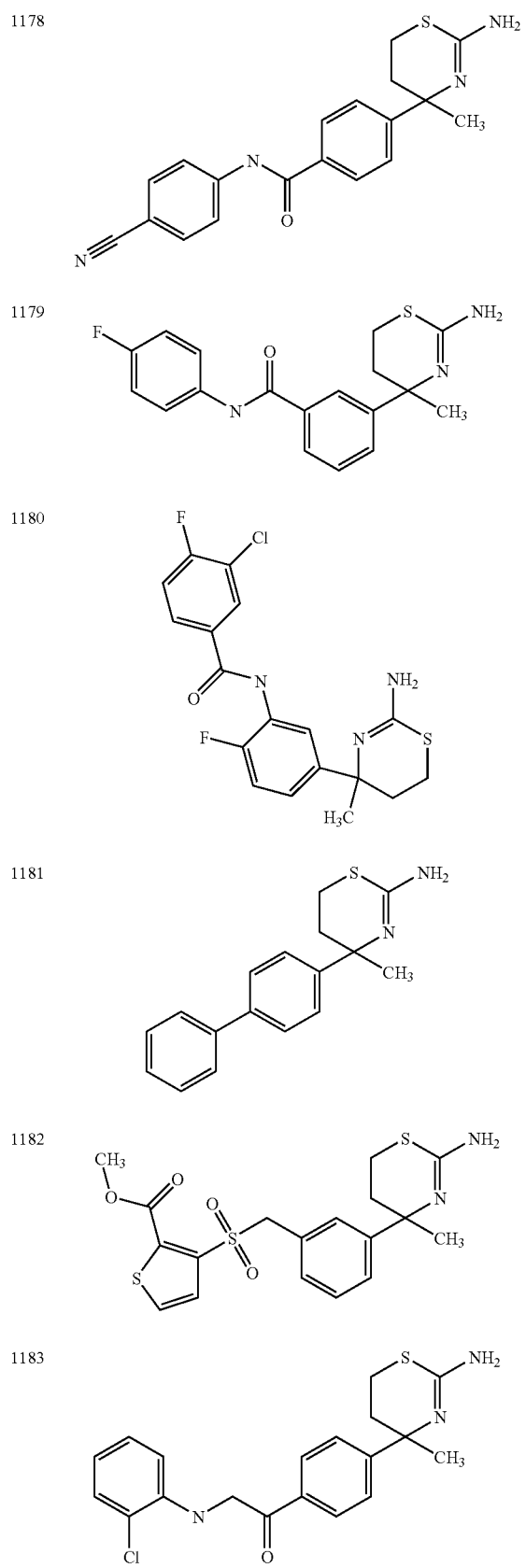
TABLE 126-continued
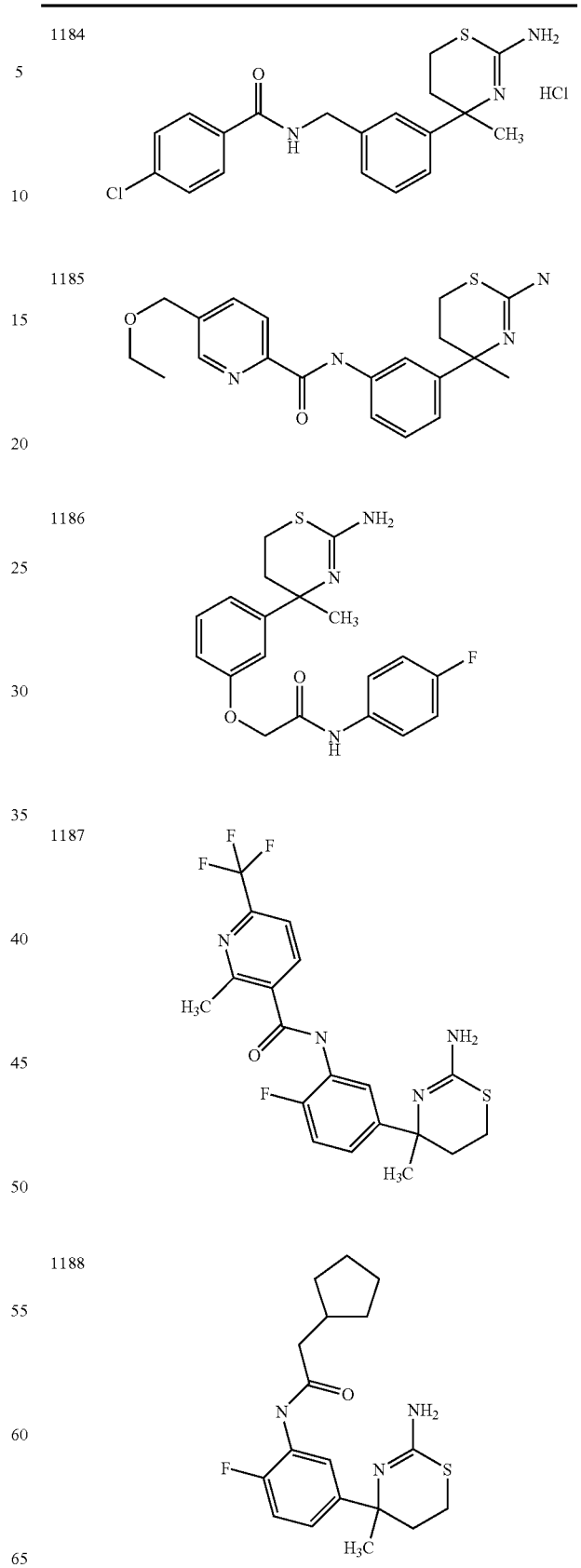

TABLE 127
1189 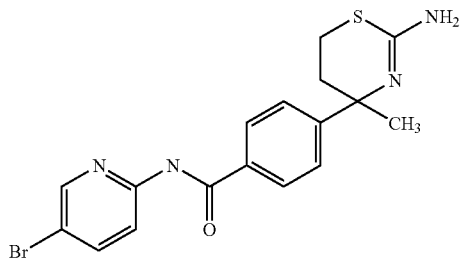
1190 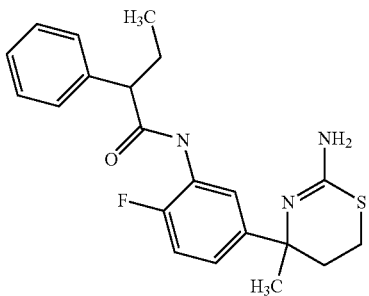
1191 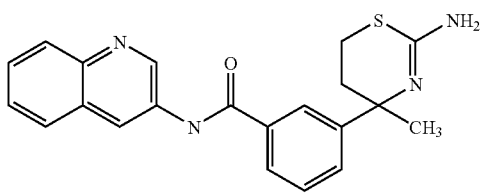
1192 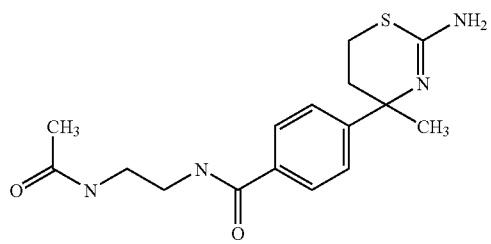
1193 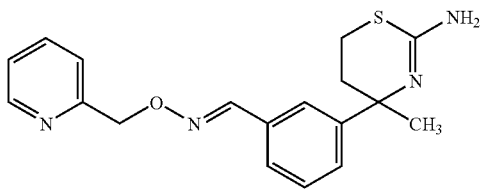
1194 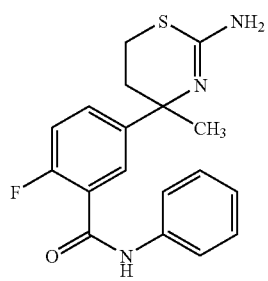
TABLE 127-continued
1195 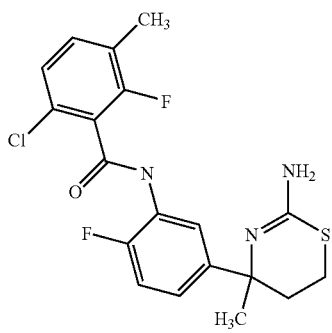
1196 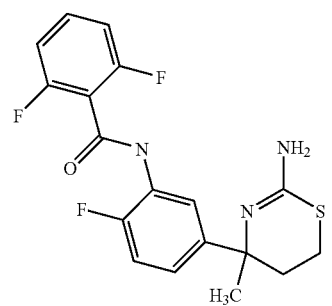
1197 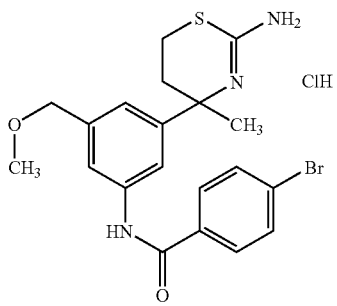
1198
TABLE 128
1199 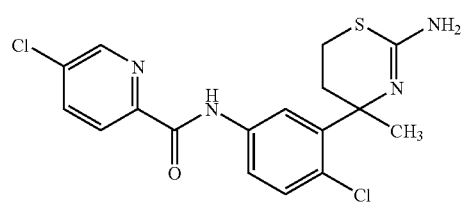

TABLE 128-continued
1200 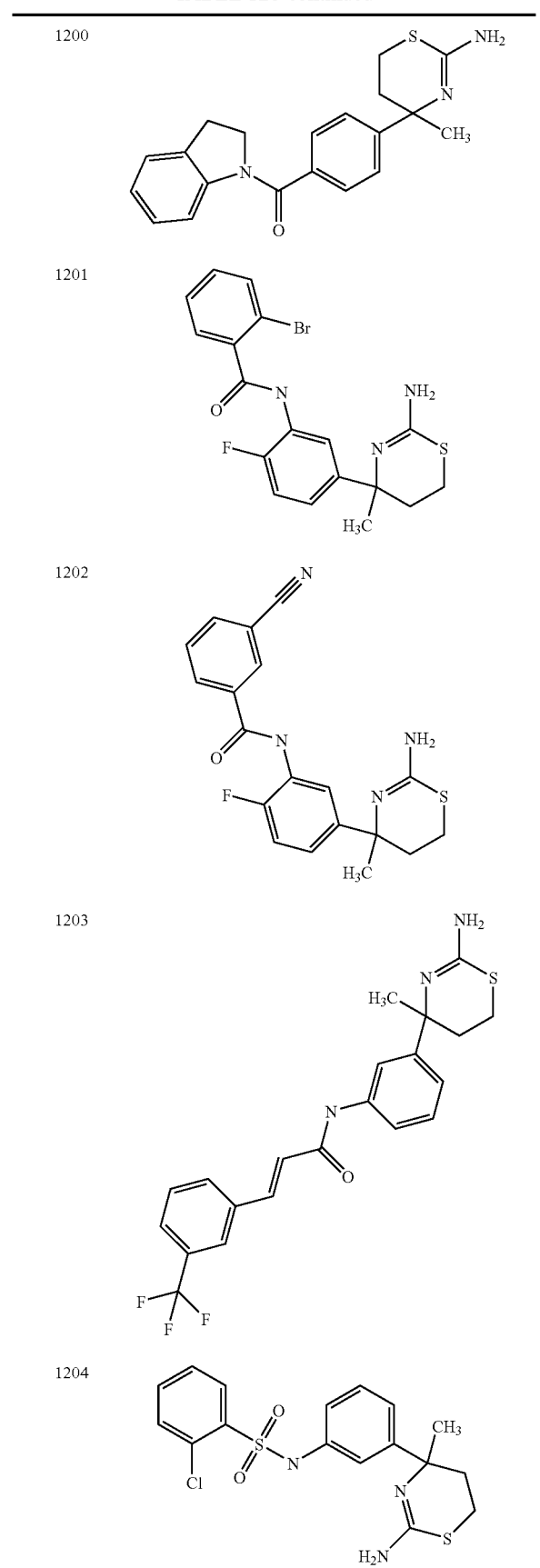
1201
1202
1203
1204
TABLE 128-continued
1205 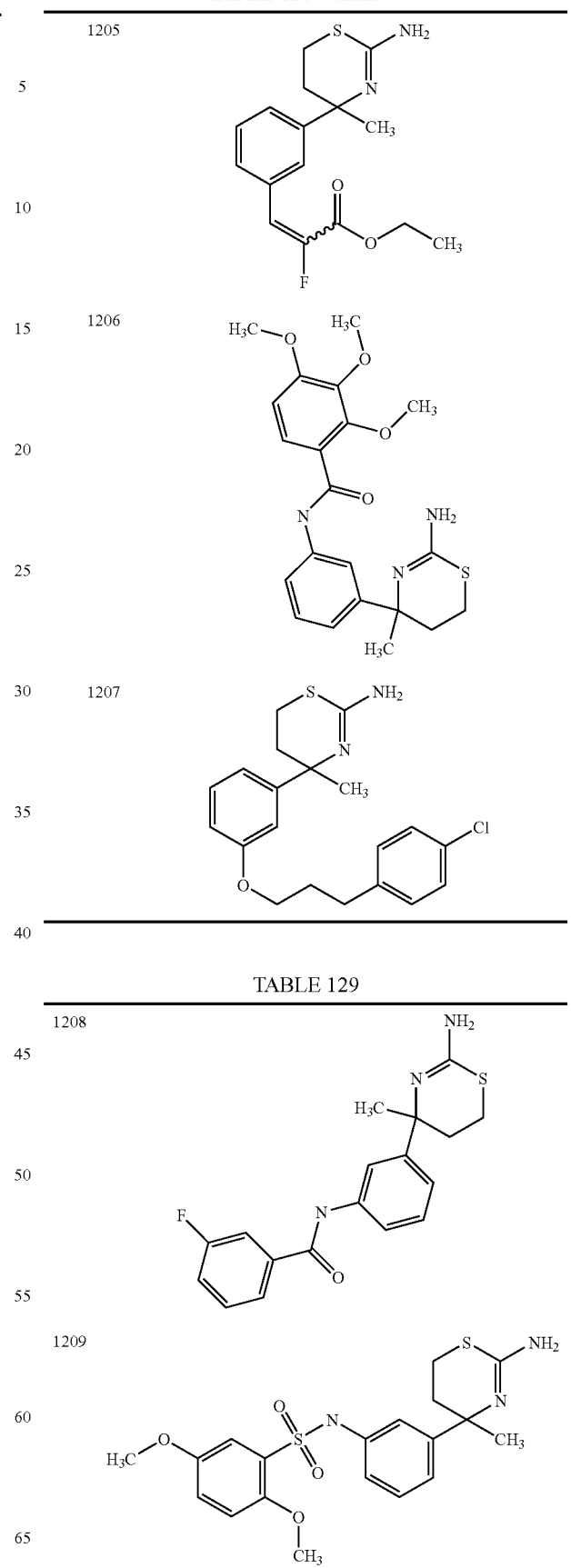
1206
1207
TABLE 129
1208
1209

TABLE 129-continued
1210 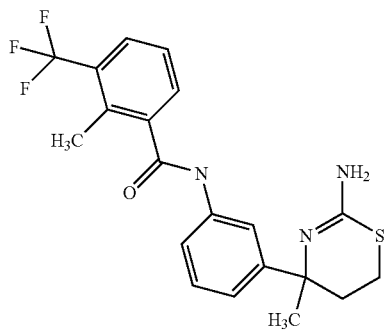
1211 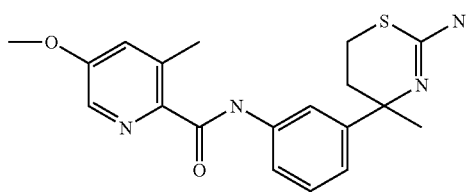
1212 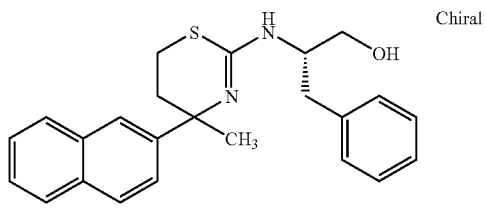 Chiral
1213 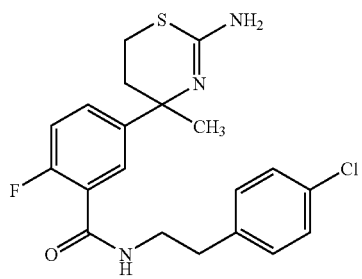
1214 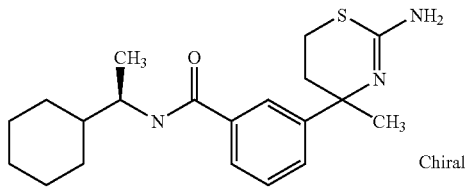 Chiral
1215 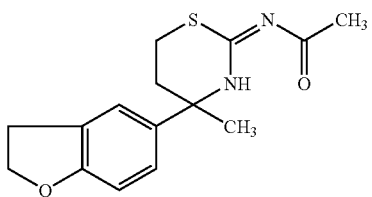
TABLE 129-continued
1216 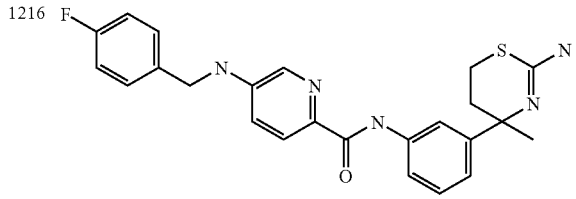
1217 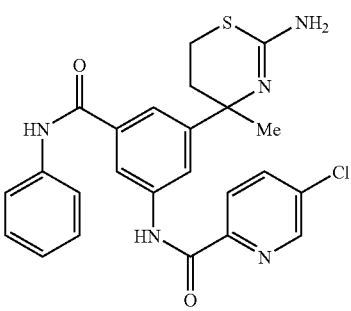
TABLE 130
1218 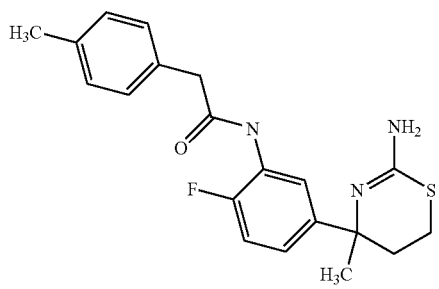
1219 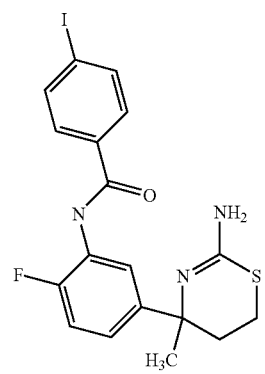
1220 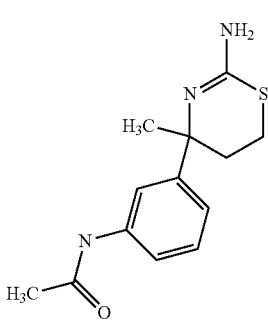

TABLE 130-continued
1221 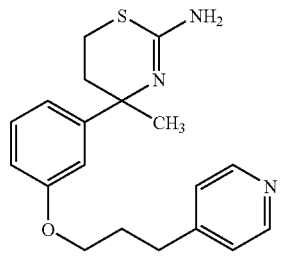
1222 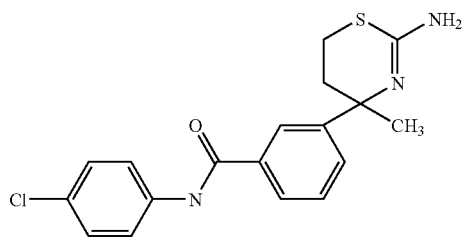
1223 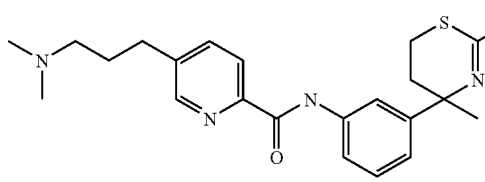
1224 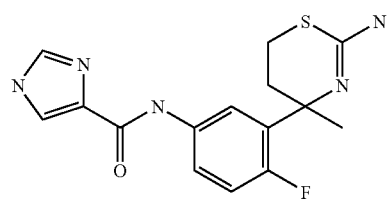
1225 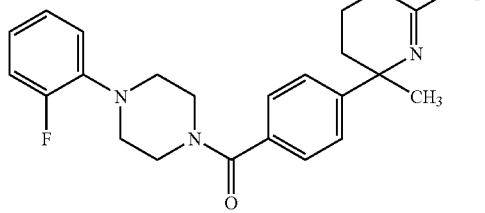
1226 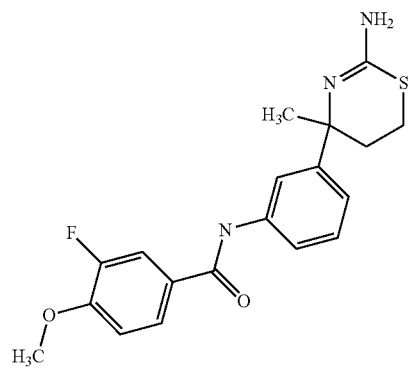
TABLE 131
1227 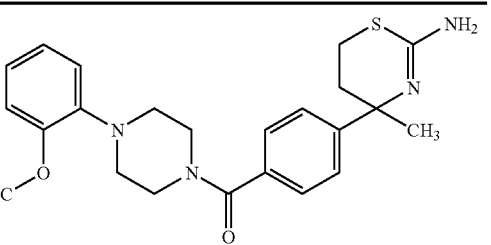
1228 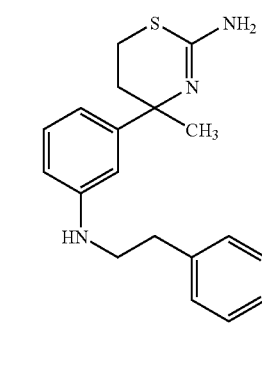
1229 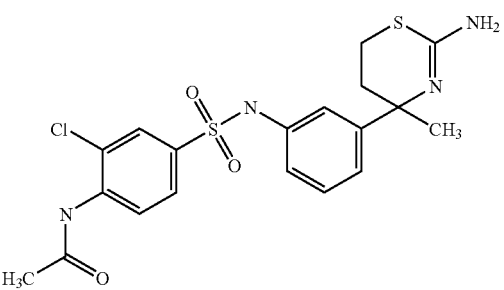
1230 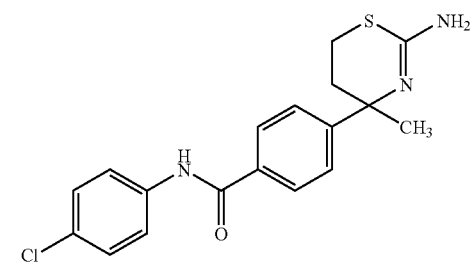
1231 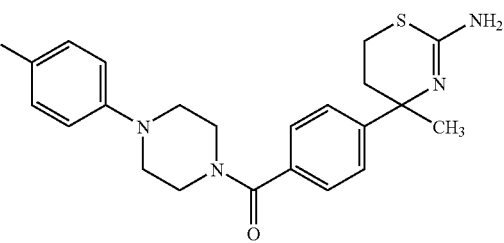

TABLE 131-continued
1232 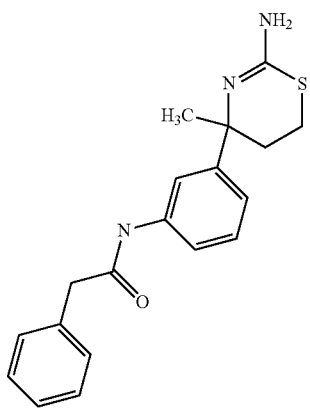
1233 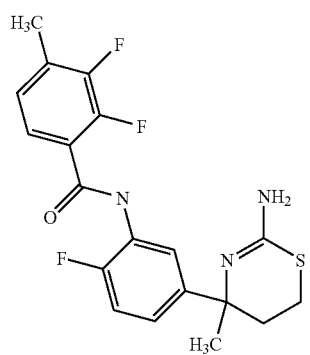
1234 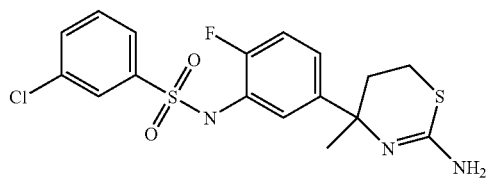
1235 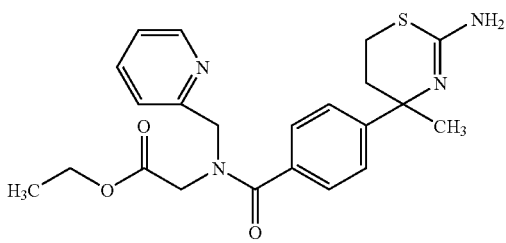
1236 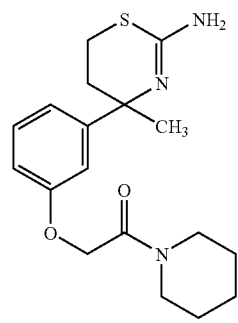
TABLE 132
1237 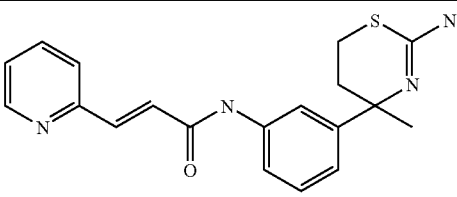
1238 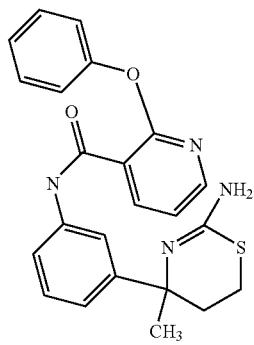
1239 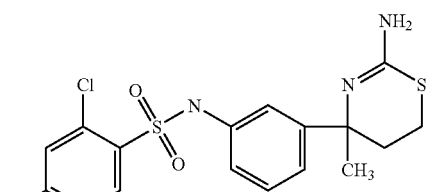
1240 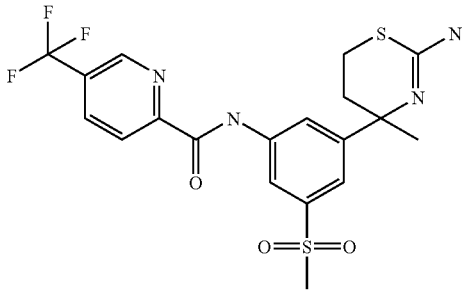
1241 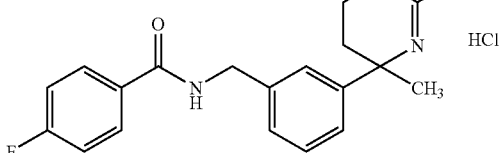
1242 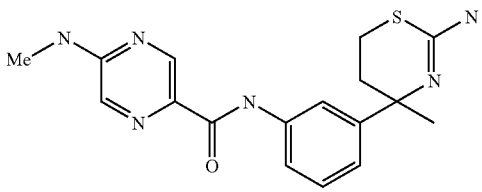

TABLE 132-continued
1243 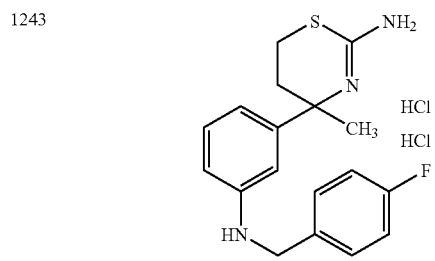
1244 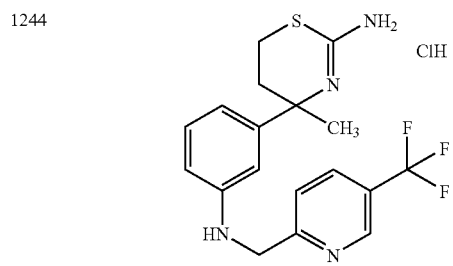
1245 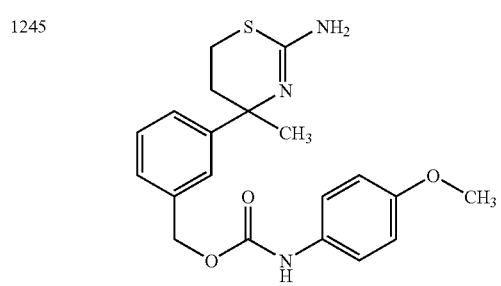
1246 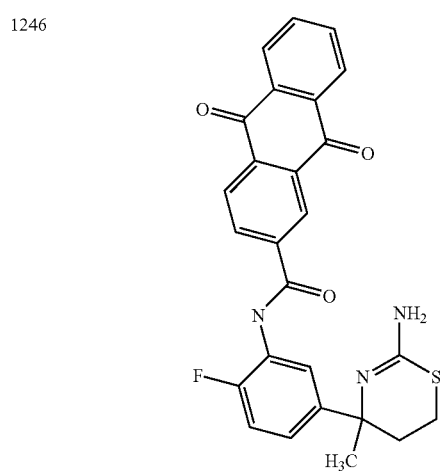
TABLE 133
1247 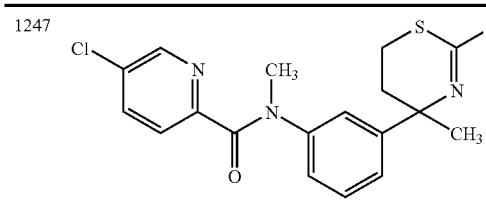
TABLE 133-continued
1248 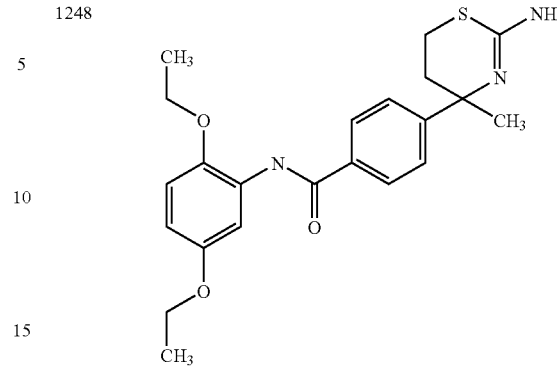
1249 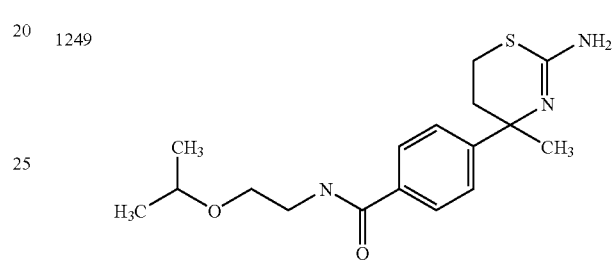
1250 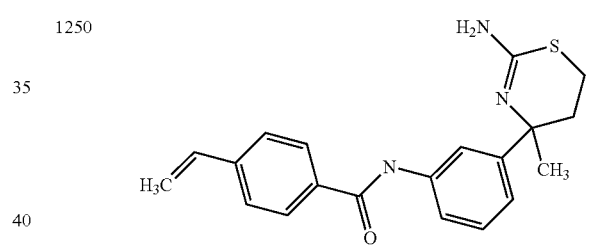
1251 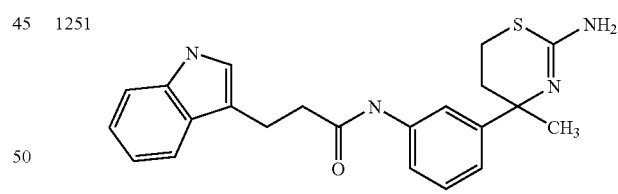
1252 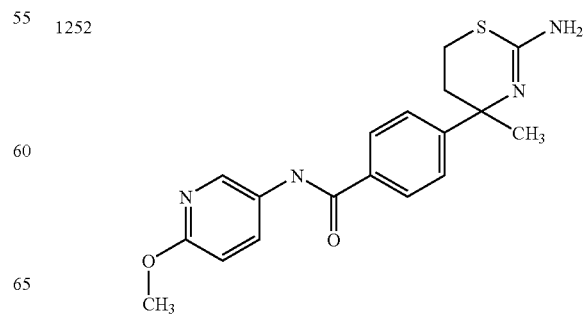

TABLE 133-continued
1253 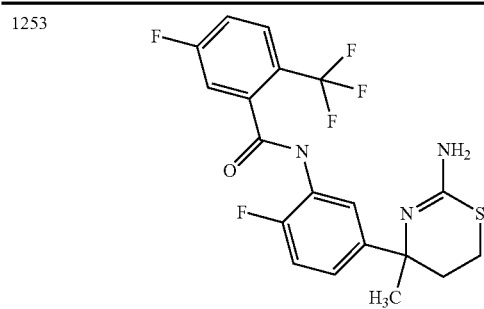
1254 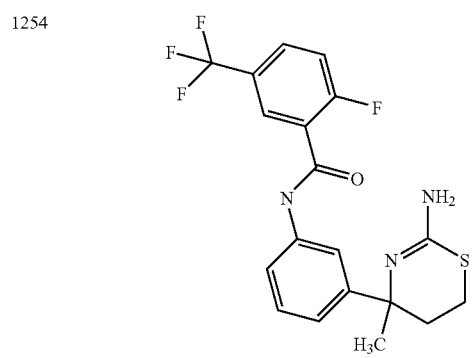
1255 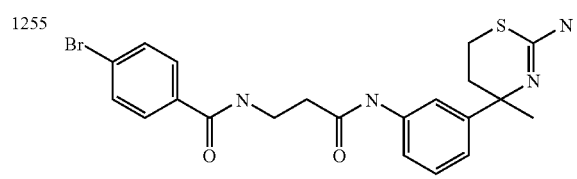
1256 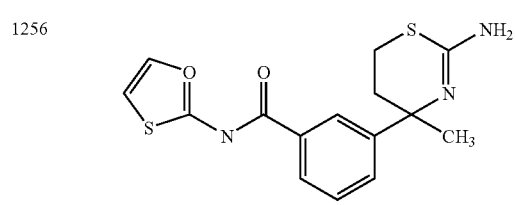
1257 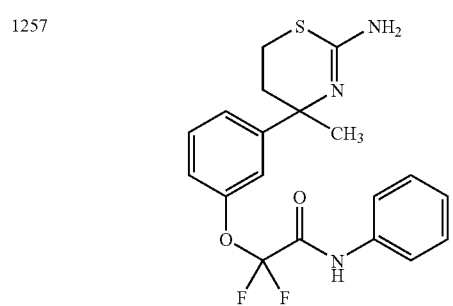
TABLE 134
1258 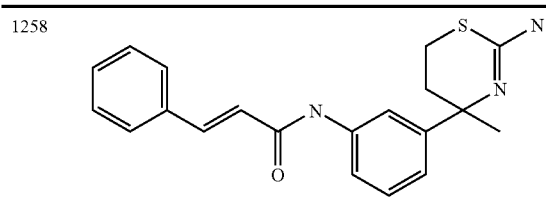
TABLE 134-continued
1259 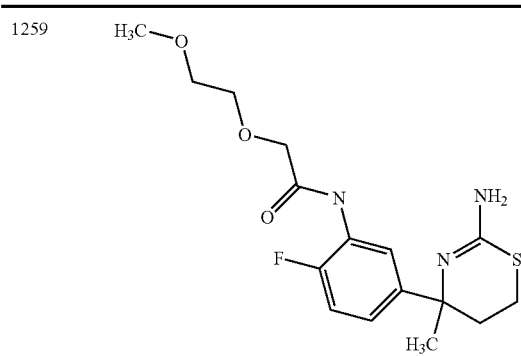
1260 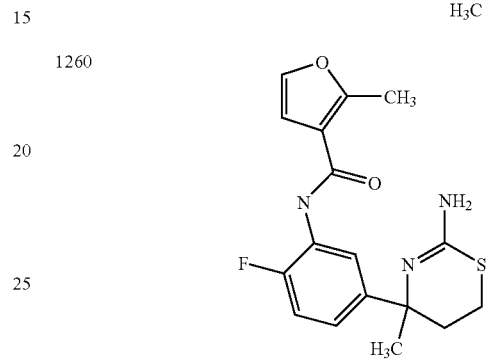
1261 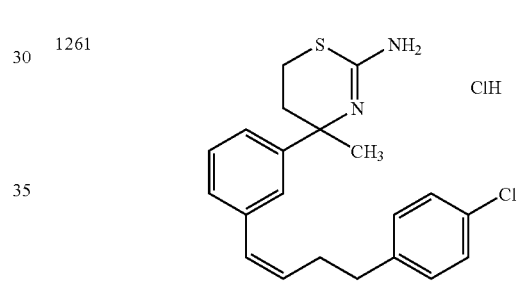
1262 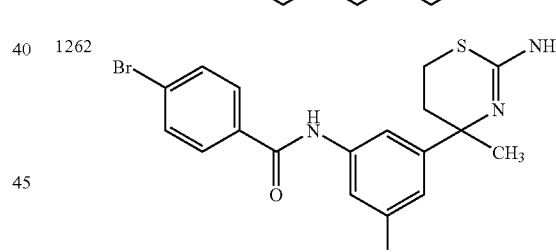
1263 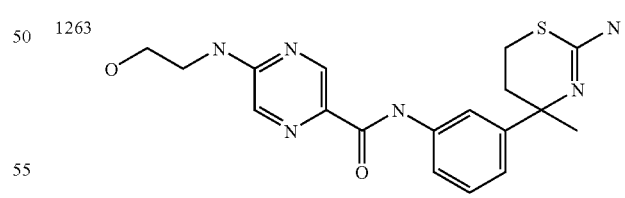
1264 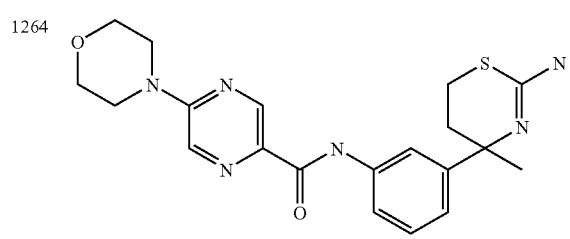

337
TABLE 134-continued
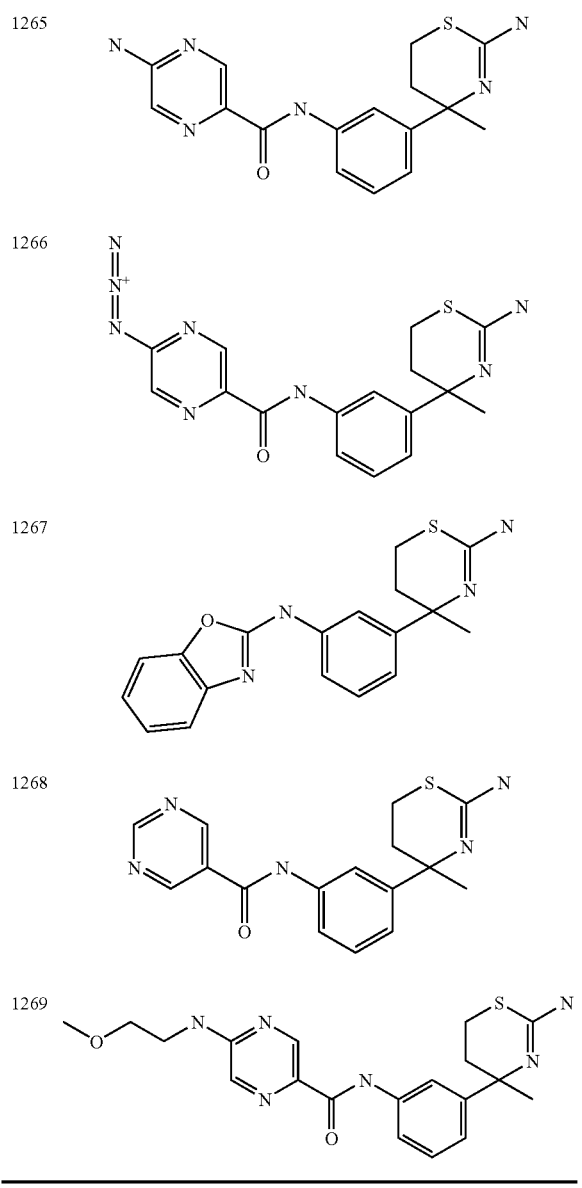
338
TABLE 135-continued
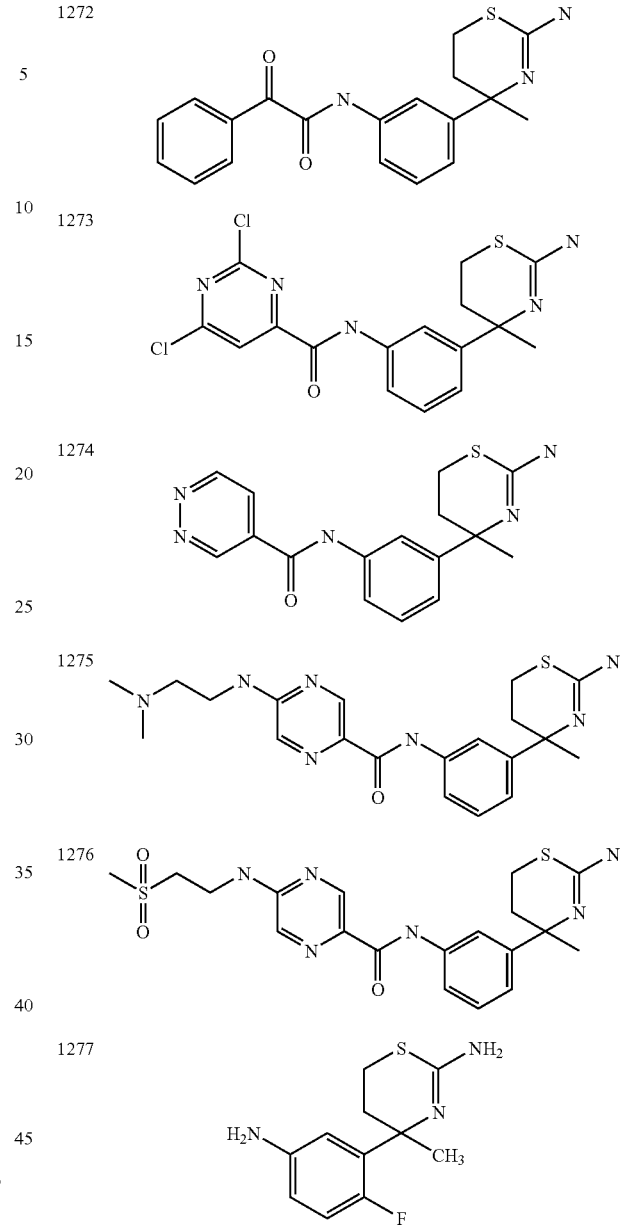
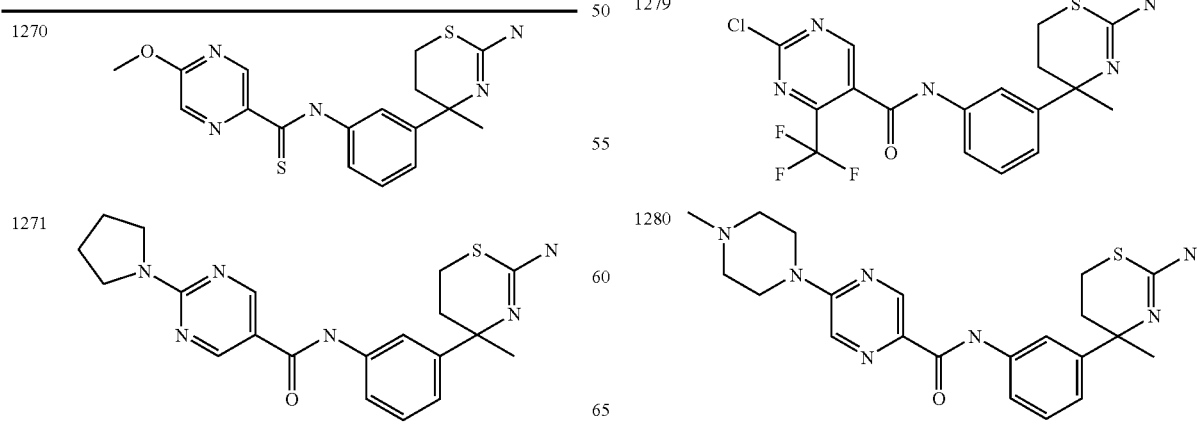

TABLE 135-continued

| No. | Structure |
|---|---|
| 1281 | (4-Cl-piperidin-1-yl)-pyrazine-2-carboxamide linked to phenyl bearing 2-amino-4-methyl-5,6-dihydro-4H-1,3-thiazine |
| 1282 | 2,5-dimethylfuran-3-carboxamide linked to 4-fluorophenyl bearing 2-amino-4-methyl-5,6-dihydro-4H-1,3-thiazine |

[Chemical formula 65]

in formula, ⤳N⤳ means ⤳NH⤳,

⤳N⤳ means ⤳NH₂, and ⤳O⤳ means ⤳OH.

TABLE 136

| Compound No. | Melting Point (° C.) | 1H-NMR (d) | MS (m/z) | UV (λmax: nm) |
|---|---|---|---|---|
| 1 | | | | 213.4 |
| | | | | 305.3 |
| 3 | 285 (dec.) | | | |
| 4 | amorphous | | | 219 |
| 5 | | | | 215, 262 |
| 6 | 147-148 | | | |
| 8 | 214-217 | | | |
| 9 | oil | | | 220 |
| 18 | 181-183 | | | |
| 23 | | | | 213.4 |
| | | | | 272.2 |
| | | | | 305.3 |
| 24 | 116-117 | | | |
| 26 | 182-184 | | | |
| 30 | | | | 267.4 |
| 33 | | | | 253.3 |
| | | | | 305.3 |
| 37 | amorphous | | | 219, 275 |
| 38 | 240-244 (dec.) | | | |
| 39 | | | | 285.2 |
| 42 | 187-188 | | | |
| 43 | | | | 218.1 |
| | | | | 275.7 |
| 48 | | | | 230 |
| | | | | 275 |
| 57 | 197-198 | | | |
| 58 | 234-240 | | | |
| 62 | 198-201 | | | |
| 69 | 194-195 | | | |
| 71 | | | | 216.9 |
| | | | | 268.6 |
| 73 | 266-269 | | | |
| 77 | | d in d20-DMSO: 1.67 (3H, s), 2.13-2.06 (1H, m), 2.63-2.55 (2H, m), 3.16-3.13 (4H, m), 3.65-3.63 (2H, m), 4.76-4.73 (2H, m), 7.15-7.08 (2H, m), 7.30 (1H, t, J = 8.0 Hz), 7.35 (1H, s), 7.42 (1H, t, J = 8.0 Hz), 7.60 (1H, d, J = 8.0 Hz), 7.69 (1H, d, J = 8.0 Hz), 7.73 (1H, brs), 7.86 (1H, d, J = 8.0 Hz), 10.52 (1H, s) | 422.543 | |
| 78 | | ¹H-NMR (CDCl₃) d: 1.76 (3H, s), 2.02 (1H, s), 2.58 (1H, d, J = 14.1 Hz), 2.78 (2H, d, J = 6.9 Hz), 3.80 (3H, d, J = 13.1 Hz), 4.54 (2H, s), 6.45 (1H, s), 6.55-6.57 (2H, m), 6.66 (1H, d, J = 8.7 Hz), 7.10 (1H, t, J = 7.0 Hz), 7.22 (2H, td, J = 7.7, 1.4 Hz), 7.34 (1H, d, J = 9.1 Hz), 7.56 (1H, d, J = 7.7 Hz). | 365 [M + 1] | |
| 80 | | | | 220.4 |
| | | | | 280.4 |

TABLE 137

| Compound No. | Melting Point (° C.) | 1H-NMR (d) | MS (m/z) | UV (λmax: nm) |
|---|---|---|---|---|
| 85 | 147-148 | 1.54 (3H, s), 1.75-1.86 (1H, m), 2.08-2.18 (1H, m), 2.33 (3H, s), 2.63-2.74 (1H, m), 2.81-2.90 (1H, m), 4.36 (2H, br), 7.13 (2H, d, J = 8.6 Hz), 7.20 (2H, d, J = 8.6 Hz) (solvent: CDCl3) | | |
| 86 | 141-142 | | | |
| 91 | | | 372 [M + 1] 296 | 201 206 216 |
| 96 | | | | 309 |
| 97 | | d in d13-DMSO: 1.64 (3H, s), 2.03-1.97 (1H, m), 2.63-2.57 (2H, m), 3.28-3.25 (1H, m), 7.22 (1H, q, J = 12.4, 9.0 Hz), 7.82-7.77 (2H, m), 8.60 (1H, s), 8.79 (1H, s), 10.37 (1H, s). | | |
| 99 | 221-224 | | | |
| 101 | 264-265 | | | |
| 104 | amorphous | | | 229, 280 |
| 113 | | 1.58 (s, 3H), 1.88 (ddd, J = 14.1, 10.9, 3.7 Hz, 1H), 2.24 (ddd, J = 14.1, 5.9, 3.5 Hz, 1H), 2.73 (ddd, J = 12.3, 10.9, 3.5 Hz, 1H), 2.88 (ddd, J = 12.3, 5.9, 3.7 Hz, 1H), 3.83 (d, J = 15.4 Hz, 1H), 3.87 (d, J = 15.4 Hz, 1H), 7.02-7.04 (m, 1H), 7.25-7.31 (m, 2H), 7.36 (d, J = 2.0 Hz, 1H), 7.45-7.50 (m, 2H), 8.52 (d, J = 5.2 Hz, 1H), 9.43 (s, 1H) (solvent: CDCl3) | | |
| 114 | | | | 214.5 306.5 |
| 115 | | d in d6-DMSO: 1.47 (3H, s), 1.80-1.74 (1H, m, 2.22-2.18 (1H, m), 2.60-2.55 (1H, m), 2.96-2.93 (1H, m), 6.14 (1H, s), 6.93 (1H, s), 7.09-7.04 (2H, m), 7.63-7.61 (1H, m), 7.68-7.66 (1H, m), 9.85 (1H, s), 11.63 (1H, brs) | | |
| 120 | amorphous | | | 213 |
| 121 | 166-167 | | | |
| 125 | >300 | | | |
| 126 | amorphous | | | 229, 271 |
| 127 | 280-285 | | | |
| 128 | 159-163 | | | |
| 129 | 219-222 | | | |
| 130 | 128-131 | 1.56 (3H, s), 1.83-1.93 (1H, m), 2.16 (1H, dq, J = 13.85, 3.41 Hz), 2.29 (3H, s), 2.72-2.77 (1H, m), 2.90-2.94 (1H, m), 4.13 (3H, s), 6.42 (1H, s), 7.10-7.14 (1H, m), 7.32 (1H, d, J = 7.91 Hz), 7.37-7.38 (1H, m), 7.60-7.63 (1H, m). (solvent: CDCl3) | 344 [M + 1] | |
| 132 | 147-150 | | | |
| 134 | | | | 228.5 |

TABLE 138

| Compound No. | Melting Point (° C.) | 1H-NMR (d) | MS (m/z) | UV (λmax: nm) |
|---|---|---|---|---|
| 139 | 287-290 | 1.77 (s, 3H), 2.10 (ddd, J = 14.0, 10.8, 3.6 Hz, 1H), 2.64-2.70 (4H, m), 2.76 (td, J = 12.8, 3.6 Hz, 1H), 2.90 (dt, J = 12.8, 3.6 Hz, 1H), 7.05 (ddd, J = 8.0, 2.0, 0.8 Hz, 1H), 7.41 (t, J = 8.0 Hz, 1H), 7.69-7.72 (m, 2H), 8.32 (dd, J = 8.0, 0.8 Hz, 1H), 8.40 (dd, J = 8.0, 2.0 Hz, 1H), 9.14 (dd, J = 2.0, 0.8 Hz, 1H) (solvent: CDCl3 + CD3OD) | | |
| 141 | | d in d17-DMSO: 1.41 (3H, s), 1.75-1.70 (1H, m), 2.03-1.99 (1H, m), 2.62-2.56 (1H, m), 2.94-2.89 (1H, m), 3.89 (3H, s), 6.88 (1H, d, J = 8.8 Hz), 7.05 (1H, d, J = 7.6 Hz), 7.24 (1H, t, J = 8.0 Hz), 7.66-7.63 (3H, m), 8.45-8.44 (1H, m), 9.90 (1H, s) | | |
| 148 | | | 362 [M + 1] 286 | 200 208 212 218 262 |
| 149 | 143-145 | | | |
| 157 | | d in d6-DMSO: 1.20 (6H, d, J = 6.6 Hz), 1.41 (3H, s), 1.65-1.77 (1H, m), 1.96-2.07 (1H, m), 2.55-2.63 (1H, m), 2.85-2.95 (1H, m), 4.04-4.16 (1H, m), 5.79 (2H, bs), 7.07 (1H, d, J = 8.1 Hz), 7.25 (1H, t, J = 8.1 Hz), 7.72-7.78 (3H, m), 7.93 (1H, s), 8.64 (1H, s), 9.96 (1H, s). | | |

TABLE 138-continued

| Compound No. | Melting Point (° C.) | 1H-NMR (d) | MS (m/z) | UV (λmax: nm) |
|---|---|---|---|---|
| 159 | amorphous | | | 285 |
| 161 | 247-251 | | | |
| 163 | amorphous | | | |
| 164 | 91-96 | 1.68 (s, 3H), 2.07-2.15 (m, 1H), 3.13-3.20 (m, 1H), 7.12 (d, J = 7.6 Hz, 1H), 7.46 (t, J = 7.6 Hz, 1H), 7.90-7.94 (m, 2H), 8.83 (br s, 1H), 8.96 (br s, 1H), 9.31 (br s, 1H), 10.36 (s, 1H), 10.86 (s, 1H) | | |
| 165 | 246-248 | | | |
| 166 | amorphous | | | 220, 275 |
| 176 | amorphous | | | 217, 278 |
| 178 | 224-225 | | | |
| 181 | | | | 261.5 |
| 189 | | | | 259 |
| 193 | 266-268 | | | |
| 196 | | | | 212 |
| 202 | 117-118 | 0.85 (3H, t, J = 7.3 Hz), 1.02-1.19 (1H, m), 1.34-1.54 (1H, m), 1.72-1.89 (3H, m), 2.04-2.15 (1H, m), 2.61-2.82 (2H, m), 3.80 (3H, s), 4.32 (2H, br), 6.85 (2H, d, J = 8.9 Hz), 7.18 (2H, d, J = 8.9 Hz) (solvent: CDCl3) | | |

TABLE 139

| Compound No. | Melting Point (° C.) | 1H-NMR (d) | MS (m/z) | UV (λmax: nm) |
|---|---|---|---|---|
| 204 | 205-208 | 1.64 (d, J = 1.2 Hz, 3H), 1.95 (ddd, J = 14.0, 10.8, 3.6 Hz, 1H), 2.45 (ddd, J = 14.0, 6.4, 3.6 Hz, 1H), 2.75 (ddd, J = 12.4, 10.8, 3.6 Hz, 1H), 2.99 (ddd, J = 12.4, 6.4, 3.6 Hz, 1H), 7.09 (dd, J = 11.6, 8.8 Hz, 1H), 7.47 (dd, J = 7.2, 2.8 Hz, 1H), 8.03 (ddd, J = 8.8, 4.4, 2.8 Hz, 1H), 8.89 (s, 2H), 9.75 (s, 1H) (solvent: CDCl3) | | |
| 213 | oil | | | 216, 272 |
| 214 | | | | 212.2 292.3 356.5 |
| 216 | | | | 242.7 |
| 220 | 191-193 | | 363 [M + 3] 361 [M + 1] | 287 285 |
| 224 | oil | 1.58 (3H, s), 1.87 (1H, ddd, J = 13.9, 10.5, 3.7), 2.13 (1H, ddd, J = 13.9, 6.3, 3.7), 2.25 (3H, s), 2.68 (1H, ddd, J = 12.1, 10.5, 6.2), 2.89 (1H, ddd, J = 12.1, 6.3, 3.7), 5.23 (2H, s), 7.28-7.48 (4H, m), 7.60 (1H, s), 7.75 (1H, d, J = 8.0), 8.56 (1H, dd, J = 5.0, 1.4), 8.70 (1H, d, J = 1.4) (solvent: CDCl3) | | 222 |
| 227 | | | | 213 |
| 232 | | 1H-NMR (CDCl3) d: 1.59 (3H, s), 1.83-1.90 (1H, m), 2.35-2.47 (4H, m), 2.60-2.67 (1H, m), 2.87-2.92 (1H, m), 4.70 (2H, br s), 6.87-6.98 (2H, m), 7.16 (1H, d, J = 6.6 Hz), 7.27 (2H, d, J = 7.8 Hz), 7.61 (2H, d, J = 8.1 Hz). | 378 [M + 1] | |
| 233 | oil | | | 224, 272 |
| 235 | 196-200 | | | |
| 238 | | 1H-NMR (CDCl3) d: 1.68 (3H, s), 1.97-2.00 (1H, m), 2.53 (1H, dt, J = 14.4, 3.7 Hz), 2.63-2.79 (2H, m), 4.52 (2H, s), 6.56-6.66 (3H, m), 7.17 (1H, t, J = 8.0 Hz), 7.43-7.52 (3H, m), 7.81 (4H, dd, J = 11.6, 5.7 Hz). | 362 [M + 1] | |
| 241 | 187-190 | 1H-NMR (DMSO-d6) d: 1.49 (3H, s), 1.78-1.86 (1H, m), 2.13-2.21 (1H, m), 2.59-2.67 (1H, m), 2.96-3.02 (1H, m), 7.11 (1H, t, J = 10.7 Hz), 7.29 (1H, t, J = 7.8 Hz), 7.45 (1H, t, J = 7.5 Hz), 7.66 (1H, d, J = 8.8 Hz), 7.74-7.78 (1H, m), 7.80-7.83 (1H, m), 8.21 (1H, d, J = 8.6 Hz), 10.25 (1H, s). | | |
| 243 | 182-184 | 1.46 (s, 3H), 1.75-1.83 (m, 1H), 2.08-2.16 (m, 1H), 2.55-2.63 (m, 1H), 2.92-2.98 (m, 1H), 4.02 (s, 3H), 7.11 (d, J = 8.0 Hz, 1H), 7.31 (t, J = 8.0 Hz, 1H), 7.77 (d, J = 8.0 Hz, 1H), 7.82 (br s, 1H), 8.41 (d, J = 1.2 Hz, 1H), 8.90 (d, J = 1.2 Hz, 1H), 10.38 (s, 1H) (solvent: CDCl3) | | |

TABLE 140

| Compound No. | Melting Point (° C.) | 1H-NMR (d) | MS (m/z) | UV (λmax: nm) |
|---|---|---|---|---|
| 244 | 222-224 | | | |
| 251 | | | 351 [M + 1]<br>311<br>275 | 200<br>204<br>215<br>285 |
| 255 | 238-239 | | | |
| 256 | oil | | | 215, 257 |
| 259 | amorphous | 1.58 (3H, s), 2.01 (1H, ddd, J = 15.2, 12.2, 3.4),<br>2.48-2.56 (2H, m), 3.07 (1H, ddd, J = 13.3, 5.7, 3.5),<br>4.24 (2H, s), 6.53 (1H, d, J = 7.6), 6.59-6.61 (2H, m),<br>7.09-7.12 (1H, m), 7.11 (2H, d, J = 7.6), 7.24 (2H, d, J = 7.6),<br>8.82 (2H, br) (solvent: DMSO-d6) | | 229<br>298 |
| 263 | | | 363 [M + 1]<br>287 | 200<br>284 |
| 267 | 114-115 | | | |
| 268 | | | | 214.5<br>298.2 |
| 271 | oil | | | 229, 276 |
| 275 | | (CDCl3) 1.66 (3H, d, J = 1.2 Hz), 1.98 (1H, ddd, J = 14.0,<br>10.4, 3.7 Hz), 2.47 (1H, ddd, J = 14.0, 6.7, 3.5 Hz),<br>2.79 (1H, ddd, J = 12.0, 10.4, 3.5 Hz), 3.02 (1H, ddd,<br>J = 12.0, 6.7, 3.7 Hz), 4.45 (2H, br), 6.16 (2H, br),<br>7.04-7.11 (2H, m), 7.38 (1H, dd, J = 7.2, 2.9 Hz), 7.88 (1H, d,<br>J = 2.0 Hz), 7.96 (1H, ddd, J = 8.9, 4.2, 2.9 Hz),<br>9.88 (1H, s) | | |
| 277 | | | | 216<br>228<br>281 |
| 279 | | | | 214.5<br>292.3 |
| 281 | amorphous | 1.55 (3H, s), 1.83 (1H, ddd, J = 13.9, 10.6, 3.9),<br>2.10 (1H, ddd, J = 13.9, 6.5, 3.6), 2.67 (1H, ddd, J = 12.2,<br>10.6, 3.6), 2.87 (1H, ddd, J = 12.2, 6.5, 3.9),<br>4.49 (2H, d, J = 5.6), 4.85 (1H, br), 6.38 (1H, dt, J = 8.5,<br>0.9), 6.59 (1H, ddd, J = 7.2, 5.2, 0.9),<br>7.21-7.24 (2H, m), 7.28-7.32 (2H, m), 7.40 (1H, ddd, J = 8.5,<br>7.2, 1.8), 8.11 (1H, ddd, J = 5.2, 1.8, 0.8)<br>(solvent: CDCl3) | 233 | 301 |
| 282 | 146-147 | | | |
| 284 | 181.5 | | | |
| 293 | | 1.57 (s, 3H), 1.78-1.89 (m, 1H), 2.10-2.19 (m, 1H),<br>2.69 (ddd, J = 11.9, 10.8, 3.5 Hz, 1H), 2.83-2.91 (m,<br>1H), 7.15-7.35 (m, 5H)<br>(solvent: CDCl3) | | |
| 299 | | | | 293.5 |

TABLE 141

| Compound No. | Melting Point (° C.) | 1H-NMR (d) | MS (m/z) | UV (λmax: nm) |
|---|---|---|---|---|
| 301 | | (CDCl3) 1.53 (3H, s), 1.80 (1H, ddd, J = 14.0, 10.4, 3.6 Hz),<br>2.12 (1H, ddd, J = 14.0, 6.0, 3.6 Hz), 2.75 (1H,<br>ddd, J = 12.0, 10.4, 3.6 Hz), 2.85 (1H, ddd, J = 12.0,<br>6.0, 3.6 Hz), 3.64 (2H, s), 4.32 (2H, br), 6.55 (1H, ddd,<br>J = 8.0, 2.0, 0.8 Hz), 6.66 (1H, t, J = 2.0 Hz), 6.70 (1H,<br>ddd, J = 8.0, 2.0, 0.8 Hz), 7.11 (1H, t, J = 8.0 Hz) | | |
| 302 | 122-126 | 1.41 (s, 3H), 1.67-1.76 (m, 1H), 1.98-2.06 (m, 1H),<br>2.55-2.63 (m, 1H), 2.86-2.94 (m, 1H), 3.19 (s, 6H),<br>5.75 (s, 2H), 7.08 (d, J = 8.0 Hz, 1H), 7.26 (t, J = 8.0 Hz,<br>1H), 7.73 (d, J = 8.0 Hz, 1H), 7.76 (br s, 1H),<br>8.16 (s, 1H), 8.73 (s, 1H), 10.00 (s, 1H)(solvent:<br>CDCl3) | | |
| 306 | | | | 231, 258,<br>289 |
| 307 | | 1.83 (ddd, J = 13.9, 10.3, 3.6 Hz, 1H), 2.13 (ddd, J = 13.6,<br>6.2, 3.5 Hz, 1H), 2.53 (s, 3H), 2.66-2.75 (m,<br>1H), 2.90 (ddd, J = 12.2, 6.3, 3.8 Hz, 1H), 7.09 (d, J = 7.8 Hz,<br>1H), 7.32 (t, J = 8.0 Hz, 1H), 7.37 (s, 1H),<br>7.63 (d, J = 7.8 Hz, 1H), 8.79 (s, 1H) (solvent:<br>CDCl3) | | |
| 308 | 167-168 | | | |
| 309 | 241-244 | | | |
| 319 | | | | 308.9 |

TABLE 141-continued

| Compound No. | Melting Point (° C.) | 1H-NMR (d) | MS (m/z) | UV (λmax: nm) |
|---|---|---|---|---|
| 329 | 238-239 | | | |
| 330 | | | | 213.4 |
| | | | | 263.9 |
| 332 | | | | 212.2 |
| 333 | 154-158 | | | |
| 339 | 217-218 | | | |
| 341 | amorphous | | | 216 |
| | | | | 249 |
| 342 | 184-187 | | | |
| 344 | | (DMSO) 1.49 (3H, s), 1.73-1.85 (1H, m), 2.15-2.28 (1H, m), 2.54-2.66 (1H, m), 2.92-3.04 (1H, m), 5.86 (2H, s), 7.03-7.25 (3H, m), 7.40-7.48 (2H, m), 7.64-7.78 (3H, m), 10.31 (1H, s), 11.74 (1H, s) | | |
| 353 | | | | 279.3 |
| | | | | 364.5 |
| 354 | 102-103 | | | |
| 356 | amorphous | 1.73 (s, 3H), 2.09-2.17 (m, 1H), 2.40 (s, 3H), 2.65-2.73 (m, 2H), 3.15-3.23 (m, 1H), 3.81 (s, 3H), 7.07 (d, J = 7.2 Hz, 2H), 7.29 (br s, 1H), 7.36 (d, J = 8.0 Hz, 2H), 7.61 (d, J = 8.0 Hz, 2H), 7.78 (br s, 1H), 7.90 (d, J = 7.2 Hz, 2H), 8.00 (br s, 1H), 10.32 (s, 1H)(solvent: DMSO-d6) | | 267 |
| 357 | amorphous | | | 224, 298 |

TABLE 142

| Compound No. | Melting Point (° C.) | 1H-NMR (d) | MS (m/z) | UV (λmax: nm) |
|---|---|---|---|---|
| 358 | | 1.57 (3H, s), 1.80-1.91 (1H, m), 2.15-2.18 (1H, m), 2.70-2.94 (2H, m), 3.94 (3H, s), 4.67 (2H, s), 6.75 (1H, s), 7.05-7.08 (1H, m), 7.31 (1H, t, J = 7.91 Hz), 7.53 (1H, t, J = 1.98 Hz), 7.64-7.67 (1H, m), 8.64 (1H, s). (solvent: CDCl3) | 360 [M + 1] | |
| 359 | 212-214 | 1.46 (s, 3H), 1.73-1.83 (m, 1H), 2.13-2.20 (m, 1H), 2.54-2.61 (m, 1H), 2.62 (s, 3H), 2.93-3.00 (m, 1H), 5.84 (br s, 2H), 7.12 (dd, J = 12.0, 8.8 Hz, 1H), 7.73-7.78 (m, 1H), 7.81 (dd, J = 7.2, 2.4 Hz, 1H), 8.68 (s, 1H), 9.13 (s, 1H), 10.59 (s, 1H)(solvent: CDCl3) | | |
| 360 | amorphous | | | 222 |
| 361 | | | | 280.4 |
| 364 | oil | | 344 [M + 1] | 227, 271 |
| 367 | | (CDCl3) 1.78 (3H, s), 2.07 (1H, ddd, J = 14.0, 12.4, 3.6 Hz), 2.61 (1H, br d, J = 14.0 Hz), 2.84 (1H, td, J = 12.4, 3.2 Hz), 2.94 (1H, td, J = 12.4, 3.6 Hz), 4.08 (3H, s), 7.07 (1H, ddd, J = 8.0, 2.0, 0.8 Hz), 7.40 (1H, t, J = 8.0 Hz), 7.63 (1H, ddd, J = 8.0, 2.0, 0.8 Hz), 7.74 (1H, t, J = 2.0 Hz), 8.18 (1H, d, J = 1.2 Hz), 9.02 (1H, d, J = 1.2 Hz), 9.56 (1H, s) | | |
| 375 | | | | 217 |
| 380 | 181-182 | 0.86 (t, J = 7.2 Hz, 3H), 1.82-1.98 (m, 3H), 2.24 (br, 1H), 2.74 (td, J = 12.0, 3.6 Hz, 1H), 2.84 (dt, J = 12.0, 4.0 Hz, 1H), 7.08 (ddd, J = 8.0, 2.0, 0.8 Hz, 1H), 7.37 (t, J = 8.0 Hz, 1H), 7.58 (t, J = 2.0 Hz, 2H), 7.76 (ddd, J = 8.0, 2.0, 0.8 Hz, 1H), 7.88 (dd, J = 8.4, 2.4 Hz, 1H), 8.25 (dd, J = 8.4, 0.8 Hz, 1H), 8.57 (dd, J = 2.4, 0.8 Hz, 1H), 9.84 (s, 1H) (solvent: CDCl3) | | |
| 383 | oil | | | 225, 269, 288 |
| 389 | amorphous | | | 292 |
| 393 | | | | 213.4 |
| | | | | 316.0 |
| 395 | amorphous | | | 217, 269 |
| 396 | 211-213 | 1.64 (s, 3H), 1.96 (ddd, J = 14.0, 10.4, 4.0 Hz, 1H), 2.44 (ddd, J = 14.0, 6.8, 3.6 Hz, 1H), 2.75 (ddd, J = 12.4, 10.4, 3.6 Hz, 1H),, 2.99 (ddd, J = 12.4, 6.8, 4.0 Hz, 1H), 4.50 (2H, br), 7.08 (dd, J = 11.6, 8.8 Hz, 1H), 7.45 (dd, J = 6.8, 2.8 Hz, 1H), 8.01 (ddd, J = 8.8, 4.4, 2.8 Hz, 1H), 8.16 (ddd, J = 8.0, 2.0, 0.8 Hz, 1H), 8.43 (d, J = 8.0 Hz, 1H), 8.89 (dd, J = 2.0, 0.8 Hz, 1H), 9.91 (s, 1H) (solvent: CDCl3) | | |
| 401 | 106-107 | | | |

TABLE 143

| Compound No. | Melting Point (° C.) | 1H-NMR (d) | MS (m/z) | UV (λmax: nm) |
|---|---|---|---|---|
| 405 | 192-194 | 1.41 (s, 3H), 1.68-1.77 (m, 1H), 1.96-2.05 (m, 1H), 2.55-2.63 (m, 1H), 2.88-2.95 (m, 1H), 4.15 (s, 3H), 5.74 (s, 2H), 7.13 (d, J = 8.0 Hz, 1H), 7.29 (t, J = 8.0 Hz, 1H), 7.44 (d, J = 8.8 Hz, 1H), 7.75 (d, J = 8.0 Hz, 1H), 7.86 (br s, 1H), 8.20 (d, J = 8.8 Hz, 1H), 10.73 (s, 1H) (solvent: CDCl3) | | |
| 406 | | | | 276.9 |
| 408 | 221-224 | 1.74 (3H, s), 2.28 (2H, m), 2.67 (2H, m), 2.91 (3H, s), 3.82 (3H, s), 6.90 (2H, d, J = 9.0), 7.19 (2H, d, J = 9.0) (solvent: CDCl3) | | |
| 409 | oil | | | 215 |
| 410 | 178-182 | 1.37 (d, J = 6.0 Hz, 6H), 1.42 (s, 3H), 1.70-1.78 (m, 1H), 2.00-2.08 (m, 1H), 2.53-2.61 (m, 1H), 2.88-2.95 (m, 1H), 5.36 (quintet, J = 6.0 Hz, 1H), 7.11 (d, J = 8.0 Hz, 1H), 7.29 (t, J = 8.0 Hz, 1H), 7.75 (d, J = 8.0 Hz, 1H), 7.80 (br s, 1H), 8.32 (d, J = 1.2 Hz, 1H), 8.87 (d, J = 1.2 Hz, 1H), 10.32 (s, 1H) (solvent: CDCl3) | | |
| 411 | | | | 218, 264 |
| 413 | 251-254 | | | |
| 415 | amorphous | | | 226, 290 |
| 417 | 137-139 | | | |
| 422 | | (CDCl3) 1.45 (3H, s), 1.70-1.84 (1H, m), 1.96-2.04 (1H, m), 2.88-2.96 (1H, m), 3.04-3.14 (1H, m), 6.86 (1H, d, J = 15.9 Hz), 6.42 (1H, d, J = 15.9 Hz), 7.22-7.41 (5H, m) | | |
| 426 | | | | 211.0 312.4 |
| 427 | | | | 216 |
| 429 | oil | | | 211 259 |
| 430 | | (DMSO) 1.07 (3H, s), 1.53-1.66 (4H, m), 2.50-2.70 (2H, m), 2.92-3.10 (2H, m), 5.48 (1H, s), 7.11-7.21 (3H, m), 7.23-7.29 (2H, m) | | |
| 432 | oil | | | 216, 272 |
| 436 | 254-256 | | | |
| 441 | 161-165 | | | |
| 443 | | $^1$H-NMR (CDCl$_3$) d: 1.55 (4H, s), 1.74-1.80 (1H, m), 2.13-2.17 (1H, m), 2.68-2.73 (2H, m), 4.33 (1H, br s), 4.48 (2H, d, J = 4.0 Hz), 4.76 (2H, t, J = 20.1 Hz), 6.52 (1H, dd, J = 7.9, 1.8 Hz), 6.63-6.65 (2H, m), 7.13 (1H, t, J = 7.8 Hz), 7.45-7.51 (2H, m), 7.79-7.82 (4H, m). | 362 [M + 1] | |

TABLE 144

| Compound No. | Melting Point (° C.) | 1H-NMR (d) | MS (m/z) | UV (λmax: nm) |
|---|---|---|---|---|
| 444 | 214-215 | 1.41 (s, 3H), 1.66-1.76 (m, 1H), 1.97-2.05 (m, 1H), 2.53-2.62 (m, 1H), 2.62 (s, 3H), 2.86-2.93 (m, 1H), 5.79 (br s, 2H), 7.12 (d, J = 8.0 Hz, 1H), 7.28 (t, J = 8.0 Hz, 1H), 7.74 (d, J = 8.0 Hz, 1H), 7.81 (br s, 1H), 8.68 (s, 1H), 9.14 (s, 1H), 10.52 (s, 1H) (solvent: CDCl3) | | |
| 445 | 92-93 | | | |
| 446 | oil | 1.57 (3H, s), 1.86 (1H, ddd, J = 13.9, 10.4, 3.7), 2.13 (1H, ddd, J = 13.9, 6.5, 3.6), 2.25 (3H, s), 2.35 (3H, s), 2.70 (1H, ddd, J = 12.2, 10.4, 3.6), 2.89 (1H, ddd, J = 12.2, 6.5, 3.7), 4.35 (2H, br), 5.19 (2H, s), 7.17 (2H, d, J = 8.0), 7.31-7.34 (4H, m), 7.50 (1H, ddd, J = 5.8, 3.0, 1.8), 7.55-7.60 (1H, m) (solvent: CDCl3) | 219 252 | |
| 448 | | d in d6-DMSO: 1.41 (3H, s), 1.67-1.75 (1H, m), 1.98-2.05 (1H, m), 2.52-2.61 (1H, m), 2.86-2.94 (1H, m), 5.79 (2H, bs), 7.14 (1H, d, J = 7.8 Hz), 7.30 (1H, t, J = 7.8 Hz), 7.73 (1H, bd, J = 7.8 Hz), 7.81 (1H, t, J = 1.8 Hz), 8.94 (1H, m), 9.11 (1H, m), 10.63 (1H, bs). | | |
| 452 | 132-134 | | | |
| 456 | 147-149 | | | |
| 457 | 153-155 | | | |
| 465 | 194.6 | | | |
| 466 | | | | 211 |

TABLE 144-continued

| Compound No. | Melting Point (° C.) | 1H-NMR (d) | MS (m/z) | UV (λmax: nm) |
|---|---|---|---|---|
| 470 | 281 (dec.) | | | |
| 482 | | 1.60 (s, 3H), 1.91 (ddd, J = 14.0, 10.8, 4.0 Hz, 1H), 2.23 (ddd, J = 14.0, 6.4, 3.6 Hz, 1H), 2.77 (ddd, J = 12.0, 10.8, 3.6 Hz, 1H), 2.93 (ddd, J = 12.0, 6.4, 4.0 Hz, 1H), 7.16 (ddd, J = 8.0, 2.0, 0.8 Hz, 1H), 7.37 (t, J = 8.0 Hz, 1H), 7.61 (t, J = 2.0 Hz, 1H), 7.75 (ddd, J = 8.0, 2.0, 0.8 Hz, 1H), 8.14 (d, J = 1.6 Hz, 1H), 8.80 (d, J = 1.6 Hz, 1H), 9.79 (s, 1H) (solvent: CDCl3) | | |
| 483 | 224-227 | | | 211, 289 |
| 490 | | 1.64 (3H, s) 2.03-2.12 (1H, m) 2.49-2.62 (m) 3.12-3.16 (1H m) 7.22 (1H, dd, J = 4.2 Hz) 7.27 (1H, bs) 7.75 (1H bs) 7.87 (1H, dd, J = 4.2 Hz) 8.04 (1H, s) 8.12 (1H, dd, J = 4.2 Hz) 10.64 (1H, s) 10.72 (1H, s)(solvent: DMSO-d6) | | |
| 491 | | 1.58 (s, 3H), 1.85-1.96 (m, 1H), 2.15-2.24 (m, 1H), 2.50 (s, 3H), 2.67 (s, 3H), 2.71-2.81 (m, 1H), 2.90-2.98 (m, 1H), 7.13 (d, J = 6.2 Hz, 1H), 7.35 (t, J = 8.0 Hz, 1H), 7.40 (s, 1H), 7.55 (d, J = 7.6 Hz, 1H) (solvent: CDCl3) | | |
| 493 | | | | 216 |

TABLE 145

| Compound No. | Melting Point (° C.) | 1H-NMR (d) | MS (m/z) | UV (λmax: nm) |
|---|---|---|---|---|
| 494 | | d in d6-DMSO: 1.37 (3H, s), 1.62-1.70 (1H, m), 2.0-2.12 (1H, m), 2.40-2.50 (1H, m), 2.79-2.83 (1H, m), 3.82 (3H, s), 4.52 (2H, d, J = 5.4 Hz), 6.19 (1H, m), 6.54 (1H, d, J = 7.8 Hz), 6.62 (1H, d, J = 8.1 Hz), 6.75 (1H, s), 7.01 (1H, t, J = 8.1 Hz), 7.14-7.25 (2H, m), 7.51 (1H, d, J = 8.1 Hz), 7.60 (1H, d, J = 7.5 Hz). | 366 [M + 1] | |
| 496 | 152-154 | | | |
| 497 | | d in d6-DMSO: 1.48 (3H, s), 1.83-1.77 (1H, m), 2.61-2.56 (1H, m), 2.99-2.95 (1H, m), 3.86 (3H, s), 6.07 (1H, s), 6.95 (1H, s), 7.03-7.02 (1H, m), 7.09-7.06 (1H, m), 7.58-7.57 (1H, m), 7.64-7.62 (1H, m), 9.83 (1H, s) | | |
| 498 | 122-125 | | | |
| 500 | 181-184 | | | |
| 501 | 155-156 | | | |
| 502 | 137-138 | | | |
| 504 | 209-219 | | | |
| 511 | 211-214 | 1.58 (s, 3H), 1.90 (ddd, J = 14.0, 10.0, 3.6 Hz, 1H), 2.15 (ddd, J = 14.0, 6.8, 3.6 Hz, 1H), 2.77 (ddd, J = 12.4, 10.0, 3.6 Hz, 1H), 2.94 (ddd, J = 12.4, 6.8, 3.6 Hz, 1H), 4.34 (2H, br), 7.17 (ddd, J = 8.0, 2.0, 0.8 Hz, 1H), 7.38 (t, J = 8.0 Hz, 1H), 7.50 (d, J = 2.0 Hz, 1H), 7.56 (td, J = 2.0 Hz, 1H), 7.70 (ddd, J = 8.0, 2.0, 0.8 Hz, 1H), 8.08 (d, J = 1.6 Hz, 1H), 9.70 (s, 1H) (solvent: CDCl3) | | |
| 515 | 204-206 | 1.61 (s, 3H), 1.90 (ddd, J = 14.0, 10.8, 3.6 Hz, 1H), 2.22 (ddd, J = 14.0, 6.0, 3.6 Hz, 1H), 2.77 (ddd, J = 12.4, 10.8, 3.6 Hz, 1H), 2.93 (ddd, J = 12.4, 6.0, 3.6 Hz, 1H), 7.15 (ddd, J = 8.0, 2.0, 0.8 Hz, 1H), 7.39 (t, J = 8.0 Hz, 1H), 7.65 (t, J = 2.0 Hz, 1H), 7.80 (ddd, J = 8.0, 2.0, 0.8 Hz, 1H), 8.89 (s, 2H), 9.77 (s, 1H) (solvent: CDCl3) | | |
| 516 | | | | 292.3 |
| 525 | 105-106 | | | |
| 528 | 173-174 | 1.60 (s, 3H), 1.89 (ddd, J = 14.0, 10.8, 3.6 Hz, 1H), 2.22 (ddd, J = 14.0, 6.4, 3.2 Hz, 1H), 2.44 (s, 3H), 2.77 (ddd, J = 12.4, 10.8, 3.2 Hz, 1H), 2.91 (ddd, J = 12.4, 6.4, 3.6 Hz, 1H), 4.50 (br, 2H), 7.11 (ddd, J = 8.0, 2.0, 0.8 Hz, 1H), 7.35 (t, J = 8.0 Hz, 1H), 7.67-7.71 (m, 2H), 7.74 (ddd, J = 8.0, 2.0, 0.8 Hz, 1H), 8.18 (d, J = 8.4 Hz, 1H), 8.44 (d, J = 1.6 Hz, 1H), 9.98 (s, 1H) (solvent: CDCl3) | | |
| 532 | | | | 305.3 |
| 533 | 180-181 | | | |
| 534 | 201-204 | | | |
| 549 | 100-101 | | | |
| 551 | 139-141 | | | |
| 554 | | | | 216 |

TABLE 146

| Compound No. | Melting Point (° C.) | 1H-NMR (d) | MS (m/z) | UV (λmax: nm) |
|---|---|---|---|---|
| 556 | | (CDCl3) 1.67 (3H, d, J = 1.2 Hz), 1.98 (1H, ddd, J = 14.0, 10.4, 3.7 Hz), 2.47 (1H, ddd, J = 14.0, 6.7, 3.5 Hz), 2.79 (1H, ddd, J = 12.0, 10.4, 3.5 Hz), 3.02 (1H, ddd, J = 12.0, 6.7, 3.7 Hz), 4.11 (3H, s), 4.45 (2H, br), 7.10 (1H, dd, J = 11.7, 8.8 Hz), 7.41 (1H, dd, J = 6.9, 2.8 Hz), 8.04 (1H, ddd, J = 8.8, 4.0, 2.8 Hz), 8.20 (1H, d, J = 1.4 Hz), 9.06 (1H, d, J = 1.4 Hz), 9.51 (1H, s) | | |
| 558 | | | 358 [M + 1] 282 | 200 |
| 559 | | | | 224 |
| 560 | | d in d10-DMSO: 1.72 (3H, s), 2.12-2.05 (1H, m), 2.71-2.61 (2H, m), 3.22-3.19 (1H, m), 6.52 (1H, s), 7.26 (1H, q, J = 11.6, 9.2 Hz), 7.55 (1H, s), 7.66-7.62 (2H, m), 7.79-7.77 (1H, m), 7.90-7.88 (1H, m), 8.07 (1H, s), 10.42 (1H, s), 11.55 (1H, s) | | |
| 561 | 235-240 | | | |
| 567 | oil | | | 212 |
| 570 | 186-187 | | | |
| 573 | 112-114 | | | |
| 577 | | d in d19-DMSO: 2.14-2.07 (1H, m), 2.88-2.70 (3H, m), 3.07, 3.26 (2H, abq, J = 12.0 Hz), 3.73 (3H, s), 5.40 (2H, s), 6.51 (1H, s), 6.85 (1H, d, J = 12.0 Hz), 7.34 (1H, d, J = 8.0 Hz) | | |
| 584 | 152-153 | | | |
| 586 | | d in d7-DMSO: 1.71 (3H, s), 2.10-2.04 (1H, m), 2.69-2.59 (2H, m), 3.20-3.17 (1H, m), 4.00 (3H, s), 7.13 (1H, d, J = 7.4 Hz), 7.33-7.23 (3H, m), 7.55 (1H, d, J = 8.4 Hz), 7.72-7.68 (1H, m), 7.92-7.90 (1H, m), 10.60 (1H, s) | | |
| 588 | 155-156 | | | |
| 593 | oil | | | 226 |
| 595 | oil | 1.56 (3H, s), 1.86 (1H, ddd, J = 13.9, 10.1, 3.7), 2.11 (1H, ddd, J = 13.9, 6.6, 3.6), 2.32 (3H, s), 2.70 (1H, ddd, J = 12.3, 10.1, 3.6), 2.90 (1H, ddd, J = 12.3, 6.6, 3.7), 5.25 (2H, s), 7.29-7.35 (4H, m), 7.47 (1H, dt, J = 6.8, 2.0), 7.56-7.58 (1H, m), 8.59 (2H, d, J = 6.0) (solvent: CDCl3) | | 220 |
| 596 | | | | 215 |
| 597 | 192-194 | | | |
| 600 | 178-180 | | | |
| 601 | 181-192 | 1.59 (3H, s), 1.85-1.95 (1H, m), 2.15-2.22 (1H, m), 2.72-2.78 (1H, m), 2.88-2.96 (1H, m), 4.31 (3H, s), 7.13 (1H, d, J = 7.25 Hz), 7.33 (1H, t, J = 7.91 Hz), 7.59 (1H, s), 7.68 (1H, d, J = 7.91 Hz), 7.75 (1H, s). (solvent: CDCl3) | 375 [M + 1] | |
| 602 | 272-285 (dec.) | | | |

TABLE 147

| Compound No. | Melting Point (° C.) | 1H-NMR (d) | MS (m/z) | UV (λmax: nm) |
|---|---|---|---|---|
| 605 | 230-233 | 1.63 (s, 3H), 1.94 (ddd, J = 14.0, 10.4, 3.6 Hz, 1H), 2.44 (ddd, J = 14.0, 6.4, 3.6 Hz, 1H), 2.75 (ddd, J = 12.4, 10.4, 3.6 Hz, 1H),, 2.98 (ddd, J = 12.4, 6.4, 3.6 Hz, 1H), 4.50 (2H, br), 7.06 (dd, J = 11.6, 8.8 Hz, 1H), 7.40 (dd, J = 7.2, 2.8 Hz, 1H), 7.59 (ddd, J = 8.8, 8.0, 2.8 Hz, 1H), 7.99 (ddd, J = 8.8, 4.4, 2.8 Hz, 1H), 8.33 (dd, J = 8.8, 4.4 Hz, 1H), 8.45 (d, J = 2.8 Hz, 1H), 9.78 (s, 1H) (solvent: CDCl3) | | |
| 608 | | | | 213.4 304.1 |
| 611 | 200-202 | | | |
| 613 | | | | 238 |
| 618 | | 1.74 (s, 3H), 1.97-2.07 (m, 1H), 2.45-2.55 (m, 1H), 2.77-2.85 (m, 1H), 2.84 (s, 3H), 2.90-2.96 (m, 1H), 7.11 (d, J = 8.0 Hz, 1H), 7.42 (t, J = 8.0 Hz, 1H), 7.57 (d, J = 8.8 Hz, 1H), 7.70 (d, J = 8.8 Hz, 1H), 7.74 (br s, 1H), 8.29 (d, J = 8.8 Hz, 1H), 10.12 (s, 1H) (solvent: CDCl3) | | |
| 620 | | | | 212, 253 |
| 625 | 107-109 | | | |

TABLE 147-continued

| Compound No. | Melting Point (° C.) | 1H-NMR (d) | MS (m/z) | UV (λmax: nm) |
|---|---|---|---|---|
| 629 | | d in d14-DMSO: 1.66 (3H, s), 2.11-2.05 (1H, m), 2.37 (3H, s), 2.63-2.53 (2H, m), 3.14-3.11 (1H, m), 7.08-7.04 (2H, t, J = 7.0 Hz), 7.43-7.35 (4H, m), 7.83-7.80 (2H, m), 10.39 (1H, s), 11.69 (1H, s) | | |
| 630 | | 1.28 (3H, t, J = 7.7 Hz), 1.96 (1H, ddd, J = 3.8, 9.9, 13.7 Hz), 2.19 (1H, ddd, J = 3.5, 7.0, 13.7 Hz), 2.74 (1H, ddd, J = 3.6, 9.9, 12.2 Hz), 2.93 (1H, ddd, J = 3.8, 7.0, 12.1 Hz), 4.05-4.49 (4H, m), 7.40-7.50 (3H, m), 7.77-7.86 (1H, m) (solvent: CDCl3) | 301 [M + 1] | |
| 634 | | (CDCl3) 1.67 (3H, d, J = 1.2 Hz), 1.98 (1H, ddd, J = 14.0, 10.4, 3.7 Hz), 2.47 (1H, ddd, J = 14.0, 6.7, 3.5 Hz), 2.79 (1H, ddd, J = 12.0, 10.4, 3.5 Hz), 3.02 (1H, ddd, J = 12.0, 6.7, 3.7 Hz), 4.11 (3H, s), 4.45 (2H, br), 7.10 (1H, dd, J = 11.7, 8.8 Hz), 7.41 (1H, dd, J = 6.9, 2.8 Hz), 8.04 (1H, ddd, J = 8.8, 4.0, 2.8 Hz), 8.20 (1H, d, J = 1.4 Hz), 9.06 (1H, d, J = 1.4 Hz), 9.51 (1H, s) | | |
| 636 | 118-119 | | | |
| 637 | | | | 229, 275 |
| 643 | 155-157 | 1.60 (s, 3H), 1.90 (ddd, J = 14.0, 10.4, 3.6 Hz, 1H), 2.20 (ddd, J = 14.0, 6.8, 3.6 Hz, 1H), 2.77 (ddd, J = 12.0, 10.4, 3.6 Hz, 1H),, 2.93 (ddd, J = 12.0, 6.8, 3.6 Hz, 1H), 4.59 (brs, 1H), 7.16 (ddd, J = 8.0, 2.0, 0.8 Hz, 1H), 7.37 (t, J = 8.0 Hz, 1H), 7.67 (t, J = 2.0 Hz, 1H), 7.71 (ddd, J = 8.0, 2.0, 0.8 Hz, 1H), 7.87 (dd, J = 10.0, 1.2 Hz, 1H), 8.73 (d, J = 1.2 Hz, 1H), 9.74 (s, 1H) (solvent: CDCl3) | | |
| 644 | 201-203 | | | |

TABLE 148

| Compound No. | Melting Point (° C.) | 1H-NMR (d) | MS (m/z) | UV (λmax: nm) |
|---|---|---|---|---|
| 645 | oil | 1.58 (3H, s), 1.87 (1H, ddd, J = 14.0, 10.4, 3.6), 2.16 (1H, ddd, J = 14.0, 6.3, 3.5), 2.34 (3H, s), 2.70 (1H, ddd, J = 12.3, 10.4, 3.5), 2.90 (1H, ddd, J = 12.3, 6.3, 3.6), 5.38 (2H, s), 7.18-7.33 (3H, m), 7.43 (1H, d, J = 8.0), 7.49-7.60 (2H, m), 7.69 (1H, dt, J = 7.7, 1.9), 8.59 (1H, ddd, J = 4.9, 1.9, 1.1) (solvent: CDCl3) | | 222 |
| 649 | 161-162 | | | |
| 651 | 193-196 | 1.59 (s, 3H), 1.90 (ddd, J = 14.0, 10.4, 3.6 Hz, 1H), 2.18 (ddd, J = 14.0, 6.4, 3.6 Hz, 1H), 2.76 (ddd, J = 12.4, 10.4, 3.6 Hz, 1H),, 2.93 (ddd, J = 12.4, 6.4, 3.6 Hz, 1H), 4.42 (br, 2H), 7.17 (ddd, J = 8.0, 2.0, 0.8 Hz, 1H), 7.38 (t, J = 8.0 Hz, 1H), 7.64 (t, J = 2.0 Hz, 1H), 7.77 (ddd, J = 8.0, 2.0, 0.8 Hz, 1H), 8.20 (dd, J = 8.0, 2.0 Hz, 1H), 8.44 (dd, J = 8.0, 0.8 Hz, 1H), 8.91 (dd, J = 2.0, 0.8 Hz, 1H), 9.87 (s, 1H) (solvent: CDCl3) | | |
| 652 | | d in d21-DMSO: 1.67 (3H, s), 2.14-2.07 (1H, m), 2.62-2.57 (2H, m), 3.17-3.14 (1H, m), 5.74 (1H, s), 7.14 (1H, d, J = 8.0 Hz), 7.44 (1H, t, J = 8.0 Hz), 7.85-7.81 (2H, m), 8.01 (1H, d, J = 12.0 Hz), 8.16 (1H, d, J = 8.0 Hz), 8.77 (1H, s), 10.95 (1H, s) | | |
| 653 | 193-194 | | | |
| 654 | oil | | | 257 |
| 657 | 199-203 | | | |
| 660 | amorphous | | | 223, 266 |
| 661 | | d in d9-DMSO: 1.30 (3H, t, J = 7.0 Hz), 1.69 (3H, s), 2.10-2.04 (1H, m), 2.20 (3H, s), 2.67-2.62 (2H, m), 3.20-3.17 (1H, m), 4.40 (2H, q, J = 14.0, 7.0 Hz), 6.83 (1H, s), 7.25 (1H, q, J = 12.0, 9.0 Hz), 7.62-7.61 (1H, m), 7.85-7.83 (1H, m), 10.42 (1H, s) | | |
| 664 | amorphous | | | 225, 267 |
| 667 | amorphous | | | 226 |
| 673 | oil | | | 224 |
| 677 | amorphous | | | 216 |
| 680 | 159-160 | 1.63 (3H, s), 1.65-1.80 (1H, m), 2.53-2.64 (1H, m), 2.75-2.88 (2H, m), 3.83 (3H, s), 4.32 (2H, br), 6.87-6.96 (2H, m), 7.19-7.33 (2H, m) (solvent: CDCl3) | | |

TABLE 148-continued

| Compound No. | Melting Point (° C.) | 1H-NMR (d) | MS (m/z) | UV (λmax: nm) |
|---|---|---|---|---|
| 681 | | d in d6-DMSO: 1.43 (3H, s), 1.66-1.74 (1H, m), 2.02-2.07 (1H, m), 2.56-2.63 (1H, m), 2.85-2.90 (1H, m), 5.80 (2H, bs), 6.91 (1H, d, J = 7.8 Hz), 6.96-6.98 (2H, m), 7.25 (1H, t, J = 7.8 Hz), 7.2-7.36 (2H, m), 7.40 (1H, m), 7.89-7.92 (1H, m), 9.42 (1H, bs), 10.78 (1H, bs). | 338 [M + 1] | |
| 683 | 166-168 | | | |

TABLE 149

| Compound No. | Melting Point (° C.) | 1H-NMR (d) | MS (m/z) | UV (λmax: nm) |
|---|---|---|---|---|
| 687 | 164-167 | 1.60 (3H, s), 1.84-1.95 (1H, m), 2.21-2.26 (1H, m), 2.73-2.94 (2H, m), 3.92 (3H, s), 4.25 (3H, s), 7.10 (1H, d, J = 7.58 Hz), 7.34 (1H, t, J = 7.91 Hz), 7.40 (1H, s), 7.57 (1H, br s), 7.66 (1H, d, J = 7.91 Hz), 8.67 (1H, s). (solvent: CDCl3) | 388 [M + 1] | |
| 692 | | (CDCl3) 1.50 (3H, s), 1.75-1.88 (1H, m), 2.00-2.10 (1H, m), 2.91-2.99 (1H, m), 3.08-3.18 (1H, m), 6.21 (1H, d, J = 15.9 Hz), 6.59 (1H, d, J = 15.9 Hz), 7.42-7.47 (3H, m), 7.59 (1H, dd, J = 8.6, 2.0 Hz), 7.74-7.83 (4H, m) | | |
| 698 | | | | 269 |
| 700 | 177-178 | | | |
| 701 | | 1.61 (s, 3H), 1.90 (m, 1H), 2.25 (m, 1H), 2.81 (m, 1H), 2.92 (m, 1H), 3.86 (s, 3H), 6.71 (t-like, J = 1.8 Hz, 1H), 7.12 (t-like, J = 1.8 Hz, 1H), 7.53 (t-like, J = 1.8 Hz, 1H), 7.89 (dd, J = 8.3 Hz, 2.4 Hz, 1H), 8.24 (d, J = 8.3 Hz, 1H), 8.58 (d, J = 2.4 Hz, 1H), 9.85 (br, 1H) (solvent: CDCl3) | | |
| 702 | | 1H-NMR (CDCl3) d: 1.65 (3H, s), 1.91-1.98 (1H, m), 2.57-2.62 (1H, m), 2.68-2.75 (1H, m), 2.92-2.97 (1H, m), 4.18 (3H, s), 6.82 (1H, br s), 7.02-7.08 (1H, m), 7.28-7.32 (1H, m), 7.44 (1H, s), 7.92-7.96 (1H, m). | | |
| 707 | 167-174 | | | |
| 709 | 99-100 | 0.82 (3H, t, J = 7.3 Hz), 1.72-1.90 (3H, m), 2.06-2.15 (1H, m), 2.61-2.82 (2H, m), 3.80 (3H, s), 4.36 (2H, br), 6.86 (2H, d, J = 8.9 Hz), 7.17 (2H, d, J = 8.9 Hz) (solvent: CDCl3) | | |
| 717 | 157-162 | 1.58 (s, 3H), 1.90 (ddd, J = 14.0, 10.4, 3.6 Hz, 1H), 2.15 (ddd, J = 14.0, 6.8, 3.6 Hz, 1H), 2.76 (ddd, J = 12.4, 10.4, 3.6 Hz, 1H), 2.94 (ddd, J = 12.4, 6.8, 3.6 Hz, 1H), 3.49 (1H, S), 3.76 (2H, br), 7.17 (ddd, J = 8.0, 2.0, 0.8 Hz, 1H), 7.36 (t, J = 8.0 Hz, 1H), 7.38 (d, J = 1.6 Hz, 1H), 7.50 (t, J = 2.0 Hz, 1H), 7.73 (ddd, J = 8.0, 2.0, 0.8 Hz, 1H), 8.22 (d, J = 2.4 Hz), 9.26 (d, J = 2.4 Hz, 1H), 10.12 (s, 1H) (solvent: CDCl3) | | |
| 719 | oil | | | 226 254 |
| 720 | 133-138 | | | |
| 725 | amorphous | 1.62 (s, 3H), 1.96-2.03 (m, 1H), 2.38-2.49 (m, 1H), 2.63-2.71 (m, 1H), 3.05-3.12 (m, 1H), 6.73 (dd, J = 3.2, 1.6 Hz, 2H), 7.35 (d, J = 3.2 Hz, 1H), 7.37 (br s, 1H), 7.57 (d, J = 8.4 Hz, 2H), 7.67 (d, J = 8.4 Hz, 2H), 7.77 (br s, 1H), 7.96 (br s, 1H), 8.01 (br s, 1H), 10.35 (s, 1H) (solvent: DMSO-d6) | | 265 |
| 728 | 179-182 | | | |
| 729 | 167-169 | | | |

TABLE 150

| Compound No. | Melting Point (° C.) | 1H-NMR (d) | MS (m/z) | UV (λmax: nm) |
|---|---|---|---|---|
| 730 | | | | 211.0 289.9 |
| 731 | 91-94 | | | |

TABLE 150-continued

| Compound No. | Melting Point (° C.) | 1H-NMR (d) | MS (m/z) | UV (λmax: nm) |
|---|---|---|---|---|
| 732 | amorphous | | | 211 |
| 735 | 166-168 | | | |
| 737 | | 1H-NMR (CDCl3) d: 1.59 (3H, s), 1.87-1.94 (1H, m), 2.47-2.53 (1H, m), 2.67-2.73 (1H, m), 2.93-2.99 (1H, m), 4.10 (3H, s), 6.62 (1H, s), 7.04 (1H, t, J = 10.2 Hz), 7.33 (1H, d, J = 4.3 Hz), 7.85 (1H, br s). | | |
| 738 | 181-183 | | | |
| 739 | | | | 285 |
| 740 | 250 (dec.) | | | |
| 743 | 148-150 | 1.60 (s, 3H), 179-2.93 (m, 4H), 4.46 (2H, br), 7.09 (d, J = 2.0 Hz, 1H), 7.12 (ddd, J = 7.6, 2.0, 0.8 Hz, 1H), 7.18 (t, J = 2.0 Hz, 1H), 7.36 (d, J = 7.6, 2.0, 0.8 Hz, 1H), 7.43 (t, J = 7.6 Hz, 1H), 8.21 (d, J = 2.0 Hz) (solvent: CDCl3) | | |
| 744 | | d in d8-DMSO: 1.47 (3H, s), 1.82-1.78 (1H, m), 2.22-2.18 (1H, m), 2.62-2.56 (1H, m), 3.00-2.96 (1H, m), 6.79 (1H, s), 6.63 (1H, s), 7.08-7.03 (1H, m), 7.51 (1H, s), 7.64-7.57 (2H, m), 9.57 (1H, s), 11.25 (1H, s) | | |
| 753 | amorphous | | | 225, 299 |
| 756 | 110-111 | 1.55 (3H, s), 1.76-1.87 (1H, m), 2.08-2.17 (1H, m), 2.35 (3H, s), 2.65-2.76 (1H, m), 2.82-2.92 (1H, m), 4.35 (2H, br), 7.01-7.25 (4H, m) (solvent: CDCl3) | | |
| 758 | 156-157 | | | |
| 766 | | | 336 [M + 1] | 203 |
| 767 | 98-100 | | 260 | 212 |
| 768 | | 1.60 (3H, d, J = 1.3 Hz), 1.89-1.99 (1H, m), 2.29 (3H, s), 2.37-2.42 (1H, m), 2.70-2.75 (1H, m), 2.96-3.00 (1H, m), 4.12 (3H, s), 6.39 (1H, s), 7.04 (1H, dd, J = 11.5, 8.9 Hz), 7.18 (1H, dd, J = 6.9, 2.6 Hz), 7.60 (1H, s), 7.82-7.86 (1H, m). (solvent: CDCl3) | 362 [M + 1] | 213 263 |
| 771 | | | 417 [M + 1] 341 | 201 |
| 774 | | $^1$H-NMR (CDCl$_3$) d: 1.77 (3H, s), 2.11-2.21 (1H, m), 2.71-2.80 (1H, m), 2.87-2.99 (2H, m), 6.91 (1H, d, J = 6.9 Hz), 7.28 (2H, s), 7.47 (1H, t, J = 8.1 Hz), 7.75 (1H, t, J = 8.6 Hz), 8.04 (1H, dd, J = 8.6, 2.3 Hz), 8.29 (1H, d, J = 8.2 Hz), 8.46 (1H, d, J = 2.2 Hz). | 400 [M + 1] | |

TABLE 151

| Compound No. | Melting Point (° C.) | 1H-NMR (d) | MS (m/z) | UV (λmax: nm) |
|---|---|---|---|---|
| 781 | | 1.63 (s, 3H), 1.92 (ddd, J = 14.0, 10.8, 4.0 Hz, 1H), 2.29 (m, 1H), 2.78 (ddd, J = 12.4, 10.8, 3.6 Hz, 1H),, 2.91 (ddd, J = 12.4, 6.4, 4.0 Hz, 1H), 3.94 (3H, s), 7.09 (ddd, J = 8.0, 2.0, 0.8 Hz, 1H), 7.34 (dd, J = 8.8, 2.8 Hz, 1H), 7.35 (t, J = 8.0 Hz, 1H), 7.68 (t, J = 2.0 Hz, 1H), 7.71 (ddd, J = 8.0, 2.0, 0.8 Hz, 1H), 8.24 (d, J = 8.8 Hz, 1H), 8.28 (d, J = 2.8 Hz, 1H), 9.86 (s, 1H) (solvent: CDCl3) | | |
| 783 | 205-206 | | | |
| 786 | | 1.66 (3H, s), 2.10 (1H, m), 2.57-2.64 (2H, m), 3.16 (1H, m), 6.74 (1H, m), 7.30 (1H, s), 7.36 (1H, s), 7.74 (1H, s), 7.98 (1H, s), 8.06 (1H, s), 10.33 (1H, s), 10.47 (1H, s) (solvent: DMSO-d6) | | |
| 790 | amorphous | | | 223, 290 |
| 791 | | d in d18-DMSO: 1.41 (3H, s), 1.76-1.69 (1H, m), 2.02-1.98 (1H, m), 2.62-2.55 (1H, m), 2.92-2.89 (1H, m), 7.13 (1H, d, J = 7.6 Hz), 7.29 (1H, t, J = 7.6 Hz), 7.62-7.59 (2H, m), 8.71 (1H, s), 9.28 (1H, s), 10.46 (1H, brs) | | |
| 792 | | | | 299.4 |
| 793 | 269 (dec.) | | | |
| 797 | | | | 213.4 312.4 |
| 799 | | | | 215, 240 |
| 800 | | | | 225, 275 |
| 802 | | 1.63 (s, 3H), 1.92 (ddd, J = 14.0, 11.2, 3.6 Hz, 1H), 2.28 (br, 1H), 2.78 (ddd, J = 12.4, 11.2, 3.6 Hz, 1H), 2.81 (s, 3H), 2.92 (ddd, J = 12.4, 6.4, 4.0 Hz, 1H), 7.10 (ddd, J = 8.0, 2.0, 0.8 Hz, 1H), 7.35 (t, J = 8.0 Hz, | | |

TABLE 151-continued

| Compound No. | Melting Point (° C.) | 1H-NMR (d) | MS (m/z) | UV (λmax: nm) |
|---|---|---|---|---|
| | | 1H), 7.56 (t, J = 2.0 Hz, 1H), 7.65 (d, J = 2.4 Hz, 1H), 7.74 (ddd, J = 8.0, 2.0, 0.8 Hz, 1H), 8.41 (d, J = 2.4 Hz, 1H), 10.03 (s, 1H) (solvent: CDCl3) | | |
| 803 | | | | 271 |
| 804 | 135-136 | | | |
| 810 | 47-48 | | | |
| 811 | 138-139 | | | |
| 813 | 204-205 | 182 (s, 3H), 1.89-1.94 (m, 1H), 2.78 (ddd, J = 12.4, 6.4, 3.6 Hz, 1H), 4.50 (2H, br), 7.06 (dd, J = 11.6, 8.8 Hz, 1H), 7.40 (dd, J = 7.2, 2.8 Hz, 1H), 7.59 (ddd, J = 8.8, 8.0, 2.8 Hz, 1H), 7.99 (ddd, J = 8.8, 4.4, 2.8 Hz, 1H), 8.33 (dd, J = 8.8, 4.4 Hz, 1H), 8.45 (d, J = 2.8 Hz, 1H), 9.78 (s, 1H)(solvent: CDCl3) | | |
| 814 | oil | | | 218, 272 |
| 816 | | | | 214.5 |

TABLE 152

| Compound No. | Melting Point (° C.) | 1H-NMR (d) | MS (m/z) | UV (λmax: nm) |
|---|---|---|---|---|
| 820 | | (CDCl3) 1.66 (3H, d, J = 1.2 Hz), 1.98 (1H, ddd, J = 14.0, 10.4, 3.7 Hz), 2.47 (1H, ddd, J = 14.0, 6.7, 3.5 Hz), 2.79 (1H, ddd, J = 12.0, 10.4, 3.5 Hz), 3.02 (1H, ddd, J = 12.0, 6.7, 3.7 Hz), 4.45 (2H, br), 6.16 (2H, br), 7.04-7.11 (2H, m), 7.38 (1H, dd, J = 7.2, 2.9 Hz), 7.88 (1H, d, J = 2.0 Hz), 7.96 (1H, ddd, J = 8.9, 4.2, 2.9 Hz), 9.88 (1H, s) | | |
| 822 | | | | 279 |
| 827 | 134-137 | | | 214.5 284.0 |
| 832 | | | | 212, 299 |
| 833 | oil | | | 212, 273 |
| 834 | | | | 217, 267 |
| 835 | 139-140 | | | |
| 836 | | | | 221.6 279.3 |
| 840 | 223-225 | | | |
| 848 | oil | | | 223, 254 |
| 849 | 143-145 | | | |
| 850 | | d in d16-DMSO: 1.41 (3H, s), 1.75-1.70 (1H, m), 2.02-1.99 (1H, m), 2.61-2.56 (1H, m), 2.93-2.88 (1H, m), 7.13 (1H, d, J = 8.0), 7.29 (1H, t, J = 7.8 Hz), 7.35 (1H, q, J = 8.4, 2.4 Hz), 7.66-7.63 (2H, m), 8.52-8.47 (1H, m), 8.81 (1H, s), 10.44 (1H, s) | | |
| 851 | 82-83 | 1.55 (3H, s), 1.76-1.88 (1H, m), 2.10-2.18 (1H, m), 2.66-2.77 (1H, m), 2.82-2.91 (1H, m), 3.81 (3H, s), 6.73-6.78 (1H, m), 6.88-6.92 (2H, m), 7.21-7.29 (1H, m) (solvent: CDCl3) | | |
| 855 | oil | | | 219 |
| 859 | | | 350 [M + 1] 274 | 200 208 254 |
| 863 | 192-194 | 1.39 (t, J = 7.2 Hz, 3H), 1.42 (s, 3H), 1.71-1.79 (m, 1H), 2.02-2.10 (m, 1H), 2.55-2.62 (m, 1H), 2.88-2.96 (m, 1H), 4.47 (q, J = 7.2 Hz, 2H), 5.70-6.20 (br s, 2H), 7.11 (d, J = 8.0 Hz, 1H), 7.29 (t, J = 8.0 Hz, 1H), 7.75 (d, J = 8.0 Hz, 1H), 7.80 (br s, 1H), 8.38 (d, J = 1.2 Hz, 1H), 8.87 (d, J = 1.2 Hz, 1H), 10.34 (s, 1H) (solvent: CDCl3) | | |
| 866 | | | | 293.5 |
| 869 | | 1.65 (s, 3H), 1.90-2.01 (m, 3H), 2.32 (br, 1H), 2.80 (td, J = 12.0, 3.6 Hz, 1H), 2.85 (t, J = 8.0 Hz, 2H), 2.92 (ddd, J = 12.0, 5.6, 3.6 Hz, 1H), 3.75 (t, J = 8.0 Hz, 2H), 7.11 (ddd, J = 8.0, 2.0, 0.8 Hz, 1H), 7.37 (t, J = 8.0 Hz, 1H), 7.70 (t, J = 2.0 Hz, 1H), 7.73-7.76 (m, 2H), 8.22 (d, J = 7.6 Hz, 1H), 8.48 (d, J = 2.0 Hz, 1H), 10.00 (s, 1H) (solvent: CDCl3) | | |
| 871 | 212-213 | | | |

TABLE 153

| Compound No. | Melting Point (° C.) | 1H-NMR (d) | MS (m/z) | UV (λmax: nm) |
|---|---|---|---|---|
| 875 | oil | | | 222, 271 |
| 876 | oil | | | 222 |
| 878 | oil | | | 211 |
| 881 | 141-144 | | | |
| 887 | | | | 262.7 |
| 892 | 251 (dec.) | | | |
| 893 | | d in d12-DMSO: 1.70 (3H, s), 2.10-2.04 (1H, m), 2.69-2.59 (2H, m), 3.20-3.17 (1H, m), 6.80 (1H, brs), 7.26-7.20 (1H, m), 7.88-7.81 (3H, m), 10.35 (1H, s)13.53 (1H, brs) | | |
| 895 | | | 378 [M + 1] 302 | 202 208 216 221 265 |
| 896 | amorphous | | | 219, 264 |
| 897 | 212-214 | | | |
| 900 | 205-207 | 1.61 (s, 3H), 1.91 (ddd, J = 14.0, 10.8, 4.0 Hz, 1H), 2.23 (ddd, J = 14.0, 6.4, 3.6 Hz, 1H), 2.77 (ddd, J = 12.4, 10.8, 3.6 Hz, 1H), 2.92 (ddd, J = 12.4, 6.4, 4.0 Hz, 1H), 7.15 (ddd, J = 8.0, 2.0, 0.8 Hz, 1H), 7.38 (t, J = 8.0 Hz, 1H), 7.65 (t, J = 2.0 Hz, 1H), 7.79 (ddd, J = 8.0, 2.0, 0.8 Hz, 1H), 8.99 (s, 2H), 9.78 (s, 1H) (solvent: CDCl3) | | |
| 906 | | | | 212.2 273.4 350.5 |
| 908 | | d in d15-DMSO: 1.66 (3H, s), 2.11-2.05 (1H, m), 2.37 (3H, s), 2.63-2.54 (2H, m), 3.16-3.11 (1H, m), 3.16 (3H, s), 7.08-6.96 (3H, m), 7.49-7.41 (3H, m), 7.85-7.81 (2H, m), 10.52 (1H, s)11.69 (1H, s) | | |
| 910 | oil | | | 211, 276 |
| 916 | 131-132 | | | |
| 926 | | 1.89 (3H, s), 2.15 (1H, m), 2.71-2.82 (2H, m), 2.96 (1H, m), 3.04 (3H, d, J = 4.9), 7.35 (1H, dd, J = 8.7, 1.8), 7.50-7.55 (2H, m), 7.74 (1H, s), 7.82-7.90 (3H, s), 10.40 (1H, br), 11.36 (1H, Br) (solvent: CDCl$_3$) | | |
| 928 | | 1.20 (t, J = 7.6 Hz, 3H), 1.53 (br s, 3H), 1.82-1.97 (m, 1H), 2.39 (s, 3H), 2.61 (q, J = 7.6 Hz, 2H), 2.99-3.07 (m, 1H), 6.93 (br s, 1H), 7.33 (d, J = 8.4 Hz, 2H), 7.54-7.58 (m, 2H), 7.87 (d, J = 8.4 Hz, 2H), 10.13 (s, 1H) (solvent: CDCl3) | | |
| 930 | 132.1-134.4 | | 328 [M + 1] | |
| 931 | | | | 299 |
| 933 | amorphous | | | 212, 259 |

TABLE 154

| Compound No. | Melting Point (° C.) | 1H-NMR (d) | MS (m/z) | UV (λmax: nm) |
|---|---|---|---|---|
| 935 | 161-165 | 1.62 (s, 3H), 1.91 (ddd, J = 14.0, 10.4, 4.0 Hz, 1H), 2.24 (ddd, J = 14.0, 6.4, 3.6 Hz, 1H), 2.80 (ddd, J = 12.0, 10.4, 3.6 Hz, 1H), 2.93 (ddd, J = 12.0, 6.4, 4.0 Hz, 1H), 7.15 (ddd, J = 8.0, 2.0, 1.2 Hz, 1H), 7.39 (t, J = 8.0 Hz, 1H), 7.66 (ddd, J = 8.4, 7.2, 1.2 Hz, 1H), 7.75 (t, J = 2.0 Hz, 1H), 7.80-7.84 (m, 2H), 7.93 (ddd, J = 8.0, 2.0, 1.2 Hz), 8.21 (d, J = 8.4 Hz, 1H), 8.38 (d, J = 8.0 Hz, 1H), 8.41 (d, J = 8.0 Hz, 1H), 10.25 (s, 1H) (solvent: CDCl3) | | |
| 936 | 169-170 | | | |
| 939 | | d in d6-DMSO: 1.72 (3H, s), 2.11-2.05 (1H, m), 2.70-2.60 (2H, m), 3.21-3.18 (1H, m), 7.20 (1H, d, J = 9.2 Hz), 7.28 (1H, q, J = 11.6, 9.2 Hz), 8.56-7.54 (2H, m), 7.69 (1H, s), 7.90-7.85 (2H, m), 10.69 (1H, s), 12.17 (1H, brs) | | |
| 941 | | | | 220 |
| 944 | amorphous | | | 219, 256 |
| 946 | | 1.61 (s, 3H), 1.91 (ddd, J = 14.0, 10.8, 3.6 Hz, 1H), 2.26 (ddd, J = 14.0, 6.4, 3.6 Hz, 1H), 2.77 (ddd, J = 12.4, 10.8, 3.6 Hz, 1H),, 2.92 (ddd, J = 12.4, 6.4, 3.6 Hz, 1H), 7.13 (ddd, J = 8.0, 2.0, 1.2 Hz, 1H), 7.36 (t, J = 8.0 Hz, 1H), 7.61 (t, J = 2.0 Hz, 1H), 7.72 (ddd, J = 8.0, 2.0, 1.2 Hz, 1H), 7.91 (d, J = 2.4 Hz, 1H), 8.49 (d, J = 2.4 Hz, 1H), 9.75 (s, 1H) (solvent: CDCl3) | | |

TABLE 154-continued

| Compound No. | Melting Point (° C.) | 1H-NMR (d) | MS (m/z) | UV (λmax: nm) |
|---|---|---|---|---|
| 947 | | | | 215.7 276.9 |
| 960 | | | | 261.5 |
| 964 | 185-187 | | | |
| 966 | oil | | | 216 |
| 968 | 107-109 | | | |
| 970 | | 1.57 (s, 3H), 1.78-1.89 (m, 1H), 2.10-2.19 (m, 1H), 2.69 (ddd, J = 11.9, 10.8, 3.5 Hz, 1H), 2.83-2.91 (m, 1H), 7.15-7.35 (m, 5H) (solvent: CDCl3) | | |
| 971 | | (DMSO) 1.49 (3H, s), 1.73-1.86 (1H, m), 2.16-2.30 (1H, m), 2.54-2.65 (1H, m), 2.92-3.03 (1H, m), 5.86 (2H, s), 7.04-7.18 (2H, m), 7.38-7.50 (3H, m), 7.66-7.78 (2H, m), 10.35 (1H, s), 11.84 (1H, s) | | |
| 972 | | 1.51 (3H, s) 1.91-1.95 (1H, m) 2.37 (3H, s) 3.00-3.05 (1H, m) 7.24 (1H s) 7.33 (2H, d J = 9.0 Hz) 7.66 (1H, s) 7.85 (2H, d J = 9.0 Hz) 8.03 (1H, s) 10.37 (1H, s) (solvent: DMSO-d6) | | |
| 974 | amorphous | | | 219 |
| 978 | oil | | | 222 |
| 984 | | | | 255.7 318.4 |
| 990 | 126-129 | | | |
| 994 | 130-131 | | | |

TABLE 155

| Compound No. | Melting Point (° C.) | 1H-NMR (d) | MS (m/z) | UV (λmax: nm) |
|---|---|---|---|---|
| 998 | amorphous | | | 229, 290 |
| 1005 | 191-193 | | | |
| 1006 | 88-90 | 2.42-2.47 (2H, m), 2.80-2.86 (2H, m), 7.78 (6H, s), 6.83 (4H, d, J = 8.9 Hz), 7.22 (4H, d, J = 8.9 Hz) (solvent: CDCl3) | | |
| 1008 | 125-126 | | | |
| 1010 | 90-91 | | | |
| 1014 | 206-210 | | | |
| 1020 | | | | 216.9 245.1 |
| 1028 | 105-106 | | | |
| 1034 | | | | 212.2 286.4 |
| 1035 | 247-251 (dec.) | | | |
| 1037 | amorphous | | | 224, 272 |
| 1039 | amorphous | | | 217 249 |
| 1043 | 277-281 | | | |
| 1044 | | (DMSO) 1.12 (3H, s), 1.60 (2H, d, J = 6.2 Hz), 1.73 (2H, d, J = 8.6 Hz), 2.65-2.90 (2H, m), 2.93-3.13 (2H, m), 5.55 (1H, s), 7.34-7.52 (3H, m), 7.68 (1H, s), 7.79-7.90 (3H, m) | | |
| 1052 | | 1.75 (s, 3H), 2.12-2.21 (m, 1H), 2.40 (s, 3H), 2.65-2.73 (m, 2H), 3.17-3.23 (m, 1H), 7.37 (d, J = 8.4 Hz, 2H), 7.40-7.44 (m, 1H), 7.77 (br s, 1H), 7.92-7.99 (m, 5H), 8.47 (br s, 1H), 8.70 (d, J = 4.8 Hz, 1H), 10.37 (s, 1H), 10.41 (s, 1H) (solvent: CDCl3) | | |
| 1055 | 169-170 | 1.56 (3H, s), 1.78-1.89 (1H, m), 2.04-2.15 (1H, m), 2.68-2.79 (1H, m), 2.86-2.95 (1H, m), 4.32 (2H, br), 6.94-7.02 (4H, m), 7.05-7.12 (1H, m), 7.25-7.37 (4H, m) (solvent: CDCl3) | | |
| 1056 | | | | 219 |
| 1059 | 262-267 | | | |
| 1061 | | | | 216 |
| 1062 | 136-137 | 1.53 (3H, s), 1.76-1.88 (1H, m), 2.03-2.13 (1H, m), 2.63-2.73 (1H, m), 2.85-2.94 (1H, m), 4.35 (2H, br), 7.23-7.32 (4H, m) (solvent: CDCl3) | | |
| 1064 | 84-85 | 1.52 (3H, s), 1.73-1.89 (1H, m), 1.97-2.07 (1H, m), 2.64-2.81 (1H, m), 2.82-2.91 (1H, m), 2.87 (3H, s), 3.77 (3H, s), 4.10 (1H, brs), 6.84 (2H, d, J = 8.9 Hz), 7.28 (2H, d, J = 8.6 Hz) (solvent: CDCl3) | | |
| 1067 | 162-165 | | | |
| 1068 | 132-134 | | | 230 |

TABLE 155-continued

| Compound No. | Melting Point (° C.) | 1H-NMR (d) | MS (m/z) | UV (λmax: nm) |
|---|---|---|---|---|
| 1069 |  |  |  |  |
| 1074 | 194-196 |  | 324 [M + 1] | 200 |
|  |  |  | 248 | 207 |
| 1076 | amorphous |  |  | 217 |

TABLE 156

| Compound No. | Melting Point (° C.) | 1H-NMR (d) | MS (m/z) | UV (λmax: nm) |
|---|---|---|---|---|
| 1084 | 146-149 |  |  |  |
| 1087 |  |  |  | 311.2 |
| 1088 | amorphous | 1.55 (3H, s), 1.83 (1H, ddd, J = 13.9, 10.5, 3.7), 2.09 (1H, ddd, J = 13.9, 6.6, 3.6), 2.67 (1H, ddd, J = 12.3, 10.5, 3.6), 2.88 (1H, ddd, J = 12.3, 6.6, 3.7), 4.48 (2H, d, J = 6.0), 4.91 (1H, br), 6.33 (1H, dd, J = 8.8, 0.8), 7.19 (1H, d, J = 7.3, 7.23-7.30 (2H, m), 7.35 (1H, dd, J = 8.8, 2.8), 8.05 (1H, dd, J = 2.8, 0.8) (solvent: CDCl3) |  | 229 318 |
| 1094 |  |  |  | 216, 322 |
| 1100 | 278 (dec.) |  |  |  |
| 1107 | oil | 1.58 (3H, s), 1.90 (1H, ddd, J = 13.9, 10.1, 3.7), 2.14 (1H, ddd, J = 13.9, 6.8, 3.6), 2.69 (1H, ddd, J = 12.2, 10.1, 3.6), 2.94 (1H, ddd, J = 12.2, 6.8, 3.7), 3.81 (3H, s), 4.62 (2H, s), 6.90 (2H, d, J = 8.8), 7.30 (2H, d, J = 8.8), 7.43 (1H, t, J = 7.4), 7.57 (1H, ddd, J = 7.4, 1.6, 1.2), 7.81 (1H, ddd, J = 7.6, 1.6, 1.2), 7.95 (1H, t, J = 1.6) (solvent: CDCl3) |  | 226 284 |
| 1109 | 134-140 |  |  |  |
| 1110 | 109-110 |  |  |  |
| 1111 | 118-119 |  |  |  |
| 1114 | 121-124 |  |  |  |
| 1115 | 167-170 | 1.63 (s, 3H), 1.93 (ddd, J = 14.0, 10.4, 4.0 Hz, 1H), 2.24 (ddd, J = 14.0, 6.4, 3.6 Hz, 1H), 2.81 (ddd, J = 12.4, 10.4, 3.6 Hz, 1H), 2.96 (ddd, J = 12.4, 6.4, 4.0 Hz, 1H), 4.49 (br, 2H), 7.19 (ddd, J = 8.0, 2.0, 0.8 Hz, 1H), 7.42 (t, J = 8.0 Hz, 1H), 7.74 (t, J = 2.0 Hz, 1H), 7.84 (ddd, J = 8.0, 2.0, 0.8 Hz, 1H), 7.88-7.95 (m, 2H), 8.22-8.26 (m, 2H), 9.80 (s, 1H), 9.89 (s, 1H) (solvent: CDCl3) |  |  |
| 1116 | oil |  |  | 220, 255, 307 |
| 1119 | 153-157 |  |  |  |
| 1120 | 213-214 |  |  |  |
| 1124 | 169-172 |  |  | 225 |
| 1125 | 195-198 |  |  | 222 256 289 |
| 1131 | 189-191 |  |  |  |
| 1132 | 175-180 (dec) |  |  |  |
| 1133 | amorphous |  |  | 219, 292 |
| 1135 | 255-260 (dec.) |  |  |  |
| 1139 | 140-141 |  |  |  |
| 1140 | oil |  |  | 218 |
| 1142 | 182-186 (dec.) |  |  |  |

TABLE 157

| Compound No. | Melting Point (° C.) | 1H-NMR (d) | MS (m/z) | UV (λmax: nm) |
|---|---|---|---|---|
| 1147 |  |  |  | 214.5 275.7 |
| 1150 |  |  |  | 221.6 279.3 |
| 1153 | 156-159 |  |  |  |

TABLE 157-continued

| Compound No. | Melting Point (° C.) | 1H-NMR (d) | MS (m/z) | UV (λmax: nm) |
|---|---|---|---|---|
| 1160 | | 1.64 (3H, s) 2.02-2.12 (1H, m) 2.54-2.63 (1H, m) 3.11-3.16 (1H, m) 7.28 (1H, s) 7.70 (1H, dd J = 8.1 Hz) 7.85 (1H, s) 8.04-8.17 (2H, m) 8.28 (1H s) 8.74 (1H d J = 5.1 Hz) 10.81 (1H, s) 10.96 (1H, s) (solvent: DMSO-d6) | | |
| 1161 | 192-193 | | | |
| 1166 | 290-295 | | 444 [M + 3] 442 [M + 1] 368 366 | |
| 1172 | | 1.55 (3H, s) 1.94-2.03 (1H, m) 2.18-2.27 (1H, m) 2.32 (3H, s) 3.03-3.07 (1H, m) 7.05 (1H, s) 7.09 (1H, s) 7.14 (1H, s) 7.37 (2H, d J = 9.0 Hz) 7.66 (2H, d J = 9.0 Hz) 10.65 (1H, s) 10.70 (1H, s) (solvent: DMSO-d6) | | |
| 1181 | 194-195 | 1.60 (3H, s), 1.81-1.93 (1H, m), 2.13-2.22 (1H, m), 2.70-2.81 (1H, m), 2.86-2.96 (1H, m), 4.36 (2H, br), 7.29-7.46 (5H, m), 7.53-7.61 (4H, m) (solvent: CDCl3) | | |
| 1184 | 149-150 | | | |
| 1185 | | | | 225.1 280.4 |
| 1193 | 182-183 | | | |
| 1194 | | | 344 [M + 1] 268 | 209 214 261 |
| 1197 | 250-255 (dec.) | | | |
| 1199 | 274-283 | | | |
| 1205 | oil | | | E 213, 273 Z 219, 275 |
| 1207 | 106-108 | | | |
| 1211 | | 1.77 (s, 3H), 1.98-2.54 (m, 2H), 2.81 (s, 3H), 2.81-2.94 (m, 2H), 3.93 (s, 3H), 7.03 (ddd, J = 8.0, 2.0, 0.8 Hz, 1H), 7.08 (d, J = 2.4 Hz, 1H), 7.36 (t, J = 8.0 Hz, 1H), 7.63 (t, J = 2.0 Hz, 1H), 7.69 (ddd, J = 8.0, 2.0, 0.8 Hz, 1H), 8.14 (d, J = 2.4 Hz, 1H), 10.13 (s, 1H) (solvent: CDCl3) | | |
| 1213 | | | 406 [M + 1] 330 | 20 209 213 |

TABLE 158

| Compound No. | Melting Point (° C.) | 1H-NMR (d) | MS (m/z) | UV (λmax: nm) |
|---|---|---|---|---|
| 1215 | amorphous | 1.64 (s, 3H), 2.07 (ddd, J = 14.1, 11.5, 3.8 Hz, 1H), 2.17 (s, 3H), 2.39 (ddd, J = 14.1, 5.3, 3.5 Hz, 1H), 2.72 (ddd, J = 12.6, 11.5, 3.5 Hz, 1H), 2.80 (ddd, J = 12.6, 5.3, 3.8 Hz, 1H), 3.21 (t, J = 8.9 Hz, 2H), 4.58 (t, J = 8.9 Hz, 2H), 6.76 (d, J = 8.4 Hz, 1H), 6.97-7.02 (m, 1H), 7.08-7.11 (m, 1H) (solvent: CDCl3) | | |
| 1216 | | | | 305.3 |
| 1217 | 263-266 | | | |
| 1221 | amorphous | | | 220, 253 |
| 1223 | | | | 226.3 280.4 |
| 1224 | | d in d11-DMSO: 1.46 (3H, s), 1.83-1.77 (1H, m), 2.18-2.15 (1H, m), 2.61-2.56 (1H, m), 2.99-2.95 (1H, m), 7.08 (1H, q, J = 12.0, 8.4 Hz), 7.72-7.66 (2H, m), 7.79 (2H, d, J = 9.2) 9.67 (1H, s) | | |
| 1228 | oil | | | 224 |
| 1230 | 232-234 | | | |
| 1240 | | | | 216.9 285.2 |
| 1241 | 194-195 | | | |
| 1242 | | d in d21-DMSO: 1.41 (3H, m), 1.75-1.68 (1H, m), 2.04-1.99 (1H, m), 2.61-2.56 (1H, m), 2.89 (4H, s), 5.75 (2H, brs), 7.07 (1H, d, J = 4.0 Hz), 7.25 (1H, t, J = 8.0 Hz), 7.72 (1H, d, J = 8.0 Hz), 7.75 (1H, s), 7.83 (1H, brs), 7.96 (1H, s), 8.67 (1H, s), 9.96 (1H, s) | | |

TABLE 158-continued

| Compound No. | Melting Point (° C.) | 1H-NMR (d) | MS (m/z) | UV (λmax: nm) |
|---|---|---|---|---|
| 1243 | amorphous | 1.58 (3H, s), 2.00 (1H, ddd, J = 14.3, 11.5, 3.1), 2.53 (1H, m), 2.56 (1H, m), 3.07 (1H, dt, J = 12.5, 3.1), 4.26 (2H, s), 6.47-6.56 (3H, m), 7.07-7.15 (1H, m), 7.12 (2H, t, J = 8.8), 7.39 (2H, dd, J = 8.8, 5.6), 8.76 (2H, br) (solvent: DMSO-d6) | | 223 299 |
| 1244 | 268-288 | 1.68 (s, 3H), 2.11 (ddd, J = 15.2, 12.0, 4.0 Hz, 1H), 2.57-2.64 (m, 2H), 3.16 (dt, J = 12.0, 4.0 Hz, 1H), 7.13 (ddd, J = 8.0, 2.0, 0.8 Hz, 1H), 7.46 (t, J = 8.0 Hz, 1H), 7.89 (t, J = 2.0 Hz, 1H), 7.97 (ddd, J = 8.0, 2.0, 0.8 Hz, 1H), 8.35 (d, J = 8.0 Hz, 1H), 8.52 (dd, J = 8.0, 2.4 Hz, 1H), 9.12 (d, J = 2.4 Hz, 1H), 10.68 (s, 1H), 10.92 (s, 1H) (solvent: DMSO-d6) | | 219 288 |
| 1245 | oil | | | 286 |
| 1247 | | | | 211 |
| 1255 | | | | 242.7 |
| 1257 | amorphous | | | 211 |
| 1258 | | | 352 [M + 1] | 228 276 301 |
| 1261 | 179-180 | | | |
| 1262 | 278-281 | | | |

TABLE 159

| Compound No. | Melting Point (° C.) | 1H-NMR (d) | MS (m/z) | UV (λmax: nm) |
|---|---|---|---|---|
| 1263 | | 1H-NMR(d in d6-DMSO): 1.41 (3H, s), 1.65-1.77 (1H, m), 1.95-2.07 (1H, m), 2.54-2.63 (1H, m), 2.84-2.94 (1H, m), 3.39-3.46 (2H, m), 3.53-3.61 (2H, m), 4.83 (1H, t, J = 5.4 Hz), 5.79 (2H, bs), 7.07 (1H, d, J = 7.5 Hz), 7.25 (1H, t, J = 7.8 Hz), 7.73 (1H, d, J = 7.8 Hz), 7.76 (1H, m), 7.87-7.93 (1H, m), 8.02 (1H, d, J = 1.2 Hz), 8.63 (1H, d, J = 1.2 Hz), 9.97 (1H, s). | 387 [M + 1] | |
| 1264 | | 1H-NMR(d in d6-DMSO): 1.41 (3H, s), 1.65-1.77 (1H, m), 1.95-2.07 (1H, m), 2.53-2.63 (1H, m), 2.84-2.95 (1H, m), 3.73 (8H, s), 5.79 (2H, bs), 7.09 (1H, d, J = 7.8 Hz), 7.26 (1H, t, J = 7.8 Hz), 7.72 (1H, d, J = 7.8 Hz), 7.75-7.78 (1H, m), 8.34 (1H, d, J = 1.2 Hz), 8.76 (1H, d, J = 1.2 Hz), 10.08 (1H, bs). | 413 [M + 1] | |
| 1265 | | 1H-NMR (DMSO-d6) d: 1.42 (3H, s), 1.70-1.76 (1H, m), 2.02-2.05 (1H, m), 2.56-2.59 (1H, m), 2.87-2.93 (2H, m), 7.07 (1H, d, J = 7.6 Hz), 7.23-7.26 (3H, m), 7.72-7.74 (2H, m), 7.93 (1H, s), 8.60 (1H, s), 9.99 (1H, s). | | |
| 1266 | | 1H-NMR(d in d6-DMSO): 1.43 (3H, s), 1.70-1.81 (1H, m), 1.97-2.10 (1H, m), 2.55-2.64 (1H, m), 2.89-2.95 (1H, m), 5.84 (2H, bs), 7.17 (1H, d, J = 7.8 Hz), 7.33 (1H, t, J = 7.8 Hz), 9.98 (1H, d, J = 1.2 Hz), 10.01 (1H, d, J = 1.2 Hz), 10.74 (1H, bs). | 369 [M + 1] | |
| 1267 | | 1H-NMR (CDCl3) d: 1.82-1.91 (1H, m), 2.04 (3H, s), 2.22 (1H, ddd, J = 13.8, 5.2, 3.6 Hz), 2.67 (1H, dt, J = 16.7, 5.8 Hz), 2.80 (1H, dt, J = 12.4, 4.7 Hz), 6.95 (2H, d, J = 8.1 Hz), 7.06 (2H, td, J = 7.8, 1.2 Hz), 7.18 (1H, td, J = 7.6, 1.1 Hz), 7.27 (1H, d, J = 1.7 Hz), 7.32 (1H, d, J = 7.9 Hz), 7.42-7.44 (2H, m), 7.80 (1H, dd, J = 8.0, 1.9 Hz). | 338 [M + 1] | |
| 1268 | | 1H-NMR (CDCl3) d: 1.62 (3H, s), 1.89 (1H, t, J = 12.3 Hz), 2.27-2.30 (1H, m), 2.69-2.76 (1H, m), 2.85-2.88 (1H, m), 7.11 (1H, dd, J = 11.4, 7.7 Hz), 7.30-7.53 (2H, m), 7.63 (1H, s), 7.71 (1H, d, J = 6.9 Hz). | 327 [M + 1] | |
| 1269 | | 1H-NMR (DMSO-d6) d: 1.40 (3H, s), 1.70-1.73 (1H, m), 1.99-2.02 (1H, m), 2.57-2.60 (1H, m), 2.88-2.90 (1H, m), 3.29 (3H, s), 3.52 (4H, s), 5.75 (2H, br s), 7.07 (1H, d, J = 7.6 Hz), 7.25 (1H, t, J = 7.7 Hz), 7.72 (1H, d, J = 8.3 Hz), 7.75 (1H, s), 7.92 (1H, br s), 8.03 (1H, s), 8.64 (1H, s), 9.96 (1H, s). | | |
| 1271 | | 1H-NMR(d in d6-DMSO): 1.41 (3H, s), 1.65-1.75 (1H, m), 1.99-2.06 (5H, m), 2.52-2.61 (1H, m), 2.85-2.93 (1H, m), 3.55 (4H, t, J = 6.6 Hz), 5.79 (2H, bs), 7.05 (1H, d, J = 7.8 Hz), 7.25 (1H, t, J = 7.8 Hz), 7.70-7.75 (1H, m), 7.73-7.77 (1H, m), 7.97 (1H, d, J = 1.2 Hz), 8.72 (1H, d, J = 1.2 Hz), 10.00 (1H, s). | 397 [M + 1] | |

TABLE 160

| Compound No. | Melting Point (° C.) | 1H-NMR (d) | MS (m/z) | UV (λmax: nm) |
|---|---|---|---|---|
| 1272 | | (CDCl3) 1.61 (3H, s), 1.85-1.96 (1H, m), 2.17-2.27 (1H, m), 2.69-2.79 (1H, m), 2.87-2.97 (1H, m), 7.17 (1H, d, J = 8.1 Hz), 7.38 (1H, t, J = 8.1 Hz), 7.48-7.74 (5H, m), 8.40 (2H, d, J = 7.5 Hz) | | |
| 1273 | | 1H-NMR (CDCl3) d: 1.58 (3H, s), 1.89 (1H, t, J = 11.2 Hz), 2.27 (1H, s), 2.75-2.82 (2H, m), 6.61 (1H, dd, J = 20.3, 8.4 Hz), 7.10 (1H, d, J = 7.2 Hz), 7.37 (1H, dd, J = 15.0, 8.8 Hz), 7.90 (1H, d, J = 7.6 Hz), 8.10 (1H, d, J = 3.2 Hz), 9.37 (1H, d, J = 4.9 Hz), 9.69 (1H, s). | 395 [M + 1] | |
| 1274 | | 1H-NMR (CDCl3) d: 1.61 (3H, s), 1.84-1.93 (1H, m), 2.30 (1H, t, J = 13.1 Hz), 2.77-2.86 (2H, m), 6.64 (1H, dd, J = 20.6, 8.6 Hz), 7.13 (1H, d, J = 7.9 Hz), 7.38-7.43 (1H, m), 7.93 (1H, d, J = 8.1 Hz), 8.13 (1H, s), 9.40 (1H, d, J = 4.9 Hz), 9.72 (1H, s). | 327 [M + 1] | |
| 1275 | | 1H-NMR (DMSO-d6) d: 1.40 (3H, s), 1.70-1.72 (1H, m), 2.01-2.04 (1H, m), 2.18 (6H, s), 2.44 (2H, t, J = 6.3 Hz), 2.56-2.59 (1H, m), 2.86-2.92 (1H, m), 7.06 (1H, d, J = 7.6 Hz), 7.25 (1H, t, J = 7.7 Hz), 7.71-7.73 (3H, m), 8.02 (1H, s), 8.64 (1H, s), 9.95 (1H, s). | | |
| 1276 | | 1H-NMR (DMSO-d6) d: 1.70-1.73 (1H, m), 1.99-2.02 (1H, m), 2.57-2.60 (1H, m), 2.88-2.91 (1H, m), 3.04 (3H, s), 3.43 (3H, t, J = 6.3 Hz), 3.79-3.81 (2H, m), 5.75 (3H, br s), 7.08 (1H, d, J = 7.3 Hz), 7.26 (1H, t, J = 7.8 Hz), 7.72 (1H, d, J = 7.8 Hz), 7.76 (1H, s), 8.04 (1H, s), 8.09 (1H, br s), 8.70 (1H, s), 10.01 (1H, s). | | |
| 1279 | | 1H-NMR (CDCl3) d: 1.73 (3H, s), 2.04 (1H, dt, J = 18.2, 6.5 Hz), 2.45 (1H, d, J = 13.6 Hz), 2.78 (2H, t, J = 11.8 Hz), 2.89 (2H, t, J = 11.5 Hz), 6.60 (1H, s), 6.99 (1H, d, J = 8.2 Hz), 7.34 (1H, t, J = 8.0 Hz), 7.48 (1H, s), 7.70 (1H, d, J = 8.2 Hz). | 328 [M + 1] | |
| 1280 | | 1H-NMR(d in d6-DMSO): 1.42 (3H, s), 1.68-1.82 (1H, m), 2.02-2.09 (1H, m), 2.23 (3H, s), 2.43 (4H, t, J = 5.1 Hz), 2.53-2.61 (1H, m), 2.87-2.95 (1H, m), 3.73 (4H, t, J = 5.1 Hz), 6.01 (2H, bs), 7.07 (1H, d, J = 7.8 Hz), 7.26 (1H, t, J = 7.8 Hz), 7.73 (1H, d, J = 7.8 Hz), 7.73-7.78 (1H, m), 8.33 (1H, d, J = 1.2 Hz), 8.72 (1H, d, J = 1.2 Hz), 10.06 (1H, s). | 426 [M + 1] | |
| 1281 | | 1H-NMR(d in d6-DMSO): 1.40 (3H, s), 1.30-1.50 (2H, m), 1.69-1.76 (1H, m), 1.82-1.88 (2H, m), 2.01-2.07 (1H, m), 2.52-2.61 (1H, m), 2.86-2.94 (1H, m), 3.76-3.83 (1H, m), 4.10-4.18 (2H, m), 4.82 (1H, d, J = 4.2 Hz), 5.91 (2H, bs), 7.07 (1H, d, J = 7.8 Hz), 7.26 (1H, t, J = 7.8 Hz), 7.70-7.77 (2H, m), 8.33 (1H, d, J = 1.2 Hz), 8.70 (1H, d, J = 1.2 Hz), 10.02 (1H, s). | 427 [M + 1] | |

TABLE 161

| compound No. | MS (m/z) |
|---|---|
| 2 | 336 [M + 1] |
| 7 | 394 [M + 1] |
| 10 | 431 [M + 3] |
| | 429 [M + 1] |
| 11 | 356 [M + 1] |
| 12 | 354 [M + 1] |
| 13 | 363 [M + 3] |
| | 381 [M + 1] |
| 14 | 394 [M + 1] |
| 15 | 409 [M + 1] |
| 16 | 425 [M + 1] |
| 17 | 374 [M + 1] |
| 19 | 362 [M + 3] |
| | 360 [M + 1] |
| 20 | 438 [M + 1] |
| 21 | 380 [M + 3] |
| | 378 [M + 1] |
| 22 | 380 [M + 3] |
| | 378 [M + 1] |
| 25 | 354 [M + 1] |
| 27 | 338 [M + 1] |
| 28 | 356 [M + 1] |
| 29 | 372 [M + 1] |
| 31 | 378 [M + 1] |
| 32 | 417 [M + 1] |
| 34 | 358 [M + 1] |
| 35 | 396 [M + 3] |
| | 398 [M + 1] |
| 36 | 370 [M + 1] |
| 40 | 416 [M + 1] |
| | 340 |
| 41 | 414 [M + 1] |
| 44 | 362 [M + 3] |
| | 360 [M + 1] |
| 45 | 365 [M + 1] |
| 46 | 362 [M + 1] |
| 47 | 416 [M + 3] |
| | 414 [M + 1] |
| 49 | 394 [M + 3] |
| | 392 [M + 1] |
| 50 | 292 [M + 1] |
| 51 | 388 [M + 1] |
| 52 | 360 [M + 1] |
| | 284 |
| 53 | 380 [M + 1] |
| 54 | 332 [M + 1] |

TABLE 161-continued

| compound No. | MS (m/z) |
|---|---|
| 55 | 412 [M + 3] |
|  | 410 [M + 1] |
| 58 | 397 [M + 1] |
|  | 395 [M + 1] |
| 59 | 412 [M + 1] |
| 60 | 422 [M + 1] |
|  | 420 [M + 1] |
| 61 | 394 [M + 1] |
| 63 | 366 [M + 1] |
| 64 | 441 [M + 1] |
|  | 365 |
| 65 | 384 [M + 1] |
| 66 | 398 [M + 1] |
| 67 | 386 [M + 1] |
|  | 310 |
| 68 | 376 [M + 1] |
| 70 | 372 [M + 1] |
| 72 | 330 [M + 1] |
| 74 | 322 [M + 1] |
| 75 | 412 [M + 1] |
| 76 | 363 [M + 3] |
|  | 361 [M + 1] |
| 79 | 310 [M + 1] |
| 81 | 386 [M + 1] |
| 82 | 306 [M + 1] |
| 83 | 336 [M + 1] |
| 84 | 380 [M + 1] |
| 87 | 415 [M + 1] |
| 88 | 426 [M + 1] |
| 89 | 370 [M + 1] |
| 90 | 354 [M + 1] |
| 92 | 417 [M + 1] |
| 93 | 407 [M + 1] |
| 94 | 350 [M + 1] |
| 95 | 406 [M + 3] |
|  | 404 [M + 1] |
| 98 | 398 [M + 3] |
|  | 396 [M + 1] |
| 100 | 332 [M + 1] |
| 102 | 424 [M + 3] |
|  | 422 [M + 1] |
| 103 | 444 [M + 1] |
| 105 | 424 [M + 1] |
|  | 348 |
| 106 | 490 [M + 1] |
|  | 414 |
| 107 | 414 [M + 3] |
|  | 412 [M + 1] |
| 108 | 332 [M + 1] |
| 109 | 412 [M + 1] |
| 110 | 404 [M + 1] |
| 111 | 469 [M + 1] |
|  | 393 |
| 112 | 377 [M + 1] |
| 116 | 408 [M + 1] |
| 117 | 413 [M + 1] |
| 118 | 372 [M + 1] |
| 119 | 424 [M + 1] |
| 122 | 338 [M + 1] |
| 124 | 471 [M + 1] |
| 131 | 412 [M + 3] |
|  | 410 [M + 1] |
| 133 | 404 [M + 1] |
| 135 | 416 [M + 1] |
| 136 | 380 [M + 1] |
| 137 | 327 [M + 1] |
| 138 | 394 [M + 1] |
| 140 | 456 [M + 1] |
| 142 | 446 [M + 1] |
| 143 | 399 [M + 1] |
| 144 | 432 [M + 1] |
| 145 | 394 [M + 3] |
|  | 392 [M + 1] |
| 146 | 433 [M + 3] |
|  | 431 [M + 1] |
| 147 | 324 [M + 1] |
| 150 | 418 [M + 1] |

TABLE 161-continued

| compound No. | MS (m/z) |
|---|---|
| 151 | 458 [M + 3] |
|  | 458 [M + 1] |
| 152 | 371 [M + 1] |
| 153 | 398 [M + 1] |
| 154 | 401 [M + 1] |
| 155 | 322 [M + 1] |
| 156 | 332 [M + 3] |
|  | 330 [M + 1] |
| 158 | 394 [M + 1] |

TABLE 162

| compound No. | MS (m/z) |
|---|---|
| 160 | 427 [M + 1] |
| 162 | 416 [M + 3] |
|  | 414 [M + 1] |
| 167 | 392 [M + 3] |
|  | 390 [M + 1] |
| 168 | 380 [M + 3] |
|  | 378 [M + 1] |
| 169 | 346 [M + 1] |
| 170 | 358 [M + 1] |
| 171 | 334 [M + 1] |
| 172 | 376 [M + 3] |
|  | 374 [M + 1] |
| 173 | 424 [M + 3] |
|  | 422 [M + 1] |
| 174 | 369 [M + 1] |
| 175 | 410 [M + 1] |
| 177 | 357 [M + 1] |
| 179 | 334 [M + 1] |
| 180 | 426 [M + 1] |
| 182 | 396 [M + 3] |
|  | 394 [M + 1] |
| 183 | 372 [M + 1] |
| 184 | 346 [M + 1] |
| 185 | 330 [M + 1] |
| 186 | 393 [M + 3] |
|  | 391 [M + 1] |
| 187 | 374 [M + 1] |
| 188 | 423 [M + 1] |
| 190 | 278 [M + 1] |
| 191 | 448 [M + 1] |
| 192 | 436 [M + 3] |
|  | 434 [M + 1] |
| 194 | 384 [M + 1] |
| 195 | 369 [M + 1] |
| 197 | 382 [M + 1] |
| 198 | 355 [M + 1] |
| 199 | 361 [M + 1] |
| 200 | 356 [M + 1] |
|  | 280 |
| 201 | 452 [M + 1] |
| 203 | 397 [M + 1] |
| 205 | 427 [M + 1] |
| 206 | 386 [M + 1] |
|  | 310 |
| 207 | 384 [M + 1] |
| 208 | 386 [M + 3] |
|  | 384 [M + 1] |
| 209 | 371 [M + 1] |
| 210 | 366 [M + 1] |
| 211 | 442 [M + 1] |
|  | 366 |
| 212 | 345 [M + 1] |
| 215 | 425 [M + 3] |
|  | 423 [M + 1] |
| 217 | 362 [M + 1] |
| 218 | 322 [M + 1] |
| 219 | 347 [M + 1] |
| 221 | 444 [M + 1] |
| 222 | 329 [M + 1] |
| 223 | 413 [M + 1] |
| 225 | 402 [M + 1] |
| 226 | 390 [M + 1] |
| 228 | 383 [M + 1] |

TABLE 162-continued

| | |
|---|---|
| 229 | 366 [M + 1] |
| 230 | 368 [M + 1] |
| 231 | 338 [M + 1] |
| 234 | 376 [M + 1] |
| 236 | 392 [M + 1] |
| 237 | 348 [M + 1] |
| 239 | 384 [M + 1] |
| 240 | 341 [M + 1] |
| 242 | 446 [M + 1] |
| 245 | 374 [M + 1] |
| 246 | 390 [M + 1] |
| | 314 |
| 247 | 374 [M + 1] |
| 248 | 370 [M + 1] |
| 249 | 336 [M + 1] |
| 250 | 366 [M + 1] |
| 252 | 401 [M + 1] |
| 253 | 397 [M + 1] |
| 254 | 434 [M + 1] |
| 257 | 321 [M + 1] |
| 258 | 398 [M + 1] |
| 260 | 440 [M + 1] |
| 261 | 308 [M + 1] |
| 262 | 466 [M + 3] |
| | 464 [M + 1] |
| 264 | 336 [M + 1] |
| 265 | 435 [M + 1] |
| 266 | 432 [M + 3] |
| | 430 [M + 1] |
| 269 | 372 [M + 1] |
| | 298 |
| 270 | 338 [M + 1] |
| 272 | 349 [M + 1] |
| 273 | 406 [M + 3] |
| | 404 [M + 1] |
| 274 | 380 [M + 1] |
| 276 | 398 [M + 3] |
| | 396 [M + 1] |
| 278 | 404 [M + 1] |
| 280 | 433 [M + 3] |
| | 431 [M + 1] |
| 283 | 322 [M + 1] |
| 285 | 340 [M + 1] |
| 286 | 433 [M + 3] |
| | 431 [M + 1] |
| 287 | 440 [M + 3] |
| 288 | 354 [M + 1] |
| 289 | 341 [M + 1] |
| 290 | 363 [M + 3] |
| | 361 [M + 1] |
| 291 | 317 [M + 1] |
| 292 | 426 [M + 1] |
| 294 | 424 [M + 3] |
| | 422 [M + 1] |
| 295 | 394 [M + 3] |
| | 392 [M + 1] |
| 296 | 389 [M + 1] |
| 297 | 448 [M + 3] |
| | 446 [M + 1] |
| 298 | 363 [M + 3] |
| | 361 [M + 1] |
| 300 | 356 [M + 1] |
| 303 | 366 [M + 1] |
| 304 | 402 [M + 1] |
| 305 | 407 [M + 3] |
| | 405 [M + 1] |
| 310 | 411 [M + 1] |

TABLE 163

| | |
|---|---|
| 311 | 388 [M + 1] |
| 312 | 428 [M + 1] |
| 313 | 453 [M + 1] |
| 314 | 368 [M + 1] |
| 315 | 322 [M + 1] |
| 316 | 386 [M + 1] |
| 317 | 328 [M + 1] |

TABLE 163-continued

| | |
|---|---|
| 318 | 362 [M + 1] |
| 320 | 327 [M + 1] |
| 321 | 392 [M + 1] |
| 322 | 404 [M + 1] |
| | 328 |
| 323 | 394 [M + 1] |
| 324 | 384 [M + 1] |
| 325 | 399 [M + 1] |
| 326 | 440 [M + 1] |
| | 364 |
| 327 | 314 [M + 1] |
| 328 | 384 [M + 1] |
| 331 | 360 [M + 1] |
| 334 | 412 [M + 1] |
| 335 | 316 [M + 1] |
| 336 | 356 [M + 1] |
| 337 | 428 [M + 1] |
| 338 | 466 [M + 3] |
| | 484 [M + 1] |
| 340 | 344 [M + 1] |
| 343 | 399 [M + 1] |
| 345 | 412 [M + 1] |
| 346 | 384 [M + 1] |
| 347 | 430 [M + 1] |
| 348 | 341 [M + 1] |
| 349 | 335 [M + 1] |
| 350 | 412 [M + 1] |
| 351 | 322 [M + 1] |
| 352 | 327 [M + 1] |
| 355 | 397 [M + 1] |
| 362 | 368 [M + 1] |
| 363 | 376 [M + 3] |
| | 374 [M + 1] |
| 365 | 366 [M + 1] |
| 366 | 409 [M + 1] |
| 368 | 384 [M + 1] |
| 369 | 396 [M + 3] |
| | 394 [M + 1] |
| 371 | 398 [M + 3] |
| | 396 [M + 1] |
| 372 | 348 [M + 1] |
| 373 | 358 [M + 1] |
| 374 | 364 [M + 1] |
| 376 | 412 [M + 1] |
| 377 | 425 [M + 1] |
| 378 | 380 [M + 3] |
| | 378 [M + 1] |
| 379 | 377 [M + 1] |
| 381 | 409 [M + 1] |
| 382 | 340 [M + 1] |
| 384 | 388 [M + 1] |
| 385 | 384 [M + 1] |
| 386 | 352 [M + 1] |
| 387 | 376 [M + 1] |
| 388 | 440 [M + 1] |
| 390 | 407 [M + 1] |
| | 331 |
| 391 | 362 [M + 1] |
| 392 | 390 [M + 1] |
| 394 | 363 [M + 3] |
| | 361 [M + 1] |
| 397 | 460 [M + 3] |
| | 458 [M + 1] |
| 398 | 408 [M + 1] |
| 399 | 372 [M + 1] |
| 400 | 374 [M + 1] |
| 402 | 372 [M + 1] |
| | 296 |
| 403 | 436 [M + 1] |
| 404 | 376 [M + 3] |
| | 374 [M + 1] |
| 407 | 449 [M + 3] |
| | 447 [M + 1] |
| 412 | 410 [M + 1] |
| 414 | 331 [M + 1] |
| 416 | 282 [M + 1] |
| 418 | 322 [M + 1] |
| 419 | 420 [M + 3] |
| | 418 [M + 1] |
| 420 | 332 [M + 1] |

TABLE 163-continued

| | |
|---|---|
| 421 | 388 [M + 3] |
| | 386 [M + 1] |
| 423 | 412 [M + 3] |
| | 410 [M + 1] |
| 424 | 370 [M + 1] |
| 425 | 380 [M + 3] |
| | 378 [M + 1] |
| 428 | 350 [M + 1] |
| 431 | 391 [M + 1] |
| 433 | 454 [M + 3] |
| | 452 [M + 1] |
| 434 | 448 [M + 3] |
| | 446 [M + 1] |
| 435 | 431 [M + 3] |
| | 429 [M + 1] |
| 437 | 382 [M + 1] |
| 438 | 400 [M + 1] |
| | 324 |
| 439 | 380 [M + 1] |
| 440 | 358 [M + 1] |
| 442 | 394 [M + 1] |
| | 318 |
| 447 | 370 [M + 1] |
| 449 | 336 [M + 1] |
| 450 | 455 [M + 1] |
| 451 | 390 [M + 3] |
| | 388 [M + 1] |
| 453 | 358 [M + 1] |
| 454 | 407 [M + 1] |
| | 331 |
| 455 | 296 [M + 1] |
| 458 | 382 [M + 1] |
| 459 | 392 [M + 1] |
| 460 | 431 [M + 1] |
| 461 | 369 [M + 1] |
| 462 | 381 [M + 3] |
| | 379 [M + 1] |
| 463 | 440 [M + 3] |
| | 438 [M + 1] |
| 464 | 338 [M + 1] |
| | 262 |
| 467 | 387 [M + 1] |
| 468 | 439 [M + 1] |
| | 363 |
| 469 | 360 [M + 1] |
| 471 | 363 [M + 3] |
| | 361 [M + 1] |

TABLE 164

| | |
|---|---|
| 472 | 378 [M + 1] |
| 473 | 414 [M + 1] |
| 474 | 334 [M + 1] |
| 475 | 317 [M + 1] |
| 476 | 324 [M + 1] |
| 477 | 437 [M + 1] |
| 478 | 379 [M + 1] |
| 479 | 394 [M + 1] |
| 480 | 370 [M + 1] |
| 481 | 431 [M + 1] |
| 484 | 314 [M + 3] |
| | 312 [M + 1] |
| 485 | 448 [M + 1] |
| 486 | 350 [M + 1] |
| 487 | 338 [M + 1] |
| 488 | 306 [M + 1] |
| 489 | 335 [M + 1] |
| 492 | 380 [M + 1] |
| 495 | 334 [M + 1] |
| 499 | 370 [M + 1] |
| 503 | 412 [M + 1] |
| 505 | 363 [M + 3] |
| | 361 [M + 1] |
| 506 | 386 [M + 1] |
| 507 | 400 [M + 1] |
| 508 | 372 [M + 1] |

TABLE 164-continued

| | |
|---|---|
| 509 | 414 [M + 1] |
| | 338 |
| 510 | 374 [M + 1] |
| 512 | 320 [M + 1] |
| 513 | 420 [M + 3] |
| | 418 [M + 1] |
| 514 | 372 [M + 1] |
| 517 | 369 [M + 1] |
| 518 | 376 [M + 1] |
| 519 | 411 [M + 1] |
| 520 | 395 [M + 1] |
| 521 | 372 [M + 1] |
| 522 | 390 [M + 1] |
| 523 | 414 [M + 1] |
| 524 | 341 [M + 1] |
| 526 | 426 [M + 1] |
| 527 | 381 [M + 3] |
| | 379 [M + 1] |
| 529 | 320 [M + 1] |
| 530 | 390 [M + 3] |
| | 388 [M + 1] |
| 531 | 410 [M + 1] |
| 535 | 356 [M + 1] |
| 536 | 372 [M + 1] |
| 537 | 377 [M + 1] |
| 538 | 408 [M + 1] |
| 539 | 411 [M + 1] |
| 540 | 354 [M + 1] |
| 541 | 342 [M + 1] |
| 542 | 361 [M + 1] |
| 543 | 344 [M + 1] |
| 544 | 412 [M + 1] |
| 545 | 366 [M + 1] |
| 546 | 383 [M + 1] |
| 547 | 430 [M + 1] |
| | 428 [M + 1] |
| 548 | 427 [M + 1] |
| 550 | 340 [M + 1] |
| 552 | 400 [M + 1] |
| 553 | 304 [M + 1] |
| 555 | 383 [M + 1] |
| 557 | 304 [M + 1] |
| 562 | 374 [M + 1] |
| 563 | 366 [M + 1] |
| 564 | 395 [M + 1] |
| 565 | 336 [M + 1] |
| 566 | 427 [M + 1] |
| | 351 |
| 568 | 362 [M + 3] |
| | 360 [M + 1] |
| 569 | 356 [M + 1] |
| 571 | 356 [M + 1] |
| 572 | 473 [M + 3] |
| | 471 [M + 1] |
| 574 | 381 [M + 3] |
| | 379 [M + 1] |
| 575 | 360 [M + 1] |
| 576 | 384 [M + 1] |
| 578 | 344 [M + 1] |
| 579 | 370 [M + 1] |
| 580 | 347 [M + 1] |
| 581 | 409 [M + 1] |
| 582 | 334 [M + 1] |
| 583 | 392 [M + 1] |
| 585 | 358 [M + 1] |
| 587 | 348 [M + 1] |
| 589 | 407 [M + 3] |
| | 405 [M + 1] |
| 590 | 410 [M + 3] |
| | 408 [M + 1] |
| 591 | 460 [M + 1] |
| | 384 |
| 592 | 380 [M + 3] |
| | 378 [M + 1] |
| 594 | 390 [M + 1] |
| 598 | 394 [M + 1] |
| 599 | 377 [M + 1] |
| 603 | 398 [M + 3] |
| | 396 [M + 1] |
| 604 | 395 [M + 1] |

TABLE 164-continued

| | |
|---|---|
| 606 | 358 [M + 1] |
| 607 | 362 [M + 1] |
| 609 | 413 [M + 1] |
| 610 | 409 [M + 1] |
| 612 | 385 [M + 1] |
| 614 | 322 [M + 1] |
| 615 | 441 [M + 1] |
| 616 | 346 [M + 3] |
| | 344 [M + 1] |
| | 270 |
| | 268 |
| 617 | 406 [M + 3] |
| | 404 [M + 1] |
| 619 | 404 [M + 1] |
| 621 | 366 [M + 1] |
| 623 | 422 [M + 1] |
| | 346 |
| 624 | 370 [M + 1] |
| 626 | 402 [M + 1] |
| 627 | 398 [M + 3] |
| | 396 [M + 1] |
| 628 | 413 [M + 1] |
| 631 | 370 [M + 1] |
| 632 | 414 [M + 3] |
| | 412 [M + 1] |

TABLE 165

| | |
|---|---|
| 633 | 322 [M + 1] |
| 635 | 420 [M + 1] |
| 638 | 408 [M + 1] |
| 639 | 386 [M + 1] |
| | 310 |
| 640 | 370 [M + 1] |
| 641 | 437 [M + 1] |
| 642 | 380 [M + 1] |
| 646 | 395 [M + 1] |
| 647 | 334 [M + 1] |
| 648 | 403 [M + 1] |
| 650 | 370 [M + 1] |
| 655 | 362 [M + 1] |
| 656 | 308 [M + 1] |
| 658 | 430 [M + 1] |
| 659 | 340 [M + 3] |
| | 388 [M + 1] |
| 662 | 330 [M + 1] |
| 663 | 334 [M + 1] |
| 665 | 316 [M + 1] |
| 666 | 345 [M + 1] |
| 668 | 430 [M + 1] |
| 669 | 377 [M + 1] |
| 670 | 388 [M + 3] |
| | 366 [M + 1] |
| 671 | 334 [M + 1] |
| 672 | 442 [M + 1] |
| 674 | 340 [M + 1] |
| 675 | 306 [M + 1] |
| 676 | 392 [M + 1] |
| 678 | 386 [M + 1] |
| 679 | 426 [M + 1] |
| 682 | 414 [M + 3] |
| | 412 [M + 1] |
| 684 | 384 [M + 1] |
| 685 | 389 [M + 1] |
| 686 | 446 [M + 1] |
| 688 | 414 [M + 1] |
| 689 | 306 [M + 1] |
| 690 | 348 [M + 1] |
| 691 | 452 [M + 1] |
| 693 | 371 [M + 1] |
| 694 | 448 [M + 1] |
| 695 | 384 [M + 1] |
| 696 | 392 [M + 3] |
| | 390 [M + 1] |
| 697 | 358 [M + 1] |
| 699 | 426 [M + 1] |
| 703 | 451 [M + 3] |
| | 449 [M + 1] |

TABLE 165-continued

| | |
|---|---|
| 704 | 342 [M + 1] |
| 705 | 372 [M + 1] |
| 706 | 368 [M + 1] |
| 708 | 383 [M + 1] |
| 710 | 396 [M + 3] |
| | 394 [M + 1] |
| 711 | 351 [M + 1] |
| 712 | 376 [M + 1] |
| 713 | 398 [M + 3] |
| | 398 [M + 1] |
| 714 | 386 [M + 1] |
| 715 | 454 [M + 1] |
| 716 | 381 [M + 3] |
| | 379 [M + 1] |
| 718 | 386 [M + 1] |
| 721 | 322 [M + 1] |
| 722 | 377 [M + 1] |
| 723 | 440 [M + 1] |
| | 364 |
| 724 | 457 [M + 3] |
| | 455 [M + 1] |
| 726 | 382 [M + 1] |
| 727 | 366 [M + 1] |
| 734 | 370 [M + 1] |
| 738 | 338 [M + 1] |
| 741 | 404 [M + 1] |
| 742 | 351 [M + 1] |
| 745 | 386 [M + 1] |
| 746 | 370 [M + 1] |
| | 294 |
| 747 | 336 [M + 1] |
| 748 | 381 [M + 3] |
| | 379 [M + 1] |
| 749 | 416 [M + 1] |
| | 340 |
| 750 | 437 [M + 1] |
| 751 | 362 [M + 1] |
| 752 | 352 [M + 3] |
| | 350 [M + 1] |
| 754 | 366 [M + 1] |
| 755 | 354 [M + 1] |
| 757 | 425 [M + 1] |
| 759 | 346 [M + 1] |
| 760 | 344 [M + 1] |
| 761 | 402 [M + 1] |
| 762 | 251 [M + 1] |
| 763 | 355 [M + 1] |
| 764 | 362 [M + 3] |
| | 360 [M + 1] |
| 765 | 392 [M + 3] |
| | 390 [M + 1] |
| 769 | 386 [M + 1] |
| 770 | 372 [M + 1] |
| 772 | 292 [M + 1] |
| 773 | 424 [M + 1] |
| 775 | 398 [M + 3] |
| | 394 [M + 1] |
| 776 | 388 [M + 1] |
| 777 | 383 [M + 1] |
| 778 | 404 [M + 1] |
| 779 | 398 [M + 1] |
| 780 | 368 [M + 1] |
| 782 | 368 [M + 1] |
| 784 | 369 [M + 1] |
| 785 | 431 [M + 3] |
| | 429 [M + 1] |
| 787 | 473 [M + 1] |
| | 397 |
| 788 | 375 [M + 1] |
| 789 | 467 [M + 1] |
| 794 | 327 [M + 1] |
| 795 | 384 [M + 1] |
| 796 | 370 [M + 1] |
| 798 | 370 [M + 1] |
| 801 | 404 [M + 3] |
| | 402 [M + 1] |
| 805 | 376 [M + 1] |
| 806 | 411 [M + 1] |
| 807 | 356 [M + 1] |

TABLE 166

| | |
|---|---|
| 808 | 354 [M + 1] |
| 809 | 400 [M + 1] |
|  | 324 |
| 812 | 425 [M + 1] |
| 815 | 386 [M + 1] |
| 817 | 377 [M + 1] |
| 818 | 398 [M + 1] |
| 819 | 352 [M + 1] |
| 821 | 336 [M + 1] |
| 823 | 362 [M + 1] |
| 824 | 363 [M + 1] |
|  | 287 |
| 825 | 420 [M + 1] |
| 826 | 430 [M + 1] |
| 828 | 377 [M + 1] |
| 829 | 437 [M + 1] |
| 830 | 370 [M + 1] |
| 831 | 327 [M + 1] |
| 837 | 324 [M + 1] |
|  | 248 |
| 838 | 377 [M + 1] |
| 839 | 376 [M + 3] |
|  | 374 [M + 1] |
| 841 | 363 [M + 3] |
|  | 361 [M + 1] |
| 842 | 386 [M + 1] |
| 843 | 466 [M + 3] |
|  | 464 [M + 1] |
| 844 | 381 [M + 1] |
| 845 | 324 [M + 1] |
|  | 248 |
| 846 | 358 [M + 1] |
| 847 | 373 [M + 1] |
| 852 | 489 [M + 1] |
| 853 | 376 [M + 1] |
| 854 | 448 [M + 1] |
| 856 | 420 [M + 1] |
|  | 344 |
| 857 | 341 [M + 1] |
| 858 | 383 [M + 1] |
| 860 | 370 [M + 1] |
| 861 | 334 [M + 3] |
|  | 332 [M + 1] |
| 862 | 358 [M + 1] |
| 864 | 392 [M + 1] |
| 865 | 398 [M + 3] |
|  | 396 [M + 1] |
| 867 | 399 [M + 1] |
| 868 | 430 [M + 1] |
| 870 | 362 [M + 3] |
|  | 360 [M + 1] |
| 872 | 428 [M + 1] |
| 873 | 351 [M + 1] |
| 874 | 341 [M + 1] |
| 877 | 399 [M + 1] |
|  | 323 |
| 879 | 332 [M + 1] |
| 880 | 363 [M + 3] |
|  | 361 [M + 1] |
| 882 | 426 [M + 1] |
| 883 | 360 [M + 1] |
| 884 | 320 [M + 1] |
| 885 | 361 [M + 1] |
| 886 | 380 [M + 1] |
| 888 | 292 [M + 1] |
| 889 | 451 [M + 1] |
|  | 449 [M + 1] |
| 890 | 400 [M + 1] |
| 891 | 292 [M + 1] |
| 894 | 347 [M + 1] |
| 898 | 412 [M + 3] |
|  | 410 [M + 1] |
| 899 | 397 [M + 1] |
| 901 | 411 [M + 1] |
| 902 | 377 [M + 1] |
| 903 | 370 [M + 1] |
| 904 | 422 [M + 1] |
| 905 | 392 [M + 1] |
| 907 | 308 [M + 1] |
| 909 | 393 [M + 1] |

TABLE 166-continued

| | |
|---|---|
| 911 | 415 [M + 1] |
| 912 | 383 [M + 1] |
| 913 | 413 [M + 1] |
| 914 | 400 [M + 1] |
| 915 | 389 [M + 1] |
|  | 313 |
| 917 | 358 [M + 1] |
| 918 | 433 [M + 3] |
|  | 431 [M + 1] |
| 919 | 354 [M + 1] |
| 920 | 381 [M + 3] |
|  | 379 [M + 1] |
| 921 | 389 [M + 1] |
| 922 | 413 [M + 1] |
|  | 337 |
| 923 | 437 [M + 1] |
| 924 | 376 [M + 1] |
| 925 | 390 [M + 1] |
| 927 | 355 [M + 1] |
| 929 | 370 [M + 1] |
| 932 | 380 [M + 3] |
|  | 378 [M + 1] |
| 934 | 507 [M + 1] |
| 937 | 388 [M + 1] |
| 938 | 366 [M + 1] |
| 940 | 388 [M + 1] |
| 942 | 378 [M + 1] |
| 943 | 413 [M + 1] |
| 945 | 372 [M + 1] |
| 948 | 462 [M + 1] |
| 949 | 383 [M + 1] |
| 950 | 388 [M + 1] |
| 951 | 412 [M + 1] |
| 952 | 378 [M + 1] |
| 953 | 318 [M + 1] |
| 954 | 383 [M + 3] |
|  | 361 [M + 1] |
| 955 | 406 [M + 3] |
|  | 404 [M + 1] |
| 956 | 292 [M + 1] |
| 957 | 398 [M + 3] |
|  | 396 [M + 1] |
| 958 | 310 [M + 1] |
| 959 | 406 [M + 3] |
|  | 404 [M + 1] |
| 961 | 362 [M + 3] |
|  | 360 [M + 1] |
| 962 | 327 [M + 1] |
| 963 | 392 [M + 1] |

TABLE 167

| | |
|---|---|
| 965 | 438 [M + 3] |
|  | 436 [M + 1] |
| 967 | 425 [M + 3] |
|  | 423 [M + 1] |
| 969 | 413 [M + 1] |
| 973 | 386 [M + 1] |
| 975 | 407 [M + 3] |
|  | 405 [M + 1] |
| 976 | 356 [M + 1] |
| 977 | 369 [M + 1] |
| 979 | 395 [M + 1] |
| 980 | 402 [M + 1] |
| 981 | 392 [M + 3] |
|  | 390 [M + 1] |
| 982 | 366 [M + 1] |
| 983 | 379 [M + 1] |
| 985 | 408 [M + 1] |
| 986 | 440 [M + 3] |
|  | 438 [M + 1] |
| 987 | 358 [M + 1] |
| 988 | 294 [M + 1] |
| 989 | 332 [M + 1] |
| 991 | 356 [M + 1] |
| 992 | 477 [M + 1] |
| 993 | 416 [M + 3] |
|  | 414 [M + 1] |

TABLE 167-continued

| | |
|---|---|
| 995 | 425 [M + 3] |
| | 423 [M + 1] |
| 996 | 416 [M + 3] |
| | 414 [M + 1] |
| 997 | 383 [M + 3] |
| | 361 [M + 1] |
| 999 | 336 [M + 1] |
| 1000 | 388 [M + 1] |
| | 312 |
| 1001 | 374 [M + 1] |
| 1002 | 400 [M + 1] |
| 1003 | 394 [M + 1] |
| 1004 | 397 [M + 1] |
| 1007 | 448 [M + 1] |
| | 372 |
| 1009 | 366 [M + 1] |
| 1011 | 419 [M + 1] |
| 1012 | 316 [M + 1] |
| 1013 | 431 [M + 1] |
| 1015 | 372 [M + 1] |
| 1016 | 470 [M + 1] |
| 1017 | 413 [M + 1] |
| 1018 | 386 [M + 1] |
| 1019 | 433 [M + 3] |
| | 431 [M + 1] |
| 1021 | 464 [M + 1] |
| 1022 | 384 [M + 1] |
| 1023 | 407 [M + 3] |
| | 405 [M + 1] |
| 1024 | 346 [M + 1] |
| 1025 | 455 [M + 3] |
| | 453 [M + 1] |
| 1026 | 425 [M + 1] |
| 1027 | 444 [M + 1] |
| 1029 | 410 [M + 1] |
| 1030 | 413 [M + 1] |
| 1031 | 404 [M + 1] |
| 1032 | 472 [M + 1] |
| | 386 |
| 1033 | 377 [M + 1] |
| 1036 | 350 [M + 1] |
| 1038 | 364 [M + 1] |
| 1040 | 317 [M + 1] |
| 1041 | 407 [M + 1] |
| 1042 | 382 [M + 1] |
| 1045 | 425 [M + 3] |
| | 423 [M + 1] |
| 1046 | 366 [M + 1] |
| 1047 | 390 [M + 1] |
| 1048 | 440 [M + 1] |
| 1049 | 396 [M + 1] |
| 1050 | 400 [M + 1] |
| 1051 | 315 [M + 1] |
| 1053 | 383 [M + 3] |
| | 381 [M + 1] |
| 1054 | 360 [M + 1] |
| 1057 | 427 [M + 1] |
| 1058 | 360 [M + 1] |
| 1060 | 381 [M + 3] |
| | 379 [M + 1] |
| 1063 | 395 [M + 1] |
| 1065 | 451 [M + 1] |
| | 449 [M + 1] |
| 1066 | 485 [M + 1] |
| 1070 | 380 [M + 3] |
| | 378 [M + 1] |
| 1071 | 345 [M + 1] |
| 1072 | 381 [M + 3] |
| | 379 [M + 1] |
| 1073 | 397 [M + 1] |
| 1075 | 342 [M + 1] |
| 1077 | 344 [M + 1] |
| 1078 | 370 [M + 1] |
| 1079 | 387 [M + 1] |
| 1080 | 370 [M + 1] |
| | 294 |
| 1081 | 355 [M + 1] |
| 1082 | 398 [M + 3] |
| | 396 [M + 1] |
| 1083 | 316 [M + 1] |

TABLE 167-continued

| | |
|---|---|
| 1085 | 439 [M + 3] |
| | 437 [M + 1] |
| 1086 | 428 [M + 1] |
| 1089 | 399 [M + 1] |
| 1090 | 398 [M + 1] |
| 1091 | 434 [M + 3] |
| | 432 [M + 1] |
| 1092 | 398 [M + 3] |
| | 396 [M + 1] |
| 1093 | 401 [M + 1] |
| 1095 | 400 [M + 1] |
| 1096 | 409 [M + 1] |
| 1097 | 384 [M + 1] |
| 1098 | 395 [M + 1] |
| 1099 | 511 [M + 4] |
| | 510 [M + 3] |
| | 509 [M + 2] |
| | 508 [M + 1] |
| 1101 | 350 [M + 1] |
| 1102 | 442 [M + 1] |
| 1103 | 397 [M + 1] |
| 1105 | 372 [M + 1] |
| 1106 | 346 [M + 1] |
| 1108 | 383 [M + 1] |
| 1112 | 445 [M + 1] |

TABLE 168

| | |
|---|---|
| 1113 | 358 [M + 1] |
| 1117 | 394 [M + 1] |
| 1118 | 336 [M + 1] |
| | 260 |
| 1121 | 392 [M + 3] |
| | 390 [M + 1] |
| 1122 | 322 [M + 1] |
| 1123 | 316 [M + 1] |
| 1126 | 386 [M + 1] |
| 1127 | 368 [M + 1] |
| 1128 | 416 [M + 3] |
| | 414 [M + 1] |
| 1129 | 341 [M + 1] |
| 1130 | 432 [M + 1] |
| 1134 | 396 [M + 1] |
| 1136 | 396 [M + 3] |
| | 394 [M + 1] |
| 1137 | 292 [M + 1] |
| 1138 | 413 [M + 1] |
| 1141 | 344 [M + 1] |
| 1143 | 384 [M + 1] |
| 1144 | 446 [M + 1] |
| 1145 | 390 [M + 1] |
| | 314 |
| 1146 | 405 [M + 1] |
| 1148 | 380 [M + 1] |
| | 304 |
| 1149 | 364 [M + 1] |
| 1151 | 442 [M + 1] |
| 1152 | 365 [M + 1] |
| 1154 | 318 [M + 1] |
| 1155 | 427 [M + 1] |
| 1156 | 368 [M + 1] |
| 1157 | 366 [M + 1] |
| 1158 | 415 [M + 3] |
| | 413 [M + 1] |
| 1159 | 414 [M + 3] |
| | 412 [M + 1] |
| 1162 | 370 [M + 1] |
| | 294 |
| 1163 | 416 [M + 3] |
| | 414 [M + 1] |
| 1164 | 396 [M + 1] |
| | 320 |
| 1165 | 361 [M + 1] |
| 1167 | 424 [M + 1] |
| | 348 |
| 1168 | 428 [M + 1] |
| 1169 | 422 [M + 1] |
| 1170 | 411 [M + 1] |

TABLE 168-continued
| | |
|---|---|
| 1171 | 390 [M + 3] |
| | 388 [M + 1] |
| 1173 | 361 [M + 1] |
| 1174 | 342 [M + 1] |
| 1175 | 430 [M + 1] |
| 1176 | 345 [M + 1] |
| 1177 | 376 [M + 3] |
| | 374 [M + 1] |
| 1178 | 351 [M + 1] |
| 1179 | 344 [M + 1] |
| 1180 | 398 [M + 3] |
| | 396 [M + 1] |
| 1182 | 426 [M + 1] |
| 1183 | 376 [M + 3] |
| | 374 [M + 1] |
| 1186 | 374 [M + 1] |
| | 298 |
| 1187 | 427 [M + 1] |
| 1188 | 350 [M + 1] |
| 1189 | 408 [M + 3] |
| | 406 [M + 1] |
| 1190 | 366 [M + 1] |
| 1191 | 377 [M + 1] |
| 1192 | 335 [M + 1] |
| 1195 | 412 [M + 3] |
| | 410 [M + 1] |
| 1196 | 380 [M + 1] |
| 1198 | 398 [M + 1] |
| | 322 |
| 1200 | 352 [M + 1] |
| 1201 | 424 [M + 3] |
| | 422 [M + 1] |
| 1202 | 369 [M + 1] |
| 1203 | 420 [M + 1] |
| 1204 | 398 [M + 3] |
| | 396 [M + 1] |
| 1206 | 416 [M + 1] |
| 1208 | 344 [M + 1] |
| 1209 | 422 [M + 1] |
| 1210 | 408 [M + 1] |
| 1212 | 391 [M + 1] |
| 1214 | 360 [M + 1] |
| 1218 | 372 [M + 1] |
| 1219 | 470 [M + 1] |
| 1220 | 264 [M + 1] |
| 1222 | 362 [M + 3] |
| | 360 [M + 1] |
| 1225 | 413 [M + 1] |
| 1226 | 374 [M + 1] |
| 1227 | 425 [M + 1] |
| 1229 | 455 [M + 3] |
| | 453 [M + 1] |
| 1231 | 413 [M + 1] |
| 1232 | 340 [M + 1] |
| 1233 | 394 [M + 1] |
| 1234 | 416 [M + 3] |
| | 414 [M + 1] |
| 1235 | 427 [M + 1] |
| 1236 | 348 [M + 1] |
| | 272 |
| 1237 | 353 [M + 1] |
| 1238 | 419 [M + 1] |
| 1239 | 416 [M + 3] |
| | 414 [M + 1] |
| 1246 | 474 [M + 1] |
| 1248 | 414 [M + 1] |
| 1249 | 336 [M + 1] |
| 1250 | 352 [M + 1] |
| 1251 | 393 [M + 1] |
| 1252 | 357 [M + 1] |
| 1253 | 430 [M + 1] |
| 1254 | 412 [M + 1] |
| 1256 | 333 [M + 1] |
| 1259 | 356 [M + 1] |
| 1260 | 348 [M + 1] |
| 1270 | 374 [M + 1] |
| 1282 | 362 [M + 1] |
[Chemical formula 66]
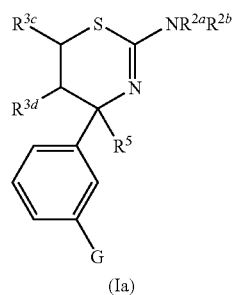
(Ia)
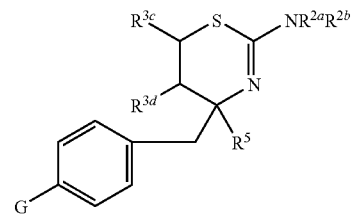
(Ib)
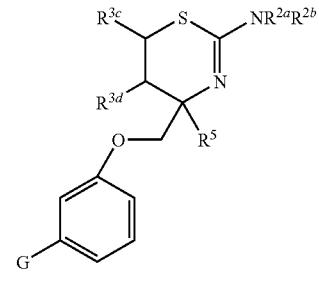
(Ic)
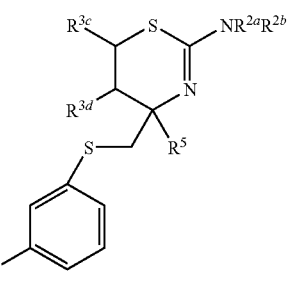
(Id)
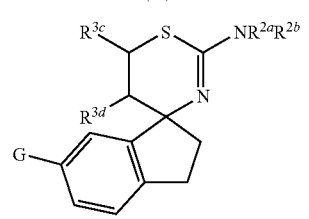
(Ie)
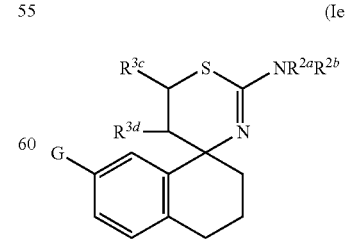
(If)
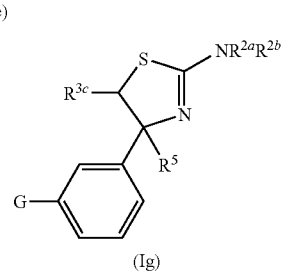
(Ig)

-continued

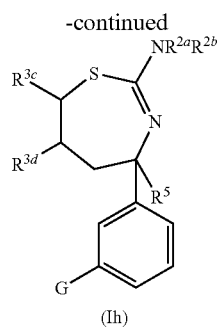

(Ih)

In above structural formula (Ia) to (Ih), the combination of NR$^{2a}$R$^{2b}$, R$^{3c}$, R$^{3d}$, R$^5$ and G (NR$^{2a}$R$^{2b}$, R$^{3c}$, R$^{3d}$, R$^5$, G) are the following compounds.

(NHMe,H,H,Me,CONHPh), (NHMe,H,H,Me,CONH-3-pyridyl), (NHMe,H,H,Me,NHCOPh), (NHMe,H,H,Me,NHCO-2-furyl), (NHMe,H,H,Me,NHCONHPh), (NHMe,H,H,Me,NHCOCONHPh), (NHMe,H,H,Et,CONHPh), (NHMe,H,H,Et,CONH-3-pyridyl), (NHMe,H,H,Et,NHCOPh), (NHMe,H,H,Et,NHCO-2-furyl), (NHMe,H,H,Et,NHCONHPh), (NHMe,H,H,Et,NHCOCONHPh), (NHMe,H,H,CH2OH,CONHPh), (NHMe,H,H,CH2OH,CONH-3-pyridyl), (NHMe,H,H,CH2OH,NHCOPh), (NHMe,H,H,CH2OH,NHCO-2-furyl), (NHMe,H,H,CH2OH,NHCONHPh), (NHMe,H,H,CH2OH,NHCOCONHPh), (NHMe,H,Me,Me,CONHPh), (NHMe,H,Me,Me,CONH-3-pyridyl), (NHMe,H,Me,Me,NHCOPh), (NHMe,H,Me,Me,NHCO-2-furyl), (NHMe,H,Me,Me,NHCONHPh), (NHMe,H,Me,Me,NHCOCONHPh), (NHMe,H,Me,Et,CONHPh), (NHMe,H,Me,Et,CONH-3-pyridyl), (NHMe,H,Me,Et,NHCOPh), (NHMe,H,Me,Et,NHCO-2-furyl), (NHMe,H,Me,Et,NHCONHPh), (NHMe,H,Me,Et,NHCOCONHPh), (NHMe,H,Me,CH2OH,CONHPh), (NHMe,H,Me,CH2OH,CONH-3-pyridyl), (NHMe,H,Me,CH2OH,NHCOPh), (NHMe,H,Me,CH2OH,NHCO-2-furyl), (NHMe,H,Me,CH2OH,NHCONHPh), (NHMe,H,Me,CH2OH,NHCOCONHPh), (NHMe,H,Ph,Me,CONHPh), (NHMe,H,Ph,Me,CONH-3-pyridyl), (NHMe,H,Ph,Me,NHCOPh), (NHMe,H,Ph,Me,NHCO-2-furyl), (NHMe,H,Ph,Me,NHCONHPh), (NHMe,H,Ph,Me,NHCOCONHPh), (NHMe,H,Ph,Et,CONHPh), (NHMe,H,Ph,Et,CONH-3-pyridyl), (NHMe,H,Ph,Et,NHCOPh), (NHMe,H,Ph,Et,NHCO-2-furyl), (NHMe,H,Ph,Et,NHCONHPh), (NHMe,H,Ph,Et,NHCOCONHPh), (NHMe,H,Ph,CH2OH,CONHPh), (NHMe,H,Ph,CH2OH,CONH-3-pyridyl), (NHMe,H,Ph,CH2OH,NHCOPh), (NHMe,H,Ph,CH2OH,NHCO-2-furyl), (NHMe,H,Ph,CH2OH,NHCONHPh), (NHMe,H,Ph,CH2OH,NHCOCONHPh), (NHMe,H,OH,Me,CONHPh), (NHMe,H,OH,Me,CONH-3-pyridyl), (NHMe,H,OH,Me,NHCOPh), (NHMe,H,OH,Me,NHCO-2-furyl), (NHMe,H,OH,Me,NHCONHPh), (NHMe,H,OH,Me,NHCOCONHPh), (NHMe,H,OH,Et,CONHPh), (NHMe,H,OH,Et,CONH-3-pyridyl), (NHMe,H,OH,Et,NHCOPh), (NHMe,H,OH,Et,NHCO-2-furyl), (NHMe,H,OH,Et,NHCONHPh), (NHMe,H,OH,Et,NHCOCONHPh), (NHMe,H,OH,CH2OH,CONHPh), (NHMe,H,OH,CH2OH,CONH-3-pyridyl), (NHMe,H,OH,CH2OH,NHCOPh, (NHMe,H,OH,CH2OH,NHCO-2-furyl), (NHMe,H,OH,CH2OH,NHCONHPh), (NHMe,H,OH,CH2OH,NHCOCONHPh), (NHMe,H,Me,CONHPh), (NHMe,Me,H,Me,CONH-3-pyridyl), (NHMe,Me,H,Me,NHCOPh), (NHMe,Me,H,Me,NHCO2-furyl), (NHMe,Me,H,Me,NHCONHPh), (NHMe,Me,H,Me,NHCOCONHPh), (NHMe,Me,H,Et,CONHPh), (NHMe,Me,H,Et,CONH-3-pyridyl), (NHMe,Me,H,Et,NHCOPh), (NHMe,Me,H,Et,NHCO-2-furyl), (NHMe,Me,H,Et,NHCONHPh), (NHMe,Me,H,Et,NHCOCONHPh), (NHMe,Me,H,CH2OH,CONHPh), (NHMe,Me,H,CH2OH,CONH-3-pyridyl), (NHMe,Me,H,CH2OH,NHCOPh), (NHMe,Me,H,CH2OH,NHCO-2-furyl), (NHMe,Me,H,CH2ON,NHCONHPh), (NHMe,Me,H,CH2OH,NHCOCONHPh), (NHMe,Me,Me,Me,CONHPh), (NHMe,Me,Me,Me,CONH-3-pyridyl), (NHMe,Me,Me,Me,NHCOPh), (NHMe,Me,Me,Me,NHCO-2-furyl), (NHMe,Me,Me,Me,NHCONHPh), (NHMe,Me,Me,Me,NHCOCONHPh), (NHMe,Me,Me,Et,CONHPh), (NHMe,Me,Me,Et,CONH-3-pyridyl), (NHMe,Me,Me,Et,NHCOPh), (NHMe,Me,Me,Et,NHCO-2-furyl), (NHMe,Me,Me,Et,NHCONHPh), (NHMe,Me,Me,Et,NHCOCONHPh), (NHMe,Me,Me,CH2OH,CONHPh), (NHMe,Me,Me,CH2OH,CONH-3-pyridyl), (NHMe,Me,Me,CH2OH,NHCOPh), (NHMe,Me,Me,CH2OH,NHCO-2-furyl), (NHMe,Me,Me,CH2OH,NHCONHPh), (NHMe,Me,Me,CH2OH,NHCOCONHPh), (NHMe,Me,Ph,Me,CONHPh), (NHMe,Me,Ph,Me,CONH-3-pyridyl), (NHMe,Me,Ph,Me,NHCOPh), (NHMe,Me,Ph,Me,NHCO-2-furyl), (NHMe,Me,Ph,Me,NHCONHPh), (NHMe,Me,Ph,Me,NHCOCONHPh), (NHMe,Me,Ph,Et,CONHPh), (NHMe,Me,Ph,Et,CONH-3-pyridyl), (NHMe,Me,Ph,Et,NHCOPh), (NHMe,Me,Ph,Et,NHCO-2-furyl), (NHMe,Me,Ph,Et,NHCONHPh), (NHMe,Me,Ph,Et,NHCOCONHPh), (NHMe,Me,Ph,CH2OH,CONHPh), (NHMe,Me,Ph,CH2OH,CONH-3-pyridyl), (NHMe,Me,Ph,CH2OH,NHCOPh), (NHMe,Me,Ph,CH2OH,NHCO-2-furyl), (NHMe,Me,Ph,CH2O H,NHCONHPh), (NHMe,Me,Ph,CH2OH,NHCOCONHPh), (NHMe,Me,OH,Me,CONHPh), (NHMe,Me,OH,Me,CONH-3-pyridyl), (NHMe,Me,OH,Me,NHCOPh), (NHMe,Me,OH,Me,NHCO-2-furyl), (NHMe,Me,OH,Me,NHCONHPh), (NHMe,Me,OH,Me,NHCOCONHPh), (NHMe,Me,OH,Et,CONHPh), (NHMe,Me,OH,Et,CONH-3-pyridyl), (NHMe,Me,OH,Et,NHCOPh), (NHMe,Me,OH,Et,NHCO-2-furyl), (NHMe,Me,OH,Et,NHCONHPh), (NHMe,Me,OH,Et,NHCOCONHPh), (NHMe,Me,OH,CH2OH,CONHPh), (NHMe,Me,OH,CH2OH,CONH-3-pyridyl), (NHMe,Me,OH,CH2OH,NHCOPh), (NHMe,Me,OH,CH2OH,NHCO-2-furyl), (NHMe,Me,OH,CH2OH,NHCONHPh), (NHMe,Me,OH,CH2OH,NHCOCONHPh), (NHMe,Ph,H,Me,CONHPh), (NHMe,Ph,H,Me,CONH-3-pyridyl), (NHMe,Ph,H,Me,NHCOPh), (NHMe,Ph,H,Me,NHCO-2-furyl), (NHMe,Ph,H,Me,NHCONHPh), (NHMe,Ph,H,Me,NHCOCONHPh), (NHMe,Ph,H,Et,CONHPh), (NHMe,Ph,H,Et,CONH-3-pyridyl), (NHMe,Ph,H,Et,NHCOPh), (NHMe,Ph,H,Et,NHCO-2-furyl), (NHMe,Ph,H,Et,NHCONHPh), (NHMe,Ph,H,Et,NHCOCONHPh), (NHMe,Ph,H,CH2OH,CONHPh), (NHMe,Ph,H,CH2OH,CONH-3-pyridyl), (NH Me,Ph,H,CH2OH,NHCOPh), (NHMe,Ph,H,CH2OH,NHCO-2-furyl), (He,Ph,H,CH2OH,NHCONHPh), (NHMe,Ph,H,CH2OH,NHCOCONHPh), (NHMe,Ph,Me,Me,CONHPh), (NHMe,Ph,Me,Me,CONH-3-pyridyl), (NHMe,Ph,Me,Me,NHCOPh), (NHMe,Ph,Me,Me,NHCO-2-furyl), (NHMe,Ph,Me,Me,NHCONHPh), (NHMe,Ph,Me,Me,NHCOCONHPh), (NHMe,Ph,Me,Et,CONHPh), (NHMe,Ph,Me,Et,CONH-3-pyridyl), (NHMe,Ph,Me,Et,NHCOPh), (NHMe,Ph,Me,Et,NHCO-2-furyl), (NHMe,Ph,Me,Et,NHCONHPh), (NHMe,Ph,Me,Et,NHCOCONHPh), (NHMe,Ph,Me,CH2OH,CONHPh), (NHMe,Ph,Me,CH2OH,CONH-3-pyridyl), (NHMe,Ph,Me,CH2OH,NHCOPh), (NHMe,Ph,Me,CH2OH,NHCO-2-furyl), (NHMe,Ph,Me,CH2OH,NHCONPh), (NHMe,Ph,Me,CH2OH,NHCOCONHPh), (NHMe,Ph,Ph,Me,CONHPh), (NHMe,Ph,Ph,Me,CONH-3-pyridyl), (NHMe,Ph,Ph,Me,NHCOPh), (NHMe,Ph,Ph,Me,NHCO-2-furyl, (NHMe,Ph,Ph,Me,NHCONHPh), (NHMe,Ph,Ph,Me,NHCOCONHPh), (NHMe, Ph,Ph,Et,CONHh), (NHMe,Ph,Ph,Et,CONH-3-pyridyl), (NHMe,Ph,Ph,Et,NHCOPh), (NHMe,Ph,Ph,Et,NHCO-2-furyl), (NHMe,Ph,Ph,Et,NHCONHPh), (NHMe,Ph,Ph,Et,NHCOCONHPh), (NHMe,Ph,Ph,CH2OH,CONHPh), (NHMe,Ph,Ph,CH2OH,CONH-3-pyridyl)(NHMe,Ph,Ph,CH2OH,NHCOPh), (HMe,Ph,Ph,CH2OH,NHCO-2-furyl), (NHMe,Ph,Ph,CH2OH,NHCONHPh), (BMe,Ph,Ph,CH2OH,NHCOCONHPh), (NHMe,Ph,OH,Me,CONHPh), (NHMe,Ph,OH,Me,CONH-3-pyridyl), (NHMe,Ph,OH,Me,NHCOPh), (NHMe,Ph,OH,Me,NHCO-2-furyl), (NHMe,Ph,OH,Me,NHCONHPh), (NHMe,Ph,OH,Me,NHCOCONHPh), (NHMe,Ph,OH,Et,CONHPh), (NHMe,Ph,OH,Et,CONH-3-pyridyl), (NHMe,Ph,OH,Et,NHCOPh), (NHMe,Ph,OH,Et,NHCO-2-furyl), (NHMe,Ph,OH,Et,NHCONHPh), (NHMe,Ph,OH,Et,NHCOCONHPh), (NHMe,Ph,OH,CH2OH,CONHPh), (NHMe,Ph,OH,CH2OH,CONH-3-pyridyl), (NHMe,Ph,OH,CH2OH,NHCOPh), (NHMe,Ph,OH,CH2OH,NHCO-2-furyl), (NHMe,Ph,OH,CH2OH,NHCONHPh), (NHMe,Ph,OH,CH2OH,NHCOCONHPh),
(NHCH2CH2OH,H,H,Me,CONHPh), (NHCH2CH2OH,H,H,Me,CONH-3-pyridyl), (NHCH2CH2OH,H,H,Me,NHCOPh), (NHCH2CH2OH,H,H,Me,NHCO-2-furyl), (NHCH2CH2OH,H,H,Me,NHCONHPh), (NHCH2CH2OH,H,H,Me,NHCOCONHPh), (NHCH2CH2OH,H,H,Et,CONHPh), (NHCH2CH2OH,H,H,Et,CONH-3-pyridyl), (NHCH2CH2OH,H,H,Et,CONHPh), (NHCH2CH2OH,H,H,Me,HNCOCOHNPh), (NHOH,H,H,Et,NHCONHPh), (NHCH2CH2OH,H,H,Et,NHCOCONHPh), (NHCH2CH2OH,H,H,CH2OH,CONHPh), (NHCH2CH2OH,H,H,CH2OH,CONH-3-pyridyl), (NHCH2CH2OH,H,H,CH2OH,NHCOPh), (NHCH2CH2OH,H,H,CH2OH,NHCO-2-furyl), (NHCH2CH2OH,H,H,CH2OH,NHCONHPh), (NHCH2CH2OH,H,H,CH2OH,NHCOCONHPh), (NHCH2CH2OH,H,Me,Me,CONHPh), (NHCH2CH2OH,H,Me,Me,CONH-3-pyridyl), (NHCH2CH2OH,H,Me,Me,NHCOPh), (NHCH2CH2OH,H,Me,Me,NHCO-2-furyl), (NHCH2CH2OH,H,Me,Me,NHCONHPh), (NHCH2CH2OH,H,Me,Me,NHCOCONHPh), (NHCH2CH2OH,H,Me,Et,CONHPh), (NHCH2CH2OH,H,Me,Et,CONH-3-pyridyl), (NHCH2CH2OH,H,Me,Et,NHCOPh), (NHCH2CH2OH,H,Me,Et,NHCO-2-furyl), (NHCH2CH2OH,H,Me,Et,NHCONHPh), (NHCH2CH2OH,H,Me,Et,NHCOCONHPh), (NHCH2CH2OH,H,Me,CH2OH,CONHPh), (NHCH1CH2OH,H,ME,CH2OH,CONH-3-pyridyl), (NHCH2CH2OH,H,Me,CH2OH,NHCOPh), (NHCH2CH2OH,H,Me,CH2OH,NHCO-2-furyl), (NHCH2CH2OH,H,Me,CH2OH,NHCONHPh), (NHCH2CH2OH,H,Me,CH2OH,NHCOCONHPh), (CNHCH2CH2OH,H,Ph,Me,CONHPh), (NHCH2CH2OH,H,Ph,Me,CONH-3-pyridyl), (NHCH2CH2OH,H,Ph,Me,NHCOPh), (NHCH2CH2OH,H,Ph,Me,NHCO-2-furyl), (NHCH2CH2OH,H,Ph,Me,NHCONHPh), (NHCH2CH2OH,H,Ph,Me,NHCOCONHPh), (NHCH2CH2OH,H,Ph,Et,CONHPh), (NHCH2CH2OH,H,Ph,Et,CONH-3-pyridyl), (NHCH2CH2OH,H,Ph,Et,NHCOPh), (NHCH2CH2OH,H,Ph,Et,NHCO-2-furyl), (NHCH2CH2OH,H,Ph,Et,NHCONHPh), (NHCH2CH2OH,H,Ph,Et,NHCOCONHPh), (NHCH2CH2OH,H,Ph,CH2OH,CONHPh), (NHCH2CH2OH,H,Ph,CH2OH,CONH-3-pyridyl), (NHCH2CH2OH,H,Ph,CH2OH,NHCOPh), (NHCH2CH2OH,H,Ph,CH2OH,NHCO-2-furyl), (NHCH2CH2OH,H,Ph,CH2OH,NHCONHPh), (NHCH2CH2OH,H,Ph,CH2OH,NHCOCONHPh), (NHCH2CH2OH,H,OH,Me,CONHPh), (NHCH2CH2OH,H,OH,Me,CONH-3-pyridyl), (NHCH2CH2OH,H,OH,Me,NHCOPh), (NHCH2CH2OH,H,OH,Me,NHCO-2-furyl), (NHCH2CH2OH,H,OH,Me,NHCONHPh), (NHCH2CH2OH,H,OH,Me,NHCOCONHPh), (NHCH2CH2OH,H,OH,Et,CONHPh), (NHCH2CH2OH,H,OH,Et,CONH-3-pyridyl), (NHCH2CH2OH,H,OH,Et,NHCOPh), (NHCH2CH2OH,H,OHEt,NHCO-2-furyl), (NHCH2CH2OH,H,OH,Et,NHCONHPh), (NHCH2CH2OH,H,OH,Et,NHCOCONHPh), (NHCH2CH2OH,H,OH,CH2OH,CONHPh), (NHCH2CH2OH,H,OH,CH2OH,CONH-3-pyridyl), (NHCH2CH2OH,H,OH,CH2OH,NHCOPh), (NHCH2CH2OH,H,OH,CH2OH,NHCO-2-furyl), (NHCH2CH2OH,H,OH,CH2OH,NHCONHPh), (NHCH2CH2OH,H,OH,CH2OH,NHCOCONHPh), (NHCH2CH2OH,Me,H,Me,CONHPh), (NHCH2CH2OH,Me,H,Me,CONH-3-pyridyl), (NHCH2CH2OH,Me,H,Me,NHCOPh), (NHCH2CH2OH,Me,H,Me,NHCO-2-furyl), (NHCH2CH2OH,Me,H,Et,CONHPh), (NHCH2CH2OH,Me,H,Et,NHCOCONHPh), (NHCH2CH2OH,Me,H,CH2OH,CONHPh), (NHCH2CH2OH,Me,H,Et,CONH-3-pyridyl), (NHCH2CH2OH,Me,Et,NHCOPh), (NHCH2CH2OH,Me,H,Et,NHCO-2-furyl), (NHCH2CH2OH,Me,H,Et,NHCONHPh)(NHCH2CH2OH,Me,H,Et,NHCOCONHPh), (NHCH2CH2OH,Me,H,CH2OH, (CONHPh),NHCH2CH2OH,Me,H,CH2OH,CONH-3-pyridyl), (NHCH2CH2OH,Me,H,CH2OH,NHCOPh), (NHCH2CH2OH,Me,H,CH2OH,NHCO-2-furyl), (NHCH2CH2OH,Me,H,CH2OH,NHCONHPh), (NHCH2CH2OH,Me,H,CH2OH,NHCOCOHNPh, (NHCH2CH2OH,Me,Me,Me,CONHPh), (NHCH2CH2OH,Me,Me,Me,CONH-3-pyridyl), (NHCH2CH2OH,Me,Me,Me,NHCOPh), (NHCH2CH2OH,Me,Me,Me,NHCO-2-furyl), (NHCH2CH2OH,Me,Me,Me,NHCONHPh), (NHCH2CH2OH,H,Me,Me,Me,NHCOCONHPh), (NHCH2CH2OH,Me,Me,Et,CONHPh), (NHCH2CH2OH,Me,Me,ET,CONH-3-pyridyl), (NHCH2CH2OH,Me,Me,Et,NHCOPh), (NHCH2CH2OH,Me,Me,Et,NHCO-2-furyl), (NHCH2CH2OH,Me,Me,Et,NHCONHPh), (NHCH2CH2OH,Me,Me,Et,NHCOCONHPh), (NHCH2CH2OH,Me,Me,CH2OH,CONHPh), (NHCH2CH2OH,Me,Me,CH2OH,CONH-3-pyridyl), (NHCH2CH2OH,Me,Me,CH2OH,NHCOPh), (NHCH2CH2OH,Me,Me,CH2OH,NHCO-2-furyl), (NHCH2CH2OH,Me,Me,CH2OH,NHCONHPh), (NHCH1CH2OH,Me,Me,CH2OH,NHCOCONHPh), (NHCH2CH2OH,Me,Ph,Me,CONHPh), (NHCH2CH2OH,Me,Ph,Me,CONH-3-pyridyl), (NHCH2CH2OH,Me,Ph,Me,NHCOPh), (NHCH2CH2OH,Me,Ph,Me,NHCO-2-furyl), (NHCH2CH2OH,Me,Ph,Me,NHCONHPh), (NHCH2CH2OH,Me,Ph,Me,NHCOCONHPh), (NHCH2CH2OH,Me,Ph,Et,CONHPh), (NHCH2CH2OH,Me,Ph,Et,CONH-3-pyridyl), (NHCH2CH2OH,Me,Ph,Et,NHCOPh), (NHCH2CH2OH,Me,Ph,Et,NHCO-2-furyl), (NHCH2CH2OH,Me,Ph,Et,NHCONHPh), (NHCH2CH2OH2O Me,Ph,Et,NHCOCONHPh), (NHCH2CH2OH,Me,Ph,CH2OH,CONHPh), (NHCH2CH2O,H,Me,Ph,CH2OH,CONH-3-pyridyl), (NHCH2CH2OH,Me,Ph,CH2OH,NHCOPh), (NHCH2CH2OH,Me,Ph,CH2OH,NHCO-2-furyl), (NHCH2CH2OH,Me,Ph,CH2OH,NHCONHPh), (NHCH2CH2OH,Me,Ph,CH2OH,NHCOCONHPh), (NHCH2CH2OH,Me,OH,Me,CONHPh), (NHCH2CH2OH,Me,OH,Me,CONH-3-pyridyl), (NHCH2CH2OH,Me,OH,Me,NHCOPh), (NHCH2CH2OH,Me,OH,Me,NHCO-2-furyl(NHCH2CH2OH,Me,OH,Me,NHCONHPh), (NHCH2CH2OH,Me,OH,Me,NHCOCONHPh), (NHCH2CH2OH,Me,OH,Et,CONHPh), (NHCH2CH2OH, Me,OH,Et,CONH-3-pyridyl), (NHCH2CH2OH,Me,OH,Et, NHCOPh), (NHCH2CH2OH,Me,OH,Et,NHCO-2-furyl), (NHCH2CH2OH,Me,OH,Et,NHCONHPh), (NHCH2CH2OH,Me,OH,Et,NHCOCONHPh), (NHCH2CH2OH,Me,OH,CH2OH,CONHPh), (NHCH2CH2OH,Me,OH,CH2OH,CONH-3-pyridyl), (NHCH2CH2OH,Me,OH,CH2OH,NHCOPh), (NHCH2CH2OH,Me,OH,CH2OH,NHCO2-furyl), (NHCH2CH2OH,Me,OH,CH2OH,NHCONHPh), (NHCH2CH2OH,Me,OH,CH2OH,NHCOCONHPh), (NHCH2CH2OH,Ph,H,Me,CONHPh), (NHCH2CH2OH, Ph,H,Me,CONH-3-pyridyl), (NHCH2CH2OH,Ph,H,Me, NHCOPh), (NHCH2CH2OH,Ph,H,Me,NHCO-2-furyl), (NHCH2CH2OH,Ph,H,Me,NHCONHPh), (NHCH2CH2OH,Ph,H,Me,NHCOCONHPh), (NHCH2CH2OH,Ph,H,Et,CONHPh), (NHCH2CH2OH,Ph, H,Et,CONH-3-pyridyl), (NHCH2CH2OH,Ph,H,Et,NH-COPh), (NHCH2CH2OH,Ph,H,Et,NHCO-2-furyl), (NHCH2CH2OH,Ph,H,Et,NHCONHPh), (NHCH2CH2OH, Ph,H,Et,NHCOCONPh), (NHCH2CH2OH,Ph,H,CH2OH, CONHPh), (NHCH2CH2OH,Ph,H,CH2OH,CONH-3-pyridyl), (NHCH2CH2OH,Ph,H,CH2OH,NHCOPh), (NHCH2CH2OH,Ph,H,CH2OH,NHCO-2-furyl), (NHCH2CH2OH,Ph,H,CH2OH,NHCONHPh), (NHCH2CH2OH,Ph,H,CH2OH,NHCOCONHPh), (NHCH2CH2OH,Ph,Me,Me,CONHPh), (NHCH2CH2OH, Ph,Me,Me,CONH-3-pyridyl), (NHCH2CH2OH,Ph,Me,Me, NHCOPh), (NHCH2CH2OH,Ph,Me,Me,NHCO-2-furyl), (NHCH2CH2OH,Ph,Me,Me,NHCONHPh), (NHCH2CH2OH,Ph,Me,Me,NHCOCONHPh), (NHCH2CH2OH,Ph,Me,Et,CONHPh), (NHCH2CH2OH, Ph,Me,Et,CONH-3-pyridyl), (NHCH2CH2OH,Ph,Me,Et, NHCOPh), (NHCH2CH2OH,Ph,Me,Et,NHCO-2-furyl), (NHCH2CH2OH,Ph,Me,Et,NHCONHPh), (NHCH2CH2OH,Ph,Me,Et,NHCOCONHPh), (NHCH2CH2OH,Ph,Me,CH2OH,CONHPh), (NHCH2CH2OH,Ph,Me,CH2OH,CONH-3-pyridyl), (NHCH2CH2OH,Ph,Me,CH2OH,NHCOPh), (NHCH2CH2OH,Ph,Me,CH2OH,NHCO-2-furyl), (NHCH2CH2OH,Ph,Me,CH2OH,NHCONHPh), (NHCH2CH2OH,Ph,Me,CH2OH,NHCOCONHPh), (NHCH2CH2OH,Ph,Ph,Me,CONHPh), (NHCH2CH2OH, Ph,Ph,Me,CONH-3-pyridyl), (NHCH2CH2OH,Ph,Ph,Me, NHCOPh), (NHCH2CH2OH,Ph,Ph,Me,NHCO-2-furyl), (NHCH2CH2O H,Ph,Ph,Me,NHCONHPh), (NHCH2CH2OH,Ph,Ph,Me,NHCOCONHPh), (NHCH2CH2OH,Ph,Ph,Et,CONHPh), (NHCH2CH2OH, Ph,Ph,Et,CONH-3-pyridyl), (NHCH2CH2OH,Ph,Ph,Et, NHCOPh), (NHCH2CH2OH,Ph,Ph,Et,NHCO-2-furyl), (NHCH2CH2OH,Ph,Ph,Et,NHCOHNPh), (NHCH2OH,Ph, Ph,Et,HNCOCONHPh), (NHCH2CH2OH,Ph,Ph,CH2OH, CONHPh), (NHCH2CH2OH,Ph,Ph,CH2OH,CONH-3-pyridyl), (NHCH2CH2OH,Ph,Ph,CH2O,NHCOPh), (NHCH2CH2OH,Ph,Ph,CH2OH,NHCO-2-furyl), (NHCH2CH2OH,Ph,Ph,CH2OH,NHCONHPh), (NHCH2CH2OH,Ph,Ph,CH2OH,NHCOCONHPh), (NHCH2CH2OH,Ph,OH,Me,CONHPh), (NHCH2CH2OH, Ph,OH,Me,CONH-3-pyridyl), (NHCH2CH2OH,Ph,OH, Me,NHCOPh), (NHCH2CH2OH,Ph,OH,Me,NHCO-2-furyl), (NHCH2CH2OH,Ph,OH,Me,NHCONHPh), (NHCH2CH2OH,Ph,OH,Me,NHCOCONHPh), (NHCH2CH2OH,Ph,OH,Et,CONHPh), (NHCH2CH2OH, Ph,OH,Et,CONH-3-pyridyl), (NHCH2CH2OH,Ph,OH,Et, NHCOPh), (NHCH2CH2OH,Ph,OH,Et,NHCO-2-furyl), (NHCH2CH2OH,Ph,OH,Et,NHCONHPh), (NHCH2CH2OH,Ph,OH,Et,NHCOCONHPh), (NHCH2CH2OH,Ph,OH,CH2OH,CONHPh), (NHCH2CH2OH,Ph,OH,CH2OH,CONH-3-pyridyl), (NHCH2CH2OH,Ph,OH,CH2OH,NHC)Ph), (NHCH2CH2OH,Ph,OH,CH2OH,NHCO-2-furyl), (NHCH2CH2OH,Ph,OH,CH2OH,NHCONHPh), (NHCH2CH2OH,Ph,OH,CH2OH,NHCOCONHPh), (NHCH2CONH2,H,H,Me,CONHPh), (NHCH2CONH2,H, H,Me,CONH-3-pyridyl), (NHCH2CONH2,H,H,Me,NH-COPh), (NHCH2CONH2,H,H,Me,NHCO-2-furyl), (NHCH2CONH2,H,H,Me,NHCONHPh), (NHCH2CONH2,H,H,Me,NHCOCONHPh), (NHCH2CONH2,H,H,Et,CONHPh), (NHCH2CONH2, H,Et,CONH-3-pyridyl), (NHCH2CONH2,H,H,Et,NH-COPh), (NHCH2CONH2,H,H,Et,NHCO2-2-furyl), (NHCH2CONH2,H,H,Et,NHCONHPh), (NHCH2CONH2, H,H,Et,NHCOCONHPh), (NHCH2CONH2,H,H,CH2OH, CONHPh), (NHCH2CONH2,H,H,CH2OH,CONH-3-pyridyl), (NHCH2CONH2,H,H,CH2OH,NHCOPh), (NHCH2CONH2,H,H,CH2OH,NHCO-2-furyl, (NHCH2CONH2,H,H,CH2OH,NHCONHPh), (NHCH2CONH2,H,H,CH2OH,NHCOCONHPh), (NHCH2CONH2,H,Me,Me,CONHPh), (NHCH2CONH2, H,Me,Me,CONH-3-pyridyl), (NHCH2CONH2,H,Me,Me, NHCOPh), (NHCH2CONH2,H,Me,Me,NHCO-2-furyl), (NHCH2CONH2,H,Me,Me,NHCONHPh), (NHCH2CONH2,H,Me,Me,NHCOCONHPh), (NHCH2CONH2,H,Me,Et,CONHPh), (NHCH2CONH2,H, Me,Et,CONH-3-pyridyl), (NHCH2CONH2,H,Me,Et,NH-COPh), (NHCH2CONH2,H,Me,Et,NHCO-2-furyl), (NHCH2CONH2,H,Me,Et,NHCONHPh), (NHCH2CONH2,H,Me,Et,NHCOCONHPh), (NHCH2CONH2,H,Me,CH2OH,CONHPh), (NHCH2CONH2CONH2OH,CONH-3-pyridyl), (NHCH2CONH2,H,Me,CH2OH,NHCOPh), (NHCH2CONH2,H,Me,CH2OH,NHCO-2-furyl), (NHCH2CONH2,H,Me,CH2OH,NHCONHPh), (NHCH2CONH2,H,Me,CH2OH,NHCOCONHPh), (NHCH2CONH2,H,Ph,Me,CONHPh), (NHCH2CONH2,H, Ph,Me,CONH-3-pyridyl), (NHCH2CONH2,H,Ph,Me,NH-COPh), (NHCH2CONH2,H,Ph,Me,NHCO-2-furyl), (NHCH2CONH2,H,Ph,Me,NHCONHPh, (NHCH2CONH2,H,Ph,Me,NHCOCONHPh), (NHCH2CONH2,H,Ph,Et,CONHPh), (NHCH2CONH2,H, Ph,Et,CONH-3-pyridyl), (NHCH2CONH2,H,Ph,Et,NH-COPh), (NHCH2CONH2,H,Ph,Et,NHCO-2-furyl), (NHCH2CONH2,H,Ph,Et,NHCONHPh), (NHCH2CONH2, H,Ph,Et,NHCOCONHPh), (NHCH2CONH2,H,Ph,CH2OH, CONHPh), (NHCH2CONH2,H,Ph,CH2OH,CONH-3-pyridyl), (NHCH2CONH2,H,Ph,CH2OH,NHCOPh), (NHCH2CONH2,H,Ph,CH2OH,NHCO-2-furyl), (NHCH2CONH2,H,Ph,CH2OH,NHCONHPh), (NHCH2CONH2,H,Ph,CH2OH,NHCOCONHPh), (NHCH2CONH2,H,OH,Me,CONHPh), (NHCH2CONH2, H,OH,Me,CONH-3-pyridyl), (NHCH2CONH2,H,OH,Me, NHCOPh), (NHCH2CONH2,H,OH,Me,NHCO-2-furyl), (NHCH2CONH2,H,OH,Me,NHCONHPh), (NHCH2CONH2,H,OH,Me,NHCOCONHPh), (NHCH2CONH2,H,OH,Et,CONHPh), (NHCH2CONH2,H, OH,Et,CONH$_3$-pyridyl), (NHCH2CONH2,H,OH,Et,NH-COPh), (NHCH2CONH2,H,OH,Et,NHCO-2-furyl), (NHCH2CONH2,H,OH,Et,NHCONHPh), (NHCH2CONH2,H,OH,Et,NHCOCONHPh), (NHCH2CONH2,H,OH,CH2OH,CONHPh), (NHCH2CONH2,H,OH,CH2OH,CONH-3-pyridyl), (NHCH2CONH2,H,OH,CH2OH,NHCOPh), (NHCH2CONH2,H,OH,CH2OH,NHCO-2-furyl), (NHCH2CONH2,H,OH,CH2OH,NHCONHPh), (NHCH2CONH2,H,OH,CH2OH,NHCOCONHPh),
(NHCH2CONH2,Me,H,Me,CONHPh), (NHCH2CONH2,Me,H,Me,CONH-3-pyridyl), (NHCH2CONH2,Me,H,Me,NHCOPh), (NHCH2CONH2,Me,H,Me,NHCO-2-furyl), (NHCH2CONH2,Me,H,Me,NHCONHPh)
(NHCH2CONH2,Me,H,Me,NHCOCONHPh),
(NHCH2CONH2,Me,H,Et,CONHPh), (NHCH2CONH2,Me,H,Et,CONH-3-pyridyl), (NHCH2CONH2,Me,H,Et,NHCOPh), (NHCH2CONH2,Me,H,Et,NHCO-2-furyl), (NHCH2CONH2,Me,H,Et,NHCONHPh),
(NHCH2CONH2,Me,H,Et,NHCOCONHPh),
(NHCH2CONH2,Me,H,CH2OH,CONHPh),
(NHCH2CONH2,Me,H,CH2OH,CONH-3-pyridyl),
(NHCH2CONH2,Me,H,CH2OH,NHCOPh),
(NHCH2CONH2,Me,H,CH2OH,NHCO-2-furyl),
(NHCH2CONH2,Me,H,CH2OH,NHCONHPh),
(NHCH2CONH2,Me,H,CH2OH,NHCOCONHPh),
(NHCH2CONH2,Me,Me,Me,CONHPh), (NHCH2CONH2,Me,Me,Me,CONH-3-pyridyl), (NHCH2CONH2,Me,Me,Me,NHCOPh), (NHCH2CONH2,Me,Me,Me,NHCO-2-furyl), (NHCH2CONH2,Me,Me,Me,NHCONHPh),
(NHCH2CONH2,Me,Me,Me,NHCOCONHPh),
(NHCH2CONH2,Me,Me,Et,CONHPh), (NHCH2CONH2,Me,Me,Et,CONH-3-pyridyl), (NHCH2CONH2,Me,Me,Et,NHCOPh), (NHCH2CONH2,Me,Me,Et,NHCO-2-furyl),
(NHCH2CONH2,Me,Me,Et,NHCONHPh),
(NHCH2CONH2,Me,Me,Et,NHCOCONHPh),
(NHCH2CONH2,Me,Me,CH2OH,CONEPh),
(NHCH2CONH2,Me,Me,CH2OH,CONH-3-pyridyl),
(NHCH2CONH2,Me,Me,CH2OH,NHCOPh),
(NHCH2CONH2,Me,Me,CH2OH,NHCO-2-furyl),
(NHCH2CONH2,Me,Me,CH2OH,NHCONHPh),
(NHCH2CONH2,Me,Me,CH2OH,NHCOCONHPh),
(NHCH2CONH2,Me,Ph,Me,CONHPh), (NHCH2CONH2,Me,Ph,Me,CONH-3-pyridyl), (NHCH2CONH2,Me,Ph,Me,NHCOPh), (NHCH2CONH2,Me,Ph,Me,NHCO-2-furyl),
(NHCH2CONH2,Me,Ph,Me,NHCONHPh),
(NHCH2CONH2,Me,Ph,Me,NHCOCONHPh),
(NHCH2CONH2,Me,Ph,Et,CONHPh), (NHCH2CONH2,Me,Ph,Et,CONH-3-pyridyl), (NHCH2CONH2,Me,Ph,Et,NHCOPh), (NHCH2CONH2,Me,Ph,Et,NHCO-2-furyl),
(NHCH2CONH2,Me,Ph,Et,NHCONHPh),
(NHCH2CONH2,Me,Ph,Et,NHCOCONHPh),
(NHCH2CONH2,Me,Ph,CH2OH,CONHPh),
(NHCH2CONH2,Me,Ph,CH2OH,CONH-3-pyridyl),
(NHCH2CONH2,Me,Ph,CH2OH,NHCOPh),
(NHCH2CONH2,Me,Ph,CH2OH,NHCO-2-furyl),
(NHCH2CONH2,Me,Ph,CH2OH,NHCONHPh),
(NHCH2CONH2,Me,Ph,CH2OH,NHCOCONHPh),
(NHCH2CONH2,Me,OH,Me,CONHPh), (NHCH2CONH2,Me,OH,Me,CONH-3-pyridyl), (NHCH2CONH2,Me,OH,Me,NHCOPh), (NHCH2CONH2,Me,OH,Me,NHCO-2-furyl), (NHCH2CONH2,Me,OH,Me,NHCONHPh),
(NHCH2CONH2,Me,OH,Me,NHCOCONHPh),
(NHCH2CONH2,Me,OH,Et,CONHPh), (NHCH2CONH2,Me,OH,Et,CONH-3-pyridyl), (NHCH2CONH2,Me,OH,Et,NHCOPh), (NHCH2CONH2,Me,OH,Et,NHCO-2-furyl),
(NHCH2CONH2,Me,OH,Et,NHCONHPh),
(NHCH2CONH2,Me,OH,Et,NHCOCONHPh),
(NHCH2CONH2,Me,OH,CH2OH,CONHPh),
(NHCH2CONH2,Me,OH,CH2OH,CONH-3-pyridyl),
(NHCH2CONH2,Me,OH, CH2OH,NHCOPh),
(NHCH2CONH2,Me,OH,CH2OH,NHCO-2-furyl),
(NHCH2CONH2,Me,OH,CH OH,NHCONHPh),
(NHCH2CONH2,Me,OH,CH2OH,NHCOCONHPh),
(NHCH2CONH2,Ph,H,Me,CONHPh), (NHCH2CONH2,Ph,H,Me,CONH-3-pyridyl), (NHCH2CON,H2,Ph,H,Me,NHCOPh), (NHCH2CONH2,Ph,H,Me,NHCO-2-furyl),
(NHCH2CONH2,Ph,H,Me,NHCONHPh),
(NHCH2CONH2,Ph,H,Me,NHCOCONHPh),
(NHCH2CONH2,Ph,H,Et,CONHPh), (NHCH2CONH2,Ph,H,Et,CONH-3-pyridyl), (NHCH2CONH2,Ph,H,Et,NHCOPh), (NHCH2CONH2,Ph,H,Et,NHCO-2-furyl),
(NHCH2CONH2,Ph,H,Et,NHCONHPh), (NHCH2CONH2,Ph,H,Et,NHCOCONHPh), (NHCH2CONH2,Ph,H,CH2OH,CONHPh), (NHCH2CONH2,Ph,H,CH2OH,CONH-3-pyridyl), (NHCH2CONH2,Ph,H,CH2OH,NHCOPh),
(NHCH2CONH2,Ph,H,CH2OH,NHCO-2-furyl,
(NHCH2CONH2,Ph,H,CH2OH,NHCONHPh),
(NHCH2CONH2,Ph,H,CH2OH,NHCOCONHPh),
(NHCH2CONH2,Ph,Me,Me,CONHPh), (NHCH2CONH2,Ph,Me,Me,CONH-3-pyridyl), (NHCH2CONH2,Ph,Me,Me,NHCOPh), (NHCH2CONH2,Ph,Me,Me,NHCO-2-furyl),
(NHCH2CONH2,Ph,Me,Me,NHCONHPh),
(NHCH2CONH2,Ph,Me,Me,NHCOCONHPh),
(NHCH2CONH2,Ph,Me,Et,CONHPh), (NHCH2CONH2,Ph,Me,Et,CONH-3-pyridyl), (NHCH2CONH2,Ph,Me,Et,NHCOPh), (NHCH2CONH2,Ph,Me,Et,NHCO-2-furyl),
(NHCH2CONH2,Ph,Me,Et,NHCONHPh),
(NHCH2CONH2,Ph,Me,Et,NHCOCONHPh),
(NHCH2CONH2,Ph,Me,CH2OH,CONHPh),
(NHCH2CONH2,Ph,Me,CH2OH,CONH-3-pyridyl),
(NHCH2CONH2,Ph,Me,CH2OH,NHCOPh),
(NHCH2CONH2,Ph,Me,CH2OH,NHCO-2-furyl),
(NHCH2CONH2,Ph,Me,CH2OH,NHCONPh),
(NHCH2CONH2,Ph,Me,CH2OH,NHCOCONHPh),
(NHCH2CONH2,Ph,Ph,Me,CONHPh), (NHCH2CONH2,Ph,Ph,Me,CONH-3-pyridyl), (NHCH2CONH,2,Ph,Ph,Me,NHCOPh), (NHCH2CONH2,Ph,Ph,Me,NHCO-2-furyl),
(NHCH2CONH2,Ph,Ph,Me,NHCONHPh),
(NHCH2CONH2,Ph,Ph,Me,NHCOCONHPh),
(NHCH2CONH2,Ph,Ph,Et,CONHPh), (NHCH2CONH2,Ph,Ph,Et,CONH-3-pyridyl), (NHCH2CONH2,Ph,Ph,Et,NHCOPh), (NHCH2CONH2,Ph,Ph,Et,NHCO-2-furyl),
(NHCH2CONH2,Ph,Ph,Et,NHCONHPh),
(NHCH2CONH2,Ph,Ph,Et,NHCOCONHPh),
(NHCH2CONH2,Ph,Ph,CH2OH,CONHPh),
(NHCH2CONH2,Ph,Ph,CH2OH,CONH-3-pyridyl),
(NHCH2CONH2,Ph,Ph,CH2OH,NHCOPh),
(NHCH2CONH2,Ph,Ph,CH2OH,NHCO-2-furyl),
(NHCH2CONH2,Ph,Ph,CH2OH,NHCONHPh),
(NHCH2CONH2,Ph,Ph,C H2OH,NHCOCONHPh),
(NHCH2CONH2,Ph,OH,Me,CONHPh), (NHCH2CONH2,Ph,OH,Me,CONH-3-pyridyl), (NHCH2CONH2,Ph,OH,Me,NHCOPh), (NHCH2CONH2,Ph,OH,Me,NHCO-2-furyl), (NHCH2CONH2,Ph,OH,Me,NHCONHPh),
(NHCH2CONH2,Ph,OH,Me,NHCOCONHPh),
(NHCH2CONH2,Ph,OH,Et,CONHPH), (NHCH2CONH2,Ph,OH,Et,CONH-3-pyridyl), (NHCH2CONH2,Ph,OH,Et,NHCOPh), (NHCH2CONH2,Ph,OH,Et,NHCO-2-fury),
(NHCH2CONH2,Ph,OH,Et,NHCONHPh),
(NHCH2CONH2,Ph,OH,Et,NHCOCONHPh),
(NHCH2CONH2,Ph,OH,CH2OH,CONHPh),
(NHCH2CONH2,Ph,OH,CH2OH-3-pyridyl),
(NHCH2CONH2,Ph,OH,Ch2OH,NHCOPh),
(NHCH2CONH2,Ph,OH,CH2OH,NHCO-2-furyl),
(NHCH2CONH2,Ph,OH,CH2OH,NHCONHPh),
(NHCH2CONH2,Ph,OH,CH2OH,NHCOCONHPh),
(NHCH(Bn)CONH2,H,H,Me,CONHPh), (NHCH(Bn)CONH2,H,H,Me,CONH-3-pyridyl), (NHCH(Bn)CONH2,H,H,Me,NHCOPh), (NHCH(Bn)CONH2,H,H,Me,NHCO-2-furyl), (NHCH(Bn)CONH2,H,H,Me,NHCONHPh),
(NHCH(Bn)CONH2,H,H,Me,NHCOCONHPh), (NHCH(Bn)CONH2,H,H,Et,CONHPh), (NHCH(Bn)CONH2,H,H, Et,CONH-3-pyridyl), (NHCH(Bn)CONH2,H,H,Et,NH-COPh), (NHCH(Bn)CONH2,H,H,Et,NHCO-2-furyl), (NHCH(Bn)CONH2,H,H,Et,NHCONHPh), (NHCHC(Bn)CONH2,H,H,Et,NHCOCONHPh), (NHCH(Bn)CONH2,H,H,CH2OH,CONHPh), (NHCH(Bn)CONH2,H,H,CH2OH,CONH-3-pyridyl), (NHCH(Bn)CONH2,H,H,CH2OH,NHCOPh), (NHCH(Bn)CONH2,H,H,CH2OH,NHCO-2-furyl), (NHCH(Bn)CONH2,H,H,CH2OH,NHCONHPh), (NHCH(Bn)CONH2,H,H,CH2OH,NHCOCONHPh), (NHCH(Bn)CONH2,H,Me,Me,CONHPh), (NHCH(Bn)CONH2,H,Me,Me,CONH-3-pyridyl), (NHCHCBn)CONH2,H,Me,Me,NHCOPh), (NHCH(Bn)CONH2,H,Me,Me,NHCO-2-furyl), (NHCH(Bn)CONH2,H,Me,Me,NHCONHPh), (NHCH(Bn)CONH2,H,Me,Me,NHCOCONHPh), (NHCH(Bn)CONH2,H,Me,Et,CONHPh), (NHCH(Bn)CONH2,H,Me,Et,CONH-3-pyridyl), (NHCH(Bn)CONH2,H,Me,Et,NHCOPh), (NHCH(Bn)CONH2,H,Me,Et,NHCO-2-furyl), (NHCH(Bn)CONH2,H,Me,Et,NHCONHPh), (NHCH(Bn)CONH2,H,Me,Et,NHCOCONHPh), (NHCH(Bn)CONH2,H,Me,CH2OH,CONHPh), (NHCH(Bn)CONH2,H,Me,CH2OH,CONH-3-pyridyl), (NHCH(Bn)CONH2,H,Me,CH2OH,NHCOPh), (NHCH(Bn)CONH2,H,Me,CH2OH,NHCO-2-furyl), (NHCH(Bn)CONH2,H,Me,CH2OH,NHCONHPh), (NHCH(Bn)CONH2,H,Me,CH2OH,NHCOCONHPh), (NHCH(Bn)CONH2,H,Ph,Me,CONHPh), (NHCH(Bn)CONH2,H,Ph,Me,CONH-3-pyridyl), (NHCH(Bn)CONH2,H,Ph,Me,NHCOPh), (NHCH(Bn)CONH2,H,Ph,Me,NHCO-2-furyl), (NHCH(Bn)CONH2,H,Ph,Me,NHCONHPh), (NHCH(Bn)CONH2,H,Ph,Me,NHCOCONHPh), (NHCH(Bn)CONH2,H,Ph,Et,CONHPh), (NHCH(Bn)CONH2,H,Ph,Et,CONH-3-pyridyl), (NHCH(Bn)CONH2,H,Ph,Et,NHCOPh), (NHCH(Bn)CONH2,H,Ph,Et,NHCO-2-furyl), (NHCH(Bn)CONH2,H,Ph,Et,NHCONHPh), (NHCH(Bn)CONH2,H,Ph,Et,NHCOCONHPh), (NHCH(Bn)CONH2,H,Ph,CH2OH,CONHPh), (NHCH(Bn)CONH2,H,Ph,CH2OH,CONH-3-pyridyl), (NHCH(Bn)CONH2,H,Ph,CH2OH,NHCOPh), (NHCH(Bn)CONH2,H,Ph,CH2OH,NHCO-2-furyl), (NHCH(Bn)CONH2,H,Ph,CH2OH,NHCONHPh), (NHCH(Bn)CONH2,H,Ph,CH2OH,NHCOCONHPh), (NHCH(Bn)CONH2,H,OH,Me,CONHPh), (NHCHC(Bn)CONH2,H,OH,Me,CONH-3-pyridyl), (NHCH(Bn)CONH2,H,OH,Me,NHCOPh), (NHCH(Bn)CONH2,H,OH,Me,NHCO-2-furyl), (NHCH(Bn)CONH2,H,OH,Me,NHCONHPh), (NHCH(Bn)CONH2,H,OH,Me,NHCOCONHPh), (NHCH(Bn)CONH2,H,OH,Et,CONHPh), (NHCH(Bn)CONH2,H,OH,Et,CONH-3-pyridyl), (NHCHC(Bn)CONH2,H,OH,Et,NHCOPh), (NHCH(Bn)CONH2,H,OH,Et,NHCO-2-fury), (NHCH(Bn)CONH2,H,OH,Et,NHCONHPh), (NHCH(Bn)CONH2,H,OH,Et,NHCOCONHPh), (NHCH(Bn)CONH2,H,OH,CH2OH,CONHPh), (NHCH(Bn)CONH2,H,OH,CH2OH,CONH-3-pyridyl), (NHCH(Bn)CONH2,H,OH,CH2OH,NHCOPh), (NHCH(Bn)CONH2,H,OH,CH2OH,NHCO-2-furyl), (NHCH(Bn)CONH2,H,OH,CH2OH,NHCONHPh), (NHCH(Bn)CONH2,H,OH,CH2OH,NHCOCONHPh), (NHCH(Bn)CONH2,Me,H,Me,CONHPh), (NHCH(Bn)CONH2,Me,H,Me,CONH-3-pyridyl), (NHCH(Bn)CONH2,Me,H,Me,NHCOPh), (NHCH(Bn)CONH2,Me,H,Me,NHCO-2-furyl), (NHCH(Bn)CONH2,Me,H,Me,NHCONHPh), (NHCH(Bn)CONH2Me,H,Me,NHCOCONHPh), (NHCH(Bn)CONH2,Me,H,Et,CONHPh), (NHCH(Bn)CONH2,Me,H,Et,CONH-3-pyridyl), (NHCH(Bn)CONH2,Me,H,Et,NHCOPh), (NHCH(Bn)CONH2,Me,H,Et,NHCO2-furyl), (NHCH(Bn)CONH2,Me,H,Et,NHCONHPh), (NHCH(Bn)CONH2,Me,H,Et,NHCOCONHPh), (NHCH(Bn)CONH2,Me,H,CH2OH,CONHPh), (NHCH(Bn)CONH2,Me,H,CH2OH,CONH-3-pyridyl), (NHCH(Bn)CONH2,Me,H,CH2OH,NHCOPh), (NHCH(Bn)CONH2,Me,H,CH2OH,NHCO-2-furyl), (NHCH(Bn)CONH2,Me,H,CH2OH,NHCONHPh), (NHCH(Bn)CONH2,Me,H,CH2OH,NHCOCONHPh), (NHCH(Bn)CONH2,Me,Me,Me,CONHPh), (NHCH(Bn)CONH2,Me,Me,Me,CONH-3-pyridyl), (NHCH(Bn)CONH2,Me,Me,Me,NHCOPh), (NHCH(Bn)CONH2,Me,Me,Me,NHCO-2-furyl), (NHCH(Bn)CONH2,Me,Me,Me,NHCONHPh), (NHCH(Bn)CONH2,Me,Me,Me,NHCOCONHPh), (NHCH(Bn)CONH2,Me,Me,Et,CONHPh), (NHCH(Bn)CONH2,Me,Me,Et,CONH-3-pyridyl), (NHCH(Bn)CONH2,Me,Me,Et,NHCOPh), (NHCH(Bn)CONH2,Me,Me,Et,NHCO-2-furyl), (NHCH(Bn)CONH2,Me,Me,Et,NHCONHPh), (NHCH(Bn)CONH2,Me,Me,Et,NHCOCONHPh), (NHCH(Bn)CONH2,Me,Me,CH2OH,CONHPh), (NHCH(Bn)CONH2,Me,Me,CH2OH,CONH-3-pyridyl), (NHCH(Bn)CONH2,Me,Me,CH2OH,NHCOPh), (NHCH(Bn)CONH2,Me,Me,CH2OH,NHCO-2-furyl), (NHCH(Bn)CONH2,Me,Me,CH2OH,NHCONHPh), (NHCH(Bn)CONH2,Me,Me,CH2OH,NHCOCONHPh), (NHCH(Bn)CONH2,Me,Ph,Me,CONHPh), (NHCH(Bn)CONH2,Me,Ph,Me,CONH-3-pyridyl), (NHCH(Bn)CONH2,Me,Ph,Me,NHCOPh), (NHCH(Bn)CONH2,Me,Ph,Me,NHCO-2-furyl), (NHCH(Bn)CONH2,Me,Ph,Me,NHCONHPh), (NHCH(Bn)CONH2,Me,Ph,Me,NHCOCONHPh), (NHCH(Bn)CONH2,Me,Ph,Et,CONHPh), (NHCH(Bn)CONH2,Me,Ph,Et,CONH-3-pyridyl), (NHCH(Bn)CONH2,Me,Ph,Et,NHCOPh), (NHCH(Bn)CONH2,Me,Ph,Et,NHCO-2-furyl), (NHCH(Bn)CONH2,Me,Ph,Et,NHCONHPh), (NHCH(Bn)CONH2,Me,Ph,Et,NHCOCONHPh), (NHCH(Bn)CONH2,Me,Ph,CH2OH,CONHPh), (NHCH(Bn)CONH2,Me,Ph,CH2OH,CONH-3-pyridyl), (NHCH(Bn)CONH2,Me,Ph,CH2OH,NHCOPh), (NHCH(Bn)CONH2,Me,Ph,CH2OH,NHCO-2-furyl), (NHCH(Bn)CONH2,Me,Ph,CH2OH,NHCONHPh), (NHCH(Bn)CONH2,Me,Ph,CH2OH,NHCOCONHPh), (NHCH(Bn)CON H2,Me,OH,Me,CONHPh), (NHCH(Bn)CONH2,Me,OH,Me,CONH-3-pyridyl), (NHCH(Bn)CONH2,Me,OH,Me,NHCOPh), (NHCH(Bn)CONH2,Me,OH,Me,NHCO-2-furyl), (NHCH(Bn)CONH2,Me,OH,Me,NHCONHPh), (NHCH(Bn)CONH2,Me,OH,Me,NHCOCONHPh, CONH2,Me,OH,Et,CONHPh), (NHCH(Bn)CONH2,Me,OH,Et,CONH-3-pyridyl), (NHCH(Bn)CONH2,Me,OH,Et,NHCOPh), (NHCH(Bn)CONH2,Me,OH,Et,NHCO-2-furyl), (NHCH(Bn)CONH2,Me,OH,Et,NHCONHPh), (NHCH(Bn)CONH2,Me,OH,Et,NHCOCONHPh), (NHCH(Bn)CONH2,Me,OH,CH2OH,CONHPh), (NHCH(Bn)CONH2,Me,OH,CH2OH,CONH-3-pyridyl), (NHCH(Bn)CONH2,Me,OH,CH2OH,NHCOPh), (NHCH(Bn)CONH2,Me,OH,CH2OH,NHCO-2-furyl), (NHCH(Bn)CONH2,Me,OH,CH2OH,NHCONHPh), (NHCH(Bn),CONH2,Me,OH,CH2O H,NHCOCONHPh), (NHCH(Bn)CONH2,Ph,H,Me,CONPh), (NHCH(Bn)CONH2,Ph,H,Me,CONH-3-pyridyl), (NHCH(Bn)CONH2,Ph,H,Me,NHCOPh), (NHCH(Bn)CONH2,Ph,H,Me,NHCO-2-furyl), (NHCH(Bn)CONH2,Ph,H,Me,NHCONHPh), (NHCH(Bn)CONH2,Ph,H,Me,NHCOCONHPh), (NHCH(Bn)CONH2,Ph,H,Et,CONHPh), (NHCH(Bn)CONH2,Ph,H,Et,CONH-3-pyridyl), (NHCH(Bn)CONH2,Ph,H,Et,NHCOPh), (NHCH(Bn)CONH2,Ph,H,Et,NHCO2-furyl), (NHCH(Bn)CONH2,Ph,H,Et,NHCONHPh), (NHCH(Bn)CONH2,Ph,H,Et,NHCOCONHPh), (NHCH(Bn)CONH2,Ph,H,CH2OH,CONHPh), (NHCH(Bn)CONH2,Ph,H,CH2OH,CONH-3-pyridyl), (NHCH(Bn)CONH2,Ph,H,CH2OH,NHCOPh), (NHCH(Bn)CONH2,Ph,H,CH2OH,NHCO-2-furyl), (NHCH(Bn)CONH2,PH,H, CH2OH,NHCONHPh), (NHCH(Bn)CONH2,Ph,H, CH2OH,NHCOCONHPh), (NHCH(Bn)CONH2,Ph,Me, Me,CONHPh), (NHCH(Bn)CONH2,Ph,Me,Me,CONH-3-pyridyl), (NHCH(Bn)CONH2,Ph,Me,Me,NHCOPh), (NHCH(Bn)CONH2,Ph,Me,Me,NHCO-2-furyl), (NHCH(Bn)CONH2,Ph,Me,Me,NHCONHPh), (NHCH(Bn)CONH2,Ph,Me,Me,NHCOCONHPh), (NHCH(Bn)CONH2,Ph,Me,Et,CONHPh), (NHCH(Bn)CONH2,Ph,Me,Et,CONH-3-pyridyl), (NHCH(Bn)CONH2,Ph,Me,Et,NHCOPh), (NHCH(Bn)CONH2,Ph,Me,Et,NHCO-2-furyl), (NHCH(Bn)CONH2,Ph,Me,Et,NHCONHPh), (NHCH(Bn)CONH2,Ph,Me,Et,NHCOCONHPh), (NHCH(Bn)CONH2,Ph,Me,CH2OH,CONHPh), (NHCH(Bn)CONH2,Ph,Me,CH2OH,CONH-3-pyridyl), (NHCH(Bn)CONH2,Ph,Me,CH2OH,NHCOPh), (NHCH(Bn)CONH2,Ph,Me,CH2OH,NHCO-2-furyl), (NHCH(Bn)CONH2,Ph,Me,CH2OH,NHCONHPh), (NHCH(Bn)CONH2,Ph,Me,CH2OH,NHCOCONHPh), (NHCH(Bn)CONH2,Ph,Ph,Me,CONHPh), (NHCH(Bn)CONH2,Ph,Ph,Me,CONH-3-pyridyl), (NHCH(Bn)CONH2,Ph,Ph,Me,NHCOPh), (NHCH(Bn)CONH2,Ph,Ph,Me,NHCO-2-furyl), (NHCH(Bn)CONH2,Ph,Ph,Me,NHCONHPh), (NHCH(Bn)CONH2,Ph,Ph,Me,NHCOCONHPh), (NHCH(Bn)CONH2,Ph,Ph,Et,CONHPh), (NHCH(Bn)CONH2,Ph,Ph,Et,CONH-3-pyridyl), (NHCH(Bn)CONH2,Ph,Ph,Et,NHCOPh), (NHCH(Bn)CONH2,Ph,Ph,Et,NHCO-2-furyl), (NHCH(Bn)CONH2,Ph,Ph,Et,NHCONHPh), (NHCH(Bn)CONH2,Ph,Ph,Et,NHCOCONHPh), (NHCH(Bn)CONH2,Ph,Ph,CH2OH,CONHPh), (NHCH(Bn)CONH2,Ph,Ph,CH2OH,CONH-3-pyridyl), (NHCH(Bn)CONH2,Ph,Ph,CH2OH,NHCOPh), (NHCH(Bn)CONH2,Ph,Ph,CH2OH,NHCO-2-furyl), (NHCH(Bn)CONH2,Ph,Ph,CH2OH,NHCONHPh), (NHCH(Bn)CONH2,Ph,Ph,CH2OH,NHCOCONHPh), (NHCH(Bn)CONH2,P h,OH,Me,CONHPh), (NHCH(Bn)CONH2,Ph,OH,Me,CONH-3-pyridyl), (NHCH(Bn)CONH2,Ph,OH,Me,NHCOPh), (NHCH(Bn)CONH2,Ph,OH,Me,NHCO-2-furyl), (NHCH(Bn)CONH2,Ph,OH,Me,NHCONHPh), (NHCH(Bn)CONH2,Ph,OH,Me,NHCOCONHPh), (NHCH(Bn)CONH2,Ph,OH,Et,CONHPh), (NHCH(Bn)CONH2,Ph,OH,Et,CONH-3-pyridyl, (NHCH(Bn)CONH2,Ph,OH,Et,NHCOPh), (NHCH(Bn)CONH2,Ph,OH,Et,NHCO-2-furyl), (NHCH(Bn)CONH2,Ph,OH,Et,NHCONHPh), (NHCH(Bn)CONH2,Ph,OH,Et,NHCOCONHPh), (NHCH(Bn)CONH2,Ph,OH,CH2OH,CONHPh), (NHCH(Bn)CONH2,Ph,OH,CH2OH,CONH-3-pyridyl), (NHCH(Bn)CONH2,Ph,OH,CH2OH,NHCOPh), (NHCH(Bn)CONH2,Ph,OH,CH2OH,NHCO-2-furyl), (NHCHC(Bn)CONH2,Ph,OH,CH2OH,NHCONHPh), (NHCH(Bn)CONH2,Ph,OH,CH2OH,NHCOCONHPh),
(NHCH(Me)CH2OH,H,H,Me,CONHPh), (NHCH(Me)CH2OH,H,H,Me,CONH-3-pyridyl), (NHCH(Me)CH2OH,H,H,Me,NHCOPh), (NHCH(Me)CH2OH,H,H,Me,NHCO-2-furyl), (NHCH(Me)CH2OH,H,H,Me,NHCONHPh), (NHCH(Me)CH2OH,H,H,Me,NHCOCONHPh), (NHCH(Me)CH2OH,H,H,Et,CONHPh), (NHCH(Me)CH2OH,H,H,Et,CONH-3-pyridyl), (NHCH(Me)CH2OH,H,H,Et,NHCOPh), (NHCH(Me)CH2OH,H,H,Et,NHCO-2-furyl), (NHCH(Me)CH2OH,H,H,Et,NHCONHPh), (NHCH(Me)CH2OH,H,H,Et,NHCOCONHPh), (NHCH(Me)CH2OH,H,H,CH2OH,CONHPh), (NHCH(Me)CH2OH,H,H,CH2OH,CONH 3-pyridyl), (NHCH(Me)CH2OH,H,H,CH2OH,NHCOPh), (NHCH(Me)CH2OH,H,H,CH2OH,NHCO-2-furyl), (NHCH(Me)CH2OH,H,H,CH2OH,NHCONHPh), (NHCH(Me)CH2OH,H,H,CH2OH,NHCOCONHPh), (NHCH(Me)CH2OH,H,Me,Me,CONHPh), (NHCH(Me)CH2OH,H,Me,Me,CONH-3-pyridyl), (NHCH(Me)CH2OH,H,Me,Me,NHCOPh), (NHCH(Me)CH2OH,H,Me,Me,NHCO-2-furyl), (NHCH(Me)CH2OH,H,Me,Me,NHCONHPh), (NHCH(Me)CH2OH,H,Me,Me,NHCOCONHPh), (NHCH(Me)CH2OH,H,Me,Et,CONHPh), (NHCH(Me)CH2OH,H,Me,Et,CONH-3-pyridyl), (NHCH(Me)CH2OH,H,Me,Et,NHCOPh), (NHCH(Me)CH2OH,H,Me,Et,NHCO-2-furyl), (NHCH(Me)CH2OH,H,Me,Et,NHCONHPh), (NHCH(Me)CH2OH,H,Me,Et,NHCOCONHPh), (NHCH(Me)CH2OH,H,Me,CH2OH,CONHPh), (NHCH(Me)CH2OH,H,Me,CH2OH,CONH-3-pyridyl), (NHCH(Me)CH2OH,H,Me,CH2OH,NHCOPh), (NHCH(Me)CH2OH,H,Me,CH2OH,NHCO-2-furyl), (NHCH(Me)CH2OH,H,Me,CH2OH,NHCONHPh), (NHCH(Me)CH2OH,H,Me,CH2OH,NHCOCONHPh), (NHCH(Me)CH2OH,H,Ph,Me,CONHPh), (NHCH(Me)CH2OH,H,Ph,Me,CONH-3-pyridyl), (NHCH(Me)CH2OH,H,Ph,Me,NHCOPh), (NHCH(Me)CH2OH,H,Ph,Me,NHCO-2-furyl), (NHCH(Me)CH2OH,H,Ph,Me,NHCONHPh), (NHCH(Me)CH2OH,H,Ph,Me,NHCOCONHPh), (NHCH(Me)CH2OH,H,Ph,Et,CONHPh), (NHCH(Me)CH2OH,H,Ph,Et,CONH-3-pyridyl), (NHCH(Me)CH2OH,H,Ph,Et, (NHCOPh), (NHCH(Me)CH20H,H,Ph,Et,NHCO-2-furyl), (NHCH(Me)CH2OH,H,Ph,Et,NHCONHPh), (NHCH(Me)CH2OH,H,Ph,Et,NHCOCONHPh), (NHCH(Me)CH2OH,H,Ph,CH2OH,CONHPh), (NHCH(Me)CH2OH,H,Ph,CH2OH,CONH-3-pyridyl), (NHCH(Me)CH2OH,H,Ph,CH2OH,NHCOPh), (NHCH(Me)CH2OH,H,Ph,CH2OH,NHCO-2-furyl), (NHCH(Me)CH2OH,H,Ph,CH2OH,NHCONHPh), (NHCH(Me)CH2OH,H,Ph,CH2OH,NHCOCONHPh), (NHCH(Me)CH2OH,H,OH,Me,CONHPh), (NHCH(Me)CH2OH,H,OH,Me,CONH-3-pyridyl), (NHCH(Me)CH2OH,H,OH,Me,NHCOPh), (NHCH(Me)CH2OH,H,OH,Me,NHCO-2-furyl), (NHCH(Me)CH2OH,H,OH,Me,NHCONHPh), (NHCH(Me)CH2OH,H,OH,Me,NHCOCONHPh), (NCH(Me)CH2OH,H,OH,Et,CONHPh), (NHCH(Me)CH2OH,H,OH,Et,CONH-3-pyridyl), (NHCH(Me)CH2OH,H,OH,Et,NHCOPh), (NHCH(Me)CH2OH,H,OH,Et,NHCO-2-furyl), (NHCH(Me)CH2OH,H,OH,Et,NH-CONHPh), (NHCH(Me)CH2OH,H,OH,Et,NHCOCONHPh), (NHCH(Me)CH2OH,H,OH,CH2OH,CONHPh), (NHCH(Me)CH2OH,H,OH,CH2OH,CONH-3-pyridyl), (NHCH(Me)CH2OH,H,OH,CH2OH,NHCOPh), (NHCH(Me)CH2OH,H,OH,CH2OH,NHCO-2-furyl), (NHCH(Me)CH2OH,H,OHCH2OH,NHCONHPh), (CNHCH(Me)CH2OH,H,OHOCH2OH,NHCOCONHPh), (NHCH(Me)CH2OH,Me,H,Me,CONHPh), (NHCH(Me)CH2OH,Me,H,Me,CONH-3-pyridyl), (NHCH(Me)CH2OH,Me,H,Me,NHCOPh), (NHCH(Me)CH2OH,Me,H,Me,NHCO-2-furyl), (NHCH(Me)CH2OH,Me,H,Me,NHCONHPh), (NHCH(Me)CH2OH,Me,H,Me,NHCOCONHPh), (NHCH(Me)CH2OH,Me,H,Et,CONHPh), (NHCH(Me)CH2OH,Me,H,Et,CONH-3-pyridyl), (NHCH(Me)CH2OH,Me,H,Et,NHCOPh), (NHCHC(Me)CH2OH,Me,H,Et,NHCO-2-furyl), (NHCH(Me)CH2OH,Me,H,Et,NHCONHPh), (NHCH(Me)CH2OH,Me,H,Et,NHCOCONHPh), (NHCH(Me)CH2OH,Me,H,CH2OH,CONHPh), (NHCH(Me)CH2OH,Me,H,CH2OH,CONH-3-pyridyl), (NHCH(Me)CH2OH,Me,H,CH2OH,NHCOPh), (NHCH(Me)CH2OH,Me,H,CH2OH,NHCO-2-furyl), (NHCHCMe)CH2OH,Me,H,CH2OH,NHCONHPh), (NHCH(Me)CH2OH,Me,H,CH2OH,NHCOCONHPh), (NHCH(Me)CH2OH,Me,Me,Me,CONHPh), (NHCH(Me)CH2OH,Me,Me,Me,CONH-3-pyridyl), (CNHCH(Me)CH2OH,Me,Me,Me,NHCOPh), (NHCH(Me)CH2OH,Me,Me,Me,NHCO-2-furyl), (NHCH(me)CH2OH,Me,Me,Me,NHCONHPh), (NHCH(Me)

CH2OH,Me,Me,Me,NHCOCONHPh), (NHCH(Me) CH2OH,Me,Me,Et,CONHPh), (NHCH(Me)CH2OH,Me, Me,Et,CONH-3-pyridyl), (NHCH(Me)CH2OH,Me,Me,Et, NHCOPh), (NHCH(Me)CH2OH,Me,Me,Et,NHCO-2-furyl), (NHCH(Me)CH2OH,Me,Me,Et,NHCONHPh), (NHCH(Me)CH2OH,Me,Me,Et,NHCOCONHPh), (NHCH(Me)CH2OH,Me,Me,CH2OH,CONHPh), (NHCH(Me) CH2OH,Me,Me,CH2OH,CONH-3-pyridyl), (NHCH(Me) CH2OH,Me,Me,CH2OH,NHCOPh), (NHCH(Me)CH2OH, Me,Me,CH2OH,NHCO-2-furyl), (NHCH(Me)CH2OH,Me, Me,CH2OH,NHCONHPh), (NHCH(Me)CH2OH,Me,Me, CH2OH,NHCOCONHPh), (NHCH(Me)CH2OH,Me,Ph, Me,CONHPh), (NHCH(Me)CH2OH,Me,Ph,Me,CONH-3-pyridyl), (NHCH(Me)CH2OH,Me,Ph,Me,NHCOPh), (NHCH(Me)CH2OH,Me,Ph,Me,NHCO-2-furyl), (NHCH(Me)CH2OH,Me,Ph,Me,NHCONHPh), (NHCH(Me) CH2OH,Me,Ph,Me,NHCOCONHPh), (NHCH(Me) CH2OH,Me,Ph,Et,CONHPh), (NHCH(Me)CH2OH,Me,Ph, Et,CONH-3-pyridyl), (NHCH(Me)CH2OH,Me,Ph,Et, NHCOPh), (NHCH(Me)CH2OH,Me,Ph,Et,NHCO-2-furyl), (NHCH(Me)CH2OH,Me,Ph,Et,NHCONHPh), (NHCH(Me)CH2OH,Me,Ph,Et,NHCOCONHPh), (NHCHC(Me) CH2OH,Me,Ph,CH2OH,CONHPh), (NHCH(Me)CH2OH, Me,Ph,CH2OH,CONH-3-pyridyl), (NHCH(Me)CH2OH, Me,Ph,CH2OH,NHCOPh), (NHCH(Me)CH2OH,Me,Ph, CH2OH,NHCO-2-furyl), (NHC H(Me)CH2OH,Me,Ph, CH2OH,NHCONHPh), (NHCH(Me)CH2OH,Me,Ph, CH2OH,NHCOCONHPh), (NHCH(Me)CH2OH,Me,OH, Me,CONHPh), (NHCH(Me)CH2OH,Me,OH,Me,CONH-3-pyridyl), (NHCH(Me)CH2OH,Me,OH,Me,NHCOPh), (NHCH(Me)CH2OH,Me,OH,Me,NHCO-2-furyl), (NHCH(Me)CH2OH,Me,OH,Me,NHCONHPh), (NHCH(Me) CH2OH,Me,OH,Me,NHCOCONHPh), (NHCH(Me) CH2OH,Me,OH,Et,CONHPh), (NHCH(Me)CH2OH,Me, OH,Et,CONH-3-pyridyl), (NHCH(Me)CH2OH,Me,OH,Et, NHCOPh), (NHCH(Me)CH2OH,MeOH,Et,NHCO-2-furyl), (NHCH(Me)CH2OH,Me,OH,Et,NHCONHPh), (NHCH(Me)CH2OH,Me,OH,Et,NHCOCONHPh), (NHCH(Me)CH2OH,Me,OH,CH2OH,CONHPh), (NHCH(Me) CH2OH,Me,OH,CH2OH,CONH-3-pyridyl), (NHCH(Me) CH2OH,Me,OH,CH2OH,NHCOPh), (NHCH(Me)CH2OH, Me,OH,CH2OH,NHCO-2-furyl), (NHCH(Me)CH2OH,Me, OH,CH2OH,NHCONHPh), (NHCH(Me)CH2OH,Me, OH,CH2OH,NHCOCONHPh), (NHCH(Me)CH2OH,Ph,H,Me, CONHPh), (NHCH(Me)CH2OH,Ph,H,Me,CONH-3-pyridyl), (NHCH(Me)CH2OH,Ph,H,Me,NHCOPh), (NHCH(Me)CH2OH,Ph,H,Me,NHCO-2-furyl), (NHCH(Me)CH2OH,Ph,H,Me,NHCONHPh), (NHCH(Me) CH2OH,Ph,H,Me,NHCOCONHPh), (NHCH(Me)CH2OH, Ph,H,Et,CONHPh), (NHCH(Me)CH2OH,Ph,H,Et,CONH-3-pyridyl), (NHCH(Me)CH2OH,Ph,H,Et,NHCOPh), (NHCH(Me)CH2OH,Ph,H,Et,NHCO-2-furyl), (NHCHC(Me)CH2OH,Ph,H,Et,NHCONHPh), (NHCH(Me)CH2OH, Ph,H,Et,NHCOCONHPh), (NHCH(Me)CH2OH,PhH, CH2OH,CONHPh), (NHCH(Me)CH2OH,Ph,H,CH2OH, CONH-3-pyridyl), (NHCH(Me)CH2OH,Ph,H,CH2OH, NHCOPh), (NHCH(Me)CH2OH,Ph,H,CH2OH,NHCO-2-furyl), (NHCH(Me)CH2OH,Ph,H,CH2OH,NHCONHPh), (NHCH(Me)CH2OH,Ph,H,CH2OH,NHCOCONHPh), (NHCH(Me)CH2OH,Ph,Me,Me,CONHPh), (NHCH(Me) CH2OH,Ph,Me,Me,CONH-3-pyridyl), (NHCH(Me) CH2OH,Ph,Me,Me,NHCOPh), (NHCH(Me)CH2OH,Ph, Me,Me,NHCO-2-furyl), (NHCH(Me)CH2OH,Ph,Me,Me, NHCONHPh), (NHCH(Me)CH2OH,Ph,Me,Me, NHCOCONHPh), (NHCH(Me)CH2OH,Ph,Me,Et, CONHPh), (NHCH(Me)CH2OH,Ph,Me,Et,CONH-3-pyridyl), (NHCH(Me)CH2OH,Ph,Me,Et,NHCOPh), (NHCH(Me)CH2OH,Ph,Me,Et,NHCO-2-furyl), (NHCH(Me)CH2OH,Ph,Me,Et,NHCONHPh), (NHCH(Me) CH2OH,Ph,Me,Et,NHCOCONHPh), (NHCH(Me)CH2OH, Ph,Me,CH2OH,CONHPh), (NHCH(Me)CH2OH,Ph,Me, CH2OH,CONH-3-pyridyl), (NHCH(Me)CH2OH,Ph,Me, CH2OH,NHCOPh), (NHCH(Me)CH2OH,Ph,Me,CH2OH, NHCO-2-furyl), (NHCH(Me)CH2OH,Ph,Me,CH2OH, NHCONHPh), (NHCH(Me)CH2OH,Ph,Me,CH2OH, NHCOCONHPh), (NHCH(Me)CH2OH,Ph,Ph,Me, CONHPh), (NHCH(Me)CH2OH,Ph,Ph,Me,CONH-3-pyridyl), (NHCH(Me)CH2OH,Ph,Ph,Me,NHCOPh), (NHCH(Me)CH2OH,Ph,Ph,Me,NHCO-2-furyl), (NHCH(Me)CH2OH,Ph,Ph,Me,NHCONHPh), (NHCH(Me) CH2OH,Ph,Ph,Me,NHCOCONHPh), (NHCH(Me)CH2OH, Ph,Ph,Et,CONHPh), (NHCH(Me)CH2OH,Ph,Ph,Et, CONH-3-pyridyl), (NHCH(Me)CH2OH,Ph,Ph,Et, NHCOPh), (NHCH(Me)CH2OH,Ph,Ph,Et,NHCO-2-furyl), (NHCH(Me)CH2OH,Ph,Ph,Et,NHCONHPh), (NHCH(Me) CH2OH,Ph,Ph,Et,NHCOCONHPh), (NHCH(Me)CH2OH, Ph,Ph,CH2OH,CONHPh), (NHCH(Me)CH2OH,Ph,Ph, CH2OH,CONH-3-pyridyl), (NHCH(Me)CH2OH,Ph,Ph, CH2OH,NHCOPh), (NHCH(Me)CH2OH,Ph,Ph,CH2OH, NHC O-2-furyl), (NHCH(Me)CH2OH,Ph,Ph,CH2OH, NHCONHPh), (NHCH(Me)CH2OH,Ph,Ph,CH2OH, NHCOCONHPh), (NHCH(Me)CH2OH,Ph,OH,Me, CONHPh), (NHCH(Me)CH2OH,Ph,OH,Me,CONH-3-pyridyl), (NHCH(Me)CH2OH,Ph,OH,Me,NHCOPh), (NHCH(Me)CH2O-Ph,OH,Me,NHCO-2-furyl), (NHCH(Me)CH2OH,Ph,OH,Me,NHCONHPh), (NHCH(Me) CH2OH,Ph,OH,Me,NHCOCONHPh), (NHCH(Me) CH2OH,Ph,OH,Et,CONHPh), (NHCH(Me)CH2OH,Ph, OH,Et,CONH-3-pyridyl), (NHCH(Me)CH2OH,Ph,OH,Et, NHCOPh), (NHCH(Me)CH2OH,Ph,OH,Et,NHCO-2-furyl), (NHCH(Me)CH2OH,Ph,OH,Et,NHCONHPh), (NHCH(Me)CH2OH,Ph,OH,Et,NHCOCONHPh), (NHCH(Me) CH2OH,Ph,OH,CH2OH,CONHPh), (NHCH(Me) CH2OH,Ph,OH,CH2OH,CONH-3-pyridyl), (NHCH(Me) CH2OH,Ph,OH,CH2OH,NHCOPh), (NHCH(Me)CH2OH, Ph,OH,CH2OH,NHCO-2-furyl), (NHCH(Me)CH2OH,Ph, OH,CH2OH,NHCONHPh), (NHCH(Me)CH2OH,Ph,OH, CH2OH,NHCOCONHPh),
(NHCH(Me)CONHMe,H,H,Me,CONHPh, (NHCH(Me) CONHMe,H,H,Me,CONH-3-pyridyl), (NHCH(Me)CON-HMe,H,H,Me,NHCOPh), (NHCH(Me)CONHMe,H,H,Me, NHCO-2-furyl), (NHCH(Me)CONHMe,H,H,Me, NHCONHPh), (NHCH(Me)CONHMe,H,H,Me, NHCOCONHPh), (NHCH(Me)CONHMe,H,H,Et, CONHPh), (NHCH(Me)CONHMe,H,H,Et,CONH-3-pyridyl), (NHCH(Me)CONHMe,H,H,Et,NHCOPh), (NHCH(Me)CONHMe,H,H,Et,NHCO-2-furyl), (NHCH(Me)CONHMe,H,H,Et,NHCONHPh), (NHCH(Me)CON-HMe,H,H,Et,NHCOCONHPh), (NHCH(Me)CONHMe,H, H,CH2OH,CONHPh), (NHCH(Me)CONHMe,H,H, CH2OH,CONH-3-pyridyl), (NHCH(Me)CONHMe,H,H, CH2OH,NHCOPh), (NHCH(Me)CONHMe,H,H,CH2OH, NHCO-2-furyl), (NHCH(Me)CONHMe,H,H,CH2OH, NHCONHPh), (NHCH(Me)CONHMe,H,H,CH2OH, NHCOCONHPh), (NHCH(Me)CONHMe,H,Me,Me, CONHPh), (NHCH(Me)CONHMe,H,Me,Me,CONH-3-pyridyl), (NHCH(Me)CONHMe,H,Me,Me,NHCOPh), (NHCH(Me)CONHMe,H,Me,Me,NHCO-2-furyl), (NHCH(Me)CONHMe,H,Me,Me,NHCONHPh), (NHCH(Me) CONHMe,H,Me,Me,NHCOCONHPh), (NHCH(Me)CON-HMe,H,Me,Et,CONHPh), (NHCH(Me)CONHMe,H,Me,Et, CONH-3-pyridyl), (NHCH(Me)CONHMe,H,Me,Et, NHCOPh), (NHCH(Me)CONHMe,H,Me,Et,NHCO-2-furyl), (NHCH(Me)CONHMe,H,Me,Et,NHCONHPh), (NHCH(Me)CONHMe,H,Me,Et,NHCOCONHPh), (NHCH(Me)CONHMe,H,Me,CH2OH,CONHPh), (NHCH(Me)CONHMe,H,Me,CH2OH,CONH-3-pyridyl), (NHCH(Me)CONHMe,H,Me,CH2OH,NHCOPh), (NHCH(Me)CONHMe,H,Me,CH2OH,NHCO-2-furyl), (NHCH(Me)CONHMe,H,Me,CH2OH,NHCONHPh), (NHCH(Me)CONHMe,H,Me,CH2OH,NHCOCONHPh), (NHCH(Me)CONHMe,H,Ph,Me,CONHPh), (NHCH(Me)CONHMe,H,Ph,Me,CONH-3-pyridyl), (NHCH(Me)CONHMe,H,Ph,Me,NHCOPh), (NHCH(Me)CONHMe,H,Ph,Me,NHCO-2-furyl), (NHCH(Me)CONHMe,H,Ph,Me,NHCONHPh), (NHCH(Me)CONHMe,H,Ph,Me,NHCOCONHPh), (NHCH(Me)CONHMe,H,Ph,Et,CONHPh), (NHCH(Me)CONHMe,H,Ph,Et,CONH-3-pyridyl), (NHCH(Me)CONHMe,H,Ph,Et,NHCOPh), (NHCH(Me)CONHMe,H,Ph,Et,NHCO-2-furyl), (NHCH(Me)CONHMe,H,Ph,Et,NHCONHPh), (NHCH(Me)CONHMe,H,Ph,Et,NHCOCONHPh), (NHCH(Me)CONHMe,H,Ph,CH2OH,CONHPh), (NHCH(Me)CONHMe,H,Ph,CH2OH,CONH-3-pyridyl), (NHCH(Me)CONHMe,H,Ph,CH2OH,NHCOPh), (NHCH(Me)CONHMe,H,Ph,CH2OH,NHCO-2-furyl), (NHCH(Me)CONHMe,H,Ph,CH2OH,NHCONHPh), (NHCH(Me)CONHMe,H,Ph,CH2OH,NHCOCONHPh), (NHCH(Me)CONHMe,H,OH,Me,CONHPh), (NHCH(Me)CONHMe,H,OH,Me,CONH-3-pyridyl), (NHCH(Me)CONHMe,H,OH,Me,NHCOPh), (NHCH(Me)CONHMe,H,OH,Me,NHCO-2-furyl), (NHCH(Me)CONHMe,H,OH,Me,NHCONHPh), (NHCH(Me)CONHMe,H,OH,Me,NHCOCONHPh), (NHCH(Me)CONHMe,H,OH,Et,CONHPh), (NHCH(Me)CONHMe,H,OH,Et,CONH-3-pyridyl), (NHCH(Me)CONHMe,H,OH,Et,NHCOPh), (NHCH(Me)CONHMe,H,OH,Et,NHCO-2-furyl), (NHCH(Me)CONHMe,H,OH,Et,NHCONHPh), (NHCH(Me)CONHMe,H,OH,Et,NHCOCONHPh), (NHCH(Me)CONHMe,H,OH,CH2OH,CONHPh), (NHCH(Me)CONHMe,H,OH,CCH2OH,CONH-3-pyridyl), (NHCH(Me)CONHMe,H,OH,CH2OH,NHCOPh), (NHCH(Me)CONHMe,H,OH,CH2OH,NHCO-2-furyl), (NHCH(Me)CONHMe,H,OH,CH2OH,NHCONHPh), (NHCH(Me)CONHMe,H,OH,CH2OH,NHCOCONHPh), (NHCH(Me)CONHMe,Me,H,Me,CONHPh), (NHCHCMe)CONHMe,Me,H,Me,CONH-3-pyridyl), (NHCH(Me)CONHMe,Me,H,Me,NHCOPh), (NHCH(Me)CONHMe,Me,H,Me,NHCO-2-furyl), (NHCH(Me)CONHMe,Me,H,Me,NHCONHPh), (NHCH(Me)CONHMe,Me,H,Me,NHCOCONHPh), (NHCH(Me)CONHMe,Me,H,Et,CONHPh), (NHCH(Me)CONHMe,Me,H,Et,CONH-3-pyridyl), (NHCH(Me)CONHMe,Me,H,Et,NHCOPh), (NHCH(Me)CONHMe,Me,H,Et,NHCO-2-furyl), (NHCH(Me)CONHMe,Me,H,Et,NHCONHPh), (NHCH(Me)CONHMe,Me,H,Et,NHCOCONHPh), (NHCH(Me)CONHMe,Me,H,CH2OH,CONHPh), (NHCH(Me)CONHMe,Me,H,CH2OH,CONH-3-pyridyl), (NHCH(Me)CONHMe,Me,H,CH2OH,NHCOPh), (NHCH(Me)CONHMe,Me,H,CH2OH,NHCO-2-furyl), (NHCH(Me)CONHMe,Me,H,CH2OH,NHCONHPh), (NHCH(Me)CONHMe,Me,H,CH2OH,NHCOCONHPh), (NHCH(Me)CONHMe,Me,Me,Me,CONHPh), (NHCH(Me)CONHMe,Me,Me,Me,CONH-3-pyridyl), (NHCH(Me)CONHMe,Me,Me,Me,NHCOPh), (NHCH(Me)CONHMe,Me,Me,Me,NNHCO-2-furyl), (NHCH(Me)CONHMe,Me,Me,Me,NHCONHPh), (NHCH(Me)CONHMe,Me,Me,Me,NHCOCONHPh), (NHCH(Me)CONHMe,Me,Me,Et,CONHPh), (NHCH(Me)CONHMe,Me,Me,Et,CONH-3-pyridyl), (NHCH(Me)CONHMe,Me,Me,Et,NHCOPh), (NHCH(Me)CONHMe,Me,Me,Et,NHCO-2-furyl), (NHCH(Me)CONHMe,Me,Me,Et,NHCONHPh), (NHCH(Me)CONHMe,Me,Me,Et,NHCOCONHPh), (NHCH(Me)CONHMe,Me,Me,CH2OH,CONHPh), (NHCH(Me) CONHMe,Me,Me,CH2OH,CONH-3-pyridyl), (NHCH(Me)CONHMe,Me,Me,CH2OH,NHCOPh), (NHCH(Me)CONHMe,Me,Me,CH2OH,NHCO-2-furyl), (NHCH(Me)CONHMe,Me,Me,CH2OH,NHCONHPh), (NHCH(Me)CONHMe,Me,Me,CH2OH,NHCOCONHPh), (NHCH(Me)CONHMe,Me,Ph,Me,CONHPh), (NHCH(Me)CONHMe,Me,Ph,Me,CONH-3-pyridyl), (NHCH(Me)CONHMe,Me,Ph,Me,NHCOPh), (NHCH(Me)CONHMe,Me,Ph,Me,NHCO-2-furyl), (NHCH(Me)CONHMe,Me,Ph,Me,NHCONHPh), (NHCH(Me)CONHMe,Me,Ph,Me,NHCOCONHPh), (NHCH(Me)CONHMe,Me,Ph,Et,CONHPh), (NHCH(Me)CONHMe,Me,Ph,Et,CONH-3-pyridyl), (NHCH(Me)CONHMe,Me,Ph,Et,NHCOPh), (NHCHMe)CONHMe,Me,Ph,Et,NHCO-2-furyl), (NHCH(Me)CONHMe,Me,Ph,Et,NHCONHPh), (NHCH(Me)CONHMe,Me,Ph,Et,NHCOCONHPh), (NHCH(Me)CONHMe,Me,Ph,CH2OH,CONHPh), (NHCH(Me)CONHMe,Me,Ph,CH2OH,CONH-3-pyridyl), (NHCH(Me)CONHMe,Me,Ph,CH2OH,NHCOPh), (NHCH(Me)CONHMe,Me,Ph,CH2OH,NHCO-2-furyl), (NHCH(Me)CONHMe,Me,Ph,CH2OH,NHCONHPh), (NHCH(Me)CONHMe,Me,Ph,CH2OH,NHCOCONHPh), (NHCH(Me)CONHMe,Me,OH,Me,CONHPh), (NHCH(Me)CONHMe,Me,OH,Me,CONH-3-pyridyl), (NHCH(Me)CONHMe,Me,OH,Me,NHCOPh), (NHCH(Me)CONHMe,Me,OH,Me,NHCO-2-furyl), (NHCH(Me)CONHMe,Me,OH,Me,NHCONHPh), (NHCH(Me)CONHMe,Me,OH,Me,NHCOCONHPh), (NHCH(Me)CONHMe,Me,OH,Et,CONHPh), (NHCH(Me)CONHMe,Me,OH,Et,CONH-3-pyridyl), (NHCH(Me)CONHMe,Me,OH,Et,NHCOPh), (NHCH(Me)CONHMe,Me,OH,Et,NHCO-2-furyl), (NHCH(Me)CONHMe,Me,OH,Et,NHCONHPh), (NHCH(Me)CONHMe,Me,OH,Et,NHCOCONHPh), (NHCH(Me)CONHMe,Me,OH,CH2OH,CONHPh), (NHCH(Me)CONHMe,Me,OH,CH2OH,CONH-3-pyridyl), (NHCH(Me)CONHMe,Me,OH,CH2OH,NHCOPh), (NHCH(Me)CONHMe,Me,OH,CH2OH,NHCO-2-furyl, (NHCH(Me)CONHMe,Me,OH,CH2OH,NHCONHPh), (NHCH(Me)CONHMe,Me,OH,CH2OH,NHCOCONHPh), (NHCH(Me)CONHMe,Ph,H,Me,CONHPh), (NHCH(Me)CONHMe,Ph,H,Me,CONH-3-pyridyl), (NHCH(Me)CONHMe,Ph,H,Me,NHCOPh), (NHCH(Me)CONHMe,Ph,H,Me,NHCO-2-furyl), (NHCH(Me)CONHMe,Ph,H,Me,NHCONHPh), (NHCH(Me)CONHMe,Ph,H,Me,NHCOCONHPh), (NHCH(Me)CONHMe,Ph,H,Et,CONHPh), (NHCH(Me)CONHMe,Ph,H,Et,CONH-3-pyridyl), (NHCH(Me)CONHMe,Ph,H,Et,NHCOPh), (NHCH(Me)CONHMe,Ph,H,Et,NHCO-2-furyl), (NHCH(Me)CONHMe,Ph,H,Et,NHCONHPh), (NHCH(Me)CONHMe,Ph,H,Et,NHCOCONHPh), (NHCHC(Me)CONHMe,Ph,H,CH2OH,CONHPh), (NHCH(Me)CONHMe,Ph,H,CH2OH,CONH-3-pyridyl), (NHCH(Me)CONHMe,Ph,H,CH2OH,NHCOPh), (NHCH(Me)CONHMe,Ph,H,CH2OH,NHCO-2-furyl), (NHCH(Me)CONHMe,Ph,H,CH2OH,NHCONHPh), (NHCH(Me)CONHMe,Ph,H,CH2OH,NHCOCONHPh), (NHCH(Me)CONHMe,Ph,Me,Me,CONHPh), (CNHCH(Me)CONHMe,Ph,Me,Me,CONH-3-pyridyl), (NHCH(Me)CONHMe,Ph,Me,Me,NHCOPh), (NHCH(Me)CONHMe,Ph,Me,Me,NHCO-2-furyl), (NHCH(Me)CONHMe,Ph,Me,Me,NHCONHPh), (NHCH(Me)CONHMe,Ph,Me,Me,NHCOCONHPh), (NHCH(Me)CONHMe,Ph,Me,Et,CONHPh), (NHCH(Me)CONHMe,Ph,Me,Et,CONH-3-pyridyl), (NHCH(Me)CONHMe,Ph,Me,Et,NHCOPh), (NHCH(Me)CONHMe,Ph,Me,Et,NHCO-2-furyl), (NHCH(Me)CONHMe,Ph,Me,Et,NHCONHPh), (NHCH(Me)CONHMe,Ph,Me,Et,NHCOCONHPh), (NHCH(Me)CONHMe,Ph,Me,CH2OH,CONHPh), (NHCH(Me)CONHMe,Ph,Me,CH2OH,CONH-3-pyridyl), (NHCH(Me)CONHMe,Ph,Me,CH2OH,NHCOPh), (NHCH(Me)CONHMe,Ph,Me,CH2OH,NHCO-2-furyl), (NHCH(Me)CONHMe,Ph,Me,CH2OH,NHCONHPh), (NHCH(Me)CONHMe,Ph,Me,CH2OH,NHCOCONHPh), (NHCH(Me)CONHMe,Ph,Ph,Me,CONHPh), (NHCH(Me)CONHMe,Ph,Ph,Me,CONH-3-pyridyl), (NHCH(Me)CONHMe,Ph,Ph,Me,NHCOPh), (NHCHCMe)CONHMe,Ph,Ph,Me,NHCO-2-furyl), (NHCH(Me)CONHMe,Ph,Ph,Me,NHCONHPh), (NHCH(Me)CONHMe,Ph,Ph,Me,NHCOCONHPh), (NHCH(Me)CONHMe,Ph,Ph,Et,CONHPh), (NHCH(Me)CONHMe,Ph,Ph,Et,CONH-3-pyridyl), (NHCH(Me)CONHMe,Ph,Ph,Et,NHCOPh), (NHCH(Me)CONHMe,Ph,Ph,Et,NHCO-2-furyl), (NHCH(Me)CON HMe,Ph,Ph,Et,NHCONHPh), (NHCH(Me)CONHMe,Ph,Ph,Et,NHCOCONHPh), (NHCH(Me)CONHMe,Ph,Ph,CH2OH,CONHPh), (NHCH(Me)CONHME,Ph,Ph,CH2OH,CONH-3-pyridyl), (NHCH(Me)CONHMe,Ph,Ph,CH2OH,NHCOPh), (NHCH(Me)CONHMe,Ph,Ph,CH2OH,NHCO-2-furyl), (NHCH(Me)CONHMe,Ph,Ph,CH2OH,NHCONHPh), (NHCH(Me)CONHMe,Ph,Ph,CH2OH,NHCOCONHPh), (NHCH(Me)CONHMe,Ph,OH,Me,CONHPh), (NHCHC(Me)CONHMe,Ph,OH,Me,CONH-3-pyridyl), (NHCH(Me)CONHMe,Ph,OH,Me,NHCOPh), (NHCH(Me)CONHMe,Ph,OH,Me,NHCO-2-furyl), (NHCH(Me)CONHMe,Ph,OH,Me,NHCONHPh), (NHCH(Me)CONHMe,Ph,OH,Me,NHCOCONHPh), (NHCH(Me)CONHMe,Ph,OH,Et,CONHPh), (NHCH(Me)CONHMe,Ph,OH,Et,CONH-3-pyridyl), (NHCH(Me)CONHMe,Ph,OH,Et,NHCOPh), (NHCH(Me)CONHMe,Ph,OH,Et,NHCO-2-furyl), (NHCH(Me)CONHMe,Ph,OH,Et,NHCONHPh), (NHCH(Me)CONHMe,Ph,OH,Et,NHCOCONHPh), (NHCH(Me)CONHMe,Ph,OH,CH2OH,CONHPh), (NHCH(Me)CONHMe,Ph,OH,CH2OH,CONH-3-pyridyl), (NHCH(Me)CONHMe,Ph,OH,CH2OH,NHCOPh), (NHCH(Me)CONHMe,Ph,OH,CH2OH,NHCO-2-furyl), (NHCH(Me)CONHMe,Ph,OH,CH2OH,NHCONHPh), (NHCH(Me)CONHMe,Ph,OH,CH2OH,NHCOCONHPh), (NHCOCH(iPr)OH,H,H,Me,CONHPh), (NHCOCH(iPr)OH,H,H,Me,CONH-3-pyridyl), (NHCOCH(iPr)OH,H,H,Me,NHCOPh), (NHCOCH(iPr)OH,H,H,Me,NHCO-2-furyl), (NHCOCH(iPr)OH,H,H,Me,NHCONHPh), (NHCOCH(iPr)OH,H,H,Me,NHCOCONHPh), (NHCOCH(iPr)OH,H,H,Et,CONHPh), (NHCOCH(iPr)OH,H,H,Et,CONH-3-pyridyl), (NHCOCH(iPr)OH,H,H,Et,NHCOPh), (NHCOCH(iPr)OH,H,H,Et,NHCO-2-furyl), (NHCOCH(iPr)OH,H,H,Et,NHCONHPh), (NHCOCH(iPr)OH,H,H,Et,NHCOCONHPh), (NHCOCH(iPr)OH,H,H,CH2OH,CONHPh)(NHCOCH(iPr),OH,H,H,CH2O,H,CONH-3-pyridyl), (NHCOCH(iPr)OH,H,H,CH2OH,NHCOPh), (NHCOCH(iPr)OH,H,H,CH2OH,NHCO-2-furyl), (NHCOCH(iPr)OH,H,H,CH2OH,NHCONHPh), (NHCOCH(iPr)OH,H,H,CH2OH,NHCOCONHPh), (NHCOCH(iPr)OH,H,Me,Me,CONHPh), (NHCOCH(iPr)OH,H,Me,Me,CONH-3-pyridyl), (NHCOCH(iPr)OH,H,Me,Me,NHCOPh), (NHCOCH(iPr)OH,H,Me,Me,NHCO-2-furyl), (NHCOCH(iPr)OH,H,Me,Me,NHCONHPh), (NHCOCH(iPr)OH,H,Me,Me,NHCOCONHPh), (NHCOCH(iPr)OH,H,Me,Et,CONHPh), (NHCOCH(iPr)OH,H,Me,Et,CONH-3-pyridyl), (NHCOCH(iPr)OH,H,Me,Et,NHCOPh), (NHCOCH(iPr)OH,H,Me,Et,NHCO-2-furyl), (NHCOCH(iPr)OH,H,Me,Et,NHCONHPh), (NHCOCH(iPr)OH,H,Me,Et,NHCOCONHPh), (NHCOCH(iPr)OH,H,Me,CH2OH,CONHPh), (NHCOCH(iPr)OH,H,Me,CH2OH,CONH-3-pyridyl), (NHCOCH(iPr)OH,H,Me,CH2OH,NHCOPh), (NHCOCH(iPr)OH,H,Me,CH2OH, NHCO-2-furyl), (NHCOCH(iPr)OH,H,Me,CH2OH,NHCONHPh), (NHCOCH(iPr)OH,H,Me,CH2OH,NHCOCONHPh), (NHCOCH(iPr)OH,H,Ph,Me,CONHPh), (NHCOCH(iPr)OH,H,Ph,Me,CONH-3-pyridyl), (NHCOCH(iPr)OH,H,Ph,Me,NHCOPh), (NHCOCH(iPr)OH,H,Ph,Me,NHCO-2-furyl), (NHCOCH(iPr)OH,H,Ph,Me,NHCONHPh), (NHCOCH(iPr)OH,H,Ph,Me,NHCOCONRPh), (NHCOCH(iPr)OH,H,Ph,Et,CONHPh), (NHCOCH(iPr)OH,H,Ph,Et,CONH-3-pyridyl), (NHCOCH(iPr)OH,H,Ph,Et,NHCOPh), (NHCOCH(iPr)OH,H,Ph,Et,NHCO-2-furyl), (NHCOCH(iPr)OH,H,Ph,Et,NHCONHPh), (NHCOCH(iPr)OH,H,Ph,Et,NHCOCONHPh), (NHCOCH(iPr)OH,H,Ph,CH2OH,CONHPh), (NHCOCH(iPr)OH,H,Ph,CH2OH,CONH-3-pyridyl), (NHCOCH(iPr)OH,H,Ph,CH2OH,NHCOPh), (NHCOCH(iPr)OH,H,Ph,CH2OH,NHCO-2-furyl), (NHCOCH(iPr)OH,H,Ph,CH2OH,NHCONHPh), (NHCOCH(iPr)OH,H,Ph,CH2OH,NHCOCONHPh), (NHCOCH(iPr)OH,H,OH,Me,CONHPh), (NHCOCH(iPr)OH,H,OH,Me,CONH-3-pyridyl), (NHCOCH(iPr)OH,H,OH,Me,NHCOPh), (NHCOCH(iPr)OH,H,OH,Me,NHCO-2-furyl), (NHCOCH(iPr)OH,H,OH,Me,NHCONHPh), (NHCOCH(iPr)OH,H,OH,Me,NHCOCONHPh), (NHCOCH(iPr)OH,H,OH,Et,CONHPh), (NHCOCH(iPr)OH,H,OH,Et,CONH-3-pyridyl), (NHCOCH(iPr)OH,H,OH,Et,NHCOPh), (NHCOCH(iPr)OH,H,OH,Et,NHCO-2-furyl), (NHCOCH(iPr)OH,H,OH,Et,NHCONHPh), (NHCOCH(iPr)OH,H,OH,Et,NHCOCONHPh), (NHCOCH(iPr)OH,H,OH,CH2OH,CONHPh), (NHCOCH(iPr)OH,H,OH,CH2OH,CONH-3-pyridyl), (NHCOCH(iPr)OH,H,OH,CH2OH,NHCOPh), (NHCOCH(iPr)OH,H,OH,CH2OH,NHCO-2-furyl), (NHCOCH(iPr)OH,H,OH,CH2OH,NHCONHPh), (NHCOCH(iPr)OH,H,OH,CH2OH,NHCOC ONHPh), (NHCOCH(iPr)OH,Me,H,Me,CONHPh), (NHCOCH(iPr)OH,Me,H,Me,CONH-3-pyridyl), (NHCOCH(iPr)OH,Me,H,Me,NHCOPh), (NHCOCH(iPr)OH,Me,H,Me,NHCO-2-furyl), (NHCOCH(iPr)OH,Me,H,Me,NHCONHPh), (NHCOCH(iPr)OH,Me,H,Me,NHCOCONHPh), (NHCOCH(iPr)OH,Me,H,Et,CONHPh), (NHCOCH(iPr)OH,Me,H,Et,CONH-3-pyridyl), (NHCOCH(iPr)OH,Me,H,Et,NHCOPh), (NHCOCH(iPr)OH,Me,H,Et,NHCO-2-furyl), (NHCOCH(iPr)OH,Me,H,Et,NHCONHPh), (NHCOCH(iPr)OH,Me,H,Et,NHCOCONHPh), (NHCOCH(iPr)OH,Me,H,CH2OH,CONHPh), (NHCOCH(iPr)OH,Me,H,CH2OH,CONH-3-pyridyl), (NHCOCH(iPr)OH,Me,H,CH2OH,NHCOPh), (NHCOCHPh)OH,Me,H,CH2OH,NHCO-2-furyl), (NHCOCH(iPr)OH,Me,H,CH2OH,NHCONHPh), (NHCOCH(iPr)OH,Me,H,CH2OH,NHCOCONHPh), (NHCOCH(iPr)OH,Me,Me,Me,CONHPh), (NHCOCH(Ph)OH,Me,Me,Me,CONH-3-pyridyl), (NHCOCH(iPr)OH,Me,Me,Me,NHCOPh), (NHCOCH(iPr)OH,Me,Me,Me,NHCO-2-furyl), (NHCOCH(iPr)OH,Me,Me,Me,NHCONHPh), (NHCOCH(iPr)OH,Me,Me,Me,NHCOCONHPh), (NHCOCH(iPr)OH,Me,Me,Et,CONHPh), (NHCOCH(iPr)OH,Me,Me,Et,CONH-3-pyridyl), (NHCOCH(iPr)OH,Me,Me,Et,NHCOPh), (NHCOCH(iPr)OH,Me,Me,Et,NHCO-2-furyl), (NHCOCH(iPr)OH,Me,Me,Et,NHCONHPh), (NHCOCH(iPr)OH,Me,Me,Et,NHCOCONHPh), (NHCOCH(iPr)OH,Me,Me,CH2OH,CONHPh), (NHCOCH(iPr)OH,Me,Me,CH2OH,CONH-3-pyridyl), (NHCOCH(iPr)OH,Me,Me,CH2OH,NHCOPh), (NHCOCH(iPr)OH,Me,Me,CH2OH,NHCO-2-furyl), (NHCOC H(iPr)OH,Me,Me,CH2OH,NHCONHPh), (NHCOCH(iPr)OH,Me,Me,CH2OH,NHCOCONHPh), (NHCOCH(iPr)OH,Me,Ph,Me,CONHPh), (NHCOCH(iPr)OH,Me,Ph,Me,CONH-3-pyridyl), (NHCOCH(iPr)OH,Me,Ph,Me,NHCOPh), (NHCOCH(iPr)OH,Me,Ph,Me,NHCO-2-furyl), (NHCOCH(iPr)OH,Me,Ph,Me,NHCONHPh), (NHCOCH(iPr)OH,Me,Ph,Me,NHCOCONHPh), (NHCOCH(iPr)OH,Me,Ph,Et,CONHPh), (NHCOCH(iPr)OH,Me,Ph,Et,CONH-3-pyridyl), (NHCOCHiPr)OH,Me,Ph,Et,NHCOPh), (NHCOCH(iPr)OH,Me,Ph,Et,NHCO-2-furyl), (NHCOCH(iPr)OH,Me,Ph,Et,NHCONHPh), (NHCOCH(iPr)OH,Me,Ph,Et,NHCOCONHPh), (NHCOCH(iPr)OH,Me,Ph,CH2OH,CONHPh), (NHCOCH(iPr)OH,Me,Ph,CH2OH,CONH-3-pyridyl), (NHCOCH(iPr)OH,Me,Ph,CH2OH,NHCOPh), (NHCOCH(iPr)OH,Me,Ph,CH2OH,NHCO-2-furyl), (NHCOCH(iPr)OH,Me,Ph,CH2OH,NHCONHPh), (NHCOCH(iPr)OH,Me,Ph,CH2OH,NHCOCONHPh), (NHCOCH(iPr)OH,Me,OH,Me,CONHPh), (NHCOCH(iPr)OH,Me,OH,Me,CONH-3-pyridyl), (NHCOCH(iPr)OH,Me,OH,Me,NHCOPh), (NHCOCH(iPr)OH,Me,OH,Me,NHCO-2-furyl), (NHCOCH(iPr)OH,Me,OH,Me,NHCONHPh), (NHCOCH(iPr)OH,Me,OH,Me,NHCOCONHPh), (NHCOCH(iPr)OH,Me,OH,Et,CONHPh), (NHCOCH(iPr)OH,Me,OH,Et,CONH-3-pyridyl), (NHCOCH(iPr)OH,Me,OH,Et,NHCOPh), (NHCOCH(iPr)OH,Me,OH,Et,NHCO-2-furyl), (NHCOCH(iPr)OH,Me,OH,Et,NHCONHPh), (NHCOCH(iPr)OH,Me,OH,Et,NHCOCONHPh), (NHCOCH(iPr)OH,Me,OH,CH2OH,CONHPh), (NHCOCH(iPr)OH,Me,OH,CH2OH,CONH-3-pyridyl), (NHCOCH(iPr)OH,Me,OH,CH2OH,NHCOPh), (NHCOCH(iPr)OH,Me,OH,CH2OH,NHCO-2-furyl), (NHCOCH(iPr)OH,Me,OH,CH2OH,NHCONHPh), (NHCOCH(iPr)OH,Me,OH,CH2OH,NHCOCONHPh), (NHCOCH(iPr)OH,Ph,H,Me,CONHPh), (NHCOCH(iPr)OH,Ph,H,Me,CONH-3-pyridyl), (NHCOCH(iPr)OH,Ph,H,Me,NHCOPh), (NHCOCH(iPr)OH,Ph,H,Me,NHCO-2-furyl), (NHCOCH(iPr)OH,Ph,H,Me,NHCONHPh), (NHCOCH(iPr)OH,Ph,H,Me,NHCOCONHPh), (NHCOCH(iPr)OH,Ph,H,Et,CONHPh), (NHCOCH(iPr)OH,Ph,H,Et,CONH-3-pyridyl), (NHCOCH(iPr)OH,Ph,H,Et,NHCOPh), (NHCOCH(iPr)OH,Ph,H,Et,NHCO-2-furyl), (NHCOCH(iPr)OH,Ph,H,Et,NHCONHPh), (NHCOCH(iPr)OH,Ph,H,Et,NHCOCONHPh), (NHCOCH(iPr)OH,Ph,H,CH2OH,CONHPh), (NHCOCH(iPr)OH,Ph,H,CH2OH,CONH-3-pyridyl), (NHCOCH(iPr)OH,Ph,H,CH2OH,NHCOPh), (NHCOCH(iPr)OH,Ph,H,CH2OH,NHCO-2-furyl), (NHCOCH(iPr)OH,Ph,H,CH2OH,NHCONHPh), (NHCOCH(iPr)OH,Ph,H,CH2OH,NHCOCONHPh), (NHCOCH(iPr)OH,Ph,Me,Me,CONHPh), (NHCOCH(iPr)OH,Ph,Me,Me,CONH-3-pyridyl), (NHCOCH(iPr)OH,Ph,Me,Me,NHCOPh), (NHCOCH(iPr)OH,Ph,Me,Me,NHCO-2-furyl), (NHCOCH(iPr)OH,Ph,Me,Me,NHCONHPh), (NHCOCH(iPr)OH,Ph,Me,Me,NHCOCONHPh), (NHCOCH(iPr)OH,Ph,Me,Et,CONHPh), (NHCOCH(iPr)OH,Ph,Me,Et,CONH-3-pyridyl), (NHCOCH(iPr)OH,Ph,Me,Et,NHCOPh), (NHCOCH(iPr)OH,Ph,Me,Et,NHCO-2-furyl), (NHCOCH(iPr)OH,Ph,Me,Et,NHCONHPh), (NHCOCH(iPr)OH,Ph,Me,Et,NHCOCONHPh), (NHCOCH(iPr)OH,Ph,Me,CH2OH,CONHPh), (NHCOCH(iPr)OH,Ph,Me,CH2OH,CONH-3-pyridyl), (NHCOCH(iPr)OH,Ph,Me,CH2OH,NHCOPh), (NHCOCH(iPr)OH,Ph,Me,CH2OH,NHCO-2-furyl), (NHCOCH(iPr)OH,PhMe,CH2OH,NHCONHPh), (NHCOCH(iPr)OH,Ph,Me,CH2OH,NHCOCONHPh), (NHCOCH(iPr)OH,Ph,Ph,Me,CONHPh), (NHCOCH(iPr)OH,Ph,Ph,Me,CONH-3-pyridyl), (NHCOCH(iPr)OH,Ph,Ph,Me,NHCOPh), (NHCOCH(iPr)OH,Ph,Ph,Me,NHCO-2-furyl), (NHCOCH(iPr)OH,Ph,Ph,Me,NHCONHPh), (NHCOCH(iPr)OH,Ph,Ph,Me,NHCOCONHPh), (NHCOCH(iPr)OH,Ph,Ph,Et,CONHPh), (NHCOCH(iPr)OH,Ph,Ph,Et,CONH-3-pyridyl), (NHCOCH(iPr)OH,Ph,Ph,Et,NHCOPh), (NHCOCH(iPr)OH,Ph,Ph,Et,NHCO-2-furyl), (NHCOCH(iPr)OH,Ph,Ph,Et,NHCONHPh), (NHCOCH(iPr)OH,Ph,Ph,Et,NHCOCONHPh), (NHCOCH(iPr)OH,Ph,Ph,CH2OH,CONHPh), (NHCOCH(iPr)OH,Ph,Ph,CH2OH,CONH-3-pyridyl), (NHCOCH(iPr)OH,Ph,Ph,CH2OH,NHCOPh), (NHCOCH(iPr)OH,Ph,Ph,CH2OH,NHCO-2-furyl), (NHCOCH(iPr)OH,Ph,Ph,CH2OH,NHCONHPh), (NHCOCH(iPr)OH,Ph,Ph,CH2OH,NHCOCONHPh), (NHCOCH(iPr)OH,Ph,OH,Me,CONHPh), (NHCOCH(iPr)OH,Ph,OH,Me,CONH-3-pyridyl), (NHCOCH(iPr)OH,Ph,OH,Me,NHCOPh), (NHCOCH(iPr)OH,Ph,OH,Me,NHCO-2-furyl), (NHCOCH(iPr)OH,Ph,OH,Me,NHCONHPh), (NHCOCH(iPr)OH,Ph,OH,Me,NHCOCONHPh), (NHCOCH(iPr)OH,Ph,OH,Et,CONHPh), (NHCOCH(iPr)OH,Ph,OH,Et,CONH-3-pyridyl), (NHCOCH(iPr)OH,Ph,OH,Et,NHCOPh), (NHCOCH(iPr)OH,Ph,OH,Et,NHCO-2-furyl), (NHCOCH(iPr)OH,Ph,OH,Et,NHCONHPh), (NHCOCH(iPr)OH,Ph,OH,Et,NHCOCONHPh), (NHCOCH(iPr)OH,Ph,OH,CH2OH,CONHPh), (NHCOCH(iPr)OH,Ph,OH,CH2OH,CONH-3-pyridyl), (NHCOCH(iPr)OH,Ph,OH,CH2OH,NHCOPh), (NHCOCH(iPr)OH,Ph,OH,CH2OH,NHCO-2-furyl), (NHCOCH(iPr)OH,Ph,OH,CH2OH,NHCONHPh), (NHCOCH(iPr)OH,Ph,OH,CH2OH,NHCOCONHPh), (NHSO2Me,H,H,Me,CONHPh), (NHSO2Me,H,H,Me,CONH-3-pyridyl), (NHSO2Me,H,H,Me,NHCOPh), (NHSO2Me,H,H,Me,NHCO-2-furyl), (NHSO2Me,H,H,Me,NHCONHPh), (NHSO2Me,H,H,Me,NHCOCONHPh), (NHSO2Me,H,H,Et,CONHPh), (NHSO2Me,H,H,Et,CONH-3-pyridyl), (NHSO2Me,H,H,Et,NHCOPh), (NHSO2Me,H,H,Et,NHCO-2-furyl), (NHSO2Me,H,H,Et,NHCONHPh), (NHSO2Me,H,H,Et,NHCOCONHPh), (NHSO2Me,H,H,CH2OH,CONHPh), (NHSO2Me,H,H,CH2OH,CONH-3-pyridyl), (NHSO2Me,H,H,CH2OH,NHCOPh), (NHSO2Me,H,H,CH2OH,NHCO-2-furyl), (NHSO2Me,H,H,CH2OH,NHCONHPh), (NHSO2Me,H,H,CH2OH,NHCOCONHPh), (NHSO2Me,H,Me,Me,CONHPh), (NHSO2Me,H,Me,Me,CONH-3-pyridyl), (NHSO2Me,H,Me,Me,NHCOPh), (NHSO2Me,H,Me,Me,NHCO-2-furyl), (NHSO2Me,H,Me,Me,NHCONHPh), (NHSO2Me,H,Me,Me,NHCOCONHPh), (NHSO2Me,H,Me,Et,CONHPh), (NHSO2Me,H,Me,Et,CONH-3-pyridyl), (NHSO2Me,H,Me,Et,NHCOPh), (NHSO2Me,H,Me,Et,NHCO-2-furyl), (NHSO2Me,H,Me,Et,NHCONHPh), (NHSO2Me,H,Me,Et,NHCOCONHPh), (NHSO2Me,H,Me,CH2OH,CONHPh), (NHSO2Me,H,Me,CH2OH,CONH-3-pyridyl), (NHSO2Me,H,Me,CH2OH,NHCOPh), (NHSO2Me,H,Me,CH2OH,NHCO-2-furyl), (NHSO2Me,H,Me,CH2OH,NHCONHPh), (NHSO2Me,H,Me,CH2OH,NHCOCONHPh), (NHSO2Me,H,Ph,Me,CONHPh), (NHSO2Me,H,Ph,Me,CONH-3-pyridyl), (NHSO2Me,H,Ph,Me,NHCOPh), (NHSO2Me,H,Ph,Me,NHCO-2-furyl), (NHSO2Me,H,Ph,Me,NHCONHPh), (NHSO2Me,H,Ph,Me,NHCOCONHPh), (NHSO2Me,H,Ph,Et,CONHPh), (NHSO2Me,H,Ph,Et,CONH-3-pyridyl), (NHSO2Me,H,Ph,Et,NHCOPh), (NHSO2Me,H,Ph,Et,NHCO-2-furyl), (NHSO2Me,H,Ph,Et,NHCONHPh), (NHSO2Me,H,Ph,Et,NHCOCONHPh), (NHSO2Me,H,Ph,CH2OH,CONHPh), (NHSO2Me,H,Ph,CH2OH,CONH-3-pyridyl), (NHSO2Me,H,Ph,CH2OH,NHCOPh), (NHSO2Me,H,Ph,CH2OH,NHCO-2-furyl), (NHSO2Me,H,Ph,CH2OH,NHCONHPh), (HNSO2Me,H,Ph,CH2OH,NHCOCONHPh), (NHSO2Me,H,OH,Me,CONHPh), (NHS2Me,H,OH,Me,CONH-3-pyridyl, (NHSO2Me,H,OH,Me,NHCOPh), (NHSO2Me,H,OH,Me,NHCO-2-furyl), (NHSO2Me,H,OH,Me,NHCONHPh), (NHSO2Me,H,OH,Me,NHCOCONHPh), (NHSO2Me,H,OH,Et,CONHPh), (NHSO2Me,H,OH,Et,CONH-3-pyridyl), (NHSO2Me,H,OH,Et,NHCOP), (NHSO2Me,H,OH,Et,NHCO-2-furyl), (NHSO2Me,H,OH,Et,NHCONHPh), (HSO2Me,H,OH,Et,NHCOCONHPh), (HSO2Me,H,OH,CH2OH,CONHPh), (NHSO2Me,H,OH,CH2OH,CONH-3-pyridyl), (NHSO2Me,H,OH,CH2OH,NHCOPh), (NHSO2Me,H,OH,CH2OH,NHCO-2-furyl), (NHSO2Me,H,OH,CH2OH,NHCONHPh), (NHSO2Me,H,OH,CH2OH,NHCOCONHPh), (NHSO2Me,Me,H,Me,CONHPh), (NHSO2Me,Me,H,Me,CONH-3-pyridyl), (NHSO$_2$Me,Me,H,Me,NHCOPh), (NHSO2Me,Me,H,Me,NHCO-2-furyl), (NHSO2Me,Me,H,Me,NHCONHPh), (NHSO2Me,Me,H,Me,NHCOCONHPh), (NHSO2Me,Me,H,Et,CONHPh), (NHSO2Me,Me,H,Et,CONH-3-pyridyl), (NHSO2Me,Me,H,Et,NHCOPh), (NHSO2Me,Me,H,Et,NHCO-2-furyl), (NHSO2Me,Me,H,Et,NHCONHPh), (HSO2Me,Me,H,Et,NHCOCONHPh), (NHSO2Me,Me,H,CH2OH,CONHPh), (NHSO2Me,Me,H,CH2OH,CONH-3-pyridyl), NHSO2Me,Me,H,CH2OH,NHCOPh), (NHSO2Me,Me,Ph,CH2OH,NHCO-2-furyl, (NHSO2Me,Me,H,CH2OH,NHCONRPh), (NHSO2Me,Me,H,CH2OH,NHCOCONHPh), (NHSO2Me,Me,Me,Me,CONHPh), (NHSO2Me,Me,Me,Me,CONH-3-pyridyl), (NHSO2Me,Me,Me,Me,NHCOPh), (NHSO2Me,Me,Me,Me,NHCO-2-furyl), (NHSO2Me,Me,Me,Me,NHCONHPh), (NHSO2Me,Me,Me,Me,NHCOCONHPh), (NHSO2Me,Me,Me,Et,CONHPh), (NHSO2Me,Me,Me,Et,CONH-3-pyridyl), (NHSO2Me,Me,Me,Et,NHCOPh), (NHSO2Me,Me,Me,Et,NHCO-2-furyl), (NHSO2Me,Me,Me,Et,NHCONHPh), (NHSO2Me,Me,Me,Et,NHCOCONHPh), (NHSO2Me,Me,Me,CH2OH,CONHPh), (NHSO2Me,Me,Me,CH2OH,CONH-3-pyridyl), (NHSO2Me,Me,Me,CH2OH,NHCOPh), (NHSO2Me,Me,Me,CH2OH,NHCO-2-furyl), (NHSO$_2$Me,Me,Me,CH2OH,NHCONHPh), (NHSO2Me,Me,Me,CH2OH,NHCOCONHPh), (NHSO2Me,Me,Ph,Me,CONHPh), (Me,Me,Ph,Me,NHCO-2-furyl), (NHSO2Me,Me,Ph,Me,NHCONHPh), (NHSO2Me,Me,Ph,Me,NHCOCONHPh), (NHSO2Me,Me,Ph,Et,CONHPh), (NHSO2Me,Me,Ph,Et,CONH-3-pyridyl), (NHSO2Me,Me,Ph,Et,NHCOPh), (NHSO2Me,Me,Ph,Et,NHCO-2-furyl), (NHSO2Me,Me,Ph,Et,NHCONHPh), (NHSO2Me,Me,Ph,Et,NHCOCONHPh), (NHSO2Me,Me,Ph,CH2OH,CONHPh), (NHSO2Me,Me,Ph,CH2OH,CONH-3-pyridyl), (NHSO2Me,Me,Ph,CH2OH,NHCOPh), (NHSO2Me,Me,Ph,CH2OH,NHCO-2-furyl), (NHSO2Me,Me,Ph,CH2OH,NHCONHPh), (NHSO2Me,Me,Ph,CH2OH,NHCOCONHPh), (NHSO2Me,Me,OH,Me,CONHPh), (NHSO2Me,Me,Me,OH,Me,CONH-3-pyridyl), (NHSO2Me,Me,OH,Me,NHCOPh), (NHSO2Me,Me,OH,Me,NHCO-2-furyl), (NHSO2Me,Me,OH,Me,NHCONHPh), (NHSO2Me,Me,OH,Me,NHCOCONHPh), (NHSO2Me,Me,OH,Et,CONHPh), (NHSO2e,Me,OH,Et,CONH-3-pyridyl), (NHSO2Me,Me,OH,Et,NHCOPh), (NHSO2Me,Me,OH,Et,NHCO-2-furyl), (NHSO2Me,Me,OH,Et,NHCONHPh), (NHSO2Me,Me,OH,Et,NHCOCONHPh), (NHSO2Me,Me,OH,CH2OH,CONHPh), (NHSO2Me,Me,OH,CH2OH,CONH-3-pyridyl), (NHSO2Me,Me,OH,CH2OH,NHCOPh), (NHSO2Me,Me,OH,CH2OH,NHCO-2-furyl), (NHSO2Me,Me,OH,CH2OH,NHCONHPh), (NHSO2Me,Me,OH,CH2OH,NHCOCONHh), (NHSO2Me,Ph,H,Me,CONHPh), (NHSO2Me,Ph,H,Me,CONH-3-pyridyl), (NHSO2Me,Ph,H,Me,NHCOPh), (NHSO2Me,Ph,H,Me,NHCO-2-furyl), (NHSO2Me,Ph,H,Me,NHCONHPh), (NHSO2Me,Ph,H,Me,NHCOCONHPh), (HSO2Me,Ph,H,Et,CONHPh), (NHSO2Me,Ph,H,Et,CONH-3-pyridyl), (NHSO2Me,Ph,H,Et,NHCOPh), (NHSO2Me,Ph,H,Et,NHCO2-furyl), (NHSO2Me,Ph,H,Et,NHCONHPh), (NHSO2Me,Ph,H,Et,NHCOCONHPh), (NHSO2Me,Ph,H,CH2OH,CONHPh), (NHSO2Me,Ph,H,CH2OH,CONH-3-pyridyl), (NHSO2Me,Ph,H,CH2OH,NHCOPh), (NHSO2Me,Ph,H,CH2OH,NHCO-2-furyl), (NHSO2Me,Ph,H,CH2OH,NHCONHPh), (NHSO2Me,Ph,H,CH2OH,NHCOCONHPh), (NHSO2Me,Ph,Me,Me,CONHPh), (NHSO2Me,Ph,Me,Me,CONH-3-pyridyl), (NHSO2Me,Ph,Me,Me,NHCOPh), (NHSO2Me,Ph,Me,Me,NHCO-2-furyl), (NHSO2Me,Ph,Me,Me,NHCONHPh), (NHSO2Me,Ph,Me,Me,NHCOCONHPh), (NHSO2Me,Ph,Me,Et,CONHPh), (NHSO2Me,Ph,Me,Et,CONH-3-pyridyl), (NHSO2Me,Ph,Me,Et,NHCOPh), (NHSO2Me,Ph,Me,Et,NHCO-2-furyl), (NHSO2Me,Ph,Me,Et,NHCONHPh), (NHSO2Me,Ph,Me,Et,NHCOCONHPh), (NHSO2Me,Ph,Me,CH2OH,CONHPh), (NHSO2Me,Ph,Me,CH2OH,CONH-3-pyridyl), (NHSO2Me,Ph,Me,CH2OH,NHCOPh), (NHSO2Me,Ph,Me,CH2OH,NHCO-2-furyl), (NHSO2Me,Ph,Me,CH2OH,NHCONHPh), (NHSO2Me,Ph,Me,CH2OH,NHCOCONHPh), (NHSO2Me,Ph,Ph,Me,CONHPh), (NHSO2Me,Ph,Ph,Me,CONH-3-pyridyl), (NHSO2Me,Ph,Ph,Me,NHCOPh), (NHSO2Me,Ph,Ph,Me,NHCO2-furyl), (NHSO2Me,Ph,Ph,Me,NHCONHPh), (NHSO2Me,Ph,Ph,Me,NHCOCONHPh), (NHSO2Me,Ph,Ph,Et,CONHPh), (NHSO2Me,Ph,Ph,Et,CONH-3-pyridyl), (NHSO2Me,Ph,Ph,Et,NHCOPh), (NHSO2Me,Ph,Ph,Et,NHCO-2-furyl), (NHSO2Me,Ph,Ph,Et,NHCONHPh), (NHSO2Me,Ph,Ph,Et,NHCOCONHPh), (NHSO2Me,Ph,Ph,CH2OH,CONHPh), (NHSO2Me,Ph,Ph,CH2OH,CONH-3-pyridyl), (HSO2Me,Ph,Ph,CH2OH,NHCOPh), (NHSO2Me,Ph,Ph,CH2OH,NHCO-2-furyl), (NHSO2Me,Ph,Ph,CH2OH,NHCONHPh), (NHSO2Me,Ph,PhCH2OH,NHCOCONEPh), (NHSO2Me,Ph,OH,Me,CONHPh), (NHSO2Me,Ph,OH,Me,CONH-3-pyridyl), (NHSO2Me,Ph,OH,Me,NHCOPh), (NHSO2Me,Ph,OH,Me,NHCO-2-furyl), (NHSO2Me,Ph,OH,Me,NHCONHPh), (NHSO2Me,Ph,OH,Me,NHCOCONHPh), (NHSO2Me,Ph,OH,Et,CONHPh), (NHSO2Me,Ph,OH,Et,CONH-3-pyridyl), (NHSO2Me,Ph,OH,Et,NHCOPh), (NHSO2Me,Ph,OH,Et,NHCO-2-furyl), (NHSO$_2$Me,Ph,OH,Et,NHCONHPh), (NHSO2Me,Ph,OH,Et,NHCOCONHPh), (NHSO2Me,Ph,OH,CH2OH,CONHPh), (NHSO2Me,Ph,OH,CH2OH,CONH-3-pyridyl), (NHSO2Me,Ph,OH,CH2OH,NHCOPh), (NHSO2Me,Ph,OH,CH2OH,NHCO-2-furyl), (NHSO2Me,Ph,OH,CH2OH,NHCONHPh), (NHSO2Me,Ph,OH,CH2OH,NHCOCONHPh), (NH2,H,H,Me,CONHPh), (NH2,H,H,Me,CONH-3-pyridyl), (NH2,H,H,Me,NHCOPh), (NH2,H,H,Me,NHCO-2-furyl), (NH2,H,H,Me,NHCONHPh), (NH2,H,H,Me,NHCOCONHPh), (NH2,H,H,Et,CONHPh), (NH2,H,H,Et,CONH-3-pyridyl), (NH2,H,H,Et,NHCOPh), (NH2,H,H,Et,NHCO-2-furyl), (NH2,H,H,Et,NHCONHPh), (NH2,H,H,Et,NHCOCONHPh), (NH2,H,H,CH2OH,CONHPh), (NH2,H,H,CH2OH,CONH-3-pyridyl), (NH2,H,H,CH2OH,NHCONHPh), (NH2,H,H,CH2OH,NHCOCONHPh), (NH2,H,Me,Me,CONHPh), (NH2,H,Me,Me,CONH-3-pyridyl), (NH2,H,Me,Me,NHCONKPh), (NH2,H,Me,Me,NHCOCONHPh), (NH2,H,Me,Et,CONHPh), (NH2,H,Me,Et,CONH-3-pyridyl), (NH2,H,Me,Et,NHCOPh), (NH2,H,Me,Et,NHCO-2-furyl), (NH2,H,Me,Et,NHCONHPh), (NH2,H,Me,Et,NHCOCONHPh), (NH2,H,Me,CH2OH,CONHPh), (NH2,H,Me,CH2OH,CONH-3-pyridyl), (NH2,H,Me,CH2OH,NHCONHPh), (NH2,H,Me,CH2OH,NHCOCONHPh), (NH2,H,Ph,Me,CONHPh), (NH2,H,Ph,Me,CONH-3-pyridyl), (NH2,H,Ph,Me,NHCONHPh), (NH2,H,Ph,Me,NHCOCONHPh), (NH2,H,Ph,Et,CONHPh), (NH2,H,Ph,Et,CONH-3-pyridyl), (NH2,H,Ph,Et,NHCOPh), (NH2,H,Ph,Et,NHCO-2-furyl), (NH2,H,Ph,Et,NHCONHPh), (CNH2,Ph,Et,NHCOCONHPh), (NH2,H,Ph,CH2OH,CONHPh), (NH2,H,Ph,CH2OH,CONH-3-pyridyl), (NH2,H,Ph,CH2OH,N,HCONPHh), (NH2,H,Ph,CH2OH,NHCOCONHPh), (NH2,H,OH,Me,CONHPh), (NH2,H,OH,Me,CONH-3-pyridyl), (NH2,H,OH,Me,NHCONHPh), (NH2,H,OH, Me,NHCOCONHPh), (NH2,H,OH,Et,CONHPh), (NH2,H, OH,Et,CONH-3-pyridyl), (NH2,H,OH,Et,NHCOPh), (NH2, H,OH,Et,NHCO-2-furyl), (NH2,H,OH,Et,NHCONHPh), (NH2,H,OH,Et,NHCOCONHPh), (NH2,H,OH,CH2OH, CONHPh), (NH2,H,OH,CH2OH,CONH-3-pyridyl), (NH2, H,OH,CH2OH,NHCONHPh), (NH2,H,OH,CH2OH,NH-COCONHPh), (NH2,Me,H,Me,CONHPh), (NH2,Me,H,Me, CONH-3-pyridyl), (NH2,Me,H,Me,NHCONHPh), (NH2, Me,H,Me,NHCOCONHPh), (NH2,Me,H,Et,CONHPh), (NH2,Me,H,Et,CONH-3-pyridyl), (NH2,Me,H,Et,NH-COPh), (NH2,Me,H,Et,NHCO-2-furyl), (NH2,Me,H,Et, NHCONHPh), (NH2,Me,H,Et,NHCOCONHPh), (NH2,Me, H,CH2OH,CONHPh), (NH2,Me,H,CH2OH,CONH-3-pyridyl), (NH2,Me,H,CH2OH,NHCONHPh), (NH2,Me,H, CH2OH,NHCOCONHPh), (NH2,Me,Me,Me,CONHPh), (NH2,Me,Me,Me,CONH-3-pyridyl), (NH2,Me,Me,Me,NHCONHPh), (NH2,Me,Me,Me,NHCOCONHPh), (NH2,Me, Me,Et,CONHPh), (NH2,Me,Me,Et,CONH-3-pyridyl), (NH2,Me,Me,Et,NHCOPh), (NH2,Me,Me,Et,NHCO-2-furyl), (NH2,Me,Me,Et,NHCONHPh), (NH2,Me,Me,Et,NH-COCONHPh), (NH2,Me,Me,CH2OH,CONHPh), (NH2, Me,Me,CH2OH,CONH-3-pyridyl), (NH2,Me,Me,CH2OH, NHCONHPh), (NH2,Me,Me,CH2OH,NHCOCONHPh), (NH2,Me,Ph,Me,CONHPh), (NH2,Me,Ph,Me,CONH-3-pyridyl), (NH2,Me,Ph,Me,NHCOPh), (NH2,Me,Ph,Me, NHCO-2-furyl), (NH2,Me,Ph,Me,NHCONHPh), (NH2,Me, Ph,Me,NHCOCONHPh), (NH2,Me,Ph,Et,CONHPh), (NH2,Me,Ph,Et,CONH-3-pyridyl), (NH2,Me,Ph,Et,NH-COPh), (NH2,Me,Ph,Et,NHCO-2-furyl), (NH2,Me,Ph,Et, NHCONHPh), (NH2,Me,Ph,Et,NHCOCONHPh), (NH2, Me,Ph,CH2OH,CONHPh), (NH2,Me,Ph,CH2OH,CONH-3-pyridyl), (NH2,Me,Ph,CH2OH,NHCONHPh), (NH2,Me, Ph,CH2OH,NHCOCONHPh), (NH2,Me,OH,Me, CONHPh), (NH2,Me,OH,Me,CONH-3-pyridyl), (NH2,Me, OH,Me,NHCONHPh), (NH2,Me,OH,Me, NHCOCONHPh), (NH2,Me,OH,Et,CONHPh), (NH2,Me, OH,Et,CONH-3-pyridyl), (NH2,Me,OH,Et,NHCOPh), (NH2,Me,OH,Et,NHCO-2-furyl), (NH2,Me,OH,Et,NH-CONHPh), (NH2,Me,OH,Et,NHCOCONHPh), (NH2,Me, OH,CH2OH,CONHPh), (NH2,Me,OH,CH2OH,CONH-3-pyridyl), (NH2,Me,OH,CH2OH,NHCONHPh), (NH2,Me, OH,CH2OH,NHCOCONHPh), (NH2,Ph,H,Me,CONHPh), (NH2,Ph,H,Me,CONH-3-pyridyl), (NH2,Ph,H,Me,NH-CONHPh), (NH2,Ph,H,Me,NHCOCONHPh), (NH2,Ph,H, Et,CONHPh), (NH2,Ph,H,Et,CONH-3-pyridyl), (NH2,Ph, H,Et,NHCOPh), (NH2,Ph,H,Et,NHCO-2-furyl), (NH2,Ph, H,Et,NHCONHPh), (NH2,Ph,H,Et,NHCOCONHPh), (NH2,Ph,H,CH2OH,CONHPh), (NH2,Ph,H,CH2OH, CONH-3-pyridyl), (NH2,Ph,H,CH2OH,NHCONHPh), (NH2,Ph,H,CH2OH,NHCOCONHPh), (NH2,Ph,Me,Me, CONHPh), (NH2,Ph,Me,Me,CONH3-pyridyl), (NH2,Ph, Me,Me,NHCONHPh), (NH2,Ph,Me,Me,NHCOCONHPh), (NH2,Ph,Me,Et,CONHPh), (NH2,Ph,Me,Et,CONH-3-pyridyl), (NH2,Ph,Me,Et,NHCOPh), (NH2,Ph,Me,Et,NHCO-2-furyl), (NH2,Ph,Me,Et,NHCONHPh), (NH2,Ph,Me,Et, NHCOCONHPh), (NH2,Ph,Me,C2OH,CONHPh), (NH2, Ph,Me,CH2OH,CONH-3-pyridyl), (NH2,Ph,Me,CH2OH, NHCONHPh), (NH2,Ph,Me,CH2OH,NHCOCONHPh) (NH2,Ph,Ph,Me,CONHPh), (NH2,Ph,Ph,Me,CONH-3-pyridyl), (NH2,Ph,Ph,Me,NHCOPh), (NH2,Ph,Ph,Me, NHCO-2-furyl), (NH2,Ph,Ph,Me,NHCONHPh), (NH2,Ph, Ph,Me,NHCOCONHPh), (NH2,Ph,Ph,Et,CONHPh), (NH2, Ph,Ph,Et,CONH-3-pyridyl), (NH2,Ph,Ph,Et,NHCOPh), (NH2,Ph,Ph,Et,NHCO-2-furyl), (NH2,Ph,Ph,Et,NHCON-HPh), (NH2,Ph,Ph,Et,NHCOCONHPh), (NH2Ph,Ph, CH2OH,CONHPh), (NH2,Ph,Ph,CH2OH,CONH-3-pyridyl), (NH2,Ph,Ph,CH2OH,NHCOPh), (NH2,Ph,Ph, CH2OH,NHCO-2-furyl), (NH2,Ph,Ph,CH2OH, NHCONHPh), (NH2,Ph,Ph,CH2OH,NHCOCONHPh), (NH2,Ph,OH,Me,CONHPh), (NH2,Ph,OH,Me,CONH-3-pyridyl), (NH2,Ph,OH,Me,NHCONHPh), (NH2,Ph,OH,Me, NHCOCONHPh), (NH2,Ph,OH,Et,CONHPh), (NH2,Ph, OH,Et,CONH-3-pyridyl), (NH2,Ph,OH,Et,NHCOPh), (NH2,Ph,OH,Et,NHCO-2-furyl), (NH2,Ph,OH,Et,NHCON-HPh), (NH2,Ph,OH,Et,NHCOCONHPh), (NH2,Ph,OH, CH2OH,CONHPh), (NH2,Ph,OH,CH2OH,CONH-3-pyridyl), (NH2,Ph,OH,CH2OH,NHCOPh), (NH2,Ph,OH, CH2OH,NHCO-2-furyl), (NH2,Ph,OH,CH2OH, NHCONHPh), (NH2,Ph,OH,CH2OH,NHCOCONHPh), (NHCH2CH(OH)CH2OH,H,H,Me,CONHPh), (NHCH2CH (OH)CH2OH,H,H,Me,CONH-3-pyridyl), (NHCH2CH(OH) CH2OH,H,H,Me,NHCONHPh), (NHCHH,H,H,Me, NHCO-2-furyl, (NHCH2CH(OH)CH2OH,H,H,Me, NHCONHPh), (NHCH2CH(OH)CH2OH,H,H,Me, NHCOCONHPh), (NHCH2CH(OH)CH2OMe,H,H,Me, CONHPh), (NHCH2CH(OH)CH2OMe,H,H,Me,CONH-3-pyridyl), (NHCH2CH(OH)CH2OMe,H,H,Me,NHCOPh), (NHCH2CH(OH)CH2OMe,H,H,Me,NHCO-2-furyl), (NHCH2CH(OH)CH2OMe,H,H,Me,NHCONHPh), (NHCH2CH(OH)CH2OMe,H,H,Me,NHCOCONHPh), (NHCH2CH(OH)CH2NH2,H,H,Me,CONHPh), (NHCH2CH(OH)CH2NH2,H,H,Me,CONH-3-pyridyl), (NHCH2CH(OH)CH2NH2,H,H,Me,NHCOPh), (NHCH2CH(OH)CH2NH2,H,H,Me,NHCO-2-furyl), (NHCH2CH(O11)CH2NH2,H,H,Me,NHCONHPh), (NHCH2CH(OH)CH2NH2,H,H,Me,NHCOCONHPh), (NHCH2CH(OH)CH2NHMe,H,H,Me,CONHPh), (NHCH2CH(OH)CH2NHMe,H,H,Me,CONH-3-pyridyl), (NHCH2CH(OH)CH2NHMe,H,H,Me,NHCOPh), (NHCH2CH(OH)CH2NHMe,H,H,Me,NHCO-2-furyl), (NHCH2CH(OH)CH2NHMe,H,H,Me,NHCONHPh), (NHCH2CH(OH)CH2NHMe,H,H,Me,NHCOCONHPh), (NHCH2CH(OH)CH2NHCOMe,H, H,Me,CONHPh), (NHCH2CH(OH)CH2NHCOMe,H,H,Me,CONH-3-pyridyl), (NHCH2CH(OH)CH2NHCOMe,H,H,Me,NH-COPh), (NHCH2CH(OH)CH2NHCOMe,H,H,Me,NHCO-2-furyl), (NHCH2CH(OH)CH2NHCOMe,H,H,Me, NHCONHPh), (NHCH2CH(OH)CH2NHCOMe,H,H,Me, NHCOCONHPh), (NHCH2CH(OH)CH2N(Me)Me,H,H, Me,CONHPh), (NHCH2CH(OH)CH2N(Me)Me,H,H,Me, CONH-3-pyridyl), (NHCH2CH(OH)CH2N(Me)Me,H,H, Me,NHCOPh), (NHCH2CH(OH)CH2N(Me)Me,H,H,Me, NHCO-2-furyl), (NHCH2CH(OH)CH2N(Me)Me,H,H,Me, NHCONHPh), (NHCH2CH(OH)CH2N(Me)Me,H,H,Me, NHCOCONHPh), (NHC(O)C(O)NH2,H,H,Me,CONHPh), (NHC(O)C(O)NH2,H,H,Me,CONH-3-pyridyl), (NHC(O)C (O)NH2,H,H,Me,NHCOPh, (NHC(O)C(O)NH2,H,H,Me, NHCO-2-furyl), (NHC(O)C(O)NH2,H,H,Me,NHCON-HPh), (NHC(O)C(O)NH2,H,H,Me,NHCOCONHPh), (NHC(O)C(O)NHMe,H,H,Me,CONHPh), (NHC(O)C(O) NHMe,H,H,Me,CONH-3-pyridyl), (NHC(O)C(O)NHMe, H,H,Me,NHCOPh), (NHC(O)C(O)NHMe,H,H,Me,NHCO-2-furyl), (NHC(O)C(O)NHMe,H,H,Me,NHCONHPh), (NHC(O)C(O)NHMe,H,H,Me,NHCOCONHPh), (NHC(O) C(O)N(Me)Me,H,H,Me,CONHPh), (NHC(O)C(O)N(Me) Me,H,H,Me,CONH-3-pyridyl), (NHC(O)C(O)N(Me)Me,H, H,Me,NHCOPh), (NHC(O)C(O)N(Me)Me,H,H,Me, NHCO-2-furyl), (NHC(O)C(O)N(Me)Me,H,H,Me, NHCONHPh), (NHC(O)C(O)N(Me)Me,H,H,Me, NHCOCONHPh).

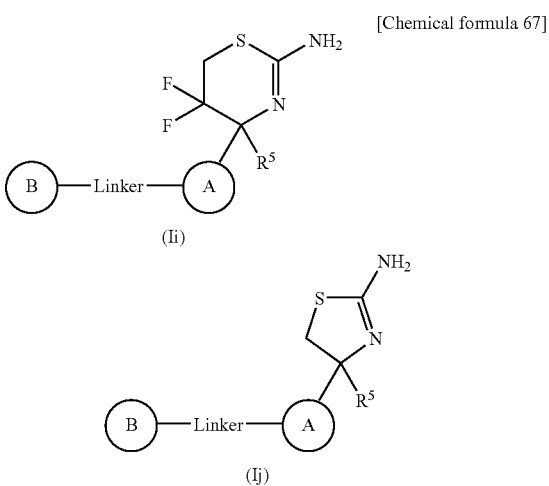

[Chemical formula 67]

In above structural formula (Ii) or (Ij), the combination of B, Linker, A, R⁵ (B, linker, A, R⁵) are the following compounds.

TABLE 169

| B | | Linker | | A | | R5 | |
|---|---|---|---|---|---|---|---|
| B1 | Ph- | L1 | (thioamide) | A1 | (pyrimidine) | R51 | —CN |
| B2 | 2-pyridyl- | L2 | (thioamide) | A2 | (pyrimidine) | R52 | —C≡CH |
| B3 | 4-Me-Ph- | L3 | (ketone) | A3 | (cyclohexyl) | R53 | —C≡CMe |
| B4 | cHex- | L4 | (ketone) | A4 | (piperidine) | R54 | —CF3 |
| B5 | cHex-CH2— | L5 | (diketone) | A5 | (phenyl) | R55 | —CH2Cl |
| | | | | | | R56 | CHCl2 |

(B, Linker, A, R⁵)=
(B1,L1,A1,R51), (B1,L1,A1,R52), (B1,L1,A1,R53), (B1,L1,A1,R54), (B1,L1,A1,R55), (B1,L1,A1,R56), (B1,L1,A2,R51), (B1,L1,A2,R52), (B1,L1,A2,R53), (B1,L1,A2,R54), (B1,L1,A2,R55), (B1,L1,A2,R56), (B1,L1,A3,R51), (B1,L1,A3,R52), (B1,L1,A3,R53), (B1,L1,A3,R54), (B1,L1,A3,R55), (B1,L1,A3,R56), (B1,L1,A4,R51), (B1,L1,A4,R52), (B1,L1,A4,R53), (B1,L1,A4,R54), (B1,L1,A4,R55), (B1,L1,A4,R56), (B1,L1,A5,R51), B1,L1,A4,R52), (B1,L1,A5,R53), (B1,L1,A5,R54), (B1,L1,A5,R55), (B1,L1,A5,R56), (B1,L2,A5,R51), (B1,L2,A1,R52), (B1,L2,A1,R53), B1,L2,A1,R54), (B1,L2,A1,R55), (B1,L2,A1,R56), (1,L2,A2,R51), B1,L2,A2,R52), (B1,L2,A2,R53), (B1,L2,A2,R54), (B1,L2,A2,R55), (B1,L2,A2,R56), (B1,L2,A3,R51), (B1,L2,A3,R52), (B1,L2,A3,R53), (B1,L2,A3,R54), (B1,L2,A3,R55), (B1,L2,A3,R56), (B1,L2,A4,R51), (B1,L2,A4,R52), (B1,L2,A4,R53), (B1,L2,A4,R54), (B1,L2,A4,R55), (B1,L2,A4,R56), (B1,L2,A5,R51), (B1,L2,A5,R52), (B1,L2,A5,R53), (B1,L2,A5,R54), (B1,L2,A5,R55), (B1,L2,A5,R56), (B1,L3,A1,R51), (B1,L3,A1,R52), (B1,L3,A1,R53), (B1,L3,A1,R54), (B1,L3,A1,R55), (B1,L3,A1,R56), (B1,L3,A2,R51), (B1,L3,A2,R52), (B1,L3,A2,R53), (B1,L3,A2,R54), (B1,L3,A2,R55), (B1,L3,A2,R56), (B1,L3,A2,R51, (B1,L3,A3,R52), (B1,L3,A3,R53), (B1,L3,A3,R54), (B1,L3,A3,R55), (B1,L3,A3,R56), (B1,L3,A4,R51), (B1,L3,A4,R52), (B1,L3,A4,R53), (B1,L3,A4,R54), (B1,L3,A4,R55), (B1,L3,A4,R56), (B1,L3,A5,R51), (B1,L3,A5,R52), (B1,L3,A5,R53), (B1,L3,A5,R54), (B1,L3,A5,R55), (B1,L3,A5,R56), (B1,L4,A1,R51), (B1,L4,A1,R52), (B1,L4,A1,R53), (B1,L4,A1,R54), (B1,L4,A1,R55), (B1,L4,A1,R56), (B1,L4,A2,R51), (B1,L4,A2,R52), (B1,L4,A2,R53), (B1,L4,A2,R54), (B1,L4,A2,R55), (B1,L4,A2,R56), (B1,L4,A3,R51), (B1,L4,A3,R52), (B1,L4,A3,R53), (B1,L4,A3,R54), (B1,L4,A3,R55), (B1,L4,A3,R56), (B1,L4,A4,R51), (B1,L4,A4,R52), (B1,L4,A4,R53), (B1,L4,A4,R54), (B1,L4,A4,R55), (B1, L4,A4,R56), (B1,L4,A5,R51), (B1,L4,A5,R52), (B1,L4,A5, R53), (B1,L4,A5,R54), (B1,L4,A5,R55), (B1,L4,A5,R56), (B1,L5,A1,R51), (B1,L5,A1,R52), (B1,L5,A1,R53), (B1, L5,A1,R54), (B1,L5,A1,R55), (B1,L5,A1,R56), (B1,L5,A2, R51), (B1,L5,A2,R52), (B1,L5,A2,R53), (B1,L5,A2,R54), (B1,L5,A2,R55), (B1,L5,A2,R56), (B1,L5,A3,R51), (B1, L5,A3,R52), (B1,L5,A3,R53), (B1,L5,A3,R54), (B1,L5,A3, R55), (B1,L5,A3,R56), (B1,L5,A4,R51), (31,L5,A4,R52), (B1,L5,A4,R53), (B1,L5,A4,R54), (B1,L5,A4,R55), (B1, L5,A4,R56), (B1,L5,A5,R5), (B1,L5,A5,R52), (B1,L5,A5, R53), (B1,L5,A5,R54), (B1,L5,A5,R55), (B1,L5,A5,R56), (B2,L1,A1,R51), (B2,L1,A1,R52), (B2,L1,A1,R53), (B2, L1,A1,R54), (B2,L1,A1,R55), (B2,L1,A1,R56), (B2,L1,A2, R51), (B2,L1,A2,R52), (B2,L1,A2,R53), (B2,L1,A2,R54), (B2,L1,A2,R55), (B2,L1,A2,R56), (B2,L1,A3,R51), (B2, L1,A3,R52), (B2,L1,A3,R53), (B2,L1,A3,R54), (B2,L1,A3, R55), (B2,L1,A3,R56), (B2,L1,A4,R51), (B2,L1,A4,R52), (B2,L1,A4,R53), (B2,L1,A4,R54), (B2,L1,A4,R55), (B2, L1,A4,R56), (B2,L1,A5,R51), (B2,L1,A5,R52), (B2,L1,A5, R53), (B2,L1,A5,R54), (B2,L1,A5,R55), (B2,L1,A5,R56), (B2,L2,A1,R51), (B2,L2,A1,R52), (B2,L2,A1,R53), (B2, L2,A1,R54), (32,L2,A1,R55), (B2,L2,A1,R56), (B2,L2,A2, R51), (B2,L2,A2,R52), (B2,L2,A2,R53), (B2,L2,A2,R54), (B2,L2,A2,R55), (B2,L2,A2,R56), (B2,L2,A3,R51), (32,L2, A3,R52), (B2,L2,A3,R53), (B2,L2,A3,R54), (B2,L2,A3, R55), (B2,L2,A3,R56), (B2,L2,A4,R51), (B2,L2,A4,R52), (B2,L2,A4,R53), (B2,L2,A4,R54), (B2,L2,A4,R55), (B2, L2,A4,R56), (B2,L2,A5,R51), (B2,L2,A5,R52), (B2,L2,A5, R53), (B2,L2,A5,R54), (B2,L2,A5,R55), (B2,L2,A5,R56), (B2,L3,A1,R51), (B2,L3,A1,R52), (B2,L3,A1,R53), (B2, L3,A1,R54), (B2,L3,A1,R55), (B2,L3,A1,R56), (B2,L3,A2, R51), (B2,L3,A2,R52), (B2,L3,A2,R53), (B2,L3,A2,R54), (B2,L3,A2,R55), (B2,L3,A2,R56), (B2,L3,A3,R51), (B2, L3,A3,R52), (B2,L3,A3,R53), (B2,L3,A3,R54), (B2,L3,A3, R55), (B2,L3,A3,R56), (B2,L3,A4,R51), (B2,L3,A4,R52), (B2,L3,A4,R53), (B2,L3,A4,R54), (B2,L3,A4,R55), (B2, L3,A4,R56), (B2,L3,A5,R51), (B2,L3,A5,R52), (B2,L3,A5, R53), (B2,L3,A5,R54), (B2,L3,A5,R55), (B2,L3,A5,R56), (32,L4,A1,R51), (B2,L4,A1,R52), (B2,L4,A1,R53), (B2,L4, A1,R54), (B2,L4,A1,R55), (B2,L4,A1,R56), (B2,L4,A2, R51), (B2,L4,A2,R52), (B2,L4,A2,R53), (B2,L4,A2,R54), (B2,L4,A2,R55), (B2,L4,A2,R56), (B2,L4,A3,R51), (B2, L4,A3,R52), (B2,L4,A3,R53), (B2,L4,A3,R54), (B2,L4,A3, R55), (B2,L4,A3,R56), (B2,L4,A4,R51), (B2,L4,A4,R52), (B2,L4,A4,R53), (B2,L4,A4,R54), (B2,L4,A4,R55), (B2, L4,A4,R56), (B2,L4,A5,R51), (B2,L4,A5,R52), (B2,L4,A5, R53), (B2,L4,A5,R54), (B2,L4,A5,R55), (B2,L4,A5,R56), (B2,L5,A1,R51), (B2,L5,A1,R52), (B2,L5,A1,R53), (B2, L5,A1,R54), (B2,L5,A1,R55), (B2,L5,A1,R56), (B2,L5,A2, R51), (B2,L5,A2,R52), (B2,L5,A2,R53), (B2,L5,A2,R54), (B2,L5,A2,R55), (B2,L5,A2,R56), (B2,L5,A3,R51), (B2, L5,A3,R52), (B2,L5,A3,R53), (B2,L5,A3,R54), (B2,L5,A3, R55), (B2,L5,A3,R56), (B2,L5,A4,R51), (B2,L5,A4,R52), (B2,L5,A4,R53), (B2,L5,A4,R54), (B2,L5,A4,R55), (B2, L5,A4,R56), (B2,L5,A5,R51), (B2,L5,A5,R52), (B2,L6,A5, R53), (B2,L5,A5,R54), (B2,L5,A5,R55), (B2,L5,A5,R56), (B3,L1,A1,R51), (B3,L1,A1,R52), (B3,L1,A1,R53), (B3, L1,A1,R54), (B3,L1,A1,R55), (B3,L1,A1,R56), (B3,L1,A2, R51), (B3,L1,A2,R52), (B3,L1,A2,R53), (B3,L1,A2,R54), (B3,L1,A2,R55), (B3,L1,A2,R56), (B3,L1,A3,R51), (B3, L1,A3,R52), (B3,L1,A3,R53), (B3,L1,A3,R54), (B3,L1,A3, R55), (B3,L1,A3,R56), (B3,L1,A4,R51), (B3,L1,A4,R52), (B3,L1,A4,R53), (B3,L4,A4,R4), (B3,L1,A4,R55), (B3,L1, A4,R56), (B3,L1,A5,R51), (B3,L1,A5,R52), (B3,L1,A5, R53), (B3,L1,A5,R54), (B3,L1,A5,R55), (B3,L1,A5,R56), (B3,L2,A1,R51), (B3,L2,A1,R52), (B3,L2,A1,R53),(B3,L2, A1,R54), (B3,L2,A1,R55), (B3,L2,A1,R56), (B3,L2,A2, R51), (B3,L2,A2,R52), (B3,L2,A2,R53), (B3,L2,A2,R54), (B3,L2,A2,R55), (B3,L2,A2,R56), (B3,L2,A3,R51), (B3, L2,A3,R52), (B3,L2,A3,R53), (B3,L2,A3,R54, (B3,L2,A8, R55), (B3,L2,A3,R56), (B3,L2,A4,R51), (B3,L2,A4,R52), (B3,L2,A4,R53), (B3,L2,A4,R54), (B3,L2,A4,R55), (B3, L2,A4,R56), (B3,L2,A5,R51), (B3,L2,A5,R52), (B3,L2,A5, R53), (33,L2,A5,R54), (B3,L2,A5,R55), (B3,L2,A5,R56), (B3,L3,A1,R51), (B3,L3,A1,R52), (B3,L3,A1,R53), (B3, L3,A1,R54), (B3,L3,A1,R55), (B3,L3,A1,R56), (B3,L3,A2, R51), (B3,L3,A2,R52), (B3,L3,A2,R53), (B3,L3,A2,R54), (B3,L3,A2,R55), (B3,L3,A2,R56), (B3,L3,A3,R51), (B3, L3,A3,R52), (B3,L3,A3,R53), (B3,L3,A3,R54), (B3,L3,A3, R55), (B3,L3,A3,R56), (B3,L3,A4,R51), (B3,L3,A4,R52), (B3,L3,A4,R53), (B3,L3,A4,R54), (3,L3,A4,R55), (B3,L3, A4,R56), (B3,L3,A5,R51), (B3,L3,A5,R52), (B3,L3,A5, R53), (B3,L3,A5,R54), (B3,L3,A5,R55), (B3,L3,A5,R56), (B3,L4,A1,R5,L4), (B3,L4,A1,R55), (B3,L4,A1,R56), (B3, L4,A2,R51, (B3,L4,A2,R52), (B3,L4,A2,R53), (B3,L4,A2, R54), (B3,L4,A2,R55), (B3,L4,A2,R56), (B3,L4,A3,R1), (B3,L4,A3,R52), (B3,L4,A3,R53), (B3,L4,A3,R54), (B3, L4,A3,R55), (B3,L4,A3,R56), (B3,L4,A4,R51), (B3,L4,A4, R52), (B3,L4,A4,R53), (B3,L4,A4,R54), (B3,L4,A4,R55), (B3,L4,A4,R56), (B3,L4,A5,R51), (B3,L4,A1,R52), (B3, L4,A5,R53), (B3,L4,A5,R54), (B3,L4,A5,R55), (B3,L4,A5, R56), (B3,L5,A1,R51), (B3,L5,A1,R52), (B3,L5,A1,R53), (B3,L5,A1,R54, (B3,L5,A1,R55), (B3,L5,A1,R56), (B3,L5, A2,R51), (B3,L5,A2,R52), (B3,L5,A2,R53), (B3,L5,A2, R54), (B3,L5,A2,R55), (B3,L5,A2,R56), (B3,L5,A3,R51), (B3,L5,A3,R52), (B3,L5,A3,R53), (B3,L5,A3,R54), (B3, L5,A3,R55), (B3,L5,A3,R56), (B3,L5,A4,R51), (B3,L5,A4, R52), (B3,L5,A4,R53), (B3,L5,A4,R54), (B3,L5,A4,R55), (B3,L5,A4,R56), (B3,L5,A5,R51), (B3,L5,A5,R52), (B3, L5,A5,R53), (B3,L5,A5,R54), (13,L5,A5,R5), (B3,L5,A5, R56), (B4,L1,A1,R51), (B4,L1,A1,R52), (B4,L1,A1,R53), (B4,L1,A1,R54), (B4,L1,A1,R55), (B4,L1,A1,R56), (B4, L1,A2,R51), (B4,L1,A2,R52), (B4,L1,A2,R53), (B4,L1,A2, R54), (B4,L1,A2,R55), (B4,L1,A2,R56), (B4,L1,A3,R51), (B4,L1,A3,R52), (B4,L1,A3,R53), (B4,L1,A3,R54), (B4, L1,A3,R55), (B4,L1,A3,R56), (B4,L1,A4,R51), (B4,L1,A4, R52), (B4,L1,A4,R53), (B4,L1,A4,R54), (B4,L1,A4,R55), (B4,L1,A4,R56), (B4,L1,A5,R51), (B4,L1,A5,R52), (B4, L1,A5,R53), (B4,L1,A5,R54), (B4,L1,A5,R55), (B4,L1,A5, R56), (B4,L2,A1,R51), (B4,L2,A1,R52), (B4,L2,A1,R53), (B4,L2,A1,R54), (B4,L2,A1,R55), (B4,L2,A1,R56), (B4, L2,A2,R51), (B4,L2,A2,R52), (B4,L2,A2,R53), (B4,L2,A2, R54), (B4,L2,A2,R55), (B4,L2,A2,R56), (B4,L2,A3,R51), (B4,L2,A3,R52), (B4,L2,A3,R53), (B4,L2,A3,R54), (B4, L2,A3,R55), (B4,L2,A3,R56), (B4,L2,A4,R51), (B4,L2,A4, R52), (B4,L2,A4,R53), (B4,L2,A4,R54), (B4,L2,A4,R55), (B4,L2,A4,R56), (B4,L2,A5,R51), (B4,L2,A5,R52), (B4, L2,A5,R53), (B4,L2,A5,R54), (B4,L2,A5,R55), (B4,L2,A5, R56), (B4,L3,A1,R51), (B4,L3,A1,R52), (B4,L3,A1,R53), (B4,L3,A1,R54), (B4,L3,A1,R55), (B4,L3,A1,R56), (B4, L3,A2,R51), (B4,L3,A2,R52), (B4,L3,A2,R53), (B4,L3,A2, R54), (B-4,L3,A2,R55), (B4,L3,A2,R56), (B4,L3,A3,R51), (B4,L3,A3,R52), (B4,L3,A3,R53), (B4,L3,A3,R54), (B4, L3,A3,R55), (B4,L3,A3,R56), (B4,L3,A4,R1), (B4,L3,A4, R52), (B4,L3,A4,R53), (B4,L3,A4,R54), (B4,L3,A4,R55), (B4,L3,A4,R56), (B4,L3,A5,R51), (B4,L3,A5,R52), (B4, L3,A5,R53), (B4,L3,A5,R54), (B4,L3,A5,R55), (B4,L3,A5, R56), (B4,L4,A1,R51), (B4,L4,A1,R52), (B4,L4,A1,R53), (B4,L4,A1,R54), (B4,L4,A1,R55), (B4,L4,A1,R56), (B4, L4,A2,R51), (B4,L4,A2,R52), (B4,L4,A2,R53), (B4,L4,A2, R54), (B4,L4,A2,R55), (B4,L4,A2,R56), (B4,L4,A3,R51), (B4,L4,A3,R52), (B4,L4,A3,R53), (B4,L4,A3,R54, (B4,L4, A3,R55), (B4,L4,A3,R56), (B4, L4,A4,R51), (B4,L4,A4, R52, (B4, L4,A4,R53), (B4,L4,A4,R54), (B4,L4,A4,R55), (B4,L4,A4,R56), (B4,L4,A5,R51), (B4,L4,A5,R52), (B4,L4,A5,R53), (B4,L4,A5,R54), (B4,L4,A5,R55), (B4,L4,A5,R56), (B4,L4,A1,R51), (B4,L5,A1,R52), (B4,L5,A1,R53), (B4,L5,A1,R54), (B4,L5,A1,R55), (B4,L5,A1,R56), (B4,L5,A2,R51), (B4,L5,A2,R52), (B4,L5,A2,R53), (B4,L5,A2,R54), (B4,L5,A2,R55), (B4,L5,A2,R56), (B4,L4,A3,R51), (B4,L5,A3,R52), (B4,L5,A3,R53), (B4,L5,A3,R54), (B4,L5,A3,R55), (B4,L5,A3,R56), (B4,L5,A4,R51), (B4,L5,A4,R52), (B4,L5,A4,R53), (B4,L5,A4,R54), (B4,L6,A4,R55), (B4,L5,A4,R56), (B4,L5,A5,R51), (B4,L5,A5,R52), (B4,L5,A5,R53), (B4,L5,A5,R54), (B4,L5,A5,R55), (B4,L5,A5,R56), (B5,L1,A1,R1), (B5,L1,A1,R52), (B5,L1,A1,R53), (B5,L1,A1,R54), (B5,L1,A1,R55), (B5,L1,A1,R56), (B5,L1,A2,R51), (B5,L1,A2,R52), (B5,L1,A2,R53), (B5,L1,A2,R54), (B5,L1,A2,R55), (B5,L1,A2,R56), (B5,L1,A3,R51), (B5,L1,A3,R52), (B5,L1,A3,R53), (B5,L1,A3,R54), (B5,L1,A3,R55), (B5,L1,A3,R56), (B5,L1,A4,R51), (B5,L1,A4,R52), (B5,L1,A4,R53), (B5,L1,A4,R54), (B5,L1,A4,R55), (B5,L1,A4,R56), (B5,L1,A5,R51), (B5,L1,A5,R52), (35,L1,A5,R53), (B5,L1,A5,R54), (B5,L1,A5,R55), (B5,L1,A5,R56), (B5,L2,A1,R51), (B5,L2,A1,R52), (B5,L2,A1,R53), (B5,L2,A1,R54), (B5,L2,A1,R55), (B5,L2,A1,R56), (B5,L2,A2,R51), (B5,L2,A2,R52), (B5,L2,A2,R53), (B5,L2,A2,R54), (B5,L2,A2,R55), (B5,L2,A2,R56), (B5,L2,A3,R51), (B5,L2,A3,R52), (B5,L2,A3,R53), (B5,L2,A3,R54), (B5,L2,A3,R55), (B5,L2,A3,R56), (B5,L2,A4,R51), (B5,L2,A4,R52), (B5,L2,A4,R53), (B5,L2,A4,R54), (B5,L2,A4,R55), (B5,L2,A4,R56), (B5,L2,A5,R51), (B5,L2,A5,R52), (B5,L2,A5,R53), (B5,L2,A5,R54), (B5,L2,A5,R55), (B5,L2,A5,R56), (B5,L3,A1,R51), (B5,L3,A1,R52), (B5,L3,A1,R53), (B5,L3,A1,R54), (B5,L3,A1,R55), (B5,L3,A1,R56), (B5,L3,A2,R51), (B5,L3,A2,R52), (B5,L3,A2,R53), (B5,L3,A2,R4), (B5,L3,A2,R55), (B5,L3,A2,R56), (B5,L3,A3,R51), (B5,L3,A3,R52), (B5,L3,A3,R53), (B5,L3,A3,R54), (B5,L3,A3,R55), (B5,L3,A3,R56), (B5,L3,A4,R51), (B5,L3,A4,R52), (B5,L3,A4,R53), (B5,L3,A4,R54), (B5,L3,A4,R55), (B5,L3,A4,R56), (B5,L3,A5,R51), (B5,L3,A5,R52), (B5,L3,A5,R53), (B5,L3,A5,R54), (B5,L3,A5,R55), (B6,L3,A5,R56), (B5,L4,A1,R51), (B5,L4,A1,R52), (B5,L4,A1,R53), (B5,L4,A1,R54), (B5,L4,A1,R55), (B5,L4,A1,R56), (B5,L4,A2,R51),(B5,L4,A2,R52), (B5,L4,A2,R53), (B5,L4,A2,R54), (B5,L4,A2,R55), (B5,L4,A2,R56), (B5,L4,A3,R51), (B5,L4,A3,R52), (B5,L4,A3,R53), (B5,L4,A3,R54), (B5,L4,A3,R55), (B5,L4,A3,R56), (B5,L4,A4,R51), (B5,L4,A4,R52), (B5,L4,A4,R53), (B5,L4,A4,R54), (B5,L4,A4,R55), (B5,L4,A4,R56), (B5,L4,A5,R51), (B5,L4,A5,R52), (B5,L4,A5,R53), (B5,L4,A5,R54), (B5,L4,A5,R55), (B5,L4,A5,R56), (B5,L5,A1,R51), (B5,L5,A1,R52), (B5,L5,A1,R53), (B5,L5,A1,R54), (B5,L5,A1,R55), (B5,L5,A1,R56), (B5,L5,A2,R51), (B5,L5,A2,R52), (B5,L5,A2,R53), (B5,L5,A2,R54), (B5,L5,A2,R55), (B5,L5,A2,R56), (B5,L5,A3,R51), (B5,L5,A3,R52), (B5,L5,A3,R53), (B5,L5,A3,R54), (B5,L5,A3,R55), (B5,L5,A3,R56), (B5,L5,A4,R51), (B5,L5,A4,R52), (B5,L5,A4,R53), (B5,L5,A4,R54), (B5,L5,A4,R55), (B5,L5,A4,R56), (B5,L5,A5,R51), (B5,L5,A5,R52), (B5,L$_5$,A5,R53), (B5,L5,A5,R54), (B5,L5,A5,R55), (B5,L5,A5,R56).

Test: Measurement of Inhibition of β-Secretase Activity

Zero point five μL of the test compounds (dissolved in N,N'-dimethylsulfoxide) were incubated with 48.5 μL of the fluorescence-quenched peptide substrate solution (Biotin-XSEVNLDAEFRHDSGC-Eu: X=ε-amino-n-capronic acid, Eu=Europium cryptate) and 1 μL, of recombinant human BACE-1 protein (R&D systems) for 3 h at 30° C. in the 96 well half-area plate (black color plate, Costar). The substrate peptide was synthesized by reacting with Biotin-XSEVNLDAEFRHDSGC (Peptide Institute) and Cryptate TBPCOOH mono SMP (CIS bio international). The final concentration of the substrate peptide and recombinant human BACE-1 protein were 18 nM and 7.4 nM, respectively. The enzymatic reaction was performed in sodium acetate buffer (50 mM sodium acetate (pH5.0), 0.008% Triton X-100). After the reaction, a 50 μL of 8.0 μg/mL Streptavidin-XL665 (CIS bio international) dissolved in phosphate buffer (150 mM $K_2HPO_4$—$KH_2PO_4$ (pH 7.0), 0.008% Triton X-100, 0.8 M KF) was add to each well and incubated for 1 h at 30° C. Then, the fluorescence intensity (excitation wavelength 320 nm, emission wavelength 620 nm and 665 nm in each well was measured using Wallac 1420 multilabel counter (Perkin Elmer life sciences). The enzymatic activity was calculated by the each fluorescence intensity ratio ([ratio of fluorescence at 665 nm to that at 620 nm]×10,000). $IC_{50}$ values of test compounds were indicated in table 170.

TABLE 170

| Compound No. | $IC_{50}$ value (μM) |
|---|---|
| 1186 | 5.7 |
| 639 | 7.9 |
| 1000 | 8.0 |
| 246 | 2.9 |
| 269 | 7.0 |
| 1010 | 2.8 |
| 417 | 5.0 |
| 161 | 7.7 |
| 220 | 1.5 |
| 1207 | 4.0 |
| 998 | 4.5 |
| 1205 | 8.1 |
| 616 | 5.9 |
| 504 | 2.5 |
| 799 | 6.7 |
| 490 | 5.1 |
| 972 | 0.45 |
| 1160 | 0.72 |
| 753 | 5.6 |
| 786 | 0.156 |
| 165 | 0.0394 |
| 1132 | 2.563 |
| 570 | 0.149 |
| 1014 | 0.165 |
| 731 | 0.278 |
| 1262 | 0.140 |
| 964 | 0.264 |
| 793 | 0.061 |
| 625 | 1.288 |
| 498 | 0.930 |
| 26 | 1.977 |
| 465 | 3.239 |
| 1197 | 0.912 |
| 395 | 1.500 |
| 896 | 8.497 |
| 660 | 4.586 |
| 664 | 3.642 |
| 176 | 1.479 |
| 284 | 0.229 |
| 912 | 0.175 |
| 212 | 0.220 |
| 163 | 2.278 |
| 1244 | 0.130 |
| 52 | 10.0 |
| 698 | 0.165 |
| 96 | 0.163 |
| 822 | 0.243 |
| 739 | 0.049 |
| 832 | 0.222 |
| 897 | 0.816 |
| 1100 | 0.037 |
| 740 | 0.505 |
| 436 | 0.160 |
| 1043 | 0.027 |
| 1199 | 0.032 |
| 73 | 0.435 |

TABLE 170-continued

| Compound No. | IC$_{50}$ value (μM) |
|---|---|
| 127 | 0.054 |
| 309 | 0.833 |
| 1135 | 2.296 |
| 1035 | 0.174 |

The IC$_{50}$ value of the following compounds were less than 100 μM by the same test.

3, 4, 6, 8, 12, 17, 18, 30, 31, 35, 36, 38, 39, 42, 43, 57, 61, 67, 67, 71, 77, 78, 80, 85, 97, 99, 105, 106, 113, 114, 115, 117, 120, 121, 125, 128, 129, 130, 134, 139, 144, 154, 157, 159, 164, 172, 175, 178, 181, 182, 186, 189, 200, 200, 201, 204, 207, 209, 211, 214, 215, 216, 228, 232, 240, 241, 243, 243, 243, 251, 255, 259, 267, 273, 275, 278, 279, 281, 282, 293, 298, 299, 300, 302, 303, 307, 314, 319, 321, 322, 326, 328, 330, 333, 335, 339, 341, 344, 345, 346, 348, 352, 363, 357, 358, 359, 359, 359, 360, 361, 363, 369, 370, 373, 378, 380, 383, 389, 390, 393, 396, 397, 402, 405, 406, 409, 410, 413, 415, 426, 442, 443, 444, 451, 452, 454, 456, 463, 467, 469, 472, 472, 479, 480, 482, 482, 483, 491, 493, 497, 500, 501, 502, 609, 511, 515, 516, 517, 527, 528, 532, 542, 544, 549, 550, 551, 558, 660, 568, 569, 576, 578, 584, 586, 588, 591, 600, 607, 608, 611, 613, 618, 620, 629, 634, 634, 637, 643, 646, 652, 657, 661, 671, 677, 681, 687, 691, 708, 711, 719, 720, 723, 725, 728, 729, 730, 732, 735, 743, 746, 756, 758, 761, 770, 775, 781, 787, 788, 790, 791, 792, 796, 797, 802, 803, 804, 808, 809, 813, 816, 819, 820, 824, 833, 835, 836, 847, 850, 861, 865, 866, 871, 876, 887, 893, 894, 900, 905, 906, 908, 910, 919, 922, 928, 932, 933, 935, 936, 939, 941, 943, 944, 946, 947, 949, 959, 966, 971, 984, 986, 988, 990, 1004, 1005, 1007, 1009, 1013, 1020, 1028, 1034, 1039, 1046, 1055, 1062, 1063, 1069, 1074, 1077, 1084, 1089, 1096, 1099, 1108, 1109, 1114, 1124, 1125, 1131, 1140, 1142, 1145, 1147, 1148, 1150, 1164, 1165, 1172, 1174, 1184, 1185, 1193, 1211, 1217, 1221, 1237, 1241, 1243, 1255, 1256, 1257, 1258, 1261, 1263, 1264, 1265, 1266, 1268, 1269, 1270, 1271, 1272, 1274, and so on.

Formulation Example 1

A granule containing the following ingredients is prepared.

| Ingredient | Compound represented by formula (I) | 10 mg |
|---|---|---|
| | Lactose | 700 mg |
| | Corn starch | 274 mg |
| | HPC-L | 16 mg |
| | | 1000 mg |

The compound represented by the formula (I) and lactose are passed through a 60 mesh sieve. Corn starch is passed through a 120 mesh sieve. These are mixed with a V-type mixer. To a mixed powder is added a HPC-L (lower viscosity hydroxypropylcellulose) aqueous solution, the materials are kneaded, granulated (extrusion granulation, pore diameter 0.5 to 1 mm), and dried. The resulting dry granule is passed through a sieve using a vibration sieve (12/60 mesh) to obtain a granule.

Formulation Example 2

A granule for filing into a capsule containing the following ingredients is prepared.

| Ingredient | Compound represented by formula (I) | 15 mg |
|---|---|---|
| | Lactose | 90 mg |
| | Corn starch | 42 mg |
| | HPC-L | 3 mg |
| | | 150 mg |

The compound represented by the formula (I) and lactose are passed through a 60 mesh sieve. Corn starch is passed through a 120 mesh sieve. These are mixed, to a mixed powder is added a HPC-L solution, the materials are kneaded, granulated, and dried. The resulting dry granule is size-adjusted, 150 mg of which is filled into a No. 4 hard gelatin capsule.

Formulation Example 3

A tablet containing the following ingredients is prepared.

| Ingredient | Compound represented by the formula (I) | 10 mg |
|---|---|---|
| | Lactose | 90 mg |
| | Microcrystalline cellulose | 30 mg |
| | CMC-Na | 15 mg |
| | Magnesium stearate | 5 mg |
| | | 150 mg |

The compound represented by the formula (I), lactose, microcrystalline cellulose, CMC-Na (carboxymethylcellulose sodium salt) are passed through a 60 mesh sieve, and mixed. Into a mixed powder is mixed magnesium stearate to obtain a mixed powder for tabletting. The present mixed powder is compressed to obtain 150 mg of a tablet.

Formulation Example 4

The following ingredients are warmed, mixed, and sterilized to obtain an injectable.

| Ingredient | Compound represented by the formula (I) | 3 mg |
|---|---|---|
| | Nonionic surfactant | 15 mg |
| | Purified water for injection | 1 ml |

INDUSTRIAL APPLICABILITY

The present invention is useful as an agent for treating disease induced by production, secretion and/or deposition of amyloid β.

The invention claimed is:
1. A compound represented by the formula (I):

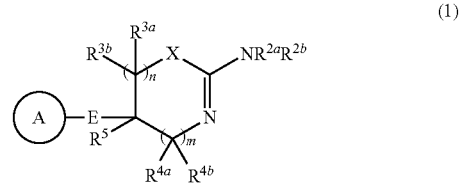

(1)

wherein E is bond and ring A is phenyl, phenyl being substituted optionally with at least one selected from the group consisting of (A) the substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;
(B) lower alkyl optionally substituted with one or more substituents selected from the group of substituent α;
(C) amino lower alkyl substituted with one or more substituents selected from the group of substituent α;
(D) hydroxyimino lower alkyl;
(E) lower alkoxyimino lower alkyl;
(F) lower alkenyl optionally substituted with one or more substituents selected from the group of substituent α;
(G) lower alkynyl optionally substituted with one or more substituents selected from the group of substituent α;
(H) lower alkoxy optionally substituted with one or more substituents selected from the group of substituent α;
(I) lower alkylthio optionally substituted with one or more substituents selected from the group of substituent α;
(J) lower alkylamino substituted with one or more substituents selected from the group of substituent α;
(K) lower alkylsulfonyl optionally substituted with one or more substituents selected from the group of substituent α;
(L) aryl lower alkoxycarbonyl optionally substituted with one or more substituents selected from the group of substituent α, azido, and lower alkyl;
(M) acyl substituted with one or more substituents selected from the group of substituent α;
(N) cycloalkyl optionally substituted with one or more substituents selected from the group of substituent α, azido, and lower alkyl;
(O) lower alkylsulfinyl optionally substituted with one or more substituents selected from the group of substituent α;
(P) sulfamoyl;
(Q) aryl optionally substituted with one or more substituents selected from the group of substituent α, azido, and lower alkyl;
(R) heterocyclic group optionally substituted with one or more substituents selected from the group of substituent α, azido, and lower alkyl;
(S) aryloxy optionally substituted with one or more substituents selected from the group of substituent α, azido, and lower alkyl;
(T) heterocyclicoxy optionally substituted with one or more substituents selected from the group of substituent α, azido, and lower alkyl;
(U) arylthio optionally substituted with one or more substituents selected from the group of substituent α, azido, and lower alkyl;
(V) heterocyclic thio optionally substituted with one or more substituents selected from the group of substituent α, azido, and lower alkyl;
(W) arylamino optionally substituted with one or more substituents selected from the group of substituent α, azido, and lower alkyl;
(X) heterocyclicamino optionally substituted with one or more substituents selected from the group of substituent α, azido, and lower alkyl;
(Y) aryl lower alkylamino optionally substituted with one or more substituents selected from the group of substituent α, azido, and lower alkyl;
(Z) heterocyclic lower alkylamino optionally substituted with one or more substituents selected from the group of substituent α, azido, and lower alkyl;
(AA) lower alkyl sulfamoyl optionally substituted with one or more substituents selected from the group of substituent α;
(AB) aryl sulfamoyl optionally substituted with one or more substituents selected from the group of substituent α, azido, and lower alkyl;
(AC) heterocyclic sulfamoyl optionally substituted with one or more substituents selected from the group of substituent α, azido, and lower alkyl;
(AD) arylsulfonyl substituted optionally with one or more substituents selected from the group of substituent α, azido, and lower alkyl;
(AE) heterocyclic sulfonyl optionally substituted with one or more substituents selected from the group of substituent α, azido, and lower alkyl;
(AF) aryl carbamoyl optionally substituted with one or more substituents selected from the group of substituent α, azido, and lower alkyl;
(AG) heterocyclic carbamoyl optionally substituted with one or more substituents selected from the group of substituent α, azido, and lower alkyl;
(AH) aryl lower alkylcarbamoyl optionally substituted with one or more substituents selected from the group of substituent α, azido, and lower alkyl;
(AI) heterocyclic lower alkylcarbamoyl optionally substituted with one or more substituents selected from the group of substituent α, azido, and lower alky;
(AJ) aryloxycarbonyl optionally substituted with one or more substituents selected from the group of substituent α, azido, and lower alkyl;
(AK) heterocyclicoxycarbonyl optionally substituted with one or more substituents selected from the group of substituent α, azido, and lower alkyl;
(AL) lower alkylenedioxy substituted optionally with halogen;
(AM) oxo;
(AN) azido; and
(AO) one of the following formulae:

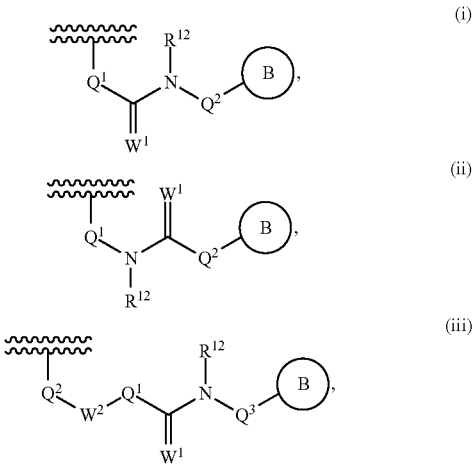

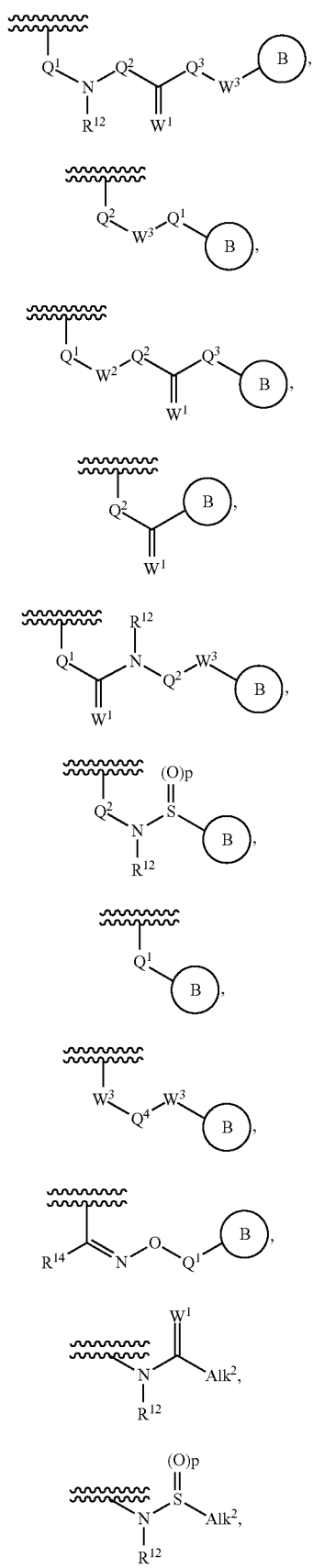

wherein $Q^1$, $Q^2$ and $Q^3$ are each independently a bond, lower alkylene or lower alkenylene, lower alkylene and lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

$Q^4$ is lower alkylene or lower alkenylene, lower alkylene and lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

$W^1$ and $W^2$ are each independently O or S;

$W^3$ is O, S or $NR^{12}$;

$R^{12}$ is a hydrogen atom, lower alkyl, hydroxy lower alkyl, lower alkoxy lower alkyl, lower alkoxycarbonyl lower alkyl, carbocyclic group lower alkyl or acyl;

$R^{14}$ is a hydrogen atom or lower alkyl;

ring B is a carbocyclic group or a heterocyclic group, the carbocyclic group and the heterocyclic group being substituted optionally with at least one selected from the group consisting of (a) a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

(b) lower alkyl optionally substituted with the substituent α;
(c) amino lower alky substituted with the substituent α;
(d) hydroxyimino lower alkyl;
(e) lower alkoxyimino lower alkyl;
(f) lower alkenyl optionally substituted with the substituent α;
(g) lower alkynyl optionally substituted with the substituent α;
(h) lower alkoxy optionally substituted with the substituent α;
(i) lower alkylthio optionally substituted with the substituent α;
(j) lower alkylamino substituted with the substituent α;
(k) lower alkylsulfonyl optionally substituted with the substituent α;
(l) aryl lower alkoxycarbonyl optionally substituted with one or more substituents selected from the group of substituent α and lower alkyl;
(m) acyl substituted with the substituent α;
(n) lower alkylsulfonyl optionally substituted with the substituent α;
(o) sulfamoyl;
(p) lower alkyl sulfamoyl optionally substituted with one or more substituents selected from the group of substituent α;
(q) cycloalkyl optionally substituted with one or more substituents selected from the group of substituent α azido and lower alkyl;
(r) aryl optionally substituted with one or more substituents selected from the group of substituent α azido and lower alkyl;
(s) heterocyclic group optionally substituted with one or more substituents selected from the group of substituent α, azido and lower alkyl;
(t) aryloxy optionally substituted with one or more substituents selected from the group of substituent α, azido and lower alkyl;
(u) heterocyclicoxy optionally substituted with one or more substituents selected from the group of substituent α, azido and lower alkyl;
(v) arylthio optionally substituted with one or more substituents selected from the group of substituent α, azido and lower alkyl;
(w) heterocyclic thio optionally substituted with one or more substituents selected from the group of substituent α, azido and lower alkyl;
(x) arylamino optionally substituted with one or more substituents selected from the group of substituent α, azido and lower alkyl;
(y) heterocyclic amino optionally substituted with one or more substituents selected from the group of substituent α, azido and lower alkyl;
(z) aryl lower alkylamino optionally substituted with one or more substituents selected from the group of substituent α, azido and lower alkyl;
(aa) heterocyclic lower alkylamino optionally substituted with one or more substituents selected from the group of substituent α, azido and lower alkyl;
(ab) arylsulfamoyl optionally substituted with one or more substituents selected from the group of substituent α azido and lower alkyl;
(ac) heterocyclic sulfamoyl optionally substituted with one or more substituents selected from the group of substituent α, azido and lower alkyl;
(ad) arylsulfonyl optionally substituted with one or more substituents selected from the group of substituent α, azido and lower alkyl;
(ae) heterocyclic sulfonyl optionally substituted with one or more substituents selected from the group of substituent α, azido and lower alkyl;
(af) arylcarbamoyl optionally substituted with one or more substituents selected from the group of substituent α, azido and lower alkyl;
(ag) heterocyclic carbamoyl optionally substituted with one or more substituents selected from the group of substituent α, azido and lower alkyl;
(ah) aryl lower alkylcarbamoyl optionally substituted with one or more substituents selected from the group of substituent α, azido and lower alkyl;
(ai) heterocyclic lower alkylcarbamoyl optionally substituted with one or more substituents selected from the group of substituent α, azido and lower alkyl;
(aj) aryloxy carbonyl optionally substituted with one or more substituents selected from the group of substituent α, azido and lower alkyl;
(ak) heterocyclicoxycarbonyl optionally substituted with one or more substituents selected from the group of substituent α, azido and lower alkyl;
(al) lower alkylenedioxy substituted optionally with halogen; and
(am) oxo;
$Alk^2$ is lower alkyl, lower alkyl being substituted optionally with at least one selected from the group consisting of a substituent α; and
p is an integer of 1 or 2;
X is S;
$R^{2a}$ and $R^{2b}$ are each independently a hydrogen atom, hydroxy, lower alkyl, lower alkenyl, amino, amidino, acyl, carbamoyl, carbamoylcarbonyl, lower alkylsulfonyl, arylsulfonyl, or a heterocyclic group,
lower alkyl being substituted optionally with at least one selected from the group consisting of a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, lower alkenyl being substituted optionally with the substituent α,
amino being substituted optionally with at least one selected from the group consisting of lower alkyl, acyl, hydroxy, lower alkoxy, lower alkoxycarbonyl, a carbocyclic group and a heterocyclic group,
amidino being substituted optionally with at least one selected from the group consisting of lower alkyl, acyl, hydroxy, lower alkoxy, lower alkoxycarbonyl, a carbocyclic group and a heterocyclic group,
acyl includes aliphatic acyl of a carbon number of 1 to 10, carbocyclic carbonyl and heterocyclic carbonyl; and
acyl being substituted optionally with the substituent α; and the ring part of the "carbocyclic carbonyl" and the "heterocyclic carbonyl" is substituted optionally with at least one selected from the group of "lower alkyl"; the "substituent group α"; and "lower alkyl substituted with at least one selected from the group of the substituent α",
carbamoyl being substituted optionally with at least one selected from the group consisting of lower alkyl, acyl, hydroxy, lower alkoxy, lower alkoxycarbonyl, a carbocyclic group and a heterocyclic group, carbamoylcarbonyl being substituted optionally with at least one selected from the group consisting of lower alkyl, acyl, hydroxy, lower alkoxy, lower alkoxycarbonyl, a carbocyclic group and a heterocyclic group, lower alkylsulfonyl being substituted optionally with the substituent α, the arylsulfonyl being substituted optionally with at least one selected from the group consisting of the substituent α and a lower alkyl, and carbocyclic group and the heterocyclic group being substituted optionally with at least one selected from the group consisting of the substituent α and a lower alkyl;

$R^{3a}$, $R^{3b}$, $R^{4a}$, and $R^{4b}$ are each independently a hydrogen atom, halogen, hydroxy, lower alkyl, lower alkenyl, acyl, carboxy, lower alkoxycarbonyl, amino, carbamoyl, a carbocyclic group, or a heterocyclic group, lower alkyl being substituted optionally with at least one selected from the group consisting of a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, lower alkenyl being substituted optionally with the substituent α, acyl includes aliphatic acyl of a carbon number of 1 to 10, carbocyclic carbonyl and heterocyclic carbonyl; and acyl being substituted optionally with the substituent α; and the ring part of the "carbocyclic carbonyl" and the "heterocyclic carbonyl" is substituted optionally with at least one selected from the group of "lower alkyl"; the "substituent group a"; and "lower alkyl substituted with at least one selected from the group of the substituent α", lower alkoxycarbonyl being substituted optionally with the substituent α, amino being substituted optionally with at least one selected from the group consisting of lower alkyl, acyl, hydroxy, lower alkoxy, lower alkoxycarbonyl, a carbocyclic group and a heterocyclic group, carbamoyl being substituted optionally with at least one selected from the group consisting of lower alkyl, acyl, hydroxy, lower alkoxy, lower alkoxycarbonyl, a carbocyclic group and a heterocyclic group, and the carbocyclic group and the heterocyclic group being substituted optionally with at least one selected from the group consisting of the substituent α and a lower alkyl;

n=2 and m=0;

each $R^{3a}$, each $R^{3b}$, each $R^{4a}$, and each $R^{4b}$ may be independently different;

$R^5$ is a hydrogen atom, lower alkyl, lower alkenyl, lower alkynyl, a carbocyclic group, or a heterocyclic group, lower alkyl being substituted optionally with at least one selected from the group consisting of a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, lower alkenyl being substituted optionally with the substituent α, lower alkynyl being substituted optionally with the substituent α, and the carbocyclic group and the heterocyclic group being substituted optionally with at least one selected from the group consisting of the substituent α and lower alkyl;

with the proviso that the compounds;

i) wherein $R^5$ is a hydrogen atom, and ring A is non-substituted phenyl;

ii) wherein n is 2, m is 0, $R^{2a}$ is a hydrogen atom, $R^{2b}$ is a hydrogen atom or acetyl, $R^5$ is methyl, and ring A is phenyl or 4-methoxyphenyl;

iii) wherein n is 2, m is 0, $R^{2a}$ is a hydrogen atom, $R^{2b}$ is a hydrogen atom or acetyl, $R^5$ is ethyl, and ring A is 3,4-dimethoxyphenyl;

iv) wherein n is 2, m is 0, $R^{2a}$ is a hydrogen atom, $R^{2b}$ is a hydrogen atom or acetyl, $R^5$ and ring A is phenyl;

v) and wherein $R^5$ is a hydrogen atom, ring A is phenyl which has only one or two substituent(s) selected from the group consisting of hydroxy, halogen, lower alkyl, lower alkoxy, nitro, amino, lower alkylcarbonylamino, mercapto, lower alkylthio, and carbamoyl, non-substituted phenyl, or non-substituted naphthyl; are excluded, a pharmaceutically acceptable salt thereof or a hydrate thereof.

2. The compound according to claim 1, wherein $R^5$ is lower alkyl, lower alkenyl, lower alkynyl, a carbocyclic group, or a heterocyclic group, lower alkyl being substituted optionally with at least one selected from the group consisting of a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, lower alkenyl being substituted optionally with the substituent α, lower alkynyl being substituted optionally with the substituent α, and the carbocyclic group and the heterocyclic group being substituted optionally with at least one selected from the group consisting of the substituent α and lower alkyl, a pharmaceutically acceptable salt thereof or a hydrate thereof.

3. The compound according to claim 1, wherein $R^{2a}$ is a hydrogen atom; $R^{2b}$ is a hydrogen atom, lower alkyl, acyl, lower alkylsulfonyl, or amidino, lower alkyl being substituted optionally with at least one selected from the group consisting of a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, acyl includes aliphatic acyl of a carbon number of 1 to 10, carbocyclic carbonyl and heterocyclic carbonyl; and acyl being substituted optionally with the substituent α; and the ring part of the "carbocyclic carbonyl" and the "heterocyclic carbonyl" is substituted optionally with at least one selected from the group of "lower alkyl"; the "substituent group α"; and "lower alkyl substituted with at least one selected from the group of the substituent α", lower alkylsulfonyl being substituted optionally with the substituent α, and amidino being substituted optionally with at least one selected from the group consisting of lower alkyl, acyl, hydroxy, lower alkoxy, lower alkoxycarbonyl, a carbocyclic group and a heterocyclic group, or a pharmaceutically acceptable salt thereof or a hydrate thereof.

4. The compound according to claim 1, wherein $NR^{2a}R^{2b}$ is represented by the formula:

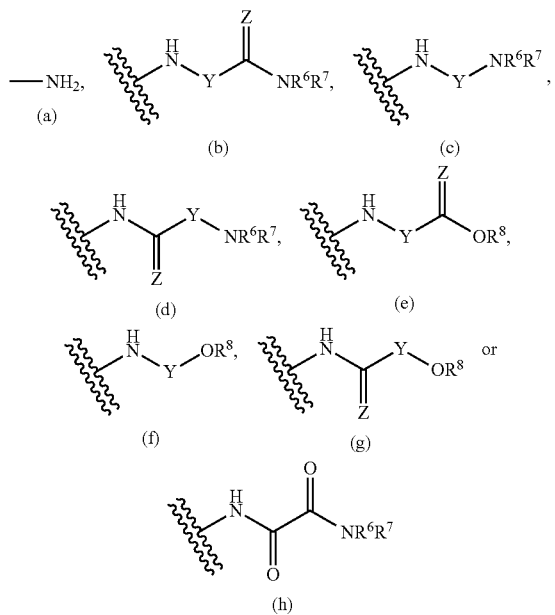

where $R^6$, $R^7$, and $R^8$ are each independently a hydrogen atom, lower alkyl, or acyl;

Y is lower alkylene, lower alkenylene, or lower alkynylene, lower alkylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, lower alkenylene being substituted optionally with the substituent α, and lower alkynylene being substituted optionally with the substituent α;

Z is O or S;

a pharmaceutically acceptable salt thereof or a hydrate thereof.

5. The compound according to claim 1, wherein ring A is represented by the formula:

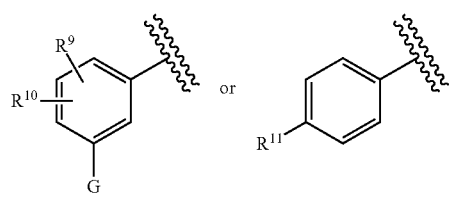

wherein $R^9$, $R^{10}$, and $R^{11}$ are a hydrogen atom or G;

G is <A>, <B>, <C>, <D>, <E>, <F>, <G>, or <H>, where <A>, <B>, <C>, <D>, <E>, <F>, <G> and <H> are the following:

<A> halogen, hydroxy, cyano, nitro, mercapto, lower alkyl, lower alkoxy, lower alkenyl, lower alkynyl, acyl, acyloxy, carboxy, lower alkoxycarbonyl, lower alkoxycarbonyloxy, aryloxycarbonyloxy, amino, carbamoyl, carbamoyloxy, lower alkylthio, arylthio, lower alkylsulfonyl, arylsulfonyl, lower alkyl sulfinyl, arylsulfinyl, lower alkylsulfonyloxy, arylsulfonyloxy, sulfamoyl, a carbocyclic group, carbocyclicoxy, a heterocyclic group, or heterocyclicoxy, lower alkyl being substituted optionally with at least one selected from the group consisting of a substituent α, a hydroxyimino group, and a lower alkoxyimino group, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, lower alkoxy being substituted optionally with the substituent α, lower alkenyl being substituted optionally with the substituent α, lower alkynyl being substituted optionally with the substituent α, acyl includes aliphatic acyl of a carbon number of 1 to 10, carbocyclic carbonyl and heterocyclic carbonyl; and acyl being substituted optionally with the substituent α; and the ring part of the "carbocyclic carbonyl" and the "heterocyclic carbonyl" is substituted optionally with at least one selected from the group of "lower alkyl"; the "substituent group α"; and "lower alkyl substituted with at least one selected from the group of the substituent α", acyloxy includes aliphatic acyloxy of a carbon number of 1 to 10, carbocyclic carbonyloxy and heterocyclic carbonyloxy; and acyloxy being substituted optionally with the substituent α; and the ring part of the "carbocyclic carbonyloxy" and the "heterocyclic carbonyloxy" is substituted optionally with at least one selected from the group of "lower alkyl"; the "substituent group α"; and "lower alkyl substituted with at least one selected from the group of the substituent α", lower alkoxycarbonyl being substituted optionally with the substituent α, lower alkoxycarbonyloxy being substituted optionally with the substituent α, aryloxycarbonyloxy being substituted optionally with at least one selected from the group consisting of lower alkyl and the substituent α, amino being substituted optionally with at least one selected from the group consisting of lower alkyl, acyl, hydroxy, lower alkoxy, lower alkoxycarbonyl, a carbocyclic group and a heterocyclic group, carbamoyl being substituted optionally with at least one selected from the group consisting of lower alkyl, acyl, hydroxy, lower alkoxy, lower alkoxycarbonyl, a carbocyclic group and a heterocyclic group, carbamoyloxy being substituted optionally with at least one selected from the group consisting of lower alkyl, acyl, hydroxy, lower alkoxy, lower alkoxycarbonyl, a carbocyclic group and a heterocyclic group, lower alkylthio being substituted optionally with the substituent α,
arylthio being substituted optionally with at least one selected from the group consisting of lower alkyl and the substituent α,
lower alkylsulfinyl being substituted optionally with the substituent α,
arylsulfonyl being substituted optionally with at least one selected from the group consisting of the substituent α, azido, and lower alkyl,
lower alkylsulfonyl being substituted optionally with the substituent α,
arylsulfinyl being substituted optionally with at least one selected from the group consisting of lower alkyl and the substituent α,
lower alkylsulfonyloxy being substituted optionally with the substituent α,
arylsulfonyloxy being substituted optionally with the substituent α,
sulfamoyl being substituted optionally with the substituent α, and
the carbocyclic group, carbocyclicoxy, the heterocyclic group, and heterocyclicoxy being substituted optionally with at least one selected from the group consisting of lower alkyl and the substituent α;
<B>
one of the following (i), (ii), (iv), (vi), (viii) and (x):

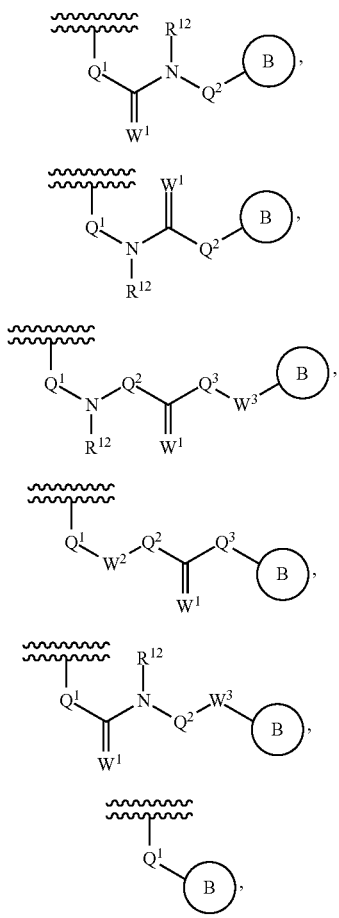

wherein each $Q^1$ is lower alkylene, lower alkylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;
$Q^2$ and $Q^3$ are each independently a bond, lower alkylene or lower alkenylene, lower alkylene and lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;
$W^1$ and $W^2$ are each independently O or S;
$W^3$ is O, S, or $NR^{12}$;
$R^{12}$ is a hydrogen atom, lower alkyl, hydroxy lower alkyl, lower alkoxy lower alkyl, lower alkoxycarbonyl lower alkyl, carbocyclic lower alkyl, or acyl; and
ring B is a carbocyclic group or a heterocyclic group, the carbocyclic group and the heterocyclic group being substituted optionally with at least one selected from the group consisting of
(a) a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;
(b) lower alkyl optionally substituted with the substituent α;
(c) amino lower alky substituted with the substituent α;
(d) hydroxyimino lower alkyl;
(e) lower alkoxyimino lower alkyl;
(f) lower alkenyl optionally substituted with the substituent α;
(g) lower alkynyl optionally substituted with the substituent α;
(h) lower alkoxy optionally substituted with the substituent α;
(i) lower alkylthio optionally substituted with the substituent α;
(j) lower alkylamino substituted with the substituent α;
(k) lower alkylsulfonyl optionally substituted with the substituent α;
(l) aryl lower alkoxycarbonyl optionally substituted with one or more substituents selected from the group of substituent α and lower alkyl;
(m) acyl substituted with the substituent α;
(n) lower alkylsulfonyl optionally substituted with the substituent α;
(o) sulfamoyl;
(p) lower alkyl sulfamoyl optionally substituted with one or more substituents selected from the group of substituent α;
(q) cycloalkyl optionally substituted with one or more substituents selected from the group of substituent α, azido and lower alkyl;

(r) aryl optionally substituted with one or more substituents selected from the group of substituent α, azido and lower alkyl;
(s) heterocyclic group optionally substituted with one or more substituents selected from the group of substituent α, azido and lower alkyl;
(t) aryloxy optionally substituted with one or more substituents selected from the group of substituent α, azido and lower alkyl;
(u) heterocyclicoxy optionally substituted with one or more substituents selected from the group of substituent α, azido and lower alkyl;
(v) arylthio optionally substituted with one or more substituents selected from the group of substituent α, azido and lower alkyl;
(w) heterocyclic thio optionally substituted with one or more substituents selected from the group of substituent α, azido and lower alkyl;
(x) arylamino optionally substituted with one or more substituents selected from the group of substituent α, azido and lower alkyl;
(y) heterocyclic amino optionally substituted with one or more substituents selected from the group of substituent α, azido and lower alkyl;
(z) aryl lower alkylamino optionally substituted with one or more substituents selected from the group of substituent α, azido and lower alkyl;
(aa) heterocyclic lower alkylamino optionally substituted with one or more substituents selected from the group of substituent α, azido and lower alkyl;
(ab) arylsulfamoyl optionally substituted with one or more substituents selected from the group of substituent α, azido and lower alkyl;
(ac) heterocyclic sulfamoyl optionally substituted with one or more substituents selected from the group of substituent α, azido and lower alkyl;
(ad) arylsulfonyl optionally substituted with one or more substituents selected from the group of substituent α, azido and lower alkyl;
(ae) heterocyclic sulfonyl optionally substituted with one or more substituents selected from the group of substituent α, azido and lower alkyl;
(af) arylcarbamoyl optionally substituted with one or more substituents selected from the group of substituent α, azido and lower alkyl;
(ag) heterocyclic carbamoyl optionally substituted with one or more substituents selected from the group of substituent α, azido and lower alkyl;
(ah) aryl lower alkylcarbamoyl optionally substituted with one or more substituents selected from the group of substituent α, azido and lower alkyl;
(ai) heterocyclic lower alkylcarbamoyl optionally substituted with one or more substituents selected from the group of substituent α, azido and lower alkyl;
(aj) aryloxy carbonyl optionally substituted with one or more substituents selected from the group of substituent α, azido and lower alkyl;
(ak) heterocyclicoxycarbonyl optionally substituted with one or more substituents selected from the group of substituent α, azido and lower alkyl;
(al) lower alkylenedioxy substituted optionally with halogen; and
(am) oxo;

<C>
one of the following (iii), (v), (vii), (ix) and (xii):

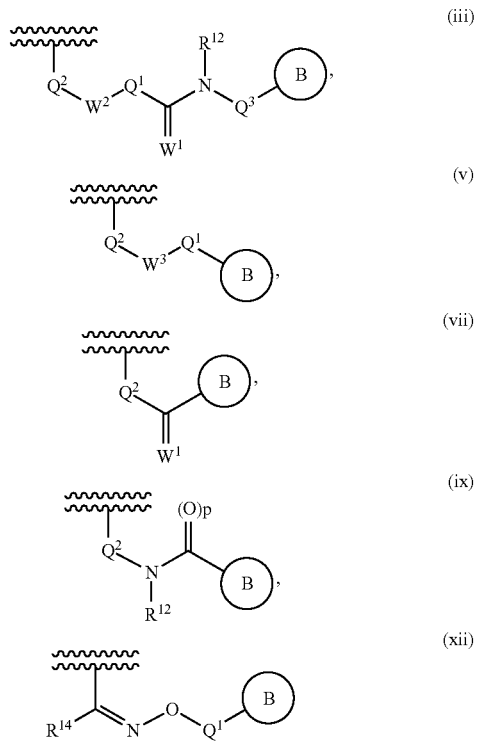

wherein each $Q^2$ is lower alkylene, lower alkylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

$Q^1$ and $Q^3$ are each independently a bond, lower alkylene or lower alkenylene, lower alkylene and lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

$W^1$ and $W^2$ are each independently O or S;

$W^3$ is O, S, or $NR^{12}$;

$R^{12}$ is a hydrogen atom, lower alkyl, hydroxy lower alkyl, lower alkoxy lower alkyl, lower alkoxycarbonyl lower alkyl, carbocyclic lower alkyl, or acyl;

p is an integer of 1 or 2; and ring B is a carbocyclic group or a heterocyclic group, the carbocyclic group and the heterocyclic group being substituted optionally with at least one selected from the group consisting of the above (a) to (am); and $R^{14}$ is a hydrogen atom or lower alkyl;

<D>
one of the following (iii), (v), (vi) and (xi):

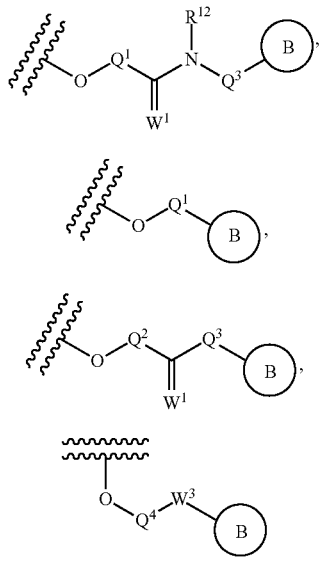

wherein each $Q^1$, $Q^2$ and $Q^4$ are each independently lower alkylene, lower alkylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;
$Q^3$ are each independently a bond, lower alkylene, or lower alkenylene, lower alkylene and lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;
$W^1$ is O or S;
$W^3$ is O, S, or $NR^{12}$;
$R^{12}$ is a hydrogen atom, lower alkyl, hydroxy lower alkyl, lower alkoxy lower alkyl, lower alkoxycarbonyl lower alkyl, carbocyclic lower alkyl, or acyl; and
ring B is a carbocyclic group or a heterocyclic group,
the carbocyclic group and the heterocyclic group being substituted optionally with at least one selected from the group consisting of the above (a) to (am);
<E>
one of the following (i), (ii), (iv), (vi), (viii) and (x):

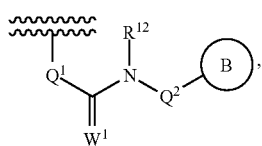

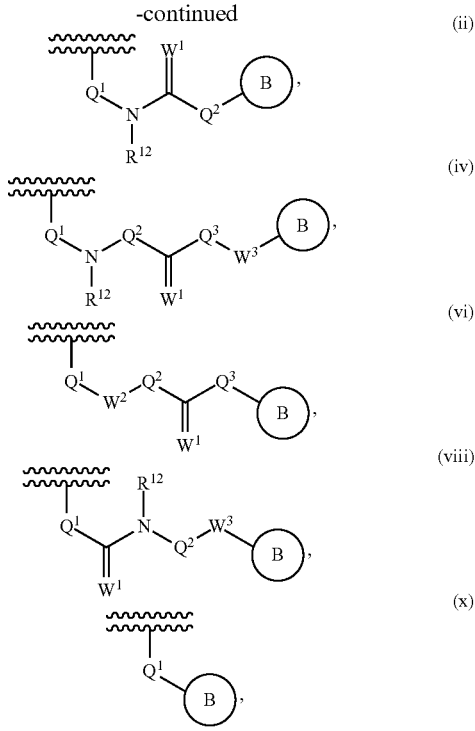

wherein each $Q^1$ is lower alkenylene, lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;
$Q^2$ and $Q^3$ are each independently a bond, lower alkylene or lower alkenylene, lower alkylene and lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;
$W^1$ and $W^2$ are each independently O or S;
$W^3$ is O, S, or $NR^{12}$;
$R^{12}$ is a hydrogen atom, lower alkyl, hydroxy lower alkyl, lower alkoxy lower alkyl, lower alkoxycarbonyl lower alkyl, carbocyclic lower alkyl, or acyl;
ring B is a carbocyclic group or a heterocyclic group,
the carbocyclic group and the heterocyclic group being substituted optionally with at least one selected from the group consisting of the above (a) to (am);
<F>
one of the following (iii), (v), (vii), and (ix):

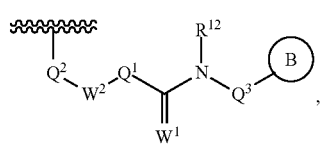

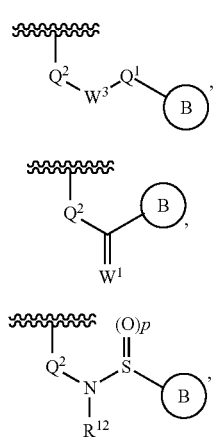

(v)

(vii)

(ix)

wherein $Q^2$ is lower alkenylene, lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

$Q^1$ and $Q^3$ are each independently a bond, lower alkylene or lower alkenylene, lower alkylene and lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

$W^1$ and $W^2$ are each independently O or S;

$W^3$ is O, S, or $NR^{12}$;

$R^{12}$ is a hydrogen atom, lower alkyl, hydroxy lower alkyl, lower alkoxy lower alkyl, lower alkoxycarbonyl lower alkyl, carbocyclic lower alkyl, or acyl;

p is an integer of 1 or 2;

ring B is a carbocyclic group or a heterocyclic group, the carbocyclic group and the heterocyclic group being substituted optionally with at least one selected from the group consisting of the above (a) to (am); and $R^{14}$ is a hydrogen atom or lower alkyl;

<G> one of the following (ii), (iv), (v), (ix), (xiii) and (xiv):

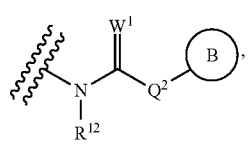

(ii)

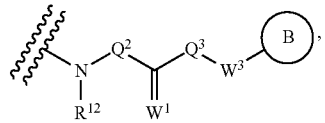

(iv)

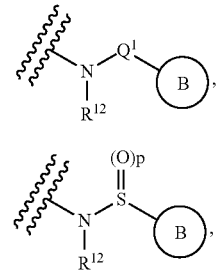

(v)

(ix)

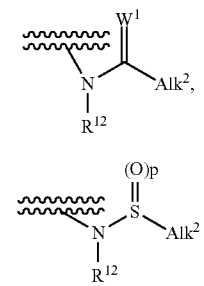

(xiii)

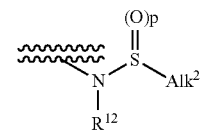

(xiv)

wherein each $Q^1$, $Q^2$ and $Q^3$ are each independently a bond, lower alkylene, or lower alkenylene; lower alkylene and lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

$W^1$ is O or S;

$W^3$ is O, S, or $NR^{12}$;

$R^{12}$ is a hydrogen atom, lower alkyl, hydroxy lower alkyl, lower alkoxy lower alkyl, lower alkoxycarbonyl lower alkyl, carbocyclic lower alkyl, or acyl;

$Alk^2$ is lower alkyl, lower alkyl being substituted optionally with at least one selected from the group consisting of a substituent α;

p is an integer of 1 or 2; and ring B is a carbocyclic group or a heterocyclic group, the carbocyclic group and the heterocyclic group being substituted optionally with at least one selected from the group consisting of the above (a) to (am);

<H> one of the following (i), (viii) and (xv):

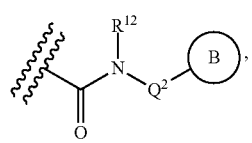

(i)

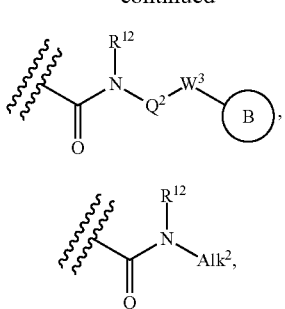

(viii)

(xv)

wherein $Q^2$ is a bond, lower alkylene, or lower alkenylene, lower alkylene and lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

$W^3$ is O, S, or $NR^{12}$;

$R^{12}$ is a hydrogen atom, lower alkyl, hydroxy lower alkyl, lower alkoxy lower alkyl, lower alkoxycarbonyl lower alkyl, carbocyclic lower alkyl, or acyl;

$Alk^2$ is lower alkyl, lower alkyl being substituted optionally with at least one selected from the group consisting of a substituent α; and ring B is a carbocyclic group or a heterocyclic group, the carbocyclic group and the heterocyclic group being substituted optionally with at least one selected from the group consisting of the above (a) to (am);

each G may be independently different;

a pharmaceutically acceptable salt thereof or a hydrate thereof.

6. The compound according to claim 5, wherein ring A is represented by the formula:

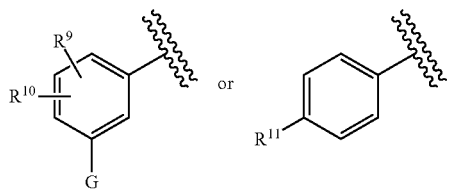

wherein $R^9$, $R^{10}$, and $R^{11}$ are a hydrogen atom, halogen, hydroxy, cyano, nitro, mercapto, lower alkyl, lower alkoxy, lower alkenyl, lower alkynyl, acyl, acyloxy, carboxy, lower alkoxycarbonyl, lower alkoxycarbonyloxy, aryloxycarbonyloxy, amino, carbamoyl, carbamoyloxy, lower alkylthio, arylthio, lower alkylsulfonyl, arylsulfonyl, lower alkylsulfinyl, arylsulfinyl, lower alkylsulfonyloxy, arylsulfonyloxy, sulfamoyl, a carbocyclic group, carbocyclicoxy, a heterocyclic group or heterocyclicoxy, lower alkyl being substituted optionally with at least one selected from the group consisting of a substituent α, a hydroxyimino group, and a lower alkoxyimino group, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, lower alkoxy being substituted optionally with the substituent α, lower alkenyl being substituted optionally with the substituent α, lower alkynyl being substituted optionally with the substituent α, acyl includes aliphatic acyl of a carbon number of 1 to 10, carbocyclic carbonyl and heterocyclic carbonyl; and acyl being substituted optionally with the substituent α; and the ring part of the "carbocyclic carbonyl" and the "heterocyclic carbonyl" is substituted optionally with at least one selected from the group of "lower alkyl"; the "substituent group a"; and "lower alkyl substituted with at least one selected from the group of the substituent α", acyloxy includes aliphatic acyloxy of a carbon number of 1 to 10, carbocyclic carbonyloxy and heterocyclic carbonyloxy; and acyloxy being substituted optionally with the substituent α; and the ring part of the "carbocyclic carbonyloxy" and the "heterocyclic carbonyloxy" is substituted optionally with at least one selected from the group of "lower alkyl"; the "substituent group a"; and "lower alkyl substituted with at least one selected from the group of the substituent α", lower alkoxycarbonyl being substituted optionally with the substituent α, lower alkoxycarbonyloxy being substituted optionally with the substituent α, aryloxycarbonyloxy being substituted optionally with at least one selected from the group consisting of lower alkyl and the substituent α, amino being substituted optionally with at least one selected from the group consisting of lower alkyl, acyl, hydroxy, lower alkoxy, lower alkoxycarbonyl, a carbocyclic group and a heterocyclic group, carbamoyl being substituted optionally with at least one selected from the group consisting of lower alkyl, acyl, hydroxy, lower alkoxy, lower alkoxycarbonyl, a carbocyclic group and a heterocyclic group, carbamoyloxy being substituted optionally with at least one selected from the group consisting of lower alkyl, acyl, hydroxy, lower alkoxy, lower alkoxycarbonyl, a carbocyclic group and a heterocyclic group, lower alkylthio being substituted optionally with the substituent α, arylthio being substituted optionally with at least one selected from the group consisting of lower alkyl and the substituent α, lower alkylsulfonyl being substituted optionally with the substituent α, arylsulfonyl being substituted optionally with at least one selected from the group consisting of the substituent α and lower alkyl, lower alkylsulfonyl being substituted optionally with the substituent α, arylsulfinyl being substituted optionally with at least one selected from the group consisting of lower alkylsulfonyloxy being substituted optionally with the substituent α, arylsulfonyloxy being substituted optionally with the substituent α, sulfamoyl being substituted optionally with the substituent α, and the carbocyclic group, carbocyclicoxy, the heterocyclic group, and heterocyclicoxy being substituted optionally with at least one selected from the group consisting of lower alkyl and the substituent α; and G is represented by the formula:

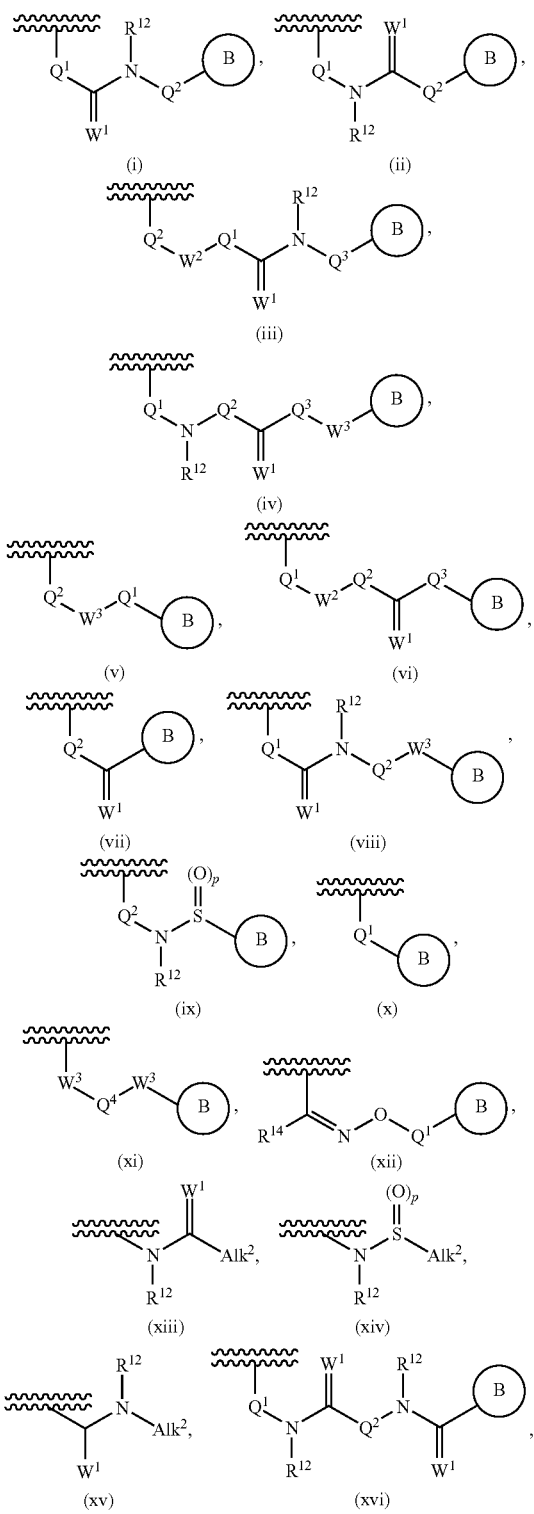

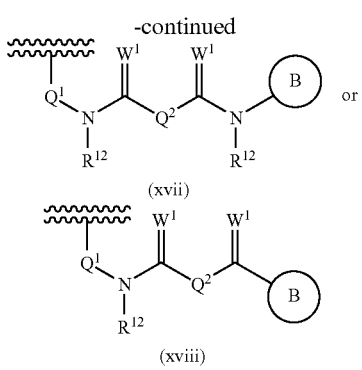

$Q^1$, $Q^2$, and $Q^3$ are each independently a bond, lower alkylene, or lower alkenylene;

$Q^4$ is lower alkylene, or lower alkenylene, lower alkylene and lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

$W^1$ and $W^2$ are each independently O or S;

$W^3$ is O, S, or $NR^{12}$;

$R^{12}$ is a hydrogen atom, lower alkyl, hydroxy lower alkyl, lower alkoxy lower alkyl, lower alkoxycarbonyl lower alkyl, carbocyclic lower alkyl, or acyl;

$R^{14}$ is a hydrogen atom or lower alkyl;

ring B is a carbocyclic group or a heterocyclic group, the carboxylic group and the heterocyclic group being substituted optionally with at least one selected from the group consisting of a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, amino lower alkyl substituted with the substituent α, hydroxyimino lower alkyl, lower alkoxyimino lower alkyl, lower alkyl optionally substituted with the substituent α, lower alkenyl optionally substituted with the substituent α, lower alkynyl optionally substituted with the substituent α, lower alkoxy optionally substituted with the substituent α, lower alkylthio optionally substituted with the substituent α, lower alkylamino optionally substituted with the substituent α, lower alkylsulfonyl optionally substituted with the substituent α, aryl lower alkoxycarbonyl optionally substituted with at least one selected from the group consisting of the substituent α and lower alkyl, acyl substituted with the substituent α, lower alkylsulfonyl optionally substituted with the substituent α, sulfamoyl, lower alkyl sulfamoyl optionally substituted with the substituent α,
cycloalkyl optionally substituted with at least one selected from the group consisting of the substituent α, azido, and lower alkyl,
aryl optionally substituted with at least one selected from the group consisting of the substituent α, azido, and lower alkyl,
heterocyclic group optionally substituted with at least one selected from the group consisting of the substituent α, azido, and lower alkyl,
aryloxy optionally substituted with at least one selected from the group consisting of the substituent α, azido, and lower alkyl,
heterocyclicoxy optionally substituted with at least one selected from the group consisting of the substituent α, azido, and lower alkyl,
arylthio optionally substituted with at least one selected from the group consisting of the substituent α, azido, and lower alkyl,
heterocyclic thio optionally substituted with at least one selected from the group consisting of the substituent α, azido, and lower alkyl,
arylamino optionally substituted with at least one selected from the group consisting of the substituent α, azido, and lower alkyl,
heterocyclic amino optionally substituted with at least one selected from the group consisting of the substituent α, azido, and lower alkyl,
aryl lower alkylamino optionally substituted with at least one selected from the group consisting of the substituent α, azido, and lower alkyl,
heterocyclic lower alkylamino optionally substituted with at least one selected from the group consisting of the substituent α, azido, and lower alkyl,
arylsulfamoyl optionally substituted with at least one selected from the group consisting of the substituent α, azido, and lower alkyl,
heterocyclic sulfamoyl optionally substituted with at least one selected from the group consisting of the substituent α, azido, and lower alkyl,
arylsulfonyl optionally substituted with at least one selected from the group consisting of the substituent α, azido, and lower alkyl,
heterocyclic sulfonyl optionally substituted with at least one selected from the group consisting of the substituent α, azido, and lower alkyl,
arylcarbamoyl optionally substituted with at least one selected from the group consisting of the substituent α, azido, and lower alkyl,
heterocyclic carbamoyl optionally substituted with at least one selected from the group consisting of the substituent α, azido, and lower alkyl,
aryl lower alkylcarbamoyl optionally substituted with at least one selected from the group consisting of the substituent α, azido, and lower alkyl,
heterocyclic lower alkylcarbamoyl optionally substituted with at least one selected from the group consisting of the substituent α, azido, and lower alkyl,
aryloxy carbonyl optionally substituted with at least one selected from the group consisting of the substituent α, azido, and lower alkyl,
heterocyclicoxycarbonyl optionally substituted with at least one selected from the group consisting of the substituent α, azido, and lower alkyl, lower alkylenedioxy substituted optionally with halogen and oxo;
$Alk^2$ is lower alkyl,
lower alkyl being substituted optionally with at least one selected from the group consisting of a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

p is 1 or 2;

if there are multiple $W^1$, multiple $W^3$ and multiple $R^{12}$, each may be independently different, a pharmaceutically acceptable salt thereof or a hydrate thereof.

7. The compound according to claim 6, wherein ring B is aryl substituted optionally with at least one substituent selected from the group consisting of halogen, hydroxy, lower alkyl, lower alkoxy, acyl, amino, cyano, carbamoyl, an carbocyclic group, carbocyclicoxy, and heterocyclic group, or heteroaryl substituted optionally with at least one substituent selected from the group consisting of halogen, hydroxy, lower alkyl, lower alkoxy, acyl, amino, cyano, carbamoyl, a carbocyclic group, carbocyclicoxy, and a heterocyclic group, lower alkyl being substituted optionally with at least one selected from the group consisting of a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, lower alkoxy being substituted optionally with the substituent α, acyl includes aliphatic acyl of a carbon number of 1 to 10, carbocyclic carbonyl and heterocyclic carbonyl; and acyl being substituted optionally with the substituent α; and the ring part of the "carbocyclic carbonyl" and the "heterocyclic carbonyl" is substituted optionally with at least one selected from the group of "lower alkyl"; the "substituent group a"; and "lower alkyl substituted with at least one selected from the group of the substituent α", amino being substituted optionally with at least one selected from the group consisting of lower alkyl, acyl, hydroxy, lower alkoxy, lower alkoxycarbonyl, a carbocyclic group and a heterocyclic group, carbamoyl being substituted optionally with at least one selected from the group consisting of lower alkyl, acyl, hydroxy, lower alkoxy, lower alkoxycarbonyl, a carbocyclic group and a heterocyclic group, and the carbocyclic group, carbocyclicoxy, and the heterocyclic group being substituted optionally with at least one selected from the group consisting of lower alkyl and the substituent α;

a pharmaceutically acceptable salt thereof or a hydrate thereof.

8. The compound according to claim 6, wherein G is represented by the formula:

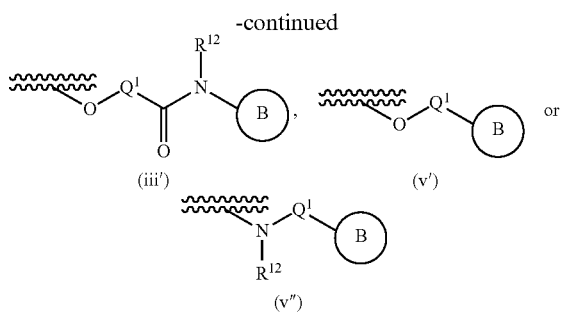

a pharmaceutically acceptable salt thereof or a hydrate thereof.

9. The compound according to claim 1, wherein $R^5$ is C1 to C3 alkyl, a pharmaceutically acceptable salt thereof or a hydrate thereof.

10. The compound according to claim 1, wherein $R^5$ is methyl, a pharmaceutically acceptable salt thereof or a hydrate thereof.

11. The compound according to claim 1, wherein $R^{3a}$ and $R^{3b}$ are each independently a hydrogen atom, halogen, hydroxy, lower alkyl, lower alkoxy, or aryl, lower alkyl being substituted optionally with at least one selected from the group consisting of a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, lower alkoxy being substituted optionally with the substituent α, and aryl being substituted optionally with the substituent α or lower alkyl;

a pharmaceutically acceptable salt thereof or a hydrate thereof.

12. The compound according to claim 1, wherein all of $R^{3a}$ and all of $R^{3b}$ are hydrogen atoms, a pharmaceutically acceptable salt thereof or a hydrate thereof.

13. A pharmaceutical composition comprising the compound as defined in claim 1, a pharmaceutically acceptable salt thereof or a hydrate thereof as an active ingredient, and a pharmaceutically acceptable carrier.

* * * * *

UNITED STATES PATENT AND TRADEMARK OFFICE
CERTIFICATE OF CORRECTION

PATENT NO.        : 8,173,642 B2
APPLICATION NO.   : 12/089409
DATED             : May 8, 2012
INVENTOR(S)       : Kobayashi et al.

It is certified that error appears in the above-identified patent and that said Letters Patent is hereby corrected as shown below:

Column 424 (Claim 1), the formula (xvii): delete "N" under W1=

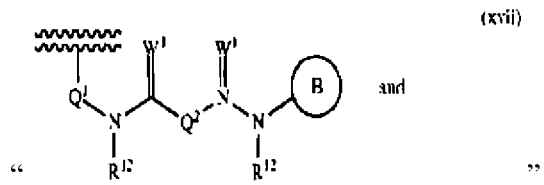

should be

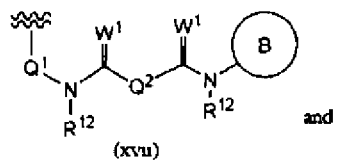

Column 434 (Claim 5), the formula (ix): insert -- S -- under (O)p=

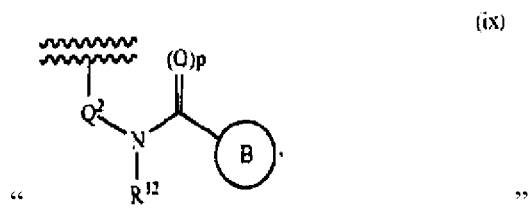

should be

Signed and Sealed this
Twenty-sixth Day of March, 2013

Teresa Stanek Rea
*Acting Director of the United States Patent and Trademark Office*

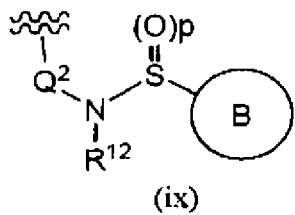
(ix)
---
Column 441 (Claim 6), the formula (xv): line should be double above $W^1$
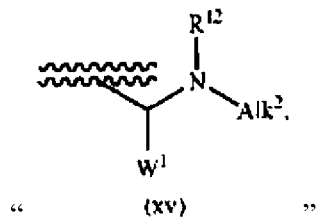
" (xv) "
should be
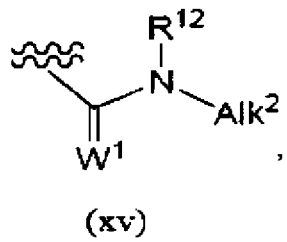
(xv)
---
Column 444 (Claim 8), the formula (ii'): delete "N" under O=
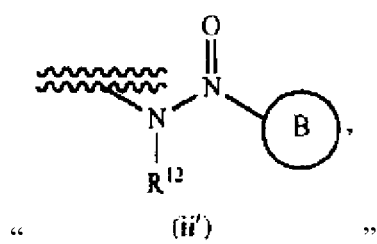
" (ii') "
should be
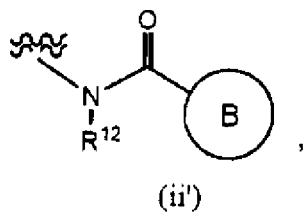
(ii')

Column 427 (Claim 1), line 38: after "substituent α", the sentence -- amino being substituted ... -- should start in the next line as shown below:

lower alkoxycarbonyl being substituted optionally with
        the substituent α,
    amino being substituted optionally with at least one selected
        from the group consisting of lower alkyl, acyl, hydroxy,
        lower alkoxy, lower alkoxycarbonyl, a carbocyclic group
        and a heterocyclic group,
    carbamoyl being substituted optionally with at least one
        selected from the group consisting of lower alkyl, acyl,
        hydroxy, lower alkoxy, lower alkoxycarbonyl, a carbocyclic
        group and a heterocyclic group, and Column 427 (Claim 1), line 63: after "heterocyclic group", the sentence -- lower alkenyl being substituted ... -- should start in the next line as shown below:

lower alkyl being substituted optionally with at least one
        selected from the group consisting of a substituent α, the
        substituent α being at least one selected from the group
        consisting of halogen, hydroxy, lower alkoxy, hydroxy
        lower alkoxy, lower alkoxy lower alkoxy, acyl, acyloxy,
        carboxy, lower alkoxycarbonyl, amino, acylamino,
        lower alkylamino, lower alkylthio, carbamoyl, lower
        alkylcarbamoyl, hydroxy lower alkylcarbamoyl, sulfamoyl,
        lower alkylsulfamoyl, lower alkylsulfinyl, cyano,
        nitro, aryl, and heterocyclic group,
    lower alkenyl being substituted optionally with the substituent α,
    lower alkynyl being substituted optionally with the substituent α, and Column 428 (Claim 2), line 37, after "hetrocyclic group", the sentence
-- lower alkynyl being substituted ... -- should start in the next line as shown below:

lower alkyl being substituted optionally with at least one
        selected from the group consisting of a substituent α, the
        substituent α being at least one selected from the group
        consisting of halogen, hydroxy, lower alkoxy, hydroxy
        lower alkoxy, lower alkoxy lower alkoxy, acyl, acyloxy,
        carboxy, lower alkoxycarbonyl, amino, acylamino,
        lower alkylamino, lower alkylthio, carbamoyl, lower
        alkylcarbamoyl, hydroxy lower alkylcarbamoyl, sulfamoyl,
        lower alkylsulfamoyl, lower alkylsulfinyl, cyano,
        nitro, aryl, and heterocyclic group,

CERTIFICATE OF CORRECTION (continued)
U.S. Pat. No. 8,173,642 B2 lower alkenyl being substituted optionally with the substituent α,
    lower alkynyl being substituted optionally with the substituent α, and Column 444 (Claim 7), lines 14 through 33: the indentation in the paragraph should be as shown below:

The compound according to claim 6, wherein ring B is
        aryl substituted optionally with at least one substituent
        selected from the group consisting of halogen, hydroxy, lower
        alkyl, lower alkoxy, acyl, amino, cyano, carbamoyl, an carbocyclic
        group, carbocyclicoxy, and heterocyclic group, or
        heteroaryl substituted optionally with at least one substituent
        selected from the group consisting of halogen, hydroxy, lower
        alkyl, lower alkoxy, acyl, amino, cyano, carbamoyl, a carbocyclic
        group, carbocyclicoxy, and a heterocyclic group,
    lower alkyl being substituted optionally with at least one
        selected from the group consisting of a substituent α, the
        substituent α being at least one selected from the group
        consisting of halogen, hydroxy, lower alkoxy, hydroxy
        lower alkoxy, lower alkoxy lower alkoxy, acyl, acyloxy,
        carboxy, lower alkoxycarbonyl, amino, acylamino,
        lower alkylamino, lower alkylthio, carbamoyl, lower
        alkylcarbamoyl, hydroxy lower alkylcarbamoyl,
        sulfamoyl, lower alkylsulfamoyl, lower alkylsulfinyl,
        cyano, nitro, aryl, and heterocyclic group,
    lower alkoxy being substituted optionally with the substituent α,